US011168335B2

(12) United States Patent
Vossen et al.

(10) Patent No.: US 11,168,335 B2
(45) Date of Patent: Nov. 9, 2021

(54) R8 *PHYTOPHTHORA* RESISTANCE GENE IN POTATO

(71) Applicant: Wageningen Universiteit, Wageningen (NL)

(72) Inventors: Jacobus Hubertus Vossen, Wageningen (NL); Kwang Ryong Jo, Wageningen (NL); Richard Gerardus Franciscus Visser, Bennekom (NL)

(73) Assignee: Wageningen Universiteit, Wageningen (NL)

( * ) Notice: Subject to any disclaimer, the term of this patent is extended or adjusted under 35 U.S.C. 154(b) by 0 days.

(21) Appl. No.: 16/245,767

(22) Filed: Jan. 11, 2019

(65) Prior Publication Data

US 2019/0211350 A1 Jul. 11, 2019

Related U.S. Application Data

(62) Division of application No. 15/511,103, filed as application No. PCT/NL2015/050646 on Sep. 17, 2015, now abandoned.

(60) Provisional application No. 62/051,361, filed on Sep. 17, 2014.

(51) Int. Cl.

| | |
|---|---|
| ***C12N 15/82*** | (2006.01) |
| ***A01H 5/06*** | (2018.01) |
| ***C07K 14/415*** | (2006.01) |
| ***A01H 1/02*** | (2006.01) |
| ***C07K 16/16*** | (2006.01) |

(52) U.S. Cl.

CPC ........... *C12N 15/8279* (2013.01); *A01H 1/02* (2013.01); *A01H 5/06* (2013.01); *C07K 14/415* (2013.01); *C07K 16/16* (2013.01); *C12N 15/8282* (2013.01)

(58) Field of Classification Search

None

See application file for complete search history.

(56) References Cited

U.S. PATENT DOCUMENTS

2002/0062504 A1 5/2002 Tanksley et al.

FOREIGN PATENT DOCUMENTS

CN 102796744 A 11/2012

OTHER PUBLICATIONS

Wikipedia: "Oomycete" and "Phytophthora infestans" (2020); downloaded from https://en.wikipedia.org/wiki/Oomycete and https://en.wikipedia.org/wiki/Phytophthora_infestans; excerpts directed to classification.*

Jo et al. Mapping of the S. demissum late blight resistance gene R8 to a new locus on chromosome IX. (2011)Theor. Appl. Genet.  vol. 123; pp. 1331-1340 (Year: 2011).*

Kumar et al. Agrobacterium-mediated transformation of five wild *solanum* species using in vitro microtubers. (1995) Plant Cell Reports vol. 14;pp. 324-328 (Year: 1995).*

Pel et al. Mapping and cloning of late blight resistance genes from Solanum venturii using an interspecific candidate gene approach. (2009) MPMI;vol. 22; pp. 601-615 (Year: 2009).*

Kim et al. Broad spectrum late blight resistance in potato differential set plants MaR and MaR9 is conferred by multiple stacked R genes. (2012) Theor. Appli. Genet. (2012) vol. 124;pp. 923-935 (Year: 2012).*

Vossen et al. The Solanum demissum R8 late blight resistance gene is an Sw-5 homologue that has been deployed worldwide in la Theor. Appi. Genet. vol. 129; pp. 1785-1796 (Year: 2016).*

Bains et al. Haploid plants of Solanum demissum. (1950) Nature;vol. 166; p. 795 (Year: 1950).*

Brugmans et al. Exploitation of a marker dense linkage map of potato for positional cloning of a wart disease resistance gene. (2006) Theor Appl Genet; vol. 112; pp. 269-277 (Year: 2006).*

E. Orlowska et al., "Revealing the importance of meristems and roots for the development of hypersensitive responses and full foliar resistance to Phytophthora infestans in the resistant potato cultivar Sarpo Mira," Journal of Experimental Botany, 63(13): 4765-4779 (2012).

Hyoun-Joung, Kim et al., "Broad spectrum late blight resistance in potato differential set plants MaR8 and MaR9 is conferred by multiple stacked R genes," Theoretical and Applied Genetics, International Journal of Plant Breeding Research, 124(5):923-935 (2011).

International Search Report issued in corresponding Application No. PCT/NL2015/050646, dated Feb. 1, 2016, 4 pages.

Kwang-Ryong et al., "Mapping of the late blight resistance gene R8 to a new locus on chromosome IX," Theoretical and Applied Genetics; International Journal of Plant Breeding Research, 123(8):1331-1340 (2011).

Seijiro Ono et al., Efficient Chromosome Number Estimation Using Flow Cytometry in the Backcross of Solanum demissum (2n=6x=72) to S. tuberosum (2n=4x=48), American Journal of Potato Research, 87(6):553-556 (2010).

Tomczynska et al., "Hypersensitive response to Potato virus Y in potato cultivar Sarpo Mira is conferred by the Ny-Smira gene located on the long arm of chromosome IX," Molecular Breeding: New Strategies in Plant Improvement, 34(2):471-480 (2014).

Tanksley et al., "High Density Molecular Linkage Maps of the Tomato and Potato Genomes," Genetics 132:1141-1160, Dec. 1992.

(Continued)

*Primary Examiner* — Cathy Kingdon Worley

(74) *Attorney, Agent, or Firm* — McNeill Baur PLLC

(57) ABSTRACT

A R8 *phytophthora* resistance gene from potato is described that produces a protein capable of inferring oomycete resistance, such as resistance to *Phytophthora infestans* when expressed in a plant. Also described is a method for providing at least partial resistance or increasing resistance in a plant against an oomycete infection comprising providing a plant or a part thereof with a nucleotide sequence of this gene or a functional fragment thereof, for example wherein said plant is a plant from the Solanaceae family, more preferably *Solanum tuberosum*.

18 Claims, 85 Drawing Sheets

Figure 1:
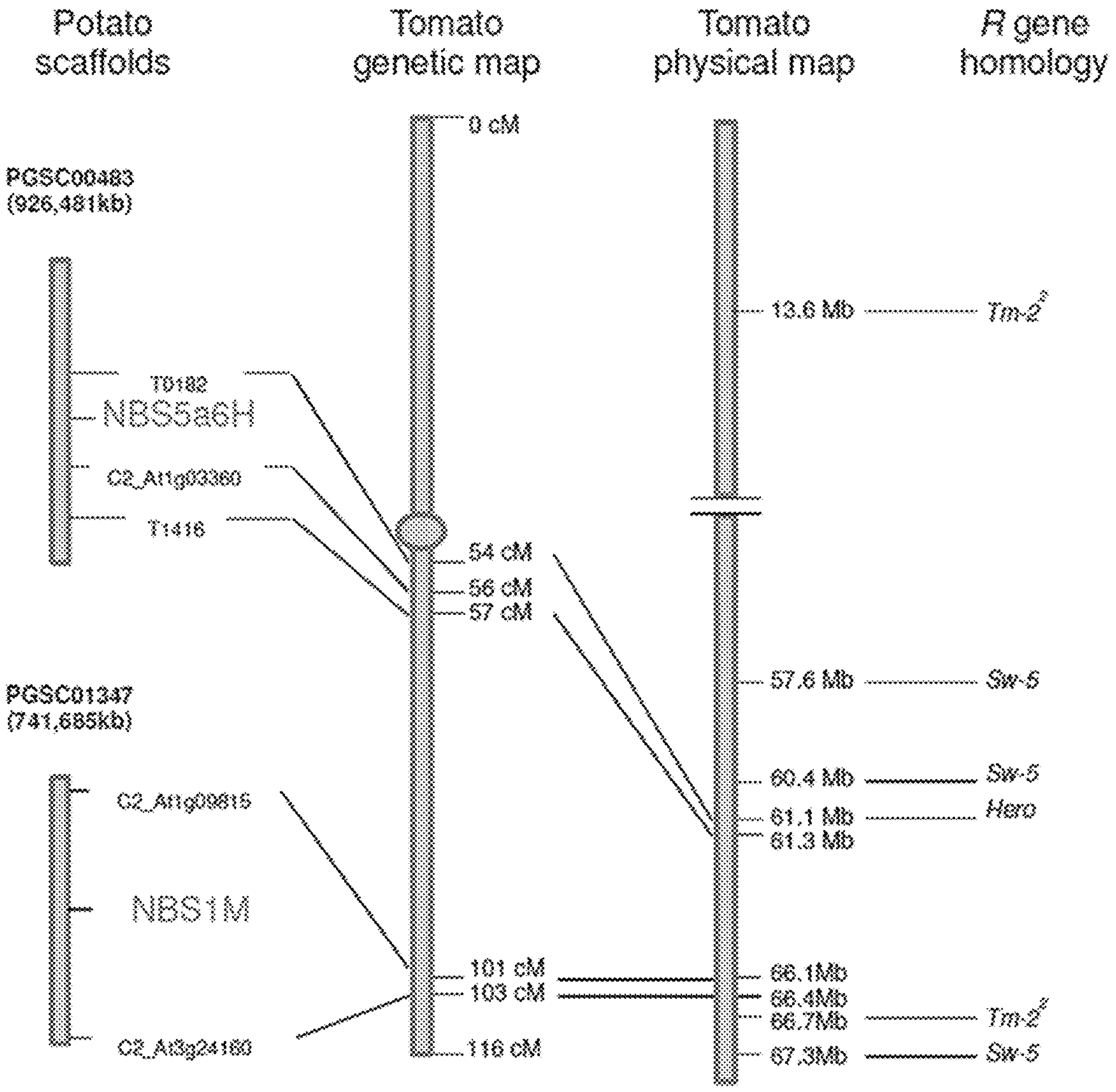

Specification includes a Sequence Listing.

(56) References Cited

OTHER PUBLICATIONS

Thompson et al., The CLUSTAL_X windows interface: flexible strategies for multiple sequence alignment aided by quality analysis tools, Nucleic Acids Research (1997) 25(24):4876-4882.
Van Der Fits et al., "The ternary transformation system: constitutive virG on a compatible plasmid dramatically increases Agrobacterium-mediated planttransformation," Plant Molecular Biology (2000) 43:495-502.
Van Der Linden et al., "Efficient targeting of plant disease resistance loci using NBS profiling," Theor Appln Genet (2004) 109:384-393.
Van Der Vossen et al., "An ancient R gene from the wild potato species *solanum bulbocastanum* confers broad-spectrum resistance to Phytophthora infestans in cultivated potato and tomato," The Plant Journal (2003) 36:867-882.
Van Der Vossen et al., "The Rpi-blb2 gene from Solanum bulbocastanum is an Mi-1 gene homolog conferring broad-spectrum late blight resistance in potato," The Plant Journal (2005) 44:208-222.
Van Os et al., "Construction of a 10,000-Marker Ultradense Genetic Recombination Map of Potato: Providing a Framework for Accelerated Gene Isolation and a Genomewide Physical Map," Genetics 173:1075-1087 (Jun. 2006).
Van Poppel et al., "The Phytophthora infestans Avirulence Gene Avr4 Encodes an RXLR-dEER Effector," MPMI (2008) 21(11):1460-1470.
Vleeshouwers et al., "A laboratory assay for Phytophthora infestans resistance in various *solanum* species reflects the field situation," European Journal of Plant Pathology 105:241-250, 1999.
Vleeshouwers et al., "Effector Genomics Accelerates Discovery and Functional Profiling of Potato Disease Resistance and Phytophthora Infestans Avirulence Genes," PLoS ONE, 3(8), e2875, 10 pages, Aug. 2008.
Vleeshouwers et al., "SolRgene: an online database to explore disease resistance genes in tuber-bearing *solanum* species," BMC Plant Biology (2011) 11:116, 9 pages.
Vleeshouwers et al., "Understanding and Exploiting Late Blight Resistance in the Age of Effectors," Annu. Rev. Phytopathol. (2011) 49:507-531.
Vossen et al., "Novel applications of motif-directed profiling to identify disease resistance genes in plants," Plant Methods (2013) 9:37, 13 pages.
Wang et al., "The utility of NBS profiling for plant systematics: a first study in tuber-bearing *solanum* species," Plant Syst Evol (2008) 276:137-148.
Whisson et al., "A translocation signal for delivery of oomycete effector proteins into host plant cells," Nature 450:115-119, Nov. 1, 2007.
Win et al., "Sequence Divergent RXLR Effectors Share a Structural Fold Conserved across Plant Pathogenic *oomycete* Species," PLoS Pathogens, 8(1):1-4, Jan. 2012.
Wu et al., "The detection and estimation of linkage in polyploids using single-dose restriction fragments," Theor Appl Genet (1992) 83:294-300.
Zhu et al., "Functional stacking of three resistance genes against Phytophthora infestans in potato," Transgenic Res (2012) 21:89-99.
Huang et al., "Comparative genomics enabled the isolation of the R3a late blight resistance gene in potato," The Plant Journal (2005) 42:251-261.
Andolfo et al., "Defining the full tomato NB-LRR resistance gene repertoire using genomic and cDNA RenSeq," BMC Plant Biology 2014, 14:120, 12 pages.
Armstrong et al., "An ancestral oomycete locus contains late blight avirulence gene Avr3a, encoding a protein that is recognized in the host cytoplasm," PNAS 102:21; 7766-7771, May 24, 2005.
Ausubel et al., "Current Protocols in Molecular Biology," John Wiley & Sons, Inc., ringbou edition, Dec. 4, 2003, 4648 pages.
Ballvora et al., "The R1 gene for potato resistance to late blight (*Phytophthora infestans*) belongs to the leucine zipper/NBS/LRR class of plant resistance genes," The Plant Journal (2002) 30(3):361-371.
Bisognin et al., "Half-sib progeny evaluation and selection of potatoes resistant to the US8 genotype of Phytophthora infestans from crosses between resistant and susceptible parents," Euphytica 125:129-138, 2002.
Black et al., "A Proposal for an International Nomenclature of Races of Phytophthora Infestans and of Genes Controlling Immunity in Solanum Demissum Derivatives," Netherlands Journal of Plant Breeding, 2:3, pp. 173-179, Oct. 1953.
Bradshaw et al., "Mapping the R10 and R11 genes for resistance to late blight (*Phytophthora infestans*) present in the potato (*Solanum tuberosum*) R-gene differentials of Black," Theor Appl Genet (2006) 112:744-751.
Brommonschenkel et al., "The Broad-Spectrum Tospovirus Resistance Gene Sw-5 of Tomato is a Homolog of the Root-Knot Nematode Resistance Gene Mi," MPMI 13:10, pp. 1130-1138, 2000.
Brugmans et al., "Genetic mapping and transcription analyses of resistance gene loci in potato using NBS profiling," Theor Appln Genet (2008) 117:1379-1338.
Champouret, "Functional Genomics of Phytophthora infestans Effectors and Solanum Resistance Genes," Thesis, Wageningen University, Wageningen, NL (2010), 162 pages.
Collins et al., "QTL for field resistance to late blight in potato are strongly correlated with maturity and vigour," Molecular Breeding 5:387-398, 1999.
Cooke et al., "Genome Analyses of an Aggressive and Invasive Lineage of the Irish Potato Famine Pathogen," PLOS Pathogens, 8(10):1-14, Oct. 2012.
Dianese et al., "Development of a locus-specific, co-dominant SCAR marker for assisted-selection of the Sw-5 (Tospovirus resistance) gene cluster in a wide range of tomato accessions," Mol Breeding (2010) 25:133-142.
Dodds et al, "Plant immunity: towards an integrated view of plant-pathogen interactions," Nature Reviews Genetics, 11:539-548, Aug. 2010.
Foster et al., "Rpi-vnt1.1, a Tm-22 Homolog from Solanum venturii, Confers Resistance to Potato Late Blight," MPMI 22(5):589-600, 2009.
Fry et al., "Resurgence of the Irish Potato Famine Fungus," BioScience, 47(6):363-371, Jun. 1997.
Fulton et al., "Microprep Protocol for Extraction of DNA from Tomato and other Herbaceous Plants," Plant Molecular Biology Reporter, 13(3):207-209, 1995.
Haas et al., "Genome sequence and analysis of the Irish potato famine pathogen Phytophthora infestans," Nature, 461:393-398, Sep. 17, 2009.
Heeres et al., "Transformation of a large number of potato varieties: genotype-dependent variation in efficiency and somaclonal variability," Euphytica 124:13-22, 2002.
Hoekstra, "Exploring the Natural Biodiversity of Potato for Late Blight Resistance," Potato Research (2009) 52:237-244.
Jacobs et al., "AFLP analysis reveals a lack of phylogenetic structure within Solanum section Petota," BMC Evolutionary Biology, 2008, 8:145, 12 pages.
Jansky, "Breeding for Disease Resistance in Potato," Plant Breeding Reviews (2000) 19:69-155.
Jeanmougin et al., "Multiple sequence alignment with Clustal X," TIBS 23, Oct. 1998, 403-405.
Jo, Kwang-Ryong et al., "Mapping of the S. demissum late blight resistance gene R8 to a new locus on chromosome IX," Theor Appl Genet (2011) 123:1331-1340.
Jo, Kwang-Ryong, et al., "Problematic Crops: 1. Potatoes: Towards Sustainable Potato Late Blight Resistance by Cisgenic R Gene Pyramiding," Plant Pathogen Resistance Biotechnology, First Edition, Chapter 9, pp. 171-191, 2016.
Kaeppler et al., "Silicon carbide fiber-mediated DNA delivery into plant cells," Plant Cell Reports (1990) 9:415-418.
Karimi et al., "GATEWAY(TM) vectors for Agrobacterium-mediated plant transformation," Trends in Plant Science, 7(5):193-195, May 2002.
Kim et al., "Broad spectrum late blight resistance in potato differential set plants MaR8 and MaR9 is conferred by multiple stacked R genes," Theor Appl Genet, Nov. 23, 2011, 13 pages.

(56) References Cited

OTHER PUBLICATIONS

Knapp, "Tobacco to tomatoes: a phylogenetic perspective on fruit diversity in the Solanaceae," Journal of Experimental Botany, 53(337):2001-2022, Oct. 2002.

Kuhl et al., "Characterization and mapping of Rpi1, a late-blight resistance locus from diploid (1EBN) Mexican Solanum pinnatisectum," Mol Genet Genomics (2001) 265:977-985.

Li, Guangcun et al., "Cloning and Characterization of R3b; Members of the R3 Superfamily of Late Blight Resistance Genes Show Sequence and Functional Divergence," MPMI 24(10):1132-1142, 2011.

Lokossou et al, "Exploiting Knowledge of R/Avr Genes to Rapidly Clone a New LZ-NBS-LRR Family of Late Blight Resistance Genes from Potato Linkage Group IV," MPMI (2009) 22(6):630-641.

Lokossou, "Dissection of the major late blight resistance cluster on potato linkage group IV," PhD Thesis Wageningen University, The Netherlands, 2010, 142 pages.

Malcomson et al., "New R Genes in Solanum Demissum Lindl. and their Complementary Races of Phytophthora Infestans (Mont.) de Bary," Euphytica (1966) 15:199-203.

Mantovani et al., "Nucleotide-binding site (NBS) profiling of genetic diversity in durum wheat," Genome (2006) 49:1473-1480.

Milbourne et al., "Isolation, characterisation and mapping of simple sequence repeat loci in potato," Mol Gen Genet (1998) 259:233-245.

Oh et al., "In Planta Expression Screens of Phytophthora infestans RXLR Effectors Reveal Diverse Phenotypes, including Activation of the Solanum bulbocastanum Disease Resistance Protein Rpi-blb2," The Plant Cell (2009) 21:2928-2947.

Oliva et al., "Recent developments in effector biology of filamentous plant pathogens," Cellular Microbiology (2010) 12(7):1015.

Park et al., "Two distinct potato late blight resistance genes from Solanum berthaultii are located on chromosome 10," Euphytica 2008, 10 pages.

Pel et al., "Mapping and Cloning of Late Blight Resistance Genes from Solanum venturii Using an Interspecific Candidate Gene Approach," MPMI (2009) 22(5):601-615.

Pel et al., "Mapping, Isolation and characterization of genes responsible for Late Blight Resistance in Potato," PhD Thesis Wageningen University, The Netherlands, 2010, 210 pages.

Potrykus et al., "Direct gene transfer to cells of a graminaceous monocot," Mol Gen Genet (1985) 199:183-188.

Raffaele et al., "Analyses of genome architecture and gene expression reveal novel candidate virulence factors in the secretome of Phytophthora infestans," BMC Genomics 2010, 11:637, pp. 1-18.

Rauscher et al., "Characterization and mapping of RPi-ber, a novel potato late blight resistance gene from Solanum berthaultii," Theor Appl Genet (2006) 112:674-687.

Rietman et al., "Qualitative and Quantitative Late Blight Resistance in the Potato Cultivar Sarpo Mira Is Determined by the Perception of Five Distinct RXLR Effectors," MPMI (2012) 25(7):910-919.

Schornack et al., "Ancient class of translocated oomycete effectors targets the host nucleus," PNAS 107(40):17421-17426, Oct. 5, 2010.

Song et al., "Gene RB cloned from Solanum bulbocastanum confers broad spectrum resistance to potato late blight," PNAS 100(16):9128-9133, Aug. 5, 2003.

Spassova et al., "The tomato gene Sw5 is a member of the coiled coil, nucleotide binding, leucine-rich repeat class of plant resistance genes and confers resistance toTSWV in tobacco," Molecular Breeding 7:151-161, 2001.

Spooner et al., Potato Systematics and Germplasm Collecting, 1989-2000, Amer J of Potato Res (2001) 78:237-268.

Tan et al., "The RPi-mcd1 Locus from Solanum microdontum Involved in Resistance to Phytophthora infestans, Causing a Delay in Infection, Mapson Potato Chromosome 4 in a Cluster of NBS-LRR Genes," MPMI (2008) 21(7):909-918.

* cited by examiner

CTATTATTTATTGCTACCAGTAGTACAGCTTCCAGGGAATACAGAAACTTCTCTATGACCTCTAAAAAGAAGTTAAACAG

AATGCCAACTAAAATTATGATTAAGGAGGATAAATAGAGAATGTTGTGACATACACAGACAAGGACGCCAAAAAGCAACT

TTCAGGAAAATTCAAAACAAAAATGAGTTGATCTCCAAGATAGTTCTCAAGACATTCAAGTTCACACCATCGCTCTTTCT

TTCAGCATGCCTCTAGGCTCTAAAATTCCAATTAATATGATTGATTCAGTATTTAATTGTTTTCAACATAGAATTGAATA

CAAAAGCTGCACCCAGCTTCCAAAGCTACATCACTGCCAATATCTTGACCATTCGTATTACTGATTAACACAATACTGAT

CAAGACCCATGAGAAACAGGGTAAAAAGAACAGAATACAGTGTCAACCACTGTTCTCATTAAATTAACTATGTTGGAGCA

CTGATACATGAATCAATCTCTCTTCTTCCTGTAAGTGCTATAAACTTATCCCTAAATAATAACAGAGGGCATTTACAGAT

CAAATTAGACCCATCATAAGCCTCTTTAAGTATCACGGTACTCCTAACACCTTTATTAGTGATGTAGAATATACTGTGTT

GTTTGATTAAGCAAAGCAAAAGTCTAGCTGGTAACCGTAACTCGGAATGAAATGCATCTATTTGAGCAGATGTCAACCTC

TTTTCCATAGTCAAACTGAGGAGCTCGTGAAGCACTGCGACTACTCTCTTTTGAGCTTTGGGATCAGCAAGTTCAAATCT

TTTAGCATTCAAGTATGGAGAAGGGAACTCCATCTTCTGCCATTTCTGAACTTCCTTAAGGTAGTTCATATTCGGCCTAA

ATCCTGCAGGATAATGCATTTGAAACGAGAAGGGACCGAAATAGTTTCCATCTTTCAATACTCTAACCTTCTCTTTTGAA

GTCAGGACCCCTTCACACGCCAACCTTTCCTCCCGGGCAGTGACAGCTAGAAAAGAATCCCAATTTTCCAACTGAAGGGA

AGTTCTTCCATTCACGTCTTTCACTGAGAAAAATTGTGGGTATTTTGGAATCAGCGACTGCCTGAAGTCATTAGGCAAGC

CCAAATCATTCTCAATCAGTTGAATGGTTTCCAGTGGCAACGTGCAATCAACCGACAACATTAACAACTTCCTTAGATTC

TTGACCAAAATAGGTTCCATTTGCGCTCTTGCTTCATCTTCTTCTAGTGCTATTTTATCAGCCTTTTCAGTCAGCATAAC

CATCGGTGGAGTTCCATTACCACCGGTGACACGGAATATCGTAGGATATTTCTCAATAATACCCATGAAATTCCACTTTT

GCACAAATCCAACTTCTTTCTCAAGGTCTCTAAGAAGGACGCATTGTTTTCTCTGTGATTGAATTATGGATTTTAAGCGT

AAAATCAATGATGGTTTCTTCTGAAGCTCCATGACTCTGTCTAGATCATTTACTCTATAGTACATTTTCTTCTTAGGTCT

CCTCCCTCCACTGGTTTTGAACATAATTTGAACCCACATATGCCCTACTCCCAGAGATGGCAATGGATGGCACAATCTTT

GCCTTCCATTGACTGTAAACCATTTTCGAGGCTCAATTAGCGAGAAGACCATCACATTTATGCATCTGGAAAAGAACAGA

GATGTGCGCAATTTAGCTAAAACAATTGAAGTGTAGTAAGATTTTGGAGAAAAGAGTTGTTTCCCCTTAAAACAAAAACT

ACAAACAGAGGCATATCAAGAATTTGAAGTTTGTGGGTCCAAGCCCAATGGATGGTGACCAACGAATTCGAACCCTTGAC

CAAGAGGGCAACAAAGCTTAAAAGATTACATTTTTACCCACTACCCAACATCCCCAAGCCGTTTCTCTTACTGGATTTTT

CAATACTCCGCGCAAAATTTACTATGTTCTTGGGAACCCCCTCCAATACCCTAAATTCCCCCCCCCCCCCCCTGAGTCTA

CAAACAGGAAATGATATAGACAGAGTCATTGAGCTTGGACTATATATGACCAAAAAAAGGACAAATTTTTCTCGACTGCT

ACTACTTATACGCAGATTAGTGCTACACTATAAGAACATCATGCTTTAAATTTGTGAAAAAAAATAAAGAAATGAAGTAA

TACAATAGAGTTGCAGCTCTTCGATAAATGGGAACAAATACATCATTAAACACAAAAAAAAAATTCACTGGAATTCATGG

TTTACTAAATATACTCAAATTGCAAGTAAATTAAAAGGGCTTCGGTCAAATTAAATAGTGATTGAAGAGACAAGGAGAAA

CTTACAAGACGGTGTGGAGCGCAGCAGAGCAGTAAGACGAATGAAAATGGCTTATTTGTTTTTCAGGTTCAACTTTGCCT

Figure 8

TTTATAATAATCATAATCTAAAATTAAGAAGGGGTAAAATTGGAATTTTATTTTAATTTTCAAATTGAAGGGCCAAAAAC

TTTTTTCTTCGACTCCAATTTTATAAAGTTAAAAAATAAATAAAAAATATTTGAAATTTATGATAAAAAATTTACTTAAA

TATGTAGAGTTAGAGTATTTTGAGCCGTTGATCTATTAAATACAAGTGCATCTATGAGCCAATTTGCTAATATTAAGATT

TAATGAAAGATAGAAAGATTGTTTTTGAAAGAATGAAAAAGAAAATATGATAGTGAAAAAAATATAACTAATTAGGAAAG

CAAGGTGAAAATTAAAAGAAGGTCAAAGTCATATGTAGCCCCTCAAAGTTGTCTTCATTATTCATTTAGACACCTCAACT

ACACCTAGTACCTATTGAACACCTCTACCACCCCAGATTTGAACCATCTAAGCATTTTTTTTATCACTTTTCATAAACT

GTGTGGCGCGTGTATTTAACCTCCCCACGTGTATCCGACGTGTATAGAATGACCATTTAACAACTACCACGTGTATCCGA

CGTGTATTTGTAAATGTCTTAATTGGGGAAGATTCCTAAATCGTTAAAATTGACAGAACACTTCTCTCTCTCTTTGCGAT

TTTTTCCCAATTGAAGCTCTCCATCTTCGCGATTTCCTCCAGATTGAAGTTGGATTCGTCTTGTTCGTGTTACAATCTTG

AAGATTTCCTTGTGTAAGTTAGGATTGTTAATGATTTTTACATGCTTTGTTAAATGAATTCCAAAAAAGCTAGGGTTTTG

TAAAAATATAGGGTTTGTGATTTTTGCGAATATTCTGTCCCTTCTTTACTATTACCCAAAAAATATGCTTTAAAACTTTG

GTTTTTAGTTGTTGTATATGTTATATGAGTATATTCCGTTATCTTAAGCTAGGGTTTGTTTGATATTTTGTAGGGCTAAC

AATTGACCATGGAGGAGAGCCTTATATTTACAAAGATTTACCATGGTGGAATCTTATCCGAGATATTTGTCCTTACTTAT

GTTGGAAACTGTGTGTCTGCACTCAGGTATATTATTAAGGACCACTTTTCCATTTTGGAACTACTGTATTATACTAAAGA

ATTAGGGTATGAAACTGTTAGAGGCTTTTATGTGAAGGATTTATTGAATAAAAAATGGGTCCTAATTACAACTGACCAAC

ATCTCCTACACCTAATTAAAGACTTAAAATATGAGGACACTTTTGAAGTATTTGTCTGTCATGTATTAGATGAACCTTAC

TTGACACTGAGGGACCTAGAGGCTATCTAACTAATGTTGGTGGTGAAGGTGTTGATGTTGACCTTGGTGAAGAGGGTGAG

ACTGTTAACTTAGGTGGAGAAGGTGAGGTTGTTGACCTAAGTGGAGAAGGTGAGGCTGTTAACCTTGGTAGTGAGGGTGT

TGATGTTAACATTGGTGAAGAGGGTGTGGATGATAACCTAGGTAGAGATGGTGTGGATGATAACCTAGGTGGAGAAGGTG

AATCTGATTTTTTGAGTAGTGATTCAGATCTAGATATACCTTCAGAAGATGGTTCAGATATTGATGAAGAGTTGAGAGCT

TTTAGACAAGAAAGAAGAAACAAAAAACAGAGAAACAAGGCTACTGAATTTGAAGAAATACCAGTTGGAGAGGCTGGTGG

TATAGATAGAGGCTTTGAGGATATTGAAAAAAATAAAACAGACAAATATACAGGAAAATTAGGTGGAGATGAGGATTATA

TTGATAGCTCTGACTGTTGGAGTGATGATAGTGATGAACAACTAAATATGGATGCTGTTAGGGGAGTAGATATACCTACT

AGAAGGAGAAGCAAAAAAGTTAGGTATGATGAAGATTGTGAAGTTTCAATATTTGAGCTTGGAATGGTCTTTGAGGGTGC

AAATCAGTTCAGGAAAGCAGTGGCAGATTATGCTGTAGAGTACATGAGGCAGATAAAGTTAAGACCTAATGAAAAACATA

GAGTGAAGGTGAAGTGCAAAAATGCTAACTGTAAGTGGTTGTTATATGCTTCCATTGACAGGGACTCAGGTGATTTCATT

GTGAAGAACTATCATCCTGTTCACAAGTGTATTCCATTAAACAGGAACAAGTTGTGTAATTCAAAGTTAATTGCTAGAAA

GTTTAAGGACAAAATTGTATCTCAACCATACATAAGGATTTGAGAAATTCAAGATTTGGTTAGAAAGACATTGGGTCTTT

ATGTTGGTAAGACTCTTTGTTACAGGGCTAAACAGAGGATTATGAAGGAAAACAACATGGGTGATTGGAATGTGGAATTT

GCCAGATTATGTGTGTAATGACCCTAAAGGTCATTTTTGGAAATTTTCATAAAATGACCGTTTTACCCCTCCCGATAGTT

GCCCCGAGTCCTAATTGTTGTATTTTCGAAGTTGGTTTGGAGGAAAATTGATGAAAAGTTGAGTTTTTGGAAAGTTGAGT

Figure 8 (Cont.)

TTTTAAGAGTTAAAGTTTGGTTAAAAGTGCTATTTCGAGTCATTTGGAGTTTCGAAACTCGAATTGGATTTTCGTTGATT

CCAGCAGTTTTAGAATGTCGAAACATGTCTATGAGAATTTACGGAGTCGAATTTGGAGTTAAAACGAAGATTTGAGGTCC

TAAGTTGCAAAAATTGTGAAATTTTGATCAAGAGTTGACTTTGGTCAACAAACGAGGTTCCGGTGCTCGAAATGGAATCC

CGAGGGCACCGTTGGATTCAGGGGGTGATTCTAAGTCTAGAATGAGTCTTGGTTAAATTTTTAGAGGCCCCGAGTGCGTT

TCGAGTTTTTGAGCCTAAAGTTAGTTTCTTGACGCCTTATCGGATACCGGGTCAAGGAGACCTCGAATTCAAATTCCGAC

GATTTCATTGAGTCCGAAATGTCATTTTCAAGCTAGTAGCATATTTGGTTTGTGTTCGGGAAGTGCCAAATGAATTTTGG

GTGAGCTTTTAAGCTTCTTGGATGCTTTGACACTATTTCAGCAAATTGTGGCAACTAAAGGGTTCATTATTAGGTTTAAA

GGTCGAAATTTTTTTCCGAAGGTTCTGAAATTTTGAGCATGAATTATAGGACTTTCTGCAAATTTTGGTGCATTTTCGCT

AACCTGAGATTGGACTTTTATCGCAAATAAGAAATAATTGTTTACAGAGTAGAAATGATATTTGACTGGGCAAAGAGCAT

GAAATTGAGCTCCGATTGAACGAGCAGGTCCGTATCATTATTTAAGACATTTACAAAAAAGAATCGGGTCATTTCACTAT

CGTATGAGGAAATTACGGCCTTTTTAGTGAAAGATTAACTGCTGTTTTTCTGGTGCATAACAGCCATGTACTGTTATAAA

AATCTCAGACTGTGTTCATTTGGTATTTTGAGCATATCGGGAGTTCTAGAGATCGGAATGGAGTGATTCTTACGGGTCTC

TTCTTGAATTAATATGAGGGTTAGTATTCAATCTTCAATTCGACATTTTCTCATAATTTCTTTATCTGGTTTTTTTTCCT

ATCCGTAAATCTCTTGGGAAAAATTGGGGTTTTATCGATTTGGACTCCCTTTTTGATGAAAAAGGTATATTTACAATCCT

TATGTTATGGGTAAACTGATTTTAACATAAAATTATTGATTCATCGATTATTTTCATCATATTAACCGCGTACAATTTAA

ACTTTCCCGGTAAAGTTAAAGTTTGATAAATTGAGAATTTCAAGGTCGATCTTAACTCCATTTTTGATGAAATTTCATAT

TTGAACTTATCTAAGCATGGGTAAGATGTTTTTCAAGAGATATTTCATTTTCGAGTCGGGGTTTCGGATCCGAATATTTT

AGGCTTCTTCAAGAACGTGGATTTTCCTTCAAATTGAGTTTGTGAATTGATTTCAACTCCGTTTTCAAATTGGGTTTCAC

CATTAGTTTCCAAATACTGTAAGGATCATTTTACATAAAAAAATTTCCATATTTGGGTATCATTTTCTGGTATGAGACTT

TTGGACCTTTTTGCCCTTTTCCCCTAAATTTCTTGATTTTGGTGTCATTGGACTCGAATTGTGATTGTGAATAATTGTTT

GAATAGATTGTCGTGATCCGGATTATACTCGAAAAGGAAAGGCTCAAGTCAAGTAACTTTTGGAGTTCGTTTCAAGGCAA

GTGGCTTTCAAACTTTGTAAAACTCTTAGACTACGCATGACTACTTTCCTAATTGTGTTGGGGAGTAATGGGTATTGAGG

ATGAGTTTTATTTGTTGATTGAAATTGTTGTAAATGAAAGATGGGGAATAAAACGAGCTAAATGTGTTATATGTGACTTG

AATTTGTTAAATAAGTCATGTGATAACTGATATTGAGGGGATAGAAGAGCATGAGTAGGCTATGATTGATACAGACATTG

ATGTTGTGACATATGATGTGTAATACTATGATGTGGTCGTGATATGGTTGTGATTGAGACAGGTGATGTGTAATACTGTG

ATGTGGTCGTGATTTGGTTGTGATTGAGACATGTGATGTGTAATACTATGATGTGGTCGTGATATGGTTGTGATTGAGAC

AGATGATGTGTAATACTATGATGTGATCGTGATATGATTGTGATTGATGACATGTGCATATTCATTATTCATCCCATGTG

TGAACTATCTGTTGCATGAGTTCTGAGACACTGATATGAGGATGGATGGATATGAGACATAGTTGAGACTAGCTCCGGCT

AGCGATTTGGATGCCGATGGGATCTGGTTCCGGCGGTGATACATGGTCCATGTGTGGCCCCCATGGGTTCTGATTTGAGT

ATTCAGCGCGGACTGATTACGTCAACAGATGTGTATCGTAGGACAAACATGCATCATGACATCATTATTGCATTTTGCAT

CGCATTTGCCTTATCTTTGTCTGTGATGTGTGGATTGTATCGGTTTACCCTTCTTATGTGGAATTTGATCTACTTGCTCT

Figure 8 (Cont.)

TATTTGTTGATCTGAGGTTGATGAGGATATACTGTTGGTTCTGGCTGTTGAATATGATCTGCTTAGTATAGGTTGGTTGG

TTTGCTGCTAGATTGAAGTTTCGGTGGTTTGGTTGGGATTGAAATGAGTTGTTTGTAGCTGCTAGTTTTGCTTAGTTTAG

AGTTACTTGCGAGTACCTGTGGTTTTTGATACTCACCCTTGCTTCTACACAATTGTGTAGGTTGACAGCTCTCTCTCAGA

TTCGGCTTAGTAGTTTCTTTAGCAGATTGAGCTTCGGGACATACTCGAGAGGTAGCGGTTCATTCCAGACGTGCCCTTGA

GTTATCTTTACTTTCAGTTTTGTTCTATTTGAGAACTATACTCTGAGACTTGTATATTTTTATTCGAATTCTGTATTTAG

AGGTTTGTACATGTGACAACCAAATTCTGGGTAGTGTTGAGTCTTAATTAAAGTCTTTCGCTTATTTATTATCTTTTATT

CTCGTATTTCTACTTCTCTATCGTTGTGGTTGGGTTAGGCTGATGTGTCCGGTGGGAAATGGATACGTGCCATCACATCC

GGATTTGGGGTGTGACAATGTGACTATGCAGATATGATCAAACAAACCAATCCTGGAAGCTCTTGTCGGGTAAAAATTGA

TAAGGAAACTGAACCAGGAAAGAACCTTTTTGTGTATTTTTATGTGTGCTTTCATGCATTTAAGCAAGGATGGTTGGAGG

GGTGTAGGAATATAATTGGAGTTGATGGTTGTTTTCTTAAGGGAGCTTGTAAAGGTGAGCTACTAGTTACTGTTGGAAAG

AATGGGAACAATCAAATGTATCCCATTGCCTGGGAAGTTGTAGATACAGAAACAAACATAGTTGGAGCTGGTTCATAAGG

TATTTAATTGCTGATCTAAACTTGGGAAGTGGTGAAGGTTTGACTGTAATGTCAGATATGCAAAAGGTATTGATTATACA

ATTTTTATATTTTAGTTTAATTTGATCTTTACTTCTTCAATTACTTATTTTGTACATATTTTTTGTTAGGGACTTATTCC

TGTCTTGTCAGAGTTGTTACCAAATGCTGAGAAAAGGATGTGTGCTAGACATATATGGAGTAACTGGCATGTGAACTGGA

AAGGAGAAGAAAGAAGGAAACAGTTTTGGAGATGCTCAAAGGCCTCCTTTGAAGTCAAGTTTGGAGAAGAAGTTCATGCA

ATGTCAAAGCTAGGTAAGAAGGAAATAACAGAGGACTTGCTACATTATGATCCCAGAAATTAGTCTAGGGCCTTTTTCCA

AACTCACTCCAAGTGTGATGTTGTAGAAAATAACATGTGTGAGACTTTCAATTCCTGGATCTTAGCTGCTAGACATAAAT

CAATTATTACCATGTTAGAAGATATTAGGCATAAAATGATGAACAAACATATAGACATGATCAAATTTGCTGAAACATGG

ATATCAGACATTGCACCTATGGCAAGGGCAATACTAGAAAGAAACGAGGAGTATTCAAATAATTGTAATGTTCAATGGAA

TGGGTTGAATGATTTTGAGATTAGTGAAGGGAATATTCATTTGTTGTTGACTTGGAGAAGAAACATTGTGACTGTAGGTT

GTGGATGTTGAGAGGTATTCCTTACCCTCATGCTATTTGTGCTTATTATTACTTGAATCAAGATCCTGATCAACATGTAG

AGCACTGGTATAAGAAGGAAACATTTCTCAAGGCTTACATCCATTTTATCCAACCTATTCCCAATATGAGGATGTGGCCT

GAAACTACAAATCCATCAATAGAGCCTCCAAAACCAAGAAAAATGCCAGGCAGACCTGGCAAGAAGAGAAGAAAGAGTAA

GGATGAGCCAAAAAAATGGGGGAAACTTTCAAGAAAAGGAGTAAAGATGACATGTACCATATGCAAGAAAACTGGTCATA

ACAAAGCTGTGTGTGCAAGAGTAAGTAATACTTCATATTCACATTTGTAAATTGCTTAAAGTTTATATATATTATAATCA

TATATTTTATTTTGTGGTGACATAGTATACGAGGGGGAGCACTTCTCAACCTACAAGTCAAGGAAATTCAAGCCAACAAA

GTTATTCTCAAACAGGAGTAAGATTTGATTTACATATTCATTTGCATTAATTTTCATCGTATAAGTTATTCATATCTCCT

TATTTTTGTTCAATAGGTTAGAACACAATCAAGTTAACAAAGTTCTGTTTGCGCTGATACCACTGTTGTGCCAAGAACTA

CTCAAACAACAGTAAGATTAGATTTAATAATTCATTTACATTTTCTGATTGATCTACAAGTTATTCATATATCCTTATTT

CTGCTATATAGTCTACAATGGGAGGTCCATCGCATTCTACTTTCAGAACCACATATGCAACTACATAATCAAGTCAACCA

AGTTCTATTTGTGCTGACACAGAATCTGTGCCAAGACGTCCTCAAAATAGGGTTCAAGTTGGGACTGGAAGAGGATTGGG

Figure 8 (Cont.)

AAGAAAAAAAGCTAATGCAAGAGTGATAGTTCTTCTAGTCAATTGCCACCTTTATCAGGTCACAAAAGACCGTACAATTC

TGCCTCATTTGCTGCTGCTGCTACTGGAGGTAACAGAAGGCTTGCAACTGGTTTTGGTGTTTACTCTAATCCTACTACTG

GAGCCCAAGTATTTAATGTATGTTTACTCTGTTTTGGTGTATATTCTGATAGCTATATTATGATCTTACCTTATCTTACA

CTTTCTTTCTTATATTACAGCCTGGTACATCAAGTGAGAAGATTCTACATGGGCCAACAAAATTGAAGAGTGCTTCACCA

ACCAATATAGACATTGTCTTTAAACCTCGTGGCCTAAAATGGAAGGGAAAAGATGCAGTCAGCACCTCACAGTTGCAACA

AATGAAAGCAAACAGGAAAAACTAAAAGTAGTTCATTTGGAAAGTTGTTATGATTTTGGCCCATGTTAAAAGGGTCTTCA

ACAAGCTACTCTTTAGTTTATTTTGAACACTCGTGTGATGTATTTTTGAACCATGCCTTTGTGTTAGCAAGACTATGTAT

TTTTGAACCATGCAAGACAATAGTTTTTTATTACCTCTCAATGCATTTGTGTTATGTATTTTTCAACCATGACTTTGTGT

TATGTATTTTCCAGCCATGCATTTGTGTTATTAGCTCAGTTTTTGAACAACAACTACACAGGGCAAGTCGATCCCAGAAC

TAATTTCAGAACACAGGGCAAGTTAGAACACAGGGCAAGTTAGAAAACAGAGGCAAGTTATAAAAGAGAAACTGATCAAT

TCACACTAGAAGTTACAAAAGAGACACTGATCAATTCACATTCAAACTTCCAATTTGATATAAAATATGAACTTAACAGA

CCAATTAAGTACAACACTAATTACGTGAAATAACTTCCTAACTATTGCAAAACTAAACAATTAAGTACTACAATTTTGAA

CTACACAATATTAAAGAACCATTTTATAGTTAGCAGACAAAGAGAAACAATCACAACTCGATTAAATTTGACATTTTCCC

AATCCCTTTGGAGTTTAACTTCCTTGAGCTTCTTGTTCAATACCATCATCTTCTCTTCATTTTCATTCAATTGAAATTTC

AAAAAATCCCTTTCTTCTTCAAGCTCTTTCACTTTTCTCTTTAGTTGATCAATCGGATTATGACCATCTATGAATCTATT

CATTAAGGATGATTCATCAATATTTTCAAGTGACGGATCAATCCATCTAAAATAGCCACATCCACCATTTTCCTACAAAC

CACATAACAGTAATAAATATACAAAAATGTTGATTTTTCAAATAATACAATAATAGTAGTTTTTGTTCAAATAACTACAA

ACCTTTGATGCTTTGCATCCAAAAAATCGACAACCTGGGTTCAATGGAGTCCTCGAAGTTTTCAGTCGACAATAGTAACC

ACACTTACATACATCGACTTCCTCGATATTCACTGAACTTTGTGACATTTGATAAAACACAACTGATTTAGAAGAGAGAA

ACGTTGGATATTTAGAGGAAGAAGAGAGAATTGGGGATTAGGGTTCTAAAATGTATTTGGGGGAAGAAGAAGATTTTAAT

GTTAAAATATCCAAGTTAACGTTGGATGTCTTAAATGCAGGGTAAAAAATGGGAGAAAAAACAATTCACGCGCCCGATTT

GCGTGAATCACAAACGATTTGCCATGTAGGCAAAAAATGCTTAGATGGTTCAAATCTGGGGTGGTAGAGGTGTTCAATAG

GTACTAGGTGTAGTTGAGGTGTCTAAATGAATAATGAGGACAACTTTGAGGGGCTACAGATGACTTTGGCCTTAAATGAA

TTTGAATCATAAATCTTTTTTGAGAAGATTGCAAGTATTACATATACAACATTAATTGTGCTTGATATATTTACAAAAAG

GAATCTAATTTTAACCTGATTTAAGTCTCTACATGATAAAATAATGAGCAACTTTCACATATAGCAAACATAAAAATCAT

ATTTGTATGTTATAGCTATAGTTTGTATAATTGCGCTCCATAACAAATTTTATGTTTGCTATTGAACTTTTGATTTGTAT

AATTCGCTACAAACATCCAATTTTATACAAATTGTTCAGTTTTGTATAAATTCATTTATACATTGTAATTTGTATAATAA

AATCTGTATTTATATAATTATAAGTGTATAGGACGAAAATATATTTATTTGTATTTGTATATACACTTTTCTCTCGCTTT

ATACAAACACAAACGCATTTTATACATTTTATACCGAAATGTATAAAATGACTAATTGTATACCGAAAATGGCTAATTGT

ATATGACAAAAAACATGGATGTTTGCTGCTAATTACAATTAAAATAAGCTATGGCTATAACATTTAATTTAAATTAATAG

TTTGCTATTTCATACAATTTTCCCTAAATTAATTCATCTTTACCAACAAAAGTATATAGAATTTTTTGCCTTTTATCATC

Figure 8 (Cont.)

TCTATAGAACTGACTGACTCTATCTTTAAAGCATCTTGCATGTTCTCTTTCCAAATGGTTATTGGCTCTTCAAAATTAAC

TTTGGCTGGCAACATGAATATGACAACATTTTTGAAGAATCCAAGCAACATAAGTTCTCTGCCACTTGTGCTCTTTTGGC

ATGCCCTTCTGTACCAGATGTCTTCAGGTATTGTGTTTTCAAGCCTAAACCTTATGCCTTCATTTGAGAAGCAGAAATTG

TGTTATGGGAACCAAAAGAAACACAATGAACTGACCCTTGAGAAAACTTATCCAGCCACTCTATGGTTGTCTCCTCGATC

CCAAGCACCGAAGCAGTCTGTTGCAAAATCTACTTTTGTAACTGAGACATTGGAAAAAAAAACTATTTAAGAAATATTCC

ATGAATGAATGATTTTGGTTTCATGAAGTTTTTCTTAATTTTAAACATATAACACAGTGCACATAATGTTACATGAATGA

ATGAATGATTTTGCACTTACCATAATTGAAATATTCATACTTGTTAAGGACTTGGAGGCTATCACATCCTGTAATCTCTT

CCACTTGGTTTTTAATATTGAAAGCTGAAAGCTTAAGTGACTCATCGCAGCAAATCAATTTAATCAACTTCAGTGTTGGG

ATATCCACGAAGCTACAAGGGATCTGACCGCACTGAATTATGCAATTGTTTATAATTAGTTGCTCAAGCACGGGGAAAGA

TTCTTCTGAGGAGCGCCATTCTGTCACGAGAACATTCTGTAAGTTCAAGTATTTGAGTGCTCGAAACTCATAATCACTGA

CATCCCAACATATGCTATATCCAGCCTGCCCATATCTATCTTCAGACTTGAAGTATACTTCACGTAGTTTGAGACTCTCA

AGGTTTCGTAGTCTTGCAAGTTGTGAAACAACTTTTTCAGTTAGGCAAAGTCTATCAAGTGACAAATCCTTCAGATTTGA

AGGGAAGACAACACATCTGGCCCGTCCTATGGATTTGTAGCCTGAAATCGCGCGTGAGAAACACAGTTCGAGAGATAGAA

GTGGGAGTTCTTCAAGATTCGGCATATCAACTTCATAACCTGGTTCAATAAAGTGGAGGTTGAGTTGTTCAATATTTGGG

AATCTCCACCAGAACTCCGGAGTCTTATCAACCAAGTATATACGACACTTCCCAAAAGTCTTCAAGTTTGGTAACACAGT

TTCTGAAGATTCTTCGAAAAGTGCTCGATCATTGTCTTCCCATTTGAAGGAAAAATCCTGTATATCCACATGTCTTAGCT

TCTGCATTTTCCAAATAGAAGGTGATGTCTCAAAGCACCCCGAAAGTTTATCATCATTTCCCACCACCTGCAAAGTTTGT

AGATCATGTAGGTGTGATACCCACTGGAAATCAAATTCTTGGGTACGAATTGCAAGATACCTCAAGTGAGTTACTACTTG

CACTGCCGTAACCCAAGAACATCTTTCCAAGTTGACATCCAACAAATGCAATACCCGAATAAATCTTAAGTTCTTAAGTA

CACTGAAAAGACGTATCCCATCACCCAGAGAGGAATGTGGATTATCAATGAACTCACTATACCTAGCATTACATTGATCA

ACAAACTCCCATTCCTTCAAGCCTGCCAACATTGGAAACTTATCCAATAACTTTTCATACTGCAACAAATGTTTAACAAG

ATCGTCATGGATATACTTGCGACGTGACCGAGGTTCCTCTGCAAGTCGGTACAGCATAAAATTTTCTTCCTGAGGTTCCT

TTGCAAGTTGGTACTGCATAAACTTTTCTTTTGCAAGTTTTCTCATGCAAAACTCATGCACTACATCATGAACAGTGCAG

TACTCGATCTCACCATTATCTTCTCTCCTTCCAGAAACAATTACTAGGCTTTTTTTCACTAGTTCATTCAAGCAAATTTT

AGATGCTTCCTCCACGTTCTCTAAGCCCATGTTTTGTACAAAATTTTCAGCTATCCAAAACTTTAGCAAATTGGACACTG

GAAATTTGTAGTCTTCTGGAAACAATCCCATGTAAAGAAGGCAAAACTTTAAATGGTCTTCCAAATAATCAAAACTTGAT

TCTAATATCTTCATGTTTTTCTCTTCTAAAACACGGGACCTTAAATCTTTTGCGATCGCAAGCCATAAAGAGGCTTCCCT

TTTCTTTGCAATAATTCCAGCAATCAAAACGATCACAAGTGGTAATCCCTTGCAGCTTTCAGCAACTCGTAATCCTGTGT

TGAGTAGCTCTGGGGGACAAATCTCTCATTGAAATACTTTCTTTTGAAGTAAGTCCCAGCTCTCATCAACCGTGAGAAAT

CGAAGAAAATATGGATCACTGTGGTGCTTAAGCTGCCTGGCCACTTCTTCATCTCGAGTTGTTAGCACTACTCTGCTTCC

ATTTTCATCATCTGGGAAAGATAGCTGCAACTCTTCCCAAGCCTCAACTTCCCATATATCATCTAAAACAATGAGGTATC

Figure 8 (Cont.)

TCTTGTTCATTAGACTCTTGCGCAACTTGTCAGGCATGTCTTCATTTCGTATACCATCCACACTGCCTAAAACTTGTTTA

AGAATCTCAGAGCACATCTTCCTCAAATTATATTCTTTTGAAATAGAACACCATGCTTGAACGTCAAAGTGTTTATCCAC

GCTTGGATGAGTGAACACCTTTTTAGCCAAAGTTGTTTTGCCTAGTCCAGGCATTCCAACAATCGAGACAACGTCTAGTT

CCTCGGTACATCCAGTCAATTTCTGTATTATACTTTCCGCATCTTCCTCAAAACCAACTATTTCCTCATCAATTGATGGA

AAACTACGAGAAGGGGTTCTTTCACTGCTCAGAACGTTCTCCATGCTAATTATACTTTCCGCATCTTCCTCAAAACCAAA

TATGTCCTCATCAATTGATGGACAACTAGGAGAAGGGGTTCTTTCACTGCTCAGAACGTTCTCCATGCCAAATATACTTT

CCGCATCTTCCTCAAAATCAAGTTTTAACTTATCAATTGATGGAAAACTACGAAAAGACGTTCTTTCACTGCTCAGAACG

TTCTCCATGCCAATTATACTTTCCGCATCTTCCCCAAAATCAAATATTAACTCATCAATTGATGGAAAACTACGAAAAGG

GGTTCTTTCACTGCTCAGAACGTTCTCCATGCCAATTATACTTTCCGCATCTTCCTCAAAACCAAATATTTCCTCATCAA

TTGATGGAAAACTAGGAGAAGGGGTTCTTTCACTGCTCAGAACATTCTCCATGCCAATTATACTTTCCGCATCTTCCTCA

AAACCAACTATTTCCTCATCAATTGATGGAAAACTACGAGAAGGGGTTCTTTCACTGCTCAGAACGTTCTCCATGCCAAT

TACTGCAGTTAGGAGTAAATATAACTATGTTACAACTGATTGCACAATCGCTTAGAATTATTTAGATTGCCAAACAAGTC

AAAATTCAACAATCTATTCATAGTTTCCTAGAAAAGATCATTTCCTAGAGGGAATACTGAAAGTCAATCTTCTCTTGGAT

ACTATTTAGAGTTAATAGTAAAAATAAAACACCTAAAATATCACTTTTTCGTGACCTCAAAGTTATAGTCTTTTAGCAAA

TTTTAACTCTCTTTGTATTAACACACTCCATTTTTAAGCTTTCCTATTCTTGAAACCACTTTCCTCAAACTACCTACCAA

CAAAAATATTGAAAGGGTGCGTGTCAGATCCTTCAGATATAGTACTCCCTCCATCTCATTGTATGTGGCAACCTTTTCTT

TTTAGTTTATCTAACAAAGAATGTCACCTTACTACTACTAGAAACAATTTAACTTTAAAATTTCTCTTTACCTACTAAAT

AATTTACAACCACACAAATATCTAAAGATTATTTAAGACCTCAAGTTTCAAAAGTCTTCATTTTTCTCTTAAATACTTTG

TCAAGTCAAACGGTGACACATAAAATGAGATGGAGGGAGTATATTTTTAAGGATCCCACAGGGTTTCTCTAGAGTCCGAG

CATCATTGCTAGCTACTTACTCTTAGTACAGTTAAGTTTATATAGCCAAAAAATATGGATAAAATCCAAGTTACCTTGCT

ATATCTGGTGTGACATTTTTGGAAAGAAAAAAAAATTCATAATCAGAAGTTCAGAACATAAACTACATGATCTTCTCAAA

TAAGACACAAAAATGTTAACTTATGATAAATGATAAATATAGACAAAATATATATACATAAAAAAACAGGAACCTAAGAA

GAAATCTGACCTTCAATTATGAGAGAGAAGCGGCAGCTTCTTATAACTTAAAAGGATTTGGAATATGAAAGCATATGGTG

AATGAAGGAGTGATAATATAGTAATTAATCGTTGAGTGGGAGTGAGAAAAAGACAAAAATGGTCCCTTATATTTAATGGT

AAGCTTAAAATAGTCCGTTAAGTATGCACTAATTAATAGTTTTGAGGGTGGGCATGGTATGGTATGGTTAATGTTTTGTT

ATTGTAATTTCGATTTTCGGTTTTAAAAACATTTAATCATTATCATATCAATTTAATTTAGTATGGTTCGGTATTTTAAA

GTTTGGTTTCGATAGTTTGTTCAACTTCGACTAATATATATTCGTATAATAGAGTATTATGACTTTGACAATTAAAAAAA

GATCTTAATTGTATCATACTAACACATTACACATGTAAAAATATATATTCAAAATAAAGTACAAACAGCCCCTTTTGCTA

ATCAATTACATTTCAATCAAAATAGAGTAGTCAAAGTTTCAACTTCTAAACATTTAGTTTATACAAATACTAGATTGCAT

ATTTGTTAGTATTTTAATAATATATTTATACTTCGATGTGGTATTTGATATTTCGGTATGTTATTTTTTAAATACAAAAT

ACCATACCAGATACTAAAAAAAAGTATACCATATACCATATCAAATATCATAATACTGAAATCACGGTATTAAAATTTTC

Figure 8 (Cont.)

GATATATTATAATAATTGGATATATACCATATCAAGCCCACCCCTAGTTTTGATCATTTAAGTAATTTGTCACAAGTTAG

CAAACATGATCTGTTATGCTTGAAGGTTCAAAATAATTTCTTTTAAGTATGCACTTAACAATTGTGGTACCTTAAATTTA

CAAAAAAATTAACAGGAAGTTTATTTTCGCTAGATTCTCGGCTCAAGAACAAGTAAATATGTGAAGAAGTTGTTGAGAAT

AAAACTAATTAACAAAAGTGTGATGTTCACATATTTCGATATAATATCAGAGTAGTCAAAGATCCTGAAATTGAATCTTA

CCATCACTATATTAAAAAAAATCACTTATTTGACCCATAAAAAAGATCGTGAAATCAAATATCACCTTCACTATATATAA

TGAAAAAGAATCAAGTTTCCACATGCAAAATGGGTAAAGACTTGTTTTTTTCTTTTTTGGATATAGAGAGATAGTAGATA

CAAAGACATATAAGCTATGTATAGACACATTAATTAAAGAGCAATTGTATGTTACATCTTGAAAGAACAAAGAGCTCAGC

TGACCATAATTTTCAAGTAATTCCCCAAAAATTCATAAATGTGTAACTTTGTCAGAATTTAAAAAATAAAGAAGGCAGA

TTCTCAATTGGAGCAGTAAGAATAGGAAGAAATTTGAAACTTACATTGAAATGAGAAAGAAAACCAGAGGTACGTAGTAC

TGCAGTGCTAATTCCTCTATGTTTATTGAAGTTCGAATAAATTTGAATTTATGTCCACAAAAATAACAAAGTCAATTTCA

GATCTGAAGCTCAAATTGAAGAAGAAAAAGAATCTTTGTTTGGTGCACATATGAGTGGTCACTTGGAAAGAGCAGGCAAT

AAGCAAGTTAAATATTCACAGTTTATTGAAAAAAAACAAAAAACAAGCAAGTTGAATGAAGGAAGAATATACTTCGAACT

TTCAACAAAGGCGGGCTCTTTCCAGCGATTGTATGCCAAATTCACTATGTGAGTCTTAACGTATTCTTTAATTTTGTAAT

ATTAAAAAATTGTGGGAAAAAAAAATCTTTTTTAAGCAAACTAAAAAAATATATATCAAAACAAATAGATTGGAAGTGA

AGGAGTGTAATTTTGAGTCTATTCTTTGACTCCACTTGGAAATTCTTACAAAATAATCGATTGAATATATATCAAAGATA

ACTAGATCAAGTGTTTGAATAAAATCTTCAAGATATATAACAACTTAATTTGCTCATAAGATTTCGTCCACATGAAAGCT

GACTCATTAATTTCGAAGCATGTTTCAATAAATAGTTCATAATAGTTCAAATAAAAAATACAAACACTTGATAGTTCAAA

TAGAAAACTCGAAAAAAGATAAATATTTCAACTGTGTTTTTACACCATTATCTCTAAATCAAATAAGACAGAACTTGGAG

ACTTTCACATCCTGTGATGTCTTCTACTTCTTTAATGTTCAGAGCTGAATCCTCAAGTGACTTCGTGCATCTCCTCAATT

TAATCAACATCTGCTATATTTTTCATCCCAGAAGCAACAGCGGAGCCATGGTTTTTACCAAGGAGTTTCAAAATATGAAA

AAATAAACACATGAAGAAATCAAAGTAATTACACATCTACTATATATAAACAATATAACTTTTTGTCGAAGATGATTCAG

ATGAACCCCTGACTCTACATGGATCCTCCCCCGCCCAGAAGCAACCATCATCGTCCTTGAACTCGAAGAATGCTCCATTA

AGTCTCTCAAGGAATCTCACCTGGAGAATTCTTGATATACTGTGGATGAAAACAGAATATTAGCAGTAAATAAGAGAGTG

AGTCCACGATGCTACGAACTAGCCAAGCAGCTCACCCTGATATCTCCAAGCAAACTCTAAACTCAGTCATGACAGCCACT

ATCACGGGTATACATTACTGTACAAAAAATGCAATAAGTGTAGTATGAGTACAAAATATAACGTGTATTCAACAAGTATC

ATTGATAGTAATGAGGGTTGGTCTTTCAAATGCTTGTGTTCCATCCTGATTAGCATATGTGATCTCAACAGACATAGAAT

AACAACATAGAAGTATATCTAACCGAACATTGTTATAAAAAAAATACACAAAACCAACCTACAGAGAAGATATGCACAGA

TTCAACCCAACAACTAAATAAAATGCGCGAATAAGAGTTATGATGCGATATAAGTAAAGCTGATTCTTTACCACAATTGT

GTCAACCAATCCCAGGTAAAACAACCCTACGCGATCACCACTCCTCCTCCCATGATCACAAAGCACAAAAACCTGATGCA

CTAGTAAAAAAAAATCTGGTGCAACTGAAATAGGATATTAGCACCCAAAAGGCCAAATCTCACTGAACCTCTCGAGTTGC

AGTGCAAACATATGTACAAGTTCAAACTCATCCTATGAACCTACTCAAATCTTGAATTCGAGCCCGTCTCATCACAACAT

Figure 8 (Cont.)

TGACTTCGGTTCTAACATTCCAAAATTCATCTGAGCCTCTTGGAACCCATGCCCCCCATACCCACAAGTCATAAAACACC

AAATGAACATACTGAAAGTCTCAAATAGGGGAAAGGGATTCTAAAACTCAAAACGAACTAATAGGTCATTACAAACATGG

GAACATAAGTCATTTGCAACCTCAAGTCAAAAGGCGGCAGTGAGCTACGGTTGTTTTCTTGATCCCAAACACTGAAGCAT

TCTGCTGCAAAATCTGCATCTGCATATCCTATAAAGAAAGAAAGAAAAATAGAGAGAAAAATCAAAATGTTACCTGAATG

AATTATTTTTTACCTAAATAAAGTTTCTCTCAAGTCCAAACAGTTTTCTGGAATACTATCCATGGTTAAACGGGCACTTA

ATGATATAGCTTACTGTCTGGTTGATACTGAATATGAAGTTGGAGACTATCACATCCTGCGATCTCTTCCACTTCATTTT

TAATGTTGAAAGCTGACTTCTCAAGTGAGTAGTTGCAGCCAATCAACTTAATCAACTTCAATGTCGGGATATCCACAAAG

CTAGAAGGGATCTGATCACACTGAATTGTGCATTTGTTTATAATTAATTTCTCCAGCACAGGGAAGGATGACTCTGAGGA

GCGCCATTCTGTCACGAGAATATTCTGTAAAAGCAAGTATTTGAGTGCTAGGAACTCATAATCACTGACATCCCAACATA

TGCTATATCCAGCCTGCCTGAATCTACTTTCCGGCTTAAAGTATATATTACGTAGTTTGAGACTTTCAAGGTTTCGCAGA

CTTGCAAGTTGTGAAAAAGCTTCTTCTGTTAGGCAAAGTCTATCAAGGGACAAATCCTTTAGATTTGAAGGGAAGACAAC

ACAGCGGGCCTGTCCAATGGATTTGTAGCCTGAAATCGGGCGTGAAAAACACAGTTCGAGAGATTGAAGTGGGAGTTCTT

CAAGATTAGGCATATCAACTTCATAACCTGGTTCAATAAAGTGGAGCTTGAGTTGTTCAATATTTGGAAATCTCCACCAG

AACTCCGGAGTCTTATCAGCCAAGTATATACGACACTTTCCAAAAGTCTTCAAATCTGGTAACAAAGTTGATGAAGATTC

TTCGAACAGTGCTCGATCATTGTCTTCCCATTTGAAGGAAAAATCCTGTATATCCACATGTCTTAGCTTCTTCATTTTCC

AAATAGAAGGGGATGTCTCGAAACGCCTTGAAAAATCACTATTCCCCACCACCTGCAAAGTTTGTAGATAGTGTAGGTGT

GATACCCACTGGAAATCAAATTCTTGGGTACAAATTGCAAGATATCTCAAGTGAGTTACTGCTTGCACTGCTGTAGTCCA

AGAACGTCTTTCCAAACAGACATCTGACAAATGCAACACCCGAATAAATCTTAAGTTATCGAGTAAAGGAAAAGTCTTTT

CCCAAACACGGGACTTTGGATGAGCAATAAACTTAAGAAACCTATCATGACATTGAGCAAAAGACTCTCCTTCCTTCAAG

CCTGCCAACATTGGAATCCTATCCAATGATTTTGTATACTGCAACAATTGGTGAACAAGATCATCATGGATAAACCTAAT

ATATTGGGGTTCCTTTGAAGGCCGGTACTGCATAAACTTTTCTTTTGTAAGTTTCCTCATGCAAAACTCATGCACTACAT

CATGAACAGTGCAGTACTCTATCTCACCATTATCTTCTCTCCTTCGAGAAATAATTACTAAGCTTCTGTTCACTAGATCA

TTCAAGCAAATTTTAGATGCTTCTTCAACGTTCTCTGTGTCCACGCTGTGTATAAAATTTTCTGCTATCCACAAGTTTAG

CAAATTGAATACTGGAAATTGATGGTCTTCTGGAAACAATCCCATGTAAAGCAGGCAAGACTTTAAATGGTCCTCCAAAT

GGTCATAACTTGATTCTATTATCTTCATGCTTTGCTCTTCTAAAACATGGGAACTCAAATCTTCTGCGAACCCAAGCCAC

AAAGAGGCTTCCCTTTGCTTTGCAATAATTCCAGCAATCAAAACGATCACAAGAGGTAATCCCTTGCAGTTTTGAGCAAC

TTGTAATCCTGTTTTAAGTAGCTCTGGGGGACAAATCTCTCCTTGAAATACTTTCTTCTGAAGCAAGTCCCAGCTCTCAT

CCACGGTGAGAAATCGAAGAAAATATGGATCACTGTGGTGCTTAAGCTGCCTAGCCACTTCCTCATCTCGAGTTGTTAGC

ACTACTCTGCTTCCATTTTCATCATCCGGGAACGATAAGTGCAACTCTTCCCAAGCCTCAACTTCCCATATATCATCTAA

AACAATGAGGTATCTCTTGTGCATTAGACTCTTGCGCAACTTGTCAGGCAAGTCTTCAGATGGGCTATCATCCATATTGC

CTACAACTTGTTTAAGAATCTCTAAGAACACCTTCCTCAAATTATATTCTTTTGAAATAGAGCACCGTGATCGAACGTCA

Figure 8 (Cont.)

AAGTGTTTATCAACACAATGATGAGTGAAAACCATTGTAGCCAAAGTTGTTTTGCCTAGTCCAGGAATTCCAACAATTGA

GTCAATGTCTAGTTCCTTCGTTCCTCCCGTCAATTGTTTAATTATGTTATCAGCATTTTCCTTAAAACCAACCACTTCCT

CATCAATTGAGGTGGAAGTTCTTTCACCCTTCAGAACGTTTACCATGTCAGTTATCTTGATCTCTTTACTGCTGGTAGAA

GTAGAAATAACTATATTAGAACTGATTGCTCGTCCTAGAATAAATAGATTGGCAAATAAATTAAAGTTAACTAATCTACT

AGGTCTATCAAATAATCAGGTCCATTTATGTAACGGTAGGGGTATATGTGAGCCACTTTTGTAACGAGGGATATATCATC

TCTAAATCGCAAAGTTGAGGGGGGATATGAGACCCTTTTCCCTTCTTTTTTTTGGGGTATAAGCTATATATAGGCACACA

TTATAGCTTAGTGCATTCATCTTCTTCTTTTCTTAACATGAATGTAGCAGAACTCTTTTATGCTACATCTTGGAAGAACA

AATAGCTCAGCTGACCATAATTTTGAAGGTCTTCACCTAATACTCCCTCAGTTCACTTTTACTTGTCCACTATTCCAAAA

ATAGAATTTAATTTTTATTTGTCAATTCTAACATATAAAAAAAAGACGATTTTTTCCCATGTTTTAACATGGAGTATTAA

TTACTTATTTCCCTAATCATTTTCCAAGACTTAATATTGTAAAAATACTCATATGAGTCATATCAATTATTGTTTCTTAA

GCATCTGCAAAGTCCAAAGTGGACAAGTAAAAATAAACCGAATAGGTAATTTCTTTTCCCAAAATTTCAGGACTTTGTAA

CTTCTGATAGAATTTCAAAAACCAAAAAAGACACGCTCTGCATAAAATTTATAAACAATTGCCGAAAGATTCGTAAATTC

AAACTTACATTCTCAAATGAGTAGAAAACCAGAGGTACGTAGTACTGCAATGCTAATTCCTGGATGCTTCTTTCACTTCT

TTACTCCAATTAAATTTGGATTTGTACTCGTAACAAAGGCGATTTCATATCTGAAGCTCAAAGTTGTTGAAGAAGAAGAA

TAGTGTTTGTTCTTCTACGATACCAATGTGTATGGAATTTGGAAAATACTTTTTCACTTTCAACAAAGGCTGACGCTATA

TATTCTTTCCCTTTTTTGAAATGAAATAAAAGTTCCACTAGTAATATTATAAGTTTTTATGGTATACACTAGATCTTTAA

TTAAATCCATGTGAGGGATCTTTTTTTTTTTTTATGTCCAGATCAACTTGCATGCACCTTAACTAATTCCACGAAATACT

TTATACTTGTCACCTCTCACCAACAACTCAACTAATTTCATAGGGTATTTGTTACCTCCCACCATCAATAGATACCAAAT

AAATTTGTACACCAAGATTAGGACAAATAGGAAGAAATCGCCTAGTGATTTTGTCTATGTAATAATTTGAACCTCGTTTT

GGAATTCACACAATGTCCAAAAGAGTCCCAAAAAGGAGTATCAAAAGGTTAACATCTGCTAATCATCATATCATATTATA

TATATATATATATATATATATATGTAATGACCCTAAAGGTCATTTTTGGAAATTTTCATAAAATGACCGTTTTACCCCTC

CCGATAGTTGCCCCGAGTCCTAATTGTTGTATTTTTGAAGTTGGTTTGAAGGAAAATTGATGAAAAGTTGAGTTTTTGGA

AAGTTGAGTTCTTAAGAGTTAAAGTTTGGTTAAAAGTGCTATTTCGAGTCATTTGGAGTTTCGAGACTCGAATCGAATTT

CCGTCGATTCCAGTAGTTTTAGAATGTCGAAACAGGTCTATGGGAATTTACGGAGTCGAATTTGGAGTTAAAACGAAGAT

TTGAGATCCTAAGTTGCAAAAATTGTGAAATTTTGATCAAGAGTTGACTTTGGTCAACAAACGAGGTTTCGGTGCTCGAA

ATGGAATTTTGAGGGCACCGTTGGATTCAGGGGGGGATTCTAAGTCTAGAATGAGTCTTGGTTGAATTTTTAGAGGCCCC

GAGTGCGTTTTGAGTTTTTGAGCCTAAAGTTAGTTTCTTGACGCCTTATCGGATACCGGGTCAAGGAGACCTCGAATTCA

AATTCCGACGATTTCATTGAGTCCGAAATGTCATTTTCAAGCTAGTAGCATATTTGGTTTGTGTTCGGGAAGTGCCAAAT

GAGTTTTGAGTGAAGCTTTCTTCTTGGATGCTTTGACACTATTTCAGCAAATTGTGGCAACTAAAGGGTTCATTATTAGT

TTTAAAGGTCGAAAAATTATTCCGAAGATTCTGAAATTTTGAGCATGAATTATAAGACTTATCTGCAAATTTTGGTGCAT

TTTCGCTAACCCGAGATTGAACTTTTATCGCAAATAAGAAATAATTGTTTACCGAGTAGAAATGATATTTGACTGAGCAA

Figure 8 (Cont.)

ACGAGCATGAAATTGAGCTCCGATTGAACGAGCAGGTCCGTATCATTATTTAAGACATTTACAAAAAAGAATCGGGTCAT

TTCACTATCGTATGAGGAAATTACGGCCTTTTTAGTGAAAGATTAACTGCTGTTTTTTTGGTGCATAACAGCCATGTACT

GCTATAAAAATCTCAAACTGTGTTCATTTGGTATTTTGAGCATATCGGGAGTTCTAGAGATCGGAATGGAGTGATTGTTC

CGGTTTTCTTCTTGAATTAATATGAAGGTTAGTATTGAATCTTCAATTCGACATTTTCTCATAATTTCTTTATCTGGTTT

TTTTTTCCTATCCGTAAATCTCTTGGGAAAATTTGGGGTTTTATCGATTTGGACTCCCTTTTTGATGAAAAAGGTATATT

TACGATCCTTATGTTATGGGTAAACTGATTTTAACATAAAATTATTAATTCATCAATTATTTTCATCATATTAACCGCGT

ACAATTTGGACTTTCCTGGTAAAGTTAAAGTTTGATAAATTGAGAATTTCAAGGCGATTTTAACTCCGTTTTTTATGAAA

TTTCATATTTGAACTTATCTAAGCATGCGTAAGATGTTTTTCAAGAGATATTTCATTTTCGAGTCAGGGTTTCGGATCCG

AATATTTTAGGCTTCTTCAAGAACGTGGATTTTCCTTCAAATTGAGTTTGTGAATTGATTTCAACTCCTTTTTCAAATTG

GTTTTCACCATTAGCTTCCAAATACTTTAAGGATCATTTTACATCAAAAATTTCCAAATTTGGGTATCGTTTTCCGGTAT

GAGACTTTTGGACCGTTTTGCCCTTTTCCCCTAAATTTCTTGATTTTGGTGTCATTGGACTCGAATTGTGATTGTGAATA

ATTTTTTGAATAGATTATCGTGATCTGGATTATACTCGAAAAGGAAAGGCTCAAGTCAAGTAACTTTTGGAGGTCGTTTT

AAGGCAAGTGACTTCCAAACTTTGTAAAACTCTTAGATTACGCATGACTACTTTCCAAATTGTGTTGGGGAGTAATGGGG

ATTGAGGATGGATTTTACTTGTTGATTAAAATTATTGTAAATGAAAGATGGGGAATAAAACGAGCTAAATGTGTTATATG

TGACTTGAATTTGTTGAATAAGTCATGTGATAACTGATATTGAGGGGATAAAAGAGCATGAGTAGGCTATGATTGATACA

AACATTGTGATTGAGACAGGTGATGTGTAATACTATGATGTGGTCGTGATATGGTTGTGATTGAGACAGGTGATGTGTAA

TACTATGATGTGGTCGTGATATGGTTGTGATTGAGACATGTGATGTGTAATAATATGATGTGGTCGTGATATGGTTGTGA

TTGAGACATGTGATGTGTAATACTATGATGTGGTCGTAATATGGTTGTGATTGAGACAGGTGATGTGTAATACTATGATG

TGGTCGTGATATGGTTGTGATTGAGACAGATGATGTGTAATACTATGATGTGATCGTGATATGATTGTGATTGATGACAT

GTGCATATTCATTATTCATCCCATGTGTGAACTATCTGTTGCATGAGTTCTGAGACACTGATATGAGGATGGATGGATAT

GAGACACAGTTGAGACTAGCTCCGGCTAGAGATATATGAGATGGACTAGCTCCGGCTAGCGATTTGGATGCCGATGGGAT

CTGGTTCCGGCGGTGATACATGGTCTATGTGTGGCCCCCATGGGTTATGATTTGAGTATTCAGCGCGGACTGATTACGTC

AACAGATGTGTATCATAGGACAGACATGCATCACGACTACATGACATCATTATTGCATTTTGCATCGCATTTGCCTTATC

TTTGTCTGTGATGTGTGGATTGTATCGGTTTACCCTTCTTATGTGGAATTTGATCTACTTGCTCTTATTTGTTGATCTGA

GGTTGATGAGGATATACTGTTGGTTCTGGCTGTTGAATATGATCTGTTTAGTATATGTTGGTTGGTTTGCTGTTAGATTG

AAGTTTCGGTGGTTCGATTGGGATTGAAATGAGTTGTTTGTAGCTGCTAGTTTTGCTTAGTTTAGAGTTACTTGCGAGTA

TCTGTGGTTTTCGGTACTCACCCTTGCTTCTACACAATTGTGTAGGTTGACAGCTCTCTCTCAGATTCGGCTTAGTAGTT

TCTTTAGCAGATTGAGCTTCGGAACATACTCGAGAGGTAGCGGTTCATTCCAGACGTGCCCTTGAGTTATCTTTACTTTC

AGTTTTGTTCTATTCGAGAACTATACTCTGAGACTTGTATATTTTTATTCGAATTCTGTATTTAGAGGTTTGTACATGTG

ACAACCAAATTCTGGGTAGTGTTGAGTCTTAATTAAAGTCTTTCGCTTATTTATTATCGTTTATTATTGTATTTCTACTT

CTTTATCGTTGTGGTCTGGTTAGGCTGACGTGTCCGGTGGGAAGTGGACACGTGTCATCACATCCGGATTTGGGGTGTGA

Figure 8 (Cont.)

CAATATATATAATAGAGAACCTTAGGCTTGTCTACGTGTCGACACCACAAACCAAAATTCTCTTTTAATTTATTTATTTA

TAAAATTAGTCTTCTCTTTTATGAAAAGTTGCGACTTTAATGAAGAGTTGTGACTTTTATGAAAAATTGTGATTTTTATG

AAGAGTTGCGACTTTAATGAAGAGTTGCGACTTTTATGAAAAGTTATGACTTTTATGAAAGGTTGTGACATTTCCGAAGT

GTTGTAACTTTTCCAAATAGTTGTAACATTTTTGATAAGGCACAATAAACATTTGTCCACTTTACCCTTTGTTGTCAATA

AATAGAGGGATTTCCTCTCATTTTAACACAACTAAAATTCTGAACCTCTTCTTCTTCTTCTTCTTCCCAATTAAATA

TTTGTATACTTTGATCATGTTGAGTGGCTCACTGACACTATTGTTTATGTTACAGATCATGGTATATATTTTTACAATCA

TTAATTTATAATTTATGCTTATGTTATTAAGCTAAATGATAAGATGTAATAATTTTCATTTTTCTTTACATTATTAATGT

TTGTTACTATGTAATTTTGTATGTAAGATAATATAGTGTTTTAGTTTTAATGTCTGATATGTTTTAAGTATTATTTTATA

AATTTTGTGATATTAAATTCTCACACGAAACGCGGGTTATTTTACTAGTATATATATAAAAGAGAACCTCAGGCCCGCCT

ACGTGGCGTCACCAAAATCCAGGATTCCCTTTTAATTTATTTATTTCCAAAATTAGTCTTCCCCTTTTATGAAAAGTTGC

GACTTTTATGAAAAGTTGCGACTTTTATGAAAAATTGTGACTTTTATGAAGAGTTGCGACTTTTTTGAAGAATTGCGACT

TTTTTGAAGAGTTGTGACTTTTTTGAAGAGTTGCGACTTTTATGAAAAGTTGTGACCTTTCCGAAAGAGTTGTGACCTTT

CTGATAAGACACAATAAATATTTGTTCACACTACTCTTTGTTGCTTATAAATATAGAGATTTTCTCTCATTTTAAAACAA

CAAAATTTTTGTACTACTTCTTCTTTTACTCCTGTTCAGTGACTCACTTCACCATTGTTTTTTGTATCAATACAATGATG

AATAGAATCGTTATATCCTGAGAGGATCTATTCCTTTAAATCTCGGATACTGAAGGGGAATAATTTTCCTAAGGGTACAC

AATGCATTTAGTGGGCTCAATTTTTTCCTTTCTGTTTCATTCTATTGTTACATATCTTGATTTTTTTTCACAGTCATTAA

TTTATGCTTATTTTATTAATTATTATTTTTGAGTATATCTTTTAAAATTTGTTGTTTATGTTTCTTCAAAGTTATTATTA

TAAGTATTTGTTAGTACATGTTAAATAACACACGTTAATTGAGTATTCATGCAAGTTTTCTCTACTAAAACTGTTGAAAG

TAGAGTAAAAGAATTCCTTAAAGATCTGTACTACCATATCTTGAAGACAAAATTCAAATTTGATATGTCATTGTAAACAC

ATAAAGATCTTAAAAATTTTATCGCACCTTGATGTGCAAAGTGAACCAGGAAAAGAAGACAAAAATTAATAAACTTTTGA

CATAAGTTCAAGGATGTGTCGGATGACCTATAGAGGAAAATGACTAGACTGCAACATCTTTTAATCCCAAAGAAATAGAT

AACTACATAATAAATTAATTGCTCATATTTAATATGAAGTAAGGACAAATTTCTCAAGTTTACTGCAAGTTGTAAATATT

TTTCTTGAAGTAATAGACGTGTTTTCGACACTGTGTGGAATAGAAGTGTAGTTCAAATTGAACTTTATCACTCTGGTGTG

TTAATTTTTAAAAAACAACTAGACAAATTGAATAGTTTTGTGTAATATTTTTTCCTTTCAAGTATATATAATGAGTTGAA

TTGTTGTCCAATATGATACATTTTCCATTTAATATTCATTTTAATAATTACTTACGATACATTTAAATGGGAATTTCAAA

ATGATATATGTAAAACAAAAGATAGTGCTGAACTTTCTACACGCTAGAATTAGAATATTTGTTTACTTTTTTCAATCTTT

TACAATTTATTTATCTCTACACCAACAATTATTTATTTATTAGAATATTTAATACTACCAGTTTATGCATTTGATTCCTC

AAAAATGTCGAATAGTAACACTTCCTAGAAGCAAAATAAAAAATAAAAAAATCAAATTAAAGATGATTGATTGAAAGATA

AATGATAAAATGTTATAATTATCACTTCCTTTGTAGTGTTTTACTTAAAATGGCTAATATGTTATAAGTATTATTTTATA

AATTTCGTAACATTATATATATAAAAGAATGTTTTAGTGGCAACATTCGTCGCTGCTAATACATTAATAGTCGCTACTAA

AAGAATACTTTAGTGGCAACATTAGTCGCTGCTAATGCATTAATAGTCGCTACTAAAAGAATACTTTAGTGGCAACATTA

Figure 8 (Cont.)

GTCGCTGCTAATACATTAATAGTCGCTACTAAAAGAATACTTTAGTGGCAACATTCGTCGCTGCTAATGCCTATAATAGT

CGCCACTAAAAATATGTTTTAGTGGCACCATCAGTCGCTGCTAATGCTTATAATAGTCGCCACCAAAAGTATGTTTTAGT

GGCAACATTAGTCGCTGCTAATGCCTATAATAGTCGCCACTAATAGTTTGTTTTAGTGACAAGATTAATCTCCGCTAATA

CCTATAATAGTCGCTACTAAAAGATTGTTTTAGTGGCAACATTAGACACTGCCAATGCCTATAATGCCACCACTAAAAGA

ATGTTTTAGTAGCAAAATCAGTCGCTGCTAATATCGATAATAGTCTCCACCAATAGTTTGTTTTAGTGACGAGAGCTCAC

TTGGACAAAACTTTCGTCCTTTTAATGTTTTTCTTTTTTTCCTTCTCATTCAATTCTTCTAAATATTTTTTGTGTGAGTT

ATTACTATTTTCGGCAAGCTTAATTTGAAGAATATGAAACAAAACATTCTCTGAATAAAAATAATATCTTAAGCTACAAA

AGATATGTCTATTAACATTGTTGTCCTTTATGTCCTAAGTTATTGCTGAACATTTGAATTATCTAGGTTAGACTCATTTT

TAATGTTTTTAATGTTCGAAAATATTTCTTTAGCATGAGTCTAGAATTCAACATTTTGATCTACTTGTACTTTCATAATG

CAACTAGAAGGGCTTTCAAAGCAGCATTTTAATAAAGAATGAATTTCTAAAAGAGTCAACAATATTATTTTGCTGTTGTT

TCAAATTAATTTTTCTCCTTCTATAAATTTTGTTAGAGTAGCAAAGTAACAATAACGAAAAGTAGTGAACGTTTGACCTC

ACCAAATAGATAGTCTCTAAAAAAAATTATTTATGTTGTTGTGGTGTACATTTTTAACGGTCTTAACGTATTTATAACTA

ATATTGATTATCGAAAATTTTTACATAATTTTTTTTCCACAAGGAGTTATTCTAACCATAAAATTATCTGATTCTATATT

TTTCATGTACAAAAAAATAAAAAATTATGTTTAATTGCTACATAAAAACATCACTTAATTTTAACAACACAATTATATCA

TCAAACATATATTATGATAAATTATGTAAAAGATAAAAATGATTAGATCTCAAAATATTTTTAATCATTCAACATATATT

TACAATTCTTTAAATATGTGATAATGTCAAATCATTTAATTTCTGTTGAAATGTTTTTAAAACCTACTAAAATTTACTCT

TTTTTTTCTTATAACAGTCGATTATTGAAAAAGTTGTTCAAAAGTTTAGAAAGATTATTTATGCCCGCGCAAAGCGCAGG

TAAATTACCTAGTACAAAAATAAATTGGAACTTCTCTACTATTTGTAAATGGTAAAACAAAAAATGGGAATTATTTACTA

TTGAAAGTAATTCAATGAGTTACAACATTCTCCTTGTTTTGTGATTCTTGTGATGTTACATAATTAATCAATTGAATGAT

TGAATATACATAGAGAGAAGGATAGTGAAGTATTCCTTTGGAAAACTTCAAACTCTATTTACAACTTTTGCAGCATGAAA

CATACCAATGGCTTGTGCTTTGTCACCTTTATATTCTTCAAAAGCTTTATCAAGCACTTCCTAGACGCGCTTCAGCCATT

TGTTTTGATTCATCGCAATTGGTCCAAAGGTCTTTCAATTCGCGTCTCACTGCCCCCAGTACCACACAAGTTCCTAGACG

ATAAAGGTTTTAAAACGATGAAAAAACTAAACAACAATTTCAATTAAGTGGTCATCAATTTCGTCATACCTAATGTGCAT

GGCACGAGATACAGGAGAGCAGGTTGACCATGTCCATTCATCAAAAACAAGCCGACATAAGTAATGCAAAGACCTGCACG

GATTTTAGGTTGATTAAGGCGAGGAATGAACGAAATGCAGCATTAGAAAAGAGAAAAAGGAGGGAGAAAGTACAAGAATT

AAAAAGAAACACGGAAAGAAAGAAACTCAGAAAGAATGATAGATAATCAACATGATTCACACGTAAAAATCAAAACTAAC

ATATGTGGCGCAAAAAACAATTTCCATAGATGTGCAGAATCATAAGCAGAGGTTTTATTAGAATAATTAGAAGCATTGAA

CGAAAGAATTGTACATTGGAGCGATAATCTCAAAATGATTTTCAATTATGAAATGAGGCTATTTCTCAATTTTACCCGTT

TTTGTGGTCTCAAACAACTAAGAGCAGCAGTAATGTATTAAGACAAAACGGATATGAAATAACACACCAACAACAAAATA

CCCAGTATAATCACACAAGTGGAGTTTGGATAAGAAATAACATAGTAAGAGCATATAAAAGCAGAAAGAACAAAAAGAAC

TACATATAAAATAAAAAATAAGAAGGAAGAAACAAAAGAGAGGTACCCACCAGTTCCATAACCAATCATCAGCCAAAGGA

Figure 8 (Cont.)

AGTATCCATTTAGTACCCCCTTCTTTTTAGCTTCATCAAATCTGCAAAAAAGATCGAGAAAGAGATCAACAAGAGGTCCA

AATGGGATAAATCAGAAGTCAAAACTAAATCGCCATCATTCTGTAGAAAGAACGAGTGAATTTAGACAAACTGGGCCGCT

AAGTTGATTTGAAAACATCCTCTACTGAATCCCACAAATATTTATCCAATTTTTGTTTTCCCATTTTTTAACCATTGTCA

TCGGAATGATTTGTAACACTTGTAAACTGGAATAATTAGAGATGTTTGCATAACAAATAAGAATTTGCATTGAAACCTAG

AGCTTCATATATCAAAACATTCATGACTAAATTCATATATACTCACTGTCCTTGTAGATGCCTATAAGAAGAATATCTTT

AAGAACAAAGGTAGAGAAGTAAGTGAAATAGAAGTTTCTTATCATTTAATCGAGGTGATGTGCTAATCTTTACATTTCTA

AAAGAGAGCAACAATTATCTTTGCAAGATGACTGAAGAGCAAAAATACCTGTATGTAAAGCAAATTAGCAAACCAGGGAA

GAGAATATCCCCAAAGCCAAGCATATCAAATCCTTTATAAGGATCTGTTAATTTAGGAACTCTCAGAAGCATCGGGATTG

ATTCTCCACCAGCTTTCTTACCTTTAGCAACCTACAAGAGAGGCCAAATCCAACCACCCGAAAAATTAGAGACAGATACT

GAAGAGCTAAATTATCTTCTGGTAAGAAGTGCGTGGCAAGAAGCGAGTTTAACCCAACTTAATAATGAAAGGATCCAGTT

TTGAGCACGTAAATGTAATTAACATATACCAAGAAAAAAACATTGAAACCATCAAAAGATAAAAGATGCATGTGTGCACA

TTTAAATCATACAGGTACATCTTTATGTTTTAAACAATCCGGAGCAGCTTCATTATAATCATTACCTAGTTCCTGTGCAA

AACAATCAAATAATTTTGTTGCATTTTGTTAATGTTCCACAATCCACAACGACAAGATAAATATCCAAAAGTGTTCAATA

AGGTTATTTAGCTGCTACTACTTTGAAGGTGTGCATTTATGCATGTTGCAGGAAGGCAATGACATCAGAGTAAAAGAAAA

TTTTAATGCCCAACATTAGTGGCATATTTTGAAAGAACAGAAACCAAGTAGAGGGAAGTTCTCCTTCCTATCTACCTTAT

AAAATGGAACTAGAAAAAGACTGAAACTTCATACAGACAGGTGGTATAACACCACCTGCCTGTAAAGGGGAACAATTTTT

AATTTTCTAGAGATCAAAGACCAAAAAGGCTTCATGCTGAAAATATTAAGAGGAAGAAAACTGGGAAGAGATAATAGCAT

TCTTACCAAGTTAATACAAATAAATTACAAGATACACCTGTATATAGGTGTGAAATCCATATAATTAAGTGTGAGTATAA

TAAATAAAACATGGTGTATTAATGCAAAGCCGAACACATTCATTATGTTCATACCTTCCATTGCCAACCTCTGGCTTCTA

AAAAGTACCATTCTCAAAACTAAAAACAATAAAAATTTAAATTAACTTAACTTTCTTCATTTCTTATACAAATCTTTATT

TAGACATCTAACTCATGATATGATTTGACAAAATATCTACATCAGCAGTACAGCTTAAAATTGTAACTAAAGAGAAAACT

TACTGAAATCATAACACTGTCATGGAATATAGCAGGAGATAGGAAAACCCAGAAGATGTCATAGACAAACGCGCAGCAGA

GAAGCACTGTAGCAACCTAAAAGAGAAAGGAAATGACAGAAATGAAAGGTATATTAGTAGACATAGGTAAAGCAAAACAA

GAAATCAACTATGTTCACTGGTGAATTTTAAAAGCTATAAACACACCTTTATATTAGGCAATTGAGCCAACTGCAGAACA

GTGATCATCAAAGCAATCCCCTGGCGAAAAAAAATTTTCATTTACTTTTAACAGTTTTCAGCTGGAGTAAGTATCTAGAA

GAGTGAAACTTGGTGATAAGGATGCATAAAACCAACTAAATATCCAACTGCAAATAAAGGTCTATCACACAAACAGTTTT

TCAGTTAAGGAGGAGATTATAAAATTAGCTTACAAGAATGTCTTGGCCAACCCAAGAGTATGATTCTTTCCTGTTTATTG

CCCAGAAGATGGCGAATCCCACACAAAGTGTTAGGACAACTAGAGACAGAATAGCGACCTCCCCAACAAGCGGCAAATTC

AATGTTTTCTTTCCACAACCTCTAAATTTGCTGCTTAAAAGATTGTATGAAGCATAGTTAAGGATCTAATCAGAAATTCT

GTACATAATATGAAATAGACATAATGGGTCAATACATCATACCTTAGTATGAGCGTCACTATACAGTTATGCAGTCCCTG

GAAAGAAACAAAAAGTTAAACAATAAAAATTCAACAACCAGAAAAAATGTTGACCAAATGCAAACCAGAATTAGTTTTGC

Figure 8 (Cont.)

TCCAAAACGTAGAAAGTGCATATGTTGCACAAATCAAGCGTAATCAAAAGTAGTCAGAATTTAGGTAAGTAACCTCCCAA

GCACCATATGGACTTGCGCATATCAACTAACAGAAAATGGAAGCTAACTAAAGCATATGGATTTGTAAGTCCACATATTA

ATCACAATTACAATATTGCATCTATAAGCAGATGGAAAGGTTAACCTTTCAGAAGATTATGGAAGGCACAATTATCATGG

AAAATGCATTTATGACTCAAAAAGTTGGCTAAAATCTACTGTTCCTACGATCTAAAGTTAGAATCATAGATAACATAAGG

TCTTTGATGCAGCCAGTATATTAAGCCTTAAGCCTAATACACCTCATCAGCTGGTGTATTCCCTTGACTTGGCGGTTAAG

AAAGCATAGCTCCATGACAATGTTACCCATAATGATCCCCTACCATTAATGAGCTTGATGAGTGCAAGTACAATATTATT

AGAGGGCCACTAAAAAGATAATATGAAAGAACAATATACTAGGCACAGCTGATGTGTTTCAAATAACTACAACTACAAAG

CTACTAATTCACTTCGCATGCCCAAAAGGAAATTTGGCCTGGTGATTAAGAGTCTTATAGAGGAAAATTCAACAATTCCA

CAGAAATGCATGAATTTTGCATATCAAGAAACATTTAACATTTGTAGCACAATTCAAGAGTCAAATGATTGATTTGAACC

ATTAAACTGATGGGCATTAATTTTAACTATTTTAACCTTGTAATCTGGCACAAGTGAATAGAAAAGGTAATCCACTCATG

TGAGTGCCTTTTTTCTAGTAAAATGTAAACCAAGTACATCTCCATGGCAAGTGGGTGGGCCTACGTAGGATGTTGTCCCA

GTGTGTTATGCCAAAATGTTAGAGAGCTGAACACTGGACGATAACCCTTTAATGATCAATTTGGACTTTTTGGTTGGAAA

ACATTATAAAACCTTTCGAAGGAGAGGAAAACCTTTAAATAATTCTAAGTTTATATCTATTTCCAAGCTCTACGTTTTAA

GTTCGGGAAGCAATGATTACTAGTGAAGACTTGAGAGTTCCCTAGATATGAAGAAAAAGTTGTTTTGATCATCTACTTTG

TTAATCATCATGGTATGTGATTGTATCCATCATCCAGGAGCTAGCACTCCCTGTCCCAGAAGCTTCTTTGAATATTTTTA

TCAGGGGTCTAAGGCAGGGAGTGGGAGCATGACAAAAGATTTGTCCACTTGAATGCTAGATTAGACCAGCTCTGAAACAG

TTACTACCGAAGCACAAAGTTGTATCATTTTCCTGAGTAGTTTTAGATTAGCAGGAAAAACTACTATAAACACGGCATGG

AAAATATTGCAAGGAGGAATATTATAGTTCAGTAACATAATAATTCAAAAAATACATCAAAATATATATTATTAGGCATT

GACAAACACATTTTTTCTAAAAATCTTTAGACATTATATTCCATTTTCTTTGCATACTATACGAACAGATGCATGATATC

ATTATCTTGCTCATCTGTCAGATACTACATGCATGGCCCCAACTTATAAACTAATTCAACAATAAAGCATAAATAAGCAG

TGCCATGAAATGAGACTTAGACGAAAGAAGAAGGAGAAAGAACGAACTTGAATACCTCGATTCCACCGATACAGAAAAGC

AATATCAGCAGCCAGACAAACCATGTGGACATGAAAAAGTAAAGCAGCACCAGAAATGTGGATGCTGAGATGACAAATCC

AATAGCAGTCCATGCAGTAATGTGCAGAATTTCACTATCATCCTCCTCCTTGACGGTCATATCATCATCCTGTAAGGAGA

GCATACACTTTTTAAGACATTACAGCTATTAATCAAGCAAGGCATCATTGGGTGTTATCAATATTTGACACAAGAACTAG

AAGTAGGAAAACCAAGAAAGACATGTTCACAATACGCTCATAACATTCAAATACAAATCATAGATATAAATAGATCACTC

GTTCAACTATATTTAAATCAGATCAACTAAGGTCATATATGAATCTTCAGTTCCATTCCCCGCTCTATTCGGGGATATTT

CACTCCAATACTAGATAATTTGTATTTTAACACAAACAAGGAGTTCCGCAAAATTAGTGTGTTAAGGTATGATAAGATTT

ATATTGATTAGGGTTTATTTAATTTTATTAGCTTGATTAGGGATTAAATCAGATTATATCTGATTTCAATATAGCAATTT

TCAAAATTACACACCTTGCGACACTTTTGAGAATATTAGGTCTTCTAACACTACACCATTTCTACCCAGTCGATATATTG

TAGCTCCACCAACCAAACAGGCCTTCATTATGTGAGTCTTGTCACCACAAAATTGTCGACAGTTTTTGAGATCCTCCAAA

CTGGGAAAGACCTCTCCAATTTCTTCTCTGGATAAATATGTCTCTCACACACCTTTACCTTTGCCGTTAAGGGAAAAGGA

Figure 8 (Cont.)

TCTATAGAACAAGCCATCTCCTCGATGTCAAAAGTTTTTCCATCAATCTGGTGGCCAAGTATACTTAGAAAGCCCATTCT

ATTCCATTCCTTTTAAATTCTTGACTTACTGGATCCAGTTTAGCTTCAGCATACCTCTTTTTTCGCTGGAGATGCTTTGT

AGGTGACACCCTATTAGTGGTATGGAAGGGAAAAATGTAAGCAGTGCACTGGTCAAGAACTAAAGTATCCAAAGGAAGTA

TGTATCAAGGATAAATTATTTGGAAAAGGGCAGAGTAGTGAAAAGATTACACAGACATATCAACCTTGGTCAATTCAGAT

GTATGTTAACTTCTGGGGCAGCTCTTGTGACGCAGGCAGCTAAGTTTTGAAAGACCAACAACTATTACCAATTATGTTAC

CTAAAATCCAACAGCCAGAGTAAACTAAATTTACTACATTATCATCAAGATGCAGTGCTGAAAAGCTAAGACAAATAGCC

CAAACAAAATCAATGTTGACAATGCTACTAGCTGAATTTAAAAGAATATAAGAAGCTGAGCATGTCAAGTTTGAGATTGT

ATCAGACAGCTTATTTTTTTATTTTTTTGTGTGTGTGTGGGGGGGGGGGGGGAGGCTCTTGTGATAGTTCATAGTTGTCA

CTTTCCTTAGATTGAGTAAACTTTTTCCAAAGAGCTGCACAAATGATTGTTCCAACAGCCATCAACCATATGAAAGACAC

CGAGTAGTCCACAATAGGGCGATCTGGCGAATATAACAGCAGCTCCACTGGATTAAGAAAAGGATTCCATATGTCAAAAG

TATTCCAAGTGAAATAAAACAAACAACAAGAAATAAGAAGATCAGAACAAAAGATATGCATCAATTAGAGAGTCACTATA

ATTGTTTGCAAATAAAAAGGCCATTTGATGTTAGCCAACACTGCGTTTAAGTCCACATTCTCATCAGCTACCACTGACAT

TTTGAAGAGAAAATCAATCTCCGATCTTCAATCTTCGTTGCATCACACTAAACCTTCATCCCAAACTCATTGCTTAACTG

TTTTTTCAAAGTATCAACCTGACATGCCTTTTGCGGTGAAGACACATCATCGAGATCCAACCATAAATAGATGAAGAATC

ATCTAAAAGCTTTCTATGAACACACAAATGGCATACGGTTCCTACAGAATACACCCAATAATATATGCAACAAGGACCTA

TTGTTTGCACCAAAAGTTAACCAGCAAGAAGTGGGATTACATCTCAATGATATATAATAAATCTATTTTCATACTTCAAA

AGCACTCATTAAAATGAATTATAATGCATGTAATATAGAAAAAGTAGATTACAACACAAGCTAATCAACATCTTGACAAC

CAAAATTAGAATCTAAAAGAAAGCTAACCTTTATAAAAACATCTAAGCAATACATATGAGGCCAGGGCTTACCTTTCTTT

CCTGAATTGATGTATTTATCAATAATATCTGCCCCCTCTTTTGAAATTGAAACAACAGGAATGGTTACATTTGATATGGT

AGAATTATTAGGACAAGCAATATCCAGAGGACCTAAATAAATGCAAGAAAAAGCAGCGTCATATCAGAAAGAGATGAAGG

GAAACATATAAAACAGACCTTGAGACCTAAGATGACAATGTGAGTCAGGGTTACAACCTCCTTCATTATTTATTAGCACA

ACACCTCCTGCACCTCCTTCTTGGGCAACCGTGGCCTTGGTTATAAATTCACATTCACCGCGACGAGCTAGTGCAATAGA

GCCTGATAACTAGAACAAATGATATTTCTGCATTATTAATGTATAACAAACAACACCACTATTATTTTCTTTTTATAGGA

CATTCTCGAGCCTATTTTTACAACAGCCAAACAGATATAGCAAATTTAGACTTCTTTGGTATTCAAAGTAAAATCAGTTT

GTAATAGTTAACTTCTGGTAGATCCTAGTGGTAACCCTTTCAGATCATTTTACAATTCAAAATTCCTCCACCACTACTAT

TTGGTTCCACTTCTGAAAAGTACCATGAAAAGGATATTTTTCCTCTAAAATACCAGTTGTATTTGTATCGCTAAAAATAA

CACAAGATCGAAGAAAGAAAAAACTAACAGAATTACTAAGACTCACAAATTGCTAATATAATTGATATTTTTGCAATTGG

GGTAATATATGGTTATTTTTAGCAAGAACTTAAAAGTATAGCTGATCACACAAATAGTTTAAAATAAAATCTTGAAAGTT

GAAAATGAAGTCATGTAGTCTTTTGTAAATGAAACAAAAAAAGAAGAAAAAGATCTAAATTTTGGAAGATGATGTAAACA

ATGATTATCACTTGAAAAACTTATAAACAATTTAAGCAATAGCTTATATGAAGATGAGTTGCTGTACAGAGAGGGGTGAG

GGTGTTGACAAGACTCACGACAGAACAAAAGGTTGTTCAGTAAGTATTTAACTATTTATCTAGTATGTGTTTAGTTCATC

Figure 8 (Cont.)

AAATTAATCAAAAAGAAGAAGGAAAGATTGTGGCTACTTTTGAGCTATCAAGAGATCATTCCTTCACCACCCTGTACATA

GTGCTACATCATCCTCAACCTATCTCCATTTCTACTCTTTTCTCCTATTTCAACCCTCCACTGCAATCCACCAGAAAAAA

GTATCTTTCCATTTTCACGAGTGAAACTTACTCTTAAGTTTTCTTATATGCTGAAAATAAGTTGTTCTATGCAGAGTAAG

TTTGAATTACTTTAACTTCCTGATAGAAGACAGAGATGGTCAATGGCTTAACATGTAGATGTTTTCACCTAAACTATATT

AAAAAAAAAAAATTGTTTCTTCACTTCTCCTTGATATAAATGAGATTGGTTCACAATTCGGCTCCTTAAATCTTTTCAAC

CTTGCTGAGATTTGCATCAATTCTTCACTCTTAAAGCAGGACTTGGCTCATAAAGAAGTATGAATTCTATTGTTTTCAAA

TATTCGCAAGTTAACAAATGAGAGATGGAAGATCATCAAGAAAGATCAAAAGAACCGAAATTGGGCCACGAAAGAATTAT

GACTATTATTTAATCAACCAGCAACACAGTTTTGTTTCGGATATCCACCTAAAAGTAAAGGTGTGTAAGGAATGTGGAGT

AAATACCTTAGTGGAGGAAGCAGAACAGCCATTCAAAGGTTGTGTATAAACAGCACGCAACCTGGAGGCACGTTTAGTAT

CAGTGGGTAATACAGACCCAAATGCCGCACTCAAGCCAACTATTGAATCTTCTTCACCACCATTAACCCACAACTTCACC

AGCATCTTTAACAAAAGAAAGGAAAAGATGATTAGCACCGGTAAGTTTCTATATGTGCAGAACAGAATGAAAATAGAGAA

TACTTCAAGTCCAGTTAAGACTAAACATCAACTAACATGGATATTGTGGTAAAATACTCATTTCAATCATTGTTTCTTAA

AGGGCATGCAAAGTCCAAAATCGACAAGTAAAAGTGAACGGAGGGAGTATAATAAATGCTAAATAAATCCTTGTATAGTA

ATCTTATAACACACACACACACACCACACACCAGAACCTCAAATTAAACTTTTTTATGGAGTGGTGTCTGAGCTAACTTG

CCCACACCTCAACTATTCCACCGAGTAACTCTGCCACCCCGGCACAGAATCAAAACATAATATATCAAATAACTCCATTT

CATAACAAATTCCACCAAATGCATGAACCCAATCCTCACCATTTCAAATCATCTTATTAGCATTACCCAAAAAAGATTGC

TTTTTTAATGATAATCGCAGTGTCCAGGCCAGCTCAACTAATTCCACGAGATACGTACCACCTCCCACCAACATGTCCAT

ACCAAACAAAGATTCTTAACTATTGAAACCCCTCAAGAGAAAACAACAAAAAAATCCATAACCCCATCATAACTTTCCAC

ATAATCAAGAAATGACAATATCAAATAAGAAAATCTACAAAACCCATAAAAGACTACATTTTTAACACAATTTCCACCCA

AAAAACAAACCCCATAATTTATTTTCTCTACACAAGAAAAGGGTTGAATACATTTACCATATTGATTTCATTGCTGCAAG

AGCTATGTGCCTTGGTAGGAGCAGAATGTGCTATTGATGATACATTTAGAAGAAAAACAAAAATAGATAGTCCAATAAAA

CGCCATGAAAATGCCATAATTATTTATTCAATGTTGATTCCTCCCTTTTTCTTCCTCAATATTTTCCCCAATTCTTGCGC

TATATTTTCTTCGCCTATTTCTGCATTGAATTTTTTTTTTTCTTTCTTTCAGGGGAATGAAGGAAGAAAGGAATTTTCTT

TCCGATGAAGAAGTAAACAAACTTTTAATGATTAATAAATCTCAAATTAAATTAATTAATTAAAAAATTTAATTATGAAT

TGGTAAAAAATCCAACTCATATTAATATAGTGTGAAATTTATGATTTGTTGCATTTATAAAAAAAATTTAAAAAAAAGAT

AAATATGAATTTATTTCATTATAAACTTTTATACTGATGAGTTAAAAATAAAGTTAATAAAAATGTAATTGTGTGTAATA

ATTACAAAAAATAAAAGACTAGAAGATGAAAATAAGAGACAGGAAAAGAAAAATAATATTAAAAGACTAATATATATTTG

ACAAACGGAAAATAAAAGAGCAATATAAATAGCTACTAAAGTATTTGATTACACAATGTAATTTTCACCTTTCCATTCAA

ATTAAGATAGTGTAATTATATTGCACCCTCTCAATTGTATTCAATATATCATATTGATCCAGTAATTACTTAGCTAAATA

TATACATATTAATTATGTAATTACACATAAGTTTGATTTTTAGGTGTTTTTCAAAATATGATTTTAGTAAATGTGATTTT

CGTTTCTAAAATAGAGTAGAAGTTCAGGTTTTTTATTTAGTTTTTTTTCAAAATCTTTTTTTTGGGAGCAAACTCTTGTG

Figure 8 (Cont.)

GAGGAAAAAGAGGCATTTGACTAGTAGGATTCGCCTAAGTGAATTTTGATTCTCTATGAATTTTTTCAAAGAATAAATAA

GAGTCAATCCAAAATTCAATTTATGCCTATGCTTATCGATCTTTCTTGATGGATGTAAAGTTATAGTGAATTCTCCAAAT

TAGAGTCAGAAGTTGAGGGGGAACCACACTTCCACCTTTCAGTTCAAAGCTGCTTTTTTCTTTATCATATATCGCATTAG

AAAGTGATAATAAGAATGACTTTGACATACTTGTTTATAGCAAGTAATCTAACTCGAAGGCTCTGCCCCTAACCTTAAAA

AATCGCATGTGCATGTCTCCCGTATACGGTTCAAGTGGCAAAAGCATTTTCTTTGCGCTAAATTTGAACTAATGATATGT

TAGACAATCTTTTACCTTAATAAACTTATGAGATATGCATATCACATTTCTTTCATGTGTTTTACATATTATTTGAATTT

CCACAAAAAAAAACATATTTTTTAAAGTCAAAAGCGCACAGTTTTTTTGAAAATATCTAATATATGCCCTTAATTGTGGA

AGAGCGATAAATTTATAAAAGAAAAATTCAAAAAGATACCAAAATCTCACATATTATACATAGGGTTTCAAATGTGATAT

ACAAATTTTTAATCTTATTTATCATTAAACTAAAATCTGTTTCTTTTTTATCAAAAATTCAAGAAAATGTATGAGTAAAT

TAAATTATTTTTTCCATAATTTCGCAATACAATTTTCCTTTGAAAAGGATTCAATTGAACTCATTTGACTCTCTTTAGCT

CTATTATATTTGTAATCACTAGTTTTGATTCACATTCTGAAAATAAATATGTTCTTTAATTAGACATTTACAATATGAAT

ATAAACCAATAAAATTATTGAATATTAAATATTGAATAGTTAAAAATAAAATAAAATTTAGCAATACACTTAATCCTAGA

TATTCTAAAAAAAACGTATTTATTATACTCCTAGTGGGATACCATACTCAAACCACTAAGATCCAAATGGATTATACTTT

TAAAATGGAAGATATAATTTAAAAAATGCACTAAACATTATGTGGAATCCTCCCCATGGTATCAACAAAGTGAGGACACA

AGGAAGTCAACTCATGATAATTTATGTCTTTAAATTTGTTTAGTTGACTTTATTTTTTGATATTCATATTGAAGCTTTGA

TTAATTTAAATTCGTGCTACATAAAGTTATATAAAGGAAAATATTATCTAACTAGATGTTTTTTATTATCTAACTAGATG

TTTTTTACATTTTAATGGAAAAATCTTATTGTTAATTAACTTGTCTTGATATTGTTTAATTAGAATGAAGTGTTTGTTAC

ATGTTAATTTACAATTAGTGACCGTGAAAAGAAAAGATGTGAATTGTCATTATTATTAGTAGAATTACAAAAAGAATAAA

GACTTTTTAAACATTCCTTGTACAACTCAAATAAAATTATTAGTGGAAAATATTGAAGAAATATTCAAATTTTTGACTAG

ACAATATAAAGTCAAAAGGCTTGTTCCATAATGAAATCTGAAATTAATTTAATTTTTCAGCATTTCCATTATATCATTTA

TTTATTTAAGCACTCAATTTATTAATTGATATTGAAAGCAAAAAGTTTAATACACGTTCAAATTATGGTTGTTAAGAACT

TAAGATAACTAACTATTATAACAAATCTCTAAAAATATTATAAGTATCTATTTTTCCTATATGTTGTGCTTTGTTTCAGA

CTCTTTAAAAATATTATGAATATATTTGTTTCAGTTCCTTAACACATATTTATCGACATTGCTAAAGAGTTCGATCACAT

TGATTTTTACCTCTAAAACTTACCTACAACAATATTTTGCCTAACAATTTTATGTCTTCTTTTTTGTTAAATATTTACAA

TGTTCTCTCGTGGAAATTTAAGTTTTTGTTGGACTTAAATAATTATACTGAAAAAAAATAATTCCTTAATTTTCATGGTC

AATGAATTGTGGCCGCTCACCTTTGTTGATAAACTATTTTTAAAGAGTTTAATTATTTTGATCATAATCAATGTATAAAG

TTTATTTATTATCATATTAAGTTCTCTTATAGTATAGTAATAAATAAAAAATTCAAATAATCCTAGTATGATAATATGCA

TATGTAATAATACACAATATAATATGAAATAAAGTAAATGAATATGAAAAAATTCATTGAATGAGACAATGTCGACTGCT

GAGAAATTGATTGTTCTGAAAATAATAATAATATTGTGATGAAAATAGTTGAACAGTATGGAGTAGATTATATTTCACCA

TCTATACAAATTGAAACAGTATTATTAAATAAGAAGGGTCACTAAAATTTGAGTTGTAATACACAAATTATTTTAAAATT

TTGTATTATATGGAAATATCTTATACCTGAATCTTCTCGATGTCTTCTTCCCATAATTAAATTATAGAATATAATACTAC

Figure 8 (Cont.)

TAAAATAAAGCTTTGCGTGATAATGGCAAATTAAAAAAATAAAAAAATTAATATCTTAAAAATATTTACTATGTAACTTT

TAAGGATATTATAGCTTGTTTGGTTAGGATTTTATTAGATTTGAAGTGCTTATTTGTTTTAGAACATAAATAACTTATTT

TTAAAAAGGGTTAGTTCATATATTTGGTCCCTCAATTATGGATATAATATATCTCATTAATCATTTTTTCCCTTTAAATC

TCAATTAACATAATATAACTAATGAACACTTTATAGGGCAATTTTTATTTTATTATTTTATTTTTTATCATATAATAAAA

GTGAATGTGCATATTGTATTGTAAGCATAATGTCATATGATACTGTCATTGTTGTTGCCATTACAGAGTCATGTCTCAAT

AACTGATTTTGTAGTTTGGCAGACTACATAGCTTTCTGATTTTTCTTATCTATATTTTTCTATTAAAATATTTTTTTATAT

TTATTTCATAATTGCAATTCAATTTTCTTATACATAATTTACTGCAGACATGCACCGGTGGAATATGATATTTAAAATAT

TAGTTGGTAAACTTTTAATCAAGTTGTTGCTATCTTACGACAATATTTGATAACTTAGACATATGAAAGTGTATATTAAA

TAATAAATACATGATACATGTTTACTATATATATATAAAATTAGCACTCGACCGTAGTTAACTTATGTTCCATGCCAAAA

ACCTAACAATTGTAGCTTTAGTTTATCTAATCTTGTTTTATTTATAGGTCGATATAATTCATTATTTTGGCTCAAACCTT

ATATTTTTGTTAAAAAATTATTTAATATATTCAAAACAAGCAATAAAGATTATGGTCCGCACTTATACGGAAAAGGTAAA

AGATAAATGTCATCTTCTCGTAATTCGTACTTGTATTGAAAAGGTCAAATTATGATAAGCCAATCAACATTACCTAACTC

TTCTTACTTCAGTTCATCACTTAATCATGGTAAATTAACATTGTTAACTTAAATGATGTTTTACAAAAGTAGGGGTGAAG

CTACTATTATAATTACGATAAATTCGACGCAAATTCTTTATATTATTTAGGAAAACTATAATTCAAAATTGATAAACTAA

AACCTTTGAATATCTTTTTATAAATTGCATACAGTCTTGCCAAATAAGCTAATAAAGCTTGGTACAATGCCAATATACAA

TCAACAAAGAATAGAAAGGAGAAAAAGCACTATCCCAAATATATATAATCCACAAAGTGTTGCACTATACCCATGCACAT

AAAGTTTATTCAACTTACAAATGCAATATGCACTATTGAGTATAATAAATGAAAAGTGCAAAACTAAGGATTTGCTTCTA

GAAACTTTACCCACAAAAAGGCATGATGAATGGATAATGCACTTTAAACTTTTGAAACACTTGAACATTGAGAATGAAAT

AACAATAAACTAGGATAATTTTTTTGTTAAGTATTTTTATATTAATATATAGGTGAGCGTTATATTAGTTAAATAATAGT

TATAACTAGGGGTGTACAAGTCAAATTGTAAAGTCAAACCGAATTGACGAACCAAATTAAACCGAAAAAAAAACTGATGT

GTGATTTGGTTTGGTTGGTTTGGCAGTTGAAAAAAAAAAACCGACCACTCTTGATTTGGTTTGATATTAAAAAAAAAGTC

AAATTGAACTCAAATCAAACCGACAATATATATATATATATATTATTTGTTTTATTTATAGATAAAAATATTATTTATAA

TCTACTTTGTTAATATATTTTTAGTTAGTTTATAGTTTTCAATGTTTATATATTTTATTTCAAATTTTGGGCATGTAAAA

TTTGTAAATATTTATTTTGTATTAATATCTGAAGTTACAATTATATTGTTATAGTTTTTCAAATTCGAAGTTAACAATTT

ACTTTGTAAATATTTTATTTTGTATTCAGTTTGACTATAACCTTTAATCTTATTAATGTAACATAATGAACATTGATATT

TCAAAAAAAATATTTTGTATTCATGTGAATTTTACCGTCTTTTCGAAATTTCTATTCATTTAACATTTTTTAGGTTTAGC

TTATAACACGGGTAAGTGAAAATATATTTGATCTCTTTTTCAAGCACCGTATAGTTGTAAAAACCGACTAAAGCCAAAAC

CAAAAAAACCAACTTTATGTGTTTTGATTTGGTTTTTAGATTTAATAAGCCGACATAATTGGTTTATGTTTTTTTTAATG

GAAAATCAAACCAAATCGACTTATGTACACCCCTAGTTATAACAATTCAATGGTAGAAATTCACAAGAATGTATCTAGAC

ATATATTTTGGTAAGCGTCACTTTGGACTTTCTTTGGTAAGCTCAAAAGACATGCATGTATACTTCGCTTGGAGGGGGAA

ATGTACATATACTCGATTTTAATGTCCCTATTAAAATTATATTTTGAGTTTATAAATTCTTTTTCATATTTATCAATTAT

Figure 8 (Cont.)

TATTTCACGATAACTTTACATATATGATGTCTGAATTTTCATATGGATGAAATTCAGACATTTTTAGTTAGAGTTTTTAA

AAATATTTTTCTTTCGTGATATTTAATTGAAAATTAGTTTATTTCGTACAAATCCTTCTTCAGAATTTGAAGCCAACCTC

ATATTTGGAAGAAATGTTAAATAATGTATAGTAATTTTTTTCTTTAAAATGATTTCTTACTAAAATTTTCTTTTAAAGAC

ATTTTTTCCTAAATTAGTAATTTTCTCCCAAATACATTTGACTTTCAAAAGGGCTTTTCACACAAAGGAAAAAAGCATTC

ATCATGATGACACAAGCCTGAAATCATCATATATTAATATCCATATACTAAAATCCAAATAATAAATTAAAATAACAATA

AAAAAATTAGCTGTCTTTTTCAATATTCAACTTACAGAGTTCCCTCAATTTGAACCCCATTTTCAATATTCTAAAAATTT

TCATATAAATAGGGAAACATAGTTTACAAGATACACACAAAAATAATAATCAAGAATTGTTATATGAGAGCTATTTCTGA

AATATTTTTAGTGAATTTTTCCCCATTTGTTAGAAATAATTTTTTTTCAAGAAAGCCTATTTTTTTTCTATTAGAAATAT

TACTATGTCTGAATCAAGTCAATATGATTCTTGTTTTGATAGACCAAGATTGGTGATTAAGAAAGTTTTAGCTAAACCTC

AAAGTGAAGGGAATGGAGCTGTTGTTAGAAGAAGCATTGGAAGGTATTAAAATTTAGGATTTTTATATTTTTCACATTTT

CTTTTTGTTGATTTTAAGTTTTGTTTCTAAATTTTATGACTTTTTTGTCATTTGGGTATTTTTCATTTTTCAATTTGGAC

AATAAAAGAAGTAACTTTAATAGGAAATTGTGTTTTGAAACTTTGGCCTTGATGTGTTTTCTTGATTTCCTTATTGGAAA

GTCTCTGTCTTAATGTGATTTCTTTCTATTTGTCAAGTCTGGATGAATAGAGTTACCTAGTACCTGTTATTGGTGGGAGT

TGACAGGTATCTAGTGTAATTAGTTGAGGTGCGGAAAAGCTGCCAAGAAACCACAATTATCAAAAAGAAAAAAAGTATCT

GTCTTTATGATTTTTTTCTATAGTCTTGTTGCTAATTGAATGTGGGGTTTTTGTTTTAAAAATTTGATCTTGCAGGCATGA

ATTGAGGAATCTTGATCCTTTCCTCATGTTGGATGAATTTTCAGGTACTGTTTTGAGTAATGTTGCTTGGACCCTCCAAA

AATGTTGTTGCACATGTGTGAGATTCTCCAAAAAAGCATAGCTTTTGGAGGATCAACACACACGACAATATTTTTGAAGA

GTTTGAGCAACATAAGTCTTGAACATCTAACTGGAATGTGTTGATTATTTTATTTTTTTGAGCCAAGTGAAGTTGATATA

GTACTGTTTTATTGTTTCAGTTTCTGCTCCTGCTGGTTTTCCTGATCATCCACACAGAGGTTTTGAGACAGTAACTTACA

TGTTAGAGGTAAAAAAATTATGTTGCCTAATTCAATCCAATATAACAGTAAGGAGAAAGGGCCGACGAAGGGTGGAAAAT

GGAAGGCCATTTCTTGTTCCCTGAGGCCGTGTGTGTGCCATGACCAAACACCCATTTGATGCTCTTTAACCTCCCCATTA

GGATGGCTCCGTTGTATTGGTATCCGAATCATCCAACAAAGTATAAGCAGCAAAGCACCAAATGGCATTCCTTGTTGAAT

TGTACTGAGGCGGATGTAGTGTTTACTTGAACCCAATATTTTTGACACAAAACATAAATAAACGCACATCAAAATCTTAA

CTCATGATTTCAAAAGTAAAACGGGCACAGAAGACGTGATAATGCTAATGTTGTGTTTTCATTTCCTTAGGGAGCTTTTA

CTCATCAAGATTTTGCTGGTCACAAGGGCACAATCAATACTGGTGATGTGCAGGTATAGAATATTCAGCTCTTAGCATTT

TTACTTACAAGCTATGTTGCTCGGATCCTCCAAAAATGCATAACTTTTGGAATATCCGACACACGTTCAATAGTATTTTT

GAAGAATCCGAGCAGCATAGCTTACAAGAACAGAAGAGATATTTTGGTTGCTGATATATGTTTCTTATTGTGGATGATAT

TGCAGTGGATGACAGCAGGAAGAGGTATAATTCACTCAGAAATGCCTGCAGGAGAAGGCAGTCAAAAGGGGTTGCAACTT

TGGATAAATCTTTCTTCTAAGGACAAAATGTAAGTTATAGTCATTTACATCATTAGAAGCTTTCAGTCTTATCACTCCTT

TTGACCTATGTTGCTCGTACTCTTTGAAAATGCTGGCACACTCGTTTCAGATCCTCCATAAATGCGCTATTATTTGGAGA

ATCTGACACGCACCTGTTGACATTTTTAAAGAGTACGAGCAACACAACTTTTGACCTGACCCCATATAGATACTTTACAC

Figure 8 (Cont.)

ACCACCACTTTATTGTACTTGGCTCTAGCATATAGTAGTAAAAAATTTTAATGTTAGCTCTTATCTACTTTTTTTGTGGG

GCAGGGGGGGTGTTAGGAGTGTACTAATATGCAGTATAAAAATCACCTCTGTTTCTGCTGTGTTTTGCTAAGCTTAATCA

TTCACTTTTGACTAAGTTCTCAAAATTTTGGACATTTTATGATGTGATATTCTAGAAATCAAGATTTAGTTTGAACCAAT

ATTTTCCCATGTTCAAGTTTATAGCCCAAAACGAAGACTTTGTGGCGAACACACGTTTGATATTGGATTGCTTTTCCTTT

TTCAATTCTTATTAAGTTCAAAGTTCAACTGCAGGATTGAGCCAAGGTATCAAGAACTGCTGAAAGAAGACATACCAAGA

GCAGTGAACAATGGTGTTGAAGTAAAAGTTATAGCAGGTGAAGCGATGGGTGTCCAATCCCCGGTTTACACACGAACGCC

TACAATGTACCTCGATTTCACCCTACAACCAACAGCTTACTATCATCAAGCCATCCCCGAGTCTTGGAATGCGTTTGTGT

ATATAGTTGAAGGAGAAGGAGTCTTTGGAATTCCGAATTCAGGTCCTGTATCAGCTCACCATTGTTTGGTTTTAGGCCCT

GGAGAGGGACTTAGTGTATGGAACAAGTCTTCAAAGCCATTAAGATTTGTTCTTTTAGGTGGACAACCTCTTAATGAGCC

TGTTGTTCAACATGGTCCATTTGTGATGAACTCACAAGATGAAATTGATCAAACTTTTGAGGATTATCAATATTGCAAGA

ATGGTTTTGAGAATGCTAGATACTGGAGGTCAGGGCACTGAAGAAATAGAGCTGAAACAATAATACAAGCTATGTTGGTC

GGAATCTTTAAAAGTGCATATAGGTGTGTGTGTTGGATCCTTCAAAAGTAGTGTATTTTTTGGAGGATTCGACATTGGTG

TGGCAACATTTTAGGAGAGTACGAGCAACATAGACTATTAGCCTCAAAATGCACCTTTTTTATGTTTCTTTTTTTCTTTT

CATAAATATATCCCTAGTAAAGAAATAATGGTCAACTTTATCTTGATTTATCATTTGAAAATTGCTTAGGTTATTGTTAT

TTATTCTTATTTTCAGTGTGGGGTTTAATAGCATATTTGGTCCCTTGATTATCAAAAAATTCCAGTTTTCTTCCTTGTGA

TATCTCACTGACATTTACCATACAATTACTTTGAAACGTGCACGTTTGATCACTTTGCTTATGAATACTCACAAAATTTC

AACACTTATTAACCATATGTTAAGTTAAGCTTGTATAAAAACACACACATTCTAATTAATTGAAGATTAAATATGTTGAG

TCATTCTATATCACAAGAATAAAAAATATTATTTATCAATTATTGAAGGATTAATGCTATTCTCCCTTCAATGTTGATAG

GTCGTGATCAAAAAGTTGATTGTTATTTCTTTTTCTTATAGTGAATATTGATTCTGAATCTATGATAATATCTTCTTGGA

TATTGATATAGTGGTGGTGGTGGGGTAAGATTCTTTGTTGTTAGTTGGTTTCTCTCTTTCTTTTCCTGTTTCCCTTAGGT

GTTCAGTAATTATTTTGGAGTTTGATTAATTCAAAGTCATGTTGAAAGCATGCACTATTGAATATGACTTCATATCCTGA

GCTTGAACCTAAGATCTCTAATTAAGATTATCGGAATAGTTACTGCTTGATCACAACAAGTTTTTATTGACAAGTTTTAA

ATATGGGAACCTCTCATAATGTTGCTAGAACTAAGAGTGTTGGTGAGGATGAAAGGAATCATTTTACATAATTTGGTGAG

AAAAGGATGTTTGCTCAGTTTCTAGAAGATGTTGATATGCACAGTTTACTGATAAGATGACCTTGACAGACTATACTGTC

TTTGTTCTTTTAGAATGTTTTAGTTTTGGAGTTGTTGAGTTGCATCACTAATGCATGTTATAATCAGCTCTCCCAAAAAG

CAAACAATTTCTTTTCGTTTCTCACCCAGTGTCTAATACCTGTATTAAAGCCCAACTAAAACATTTACATCAGAAAGTCC

CATATTGTGAGTACACTACTCCCTAACAAAGGTGATTCCATACACTCGAGTTCAAAAGCTCTGATTGAATATGAAATAGT

ATTTATCACTCACTCTACCACAACATTTGTTGGTAAAAAGTGGCAACAATTGAACAATCAAGAATGACAAATACATAAAG

CAGCACACAGAGTTACATTGGTAAAAGAAACATTTTTAATTTCAGCTGCCATATAGAATATAAATATCAAGTTCCTGACC

ATTACAAAAGTACTCCATCCATTAACAAATCAATAAACAGTAACACCAACAAAAATAATTTAATGAACCATTCTTGTAAA

ACTTAAGGGGAATCAAGAAAACATAACATGAATCACCTAGAACAACAAGAGTAGCCCTGCTTTTGTTTCGATCCATCGGT

Figure 8 (Cont.)

ACCATCRTTGACCAGGTTAACTCTGTTGACAGATAATTCTGCTTTATAAGAATCGGAATTCAAAACCTTTCTACTAACAC

TATTATAGATCTCTCGAATCACAATCTCGAAAGCCTTGTTTACGTTTGTTGAATCGAGGGCAGATGTCTCCATGAAGAAC

ATCCCTTCTGATTCTGCCAGGCTTTTGCCTTCTTCTACGCTCACAGCTCTTATGTTCTCCAAGTCACATTTGTTTCCCAC

GAGCATCCTTGCTACCGTTGTATCAGAATGAGCTGCATGTAAATGGTTGTTTCAGTTATAGAACGATTGGGAGTATGAAG

AACATATAGAACACCACCGTAACATGTAATTTGAACACCTAATATACAACGGTATAAATAAAAGTTGGGATTCTCGACAG

CAGAAAGTATCATTCCAAGAAAAAATGTGAATAAATAAGCTCGTGAATGCAAAGTTTAAGTACAGCACCTGCACATATAA

AGAGTCTGTAAACCTTAATATTACTACCTATATTTCCTTCAAAAGTATGTATCTGAATTTTCTCAAGTTGTTATTAGCAA

CGTCATTGTCTCCTTTCATGAGGAAGAAAAATGCTGCACCTTATTAACACTGACTTCGATTTTGATGACATAATCCTCTG

CTCATTTCATCCCGTGATTAAATGAAGCTTCTGGAGTACAAACCTCATTTGTGGTTTTATATGCTGCAAATGTTAACATT

CTATTTATCGCATTTCCCTGGCCCTGGGCTCTTTAATGCCCTTAACTCAAGCTAAAATCTTCTACTTGGGCAAACGGCCT

TGTATCTGGCCCACTCATTTTGATAGATCAAGAGTTAATACTCCTCTATTTTATGGACATTAAGTTCTAAAAGTTTTCAA

CTTTGGAAACAGTGAGCACAAAGTCATTCATTTTCAAGATTCAAATGATATTTGCAAGACAAGAACAGATTTGAATAACA

AAATAAGGTCGTGCAAGTATCACATAGCAGCTCACGGCTCAAAGCAACACATATACATTCCCGTCCAGCCAAAAGTTAGT

TAGCTAAGGGCTTAATAGAGAGACTACCTAAGTTATAAATATGGCACCACTTAACATCAAAAGAATCTCAGAGATTTTTT

ATCAATCCCCGAGACTCCTTAGTCTACCATAATGCCATACGTAGGTAAGCCAGGCAGTTGGTCCTAATTATTTTCACAAT

CAAGCAAATAAAACAGATTCCATATAAGTATGATCTGTTGACAAGTTCATTTAGATTGGCTTTTCGGAGAAAGAAAAGCA

TGACTTGATTTCCAATTCCTAATATACATCCAATTGACAGTCTGTCTAATTCGTTCTTATCATAGGTTCCCAACTGCATC

TAGACAAAATTGAGCATAACAGCTACATTGGCATATATACCGCTTTCTTGGCCATTGCTTCAAGTAACAATGATCCATAA

TCAAGACTCAAGGTTTTTCTAGCTAACATTACCATTTGTTTTTATGCCTGGTAAGTAGTTTTTCACTAAAAAGATTGAAT

TAGACTTGATAGCAACTGTAAAATCTTACTTTATTCAGTCAAAGAGAAAAGTGATAGGAACCAAATCCACAGAAGAAGAA

AAAAAGCAAAGGACAAGATTCAAAAAATATAAATTCAACACATTCATTATTCAATTCTGGAAAAACTCAATTAAAATTAC

CCTTATGGCTTATTCCATCATCCTAAATAGTTAAAGTAGCCAAGACTTTTCGGATCTACAAGATATCTTACATACTTATA

AGTTATAATCAAGAACCAAGAATGTGGAAGTCAAATTCCAGAATCGCCATCATATCATAACACCATCAAATCTCAAAAAC

TGAACTTCATACTACCAACCTCAATATATCTCAAAAAGGTGAGAACCTTTGTATTAAACTTTGATGGGAACTCAACATAT

GCCAAAACCAAGTTGAAAAGTGGGAATTCAACATGAACCAAAACCAAGTTTAAATTTTTTTGTAGCAACAGAGACATATG

AATACAACAATCAGATCTCGACTCACTTGTCAATTTATCCAATAACTAATTATAAACAAAATGAATAATGTAGAAGTCAA

ATCAAAAGAACTACCATTCTATCATAACACCATCAATTCTAAAAAAACTAGACTTTACAGCCAATCCACCAAAAAGGTGA

GAACTTTCTGTGCACAAAGAAAAGATAATGCATAAAGCTTAGATGACAATTCAACATAAACCAAAACCAAGTCTAGAAAA

AGAGAAGAATTTTAGCAACAGATGCCAAATCTAAGAATTACCATTATATCATAGCACAATCAAAATCTCAAGAACTAAAC

TTTATAGCCAATCCACCAAAACCTCACTATATTTCAAAAAGGTGAAAACTTTTTCTTGCACAAAGAAAAAGATATGCATA

AAACTTTGATGGGAATTCAACATAAACCAAAACCAAGCTAAACAAAGAAAAGACTACTAGCAACATAAACAAGAATGTAG

Figure 8 (Cont.)

AAGTCAAATCTAAGAATTACCATTCTATCCTAACACCATCAAATCTAAAAAAAACTAAACTTTACAGCCAATCCACCAAA

AAGGTGAGAAATTTCTATACACAAACCAAAGACAATGCATAAAACTTGGATGGGAATTCAACATAAACCAAAACCAAGCT

AAACAAAAGAATTTTTTCAGCAACATAAACAAGAATGTAGAATTCAAATCTAAGAATTACTATTCCATCATAACATCATC

AAATCTCAAAAGACTAAACTCAAGCCAATCCACCAAAAAAGGTGAGAACTTTCAATGCACAAACCAAAACTAATATAAGA

ATTCAACATAAACCAAAACCAACTTATAAAAAAGAGAACTTTTAGCAAAAAAGATACATACTTTTGAGTTCATCAAGCCA

ACGAGGGATGCTATCAAAAGTTGTCCTTCTTGAAATATCATAAACAACAAGAGCACCAAAAGCACCACGATAATAAGCAG

AAGTCACAGCTCTAAACCTTTCTTGTCCAGCAGTATCCCAAATCTGAGCTTTAACTTCTTTTCCATCAATTTCAAGAGTT

TGGGTCTGAAACTCAACTCCAATAGTTGCTTTTGAATGCAAATTAAACTCATTTCTTGCATAACGTGTAAGCAAATTAGA

TTTCCCAACTGCAGAATCACCAATGATTACAATCTTGAAAAGGTACTCCTCACCCTCATCATCTGAAGAGTCCATTTGGT

GAAAAATTGAAACTTTTTTATGTTTAGAGAGAGAAAGAATTGGAAAATGGTGATCTAGAGAGAGAGGGGGAAAGGAGTGT

TGGGGTTTTGTGCAAAGAAGTAATGGTGGCAGAGCTGGCAAAGATTATACAGAGAATTTGAAAGAAGTGGTCTTGCTGGA

TTTTTATTTTTTGTTATTTTGTTTTTTATTGTTTTTTTAATAAAATAAAATCATAAGTGGGTGTTCTTTTTTAGGTAAAT

AAAAAGGAATATATAATAATTATATAACCTTTTGTTTGAAAAGAAAACAGGCGGTTGAAGACTTGGAGTCTAATAGTTTT

TTTATTAAAAAAATAACTTTTTATGATAACCTTTTGCCTTTTTCCTTCTTTTTATTGGTGTAATCCTTGTGATATATATG

ATTTAACATATTTAAATTATTCAATATAAGAAATTATGTGTTCATAGTTTTTTTAGGTAAGAAATATGTTAACTTTGAGC

TATTTTTAGAAGTACATTATGTACTCACAAATTAAAAAAATTTCGTTTTGACTATAAATTTTAGGAGTATTCACTTTTAT

TTACAAAATACATATCTAAACATATCTTTACATTTCAAACAGTACTATTTTTCAACATAACTTCAAAAGTTTTTTTTTTT

CTTTCAATTTATGGCTAAACGTTAGCAAAGTTACACCACAAGCTTAGTATAATACTTGGGTTATTAAATATGATAGAACA

ATTAATAGTTCTAAAGATTTGAATGAAGAAAAGAGAAAAAAAAATGGCATGTTTCAAGTAATTACAAGTTAAATTATATA

TATTATCACTCTCAAAAATTAAAATTCGAATATATCAATAATTGAGAGATCAAAATTGTTAGTATTGGCTATTTCTTTTT

TTAGGGGAACAATAAAAGTTTCTCACATTTGCATAGAAAAAGACTCCATATGATGTGAGAAAGACTTAACTTCGAATTGC

CAGTGGGGTGGGGGTGGGGTGTTGTACAAGAAGTGATGGCAAAGCTGGCAAAGATAGGTACAGATAATTTTGTTAAGAAG

TGGTGTTGCTGGATTTTATTAATTTTCCTTTTCTAGGATGATTTTATAAATGGAAGAATAATAGTCAATTTGTTCTATTG

TCTTAAGCAGAATATTTTTGCAAGACTAATGGTAAAAGTACACACCATCCTGCTTTTTTTGGATAATTAAACGGTAAATT

GTTTAATTCTTATGTGAATTTGAACATCAATTTCTCTTTATAAAAAAATTCAAGCTAATATAAAGTGCATGAAATTAGTT

CTTGAGTCGGTTATGATTAAAACTCATGGAGGACCACATTGACTCAATAATTGAGAAATGATTGTAAAAAATCACATGGA

CCATGTTTTTCATGGACATCCACTCCCTATAATATGATAATATTGTCATTACATTTTCAATGAATGATCCAAACAAAAAA

ATAAGATATTGTTCAAGAAGTGAATATATTTTTCCACTATGGCTACAAGAATTACCATCAATTTTGAAGAAATAAAGGAT

TTAAATACCACTTCATCCAACACACTACATTTGTTGAAAGGAAAAAAAGGACTATTAAGAGAACTTATGTTGCTCGAACT

ATTAAAAATATCAACGGGTGCAAGTCAGATCTTCCATGTGCATTTTTTAAAGAAGCTTATACGAGATACGACGGTCTTTT

TGGATAGTCCTGACATGAAAATTGAATCTTGATCCAAACAAAAGAGACAAGATATAATTCAAGAATTCAACATAAATTAC

Figure 8 (Cont.)

AACCAATACAATCTTGAACAAATGAAGGAAATGAACAACTAATATAACTTCAATCAACACACATCACATTTCAAATGAAA

ACAAAGACTAAAACAACTTGAAATCATAACATTTATAAGAAAACTAATGAATATTGTACTAGTTTATAGGCTAATTTTGA

TGAAGCATATAAGATGTAACTCTGTTTACTCATTTAGAACACCATTGCCTTGACCTTTCAAATCCATTCTTTCCAAGTTG

ATAATCTTGATAAGCCTGCATAATCTCACTCTTAGTGTTCATAACAAATGGACCATACTGCACGACAGGCTCGTTAATCG

GTTGCCCTCCTATCAGAACAAACCTCAATGGTTTTGAAGATTTGTTCCACACACTTAGGCCTTCACCAGGGCCTAAAACC

AAGCAATGGTGAGCTGGTGTAGTAGTTGAATCCGAAGAACCAAACGCCTCTTCTCCTTCAACTATGTAGATGAAGGCATT

CCAGGTCTCGGGGATCTGTTGGTGATGGTCAGAACCTGGTTTTAGGGTGAAGTCAAGGTACATTGTAGGCGTTCGTGTGA

AAACTTGGGATTTTATGCCCATGGATTCCCCTGCTAAAATAGTAACCGAAACGCCATCTTTTTCCACTTTTGGTATATCT

TGGTGTAGCAATTCTTGATACCTTGGCTCAATCCTGCATCATGGACGGATAAAAGGAGGGAAGTTACAAAAACGGGGCAA

TGAAGGCTCGTGAAGTAGACAACAAGCAGCAAGACAAGGATCATTAGTTGTTGTGTCTATTGCATGGTGTAGCCTCACAC

ATTGAAGGCTGGTTAGTTGAACACCCTTTGTCGACTCGTAGAGTCAAACCATACTTTAATACATATATATTAGATCTTAA

ACGCCTAAATTTTATGAATTTTGATCAAAGTACATGTAACAGGAATATGTTCTAAAATGAAATAGATTGTTCAAACACTA

TATTTTTTTAAGCCAAAGTCAAGATTGAATCAATGTAACTTACATTTTGTCCTTGGAAGATAGATTTATCCAAAGTTGCA

ACCCCTTATGAGTACCTGGTCCAGCAGGCATTTCTGAATGAACTATACCTCTTCCTGCTGTCATCCACTGCATTAAACCA

AATGGAAAATCATAAACACACTTAAATTTCATAAATTCGATATCCGGTCGCATCATGAAGTCCACTTTAGGAGGTAACAC

ACTCCTTTTCAAATGTGACTACATTTACAAGCCTTGAACTCGAGACCTCTAATTAAGGACGAAATAATACTTACTATTCT

ACCACCATGAATTTTGATGGTAAACATTAATTGGTTACATTAGTAAAATGAGTAGCTAACAATCTATCACATGTTATATA

ACGCTGATACTATTAAAAATCTTTACACTGTCAGTGCACATAACTTAAATACTTAAGAGGTATATATGGTGGTGTTGTTA

GCAAACACATTACCTGCACATCACCAGTCCTGATTGTACCCTTGCGACCAGCAAAATCTTGATGAGTAAAAGCTCCCTAA

AATTAAACACCACAAAATTACATTAGAATTTTCAATCTCCATAATCCATACACCAACACAGAGTTTAACTTATATACATC

ACCAATACCTGATAGTATATATCAATTTTTTTTGTCGATGTACAAAAGTTAAACTTTCTACCCAAAAAAAGGAAAATAAA

ATGAATTTTTACCTGCAACATATAAGTGACGGTCTCAAAACCTCTGTGTGGATGGTCAGGAAATCCAGCAGGTGGTGAAA

CTGCAAGAAGCCAAAAATAACATAGCTTTCTAATTAGTCAAAAATAAAAATAAAATTCACAAAATAATATACTAAAAGAA

TAAAATAAAAGAAAAAATTACCATTAAACTCATCTAACATGAGGAATGGATCAAGATTCTGCAATTCAGGCCTGATCAAA

TTCCAAATTTCATAACAAATATATATAAAAAAAAAACAATCAGTATTCGATTCGTATTGCTGACAAAAGTATGATATTTA

ATTGGAGAAGAGTAAAAACGTCGTTAGAGATTTCTCGATTATCAAAACATAAAAAATCAAGAAAAAGGAAGGAAGTACCC

AAAAATAATTACCTTCCAATGCTTCTTCTAACAATAGCACCATCACCTTCATTTTGAGCTCTAGCCAAAACTTTCTTAAC

AACCAATCTTGGTCTACTAAAAATAGAGGACATAGACATTTTGATGTTTTTAATGTTTGTTTCAGCTAAATTTATTTTTT

GTTTGTTGTGTTTTCTTTTGATTGTGCTAATGTGGCTATTTATAGGCAATTTATTCTTGAGGATTCATATTCATTGAATA

TTGATGACGAAATATATTACATATTATTTTCGTGTGTTGAATAGAAGTTTCAAGTGGGGCCTACTTAATTTTTTTTTTTG

ATGATTTCATGCTGATGTTATTATGACGTGGTTTCTTATTAAAAAAATTATTTGGATAAAAAATGAGGAATATACTATCG

Figure 8 (Cont.)

TATGAATTTGTAGAGTTAATTGACTAAAAAGAAAAATAAGTTAAAAGAATAAATAAGATAAATACTAGAATTATTAGATA

TTAAAGAATTCAAAATAATATTAAATATGCATGAATTATAGATTGAATAACTAAAATGGAAAATAAGTTAAAAGAATAAA

TAAGATACTAGAATTATTGGATATTAAAGAGTTCAAAGAATACTAAAACTATCATACTTAGGATTTGAACTTTTGACGTA

AAATAATCTTTTGACTCATTTTGTTGTAATACTAAAAGTATCTTTTGATATAAAAAAAGATTCTACCATTTATATGTAAT

CGAAGCATATATTATGGAGTAGTTTTTTTAATGAGGAATTCAATAATATATACCTAGTTCCTCTAATTTCATGAGTTAAC

TCTTAAATATTTAAGGATTCAAATTAATACTAAAAATGTCATACTTATGATTTGAAGTTTTGACGTAAAAATCTCATAAA

AGGTAGAAGGTAAATTTTAAGTACCATTTATACGTAACAAAATGAAACTTCTTTTGGCAAGAAATTCAATTATATATCTT

GCCAACTACCTTTCCTTTGTGATTTCACAAGTTACCAATAAAAATTGTGATTGAATCAATAGAATTTCCTCATTTTAAAA

AGTTTTAAATTTAAAGTCAATATATATATAAAAGAATTACATTAAAAATTAAATTGTTTTCCTTAAATAACTTTACGTGA

TATAAATTCAAAAATTAATTAAATAAAATTTTATATAAATATGAAACATTAGGTGGAGGAGGATGTTACTTTTGAATTGA

ATGTTTATACATAATTATTTAAGAAAGAAACATCTAGCAACTTCAAAAATCAAAAGAGAAACAATGTTTGGTAGTTGTCG

GCATGTAAACTTTGTTTATTTTTGCTGCCTTTGATTCGTTGACCGTTGACGTGACCAATATCTATTCAAAAATTATAAAA

ATAATAATATTATAAATTTTTATTTTTTTATATATGATAAAAAAATATACATCGTAAAACGTTAATAAAAGTTTTTATCA

TTTGTCTCTAAAATAGAAAACCATAACAACTAAAAGAAACGAAAAAATAATATTGAATAATATACAATTTATTTATTTTT

ATTGATGTACAAAAATTAAAATGTTCACTGATCCAAAAAAGATTCAAAAAAAATTGTATTTGATTTAGTAATAATAAGAC

AAATCATTTGTTCATAAATACTTTATACTCATCCCGTGTTAGAAGCAAAACTTAATTCATGAACTTAAGAATCACAATTT

ATGTTTTACATATTATTTTCATTGTATTTGATTTACAAGATATTTTATAACTTTTATTTTATAGATAAAAATTTATTAAA

AATTTTAGAACAACTTATGTCCGTGGACAATATTTAACACCATGTCCTTGTTCTAATTTATAATTCTCTTTCAGTTTGCA

AATCTTAACTTTAACTAAATTTAAATTTTTAATCGATAGAAAATACTAGTCATAAAAGGATAAAAATATCTTTACCCATA

CATATAGATGTATAATGAAGATAAGTGTTAAAAGAGATTTTTTGATTGAAATAATTCATTATTTAATATTTTATTGTAAA

AAAAGTCACTAAAAATAAGTACGAAAATAACTTTAATAAAAACAATTTGAAGAAAATTTTCATTATTTGTTAACCTTCAT

GCCCTATCAAACAATACAAAAAGACTATGTTTTCTTTTAATTTTTCATTTTTTTACACATCTAATATAAACATCCTTTCA

ATAGCGTATAGACATTATTTCATTCTTCAACAAATAAACACTATCAACTAACAAATAAACGTATAAAACGTTACCAGTAA

TAACAAATTCAAAACTCATTACTCTCATCTCGACTTTAATGTAAGTTAAATAAATTTAAGATCAGACTCTAAAACCGTTA

CAATTCCAAAAAAAACTAAAAAATGATAAAATATCCACAAAATACTTATGGTGGGTCCCAACTTAAAAACTTTTAATTAC

TTATGTCCCACTAGCCTTTGACTTAAAAAAATCTCAAATAATTGAATCAACAATCCCAAAAAAATCCCAAAAAATTCTCT

AAACCAAATATTTCAATGGCGAAAAAAGCAGTGTTAATTGGAATCAATTATCCAGGAACAAAAGCAGAACTTAGAGGTTG

TATTAACGATGTTAATCGAATGTACAATTGTTTACTTAATCGTTTCGGATTTGCTGAGGAAGACATTACTGTTCTTATAG

ATACTGATGATTCTTACACACAACCAACAGGACGGAATATACGTAAAGCTTTATCGGATCTTGTTGGATCTGCTGAATCA

GGGGATTGTTTGTTTGTGCATTATAGTGGACATGGGACTAGGTTACCTGCTGAAACGGGTGAAGAAGATGATACTGGTTT

TGACGAGTGTATTGTTCCTTGTGATATGAATCTTATTACAGGTAATTCTACATTTTTTTTATTTAAAGCACTTTTTTTTA

Figure 8 (Cont.)

AGGATTTGGAGTAGGGGAAATGGGGCGGGGATTATGAAGTGGGGAATTGGAAATTCAGGTAGCTGGTGAGCTACTGAGAT

TGTACTTGATCTATATGATGGGTTTGTTCCAAGATTGTTTTTTTTTCTTTGTGTTTGTTGAATTTGTTGGGGAGTTAGT

TGGTTTGATCTAAATGATGGGTTTGTTCCAAAAATTGTTTTTTTTTGTGTGGTATGCATTTTAATGCAGCTATTTGAGCA

TTTCTTTGATCAAAATTAGGAATTGAGTAGTCAGGTAGCTAATCAACTGAGCTAGTAAGAGTGTACTTGATCTAAATCAT

GAGTTTGTTCCCAAAAAAATGTTGTTTTTTTTTGTGTGTGTGTTGAATTTATTGGGGGTTAAGTTGTATTGCTTTGATCT

AAATCATGGGTTTGTTCCAAAATTTGGTTTTTTGTGTTGTGGGTTGAATTTTATAGGTAGTTACTTGTATTGCTTTGATC

TAAATCATGGATTTGCTCCAAGATTTGCTTTTTTGGTGTTCTGTGTTGAGTACTACTTGTATGCTTTGGTCTATAGATCA

TGGGTGTCTTCCAAAATTTGTTTTTTTTTTTGTGTTGTGTCATGTGTGTGTGATATGAGTTTTATTGCAGGTACTTCTAT

TGCTTTGATCTAAATTATGGATTTGCTCCAAATTTTGCTTTTTGTTTGTTTTGGTTTGGGGGTTGGGGGGTAGAGTTGAT

GTGGTAAGGGATCTAGGAGATTGAGATCTTGAAATGGTTTTCTTAAAAAATGATCTTGAAAGGTTGAGTTGATCTGTTTT

GATGATAATTCAGGTGGATTGAAGATATAAGGAGATTTGTAAAACGAGGAAATGGGATTTTAGAAATGAGAATTTGGGTT

TCTAGAGTAATTCAAATAGTTGAATGGGGGACGAGGAACAGTTGGAAAAAAAGAGGGAGTATAGTTTACAGCATTGTGAT

ATGAATCTCATTTACAGGAACTTAACTATTTCCTTGAGCTTAATCATGGGTTGTTCCAAAATTTGTTTTTTTTCTTCGTG

TGTGTGATTTGTAGATTGGTATGAGATTGAGATCATCATATAGAATATTGTGTAAAAAAGGATCTTGAAAGTGCTTAGTT

GATCTGTTTTGATGATTATTGAGACGGATCCCGAGTTTTAGGGAGATTTGTGAAATGGGGAACCAGGATTTAGAAATGAG

AATTTGGAACCAGAGCTATTAAAATTGTTGAATGGGAGATCAGAAAAAGTTGGCAAAAAAGAGGAGAATAGTCATGATCC

CACAAGTGGGGTCTTGAAAGGGTAGGATGTACGCAAACCTTACCCTTGATTTCCGACACTCGGCTATAGAATTTATTACC

TCTTGGTTTTATAATATTGGAAAAGTAACAGGCAATTTAATATTGAACTGTTGGACGTGTTGTTTCATCCTTGATCAGAT

GATGATTTTAGAGAGCTCGTTGACAAAGTTCCTGAAGGTTGCCGGATCACAATTGTATCTGACTCATGCCACAGTGGAGG

CCTCATTGACAAAGCTAAAGAGCAGATAGGGGAGAGCCACAAGCAAGGTGATGACGATGAAGGCCATGGATCTGGTTTTG

GATTCAAGAATTTCTTACGTCGAAATGTTGAAGATGCATTTGAATCCCGGGGTATCCACATTCCACGTCGCCACCATCGC

CGTGAGGAAGAAGAGGAGAACTTTGCTGAGAGTAGTGTGATTGAGACGGAAGACGGTGATCAAGTTCATGTGAAGAGCAA

GTCCTTACCTCTTTCCACTCTCATCGAGATACTTAAGCAGAAAACCGGTAAGGATGACATTGATGTTGGGAAACTTAGGC

CAACACTCTTTGACGTCTTTGGTGAAGATGCAAGTCCTAAGGTGAAGAAGTTCATGAAGGTCATTTTTAACAAGCTACAA

AAGAATAACGAGCAGGGTGGAGGTGGTGGGTTCATGGGTATGGTTGGTAACTTGGCTCAAGAGTTTCTGAAACAGAAACT

TGATGAAAATGATGAGAGCTATGCGAAACCGGCCATGGAAACACACGTTGAAGGTAAGCAGGAAGTTTATGCCGGTTCAG

GTAATAGAGGTCTTCCAGACAGTGGCATTCTCGTCAGTGGGTGCCAAACAGACCAAACATCTGCAGATGCCACCCCTGCA

GGCGGAGATTCTTATGGTGCTCTAAGCAACGCAATTCAGGAAATCCTAGCTGAATCAGATGGTCCAGTCACCAATGAGGA

ACTTGTTAGCAAGGCTAGGAAAAAGATGCAGAAACAAGGCTTCACACAACGTCCAGGCCTCTACTGCGATGATCATCACG

TTGATGCTCCTTTTGTTTGTTGATTCTGCTGTGCTATGCCTTCTCGAGTAGCTGTTGAAAATACGACTGTGAAGTTAACG

AGGTGTTATATAACTACATCCTTTTGTGTATTTGTGTGATTGTTTGTGCTTATGTTGGAGTAGCTCTTCTACTCTGGTGT

Figure 8 (Cont.)

TGCAGAAGAACCATTCTCCATCATGTGAATGTGTATTTGGCTCTGTTTTTTTTTCCTTTTAAATTTGGTCAGAGAATAAG

GTATTAAAGAACCACAGTTTTCGGTATTGTTTTGGATATTTGAAAGTTTAATCTGGAGAACTTGTCTTGTATACTGAATA

TACTGAATGTGTTATAATTTAATGCAACTGAATGTATAAATTTCTTATCATGTGCCATCATAAGAATTGACCTTTGTCTT

GTGAAACTAGGGAACAGAACGAAAGGAGGAGCTGAATTTCAAAATTTTGGTTTACATAAGAAAATATTCACCTGAATTGC

ACTTTCATATTACATCTTGGATATATATAGTAATCAAGTACAACAAATTCTTGCACGCATAACACAATATCGCAATGCAT

GTAAACAATATTACTCGCGCTAGAACTCAGATATGGTTATTTAAATTTCAAAGAGATTTCACTCATTCGATAACAGTCAT

TCTTCAAATTTTACTTGTACAAGTTTCAAAGATATATATCAATAACTCCAGTTGTGTCCATGACTCCATTCCAAAGCTTT

ATCCACTTGGAAAAGTAGAAGTACCAAACTAAAGCAACAAAATTAGCTAAGCCGCGATCTACTTATGTTCCTTCTTTGGT

TCAATATCACTTGGATTTGGGACTGGTTGAATTCTTTGGTAAGGTTTCCTTGTCAATGTTTCACCCTTCAGAGCTGCAAC

ATATCTGTCATTTGTGTTCTCCTTTCTCTGCAGTTCGCCAAGGTACTCAGCCAACCTCTCTTTATTAACTTTACCCATCA

TCTGTTACAAAAATCAAAACAATGTATGTTTAGGAATTCAACAATCGTAAGTCAAAGTACTAAGCTATAAAAGAAAGCCA

ATGAAACCAGAAGAAACCACTGTGAGTCCATTTTTTTATCTACTGTAAAGCTTTATCTACTTAGCTCTTCATAAAAAAA

AGCAAAGTCGATGTTCTTTCAAACAGCAAATGACTGAACAAGATAGAGAAGTGAACATTATAGCTATTTGTAGTTCCCAT

AGACAGCAGGTGGCCGATTTCATCAAAGGTGTAAACCAAAGTTACGTGGAAGTGCTCACAACTCTGTTTTAGTTTTTAAC

AAAGACAAGACATAAATGGGTATATTCAAATGCTGTGTTCATCTTCACCTACAATATATCATTCAAAACCAAACTAGAAA

AAGAGAAGGGCCATTTGTAATATGAAAGAAAAGGGTCTGAAATTAAGCTTTATTCTCACTAAAATAGTCCTGCTCGGCAG

TCAAGCCACTTCACTCAATAGAGGTTCTTTGGGGACTTAAAGAACTTAGTTGTCCTTCCTTTCCAATTTACAAGTTCCAA

AAATACAAGCTGGAATTGTTATCCTTATCTATCTATTTGCCTTCTCAACAATTCTCTGCTCTTGCCAACATTCCGATGCT

CCATTTACTCACCCTGGCATGGTCCAAGCACCCAAAGGCAAGCCAAGGTAGATAGTGATGGATTCTTCCACCTTACGGCC

CAAAATGCTGGTAGAATCTGTACGTTAAAAGGTAATAACATTCGAGTCGTTTACAGCTTAACATGCACAAGTCAATATAT

TTAACCCATGCTCTCAAGTAGCTTTAGCAAGAAAGGCCAGCTAACATGGTCATATGCCTTGAAGTCTAATTTGCACATTG

CCCCAGCATCAGTAAACTTTATCTTGGACTCCAACTCTCTAAGCTCATATTAGCTACTAGCACTCCCACAAAGAAAAAGG

ATTTTGTGATTTAGATACCAATTTGTCTATTATTGCCCTCAACCTTCCATTGAGGATTTTGGCAATAATCTTGTAACTAT

TGCCAAATAGAATAGAGGTCAAAAGACTCTAATCAACACCCTTTCCTCTTCAGGGATTATAGCAATAAAAATCACATTTA

GGCTTCTATCTAGTTTCTCCACCTTAAGAAAATACTTGAAGCTGGTCTTTGAATCTTCCTTAATGATTGGTCAAGAAAAA

AATGATAGGTCAACATATTCAACAAAAAGCCCTTGGTGAAACTATTGAATTCCAGAGACTTCGTTTCGTACACTGCTTAG

ATAGCAAGCCATACATTTTCTCAGTGAAAGGTCTTTCAACTCAGTCCTCTTCTGCTCCACTTATAATGTATTCCCCAGTT

CCTCAACATACCATTCATGCCTTCACTTCTTTGTCTCTCTGAACAAATTCTTGTAGAATTTCAGGATCAACATTTTAATA

TTTGTTTTGACTACAACTTAGAAAATACACCTGACAATCTAATATCTTAAACTCCCTGATCTGTCATATGGTGTCTCATA

AAACATACAGAGGAACCTATCAATAAATAAATAAATATAGAGGAGGTGTTCCAACCAAATTCTCAGAAGTAATTCAATTC

CTTTACACTCTTCGTTCTCTATCTACCAAGACTAGCTATCGATTGCTATTTTCTATAAGTTAAATATCAATCACTTTATC

Figure 8 (Cont.)

TACACTAAAAAATAAAGCTCCAAACATCATTTTCTTTTTAAAGGTAACAAGTACATCAAACAACAAGAAACATTATCAAA

TGATACTGCCAGGTTACCTTTCATTTTCATAGATCAAAAAGCACAATCATCACAGCAGAATGTACAATAGACATGAGGTG

CATACTGATCTCGCCATATGAAAGTTTGCTCCAGATATACCATTACTATTAACAGAGCATCTTTCAAAGGCCTTTGCTTA

GCTAACTGTTATGAAAGATGTTCTGGTAATAACAGTCAGCTAGGCAAAGGCGAAAGGGAGTACAATACAGAATAAGAACC

AACAACACAAATCAATATGCGTACAATCATAACAGCAGAAGCTACAACACATATGAATCAATAAGCATCTGGTAAAAACA

ATTCTACTAGGTGAGGGGACTCTAAAACACATTAGAAAATGATAACAACAAGGCAATTCTTGGTATAATCATCACAGCAG

AATGTACAACACATGTGAAACAGATACACTCATCCTACCAGATTGAAGATGCTCCTGCAATAACACTCAGCTAAGTAGCA

GCCAAAGGAAGTCAAAGCAAAGAATGATTTTTCTTTCCTTCGAGGCTCCAGGGTAAAGATACATTTTTTACGAAAAATTG

TTAAAAAAATTCAGTTTATGTTAGCAAAAACCATGTTCCCTTCTTTTTCTGATATTTTTATAATGGATTAGTTTAATGAA

TAACAACGAATCAACTGATTGATGGTCTATCTCTTTTAGACTATAGTTAATGGATATTCTTAAATCATAATTGTAATTAT

ATAGACTATGATTCCATACCAGAAATTTTTTAAACAATACACAATAAGAACCAATAATACCAAGTCAATTTACGTATAAT

CATAACTGTAGAAGCTACATCACATACGAATCAGTTATTCATCTGGTAATAACAATACTACTAGAAAAGAAGACTCTAAT

ACACATTAGGAAATATTAATGACAGCAGAATTTCCATCCAATCATTAAACCACAATATACAACACATATAAAGCAGATAC

TCATCCGTCCATAACAGTTAGCTAGGCAAAAACAAAGGCCAAACGGAGTACAACACACAATAAGCCAAGTAAATTTACAT

ACAACCAAAACTGCAGAAGCTACAACACTTATGAATCAGATACTCATCTGGTAATAACAATACTACTTGGTGAAGGGACT

CTATGTTAATATCAAAGCAATTTCACGTAGCAGAAGCTACAATACTTATGAATCAGATACTTATTTGGCAATTACAATAC

TATTAGGCGATTGATAATCCTAAGCAATTTCCCGTATAAAACAGCAGAAGGTACAACATACATGAGCACAAACTGATCTA

GTTTTAGCAATATGAGTATTCGAAGGGGAAGTGAACATACTAGGGTTTCGGGGCGAGCGTTCTTCCGGAGTTTGGCTTCA

AGTTCAGGACTGCGAGTATTGGTGGCTGACATAACGCAGAAACCAATAATCCCCGGAATGACGCCGCAAACGGTGGCGAA

TCCGATGAAGAACGGCTTCGATTCCTTCGTTCTCCTCACTAACCACCGCCATGTTCCACTCTTCTCCCACAGAATCGACA

TCGACTTTTCTGATGATTCTCTCAACACTTTTCTTCTGCTATTTTCTAGAGTAGAACAGTGCAAGGGAGAAATAAAAATG

ACAAAAATGGCTCCTTATATTTGCGGAACATTCAAAATAGTCCTTAAGTATGAATTGATTGACAAAAGTTAAGATCCAAG

TATATTTAGTAATTTATATTTTATATTTATAAATAAATTTGAAGGAAATAATGCAAAAAAGAAAGATTTTTGTAATTTTA

AACATCAAGAAATCTTTAAAAAAACAATAAAAAGAACAAACTATATAGAGTAAAAAATATCAAAAATTGCACTTTAAAAA

AGGTATATAATTTTGATTTCGATCTATCTTAAGTGGACTAGAATTGATATCTTAATACCGATTCTTTGGTCCAAAGCGGA

CAGCTCAGGAGTGAAATGATTGTGTGTATTAGTTGAACCACGAACCAACTACCCATAGAAGAAAATTATGTTCTAAAAAG

GATGGtTTTTTTTTAATAAAAAGAGAATTCTTTGAACTAGTTTGCCTACAATTTTACACTCATTTGTTAGTACATTTCAT

TGTTAGTGAATCTCCTATATGGCTTTATACCAAAGGAAACAGAGAAGAATCTGTCCAAACTTTGGAAAATATTGCATCTC

CAGCAACAAGAAGCAGTAAATTTAACCTTGAGCTTTTTCGGATCGTTCATCGAATTAGAAAATCAAGAACTACTCAACAA

CAACAACAACATGGTTGATGTGTATTGAGCTATCAAGATGTTAATGGAGAGAAATTGGTCAAAAGTATAAAGCTGCATAA

AAACAAGAAATCAGTGACAGACCAACTGATATATATTTGTCTCCAATCATACATAAAAAGAGTTTATCAATGAAAACAAA

Figure 8 (Cont.)

CATAGAAAATAGTAGTAGTGTTACAATAAAAGAGAAATGGGCTAGACTTCAGTATGAGCATGGCTGCAACAATTAGCTAT

TAAAACCTCACTAATCTGACTATTCTTTGACGAGGTGTATACGATTACATCCTTCAATCTCTTCGATCTCTTCCTTAATT

CTCACAGCTGAATCCTCCAGAGATTCTTTCCAGGACCCAATCAATTTAATCTGTTTCAATGATGGATTATCAGCAAAGCT

AAGTGGGATCTCCTCTAGGTCACCACACTTTTTTATAACAAGTGTTTCAAGCAAGGGAAATGATTCCTCCGAGGCATCCC

ACCTTGAGATACCTAACTGCACCAATTTCAACAACTTAAGTTTATGAAACCTGATATCTCCAAGGCACCACTCTTCTGAT

TGAGGAAAACACACGTCCTGTAATTGGAGATACTCCAGGCTTGGTAGTTCCGCAATGAAGGAAATAGCACTTTCAATATG

AATTCCTTTAAGTACCAGCTTGTTTAAATTTGAAGGCACCTGTAACCCGGATAGAATGCGGGGATGCACAAAGGAAAGTT

GAAGTTCTTGAAGCTGGGTAAGATTCTCCAATTTGGGACAAAAAGGCTCTGCAGAATCTTCATCATCCTCAAGTGTGATT

TGAAGTTGTTGAAGATTAGGACACCTCTTTGATAACACATCCAGACTATCAATCGGAAATCCAACAATTTTCTTTAATAT

CCTCAAATTTTCTAATTTAGAGGATCCTTCAAAGAGCCCCTGCTTATCAAAAACTGCCCAACCAAAATGAGCATGCCTTA

ATTTTTCCATTTCCAAAAAAGACACTGGTAACCGTACACCATAAGGAAAATTCCTCACAATTAAAGTTTCTATATGGGGC

AGATGTGTTCCTGGATCAAAATAGAATTTATCTGCCCAAACTGCGAGGTACTTCAGCTGATTTAGTGGTTTGAATGTAGC

AAACGACAAAAACTCCACAGTATAAGAAATCAAATCCAAGACTTTAAGAAGTCGCAATTCAGTAATCTGACAGAAGGGAA

TCACATCAATAGATTCTCCACCATTAGCCGTTATCAGAGACCTCAAGTGTTGGTGGAAAGGCTTCTGTGTTTTGGAAACC

AGAGATGCAAACTTGGAAAGCTCTTCACTGAAACTGAAGCTCACTCGACTTCCCTTCCAATCCAACGGTTGAAACTGGAT

ATATTGACCCTTCACTGCAAGCATAAACTTTTCTTCTCTACTCTTCTTCAAGCAAAAGTGATGCACAACATCATGAACCT

GGCAGCATTTGACTTTACCATTATAACCTTTCTTTGAAACAATTACCACGTTACTGCTAATGAGATCCATCAAGTAACCT

TCAGCTTCCTCTTCCATTAATCTCCCAGATTCAGTGTTCTCCACGAATCCTTCAGCAATCCATAAACTTATCAATTTAGA

TGCTGGAATTCTTGCGTCCTCCGAAAACATCCCCATATAAAGAAGACAAGGCTTTAAACAATCGGGTAAGTTATCAAAAC

TCAACTGCATAGTCGCCAGACTATATTCTTCGAACTCACTGTCAAGATAGTCAAATAAAGCATCTTTCACCTCATTCCAC

CAAGATTCTTCCATTTTCCTTTTTTTGATTATTCCAGCTACCAAGACAACCACTAGGGGGAGTCCTTTGCATTTTTCTGC

AACTGCTTGACTCACATATTGTAGTTCAGGCGGGCAATCTTCCTTTTGAAACACTTTTTTCTGCAACAATTGGCAACTCT

CTTCTGTTGTGAGGAATGGAAGAGAATAAGGATCAGTATGGTACTTGACTTGCTTACCCACTTCTTCAAGTCGAGTTGTT

ACGACTATTCTGCTTCTCATTCCAACATCTGGAAAAGAAAGCCTTAAGTCATCCCATGCCATACAATCCCACATATCATC

CAATACAATGAGATATCTCTTTCCCATTAATTTTCTCCTCAACATGTCGGCAAGAACGTCAACCGTATCTTCCTTGTGTT

TGGAACCTGTAACTTGACTAAAAATATCTTGTAATAGCTCTCTCCGATTATATGTTTGAGAAATGATGCACCATGCTCGA

ACATCAAAGCGAGAAACAATGATGTCATTATTGTACAGCTTTCTAGCAATTGTCGTTTTCCCTTGTCCCCCCATGCCTAC

AATTGGGACGACGTCTAGCTCATTTGTACCTCTAATCAGATAATCAATTAGTTCTTCTGCTTTATTCTCAAAACCGACTA

CCTCCTCATCAGTCACAGGATTGCTATGTCGAGCTGGCAGATGTTTAAATGGAGCAGCCACGTAGTGAGGATTAAAAGGA

ATGTCCGCTGACCACATCTCAGTCACCTCTGCATTAATTTGCTTGATCTCTTTTAAAATTGTAGGAAGTGAGCAAAAAAT

ATGCAAAAAAAGCATTATACTGAGCAAGAATAGAATCAACGGCAACCTCAGCCTCATATGCCAAATTGATGGTACGTCTCT

Figure 8 (Cont.)

GAAGATCTTTAGGAATTTTATGTTCGTGGTGCACGATATCTCTGAAAATGGATGATAGCTCCTTCTCTAAAATGGATGTA

AGAGATGATAACTCTTTCTCCAAATTCCCTAAAAGAGGTTTCATCAAGAAATCTAAACCAGACTTAGATTTCGACATCTC

ATTCAGTTTCTTTAAAAGAGAATCCAGAAAGCTCAATCCACCAAAGGTGGGGAATTGAGATGGAGTAAATTTTAAGGATT

TGTAGTACGTCTCAACTTGTGCCTTCAGATCTTTAGTCTTCTCCAATATCTGTATCGAGCAAAGACTTATTTTGCTAGTG

TCATCTTTGTTTATAGATCTAGGAACAAGCTTTTGAATTACATATAGAACATCACCCGCTATAGCTCCAACCTTTAACAA

GACCTCATTCAACCAGTTACCATTAATAACGTGATTTGACACATCAGCATCAAGGAAAACCAACAAGAATTCTATTGCCA

CATCAATATTTTGAGCAGAGATATTATTAGGAAAGTTCTCGAGTTTTTTGTTTCTGAGATACATCAACAGATTGCAGAGA

TGATGTGAAAATTCTTTTGGTAATTTCTTGTCCTTAAAAGTTTTTGATTGAGTAAACTTTGAAGCCATTAGTTCACCATG

AAAAATCTTCTTCATTTCCAACTCCGCAAACACAATCAATGATAATAGATAAGGAGGTTTACTAAAGATGTCATTTTCTT

CATTAACTTCACGTTCAGTAACATAATCTAATACGGCCAAACAATATTGTCTTACATTGTTAGTCATGAACTGAATTCGA

GTCTCCAAACATTCCAGCTTCTCATAGTCGACATAACCATTTATCTCTGTGGCATATATGTATTTCAAAAATCTCATTTT

CTTTTGAACAATTTTCAGTTCCTTTATAGATCGATGTATTGCAAGTTTTTTTTGGAATGGCAGGACCTACCCTTTTGCA

AGAACATCATCAGTACATCATTTAGAATTTTTTCCAGACAATCCATATATTTCGACAGATCAAAATCATTCAACTCATAA

TTGTAACTTAAACTGGTATTACCTTGAAAGAATTCCAACAAATGTGATTCTAGCCTTTCCAGATTAAGGTTAGTTTTACA

TTCATCTGGAATCCTATGCAATACCCGGTGAAGTATTTCCCCAGTCAATTTGGCACTCTTTGTGAGTTCCACCAAGGAAT

CAGGCAAAAGAACATCATGATACTTTATAAAGGTTCTAAAAACTCTTAGCACCATTTCAAGTTCCTTAATTCGCAATATC

TCGAACCAATCCAGATTACCTCCACTCTTGATCCTTCTCAGGTGGTCTAACATTTCCTCAATTTCATTTTCAGCCATTTC

TGTAGAAAAATTCCTGCAAGTTCACCAACTTTTGGAATTAGGTTCTTGAAGCCATCTTAATGCTTTTGAAAAGTTATAAA

TATTTACAATTTTACATCTTATTTACCCTTTTCGTATTGTCATTTAACTAACAATTATTATCGCATAAAATCGTCTTTTT tCTTGTTGTCATTTATGAGATAGTAACTATTAGTTGAGTGGACCATTTGAGAAATCAACTCTCTAATTATGTATCTATGG

GAAAAAGATGACTTACCGTTAGTTAACAAGTATCTTCAATTTCTGATCCAATCATAAAAGGGAGCAATAGAGAAAAACAA

ACATTATAAGGTAAACCAGAGAGTAATAATTCTCAGATTTGGATTCCAACAAAGATATATTTCCAAGTTTACATAATAGG

TGAAACAAGAAAAAATTTATTGAAATAAAATGGATGAAGGTTTGAAGGAAGAAGGAAGAGTCTTCTTCTCTCTCTATAAT

ATTTCTTATACCTAACAAGAGATGAATTAAGTCGGTAGCTGTAAAGTGACTCAATAATACACCCATATTATTTGTCTTTT

TCTTTAGGGGTTGTTTGGTTGGAGCAAGTTATTTCGGGATTAATTATCGCGAAATAAGTTACTTGATCATGTATATGTGA

TCATAATTTATATATTCCATCACTATGATATGGGATACATAATCGGAGGACTACCAAATATGGCTCCAACCAAACACAAG

ATAAAATAATTCTGCATTTTATCCCAAAATTATTATATCTCATACTTCACACCAAATGACTCTTTAGGAAAATCCCCCAA

AATTTTATTTGGTTTGGCAGTTTCATAGTTAAATTATGCACTTATATGATATTTGCTTAGCATATAATTAAGGAATTTTA

TGGTTGGGTATTGGGTCGGACATGAAGTTATATTTTTTCTAATAAATATGAAAATGCACAAGTTGTGAAAACTTTGAAAT

TCAATTCTTATGCAATTTTACCAAATGAGTAAATCATTTCGTTAACAAGATATCATAATATCTAAAGCATCGCATCGATG

AATTATATATCTTTATGTTTCTTTTAACTTTCAAATGTACATAAACTTATAAAGATCCACTAGTCAACAATAGTAGTAAT

Figure 8 (Cont.)

TAGTAATTCTTTCACATGATACGACGGACAATTTATTCACGTCGAACATGAGTTTATTTTTGTAAAACTGAAAATAATGA

TTTGTTCTTTTTTACAAAATATAAACTTATGAATAAGTTTTTATATTTTTTTtaAAAAAACATAATTCAAAAAAGGATAAA

TCATATGTCATAAATCAAACAAGGATAAAAAAGGAGTGGTGATAATTCTTCCATAGATCTTGTGAATGGAGTCTGTTCTC

AGAACAGGGCCAATCATAATACAAAAGATTGATTTTTTTGGTTCTTAAGGGTCAAATGCCCTTATTTATTCATTTCATGT

CGTACTATATACATTTTTTTGTTTCCACCCAATGTCCGGTACCCACATTGGAGCCCGATACAATGGATTCACGACGTAAT

AAAGTCCCACATTGGGGGTGAAACGCTCCCTAACATAGACGACTCTGTATTCGGAGGGGACTCGAATGTCATACTATATT

TTTACTATATCTTAAGTTCATATGTTGCAAAGTTCAAATGATCGATGAATGACAAGAACAAATTTATTAGCTTCATTCTG

TATGAATTTCAACTTCTAAAAGAGGCACCTGAACACATAATAAAGAGATCCTTCAACATTGCACCTACAGCAACAAGAAG

CAGTTTAACCTTAAAATTTTTCGGATGTTCATCGAATTAGAAAATCAAGAAGTACTCAACAACAACAACAACAACAACAT

GGTTGATGTGTATTGAGCTATGAAGATGTAAGTGGAGAGAAATTGGTCAAAATTATAAAGCTGCATAAAAACACGAAATT

AGTGAAAGACGATCTGATGTATATTTGTCTCCAATCATATCATACATAAAAAAGAGTTGATCAATCAAAACAAACATAGC

AAACACTACTAGTGTTACAATAACAGAATGAGCTAGCAACAAAATAGACTTCAGTATTCTTTGACAAGGTCTATACGGTC

ACATCTTTCAATCTCTTCGACTTCTTCTTACGAGGTCTATACGGTCACATCCTTCAATCTCTTCGACTTCTTCCTTAATT

CTCACAGCTGAAGCCTCCATAGATACTTTCCAAGACCCAATCAACTTAATCTGTTTCAATGATGGAATATCAGCAAAGCT

AAGTGGGATCTCCTCAAGGTCATCACACTTTTTTATAACAAGTGTTTCAAGCAAGGGAAATGATTCCTCCGAGGCATCCC

ACTTTGAGATATTTAACTGCACCAGTTTCAACAACTTAAGTTTATGGAACGTGATATCTCCAAGGCACCACTCTTCTGAT

TGAGGAAAACACACATCTAGTAATTGGAGATACTCCAGGCTTGGTAGTTCCGCAATGAAGGAAATAGCACTTTCCATATG

AATTCCTTTAAGTACCAATTTGTTTAAATTTGAAGGCAACTGTAACCCGGATAGAATGCGGGGATGCACAAAGGAAAGTT

GAAGTTCTTGAAGCTGGGTAAGACTCTCCAATTTGGGACAAAAAGGCTCTACATCATCCTCAAATGTGATTTGAAGTTGT

TGAAGATTAGGACACCTCCTTGATAACACATCCAGCCTATCAATTGGAAATTCCTCAATTTTCTTTAATATCCTCAAATT

TTCCAATTTAGAGGATCCTTCAAAGAGTCCCTGCATAGCAAAACCAGCGCCAGCAAAATGAACATGCCTTAATTTTTCCA

TTTCCCAAAAAGACACTGGTAACCGTACACCATAAAAACAACTCGTCACAATTAAAGTTTCTATATGGGGCAGATGTGAT

TGTGGATCAAAATAGAAAGTACCTGCCCAAACTGCGAGGTACTTCAGCTGATTAAGTGGGTTTAATCTAGCTAACCACAA

AGACTCCACATAATAAGAACTCAAATCCAAGACCTTAAGAAGTCGCAATTCATTAATCTGACAGACGGGAATCACATCAA

TAGATTCTCCACCATTAGCCGTTATCAGAGACCTCAAGTGTTGGTGGAAAGGCTTCTGTGTTTTGGAAACCAGAGATGCA

AACTTGGAAAGCTCTTCACTGAAACTGAAGCTCACTCGACTTCCCTTCCAATCCAACGGTTGAAACTGGATATATTGACC

CTTCACTGCAAGCATAAACTTTTCTTCTCTACTCTTCTTCAAGCAAAAGTGATGCACAACATCATGAACCTGGCAGCATT

TGACTTTACCATTATAACCTTTCTTTGAAACAATTACCACGTTACTGCTAATGAGATCCATCAAGTAACCTTCAGCTTCC

TCTTCCATTAATCTCCCAGATTCAGTGTTCTCCACGAATCCTTCAGCAATCCATAAGCTTATCAATTTAGACACTGGAAT

TCTTGCGTCCTCCAGAAACATCCCCATATAAAGAAGACAAGGCTTTAAACAATCAGCTAGGTTATCAAAACTCAACTGCA

TAGTCGCTAGACTGTATTCTTCGAACTCACTGTCAAGATAGTCAAATAAAGCATCTTTCACCTCATTCCACCAAGATTCT

Figure 8 (Cont.)

TCCATTTTCCTTTTTTTGATTATTCCAGCTACCAAGACAACCACTAGGGGCAGTCCTTTGCATTTTTCTGCAACTGCTTG

ACTCACATATTGTAGTTCAGGCGGGCAATCTTCCTTTTGAAACACTTTTTTCTGCAGCAATTGGCAACTCTCTTTTGTTG

TGAGGAATGGAAGAGAATAAGGATCAGTATGGTTCTTGACTTGCTTACCCACTTCTTCAAGTCGAGTTGTTACGACTATT

CTACTTCTGATTCCATCATCTGGAAAAGAAAGCCTTAAGTCATCCCATACCATACAATCCCACATATCATCCAATACAAT

GAGATATCTCTTTCCCATTAGGCTTTTCCTCAACCTGTCAGCAAGTTTGCCTACCTCATCTTCCTTGTCCTTGGAGCCCG

TAACTTGACTGAAAATCTCTTGTAATAGCTCTCTTCGGCTATATGTTTGAGAAATGATGCACCATGCTCGAACATTAAAG

CGAGAAACAATGATGTCATTATTGTACAACTTTCTAGCAATTGTCGTTTTCCCTTGTCCCCCCATGCCTACAATTGGGAT

GACGTCTAGCTCATTTGTACCTCTAATCAGATAACCAATTAGTTTTTCTGCTTTATTCTCAAAACCCACTACCTCCTCAT

CAGTCACAAGATTGCTATGTCGAGCTGGCAGATGTTTAAATGGAGCAGCCACGTAGCGAGGATTAAGAGGAATGTTTGCT

GACCACATCTCAGTCACCTCTGCATTAATTTGCTTGATCTCTTTTAAAATTGTAGGAAGTGAGCAAAAAATATGCAAAAA

AGCATTATACTGAGCAAGAATAGAGTCAATGGCAACCTCAGCCTCATATGCCAAATTGATGGTACGTCTCTGAAGATCTT

TAGGAATTTTATGTTCGTGGTGCACGACATCTCTGAAAATGGATGATAGCTCCTTCTCTAAAATGGATGTAAGAGATGAT

AACTCTTTCTCCAAATTCCCTAAAAGAGGTTTCATCAGGAAATCTAAACCAGACTTAGATTTCGACATCTCATTCAGTTT

CCTTAAAAGAGAATCCAGAAAGCTCAATCCACCAAAGGTGGGGAACTGAGATGGAGTAAATTTTAAGGATTTGTAGTACG

TCTCAACTTGTGCCTTCAGATCTTTAGTCTTCTCCAATATCTGTATCGAGCAAAAACTTATTTTGCTAGTGTCATCTTTG

TTTATAGATCTAGGAAGAAGCTTTTGAATTACATATAGAATATCACCCGCTATAGCTCCAACCTTTAACAAGACCTCATT

CAACCAGTTACCATTAATAACGTGATTTGACACATCAGCATCAAGGAAAACCAACAAGAATTCTATTGCCACATCAATAT

TTTGAGCAGAGATATTATTAGGAAAGTTCTCGAGTTTTTCGTTTCTGAGATACATCAACAGATATTGGAGAAGATCTGAA

AATTCTTTTGGTAATTTCTTGTCCTTGAAAGTTTTTGATTGAGTAAACTTTGACACCTTTAGTTCACCATGAAAAATCTT

CTTCATTTCCAGCTCCACAAACACAATCAATGATAATAGATACGGAGGTATATTAAAGATATCATTATTATCACTAAATT

CAATATCAGCAACATAATCTAATACGGCCAAACAAAATTGTCCCACAGTGTTAGCAATGAACTGAATTCGAGTCTCCAAA

CATTCCAGCTTCTCATAGTTGACGTTACCATTTATCTCTGTGGTATATATGTATCTCAAAAATATCATTTTCTTTTGAAC

AATTTTCAGTTTCTTTATAGATAGCTGTATTGCAAGTTTTTCTATGGGATAACAGGACCTACCCTTTTCCAGGAACATCA

TTAGTACATCATTTAGAATTTTTTCCAGACAATCCATATATTTCGACAGATCAAAATCATTCAACTCATAATTGTAACTT

AAACTGGAGTTACCTTCAAAGAATTCCAACAAATGTGATTCTAGCCTTTCCAAATTAAGGTTAGTTTTACATTCATCTGA

TATCCCATCAAATACCCGGTGAAGCATTTCCACAGTCCATTCGGCATTCATTGTGAGTTTGACAAAACAATCAGGTAAAA

GAACATGATACTTTATAAAGGTTCTAAAAACTCTTAGCACAATATCAAGATCCCCAATACGACGAATCTTGAAGAAATCC

AGGTTACCTTCAATTTTGATCCTTCTTAGGTGATCTAACATTTCCTCAATTTCATTTTCATTCATTTTTTGTAGAAAAAT

TCCTGCAAGTTCACCAACTCATGGAATTAGGTTCATGTCTTTCAATATCTAGTGTTTGAAGCTATGTTAATGCTTGTGAA

AAGTTATACATCTTATGTACCATTTTCATATTGTCAAATGTCACTTAACTAATTATTATCTGAGAAAATCGTCTTTCTTA

CATTTTCAATTTTATGAGATACTAACTAATAGTTGAGTGAACCATTTGAGAAATCAACTCTCTAATTCTGTATCTATGGG

Figure 8 (Cont.)

AAAAAAGTAATTCATGAAGAAGATGACTTACAGTTAGTTGACAAGAATCTTCAATTTCTCAGATTTGGATTCCAACAAAG

ATATATTTCCAAGTTTACGCAATAGGTGATATAAGAAAAAAATTCATTGAAATAAAATGAATGGAAGTTTGAAGGTTTGA

AGGAAGAGAGTTCTTCTGTCTCTCTAATAATTCTTATACCTAACAAGAGATGAATTGTAGTAGCAAGTTGCTTTAGGTGG

TAGCTGTAAAGTGCCTCAATAATACAACTATATTACTTAGTCCTTTTTTTAAGGGTCGTTTGGTCGAGAATAAGTTATTT

TGAGAGTAATTATCTCACAATAAGTTATTTAACATGTATATGAAATAACTTATTCCATCACTAAAGTATAAATATTGGGA

TAAATAATCAAAGGACTATCTAGTACCTCCAATCAAATACATAATAAAATAATCCTATATTTTATTCCAAAATTTTTATA

CCTCATACCTCACGCCAAACGACTCCTTAGGAAAATCCCCCAAAATTATGTCCGATTTGCTAATTTCATACTTAAACTAT

GAACTATTTTGATATTTGTTTAGCATATAATTAAGGGGTATTGGGTCGGACATGAAGTTATTTTTTCTCATAAATATGAA

AATTCTCAAGTTGTGAAAACTATCAAAAGTTATCTAATTCTTAAGCAATCTTACCGAATGAGTAAATCATCATTTGTAAA

TAAGATATCAAAATATTCTAAAGCATCGCATTGATGAATTACATATTTTCATGTTTCTTTTATAAATAAATATTCACGAT

TACAAACTTTCAAATGCACATAAATTTATAAAGATCCACTAGTCAATAATAATAGTAACAAATAATTACTCTTTAAGTTA

ATATTTTCACTTGGCACGGACAATCCATTCAAATAGAATATGAGTATTTCTATAAATTTAAAATGATGACTCCTTTTTTT

ATATATATAAATTATTAACTTATGAGTCAGATATTATTTAATATTTAGAAAAAGGCAAGTTGTATCAGCAAGTTGATTTA

GGTGGTAGGTGTAAGATTAATGCTGTCTCCTTCTTTAAAATAGATTGAAATTCATGTATTAGACTAGTATTCACATGCTT

TATTGACCAAATAATGTCAGAACAATTAGACTAAGAATAGTCATCGAGATCTCAAACAGGGATTAAAAAAAGTAGTGGTG

ATAATTCATCCATACATCTTTCGGGATAACACATATTTACCAATTAAATTAGGCTTAAGTCATTCACGATTCCTTAAAAG

TTATTTGTATATTTCAGTTAGACATCTTAACTAGGACTATTACCTATTGAACACTTAAATTGTTTAAAAAATTACCTATT

AAATACAAAATGCTGATATGACAAAATAAGTGTTTTTCACTTCCTATGGGTGCGTGAAAGTTTTTGAAATACTGTTTTAT

TTTTATTTTTTCCAAAAAAACTTACACTTTTTCTTCTTTAAGTGACACTTGGCATTTAAATAAACTAAAATAATTTTTTA

ATATTTTTTAAAAAAAATTCTTAATTCAAAAAAGAAAGAGCACCCCTACCCTTCAAGTCATCTTCTTCTCTAAATTTAAA

TTTTCAAAGACAACTAAAGAATCTTCATTTTTTTTGTTTTTGTTTTTGTTTTTCCATTTCTTTTCAATATTCGTAAAAAA

AATTGAATCAAGTAACTGAATTTGCAAGAAAGATAATGAAAGTAGATTTTTGAACATTGGGATAAAAAAAGTAAGTCGAC

GCTCCATCTCCATTTTCGGTCACCTTCAAATAAATATTACCATTCCGAGAAAATTGTAAATTCACTAAACTTATCAAAAA

CAATATCAAATAATTCGCTAAATTAATTTAGGTCCTCTTGATTTCTCCTTACAATCAATTTCAAGATGATTAACCATTAG

CATACTTCCTTTATTCATCACTCTTGTACCAACTCTTTGAATATCTTTCTCTATCATGTATTAGGAATGAAAAATAATTT

TCGATAAATTAATTTGGGTCCTTTCGATTTTTCTTTGCAATCAATTTTCGGATGAGTAACTATTGACAAACTTCTTCATC

ACTATTGTATCAATCTCTTTGAATATTTTTCTCTCACACATATTAGGAATACAAAATATTTTTTTTAAAAAATTGAATCT

GCAAGTAATTTGCAGTGAAGGTTTTTGTGGTTTGAGAAAAAAAATTGATGAGAAGAAGATGAAGAACAAAGGGGGGTTGG

GTAGGGTGGGGTTAAGTAAAATGGGTTGTCATTTCATTTATTTTTTTATTAAGAAATAGATATAAAATTTATTTGAAATA

ATTTTCATTCTTTTTAACATAAAAAAAAATAAAAATCTATAGTTGTTGGGGTCAAGTGACACATGTCATCTTTTAATTAG

TTATTTTAGCCACGTCATAGCAAGTGTATCACACACACTTTAACTTTTTTACTGATTATCAAAAAAGGTCTAATAGGAAC

Figure 8 (Cont.)

AGGTTTTAGATAGATAAAAGTGTTCAATAGGTACTAGTCCTAGTTGAAGTGTTTAAGTGAATTATGCGGACAACTTTAAG

GGGCCGCAGATGACTTAAGCCATTAGATTATGATCGAAATTCCATAGACACACCTTAACTAAATCAGGGGCGTAGGCACA

TGTATGTCAGGGTGTCCAATTGGACATCCTTAGTTGGAAAAAATTTCGCATATACAAGTAAAATGATACACGAAATGATT

AAATAATATATTTTGGACACCCTTGACATAATAGGTTGTTATAGCCTAGTGATTTAAGATGTCTTGAATGTGTGTTTATA

CATCTTTAATGAGTCAGTGTTTGTGTGTTCAAATCTCACTTGCAACAATTTTTTTCCCTTTTTAAAAAGAACTTTTGTTG

TTTAATTTTTAGACCCTCTTCGTGAAATTTCTAGCTCCGACATTGAACTAAAACTAAGGTCCTATTATCCCCTGAACTCA

TTTTTTTGATAATTTTGTACACATTTTAGCTTGGCATATGCACTCCGTGACTCCACACAATTGAGGTGCGTGGGAGATAT

TTTAATGCCACAAGCCAAAATGATGTACAAAATTAAAAAAAAACATGGGTTCAGGAGTAATAGGACATTAGTCTAGTTAA

GTTGTGTCTCTGAGATTTTGGTCATAGTCTAGGGAGGTATTTGTACCTTTTTTCCCTACATCTTCCTTGTAAATGGAATG

TGTTACCAATGAGGGTCATAGTGGAGTGATTAGTATTCCTTCGTCCTTAACCAGATGCCTTGGATTCGAATCCCCCTTGA

TACATAATCGTCTTTGTTAAGGAGCGTTTTCCCGTATACTAAGTATGTTATTGTTATTGTATCGATAGAGACAACCAGAT

GGTTCGAAACCACTAAAAATCACCATCTTCAGATAAAAGAAATATTAGATGATTATAAGAAAATCCTGATATGGGCATAT

GAACACATAAAATAAGGCCATAAAGAGATTTACTCTAGAAACCAATTTAGACAAGCAAAACATATATATCTGGCTTACCA

TAAACATGACCAAAAAGTTTCTTAATTAATTTCCAGGACCTGAGCCTAAATATATTCTCTTTGTATCAAACAAGAAATCC

TACTGAATTTATTTTCTTCTCAGAACTAAAAATGCCTTCTCCACTTGGCCTCCAAAAGAGCCTTCCATATCACAACTTGA

TCCCAAAGTTGATGAGAAGCAAGCTATATATTACGAACATTGAAGTTCAACGTGTTAATTTCCCTGAAAGTACAATCGTC

AAATTAATCTTTTTATTAGCTAAGAAATGAATTCCAGCTAACTGTCTGTAGTTGTGTAACAAGTATCACAATTTGATCAA

TCTTGACGCTATTCAGATTGCTTACACTCTTCATCCTTCTTAGCTGATCTAACATATCCTCAATGTCGTTTCGAGCCATC

TTTCGTAGAAAATTCCTGCGAGTTCAACAAACACTTGGAATATTAATTTCATTAATTATGAGCAACATTTCTATTCGTGT

CTTTCAATATCTGCCACAGGAACATGATCTTTATTATAGGATAAGAAGTTTAAAGTCGTACATTTTTAGGAGGTCAATCA

TTATGTGATTAGTAAAAAAATGAGAGAACTGTAGAGAATAGCAGAAGAAATGTATAATTGGGAGACCTTCTACTAGCCAA

TAATTCGAGTTTTCAATAGACTGGAATTATGAAGTCTCTATTATTTTATATATATATATATATATATATATATATATATA

TATATATATATATATATACTCTATGATACAGAAAAAGGAGGAGAGAGCAGAGTACATATGTACATATAAGGGAAAAGGAG

AAATAATAATCCTCATCAAGACTTTATAGCCACAAACTTTTTGACCCCCCAAATCTTCCCTGTGGGTCTGGCCTATGTTT

AAAAATTAGAATATAGGAGGACCATTTTATAACTTAATAATCATGGAATTAAGTAAGCGTTACGAAAATTTAGCAACTCA

GGTCGAAAATTCAAATCATGTTTTCTTGAAAAGATTGAAATTTGAAATTAATCTCAAATCTAAACTTTGATTTGGAATCA

TATCTTCATATTACATATTCAAATGTGAGTTCAAGTTTAAATATGTCCAGCTTGTAATAATTTTATCAACCTAACATAGA

CATTGACAATCGTGAGATTTCTAGAAGATTAGAAGAAAAAACAACCTTGAAAGAGAATAAGTACATTTCAATAAGAAAAG

AAGTTTTAGTAGCTCGATTTTATCGACTAACTGAATTCTCATTTTATTGATGAGGATCACATTTCATTCCATCATTCCAA

AAGAAAAAACCTCAAATGGTTAATTATTGAATTTTCAATTTGTTAGTTATCTAAACTCTTTCACGAGGATCCAATTTCAT

TCTCTGAAGTTCTTCAGATTTTTGGTAAAATTCAATTCATTTCAGAAAAAAAATAATCTTAAATTCTTAAAAAATTGACA

Figure 8 (Cont.)

CATATGGTAAAAATTCGATCCATTTCAAAGAAATATACTATATTTATGTATACAACACCCACTATATACAGCTATATAGT

GTTGGAAAACAAAAACGTAGAGAATTATTCATTCATCAACAAAGTATATCCACACACGCCAACATATATATACAAGTCCT

ATATATCACAAAAGTGAAAATAAAAGTTGAACAAAACACTAGACGATATCCGACTTCGCTAGCCAAAACGCTAGCGAAAA

CGAAATGAACATATGAGCAATCGAACATGAAAACGAGATGAACATATGAGCAATCGAACGCGACTTCGCTGTCGGAGCTT

AAACAAAAACTCTAGGGACAGATTCGATAGGTTTACAATGAACTTCTCTAAGGAGAGTGCGAATGCCTTTGCCTCCAGCA

TTAGCAAGTGGGTGAATTCCATGGGCAGGACCTTCCATGTATGCCCTCTTCTCCCTTTCTTCATCAAATGACGCACCAAA

ACGTTTCTCCACATCTACATCAAATTTTAAAAACCTCGTAAAAAACGCTATGTTAAATAAACATACTATTAAGACTAAGA

CATAATCCTAAACACCCAAATTCATGTAAGATAGATCAAATAGTCAACCAACTAAACTATTAAAATTCTCCGAAGAAAAG

TGACTCAAAACTACTCAACACCAAATTCATGTATCACACACTAATATCCCTTCCAAATCTATCCGAAAGAGGTTTAAAAC

GGAAAAGGGAAATAGGGAGGCGATTACAACGTGAAAAATTAAATCCTCACCAATAAGATAGATCAAATAATCAACCAACT

GAACTATTGAGGTTTTCCTAATTAAGAAAGGGTCATTTAAAATTTAACTTAAAATTTTTTCATGCTACTCCTAGTTAGAC

AATTTACAACTCTATTAGATGATTTTCTAACTAAATAATCGTCTATGACTTGTTTCAGACCACAAAGTTTTTTTGAGCTG

TGTGTCTAGCAAACGGAGCTACTCCTATTGGGACGGTAGGTATTAATTAATGCTTTATACTAGCAACCTATATAATTATA

ACGAGTTCAAGTTCTATACAATTAGATTATATTATCACTTCAAAAGTAATTAATAACATGTATCAATCATAATATGATAA

GTAATTTTTGTGTACCTTGAGCAAGGTTCTGATCGAGTTGACCATCTCTAGTAAGCGCCATCATAACTTGAGGAATTCCC

AAAGGAAGTGTATCACCTCTATCAACCTGCCAGAAATGTATCACTTTGCCATAAGTTTTCACGGTTTTTTCATGATCTTG

TCGTTGAATCGGGCCTGGAACACCGGGCATGAACAGGACACCGCTTTTCACCTCGTACAAAGATGTTGATGAATTTTATT

GATAGGACCAAATCCTTGAATGGTAGCTGTTGCAGTCTCAAGAATTGCTGTTCCTGTTTGCGTAGGTTCACCTGGAACAT

CTGGATGAGTCGATACATTTATTCCTTCCATTTTTTTTCCTTTCAAAAATCTCAAATAAATTCAGAATTCGAAATTATAG

TAAAGTATTTTGTTGTGGTGATCTGTTAACTTATTTTTGGCCTAGAAAGAAGAGGCAGCTAGCTTATAGATAGGAATATG

ACTAGCATGCAGACTAACACGTGGCACGACACGTGGCGATACAACTGGTTACGTGGCAGTACAGGTGTCTTTTGTTTGGG

TAATTTGAAAGCTGACTCCTTATACTCCTACTCATGACTTGTTCTCTAACTTGTGTGACAAATGTTTTTTTTTAATGAGC

TCTGATGTGTGACGTTCAGACAAATATGTTATTAATTTACTTGTTTTGAGTATAATTTATATTTTAAAATTTTATAATTT

ATATTAAATAATATATTTACTTTCTTCATAGATTGGAAAGTTGCGATGTATTCGGAAGCGGCTCCCCTCCTGTATACATC

TTAATCCATCACTTTAGTAGCAAAATTGCACACCTAATGTAATTCAAATTTGATAAAATTTAGTAATTTTCTCAAATGTT

GCTTTGCTTTCCTACAACTTGTCATGTCAATTTTCATCTTCTTGAGATGGTAAGGTTTGTTGTTGCCAAAATCTTTTTGG

GCCAAGCCCATCAACATTCCAATGTCCAATTCTGACTAAGCAAGCCCAATACGAGATGACATACTTGTAACAAACCCCAA

TATTCACATCCCTAGCTATCGATGTGGAAATTCTCAACATGAGAACGGATGTTAATTCACACCTCTTTGCATAAGGTAGC

TCTGCCATTGCCACCAACACAAATACATGACACCATCACAATATATCATCCTGATAAAATGCGCACATCGTAGAACCTTA

ACAATTATGAGACGTTAGGATGGTAAAAAAAAAAGAATGTATTCATCGATCTTTCTATCGATGTGAGAACTCATCATTAA

GTGCAGAGTTATTTAATTTTGTAAATAATGATATAGTTTTAATAAGTAAATTTTCAGTTACGTATTACGATGCCAAAACC

Figure 8 (Cont.)

TACCTATGACCACATTTAATTGTTCTTTTTAATATTGGCACCAACTTTTCTTACATTAAGCCATATAAGTATGAAACAAC

TTGGGCAGCTTCACGATCCTTAACGCATTTCCAACTGAAATAGAAGAAACCAAATCAAGGGTGTGTTTGGCTTGGAGAAA

AAAAAAACAATTCCATCTTTGGTTCAAATTTTTTGAAAAATACTTTCTCTAAAAAAAATATTAGTCCAATGCACAAAGAA

AAAAAAACAAGATTCACGAATAATATTCCACATTGATGATTTGCTCTCTGCCTTTCAGCACAAACTATCCCACCCCATAA

CGCCCTGACGACCCAACACTTTACCACCCACCCTCCAGTCCTCCATCGATCCACAACATAGTGTTCGCCAAAATTAATTA

TACACTAATATTTTTGGGACAATATTTTTTGTTACGTACCAAAACACGAAGAATATTTTTCTTCAACCAAATACACCCTA

AGAAGTAGCTAAAACTAATAACGTGACTCCAAATCAAAGCTTGCATGAAAAATCTAAGCCTTGCATTTCACGTGCCTCTC

TCAAACGACTCTTATTATTAAATTGAAAATTTTCGATTATCAAATACACAACAACTAAAAAAAGAGATTATATTCCCAAA

AAAAAAAAAATCATCAATGAACTCTCAAGAAATTCAACCATCAAATTCTACACAAATTCAAAGTGTTGAAATATCAATTC

AAAATCTCATAAAAAATTGGGACAAAAAGCAAAGATGGAATTTCTTTATCATGAATCCTTCACAACAACCAACAAAACAA

CAATGGAGAACAAATTTAACAAAGTTTTTAGAATCCATACCTCTTAGAATTTTCACCATTGTGTTACTCATAATTGATCT

TGTTTTCACAAGTTTTGAGCTCTCTTCATCTTTGATATCCTGCCCGCAAAATCGGAACGCGATAAATCAAGAAACGGAAG

AGGTTTGGTACCATTGGGCAGGTAATATTAGATAGTTTGTAATATATATGAAGTAACATTTTCTTGTATCAAAAGGAAAA

AAATGAGTTTGAAAGCCTTTATATTTTAATCTTATTAGTTACAAACTATTTAGCGACAAATTTTATAGCTAATTCATGTT

TTTTACGATAGAGATATATGTAGCTTTGTTGTTTCCTAACTTGAAAATTGTGATATTTAAAACATAGTCACAATTTACAA

TTGTATTTAAATTTTAGTTACTTTTCTTCTTTCTTCTTCTTGATTTTCCTTGTTGTTGGCCCTTATAAATACATATACAA

CATTTCTACTAAAGATATTATTTTTGATGCTTCAAAGCTTTAAATCAATTCCATCTTTCTATTTTCCGAACAGGTATAGG

GATCTTGGGATTGTTATTTCTGAAGAGTGTAGGCCTTGTTGTAGGTCTAGGGTACGCATTTTTTCGAAGACCAGGGTACT

TGCTAGATGGCATAGTTATTATGGTGGCATTATTTTTGGAAGCATATTTGGAAAAAAATGGAGGCGGATTACTTGTTGTT

GTTAGCTTATGGAGAGTTGTTAGAGTTGTTGAAAGTGCTTTTGAGTTAAGTGATGAAGCAATTGAAGCACAAATTGAAGA

AATTGTTTGTCAATTTGAAGAATTGAAAGAAGAAAATAAAAGATTGATGGATAGTGTTGTTGAGAAAGATAAACAAATTG

AAATACTTCAACAAGAATTGGATCAATACAAAAAATCAACTTACTAGAGATGCAACTAGAATTTTATCTTGTTTTTAGGT

ACTATTTTTATAATTTATATATATATATATATATATAAAATCAATCAATCGATAGAAACTTTTAAGTTATCTGAACAAGT

AATAATTCATATTAAAATTTTCCCAAAAAGCAGATTGAACATGAAAAATAAGTTCATATTAAGTATGGGTCCAACATCAA

TTGATACTTCTTGATCTTAGGCATATTTTCATTTTAATTGAGGATTCTTGTAATAAAATATATAAATATCGAGCATGAAT

AACCTACATGTCATGTTGGTACCCCAAGTGGCATAAATTGTCAAAACTGTGCAGTTTATTGCCCACTGAATGAATAAAGA

GCTGGTCCATATATATTAAGAACCTGTTTAATTTGGCCTTTGATTCCATTCCCTTTGTTTGCTTTTTTCCCTGCAAAAGT

TTTTAGCTTTTGGTASAAGTGTAGTGACCAATCAGAGGAAACTTTTCTTATTCACCAATTAAAaCTATATGATAAATTAA tAACAAGCTTTTGaAATGTAATTCTTATTTTTAGAGTTTAGGATAAAAAAGGAGTATATGATTTAAAATATCTCATTTTT

TCAAATTTTATACCTGAACTATCTGTATGCTASTTTTCTATTTGAATTATCACKTAAGCTTGAATCWCTTTTCTATTGAA

ATATCATCATTGTTCGGGAGCAACTGATAGTTGTGGTTTGTTTTGATAAATAGTTGATGATAGTTTAGGTGAATACTCGC

Figure 8 (Cont.)

ACACCGAATAGTTAAGATATAAAACTCGAAAAAATCAAAATACTATAGTTGTGTTTTGACCCTTTACTCTTCTTCTTTTT

TTAATGTGAAACTCAATGGATCTTTACTTACTTTTATAAAACAAAACTTATACACTACGCATGGATGAATTTAGAAGTTT

AAATACAGATTCAATTGAACCCAATAGTTTTTGTATAAACGATACATTTGTGTGAAGAATTTCATTAAATATATATTCAT

ATTAGATTTAAAGCTCAATTATTATTATTTGAAGTCGTTATTCTATAATTTTAAACCCATAAAATTAAAATCATGACTCG

CCTTAATCATCACATATTAATCAAAACCACTCGCGTTAATTAATTATGTGGATATAATATCCATTGTTTTAACCTAATAT

ATAATCTTAAATATGAACTTTTTATATATAAAAGATTGATTTCTTTTGTAATTGTGGGAAAAGGGAGGAAGTTATAAGC

AACTTGTAAATTAATATAATTGAACCCTAGTTTGCCTATCATCCATCTATTCATTCGAGGTGGGAATAAAAAATAAAAAA

ATTAAAACCTTCTTTTATTAAAAAAATATAACCTTACAATTATAGTAGTCATATTCTTAAAGGGAAAAGGGTGCAACTTG

TGCAATTTTTAGTACACTTAATTAGGTCATATACATGCATCTAGTTGTTGAATCGATGTGAGAGTTGAAATAAATTATTA

TTAAGAGAGAATAGTGGGAAAAGGGTTGAAATTTGTGTAATTTAGAACCCTTATTTGTACCATGTAGCTATTCAATCGAC

GTAAGAGTCAGAAAATTGTGATAACAGTCAGACGACACTCCAAAAAATAAAAATATATAAGGGTACAACTTGGATGATTT

AATTTTTTAAATTTTAAATCGTCTAGTCATTGAACTCGAGTTTGTATAAAAGAATGATTTGTACTTACGTATAGTGATAT

AGGTCATCAACTGTCAATTATAATATAGAATATTCTATTTTTTTTTATTTGAATGAAACAAGAAGATTTAAATGAAGGAT

ATTCTTTTTACCAATAATATAAGCTAGAATTAGTAAGTTTCTATGATAAGCAATTAATGTTTTTTTTTCTTCTTCTTTTC

TAATCTCTGTGGGCATATTTATGAGAGTAAGGGTATGTTTGGCCTGTTGAAGTTTGGTAATTGAGTATTTAAGGTTCAAA

AATTCAAATAAAGTTAGCATATGACTTTCTGGAGTATACTTTTTTCTAAATTATAAACTATAGTGTTTAAATTTATGTAT

AAAAAAAATATTAGTGTTCAAATAAGGTAAGCATAGGACTTTTTGAGATAGACTAATAAATATTTTTTCAGAAAAAATAA

TAATTTTCACACTAGGAAATGTCAATATCTAAAATAATAATAAAAATACTGGACATGGTCAATACAAATATAATACACAG

GACATACTATGTTCTAGGAGAAGTGCATATGAACATGAAAAAGAAAGAACTATTCAATATGAAAAAATAAAAGATAATTA

ATCTTCTAATTATTTATCAAGGAAGTAATCAAAGTGTCATATATAATTATTAGTAGAATCCTAAAATTTACAAATGATGA

TTTTTTTAATTATGAAAAATAGTTTAGTGACTTTATATTACTTATATTAAATAGAATATTTCTTAAATCACAAAAGTTAT

ACTTTCTCTAATTCACTTTATTTGTCGTATTTTATTTTGTACACAATATTAATTAAAGGATTATTTGACTAAATTAGCTT

TGTTTATTACTCCTTTTAATTTAATATATACTTCCCTCTTTGTAAAGTAGCAATATGCATGCACACTTATTAACCTACTT

GTATATATGCCATCAAAACACTTAATTAATGGGACCAATTCATTTCTCGACCAATAATATCATAACTTCGACATTATAAT

ACTCTCTTCGTATTAATTTATGAGACATCTTTCAAATTTCAAATGTTAAATAATTTTTTTAATCACTAGCTTTTTATATG

TCTTATAAATATTTAAATCATTAATAAAAAGATAATTACTATAATACTATTTCTACAAATCCTTGTGGAATACAACAAAC

TTCTCGTGACTTGAGTATATATACGTGCAATTGCTAGTATAGTACTATATAGTGTTGCTTCACATGCATTGTACAGGATG

CTTTGACACACCACATTGAGCAGCAAGTTGAACAATATGGATTGAGGCCGGGTCAGGCCTGCACCTGTTCGGATCGACCC

GGTGAGGACCCGCCAAATGAAACAACCAATGTAGAAGAGGAAGGGGCCGGTTAATTAGGCAAAGTATGTGTCTGTGGAGA

GTAGATTGTATGAATAGACCTTCGTTACAAAATGAATATTATGATCAAAGCAGGATGACAAGAAAATATGACAACTGAAT

AGGAAGATACAAGCAAATGTAGTAAGAGTTCGATAGTATACACATAAAAGAATAAGAAACTACATGATTACTAAATACTA

Figure 8 (Cont.)

CTACTAAAAGCGAGAAGAGGGAAGGAGAAGACTGGCCCCACGTCTCCCATACATATAGTACGAGAATACTTGGATATCTA

CTAACTTTCTACTTTAATCATCGATCTCCAGACTTTCCTATCTTGATACTAGCTATGATCACCTCGATCCCTTTAGTTCT

TTTTCAACCTACTTTTACATCCCCTAGCTCCTACTATAGTCAACCTCTCATACCATCTACCCGATGTATCTGCACACTCC

ATATTTACATGTTTGAACCATCTCACTCTCATTTCCCTTATTTTGATTGTCGCAAAAGCCACTCACATATTTTCCCTGTA

TAACTTTATTCCTAATCATATTCCTCATAGTATGCCCACACGACCACTCTTCTAAACGTGGATATTCTTGACTAGCTAGC

CACCCCTCTTCCCAATACAACAATGTCGATCTAACCACTATTCTGTAACTTACCTTTAAAACTCTACTACATATTCTTAT

CACACAAAACATACCACATCGTGATCCATCTCCTCGTTCTCTTGAATTATGAATTCAAAATACTTGGATATCTACTAATT

TTCTACCTAAAAGTGAGAAGAGGGAAGGAGAAGACTGGCCCCACCTCTCTCCCATACATTTAGTACGACAATATAACTTG

GATATCTACTAACTTTCTACCTTAATCTTCGATCTCCAAACTTTCCTATGTTGGTACAAGCTATAATCACCTCCCTTTAG

TTCCTTTAATTTCAACCTACTTTTACATCCACTAACTCCTGCTATAGTCAACTTCTCATCCCACCTACCCGACATATCTG

CACACTCCATCTTCACATGTTTGAACCATCTCAATCTCACTTCTCTCATTTTGATTGTCACAAAAGCCATTCACATATTT

CCCCCATATAACTTTATTCCTAATCATATCCCTCATAATATGCCCACACCCCATCTTTCCCCGTATAACTTTATTCCTAA

TCATATTCCTCATAGTATGCCCACACGACCACTCTTCTAAACGTGGGTATTCTTGACTAGCTAGCCACCCCTCTTCCCAA

TACAACAATGTCGATCTAACCACTATTCTGTAACTTACCTTTAAAACTCTACTACATATTCTTATCACACAAAACATACC

ACATTGTGATCCATCTCCTCGTTCTCTTGAATTATGAATTCAAAATACTTAAAACTTCCTCTCTTTGAAATAACTCATGC

ATCATTTTTCATGAATTACGTTATTAAACTTACACTCTAGATAAAAATAATAATTCACGACATGATCTAATAACGACAAC

GTGCCACGTAAATTGAAACAGATAAATTATAAATATAATAATTTAGTAGGATAGGATGTAGTACACATTGTATATTAATT

TTCTATTAAAAAAAAaGAAGGTAAAGACAAAATCACAAAAACAACAAAACCCCATTGGCTGATCCACTCTCTTTCTCACA

AGACTTTTCATCAAACAAGTGTAGCACTTTTTCATTTTTTTTATTCCCAACTTGCTCTTCCCTCTTACCCCCTCACCCCA

CCCACCCACCTCTCTCTCTATTAAGTTCTCCACCTCCAAATCTTAACAATCCAATTCAAAACAATTCTCAAATGTATCCA

TCATCAACATCTTCTTCATCACAAGGTTCAATGAGCCACACCAGCACCACCGCTGGCGGCGGTGGCGGTCTCACTCGCTA

CGGTTCAGCTCCGGGATCATTTTTAACTACAGCAGTTGAATCCGTCGTTAACGGTAATCACGAGTTCGCTTCTCATGGAT

CTCATCACTCAAACCTTGGTCCTTCACGGTTTTTCCCGTCCAATTTAGCATCTAATTCGTTAAATTCTGAATCTACAAGC

AAAGCGAAGGAACAATCGAATTTACAGAGGTCAATTGGTTTCAACGACTTAACAATCGGCGGCGGCGGCGGAGGTTTGCC

GACGACTTCAACCACGCCGTTGGTTCGACATAGTAGCTCACCGGCGAGGTTTCTTAATCAACTTGCTACTGCTGCAGGTG

ATACTGGTAAGTTTTCAACTTTCCTTTTTTCCTAATTGAAATGTGAAATGACGAATTTGACCTTCCTGTATATGATTCCT

TCTGTTTGCtTTTTTTTTTTCCCCTGCTAAAGTCTTCAGCTTTTGGTAACTTTTTAACCAATCAGAGCAGACTTTGCTAA

TTGACTAATCACAACCGACTTTGCATAAATTAACAAACTTTGAAATGTGTTTTACATTTTTAAGTATTCCTTTGGTTATA

TCTTCTAGAAACAAAATTTAAGAAAGAAATAATTTTTTCTTTTTCCATGCTTAAACATGTTAGGACAATTCCATAGTTAT

TCGAGTATATCACATTACTAAGGGTGAAATGAGAAGTTCGAAATTCAAAAAATCAATTTTGTTGAAATAGACTAAACATA

TAAGAGTGTCGTACAAGACGGAGTCTTAGTTTTATACTAGTCAAATTCAGTTAAGATGCTAGTTGTGTAGTAAATGATTA

Figure 8 (Cont.)

AAATTTGACGATGGATAAATTAGAACCACGAGTTCATGAGTTCAAGTTGTGGAAACAATCTATTACAGAAATGCAAGGTA

AAATTATGCGCAATAAACTCTTGTGACCCTGACATAGCAGAAGCTTAATTAGTGCATCGAGCTACCTTTAAAAAAAATTG

TAATTAGCTATAGATGAAAAGAGAAAGTAGGTTTCTTGCAGATAGAACCAATTAATGGAGGATTAACTTATATTGATTAT

CATTGGACTATATTAACTTCTTAATGAATTGTCATGAGATTAGAGTACAAAAGTAAGATTTACTTATGTCACAATTAGAC

GTTATAAACTGACTAGTTGAGCACTTAAACATAATTAATTACTCAAAAAAGGACACATAAAAGAGTAAGTGGGGAAAGAT

GCTTAGAGTTATTGAATTTGTCTTATCTAATTATCTAATTACATACAACAAGTTGCTAAAAAGAATTACCAAAAGATTAA

AAGAGAGCTATGCAAATGCTAAAGATATACTTGGTACTCAAAGAATCTTTAATACCTCCTTACAACTTGCAAATTCTTTT

TTTTTTCTTTCCTTCCATATGATTAGTACTTTTAACATTTAAACTTAGAAGTACTTCATTTGTCTCACTTCATGTAGTTA

CTAAATTGGTGAGTTAAAAAGGAATTCTTTAAATATTTTGAATTATGAATTATTGAAATTATAGTACATATCAAGTAATT

TTTAAATATGTAAAAAAATTATTTTTAATTTTTTtAAAATTATGTGTCCATCAAATATTGAATCATCTCACATAAAAAAG

TATATCATATCGACCAAAAGTTTAGCTAGTTCTACTTTTCCTATGGTGAGTGTCATTTTTGTGTCTATTCTTTGTATCTG

TCTACGATAATAACAATAACATACTTAACATAATCTTATAACTGAAGTCTCGAAAGAACAGAGTGTACATATATTTTATG

TCTATTTTGTAGAAATTAAAAGGCTGTTTCCCATAGACTCTCGACTTAAATAAAACATTTTAAAAACAGTTTGATTTTTT

TTTATCTGTCTACCTTCTACAATTTCCAACAAAACTTTCCAATCTTGACAAAGATGTCAAAACCAGATTTCAGACTTCAG

TAGTTCGTGTTTGTAAATTGAATCCATAGTATAATTCAAGGATTATACTCCATCTCATCCCAATTATCATTCGTTTGGCA

AGTTGAAGTTATTTAAAAGTATTATTCATTTTAGGAAAAAACAAAGAAGTGATTTTGCTAATCCATCCGTTCCAATTTAT

GTGTCATAATTTGATTTTGTACAAACTTTTGAAAAAAAAGTAAATACTTCTAAAAGTTTTGGTTTTAAACATCCCAAAAC

ATATATGTGACTTTTATAAGACGTGTATACCATAAAAGCTTCAGATTAAAAACATGTCATTATTTCTGAAACATATAAAA

AAGAACCTGATAGTTTTGGCCAAAATTATATATTTATCTTGaAAAATTCATTCAACATAAATAAATTCTTGTTTACAACC

AACTTAATGATTTAGAATTCGAAAGTTATATACTTCAAATATAGTTAATTAGTATAAAAAGTAGAGGGGAACAATCTTGG

GTTAGCTTAGAGTAAATGGAATTAGTTTCCTAAATTAGAAGGTATATAACGTAAGCAGCCGCAAATTATTATTGTTTTTT

CTTAAACAAAATAACTTATCCATCAATAGGGCAAATTAGGAGATTAGTGGAGCTAATTGTCAGTATTTCTTAATCCTGTC

TCAACTCTTAGTGACATGTAAAGGTGGGTTCCACATTTGGGGAAAGTGAATGCATGTGTGTCTGCTAAGTTTCCAATCGC

CCACAACATTTGGCTAATGAAACCACTGGTATTAATTAATTACTCATTAATCATGGTGGATCCTTCTTTAAGATAGAATC

TCATTAGCACTAATTAATATATATTTTTTTAAAGtTTTTGGAGGTAGGATTTGGGGGTTGGTTTGGGGTGGGGGTAGAAG

GGAGTTAGATGCAACTTGTGCAATTTGACACTCTTGAGCTTATAAACAATAATATATTCAGTATAATTGTGAGGTTTGAA

GACGATAAAGTGTGTGTACAACTTTAAAAAGTTATTTTCAATAGATCCTGACACGATACATCTAAGTTTATATATCAAAC

AAATTTGTTACCTTTTAGTTTTTTATAACTATTATTATTTAAACCAACTTGCATGTATCTAATTAATTACATATCTAGTT

AATTATATAAGAGTATTTGTTACCTCATGTCAACACATACAACAACATACCTAACAATTACAAAGTAAATTTTTACTAGT

AGAGTTTAGATAGGGTGAAATGTATGTAGGTCTTATTGAAATAGAAATGTTATAAGAGTTAAATTTTAATTCTTTTTAGT

CTAAGGAGTAAGGGGTTTGATCTTAGTGGTAAAAGTATAACGTGCGATATGTTAAGTGTAGATCATGAAATTTTGCCTCA

Figure 8 (Cont.)

GGTAAAATTTTTTATATTCAAGTGGAGAAGATCAGAAAGATGAATTCATTATCCTTTGAATTGTGAATCATGCATCACTG

ATCCTTGTTGTTTTCGATTTAAAAAAAATATTTGACCTTTGTATTAATATAATTAATGGTGCCTAGATCCTTAGAAGCAG

GGAAGGGAGAAGGAATGATACTACTTGTGTGAATTAATTTGATATGAGGTGGGAGACAGAAAGGCTATGCTTTTATTGTC

AACTATCAAAAACTCTACAACTCATTTTGGTCGATTTAATTAAGTTGCTTGAACTTTTCAAAATTGTTGTTGTATCCGTG

TCAGATTCTTTAAAAATGTACTATTTTAAAGATCTGACACATACCCTTCTACATTTTTGAAGAATCCGAGCAATATAGAA

ATAGATTCTGCTTTCATCTAAAAATGTGGTTTAATCTATGATTTTTTGCCAACAATATATGTTGATTTGGAATAGGACAT

ACAATGTGTGTATGTTTTGACCTCGAAATAAGGCAATTTATTCTCTATTAATTTTTTTtAATAATTATAATCTACTCTAG

GTTAGGTTTAGGTCTGCTATTAGACCTTTAATCGTTGTATTAGTTTCTTAAGTTAATGTGTGTATGAACTAAGTCATGTT

CATTATGTCACACAAACTTGAATGAGTCAATAAAGTGGTGTTGGGGTTCCTTTATTCATTTTTTCCACTTGTAGAAATTG

ATACATTAGAGGTTGGTGTGCTTCTTGAGCACGAGTCTATTCCATTAGTTATGTTGTAGTTTTCTCTTCTTCAACCCAAA

TAAAATAGTAATAAATAAATAAATTAAACAAGTACAACTTGGGATATATTACTCGTTTTGTTCCATTTTATATAGCTTCA

TTTCTTTTAAATTTATTCCTATAATAATAATAATAATAACAAAAACATATAAGTGTAATTCCACAAATAAGGTCTAGGGA

GGATAAGATGTACCAGACTTTACCCCTACCTTTGTGGGATAGTGAAACTTTAGGCTAAAAAAAATTATTTGAAGTAAGAT

CGTAAGAAAAATATTTTTAACGAAATATCAAGATACAAAATATTTTATAACTGTATAGTAATGTAATAGACAAAATTGAA

GAACTTTTAGGGGCCAAAAAATGTTTTGTGGTCTTTGTATTTTATACGAGTATTGTACAAGTAGAGATATAAGTGGCCAT

TTTCGAATTATTAAGTAGCTTTATAGAACAAGTTGTCACTTGGGCCCCAATGAGCAATATAGATATTATTATTTTCTTGT

TTCCTTAATCATAATCTTAGCAAGAATCTCCTTATTGGAGGAAGTGAGCAtTTTTTTTTGGTGGGGTCCAAACTTTCAAA

TAGCAAGTTGACATTATATAAAATTCTACTAAAGTACCAACTAGCCAATAAAATAATGAATAAAGAAAAGGGAAGGGGTT

TTGTCCCTTTATTTAATTGATGGTGATTGTGCCTACGATTCTTTGAATCCATTTTTACTTATTTTGAGGTCAAGATGCAT

TCACCAAACAGCTCCTAAAATTCCATGACTGGTGAGTTATCACGTGCATGGGTATTTACTTGACCCGTTATTCCCACTTG

CTCTATCCATTATTATCATCATATATATATAATTTATATCTTAGCCGCCACCTAAAACCAGCCCAATGTTTTTGAGTGCT

TTACTAGTTTTACAATAATTGATGTTTTTTTACCAGACTCCTTTTTCTCCCCTTCTAAGATATTTTCTGAAACTTTTATG

GTCAACTGTTTAGCAGATGATCCTATTTTTATTTGTTCTTGTAATTTATGAACCTTCTAGATAGTAAATTGAAAATCTTA

TAAGAAATGACTTGCTTATGATCTTAAATTTTGTAGACATTAAACAAACTTAAATGTTTTGTTAGTTTCACAGGTTATAT

TTTCACAACTTCTGAAAATAGTGATAAAATTTAAATGATGACTTATATAAAAAAATTATTTAAATCTAGGACTTTTACAT

TTACTGTTCACATTCTGTTCTGTCGAGTGGTCAAATGAAGGGGTTTAAGCACCATAAGGTCCTAGGTTCAGTTCCTAACA

AAGACAAAACACTAGGTAATTTTTTCCCCCATATATCCCATGAAATGGAGCTTTAGTAGATCAGTTCGTTTTGAGCAGAG

GGTCTACCGGAAACAACCTCTCTACCTAACAAGGTAGGGTAAGGTCTGTGTATATCTTGTTGTCGTTGGTTTTATCTTTT

GTTTGAGTAGTAATATTCTAAGTTGCTCGGACTCTCCAAAAATGATGCGCACCCGTGTGGGATCCTTCAAAAATACACTA

TTTTTGGAGGATCCGACACGCACCTGTCAACATTTTGAAAGAGTCCGAGCAACATAGGTAATATTCATACCTAGTCAAAC

AAAGACTTCAATTTAGTTATCGAATGAAAGTCGAACAATTTGATGTGGAAAAGAGAATCTCTTTATGTTATGTCTGTGAT

Figure 8 (Cont.)

ATCCTTTAATTTTGTCAAAGAAGATCTTAATATATAGAGCCAAATGAAACCAAATACTTTTCCATGGAGACTACAAGGGT

CACACTAGAACTATCAGCTTTTGTGGTGACATTTTTGAGTCACACCCACGAAAAGATTCATATCTAATATATTGTAAAGA

TTTTAATTTGGTAAAAAAGACCTCGTTACCATAACTCGTAATATAATTCTAGTTTGACTTGACGTTAGGATTTTCAGTTT

CAATGGGGAGAGGAAGCTATAACTCAAAAGGCGGTGGAGATAGTGGCCGGGGAATAACAAGGCTGAACTCTCAGCTCAGC

TTCACTAGGCAAGAAGCTCTCTCTCAAATAGCAGAGGAAAATGAGGATATTGAAGGGACCAGTATAGCCAATGGCCACAG

AAAGTCAACACATTCTTATGCCAGTGCAAGTAGTTTCGCAATGGGTTCTTGGGAAGATAACAACTCTATAATGTTCTCTG

TCACACCTAGCAAACGAGCCAAGCAGATTAGCAATGACATGGTCAATGGGCTCGATGATGGGGAAACTCAGGTAATATAA

CTGAAATTTTGTGAAAGTATGTTTCTCTGGAGAAATTGTATTTTTAGTTGCAAGTGTTCAAGGGTCATGTTTTCTTTATC

CTGAATTCTGGAGTTGTGCATGTGATATGCCTAACTTTAACAACATTTATGTGAAAAAATGAGATGTCATTTTAATGATG

TTAGCCTTCTAGATGAAAAAATGTCTTGTGCTTTGATTTGGTGACCCTTCAAAAAGCTGACGATTTGTTTTTTCTCTTGC

ATTCTTTTATTCCTAATTCCCTACCTTTCTTCTTTCTTCCAGCTAATATGAACTTGACAGTCACTATCAGAAAACACATA

AACCTTCACTGTTTGACGTCTGTGTTTTCAACATGTCAACGGCGATAGATATACTTCCTCTGCATTTTTCCCCTTAACAA

CCTTACTACTACATTCTGTATGTGTTTGTTTTCTTTCTGCAGAAGAATGTAAATTAAAACAGACAAAATAATCCATGTTG

GCATACTCAATCATGTTTCTCGTGCGCAACTCTCGCAAATATTGATGAAAACTGCATTTTTGTTTCTTGTGAGAGGATGA

ACTGATGTTTTACATTTTTGAATCATTTTCAGTTTCAGTTTGGCTTGTCTCAGACAGCACTAGAAATGGCATCTATGGAT

AGATTGCTGCACATCCCCGAGGATTCTGTTCCTTGCAAAATTCGTGCCAAGCGTGGTTGTGCTACTCATCCTCGCAGCAT

TGCAGAAAGGGTAATCTTCATATTTCTTAAGTCATTCCTTTACTCTTGGCCCTTATAATGAACAAAGAAATAAAAATCCA

ATTGAACTTTATCAATTTAtTTTTCCCTTGCTCCGTTTCATTTTATATGGCTTTGATTGAGAATGACGTTCAAGATACTA

TCTGAAGCTGATGCAATTTGTCCAGCCACTGATTTTAAATGGCAATTTTTCCATTATGTAACACTAGATGTAGTTATCAA

CATGTAGTAGTTGCGGCATTTGAAATACTTTTCCTCAAAATTTGGATCATCATAGCTATGTTTTGtTTTTTCTAATACGT

GATAATGAACATTCTTTTCTTTTCTTTTCTTTTCTTATCTTATGCAGGAAAGAAGAACCAGAATTAGTGGGAAACTAAAG

AAGTTACAAGATCTTGTTCCAAACATGGACAAGGTATAGTTTGCTCATTTCACATTAACTTTTGTGTGAGAGAAGAGTAT

CACGAGAAATGTCTTTATGGTGTTGGAGGGGGATGAGTGTCATTAAGTTTTAAGCCGAACTTGCAGTATAGCTCTGCAAT

TATAAATTATAGCTATCTATGAAGTGCTTCATATACTATAACTCTGTAATCATGTTTGCTTGGAACAAAGAAAATTAGCT

ATTGGAAGTGGCGTGCTATTCAATTGGATAATTGTTACTTGACGTGCTAAAATGCTGTTAAACCATCAATTTATTGAATA

TTTATAGATTTGTGTAAACAAAAAATTAGTCTTTCAGTAATCTTGATTGTATGCTTTCTTTTCTTATGTTCCACTTCACA

ATATTTTCTCAGTTGGCACTTATTGCAACATGCTTGAGCTGCAAATTTTATCGCAGCAAACGAGCTACACTCCAATATTA

ACAATATTTCCTTGTTTGTTTTTGCAGCAAACGAGCTACGCTGACATGCTGGATCTAGCAGTGCAGCACATTCGAACCCT

TCAAGATCAGGTTCAGGTGGGTGATTAAATTGATCAACCTTACTGCTTTGCAGCTTTACGTAATCTATCATGCTGCATGC

ACCTAGGTACAAAATTAAAATACTTATACTCTGTTGCTCAGACTCTTCAATGATACTGTTGGATGTGTTAGATTTTATCC

TCCAAAAGCTATGCATTTTTGGAGGATCAGACACTAGTACAACAATTTTGGCCCGAGCAACACATCTTATATTCTCACAT

Figure 8 (Cont.)

GATGTTTACACCAAACCGAATAATATAACCTTAATGTTTTTGGGATAGATAATGTCTAATATATTTTGCAAAAAAAATGA

TAAATTTTCTAGCCCCACCTTTATAGCTGTGATTGAAGTAGTAGAAACATATTTTTCACATTTTCTTTTTCTTATGCAGA

ATCTGAATACAGAACTTGAAAACTGCAAATGTGGATGTAAGAAATCAAGTCAATAACAAAATGGAAGGAAGCACTTTAGC

TGAAGATCGACTTAAAAGGATTTTTGTCACCATGATTTTGCCTCTTAGAAACTCAAATTTGTACATAAGGAAGTAAATTT

CATACTAGTTTTTTAAAGCTAAAAGGCGAACTCtTCttttttttttttGtTTTtTTTcCtTTTCCAGTTAGAAGACTAC

GTATATGATTGTTTTGGATTATTTGTAGtTTTTTTTTttCCATCTAACATTTACATTTTTAATTTAGTTTTGAGTTTATT

TTGGTTGAGGATCATAAAGCTAATTGATGATGTTGTACAACAACTTTCTCTATTTCATTTTTATGTAAAATGAGTGGGTA

AGACATTTTCTTGCTTTCTGTTATGTTCTTCTTGGAAAACGACCATTTACAATTTTAAAATAAGAAAAGTAAATCTACTC

TACAAGGATTTCATTGTTTTATTTATCGAACTGATCATTTTCTGTGAAAAAAACTCATTTAATTAATATAACGTTTGTAT

TGAGCCACAAAATCGATATTTCCCTTCTTACCCATGTATATCATGAATATATGTGATTCAACAATGCGGCGCTTTAGGAT

ATTTCGATATTTTGTTTATGAACGATGATTTGCTCATTCGGTAAGATTGCATAAGAATTGGGGGATTTTTTTTATATCAA

TGTGATTTCGTATCGTATATCCAAACAAAATTTCAACTTCATATCAATATGATTTCATATCGCATATCCAAATGGGGCCC

CAAATTTGTAAaAAAAAATTATTGTACTTGTTCTATTAATCAAATCTTTCATTGTGAAAGATGAGCAAAATGAATTGAGC

TTGAATAGTTAAGTTGAATAAAAGTTCATTGTTGAACTATTGAAAAAATAGGTGAATAAGGTCATTTGAAAAGTCAGTAA

TTTTTTGTTATTTCACTCAAAAAGTCATTCAAGTTCAAAAATAATTCTCTGTCGGAATCTGAATATGAGAATTATTACTC

TCATGTTTACCTCATAATAATCTGCTTTCAATTTTAATTATGATTGAATCAGAAAATTGAAGATACTAAACAGGCATAAC

AGAAGACAAAAGTTCCAAGTTGGTTTCACTTGTTAACTAACTGTAAGTTATCTTCTTCATGAATTACTTTTACCTATTGA

TACAAAATTAGGGAGTTGATTTCTTAAATGGTCCACTCAACTAATAGTTATTATATTAGGAAGCCAGTTTCTTTGTTGAC

GAAAATTGGAATTAAaAAAAGAAAGTCTGAGATAATAATTACTCCCTCCGTCCCATTTTATGTGGCAACATTTGACCGGG

CACGGAGTTTAAGAAATAAATGAAAACTTTGAAATGTTTACCAAATTGACCCTTCAAAAAATAGTCATATTAAAAAATAG

ACTTACTTTTCTCTCTCCTCATAAGTGTATAATTAAGTGGGATCAATAAGGGTAAAAGAGGAATTGTACCTTTAAGTACT

TACCATATAAGAAAATGTGACATTCTTTTTGGGACTCATATGTGAAAGAGTTCTCAAAAGCTTGAAAATCTAAAAATCGA

TTTTGTGAACCTATGACCCTAAAACCCAAACAATGAACTTGATCCTTCAACACGCAATTACAACTTCAAGCAAACTTCAG

CACACTTTGAAACTGGAGTTCCAAAGTCCGAACAACAACTCAAAAGAGAACAATGGAAGAATTATATTTGATTTTCTTTT

TGTGATAGGGATAAACAAGGAAAAACAACATTATTGAGAGGAAGGTATTTTTGCAATGTTGGACTGCCATGTCAGTTCTA

ATGGCAAAGATAACGTTTTAAGGATGTTTGTGACATAATTAAAAGGTATATATAAGCTATTTCAAATAGTTTAAGAGTAA

TTTTGACCATTTTCCGTATAATATATTATATATGGAATAAGACATAATTCTCAAAGACAATGATAGAGTTGATGGACGTT

TTTACTAAAGCAATCAATAGCAACGAAGCACTATCATTAATTAATAAAGCACTAATTGTTGTTTGCCTACCATTAATTAA

TAAATTAATAATGCAATAATTCAGAACTCATACAATACACATTTCACTATGTTTGTGCCATTGCAAACTCTAATTATTGT

TTGATCTCATTTCCCATCTCTATGTACTAGATATAGACAACACCTTGTAACATAGGATTCGGCTATACAATCAATCAGTT

AACAATCGATTGATCTACTATTGAGCTATTGAGGAATAACAAGAGATTCGATAAGTTAAGATTAAGGTGAGTTCCATTGA

Figure 8 (Cont.)

TTCATAATTTATTTTCATACTAAAGGAAATTTTTATCCTCTAAATCTATATGTCCCCCCTTTCCAATTTAAGTGCTTGAG

TTTGACCAGTGGAAGAGGTTTGGCTTGTTTCTCTTTGGGATAAGGGTCTAAAAAATACCCCAACTTTGGTCGGATTTGCT

GTTGCGATACTAAACTTTCATGAGAACCTATTACCTCCCTAGACTATTTAATACCGTATTTTAAACATATATATTTGTCC

ACGTGACATAAAAAATAATGCAAAATTATAAATAGTAATGTGTCCATGTGGGCACATATATACCTTTAAAATACACTATC

AGGGGATaAAAAATACGGTATTAAATAGTCTAGGGAGGTAATAGGTCCTTATGAAAGTTTAGTATCGCAACAACAAATCC

GACCAAAGTTGAAGTATTTTTCAGACCCTTATCCCTTTCTCTTTTTTCTGTATGTTTCATATGGTCTTCCACTGTAATGC

CCTATATAAGTATCATCACTTGCGTTTGTAGCTTGGTGGTTGTTTTCCCCTTTAATTTTCTATAATCCTTTCATCTAACA

CCTTCTATGCAAATATCTCACCAAGTCCCTCATTGTTCTTTCTATTAATTATATTTGTAACAAGTTAGGTACATATGACT

TGTATGCACTAGCTTGAGGAGAGTGTTAGAATAGGAATAGGAGCACGAATAATATATACAATTCTACTTAGAATAAGAAT

AAAAATAGTATACAATGTAGTGTCCTAGTTGGAAAAAGAGTCGAACATAATAGGTCTCTTGAGGCATTACTAATATCATG

CCTTTTTTCACTGTCATGAAAATTCCCAGTCGCACCCTTTTCACTACATGGAGAATTATTTTGACTAGTCGAGGAAAGAG

TTCGACTACTAGTTGAATTTTTGTGTGCAACCAGTGTCCAGTTTTTAGTTGCATTCTTGTTTTCAACTTGCAAAACATGC

TGCCCAGAATTTTCAGCATCTTCAACATCAGATGTATCCATTAGTTTTTGTCTTGAATCCATTAATTTTTGCCCTGAACC

AACTCGCGGTGCATCAACCCTAACTTTTGGTGTCCCCCTGCGTTTTTAGTTGCATTAGACATCAAAGTCAGCCCAACTTC

TTTTGATTGCACCTCATTAGTAGCAGCCCGTTGGTTATTGCAATCACCTTTATTTTTGGTAGTTGTTTGAACACCAATAT

TACTTGTATCAACATCCATTGAGTCAACACGATTTTGCTCAGAAGTGGCAGCAACCAATTGTCGATCTAAAGAAGTAGCT

TTACTTTGATCGATATCCACAATCTTTCtTTTTTCATTTAGTATTTCTCTCGCATCACCTTGATACTTTTCCTTATCGAT

AGTACCTTTTAAAGCAACTTCAATGGTATCATCAATTTGTTTGTTATTTTGATTTCTTTTCGAGATCAAACGACAACTAT

CTTCATTGTGACCTTGGTGCTTACAATAATTGCAATACAAAGGTAGATTATCATATACAATCTCTTGAtTTTTtTTAGAT

AATACTACTTTTGTCCTAATTTATGTGTCACATTTCATTTTTTAGAGTCAAATAGTTTAAGTTTGATCGAGAATTTGCCC

ATGGAATCTTCAAATTTTTTAAAATGAAAATATACATATTTGTAAACTATGTCAAAAGTATTATAAGTCACAATAATTGA

CAATTCAAAATATTTAAAAGATATATGGAAAATTTATGATCAAAGATAGACTTGTTTGAATCTCGAAATCTAAAAATATG

TCACATAAAATGAGAGCGGAAGTAATTATTAGTTGAGTGACCATATGAAAAGGGTAAATAGGCACTGTTTGTAAGACAAA

ATGGTATATATAAGGGTAAATAGACACTGACACACTGTTTGTAAGACAAAATGGTACAAAATTGCTCTTAATGAAACTTA

TTCCAAGAGTTGGTGAACTTGCAGGAATTTTTCTACTGAAGATGGCTCAAAATGAAATTAAGGAAATTTTAGATCACCTG

AGAAAGATTAAGAGTGGAGGTAATCTGGATAGCATCAAGATTGCTCAAATTGAAGTACTTGAAATTGTGGTAATGTATCA

TAATTTTCTTTTGCCTGATTCCAGAGACATAATCATACAGAAGGCCAATTGGATTGTGAAAATGCATCGGTGGGTATTAG

ATAGAATTCCAGTTCCAGATGAATGTAAAACTAACCTTAATCTAGGAAGGTTATTTTCACATTTGTTCAAATTCTTTGAA

GGTAAAACCAATTTAAGTTACAATTATGAGTTGAAAGATTTTGATCTGTCGAAATATATGGATTTCCTTGGAAAGACTCT

TAATGATGTACTGATGGTTTTATTGGAGGAAGAGGTTAGGTATGACCCTCCTGAGGAAAACCTTGAAATGCACGTATTTA

TAAAGCAACTGAAAATTGTTCAAAAGAAAATGAAATTTTTGAGACACTTATATGACACAGAGATAAATGGTTACATCAAC

Figure 8 (Cont.)

CATGAGAAGCTGGAATGTTTGGAGACTCGAATTCAGTTCATGGCTAACAATGTGGGACAACTCTGTATTGCTGTTTCAGT

TATTCTTTTTTCTGATTTTGTAGATGATACAAATGAGGGTGAGGTTGACAGATATGACACGTATAAGTATTATATCTTCG

ATAAATCTCCATATGTATTATGCTTGATTGTGTTAGTGGAGCTGGAAATGAAGAAGATTTTTCTCAGTGAACTAAAGGCT

TCCAAGTTTACTCAATCAAGAACTTTCAAAGATAAGAAATTACCAAAAGAATTTTCTCATCATCTCCATAGTCTGCTGAT

GTATCTCAGAAACAAAAAGCTCGAGAACTTTCCTAATAATAAATCTTCTCAAAATATTGATGTAGCAATAGAGTTCTTGT

TGGTTTTCCTTGATGCTGATGTGGCAAATCATGTAATTAACGGTAACTGGTTGAATGAGGTTATGGAAAAGGTTTTAGAT

ATAGCGGGTGATGTTCTATATGTAATTCACAAGCTTCTGCCTAGCTCTATAAACAAAGATGACAATAGCAAAATAAGTCT

TTGCTCGATACAGATATTGGAGAAAACCAAAGATCTGAAGGCACAAGTGGAGACGTACTATAAATCCTTCAAATTCACTC

CATCTCAGTTTTCCACTGTTGGTGGATGGAGCTTTCTGGATTCTCTGATACGGAAACTGAATGAGATATCGAAATCTAAA

TCTGGTTTAGATTTCCTGATGAAACCTCTTTTGGAGAATTTGGAGAAAGAGCTATCAGCTCTTGCATCCATTTTAGAGAA

GGATCTGTCATCTTTATCATCCATTTTCAGAGATGTCGCCAAGGTGCACCATGAACATGAAATTCTTCAAGATGTTCACA

GGCGTACTATCAATTTGGCATATGAAGCTGAAGTTGCCATTGACTCTATTCTTGCTCACTATAATGTTTTTTGGCATATT

TTTTGCTCACTTCCTACAATATTAAAAGAGATCAAACAAATTAATGCGAAGGTGACTGAGATATGGTCAGCAGACGTTGC

TCTTAAACCTTGCTATGTGGTAGCACCATTTAAACATCTGCCAACTCTAGATAGCAATCCAGTAACTGATGATGAGATAG

TGGATTTTGGGAATTACACAGAAAAAATGATTCAGTATCTGATTAGAGGTAAAAATGAGCTAGACGTCATCCCAATTGTA

GGCATGGGGGGACAAGGGAAAACGACAATTGCTAGAAAGGTTTACAATAGTGACAACACTGTTTCTCATTTTGATGTTCG

AGCATGGTGCATCGTTTCCCAAACATATAACCGGAGAAAGCTATTACAAGAGATTTTGAGTCAAGTTACCGGTTCCAAGG

ACAAGGGAGATAAGGATGACATCCTTGCTGATGAGTTGAGGAAAAGCTTAATGGGCAAGAGATATCTTATTGTATTGGAT

GATATGTGGGATTGTATGGCATGGGATGACTTAAGGCTTTCTTTTCCAGATGTTGGAAATAGAAGCAGAATCGTAGTAAC

AACTCGACTTGAGAAAGTGGGTGAGAAAGTCAAGTACTACACTGATCCTTATTTTCTTCCATTCTTCACAACAGAAGAGA

GTTGCAAATTATTGCAGAAAAAAGTGTTTCCAAAGGAAGATTGCCCGCTTGAACTACAAGATGTAAGCCAAGCAGTTGCA

GAAAAATGCAAAGGATTGCCTCTGGTGGTTGTCTTGGTAGCTGGAATAATCAAAAAAAGGAAAATGGATGAATCTTGGTG

GAATGAGGTGAAAGATGCTCTCTTTGACTATCTTGATCGTGAGTCAGATGAATATAGTCTGGCGACTATGCAATTGAGTT

TTGATAACTTACCCCATCGTTTAAAGCCTTGTCTTCTTTATATGGGGATGTTTCCGGAGGATGCAAGAATTCCAGTGTCT

AAATTAGTAAGTTTATGGATAGCGGAAGAATTCGTGGTGAACATTGAATCTGCTGAAGATTACCTGATGGATCTCATTAG

CTGTAACATGGTAATGGTTTCAAAGAAAGAATATAACGGTAAGGTTAAATACTGTCAGGTTCATGATGTAGTGCTTCACT

TTTGCTTGGAGAAGAGTAGAGAAGAAAAGTTTATGTTGGCAGTGAAGGGGCATTATAGCCAGTTTCAACCTTTTGATTGG

AATGAAAGTCGAGTGAACTTCCATTTGAGTGAAGAGCATTCCAAATTTGCATCTCTGGGATCCAAAACACGGAAGCCTTT

CCACCAACCGTTGAGGTCACTGATAACGAACCAAAAATCTTTTCATGGGATTCCCTTAAGGTCTTGGATTCATAAGATGC

GGCTTCTTAAGGTCTTGGATTTGAGTTCCCATGAAGTGTGTTATTTGTTTTCAGATACATTGAAAACACTAAATCACCTG

AAGTACCTTGCAGTTTCAGCAGAGAGATTCTATTTTCATCCAGAATCACATCTGCCCCATCTTGAAACTTTAATTGTGAA

Figure 8 (Cont.)

GAATAATTGGACAAATACAGTAGTGTTACCATCATCTTTATGGGAAATGGAAAAATTAAGGCATGTTGAGATTAGGAAAG

CTGAATTTGATAAGCAGGGGCTCTTTGAAGGATCCTCTAAATTGGAAAATTTGAGGATATTAAAGAATATTGTTACCTTT

CCAATTGATAGGGTGGATGTGTTATCAAGGAGGTGTCCTAATCTTCAACAACTTCTCGTCGAATTTGATGGACATTCTGC

AGATTATTTTCATCTCACATTGGAGAATCTTACCCAGCTTCAAATACTTGACCTTTCCTTTAAGGGACCCCACATTGTAT

CTGGGTTACAATTGCCTTCAACTTTAAACAAGTTGGTACTAAGAAGGACTGGTATAGGAAACCTGATTTCCTTCATTGCG

GGACTACCAAACCTGGAGTATCTCCAATTACACAACCAGGATCGTGTTCAAATCAGAGATTGGTGTCTTGGAGATATCAC

GTTCCATAACCTTAAGTTCTTGAAATTGGCGTGGTTAGAAATCTCAAGGTGGAATGCCTCGGAGGAATCCTTTCCCCTGC

TTGAAACACTTGTTATGGAAGAGTGTGACGACCTCGAGGAGATCCCCCTTAGCTTTGCAGATATTCCAACACTGAAACAA

ATTAAGTTGATTAGGTGTGAGAACAAATCTCTGGAGGATTCAGCTGTGAGGATTAAGAAAGATGTTGAAGAGAATGAAGG

AAACGACCGTATTGACCTCATTATCAAAGTAAGTAGCAACAAACTCCTATGTTCTGTTTTTGAGTATCTATATGCATCTA

ATGTGCAAACAATATGTTTAATACAGGATAGGTGAGGAAATCCAAAGCAGCTGTGAGTAAAGTATGTACTTGTCACGACA

ACATGGTAGTCTTTCAGTTTCTTTTCTTGTTCCTTTATGTTTTTTTCGGGATAAAATGCTTGCTTTCTCTTAATTGCTCC

ATGTCGATCTCAAAGTAATGAGGATGTGTTTGAATTTGACAATTGCTCAGAAAACTGCAGCAAAAGCACAAACAGCATGG

ACCGAGGTCACTCTTAGCAAATTGTTGTAACCATGCTCATGCTGGAGTCTATTAGCCAGAACACCCATCCTTGTGACACT

ACTACTGATTGCTAAGGGATTTTTTATTGTTCGACATAGACGACTCATTCCTACTGGGAAGGGAAGGATTATGCCTTGAT

TCTCTTTTTCCAGTATGTTTCAGATGCTCTTCCACTGTGATGCCCTATATAAATATCATCACTTGCTTTTGTAACTTGGT

GGTTGTTTTCCCCTTTTATTTTCTATAACTAGTTTCAGGACACGTGCATTGCACATATATCCCATGTGAATTTTTATATG

ATCCCTTCATCTTTTGTATCTTGATGGCTGTAGCTTGAAAGCTCCGACAGTATAGCGTATGTGTTCATCAGTCACCTCAG

AGATGAAACCACCATCAGCTAACTCCTCAAACTTCACCTTCCTAAGTGATTTTTTTTGTTATTAACGTGCACAAAACTCT

GTTTTCCAACAATATAATTGGAAACTTTCGAAAGCATTGTCATATATACTAACACGTCCATCAGTCACGAGTGGTGATCA

TGATTCGGTGGCCTTTTCTGTCTCTGGGGAAAACATTCATGACGGAATCCACAACGTCTGTCATCCAAGCATCATCCAAC

ATGATAAGACATTTACCTCCTTTGTCAATGAATTCACATATTCTGTAGTGAGTTTGTTGAACACTTTCAGAATACTAAGA

AAGACCCCGAATATCAGGAAATACTCAAAGGAAACCTGAGGGCCTTTAAAGATTTTTATTGCCCATGTCGACTTTTAAAG

TCCAGGCAAGTGCACCACAGGGATAAGTACAAGCAAGGAGGGCTAAACGTCATCTCTAGGGAGGTAAATCATTGGTTCCT

TCAGCAAGTCATTTGATCATTATTTTTGTTGAGGATAAGAACTATATATTACCCATATATTTGACCTTACGTCTTCTATT

AAACATTTTCCCATTTCATTTCAATAAACTTATTTCTAGTTTCACCTAATAGTGATCTCATAAATATATCTTTATTGGAA

TCCAAATCTGAAATCTTTGGTTTACGAAATAGGAGTGCCTAAAAATCCTTGAGTACGTGAAATTACATAGTAAAATCACT

CAACTTAGGAGTTATTTGATGTGAGGTGAACGATATAATAAGTTGTTCGGAAATCATCCCATTTGATTCCATTATTTTTT

TTAAAAAAGGCATATATGTGGCAATTTTCGCTTTGTGCAGATAAGATAACTAGGGAATAATGAAAAAAAATGAGTAACAC

AAGACACTAGTACAGTAAACATGGGGTCAACAAGTCTATGCATTATTTTTCTTCTTTAACCTTCTATGTTACACATGCAA

AACTAATTTTAAGTATAGAAATCATTTACTCGATATAGATATTCGAGAAAACTAAAGATCCGAAGGTAAAAGTGAAGACG

Figure 8 (Cont.)

TACTACAAATCCTTAAAGTTCAGTACATCTCAATTTTTCAATATTGTTACTTTGAGTCGTTTGTTGGTCTATATCACTAA

TAACAATATCAAATTACATCAGAAATGATCTATAGTGACAATTAATTAACGACAATAGATTAACTGTTGAAAATATGTAT

TTTTAGAGGCAATAAACAATCTTTGTAACTGTCTCTAAAGCCAATAGCGACATTAGATCTAAGGATAATTAACTAATGTC

GGTAAAAGCTTTATCACTATTTACTGCCGCTAATAGATGTTTTTGTTGTAGACTTGTAGTGATCATCATCTTTATATTCC

ATGAATAAAAAATTTGGTTGGTAAGAGTAATTATTATATTTGATATAAATGGTCTAATTTTGGTAAAAAATAATAATATC

AATTATAAATTTTGTTTAAATATGAAATAAATGATTGGTAGATATAAAATAATTTATTTTTAACAAAATATAAACTTGTT

AGTTAATTTTTGTATATTAAAAATGTGAAATCATGATACGAAATTTCCAAATCAAGATTTTTGGAAAATTTGAGATTTCA

TCTCATTATTTAAAATCATGAGATAAAATTATATGTTCAAATGTTGATTTCAATTCATTATTTGATGAAATCACATGTTT

AAACACCTACTTAAATAAAGCTCCGCTAATGAGCCAATTTTAAAAATTGAGTTAGGCCTTAAGTGTCATGTGATACAAAT

GAAATTTCAAAAGTCAATCTTTTTTTTTATAAATTCTTTTTGATATTTAAGTTATCAATTATTGTGATTTATAATATATT

TAATTTTATGTATTTTATATAATATCTCTATCTCTTTATCCCAATTTATGTGTTATAGATGAAATTTTGAGAGTTAACAA

AATCTTTTTATATATTTTCAAATATTTTGAAGATATTAATTATTATGATTTATAATATATATAAAGTGATAAAAGACAAT

TTTTTTTAAAAAAGAAAACTTTAAATTGCCAAACTAACCCTGGCTACAAGCATGCATGTTGAAACTTGAGAAGTTATTCA

AAATTTTATTTCTTCTATCCTAATTTATGTGACATTAATAAAATTTTAGAGTGTCGATAATTTTTTAATACTATTTTTAA

ATATTAGTAATGAACAATCATATTATCATTTAAATTTAGCCTTAGTACTGAAATATGAAATATTAAATTTTATTCTACAT

GATCTCAAACACAATAACAAAGAAAGCCTAAAATAACTACAAATGAATACTAAATATGTCTCCAAAAAAAAAATGAATAC

TAAATATTATTGATGGGACGTGTGGGTCTGAGTAAGTGCTAACATCAACACTTTTATGCCTTTAAGGCATTGAAAAAAGC

CTCATATTTCAATATATTTACCAATATGTACCGGTTGATTTCTTGTAAAAAGGTACAAAAGAAGGGGCAAATAAAGCTTT

GAAAAAGTACTGCATTATCAACAAAAGGACACAATAGGAATTAGAGGGAAAAAATCATGAAACGCACAATTCGCAAAGCA

AATTGTATAAGCATTCACAGCAAAGTATAAAGCAGAATTAGATAGTAACTTATCAAAGTATCCTTGTCTAGGAAGCAAGC

ATGTTGACGAACAGTTATCAGGAAACAAAGTCATCCACAGATTGCTAACAAAAAAAAAAaTTGGATAAAACTTCAAGGAG

TATTTTATGAGAAATATGAGAAGTGAGGAGAATTTGATCAAAGAGAGAAAACATAGCAATTGTTCTTTAAAGTTCTACGG

AACAAAATGAAGAAGTGTATGTTTGAAAGCCACGTGGAATATGGATAATGCTCTAAATTACTTATTTGATAGGAAGACTA

ATATACCCTTAGGTGAGAATTTATTTCCAAGAAGCTAACATGTTGATACTGAGCTGCTTCTCATGCTTCTATAATAGTAG

AATAATAATCTAATCAAACATAGGAGGAAAATTTGGGCTCAAAAAGTCTTTTGCACATTCTGTAATTATTATTTTTATCA

TTTATTGTAAAAGAGCATTGTAAAGTACTTGACAAGTGACTCTGTTATTGCTTGATAAGTCACCTCATAGGCCCCATTTG

CATGTGTGATTGCTTTATTCATTTGTATTTTCCCCTTTAATTTCTAAGCAGCACCTGCAAAATGTTAGCAATATGTGTTT

AAAAATCAGAATTACTGATTTCAATAAACTTTGCAGAATCACGAAGTAACTAAAGTTTAATAAACCAGTAAGAATAAAAG

AACATAAATTAATTGACAAAACTAAAATCTGTAAAAAACGTACCACAATCTGAAAAAACAGAATCAGAAAAAGATCAAGC

CCACTGAATGCACAGTATTCCCTTAAGGAAATTATTCCCCTCTAGTATTCGAGGTTTGATTTGGAATATGTCCACCCAGA

ATAGAATGATCTCAATCACCAGTGTATTGATACCCAAAACTCTGGTGTCAGCGAACCACTTTACAGCAGTAAAGTACACG

Figure 8 (Cont.)

AAAATTTTTTGTGCAAAAGAAGAAGAAGAAATCAGAAAAATTCATTAGGAATAAGTCCGAGGAATCAATGTATTTATAGG

GAAGAGGAACTGGTTCCGAAAGGTTGTAATCCTTTCAGAATCCACACGACCATTCATGAAAGTTTGCAACCTTTCAAACG

GTCATGGCTGTTTCTGAAAGTTGCAACCTTTTAGAACAGTCACTTCCAACGGTGAAAAATTCAAATAAAATGGGAAAGAT

TTAAATTAAACGGATCGCGCGTGGATCCGAGTCGGGTCGGATCAATTAACTAATTAATTGAATCGGTTAATTAACTAATT

AAAACGTTGGTCATTTAATTTAATTAATTCAATAAATAATTAACAAATTTTGTCCAAAAAATAATCTCTTGATCATTTTC

CGAAGCTGAAGCCGAGCGAGCGACGACGGCACGAGGGAGGTCCCTCTTTCCAACCCTTTTAACAATTAATAGGAGTGTTT

CTATATTTAAACTCTCATATTTTTCTTTCCACCACAGATGAGGGACAAATGCCTTTTCAATAAAGCATAAAAAGACTTTT

CAAGTTCTCAACTCTTCAAGTTCCCAACTTTTCAAGTTCCTCTCTTCTCATCTTTCCTCCATTTTCCATTAAGTCTTGCT

ACATACCCAACACAAAATTCATTTAAGGAAATACCTACTGAAGTTATTTTCTGGTTGAATATAACACCTTTCATTAATCA

TCAACTAACAAACATAATATTTTAGCAGTATAAAATACTAAAGGTAAATTAAATATATATGGAAGAAAACTTCAATAGTG

ACTTTAGTGAGATCAATACTTGGATGACCGTATAGGGAATTAACTCATATTCGAAAACTAAACTGATGGATTTGTTTACA

AAGAGTATTACCTCAGGAAATGTTCGAATCTCTCAAGCAATAAAGTGGAGTTCGATTCAAAATGCCAAATGGTGTTTGAA

AAGATAGCGTTTTAATTCATGGCCTTTCATTTACTTGACAAGTTACCTCATGGTCCATTTGCCTGCTTGAAGAATAACAA

AAAGTAGAGTTCTTTTGTACCAATATTGTCTCATGGGTCATATTCATGATTAAAGTTTAGAAGGTAACAACTTCAAAAAT

AGCATTAAATAAATGTTCCATTTAATTTGTTATAACTAACATTTATGTCTCTAAATATGCACTATATATCTTTCTTTTCA

CTTAAAAGTTTGCGTTTAGATATACGGTATGATTAAAGTCATGATTTCAAATCAATATTTAAACATGCGCTTTTGAATTA

TGATTTCAAATCCCAAATTCTTCAAAAGAGAATGACTTGGAATTTAAATTATATTAAATATAAAATTTGATACATAATTA

AGTTTATATTTTTTTTTaAAAAAAAAGATTCATCATTTTAAATTTTGCATAAAAAAACTCATGTTTGTCGTGAATAGATT

GTTCGTACAATGCAAAATGATTGCATGAATAGCTAGTTACTGCTATTGGAGATAGTGGATTTTTATAAGATTATATGTAT

TTGATAATCACAAACATCTATTTATGAAAGGAACATGAAGATATATGATTCATTAATGTGGCACTTTAGGATATTCCGAT

ATCTTATTTATGAATGATAGTTTGCTCATTTGGTAAGAATGCATATTTTTGAGTAAATTTGAAGATTTTCACAGCTTGTT

GGTTTTTCATGTTTATGCAAAAAATACAATTTAAGAAATTAAAATTGCATGTCCAATCAAAACTTCAACTTTATATCAAT

ATGACTCCCTACCATAATTTCATATTGCCTCTCTAGCTAAACGAACCCCAAATTTGTAATTTTTTATGTTTTATCGTACT

TGTTCTATCATTCAAATCTTTCATGGGGAAAGATCAACAAAATGGATTGAGTTCTACACATTACATGCATAGTAAGGTTG

AACAAGAAATTCATTGTTTAGACGGTTGTTGAACTATATATAATTTAGGGGGATTTTAGTGTATTTTCCTAGAAAAAGAC

AAATAATATACCTCCTTTGTCCCATTTTATGTGGCACATTTTCTTTTTAAGTCCGTCCCAAAAAGAATGTCAACTTACTA

TAATTAGAAATAATTTCACTTCAAATCTTAATGAAATGATTTATAACCACAAAATTCAAAAGTCTTTTTTAAAAATAGTG

TATTAAGTCAAACGGTGCAACATAAAATGAGATGGAAAGAGTAGCTGTATTATTAAGCTACGTTACAGATACCACCTAAA

ACAACTTGCTAGTACTACAATTCATCTCTTCCTTCTTCCTTTAAACCCTCCTCCATTTCATTTCAATAAACTTCCTCCAA

TTTCTTTGTTGGAACATAATCCAGATCTGAGAATTATAACTCTTTTTTTACCTCATAATATTTGTTTTTTCTCTTGATGA

AACCTGCTTTCAATATTAATTATCATCTCTTTTGCTCCTTTTTATGATTGGATCACAAAATTGAAGATATTAAAGAGGTA

Figure 8 (Cont.)

TAAGAGAAGACAGAATTACAAGTTGGTTTCATTGTAAGTCATCTTCTTCATGAATGACTTTTTTCCTATGGATAGAAAGT

TGATTTCTCAAACAGTCCACTCAACTAATTGTTACTAGTATATTAGCTAGAAAGCCCTTTTTTTTTGTTGTAAAAATGTG

ATTTTTCTTCTATGCATTGTTTAATTTTATACAAGTTAAATGTTTATTTATGCACATCCAAAGTTAGAGGGCATGAATAT

CAAGTTAAAGAATATATGTATGTATTATGCCTCCAACAAATCCTTGAAGTTCTGTATTCCATCTCAGTTTTTCAACATTG

TTAATTACTTTGAGTCGTTTGTTTTCAATATCATTGATAACTATATCATCATGTTTATATTTCATAAATAAAAAATTTGG

TTGGTAAGAGTAATGGTTATATCTGATATAGATGGTTCAAAGGTTGGTAAGAATAATAATATCGATTATAAATTTTGTTT

ATACATGAAATAATTAAGTGATTGATAGATATAAATGACTTTTTTCTTATAAAATATAAAGTTATGGGTCAATTTTTATA

TATGAAAAATGTGAAATCATAATATGAAATTTTTAAATCAAATTTTGGAAAATTTTGAATTTCACCTCATGAGCTAAAGT

TGCATGTCCAAACATTGACTTCATCTCATGATTTCAATTCACGAGATAAAATCGCATGTCCAAACACCTACTTAAATAAT

ACTCCCCCCCCCCCTCCTTCCCCCCATGAGCCAATTTTAAAAGTTAAATTAAGCCTAAGTATTAGTTGATCATCTTACTA

AAATTAGTTGTCCATTATTAGTTGTTCACCTTACTAAATCAGAAAAGTATTAATTAAAATTTTCTTATATTACCCTTTCA

ATTAATTTTTTAAAGTATTCACATTCGCTTATAAAATATCAAGAAATTTTTTAAGGGATAAATTGGTAAAATTATTTTTT

TATTTATAATTTCTTAATATGCATGCGAAAGATAATTTTATTAAAGTAAAGACTAGACTTCTTTTGTACCAATATAACAA

GTCGCCTCATAGGTCATATTCATAATTACAGTTTAGGAGGTAAAAAAAATCTTTTTAAAAGGCATCTCGGCGACTGAGAA

CCATAAGGTGAGCGCCAAAACGCTAGCACCAACTGCTTCCACAAACATGCATGATAAGGGGGTGTGGGGACAACCAGGCC

ACCACTTTATTTGAAATATGAGCCGCTAAAATTTATCCCCTTTTGAATGTATTTACCCCTATGAACCTGATGCATACAAA

ACTTCAAAAGTAATATACGTTCTATTTTAGTTGATCATTTTTCACACACATATTAATAATCATAAATAGAAAGATAATTT

TGTTAATTCACCCAAAAATAATTCGTAGAATTTTTTACAAATAAATGTGAACACTTTCAAAAAGAATAAATTACAAGGGT

AATACACGAAAAATTTAATTAATGTTTTCTTGATTTAGTAAGGTGGAGTGATGAACAACTAATATGAGACAACTATTTTT

AGTAAGATGGTCAACTAATATGGGACGAAGGGAACAATACATAAATGCATGTTTCTTTTAATTTGACTTCAATTGATTTT

TATGTCTTTAACTTTGATTGTACACAATAATATATCTTGTTTTTCACTTGTAAGTTTGCGCTTGGACATATAATATGAAC

TCATGATTTTAAATTCCAAAcTCCCCCCCCCCCCTCCCCAAAAATAAAACATAATTTGGAATTTCAAATTATGATATCAA

ATTTTGTAAAATAGAAAACTTGATCCATAAATTTATATTTTGTAAAAAAAAAATAGGACTCGTGCTCAACGTGAATAGAT

TGTCCGTACCATGTGAAAGGATTATATTAAGGAATAACTAGTTGATTAATTAGTGGATCGTTATAAGATTAATCGCATTT

GAAAGTTATTTATAATCACAAATATTTATTCAAGGAGATATGTGATTCATCAATGCGTTGCTTTAAGATATTTTTTTATC

TTGTTTATGAATGATGATTTACTCATTTGATAAGATTGCATACGAATTGGAGAAATTTTGATAATTTTCACAACATGTGG

CTTTTCATGTTTATGAGAAAAAAATATAACTTAAGAAATTTCAATTGCATATCAAACAAAATTTCATCTTCATATTAATA

TAATTTCATATCACCTGTCCAAATTAAACATGCCCCAAATTAATAATTTTTTACTTTATTGTACTTTATTCAATTTAAAA

AATAATTCATCCGACTACTTTTTAAGGGGTACCTGCAATCTCAACCAGCTAGCTGTTTTCTCATCATTTCCATAGTCTGT

TGATGTATCTCAGAAACAAAAAGTTCGACAACTTTCCTAATTATAGCACTGCTCAAAATATTTGTGTAGCAATAATAGAG

TTCTTGGTTGTTTTCCTTGAAGCTGATGTGTCAAATCATGTTATTAATGGTAACTGGTTGAATGATGCTATGGAAAAGGT

Figure 8 (Cont.)

TGGAGCTATAGCGGGTGATGTTCTATATGCAATTCAAAAGGTTCTTCCTAGATCTATAAACAAAGATGACACCAGCAAAA

TGAGTCTTTTCTCCATACATATATTAAAGAAAACTAAAGATCTGAAGACACAAGTGGAGACGTACTATAAATCATTAAAA

TTCACTCCATCTCAGTTCCCCACTGTTGGTGGATGGAGCTTTCTGGATTCTCTTATACGGAAACTGAATGAGATGTCGGA

ATCTAAATCTGGTTTATATTTCCTGATGAAACCTCTCTTGGGGAATTTGGAGAAAGAGCTATCAGCTTTTACATCCATTT

TAGAGAAGGATTTGTCATCTTTATCATCCATTTTCAGAAATGTCGCCAAGGTACACCATGAGAATGAAATTCTTCAAGAT

CTTCACAGGCGTACTATCAATTTGGCATATGAAGCTGAAGTTGCCATTGACTCTATTCTTGCTCACTATAATGTTTTTTG

GCATATTTTTTTCTCACTTCCTACAATCTTAAAAGAGATCAAGCAAATTAATGTGCAGGTGACTGAGATGTGTTCAACAG

ACGTTGCTCTTAAGCCTTGCTATGTGGTAGCACCATTTAAACACCTGCCAACTCGACATAGCAATCCAATGACTGATGAG

GAGATAGTGGGTTTTGGGAATGATACAGAAAAAATGATTCAGTATCTGATAAGAGGTACAAATGAGCTAGACGTCATCCC

AATTGTAGGCATGGGGGGACAAGGGAAAACGACAATTGCTAGAAAGTTGTACAATAGTTACAACATTGTTTCTCATTTTG

ATGTTCGAGCATGGTGCATCATTTCCCAAACATATAACCGGAGAGATCTATTACAAGATATTTGTAGTCAAGTTACCGGT

TCCAAGGACAAGGGGGATAAGGACAAGGACAAGGGGGACAAGGACAAGGACAAGGACAAGGGGGATAATGATGACATCCT

TGCTGACGAGTTGAGGAAAATCTTGATGGGCAAGAGATATCTCATTGTATTGGATGATATGTGGGATTGTATGGCATGGG

ATGACTTAAGGCTTTGTTTTCCAGATGTTAGAAATAGAAGCAGAATAGTAGTAACAACTCGACTTAAGAAAGTGAGTGAG

CAAGACAAGTACCATACTAATCCTTATTCTCTTCCATTCCTCACAAAAGAAGAGAGTTGCAAATTGTTGCAGAAAAAAGT

GTTTCAAAAGGAAGATTGCCCGCCTGAACTACAAGATGTGAGTCAAGCAGTTGCAGAAAAATGCAAAGGACTGCCTCTAG

TGATTGTCTTGGTAGCTGGAATAATCAAAAAAAGGAAAATGGAAGAATCTTGGTGGAATGAGGTGAAAGATGCTTTATTT

GACTGTCTTGATCGTGAGTCGGAAGAATATAGTCTGGTGACCATGCAGTTGAGTTTTGATAACTTACCCAATTGTTTAAA

GCCTTGCCTTCTTTATATGGGGATGTTTTCAGACGACGCAAGAATTCCAGCATCTAAATTGATAAGTTTATGGATTGCTG

AAGGATTCGTGGAGAACACTGAATCTGCTGAAGAGTACTTGATGAATCTCATTAGCAGTAACGTGGTTATGGTTTCGAAG

AAAGAATATAACGGTAAGATCAAATACTGTCAGGTTCATGATGTAGTGCTTCACTTTTGCTTGGAGAAGAGTAGAGAAGA

AAAGTTTATGCTAGCTGTGAAGGGAAATCGTAGCCAATTTCAACCTTGTGATTGGAAGGAACTTCGAGTGAGCTTCAACC

AAACACGGAATCCAAAACACAGAAACCTTGTGATTGGAAGGATAGTCCAAGAGCATTTCAACTTTGCATCTCTGAGATCC

AAAACATGGAAACCTTGTGATTGGAAGGAAAGCCAGGTGAGCTTCAACCAAACACCGAATCCAAAACTCGGAAACCTTGT

GATTGGAAGGAAAGTCAAAGAGCATTCCAAGTTTGCATCTCTGGGATCCAAAACACGGAAACCTTTCCATCAACAGTTGA

TGTCACTGATAACGAACGGAGAATATTTTGATGGGATTCCCCTCTGTCAGATTCATAAATTGCGACTTCTTAAGGTCTTG

GATTTGAGTTCCCATAGAGTGAATTCTTTGTCATTAGCTAGTTTCAAACCACTAAATCACCTGAAGTACCTTGCAGTTTT

TGCAACTAAATTTGATTTTCATCCCGAATCACATATGCCGCATCTTGAAACTTTAACCGTGAATAATGATTGGGAAAATA

TAGTAGTGTTACCAACGTCTTTTTGGGAAATGGAAAAATTAAGGTATGTTGAGATCGAATATGCTGAATTTGATAAGCAA

GGGGTCAGTGAAGGAACCTCTAAATTGGAAAATTTGAGGATATTAAAGAATATTTTTAGATTCCCAATGATAGTGTGGAT

GTGTTATCAAGGAGGTGCCCTAATCTCCAACAACTTCACATCGGCTTTGGGGACTATAATTATTCTGCGGAGTCTTTTTG

Figure 8 (Cont.)

TCTCACATTGAAGAATCTTAGCCAGCTTCAAAAACTTCGCCTTACCTCTAAGTGGCGCCGCACTGTATCTGGGTTACAAT

TGCCTTCAAATTTAAAGATGTTGGTACTAAGTGGGACTGATATAGGAAACCTTATTGCGGGACTACGAAGCCTGGAGTAT

CTCCAATTACAAAATGTGTATTTTCCTCCTTCAGAAGAGTGGTGCCTTGGAGATATCACGTTCCCTAAACTCAAGGTCTT

GAAACTGGCGGCGTCACATATTTTGAGGTGGGATATCTCAGAGGAATCATTTCCCCAGCTTGAAACACTTGTTATAAGAG

GGTGTAAGAATCTCGAGGAGATCCCCCTTAGCTTTGCAGATATTCCAACACTGAAACAGATTAAGTTGATTCGCTGCAAT

AAATTTCTGGAGGATTCAGCTGAGAGGATTAAGAAAGATGTTGAAGAGAATGAAGGAAACGATCGTACTGACCTCATTAT

CAAAGTAAGTAGAAACAAACTCATATGTTCTGTTTTTGAGTATCTACCTGCATCTAACTTGACAGCAATATGTATAATAC

AGTATTATTAGGGTCATTTGGCAGCTGTGAATCAATTATGTGCCTGTAATCACAACAATGGTAAATATTGTTTCTGTTTT

TTTCTTGTTCCTTCTTCTAATTTAATGTTTGCTTTTGCTTAATTGCTCCATGTTGATCTCAAACTAACAAGGATGTATTT

CAATTTGATAATTGCAGCAAAAGTACAGCCAATTGTTGTAGCCGTGCTCATGCTCATGTATATTGTGCGCCTAGTGCCGA

CATCCCTGTCCTTTTTCTGTATGTTTTAGATGTTCTTTTACTGTGATTTCTTGTTGCCTTTTATAAACATCATGCCTTTG

TTATGTAGCTTTATTATTTTACAACCTGTCAAAACATTGCTTCTTGTTTGTTTTTGTAATATAGTAGTTGTTTCCCTTCA

TCTTACTCCTATACAAGGTGAATTGAAAGATGAGTATTCCTGAATGAAAGCTGTTTTGATAGCTTAGTACTAAATAGTTT

AGGAGCAATCCATAACATACGTCTCACTTCATAAATAAGTATTGAGTACACGTACAAAAGCTATCTATGTTGTTTGGACT

CTTCAAAAATGTCTTCCGAGTGTATATTGGATTGTCCATTTTACATTTTTGGAGGATCCGACATGGGCACAATAATATCT

TTGGAGAGTTTGAGCATCATAAGAAGCCAAATAGATAACACTTGTCAAACCTCTATTCAGCTTTCTAGGGAGGACAATGG

CAGAGTCTCCCAAGTTGACGACATGTATGCATGTCTCTCACCTTTGACAACATCACCAGAGGTATACGATTCGAGTTCTT

TCATGTCTTCCGTTGTCAATTTTACAGATAAGGCTCCTATGTTTTCGTTGAAGTTTTCAATCTTCGATGCACCTGGTATA

GGGCATACATCATCTCCTTGATGAAGAACCCATGCCAATGCTAATTGTGAAGGGGTGCAATTAGATTGATTTTCTCAAAT

ACTGGCTTTATGCTCAAAATTCTCTGGCTTGAACCTAGAGAAATTCTACAAAGCAAATCAGCAAATAATAAATTAATGTT

GCAGTCGAAATAGAAAGATTCATTGATGAAACCATTACATAGCTATATATATATTTCACGGAGCAAAAAGGTTGTGCCAA

AAAATTTATCCGTTAAATTGTGCGTTAAATCAGTCGCCAGATGCATCTCATGAAATGTTCAACGAAAGGGCGAGTGGGAA

GTTTAGGAGAATTTTTCCTGAACTTGGAATAACAACTGCAATTATAACTATGCCTCAATCACAAATAAGTTGCAATCGAC

TATATGAAATCTTGATTTCTCCACTTAAGTTCAACTAACGTCATCATCATACCAAATAAAATAAAAGCAAAAAATAAGTT

AAATATATAAAACAATATTAGAAGTTCTTAGAAAAAGACTAAATCCTACTCTCCACGGCTAGATATCTCCTATATATGGT

TCTATGTCTTCTATTGTGCCATATTTTTTTGCTAAGTATGCATTTATCCTTAGAAATTTGTAAGTATTTCAAAATTCTAC

CTCGTCTCCTTTTCAACACCTCCACTCGCCTTAGTTTCACACCTACAAACCAGTGCATCCGTAGGTCGACACAAGACATG

TCACACCATCTCAAGCGCACAATGCTACTTGCACTTCTAGCGAATATGGATCATTTTAAATTTTATTTAATATTATATGA

TCGCATATCCATCTTAGCAGTTGGTCAAATTACTGCATGCTTGGTAAAACCAGATTACTCCATGCTTAGTTAGTGTCGGC

CTGTCGGGCAGTTTAATTCAAAGACATCAGCATGTCCATAAACCAGTAGAATTTCCAGATTTCAAGAAGACTTAAGATAA

GGACATCCAGTTGATGCTCTCTGTAAAACATCAATGCACAAAGAAATAACAGGATACTAAATTCAAATGCAACTACAAAT

Figure 8 (Cont.)

ATCCAGTTGATGCTCACTGCACATTCGTATAAATGTCTATTAAACAGGAAACACAAAAGCAGTCACAGTTTTGATTTATG

TGGTCTAACCTTGCAAAAGTCACCATCAGGCAAGATTTCAATCAACTTTGCCCCTGCTGAGAAGAATCCTCGTCCGAGAG

GACTATAGGGGACAATCCCTATGCTAAGGTCAAAAAAATCAAAAACTGCTAATCTTGAACTCAAATCTAAAATAAAAAAT

GTAGAAAGGAAAATACTTGTTATTATTTAGATACAAAAATTTCATACTTTCTTTTAACAGACACAGTGTCCCAGCTAGCT

TGCACGAACCTCAATCATTCCAAGGGGTACCCGCAACTCTATCCACCAAATATTAGATAGCTAGGAAGACATCACCTAAT

TTATACCTTTACTATCATTTGAACTTGAAACCTCATGGTTCTCGACCCCTATCATCCACAACTAGCCAAATACATATCAC

TCGTCAAACCCCTACTCAGCTTTCCAGAAGGACAATGGTGACGCGCATCTCTGAATTTATCCAACAAAATAAGATTTACC

AGTGTCAATTATAAGACTCTAAATAAGTAGAACTGATTTATTTGCAGTAAGAACAACAATGTGATTAATAAAGGACAATG

TGAAAGTTCAGGTAGTCAATTAATTAGTTTTCTCTGTAGCCAACTGTCCTCTCCTTCCACACACTTTGATTAATCATTAA

TAATAGATACTAACCTTCCAATTAATTAGTTGTCTCTCTGTAGTATATCATAAGCCATGTTATTTCATTAAATAATGCAA

CCATTGACTTTGAAAGCCAATGGGAATGCATATTAACCTGTCTAAAAATTAATATGATAAACCCAAAAATTATTCATTAA

ATAATACAACCATTGACTTTTTTGTAGGATTTAGATCCAGTCCTTTGGCTAAACCATAATTATACATCCACTAATCTTGT

TAGAGTATATGACACAAACATTTCCTCATTGTTCCAAGTTAATTATGCTCATATTAATCTTTTCTTGTTAGCTTAATCCT

ACTCCAATCTTTATCAGGTATTTTTCAATAAACATTTTTCTAATCTCCCTATGAATTTTTATCCTTTCTTATATATAAGT

TATCAACAACTCTTTTTCTATGATTGGATCAGAACTTGGAGATACAAAAAGGCAAACGAAGATCGATTGATCGACTACTC

GTCACGCTTGAAATTAGTAAGATATATTGAATGTTAACTTTCTATTGCTCTCCAAAATCTCGAACTTCTTAAATTGATAC

AACAACTGAGTTATTAATCCATTTTACCAATAAACTTCATGGTTCCAAAACTACAAATATTGTGAATATGGTTTTGATGT

ATATTAATGTAGACATTTATGATTATCTTGTATGAAACAATATGGCACTTCAAAACACTTGTGTTTTTATTCCTTATATG

GTTTAGATAATTAAAAAATGATATCACCCATAATAATTAGTTTTTGCTCCGTTGAACCAGTTAAAGAAGTGTTTTATATT

TGTTTTCCTCTTTAAATTTCTATTTAAAAAAAAAGTGATCAACAGCAGATGGCTGGTTATATGTTTTTATATATACAAAT

TGGGGGTAGGGATTTAAACTTAAGGTGAAAATTCTGATATCCAACCAACTGAGCGACTAATCGTGCTATCCTTCTCCACA

CACATTTTTTTTTATTAATCATTGGGTATGCATTAGTTATTTCTCTGTACTAGTAATTAATAGGGAAAAATTCGCTAAAA

TATGTCATCCAACTTTGAGAAAAAACAAACCTCATTTATGTCGTCCATTAATAGTTGGGTTCAATCATGCCTTTGTCATT

ACATAAATGACCCATTATGCCATTATTTTTTAATATTCAGATTTTGTGGTTTTGCAACACCATTTTTCCATATGGCCTCT

TATTAGAGGTCCACGTCACCAAAATTAAACTGGTCAAAAAAAAATTCAAATATGTCATGGAACTGTGACAAACGGTTCTA

TGTCATTCGTTAATTGTTGGATCCAACCATATCACAGCCGTTAAATTTGAAATTAAAATCCAACCCATTAATACCAGACC

CGACCCACCCTAACCCATTTCCCTTTTATTTCTCCTACAAACGCTTGGATCCAAAATTTCTCCCATTTTAATGATGAATT

TATATGTCAGTTTCTTGTCAATTGATCAATTTAAGGGTCTGGGGAGAAATAAAAAGGGAATAGGTTAGGGTGGGTCGAGT

GTGAATTTATGGACCAGGTTTTAATTTCAAATTTAATTAAATTAGGTTGGTTTATTTTGGCACGTGGACCTCTAATAAGA

GGCCACGTGAAAAAAAAAAAATTTGCGAAATGATCAAACCTGACCATTTAAAAGTAGCATGAATGGGTCCCTTCTGTAACG

ACAATGGAATAGTTGAGCCCAATTATTAACAGATTGCATAAATAAGACCTTTTTTCTAAGTTTGATGGTGCATTTAAATT

Figure 8 (Cont.)

TTTTTTATCAGTTTAATTTTGGTGATGCTGACCTCTAATAAGAGACCACGTGGAAAGAACGATTTTGCTAACCATCAAAC

CAGCTGCCTGTTAAAAAATAATGGCACGAATGGACCGTTTGTGTAAAGCAGTGACATGATTGAGCGCAACTATTAACGGG

AGGCATAAAAAAGTCTTTTCCCAAAGTTTGATGGCAAATTTTAACTCTTTTACATTATTGTTAACTCAAACACAATTTAA

AGAATTTTTATGTGATTTTTTAATAGTTGATATCTAGGCACGTGCAACGATACTAGTACTACTATATTATAATACCTAAG

TGTTAGTCAAAGCAAGTATTGTGAACATAAAAGCTACGACAATTGTATGGAATATGATTCCCTTTTATAAGTGAGGAAAT

TCATTTTCTCCCTTTTAGATGAAACTTGTTTCAATTTCTCGACTTCCATCACAGTTTAGACACACAATAGATGAGCTTGA

GATCTAAAAATAAGCAATTTTAAGTTGATGTTTCATTTTCCATTTCTATATGTTAAGTTAGTCGGTAGAATAATTATAAT

GACCATCTTGTCAGGGCCAAGTTTTCGTGATATGCATCGTGGAGCTCAAAAGTGTAGTGAACTTATGTTCTGTATTGTCA

CTTTTTTTAAAAACTTATTTGGGCTATTCCTATGTGTGATTCAACTAAGATGCTTGTCAATCCTTTTCTTTGACCTGTTC

TTATCGGTCCACCCTCCATCATTAGCGTCACACATTTGATATTAGTTTTTTTTGTTTAAAGAAAATGACTATTAGTTGAG

TGACCATATGAAAGTTGAGTGAAATGTGATTTTATGAGATAATATGTCACGCCCCGAGCCTACACCCTGGGCGGGACCGG

CACCCGGAGACCATTCCTGGCCCCAAGCGAACCCTTGGCCTGGCTTTCTTAACTCAGCGGAAACCTAACTCAACAGAATA

ACTCAATGCGATGCAATATTGCAAAACAACTTAACATAAAAAGTATGGCCATAAGGCAACCCGAGTCTCAAAATAGGATG

TTTACATATATACATAGATAAGAGACTTAAAACTAGCTGACTGACTGTCTGTCTGTCTATGAAGCCTCTAAAAAAAAATA

CTGAGATGGATGTTGGGACAGACCCCGCAATATCCTAATAAGACAAAACTAAGAACACAAAGTAATTGAGTCCTCCGGAA

TGCAAGGAGGCTCACCACTGACTCTGGAGTGCTCAGCTGGATCAACGACGTACAGGATGCTGATCCGGGGTACCTGAATC

TGCATCATCAAACGATGCAGGCCAACTGGCATCAATACATGGAATGTACGAGTATGCAAGATGGAAAACTAAGCAACAAA

GGCTAGAAGGAAATCTGGAAGAAACTGAACAACTTACCTGGCTCAACTCAACCTGACTGACTTCTTTCAATATAAGGCAA

TTTAAAACAAGTGCGATATAAAGAAAGACTGCTTAAAACATGCTATAAACTCTGTGTGTATACAAAGATACAATAGGCCT

GAAATGTATATAGAAATACAATGAACTGATGTATATAAAATACAATAACTGTAGTGGGAGTTTCTCTAACCGACAACCAT

CACATAAGAGCTATAGTGATGATACAGCGATCGACCTCACGCTGCCAGAGCATCTTATACCCGGCCAAAGGTATAAGACC

TGAACTGCCTAATGGATCCACTAGTCTAATCTGAAAAGGATTCATCTAAAAAGTATGATCCTTTTCTACCCATGGTGGCT

AACATGGTTCTATGGGGGCTGTGGGTTCTTTGAACGCTCCCCCAATTCGGTGCTCGATACTACTCCCAAAATGTACTGGC

TCTTATGTTTTTAAAACATATTTATTCCTGCTGATATGAGATAATTACTCAAAAACTAGCCCGAAGGCTCCTTTGGAAAT

CTTAGTTTCCAACCTTGTCTAAATGTAAAAACATTTATTTAAAACTTCTTTGGGAATACATAGTTCCCCAATAACTTTGA

GAAAAGAACTCAACTTTAAACTCATGACTTAACTTGAAACTGAGACTCTTACTCGACTTGAAACTCTATACTCTTTTACT

TGACTTCTAACTATCTTTCCTTGAATCGGAACTATGAATTCAAGGGATTCGATCACATGTTGAGGAGGGATCCTTGAACG

CTTAGACGTACTTAGGAGTGTCGGAAACAACTATAAAACATAGGTATAATACTTGGAACTTGCATGAGAAAGTGAGAAAA

GGAATGGGGAAACTTGGCTAAAACTTCAGATTTCTGGTGACACAGGTGTGACTTACGGACGCCATCGACGGACCGTAGAT

GGACTTACGGTCCGTCCTGCAGGTCCGTAGATCGCTTCAGAAACTTCCCCAGAATTCATTTCAGAAAATGACTAAGTGTT

GACCTACGGTCCTGACTTACGGTCCGTAGGTCAGGTCACGGACCGTAGGTCGTGACCGTAGATCGAAGCCCCAAAAACCC

Figure 8 (Cont.)

AACTTCTGTTCCGATTGACGGTTGACCAGTACGGACCGTCAATCGATCTACGGTCCGTAGGTCAGGCCCGTAGACGGGAA

TCATCAGCCCAGAAATTTCTGTGAAATAAGGATGAATCAACTTCACAAGGGTCATAACTCTAGAATCATAATTCCCTCAA

CATACAATAGGTTTCAACTTAAATACTCGACCCCAATCATGTCTCACGAAGAACAATAACTTCAACAACAAATTCCATCT

TTTCTCAAATCATAGAATAAACTTGGTGTGTGTGAGGGAAAGGATCAACCCACACGAAAACTCACATACCTTGATAGGGA

TCACCCCCGACGAAAATCCACAATGATCTTGTTGATCTCCTCTTTCTTCTCTTCTTCTTCTTCTTCTCCTTCTCCTTCTT

CTCTTCTTCAATCTCAAGAACCCTAACTCTTTCTCTTTCAAAATGGGACAAAAATGATCCAAAGATCATTCTAATACAAC

AATATGAGCTCAATTAAATGATTTGTGAAAGGACCAAAATGCCCTTAAATTTCCGGACGGATTTCCCTTCCAACTGCCCA

ACTTCTACAAAGCATAACTCGCTCATACGAACTCGGAATCGAGTAAACTCAGTGGCGTTGGAAAGATTGTTCCAAGGGCT

TCGCAACCATAACTGGAACTACTCCTAAATCATCCTGGGCTAGGAGTTACGACTACTCAAAGTTGGCCAAAAACTCATTG

ATTTCCACACTTAGCCAATTTTTTCCAGATTCGTCATTTTTTCCAAAAATGACTATTTCCAAATTTCAAGCTCCTTCTAA

GCCACTTCAAATTGTCGGATGTTACATAATATGCACTATTTGAATTAGATGAAATGGTACATAAAATGTATTATCTTTCA

TAAGCATTGACATAGCTACAAACACTAGATATTGAAAGACGTGAATAAAATGTTGTTGTTAATGAACCTAATCCAAGAGT

TGGTGAACTTGCAGGAAGTTTTCAAGAGAAGATGGCTGAAAATGAAATTGAGGAAATGTTAGATCACCTGAGAAGGATCA

AGAGTGGAGGTAATCTGGATAGCGTCAAGATTGATGAAATTGAGAGGCTTGAAATGGCACTAAGAGTTTTGAGAACCTTT

ATAAAGTATCATCATGTTCTTTTTCGTGATTCCATAGTCAAACACAAAAAGAATGCCAAATTGACTATGGCAATGCTTCG

CCGGGTATTGGATGGGATTCCAGATGAATGTAAAACTAACCTTAATCTGGAAAGGCTAGAATCACATTTGTTGGAATTCT

TGGAACGTGAAGCCATTTTAAATAACGATTATGAGTTGAATGATTTTGATCTGTCGAAATATATGGATTGCCTCGGAAAG

AATCTAAATGATGTACTGATGATTTCACTGGAAATGGTTAGGTTTGGCCTTGAAATACACGGATTTATAAAGGAACTAAA

AATTGTTCAAAAGAAACTGAGATTTTTGAAATACTTATATGCCACAGAGATAAATGGTTACGTCAACCATGAGAAGTTGG

AATGTTTGGAGACTCAAATTCAATTCATGGCTAACAATGTGGGACAACTTTGTCTTTTTACTTTAGGTTATGTTGATGAG

GATGAGGATGAGGATGAGGATGAGGATGATATCTTGAATAAACCTCCTTATTTATTATTCTTGATTGTGTTAGTGGAGCT

GGAAATGAAGAAGATTTTTCTTAGTGAACTAAAGGCTTCAAAGTTTACTCATTCAAGAACTTTCAAGGACAAGAAATTAC

CAAAAGGAATTTCTTTTCATCTCCACAGTCTACTGATGTATATCAGAAAAAAAAAAGCTCGAGAACTTTCCTGATAATAT

CTCTGCTCAAAATATTGATGTGGCAATAGAGTTCTTGTTGGTTTTCCTTGAGGCTGATGTGTCAAATCATGTTATTAATG

GTAACTGGTTGAATGAGGTTATGGAAAAAGTTGGAGCTATAGCGGGTGATGTTCTATATGTGATCCAAAAGCTTCTTCCT

AGCTCTATAAACAAAGATGATACTAGAAAAATAAGTCTTTACTCGATACAGATATTGGAGAAAACTAAAGATCTGAAGGC

ACAAGTGGAGACTTACTACAAATCCTTAAAATTCACTCCATCTCAGTTCCCTACTGTTGGTGGATTGAACTTTCTGGATT

CTCTTATAAGGAAACTGAATGAGATGTCGAAATCTGAATCTGATTTAGGTTTCTTGATGAAACCTCTTTTAGGTAATTTG

GAGAAAGAGCTATCTACTCTTATATCCATTTTAGAGAAGGAGCTGTCATCTTTATCATCAATTTTCAGAGATGTCGCAAA

GGTGCACCATGAACATAAAATTCCTAAAGATCTTCAGAGACGTACTATCAATTTGGCATATGAAGCTGAGGTTGCCATTG

ACTCTATTCTTTCACAGTATAATGTTTTTTGGCATATTCTTTGCTCTCTTCCTACAATCTTAAAAGAGATCGAGCAAATT

Figure 8 (Cont.)

AATGCGAAGGTGACTGAGATGTGGTCAGCAGGCATCACTCTTAATCCTTGCTATGTGGTAGCACCATTTAAACACCTGCC

AACTCGACATAGCAATCCAGTGACTGATGAGGAGATAGTGGGTTTTGGGAATGACACAGAAAAAATGATCCAGTATCTGA

TTAGAGGTACAAATGAGCTAGACATCATCCCAATTGTAGGCATGGGGGGACAAGGGAAAACGACAATTGCTAGAAAGGTG

TACAATAGTGACAACATTGTTTCTCATTTTGATGTTCGAGCATGGTGCATCGTTTCCCAAACATATAACCGCAGAACGCC

ATTACAAGAGATTTTTAGTCAAGTTACTGGTTCCAAGGAAAAGGGAGATAAGGATGACATCCTTGCCGACATGTTGAGGA

AAAGTCTAATGGTAAAGAGATATCTCATTGTATTGGATGATATGTGGGATTGTATGGCATGGGATGACTTAAGGCATTGT

TTCCCAGACGTTGGAAATAGAAGCAGAATAATAGTAACAACTCGACTTGAAGAATTGGGTAAGCAAGTAAAGTACCGTAC

TGATCCTcgggTATTCTCTTCCATTCCTCACAACAGAgAGAcGAGTTGCAAATTACTGgCAGAAAttttAAAGTGTTgTC

AAAAGGAAGATTGTCCGCCTGAACTACAAGATGTGAGTCGAGCAGTTGCAGAAAAATGCAAACGACTGCCTCTAGTGATT

GTCTTGGTAGCTGGAATAATAAAAAAAAGAAAATGGAAGAATCTTGGTGGAATGAGGTGAAAGATTCTTTATTTGACTAT

CTTGATTGTGATTCCGAAGAATATAGTCGGGCTACTATGCAGTTGAGTTTTGATAACTTAGTTGATTGTTTAAAGCCTTG

TCTTCTTTATATGGGAATGTTTCCGGAGGATGCAAGAATTCCAGTGTCTAAATTGATAAGTTTATGGATAGCGGAAGACT

TCGTGGTGAACATTGAATCTGCTGAAGATTACTTGATGGATCTCATTAGCAGTAACGTGGTAATGGTTTCAAAGAAAGAA

TATAACGGTAAGGTTAAATACTGTCAGGTTCATGATGTAGTGCTTCACTTTTGCTCGGAAAAGAGTAGAGAAGAAAAGTT

TCTGCTTGCTGTGAAGGGAAATCTTAGCCAGTTTTTACCTTGTGATTTGAAGGAAAGTCGAGTGAGCTTCATTTTGAGTA

AAGAGAATTCCAAGTTTGTATCTCTGGGATTCAAAACACAGAAGCCTTTCCACCAACCATTAAGGTCACTGATGACAATC

GGAAAATCTTCTGATGAGATTCCCTTGAGTTCTTGGATTCATAAATTGCGACTTCTTAAGGTCTTGGATTTGAGTTCCCA

TAAAGTGTATTATTTGTCGTCAGCTACATTGAAACCACTAAATCACCTGAAGTACCTCGCAGTTTGGTCAGAGAAATTCT

ATTTTCATCCAGAATCAGATCTGCCCCATCTTGAAACTTTAATTGTGAAGACTTGGAGTAATATAGTACTGTTACCAGCG

TCTTTTGGGGAAATGGGAAATTTAAGGCATGTTGAGATCGTTGAAGCTAAATTTGATAAGCAGGGGCTTTTTGAAGGATC

CTCTAAATTGGAAAGTTTGAGGATATTAAAGAATATTGTTAGCTTTCCAATTGATAGGGTGGATGTGTTATCAAGGAGGT

GTCCTAATCTTCAACAACTTCACATCGAATTTCACGGGGGTGATAGTGATTCTGCAGAGTCTTTTTGTCTCACATTGGAG

AATCTTACCCAACTTCAAATACTTTGCGTTTCCTTTGAGCGGCCCCACATTGTATCTGGGTTACAATTGCCTTCAAATTT

AAAGAAGTTGGTACTAAGAGGGACTGATATAGGAAACCTGATTTCCTTTATTGCGGGACTACCAAGCCTAGAGTATCTCA

AATTACAAGATCCCTATTTTCCTCAATCAGAAAAGTGGTGCCTTGGAGATATCAAGTTTCATAAACTCAAGTTGTTGAAA

CTGGTGAACTTAAAGATCTCAAGGTGGAATACCTCGGAGGAATCCTTTCCCCAGCTCGAAACACTGGTTATAAAAAGGTG

TGACCATCTCAAGGAGATCCCTCTTAACTTTGCAGATATTCCAACGCTGAAACAGATTAAGTTGATTAGGTGCCAGAACG

AATCACTGAAGGATTCACCTGCGGAGATTAAGAAAGATGTTGAAGAGAATGAAGGAAACGACCGTATTGACCTCCTTATC

AAAGTAAGTAGAAACAATCTCCTATGTTTTGTTTTTAAGTATCTACCTGCATCTAACTGGACAACAATATGTATAATACA

GAATTATTAGGGTCATCTGGCAGCTGTGAGAGTCAATCATGTGCCTGTAATCACAACAATGGTATATATAGTTTCTTGTT

CCTTCTTCTAATTTAATACTTGCTTTAACTTAATTGCTCCATGTTGATCTCAAACTAACGAGGATGTATTTCAATTTGAT

Figure 8 (Cont.)

AATTGTTGCAGCCATGCTCATGCTCAAGTATATTGTGCGCCTAGAGCTGAAATTCCTGCCCTTTTTCTGTATGTTTTAGA

TGGTCTTTAACTGTGATTTCTTGTTGCCTTTGTTATGCAGCTTTATTATTTTACAACCTGTCAAAACATTGCTTCTTGTT

TGTTTTTTGTAATATAATAGTTGTTTCCCTTCATCTTACACCTGCAAAATTCAATAAAGTATACAATTGAAAGCTGGTTG

AATACAAGTTTATATACCTCCCTATTATCAATCAATAGAATACTGAATGAAAGTTGTTTTGATAGCTTAGTACTAAATAA

TTTAGGAGCAATCCATAACATACGTCTCACTTCATAAATAATCATTGAGTACATGTACAAAAGCTATCTATGTTGTTCCG

ACTCTTCAAAAATGTCACCAAGTTTATATTGGATTTTCCATAGAGGATCGACACATGTGCAACAATATCTTTGGAGAGTT

TGAGCATCAGAAGAAGCCAAATAGATATCACTTGTCAAATCCCTATTCAACTTTCTAGTGTGGACAATGGTGGAGTCTCT

GAATTTATCCAAGTTGACGACATGTATACATGTCTCTCACCTTTGACAACATCACCAGAGGTATACGATTCGAGTTCTTT

CATGTATTCCGCTGTCAATTTTATGGATAAGGCTCCTACATTTTCGTTGAAGTTTTCAATCTTCGTAGTGCCTGGTATAG

GGCATGCATCATCTCCTTGATGAAGAACCCAAGCCAATGCTAACTGTGAAGGGGTGCATCATTTCCTTGCAGCTGTTGTC

TCGAAATTCATTTCCAATTAAAGTATTTCAGAAATTACTTGTTATGAAAGTGTTTATCATAAATTGAAGAAGTTCGTAAA

ATGACATCAATAAAATCGTAAAACAAAGAGAAGCAAAAATGGAAGAGTAGCATAGACTTAACAAGGTGTGTCGCACAAAA

CATGGACTGATATACCAAGTACAAGTAGTACTTTTGGATAACAACTTGACTCTATAAACTACGATCAATGAAATAGGATT

TACCTGAATCATATAATGCAACTACTTCTTAAAAATTAAGAGTGATATGAGTACACTACAAAAATATAACTTTGGAACAA

AGATGTCAAACCGTGACTTCAATTGGCAACTGAGTATCGATGCGATGAACATAATACATATGTCATTACCAAAGTGTCAA

TTTTCTGCTGAATGCTTCTCAAAGTGAGAGAGTCTTTCCATTATATAGAGAAAATAAAGATTACACATCCCTAAAGATCC

GATCCGCCATTCCCTACCCCTAAAGATCAGCTATCTATCTCTACAAATCTGCTATTGAATCCCTCTAAATCTGCCTTGCT

ATCCCTCCAAATCAGCTATTCTATCACAATATTTATTCCTTTGATTCTACAACAAATGTATATGATCATGCTAATTTATA

TCACTGTATAATTACATTAATATATACAATCATTTAGTTGTCCATCATGCTAACACAAAGTAAGTAGAAACAAACTCATA

TTTGCTGTTTTTGAGTATCTAATATGCAAACAGTATCTTAATTACTAGTCACGACAACATGGTATTCTTTCAGGTTTTTT

TACTTTTTCCTTTATGTTCTTTCTTTTTCAGATAAGATGCTTGATTTCTCTTAATTGCTGCATGTCGATCTCAAACGAAC

AAGGATGTGTTTGAATTTGACAATTGCTTAGAAAACTGCAGCGAAAGCACTAACAGCATGGACCGAGTTCACTCTTAGCA

AATTGTTGTAATCATGCTCAAGCTGGAGTCTATTAGCCAAAACACCCATCCTTGTGACACTATACTGATTACTAAGGTTT

TTTTTAGGGAAAATGCATAAGTACACCCCCTTCCTATGCCCAAAATCCCTGAGACACACCTAACCTTTACTAAGGTCCTA

TTACCCCCGAACTTATTTTATATATAATTTTCTACCCCTTTTCGGCCTATGTGGCACTATCCTTGAAAAAATTGTCAACA

CGCGATGGGCCCACAAGATAGTGCCACGTAGGCTGAAAAGGGGTAGAAAATTATATATAAAATAAGTTCAAGGGGGTAAT

AGGACCTTAGTAAAGGTTAGGTGTGTCTCTGAGATTTCGGGCATAGGTTAGGGGGGTACTTATGCATTTTCCCTTTTTTT

TATTGTTCGACTTAGACGATTCATTCCTGATGGGAAGGGAAGATTTTTTTGCCTTGTTCCTTTATTTTCCTATATGTTTC

AGATGGTCTTCCACTGTGATTTCATGATGCCCTCTATAAATATCATCACTTGCTTTTGTAACTTGGTGGTTGTTTTCCCC

TTTTATTTTCTATAACTAGTTTCAGGACGTGTGTTGCACATGTACTCCCCAGAAAATTTTTCGAACTAAGACTCAAACCG

TTCTTCATAGTGAGTGAGATTTTTGCAAGGAATTTGAAAGTTCTCGAGTGTTAAGGTCACTATATGTAGCACCTTAAGTT

Figure 8 (Cont.)

CCAAGAAGAATCGAAGAGAAAAGCATTCAAGTCATTCCTAAGTTTTTCTTAAGTTTTGGGCAACTTCAAATGACTATAAA

TTTTAGTACAGAATGAGTTAGGAGACCCATAAGATGTTAAATTAAAGCCCTTCGAGTCCTCTTTCCAACGCCACCGAGTT

TGATCAATTCCGAGCTCTGAGTAAAAAGTTATGACGATTTACTAACGTCGCACAAATCTAGTGAGGACAATGGTGGAGTC

TCTGAATTTATCCAAGTTGACGACATGTATGCATGTCTCTCACCTTTGACAACATCACCAGAGGTACACGATTCGAGTTC

TTTCATGTCTTCCATTGTCAATTTTACAGATAAGGCTCCTATGTTTTCGTTGAAGTTTTCAATCTTCGTAGTGCCTGATA

TATATAGGGCATACATCATCTCCTTGATGAAGAACCCATGCCAATGCTAATTGTGAAGGGGTGCAATTAGATTGATTTTC

TCAAATACTTGCTTTATGCTCAAAATTCTCTGGCTTGAACCTAGGGAAATTCTACAAAGTAAATCAGCAAAATAATAAAT

TAATGTTGCTTTTAATTTATCTCTCTTCTTATCATTACTACAATTTATTGCTTTTTCATCTCCCCTCATCATTACTATAA

TTTAATTTTTTTTTTAAATTAGATTTTTTACCCTCTATATTTTAATAATTTTTTTAAATGAAAAATCTTATTTACTACCC

TCTTTATTATCATAACTAGTTAACATGTTCGCGCTTCGCGCGATCATAACAAATATTTTTAAGACAATTTCTTTTATAAA

TTAGCACATACTAAAAAAAGAAGAAATATGATCAATACTTTGGTAAAAGCTTTAAAATGTTTATGATAATTGTTTCAATT

TATAAGATACTATTTTCGTATTATTTTGTAGGGGTGAAAAGAATATGTTTAATATTTTGAAAAAAAAAATGCTAACTTAA

TTTTCTGCTTAATTTTTTATTTGTCGTGGATCATCAAATGAAACGTAAATAATCTTTCCTCCTCGTTTTTTAAAAGTAGG

AATGCTTATTTTATATAAGGAACTACTGAACTTAGACCCTTTTAGATATAATTCTTCAATATGATTTGTTTAACAAAAAT

ATACTTGTTAGGTACGTAATCTTTCATAAAATTCTTTATTTTTAAAAAAAGATTGTGCAAGTTAAAATATGAAAAATAAC

AAAAAGCATGTCAATAGTAATACAAAGGAAAGAACGACTAACTATTTTCTAATCAAATAAAATATAAATATAAAAAATCA

TAATAATTAAATTGAAAAGCAATCAATATTAATATTTCAACAAACAACTCGATACAAAACATATCATCATTTTTATTTGT

TTTAATTATCAAAGAATAATTATACAAATAATAAATAGTGAATATTTTAACTTTTGAGGAGTTACAAAACTCACTAAATA

TATAATTATTTAGAGAAAATCACAATTTAAATAATGACAAAAAAAGGCAAAGAATGGGAGAAAAAGAATAAGTAGGACTT

TTAGTATATAAGAGTTCCTGCTATCGTTTGTTTTTATATCATATCGAAATTATTTATAATTTTTTTCGTCTTCACACAAA

TAATAAAAAAAGTTTATCTTTATTTACACAATATATTTCACTAAAATAATACTTCAATTCATTTTAGTGTGTATTTTGTA

TGTTTTGTTGAGGTCATTTATTTAATTACTAAAAAGTTAGAAAATAGAAAAATATATTTCATTATTTTAGTACAAACTTT

AAAAATCTCAAGTTTTAATAAATAATACTCACTCCCTCTATTTCAAAATAAGTGAATTGTTCCAAGTTTAAGAGAGATGT

TGAAAAATTCTTCCATTTTTGCCCTCATTTACAATGTTAAATAATTATAAAAGAAATGACCTTTTAAATACAAAATGTGT

ACATAACGTCATCAGGAAAATAAATTATTTATTTTAAAGTTATTTAGAGCGCATAGATAAATGACTTAATTTTGAGTAAT

TTTAATATATGACGTAAATGAAAGAAAAATGGAAAGACGTCTTAAAAAAAGAGAGAAAGAATTAAGTAAAAGGAAATTGA

GGAGACATGTTAATTTAGAAAAAAATATAAATAGATAAAAAAAATTATAAGTCATGAGATGGATCAACCCTTTAATAAAA

AGAACAACGCAACATAGTAGTATTTCCTATTAATTTTAAACAAAATTAGAGTATGTCTTGTTACCAAAAGCTTACAACCA

CAAATAAAGAAAAAAACATATGCTCCCATGAAAATGTTCTACGTGTAAATCTTGAATAGCTGATGTGCAAATGATAGACT

AAAATCTAAATCTATTATATGTTGGGAAAACTAAATGTAGAGGTGATGAAAAGAATCGTAGAAAGGAGTTGAGGAGATAT

GTCATTATTTAAGTAGAAAAAAGTGAATAAACTAAGGTTTTTGTAATTTATGAGATATAATTAGCTGTAATAAATATTAT

Figure 8 (Cont.)

ATTTTTTTTTAGTTATCAAACAAATTAATTAATGAAGAGAGTAAATCATTTTTTGAGTTTCATAATCAACTTAAACAAAT

ATCAATTTTCTCTAAAACTTAAGAAAATATGTTCATTGTAATTAGATATTGGCAGAACAAACTTGGTTCATTTTGAAAAA

TTTCACTAAATTAGAAGAATTAAATGTTTTGTGAAATTTGAATCCAACAATAATATATATCGACTAATTTTACACAAGTG

TTAACAAATAAGAAACAAAAACTTAATGGAGGGGAACTCATCTCCTTTTTAGTTAATTCAAAATCCACAAAAGAAAAAAA

TTTGTTATATCATCTAAATTAGAATGAAAAAAAGCAGATAATGCTAAACAAAAGATGATAGAATCTTGATTGAGAAATTA

TGTCATATTAACATGTTATATACATAATATATATCGATATAAAATATGAATTGTATATGCAAAAGACAAAAGTTTATATA

ATGAAAGTATCAATTAAAGTTTTCTTTAAGCAACAAAATTATAATATGTGGAAGATCATGTTGCCCTTGATACAAAAAGT

GTGCTTTGTAATATAATCTTGTTCTTGAAGGGTACATATCTTGATGGATAAATAATTAATTGAAAAATTATATAAGCAAC

AATAAGTGCATCTATATATTTGTAAATTATTGAAACTTCTACTTTTTCAAATCTTGATGAATCTCCCACCGTCATTAAAC

TTTCTTCATTTTGATGACTTGTAGCAAATTAATTTTTGAATCTCTTTTGGCGAATCTTACACCGCCTTCAAACTTTCTTC

TTCATCTTGATAAACTTTTGCTTGGCAATTGTAACACAAGAAGAAATTCTAAAACATATATCTATAATCTTCATAAAAGC

TGAAAAACAAAAAAAATATATTAACAATATGAAGTTGGAGAAAATATAAATGGACATGCAACAACACCATAGATGATTGT

TATTTATAGATGAGAATTAAGTAGAAGGAAGTTGAGGAGACGTATTATTTAATTTGAGAATTCAAATAGGTAGAGGTTTT

TTTGTAACTTTCATGTGATATAATTATATGTAATGAATATGATTGATTTTTTTAATTTTTTAATGATTGATTAATGAAAA

AAATGAATGGAAAAACTCAAAAAAGGAAGAAAAAAGATAAATAGCTTTCTAGACCATTGAGAGGTGTCACATCACCTTGT

TTAGATCTTTATTATATATATATATAGATTTTTGTAATTAACTAAGTAATACAACCTTTTATATAAATTAAATAATAAAAAT

AAAATATTAAAAAAATATTTTTTCGTAATTGTAATTAGAAGAAGGACAAAAAATTAATTTTTTTTTATTAATAATAGAAA

TTAGAGAGGTATGAATTACGAATAATTATTCCTTGTAAGTTGGCATGTGAAGAGTCTTTGTTGTAAATGTTTTTTCATTA

ATATAATATTTATTGTAATAAATTAAATAATTGACTTTTACAATAAAATAAGTAATTTAAATAAAAAGAAAGGCCAAAAA

AATGAGAAAAAAGATAAATACATATGAAGATCATAGAGAGGTGCCACATCACCTTGTCTATGTTTCTCCTTTATATTATA

TTAAGTTAAGATTTATAATTATTATTGAAGAAAAATTTCTTCTTTAAAGTTTTTTTTTTATGGATCTATAAAATCAGTAA

AAATAATAATTCAAATACCTTAATTGTCTCTCTCCTCACATTACTACAAATTTTTTTCTTAAACTTTTTTTTTTTACCTT

CTATTTTAAAAAAAAAAAGATTCTAAAAATAATAATATTATTCATTTCTCTTCCTTATTATCATAATTTATTATTATGCT

TAATTTTGTAACTATTCTCTTTTACTCTTCTAAAACGTTGTAGAATTTATAATTTTAATTTTAATTCAAATGTAGTAATT

TCACATTTTGTTTGTCAAAGTAATATCCTAACTTAGATTTTTTTTTATCGTGATTTACTAAATTCATATTTGATTTACAA

ATTGAAAGAAAAGGAATTGAGAAACTATGATTATCTTAATGCTTTGAAGGCACATGATAACTTAAAAAGATGTGATTATT

TTTCTCATCTCAAAATAATTAATATATTTTGTATGCATATGCTATAATAATAAACCTTTTTTTTAAAAAAAAATTATAAA

AAGGATTCAACTTTATTGCTATTGGCATTCTGATAAAGTTTGTTTAGAAAACTTTTCTCAAATTTGTTATATGCATTTTG

ATAAAGTATATAGTGCCTCAAATAATTAGTTTCTTTAAATACTTTATATTATTTGTGTAATTGGGGTTGTACATCTCTCA

ATCTATTCTTTTTTTTATATAAAAATAATAAAAAATTATTTATCTCTCTTCTTTATTACCCTAATTAATTATTCTTATTC

ACAAAAAAACTCTTTTTTCTTAACTGTTATTATTCACAAAATTTCTCTTTTTTTTTAAAAAAAAAAATATATTCTCTTGA

Figure 8 (Cont.)

TCCGTAAAAATAAGATATCTCTTGATTTTTAAATATTTTTATCCTTTATATTTTATGTTAAAAAAACTCAAAAGAAGTT

ATCCTTTTTCTCCTTTTCATGATTTTTAAAGATTTTTCTTATTTATATTTTATGTTTAAAAACTCAAAAAAAGTTATAAA

TAGTATCTAATTTGATATATTTTTAACATAATTATAGTATTCACCTTATATTATGATTATAATAAATATGTTTACCTTAT

TGATCTCTCTTCTTACCTTTACTATAATTTATTGCTTTCATCTCCTCATCATTACCTATAATTTAATATTTTTTCTTAAA

TTAGTCTTTTTACCTTCTATTTTTATAAATTTTTAAAAGAGAAAATCTTATTTATCTCTCCTCCTTATTATCATAATTTA

CTATTATTATTGAAATTTGTTTTCTTCTTTAATTTTTTTTTCTTTTATTCTATAAAATAAATGAAATAAAATTCAAATAT

CATATATGTCTCTCTCCCCAATCCCCATATTACTACAATTTATCGCTTTTTCTTAAATTTCTCTCTCTAATATATATTTT

AAAAAGATTCTAAAAAATAATAATATTATTCATTTCTCTTCCTTATTATCGTAATTTATTATTATGCATGGAATTTCTAT

TTTTTCTCAATTTTATTTCTTTTTATCTATAATATTTGTCAAAAAATTATCTATTTAACCAAGAATCATTATTATTTTTT

TCCTCTTATTCTTGACTTTTAAAATATTTTTTCTTATTTATGTGTTATGTTAAAAAAATTCAAATTCAAAAAAATTATAA

AAAATATTATCTAATTTACTTTTTAATATAGTTGTGCTCACATTTATAATATGATATTACATTTCAAATAATAATAATAT

ATATATTTATATATACACACACACATACATATATTTATATAACTTTTTTTTCTATTTAAAATGCTATATAATAAAGAAGA

AAGAGAGAGAAGTAGTTAAAGAAAAATAAATAAAAAGTAACGGTTTTACATTTTTTTCCTTTCATGTGTTTATTTTTATT

GTAGTTACTTCCAAAAAAAAATTCTTTCCTTTTTCTTCTTTACCTTCCTTTTACTTTTTACTCAATTCACTACTATACAT

CTTCTTCCTTTTATTTTGCTATTTCCTGCCTCATCTCCTTATATTTTTTTTCTAATTATATCACACTAAATTTATTCTTT

ACTATTAGAAAAGATTCACTACTATCTTCTTCCTTTTATCTTGCTATTTCCTGCCTCATCTCCTTATTTTTTTTGTAATT

ATATCACACTAAATTTATTCTTTACTATTAGAAAAGAAAATCAAAAAAATATTTTTCTTATAACTTTTCATTTGTGAAAA

AGAAAAAGAATAGAATTAGAGAACTAATACTTCATGGTGGCATCATTTTTACGGTTTACAAATTGAATGTTAGAGGACAT

TTTGATGTCTTTCGATCTTTGGTATATTGAATTCCTAAATAGGATTTCATTGTACAATTTTGATAGATCTGTTGATATAA

TTCTTGTTGGCATAAAATGATTAAATTTGCACAGGTATATTCTAATGAATTCATTTATATAAACAAATCAAATTTTTAAT

TTACCTGAAATAGTAAATCTTCTTGTGGAATGATTCTTCATTTTTCTCAATTTACCTCCATATTTGAGGTAGTAAAACTT

TTCAAAAATTCAATTTACCTGACGTAGTATATCTTCTATTGCAATAATTTTTTTCCATTTTGTCAACTTACTTTTAGATT

ATGTGCTCTCATGCGTAATTTCATTTGTATAAACAAATAAAAAAACTTGATTTACATGAGGTAGTAAAACTTTTTTCTTT

TTGACAATAATTTTTGAATTTTGTTGGTTACTTTTAGTTTATGTGCTCTCCTATTTTATAATTTATAATTTTTAATTGAT

TGATTGTACTAAGTTCTTGACAATCGTTACAACTCTTAATTCTCCATTACAACAATAAAAATATCATTTTTATTAAAACT

TTTCATTATCCTCTTTAAGAAATATCATTTATGTTAGATGTATTTAGTAGATTATTATATTAAGAAATGACTAAAAGAGT

TCAAAAAATTGAGAAAAAAATAAAAATAAAATGGTGGCCATATAGGCATGCCACATCAACTTTTCTAGATTCAGCTTCAT

ATATATATATAGAGTTTATTGGTGCATGCAGCAACTCCCAAGCCGTTGGTGGCTTAAGTGTCCCTTTATTTTCATTCTTT

ATTCCTCCATTATACCTTGTAACATATGTAACTCCTAAGGTTATTATCTTCACTATTTAGTACCCCCATTATCTTCCTAT

TTATTCCTAGGAAGACTTCTTCTACTATAAATAGTGGTGATCTTCATTTGTTTTACATATAAGAAAATATAGAGTGCATA

AAGTTTGTTAAAAAAAGAGAGTTCTTATTAGTTGAAGGGATGTGTTTTTTTTGTGGAGCTTTGGACTAAACTCTTGTCCA

Figure 8 (Cont.)

```
TAGTTGTTGAGTTATCTTTTGTGAATAGGTTGTTGTATCCTGGAGGGGACAAGTAAAGAAGGACTACTGCTGGACCAGTG
AAAACATTTGCTGCGTGGGCTTGAATCTCCTTAAAGAGAGCGAGATATCCGCACCTCAGCTTGAAGAGATTTATTTCTTC
ATTTTTATTTTCAATTGTAATCTTGTAATTCTGTTATTTTGTAATTTTTCACTAAGGACTTTAAGTTTTCACTAACAATG
AATAATTAGTTTATGCTCTGTTGAACCAATTAAAGAAGTGTTTTATTTTTGTTTTCCTCTTTAAATTTATTTATTTTTAA
AAAGAGTGATCAACAGCAGATGGCTGGTTATATGTCTTTATAGATACAAATTTGGGGTAGGGAGTTGAACCCTCATAACT
GAGCGATTAATCCTGCTATCCTTCCACACACACTTTTTTAGATTAATCACTGGGAATGCATTAGTTGTTTCTCTGTACTA
ATAATTAGTAGAGAAAAAGCTCAAATATGTCATTCAATTTTGTGGGAAAAAAACCTTATTTAATAGTTTGGCTCAATAAT
GTCATTGTCTTTATATAAATGACCCATTATGCCATTGATTTTTAACGGTCAGAATTCATGGTTTTGAAACACTATTTTTT
CCATATGGCCTCTTATTAGAGGTCCATGTCACCAAAATTAAATTGATTGAAAAATAAGTTCAAATATGCCATTAAACTAT
GACAAGATATTCGTCTATGTCATTCATTAATAGTTGGATTCAACCATATTTCTAGTCAATTGATCAATCTAAGGGTTTGG
GGATAAATAAAAGGGAAATAGGTTAGGGTGGGTCCAGTGTGATGTTATGAGTCAGGTTTTAATTTCAAATTTAATTAAA
TTAGGTGGTTTATTTTTGCATGTGGACCTCTAATAAGAGGCCACATGAAAAAAATAATTTTGCGAAATCATCAAATTTGG
CCGTTAAAAAAGTAGCACGAATGGGTCCTTTCTATAGCGACAATGGAATGGTTGAGCCCAATTATTAACAAATGGTATAT
ATGAACCTTTTTCCAAAGTTTGATGGCATATTCGAACTTTTTTGATCAGTTTAATTTTAGTGATGTGGACCTGTAATAAG
AGGAAAGAAGAGTTTTGCTAAGCGTCAAACCTGTATGTTAAAAAATAATGGCACGAATGAACCCTTTCTCTAATGCAGTG
GCATGATTGAGTCAGCCAACTATTAACGGGTGGCATAAACGAGTCTTTTTTCCAAAGTTCGATGGCATAGTTGAACTCTT
TTACATTACTGTTAATTCTTTGTTTTTTTTAAAAATAAATTAATATGACCACATGGGTCAGGCTTTTATTGAATTAATAA
AAACAACTACAACTTCCTAGAAAGCTAACAGTAAAGAAGAAACAAAAAGAAAAAATAAATATCTGGAAAGTCTTATGGGT
CTCATTTCTGCTTAGGATTTGCAAGGATGTGGATCCATATTTTGAGAGTATTTGGGATGATGTACTATTTCAAGACGTCT
TCTTCGTTGTCGGTGTTGTTGTAGGACATCAGCCTAGTTCCAAATCTTTGAACATCGATTGGGAAATCCACTAGCTTCTG
CTAAGCTGGTAACTCCTCTTGACTTGTACTGAACATTTTTAATCACCATTTTCAGATGTATAATGACCGACTTTGTTCTT
GTTGTATTTCCTCTTGATCTAGCCCCCATTTGTTGCTTGGTCTTGTTTAGGACTGTGTAATCTTTCTAGTTTCTGATTCT
GAGGATTGGAATTTGTGATTTATCCGAATTCAATATCTTCCGTCCTTTGGTGGGGAGATCTTGAAAACTGTGGTAATGGA
CTGGGTTATCTTGTTCAAGTGCAATGCTTGTAATATAGTCACCTAACTGATTTGCTTCTCTGTATGTGTGTGTAATTTCC
ATCTGTAGTTGTTGCATTGTATTCTTTATTTCTTCCACCTGTTGTACTAATTCCCATGGCACTTTCCACACTTCCTGGAT
GATGTTCTTTAGTATTAAAGAATCTCATGTTTCTATTCTTGCATTATGTATATCTCTTGATAAACAACAATGCACTGCCT
TTTGTGCTACTATGGTTTCTACAATCATATTGGTGTTTTCCCCTATTTGTCCTGCCTCTGCATACAATAGATCTCCTCTA
TCATTCCTTAGGCAGAACCCGTAAGAGCTCAATCCTGGATTCCCTTTGCTTGCTCCATCAGTATTTATCTTTATTCTGCC
TGTTTCTGGTTTCTTCCAATGTGTCAAACAATGATATAGTCTTGGTCTGTAATTACTTAGCACTTGTATCATTGATGGCC
AATCTTTTGGAACAGAGGAGATACCATTCTATTATATGTAGTATCTCCTCCATGCTTCCTATAATTCCTTCTCTTCCATA
ATGATTGCTGGGATGGCTTTGAAAATGCTGTGGGGGTTGATTAGTTGTCCACCACTTACGTATGACTTGTTGCAGTTGCA
```

Figure 8 (Cont.)

ATCCTTCAATGTTATAACCTGCACAAGAAGAAAACTGTCTCCATAGCTTAGTAGCTATTGGAGATGTTAGAAAAATATGT

GACATGGTTTCTATTTTATGATCCTCACAACACCAACATCTTGATACCACACTAATTTTCATCCTTTTTAGATTATCGTC

AGTAGGTATTCTTCCTTTCCATGCTCTCCATAAAAAGAAATTAATCTTTATAGGCAACCCTTTAGTCCATATATAGTCCT

GTATTTTCTCCTTCTTCCGTCTTAATTCATTCCATGCTGATTTGACTGTGAACTTTCCATTTGAATTTCCCATCCACCAT

GATGTGTCATTATCTACATTGACTAGTTGTGGGCTGATGTTATCAAGTATATGCTGCACCATATCTACTGATAAGACTTC

CTGTAGTTTCTGCACATTCCAATAGCCATTTGTAATGAATTGTTTCACTTCTACCTCCTCATCCAATACATTTTCATTGT

CCACGAAATGAAGGCCCCTGCTTAGTCCAATTATCAAACCAGAAGCTAGAATTTCCAGCCTTAAGTTGCCACCAAATCAA

ATGTTCTAGTTCTTCTCTAACTTCCACCATCTTTTTCCAAACAGGTGAACTACCTTTTGCTTGAGCTATGACAGGGTGAA

GTTTCTTGTTGTATTTGTTTACCATATCAGCACTCTATAGTGATCTAGTTGTCCTTAGATTCCACCATAGTTTTCCAAAC

AATGCCTTTGATGTATCATGTAGTGATCTAAACCCTAAGCCTCCTTCAATTCTAGGTAAACACATAGCTTCCCAGGTAAC

CCAATGTTTTCTTTTCGGACTTGATGTATTACCCCAGAAGAAAGTTGCAAAATTTTTATGAATATGTTCTATAACTCTTT

TAGGGGGATTCATGGCTGATAGGAGATATACAGGTATCGACTGCAAAACATGTGATATCAAAATATATCTTCCTCCAAAA

TATAAGAGTTTATTTTGCCAAGACATCATCCTTTTCATAACTTTCTTCACCAGATCTTCAAAAAATACTATCTTCTTCCT

ACCATAGAAAATCAGGCATCCAAGGTAAGTAAAAGGAAAAGTCCCCTTTCTCATGCCAGTTTTTCTTCTATCTTCTTTAA

CATTACTGTTAACTCAAACACAATTTTAAAGAATTTTTATGTGATTTTTTAATAGTTCATACTCATCATCATGGGGTGCA

CATACAACACGTGTGCCTAAATACTAGTATATTATAATACCTAAGTGTTAGTTAAAGCAAGTATTGTGAACATAAAAGCT

ACAACAATTGTAAAGAAAATGATTCCCTTTTATAAGTGAGGAAAAAAAATTTCCCCCTTTTAGATGAAACTTGTTTTAAT

TTCTCGACTTGTATCACAGTTTAGACACACATTAGATGCTCATGAGATCTAAAAATAAGCAATGATAATGACCATCTTGT

CAGAGCCAAGCTTTTGGGATATGCCTCGTCGAGCTCAAAAGTGTAGTGAACTTGTGTTATGTATTTGTAACTTTTTTTTT

ACTTTCTTCTCCTATTTGGGTTATTCCTATGTGTAATTTCAACTAAGATTCTTGCCAGCCTAAATTCTTGTCAATCCTTT

TCTTTGACCTGCTCTTATCGGTCCGCCCTCCATCATTAGCATCACACATTGATATTAGTCTTCTTTTGTCTAAAGAAAAT

GACTAGTAGTTGAGTGACCATATGAAAGTGAGTGAAATGTGATTATCTGTGATAATATGCACCATTTGTTAGATGAAAAT

GGTACATAAAATATACTATCTTTCTCAAGCATCGACATATATAGCTACAAACACTAGGTATGAAAGACATGAATAAAAAT

GTTGTTAAATAAACCTAATTCCAAGAGTTGGTGAACTTGCAGGAATTTTTCAAGAGAAGATGGCTGAAAATGAAATTGAG

GAAATGTTAAATCACCTAAGAAGGATCAAGAGTGGAGGTAATCTGGATAGCGCCAAGATTGATGAAATTAAGGGACTTGA

AATGACGCTAAGAGTTTTGAGAACCGTTATAAAGTATCATCATGTTCTTTTTCGTGATTCCTTTGTCAAACACAAAAAGA

ATGCCAAATCGACTATGGCAATGCTTCACCAGGTATTGTATGGGATTCCAGATGAATGTAAAACTAACCTTAATCTGGAA

AGGCTAGAATCACATTTGTTGGAATTCGTGGAACGTGATACCATTTTAAATAATAATTATGAGTTGAATGATCGTGATCT

GTCAGAATGTATGGATTGCCTCGAAAAGAATCTAAATGATGTACTGATACTCTTCCTGGAAAGTGCTAGGTCTGACCCTC

CTGAAGAAAACCATGAAATACACAGATTTTTAAAGGAACTGAAAGTTGTTCAAAAGAAACTGAGATTTTTGACATATTTA

TATGCCACAGAGATAAATGGTTACGTCAACCATGAGAAGTTGGAATGTTTGGATACTCGAATTCAGTTCATGGCTAACAA

Figure 8 (Cont.)

TGTGGGACATTTTTGTCTTGCTTTTTCTGATGTTGTAAATGATATTGATGACTATGAGGATGAGGATGTGTATAATGATA

TCTTCAATAGACCTCCTTATCTATTAGTCTTGATTGTGTTAGTGGAGCTGGAAATGAAGAAGATTTTTCTCAATGAACTA

AAGGCCTCAAAGTTTACTCATTCAAGAACTTTCAAGGACAAGAAATTACCGAAAGGATTTTCTCATCATCTCCACAAACT

GCTGATGTATCTCAGAAAAGAAAAGCTCGAGAATTTTCCTGATGATGTCTCTGCTCAAAATATTGATGTGGCAATAGAGT

TCTTGTTGGTTTTCCTTGATGCTGATTTGTCAAATCATGTTATTAATGGTAACTGGTTGAAGGAGGTTATGGAAAAAGTT

GTAACTATAGCGGGTGATGTTCTATATGTGATCCAAAAGCTTCTTCCTAGCTCTATAAACAGAGATGAGACTAGCAAAAT

AAGTCTTTTCTCGTTATGGATATTGGAAAAAACTAAAGATGTGAAGGCACAAGTGGAGACTTACTACAAATCCTTAAAAT

TCACTCCATCTCAGTTTTCCACCTTTAGTGGATTGAGCTTTCTGGATTCTCTTTCAAGGAAACTTAATGAGATGACAAAA

TCTAAATCTGGTTTAGATTTTCTGATGAAACCTCTTTTAGGTAATTTGGAGAAAGAGCTATCATCTCTTACATCCATTTT

AGAGAAGGAGCTGTCATCCATTTTCACAGATGTCACAAAGGTGCACCATGAACATAAAATTCCTAAAGTTCTTCATAGAC

ATACCATCAGTTTGGCATATGAATCTGAGGTTGCCATTGACTCTATTCTTTCTCAGTATAATGTTTTTTTGCATATTTTT

TGCTCACTTCCTTCAATCTTAAAAGAGATCAAGCAAATTAATGCGGAGTTGACTGAGATGTGGTCAGCAGACGTTGCTCT

TAAGCCTTGCTATGTGGTAGCACCATTTAAACACCTGCAAACTCGACATAGCAATCCAGTGACTGATGAGGAGATAGTGG

GTTTTGGGAATGACACAGAAAAAATGATTCAGTATCTGATTAGAGGTACAAATGAGCTAGACGTCGTCCCAATTGTAGGC

ATGGGGGGACAAGGGAAAACGACAATTGCTAGAAAGGTGTACAATAGTGACAACATTGTTTCTCATTTTGATGTTCGAGC

ATGGTGCATCATTTCCCAAACATATAACCGGAGAACGCTATTACAAGAGATTTTTAGTCAAGTTAGCGGTTCCAAGGACA

AGGGGGATAAGGATGACATCCTTGCTGACGAGTTGAGGAAAATCTTAATGGGCAAAAGATATCTCATTGTATTGGATGAT

ATGTGGGATTGTACGGCATGGGATGATTTAAGGTTTTGTTTTCCAGACGTTGGAAATAGAAGCAGAATAGTAGTAACAAC

TCGACTTGAGAAAGTGGGTGAGCAAGTCAAGTACCATACTGATCCTTATTCTCTTCCATTCCTCACAACAGAAGAGAGTT

GCCAATTGTTGCAGAGAAAAGTATTTCAGCAGGAAGGTTGCCCACCTGAACTACAATATGTGAGTCTAGAAATTGCAAAA

AAATGCAAAGGATTGCCTCTTGTGGTTGTCTTGGTAGCAGGAGTAATCAAAAAAAGAAAATCGGAAGAATCTTGGTGGAA

TGAGGTTAAGGATGCTTTATTTGACTATCTTGATAGTGAGTCAGAAGAATATACTTGCGCGACTATGCAGTTGAGTTTTG

ATAACTTAGCAGATTGTTTAAAGCCTTGTCTTCTTTATATGGGGATGTTTCAGGAGGATGCAATAATTCCAGTATCTAAA

TTAATAAGTCTATGGGTTGCAGAAGGATTCGTGCAAAACAGTGAATCTGCTGAATATTACTTGATGGATCTCATTAACAG

TAACGTGGTAATGGTTTCAAAGAGTAGTTATAATGGAAAAGTGAAACACTGTCAGGTTCATGATGTAGTGCATCACTTTT

GCTTGGAGGAGAGTAGAAAAGAAAAGTTTATGCTGGCAGTGAAGGGGAATGTTGTCCAGTTTCAACCTTTGGATTGGAAT

GGAAGTAGAGTGAGCTTTAGTTTCAGTGAAAAGCTTTCCAAGTCTACATCTCTGAGATCCAAAACACAGAAGCCTTTCCA

CCAACACTTGAGGTCACTGATAATCAGAGAATATTATGATGGGTTTCCCTTTAGGTCTAGGATTCATACATTGCGACTTC

TTAAGATCTTGGATTTGAGTTCCAATAAAGTGAGTTATTTGTCGACAGCTACATTGAAACCACTGAATCACCTGAAGTAC

CTTGCAGTTTTGGCAAACGTATTCTATTTCGATCCAGAATCATGTCTGCCCCATCTTGAAACTTTAATGGTGAATAGTGA

TAATTTGGATTATATAGTACTGTTACCAGCGTCTTTTTGGGAAATGGAAAAATTAAGGCATGTTGATATTTTTAGTGCTG

Figure 8 (Cont.)

AATTTGATTTGGAAGAGGATAAGCAGGGGCTATCCTCTAAATTGGAAAATTTGAGGATATTAAAGAAAATTCTTAGATTT

CCAATTGATAGGATGGATGTGTTATCAAGGAGGTGTCCTAATCTTCAACAACTTCACATCGAATTTTACGGGGGTGATAG

TGATTCTGCAGAGTCTTTTTGTCTCTCATTTGAGAATCTTACCCAGCTTCAATATCTTTTCCTTTACATTGAGAGGCCCA

ACATTGTATCTGGGTTACAATTGCCTTCAAATTTAAAGAAGTTGGTACTATGTGAGACTGATATAGAAAACCTAGGTTCC

TTCATTCCGGGACTACCAAGCCTGGAGTATCTCCAATTATTGGACCCGGATAAATTTGTTCAAAACAGAGATTGGTGCCT

TGGAGATATCACGTTCCATAACCTTAAGTGCTTGAAACTGTCGCGCTTAGATATCTCAAGGTGGGATGCCTCGGAAGAAT

CCTTTCCCCAGCTCGAAACACTTGTCATAAAAAGTTGTCACCACCTCAAGGAGATCCCCCTTAGCTTTGCAGATATTCCA

ACACTGAAGCAGATTAAGTTGATTAGGTGCGAGAACGAATCTCTGAAGGATTCAGCTGCGGAGATTAAGAAAGATGTTGA

AGAGAATGAAGGAAACGACCGTATTGACCTCATTATCAAAGTAAGTAGAAACAAACTCCTAAATATGTTCTGTTTTTGAG

TATCTAATGTTCAAACAATATGTTCAATACAGGATTGCTGAATCAAGTATGTGCCTGTAACCACAACAATGGTATTGTTT

CAGTTCTTTTTAAATTGATGCTTGTTTTCCCTTAATTGCTCTTAAACTCACGAGGATTTGTTTGAATTTGACTACTGCAG

CAAGTTCATGACGGCTTGCGTCCACACATTATCCCGCACAATGAAACGTTTGCCTTCTCTGTCAATGGATTCACATACTA

TTTTTGGCAATTCCTTCACATCCATGTCTTGATATTCTGAAGTGAGCAAGTTTCTTCAAGTCTTTTAGAGTACTAAGAAA

GACCCCATTTAGTTTGTATTACGGGCCTACGTTCAGGAAAAACTCAAGGGAAACCTGAACATCTTTAGAGATTTTTTGGT

TGGATGTGATCTTGAAACTGACTCTTTCTTTTGAAATATTGCAATTTGTGGCAGCTATTGAAATATTCTTTTTTTCACTA

CTGCCCCACGTATTGTCCTTTTTTGTTCTTTCATTTACTTGACATTTGGAGACTAGATTGTGTTACGACCCAAATTCCAA

GAGCCGTTACAAAAAAACATAATAGATGTTCACACTGATGCTTTGCGCTACCAAATATATGTGTTTTTACCATCAACTCC

AAACGTATCGTTCCCTTAGTCTATAACAATGGCATCTTCACATTCTTTACTAGATTTACTGTGTCTTAATTAAAATTATT

TAAATATCTTTGTATATTCTAATTTAATCAGACATCGGCCGGGCCCACGGAGAAGACTTGGGGTAAAAAGAAAAAAGTGT

ATGTGTTGGAAAGTTGATGGAGTCTTTTCACCTTTTCCCTTAGTGCTCTCTGCTTTCTCCTTTTCTCTTCAATAATAATG

CAGAACTCATAAAGAAAGATTATGTGTATTTGAAATTTTTTTAATCACAAACATTTTTTTTATAAAAGGAACATGAATTA

ATAAAGCACTGATTGTTGTTTATCTACCATTAATTAATAAATTAATAATGCAATAATTCAGAACTCATACAATACACATT

CCAGTCTGTTCGAGCCATTGCCAACTCCAATTATTGTTTGATCTCCTCACCCATCTCTCTGTACTAGACAACACCTTGTG

CCATATAGGATTCGGATCTACGATCAATCAGTTAACAACCGATCGATCTACCACTAAGCTACTGAGGAACAACAGGAAAT

TCGATAAGTTAAGATTGAGGTGAGTTCCATTGATTCATAATTTATTTTCATACTTCAAGGAATTCCGTATCCTCTGAATA

TATATACCCCCTCTTCCTAATTTAAGTGTCTTAGTTTGACGAGGAATTCAATACACAAGTCATAATGAATAAAGCTAACA

AATTCTTTTCCGTTCCACCAAGTCTATCCTACAGCCAAGTAAACGAAAGAAGGAATGAAAAAGGAGAAACAAATTATACA

AGTCACGAGTACAGTAGACTCGTATTGGTATATAAAACTTTTAGTTTTTTAGATTGAGTTATATCTAGGTGTCATATTTT

TCTAAGGTATCATAGCAAGATCCATTCTCGTTTGGACACATGATCCATGCTCCAGTTGGGTCTGAATATAAACAGGGGTG

TTATAGTCCCACATTGATTGGGAAACAGAGTGGTAATTTGCTTATATGTACTTAAATAATCATTCCCTAATGAGTTACAC

TTTAGGGGTTGAGTTTCGCTCAATGTCATATCTCTAGAATCATTTAAATAGTTTTTCTATAGGGAAACATGTTTTCAATA

Figure 8 (Cont.)

TTAATTATAATCATATTTGTTCTTTTTAATGATTGGATCAGAAAATTGAAGATACTAAAGATGCATAAGAGAAGAAAAAA

TTACAAGTTGGTTTCACTTATTAACTAACTGTATAAGTCATCTTCTTCATGAATGATTTTTTTCCTATAATTTTTTTTTC

AAATGGTCCATTCAAAAGAATTAGTTAAGTGATTTTATGAGATAATAATTATTAGTTAAGTGACCATATAAAAAAAGATA

AATATACACCATTTGTTAGATGAAATGATACATGAGATGTATAATCTTTCACAAGCATTAAGATATTGAAAGACATGAAT

AAAAATGTTGCTCTTAATGATCCTAATTCCAGGAGTTGAATAACTTGCAGGAATTTGTAAACAGAAAATGGCTCAAAATG

AAATTGAGGAAATGTTAGCTAACCTACGAAGGATGAAGAGTAACGGTTCTCAGAGTAGCCTCAGGATTAATCGAATTGAG

AAACTTGAAATGGTGCTAAGAGTTTTAAGAACCTTTATAAAGTGTCATTGTGTTCTTTTTTCTGATTCCTCAGTCAAACT

CACAAAGAATGCCAAATCGATTGTAAGAATGCTTCGAAGGGTATTCCAAGGGACTTCATATATCAAAGTAGATAAGTGTA

GTTATGAGTTGGTTAGGGAAAGGCAAGTACCACATTTGTTGGAATTCTTTGAAGGTAATACCAATATAAGTTACAATTAT

GAGTTGAATGATTTTGATCTGTCAGAATGTATGGATTGCCTTGGAAAGAATCTAAATGATATGATAATGATGTTCTTGGA

AAGGGTTAGGTTTGACCCTCCTGAAAAAAACCCTGCAATACACAGATTTATAATGCAACTGAAAATTGTTCATAAGAAAA

TGAAATTTTTGAGATACTTATATGCCACAGAGATAAATAGTTACGTTGACGATGAGAAGCTGGAATGTTTGGAGACTCGA

ATTCAGTTCATGGCTAGCAATGTGGGACAGCTTTGTCTTTCTGTTTCAGTTAACGTTGATGCTGATTTTTTATATAATAC

ACATAACGGTGAGGTTGAACCATATGGGTGTGATATCTTGAATAAACCTTCTTATCTATTATGCTTGATTGTGTTAGTGG

AGCTGGAAATGAAGAAGATTTTTCTCAATGAACTAAAGGCTTCAAAGTTTATTCAATCAAAAACATTCAAGGACAAGAAA

TTTCCAAAAGAATTTTCACATCATCTCCACAGGCTGCTGATGTATCTCAGAAACAAAAAGCTCGAGAATTTTCCTGATAA

TATCTCTGCTCAAAATATTGATGTGGCAATAGAGTTCTTGTTGGTTTTCCTTGATGCTGATTTGTCAAATCATGTTATTA

ATGGTAACTGGTTGAAGGAGGTTATGGAAAAAGTTGGAGCTATAGCGGGTGATGTTCTATATGTAATCCAAAAGCTTCTT

CCTAGCTCTATAAACAGAGATGAGACTAGCAAAATAAGTCTTTTCTCGTTATGGATATTGGAAAAAACTAAAGATGTGAA

GGCACAAGTGGAGACTTACTACAAATCCTTAAAATTCACTCCATCTCAGTTTTCCACCTTTAGTGGATTGAGCTTTCTGG

ATTCTCTTTCAAGGAAACTTAATGAGATGACAAAATCTAAATCTGGTTTAGATTTTCTGATGAAACCTCTTTTAGGTAAT

TTGGAGAAAGAGCTATCATCTCTTACATCCATTTTAGAGAAGGAGCTGTCATCCATTTTCACAGATGTCACAAAGGTGCA

CCATGAACATAAAATTCCTAAAGTTCTTCATAGACATACCATCAGTTTGGCATATGAATCTGAGGTTGCCATTGACTCTA

TTCTTTCTCAGTATAATGTTTTTTTGCATATTTTTTGCTCACTTCCTTCAATCTTAAAAGAGATCAAGCAAATTAATGCG

GAGTTGACTGAGATGTGGTCAGCAGACGTTGCTCTTAAGCCTTGCTATGTGGTAGCACCATTTAAACACCTGCAAACTCG

ACATAGCAATCCAGTGACTGATGAGGAGATAGTGGGTTTTGGGAATGACACAGAAAAAATGATTCAGTATCTGATTAGAG

GTACAAATGAGCTAGACGTCGTCCCAATTGTAGGCATGGGGGGACAAGGGAAAACGACAATTGCTAGAAAGGTGTACAAT

AGTGACAACATTGTTTCTCATTTTGATGTTCGAGCATGGTGCATCATTTCCCAAACATATAACCGGAGAACGCTATTACA

AGAGATTTTTAGTCAAGTTAGCGGTTCCAAGGACAAGGGAGACAAGGATGACATCCTTGCTGACAAGTTGAGGAAAATCT

TAATGGGCAAAAGATATCTCATTGTATTGGATGATATGTGGGATTGTACGGCATGGGATGATTTAAGGTTTTGTTTTCCA

GACGTTGGAAATAGAAGCAGAATAGTAGTAACAACACGACTTGAGAAAGTGGGTGAGCAAGTTAAGTACCATACTGATCC

Figure 8 (Cont.)

TTATTCTCTTCCATTCCTCACAACAGAAGAGAGTTGCCAATTGTTGCAGAGAAAAGTATTTCAGCAGGAAGGTTGCCCAC

CTGAACTACAATATGTGAGTCTAGAAATTGCAAAAAAATGCAAAGGATTGCCTCTTGTGGTTGTCTTGGTAGCAGGAATA

ATCAAAAAAAGAAAATCGGAAGAATCTTGGTGGAATGAGGTTAAGGATGCTTTATTTGACTCTCTTGATAGTGTGTCGGA

AGAATATAGTCGTGCGACTATGCAGTTGAGTTTTGATAACTTAGCAGATTGTTTAAAGCCTTGTCTTCTTTATATGGGGA

TGTTTCCAGAGGATGTGAGAATTCGAGTGTCTAAATTGATAAGTCTATGGGTTGCGGAAGGATTCGTGCAAAACAGTGAA

TCTGCTGAAGATTACTTGATGGATCTCATTAACAGTAACGTGGTAATGGTTTCAAAGAGAAGTTATAATGGAAAAGTGAA

ATACTGTCAGGTTCATGATGTAGTGCATCACTTTTGCTTGGAGGAGAGTAGAAAAGAAAAGTTTATGCTGGCAGTGAAGG

GGAATGTTGTCCAGTTTCAACCTTTGGATTGGAAGGGAAGTCGAGTGAGCTTCAGTTTCAGTGAAAAGCTTTCCAAGTCT

ACATCTCTGAGATCCAAAACACAGAAGCCTTTCCACCAACACTTGAGGTCACTGATAGGAGAATATTTTGATGGGTTTCC

CTTAAGGTCTTGGATTCATAAATTGCAACTTCTTAAGGTCTTGGATTTGCGTTCCGATGCAGTGAGTTATTTGTCAACAG

CTACATTGAAACCACTAAATCACCTGAAGTACCTTGCAGTTGTGGCAAAGAAATTCTATTTTGATCCAGAATCACGTCTG

CCCCATCTTGAAACTTTAATGGTGCATAATTATTGGGATGATACAGTACTGTTACCAGCGTCTTTTTGGGAAATGGAAAA

ATTAAGGCATGTTGATATTTGGAGAGCTGAATTTGATTTGGAAGAGGATAAGCATGGGCTATCCTCTAAATTGGAAAAAT

TGAGGATATTAAAGAACATTCTTAGATTTCCAATTGATAGGATGGATGTGTTATCAAGGAGGTGTCCTAATCTTCAACAA

CTTCACATCGAATTTTACGGGGGTGATAGTGATTCTGCAGAGTCTTTTTGTCTCACATTGGAGAATCTTACCCAGCTTCA

AATACCTCACCTTTCCTTTGGGGGGCCCCACATTGTCTCTGGGTTACGATTGCCTTCAAATTTAAACAAGTTGGTACTAA

GTGGGACTCCTATAAAAAATCTGATTTCCTTCATTGCGGGACTACCAAGCCTGGAGTATCTCCAATTACTAGATATGTAT

GTTCCTCAATCAGAAGTGTGGTGTCTTAGAGATATCACATTCCATAAACTTAAGTTGTTGAAACTGGGGTGGTCAGATAT

CTCAAGGTGGGATGCCTCGGAGGAATCATTTCCCCTGCTTGAAACACTTGTTATAAAAAAGTGTAGTAACCTAGAGGAGA

TCCCTCTTAGCTTTGCAGATATTCTAACACTGAAGCAGATTAAGTTGATTTGGTGCGAGAAGAAATCTCTGGAGGCTTCA

GCTGTGAGGATTAAGAAAGATGTTGAAGAGAATGAGGGAAATGACCGTATTGACCTCATTATCAAAGTAAGTAGAAACAA

ACTCCTAAATATGTTCTGTTTTTGAGTATCTAATGTTCAAACTATATGTTCAATACAGGATTGGTGAATCAAGTATGTGC

CTGTAACCACAACAATGGTATTGTTTCAGTTTGCCTTTTTTAATTGATGCTTGTTTTCCCTTAATTGCTCTTAAACTCAC

GAGGATTCGTTTGAATTTGACTACTGCAGCAAGTTCATGACGGCTAGCGTCCACACATAATCCAGCACAATGAAACATTT

GCCTTCTCTGTCAATAGATTCACATACTATTTTTGGCAGTTCCTTCACATCCATGTCTTGATATTCTGAAGTGAGCAAGT

TTCTTCATGTCTTTTAGAGTACTAAGAAAGACCCCATTTAGTTTGTAGTACGGGCCTACGTTCATGAAAAACTCAAAGGA

AACCTCAACATCGTTGGATGTGATAATTCAAATTGACTCTTTCTTTTCGTTATTATTGGTTTTATTAGTCGTTGTCTTAT

AACAGACTCTCTAGCTAAAATCGGAGAAACAGGAAACTTTCTTCACTGAGGTTGAGGTTGTCTCTTTGCATGACAAGTTA

GAGTTGCAAAATTAACTCAACTACAAAAAAAAATTTCTTGTTGAATATAAGCAAACCTCACAAATTTACAAATTTTCGCAG

CATAGAAAACTCGAAGGTTTTGATAAGAGTCTTAGATTTAAGCTCATCGACATAATACTTTACTATGCACTAAAACTTTT

GAACTTTGTTATTGTTGTATTGTCCTTTTTTGTTCTTCATTTACTTGACAATAGGAGACTAGATTGTGTTACGACCCAAA

Figure 8 (Cont.)

TTCCAAGAGCCATTACAGAAAACATAATAGACGTTCACACTGATGCTTTGCGCTACCAAATGTATGTGTTTTTAACCATC

AACTCCAAACGTATTGTTCCCTTAGTCTTAGCAACGGCATCTTCACATTCTTTACTAGATTTACATGTGTCTTAAATATC

TTTGTATATTCTAATTTAATCAGACATAGGCCGGGCCCACAGAGAAGACTTGGGGTCTAAAAGAAAAGTATATGCATTGG

AAAGTTGATGGAGTGTTTTCACCTTTTCCCTTAGTGCTCTCTGCTTTCTCCTTTTCTCTGCAATAATAATGCAGAACTCA

TAAAGGAAGATTATGTGTATTTGAAATTTTTTAATCACAAACATTTTTTTTTTATAAAAGGAAGATGAAGATATGTGTGA

TTCAACAATGCGGCGCTTTAGAATGTTCTGATATCTTGTATATGAATGATGGTTTGCTCATTTGGTAAGATTGTATAAGA

ATTGAAGAAATTTGATGGTTTTCACAACTGATGGATTTTTCATGTTTTATGAGGGGAAAAAAATACAACTTAAAAAGTTA

AAATTGCATGTCCAATCAAAACTTCAACTTCATATCAATATGATTTCATACCATAATTTCATATAGCCTATCCAAATGAG

CCCTTAAAAAATTGTAAACTTTTATTTGTAAAATCGATCTTCCCTTTTTCCCCATGTATGACATTAACTCTCTACTGTAG

TTAAATTCTTTTTAAAATTTGTGTAAGTAACAAATATAAAACTATATATATTTAGATGAATATATTTAGAATTCGATACT

CTAGGATGTGAAAGCAGAATGTGATTTATTGGACAAAGGTCTGAATATTTTTTACTGCAAAATTTGAGTTTTTTTACGTT

CCTCTCCTATTTGGGCTATACTGATGTGATTCGACTAAAATGCTTGTTAGCCTAAATGCTTGTCAATCCTTTTTTCTGCT

GATCTGCCCTCTTCGGTCCGCCCTCCATCATTATTGTCACACATTTGTTATAGTGGGTCTTTTTTTAATAATATATTATG

GAATAAAGTTGATGTCGTTTTTACTAAAGCAATCAATAGGAATGAAGCACTATCATTAATTAATAAAGCACTGGTTGTTC

TTTACCTACCATTATTTAATAAATTAATAATGCAATTATTCAGAACTCATACAATACACATTCCAGTCTGTTTGAGCCAT

TGCCAACTCTAATTATTGTTTGATCTCCTCACCCATCTCTCTGTACTAGAAAACACCTTGTACCATATAGGTTTTGGATC

TACGATCAATCAGTTAACAATCGATCGATCGATCTATCACTGAGCTACTGAGGAACAACAGGAAATTCAATAAGTTAAAA

TTATATTGAGGTGAGTGTTTTACTCGAAAAAATAAAAATGAAAATGGACTTTTTTTCGAAAAATCGATTAAACTTATGAT

TTGAAGAGAAATCGATTTTCCAAAAGAAACAGAGTCGCCACTTAATTTTTTAGTAAAAATCAAGAAAAAAACTTAAGGTT

TTCAAAAGATTTAATCAGATAAAATCAATTGAAAATAAAAGGGTTTGGAGTTCAATGTACATTCCGAGAAGGTGTTGGGC

CCTCGAAATGTCCGCTAACTTGCGGTTGACCGGCGATTTGACTAAAAATGACTTTGACTAAATTTTGAAATTTTAACCAA

GTAAGAAAAACTCATTTATTATAACTTGCAGTATAGCTGTGCGATTATAAAGCATAGCTATTTATGAACTGCTTCATTTA

CTATAACTCTGTAACCATGTTTGCTTGGAACAAAGAAAATTAGCGAATTGGAAGTGGCAAATGGTACTTCCAAGACTTCT

ATTCAATTGGATAATTGTTACTTGACGTGCTAAAATGCTGTTAAACCATCAATTTATTGAATATTTATAGATTTGTGTAA

ACAAAAAATTAGTCTTTCAGTAATCTTGATTGTATGCTTTCTTTTCTTATGTTCCACTTCACAATATTTTCTCAGTTGGC

ACTTATTGCAACATGCTTGAGCTGCAAATTTTATCGCAGCAAACGAGCTACACTCCAATATTAACAATATTTCCTTGTTT

GTTTTTGCAGCAAACGAGCTACGCTGACATGCTGGATCTAGCAGTGCAGCACATTCGAACCCTTCAAGATCAGGTTCAGG

TGGGTGATTAAATTGATCAACCTTACTGCTTTGCAGCTTTACGTAATCTATCATGCTGCATGCACCTAGGTACAAAATTA

AAATACTTATACTCTGTTGCTCAGACTCTTCAATGATACTGTTGGATGTGTTAGATTTTATCCTCCAAAAGCTATGCATT

TTTGGAGGATCAGACACTAGTACAACAATTTTGGCCCGAGCAACACATCTTATATTCTCACATGATGTTTACACCAAACC

GAATAATATAACCTTAATGTTTTTGGGATAGATAATGTCTAATATATTTTGCAAAAAAAATGATAAATTTTCTAGCCCCA

Figure 8 (Cont.)

CCTTTATAGCTGTGATTGAAGTAGTAGAAACATATTTTTCACATTTTCTTTTTCTTATGCAGAATCTGAATACAGAACTT

GAAAACTGCAAATGTGGATGTAAGAAATCAAGTCAATAACAAAATGGAAGGAAGCACTTTAGCTGAAGATCGACTTAAAA

GGATTTTTGTCACCATGATTTTGCCTCTTAGAAACTCAAATTTGTACATAAGGAAGTAAATTTCATACTAGTTTTTTAAA

GCTAAAAGGCGAACTCTTCTTTTTTTTTTTTTTTTTTCCTTTCCAGTTAGAAGACTACGTATATGATTGTTTTGGATTA

TTTGTAGTTTTTTTTTTCCATCTAACATTTACATTTTTAATTTAGTTTTGAGTTTATTTTGGTTGAGGATCATAAAGCTA

ATTGATGATGTTGTACAACAACTTTCTCTATTTCATTTTTATGTAAAATGAGTGGGTAAGACATTTTCTTGCTTTCTGTT

ATGTTCTTCTTGGGAAACGACCATTTACAATTTGCAAAGAAGAAAAGTAACTCTACTCTACAAGGATTTCATGTGTTTTA

TTTATCGAACTGATCATTTTCATTGAAAAAAAGTCATTTAATTAATATAACATTTGTATTGAGCCATAAAATCGATATTT

CCCTTCTTACCAATGTATGTCATGAATATATGTGATTCATCAATGTGGCGCTTTAGGATATTTCGATATTTTGTTTATGA

ACGATGATTTGCTCATTCGGTAAGATTGCATAGGAAATTGACTCTTTCTTTTCGTTGTTATTGCTTTCATTAGTCGTTGT

CTCATAACAGACTCTCTAACTAACATTGGAGAAATAGGAAACTTTCTTCACTGAGGCTGTCTCTTTGCCATGACAAGTTA

GAGTTGCAAAATAAACTCAACTACAATTTTTTTTTCTTGTTGAATATAAGTACACCTCACAAATTTACAAATGTATGTGT

TTTTGACCATCAACTCCAAACGTATTGTTCCCTTGGTCTTAGCAACGGCATCTTTGCTTTCTTTACTAGATTTACATGTG

TCTTAAAATTATTTAAATATCTTTTTATATTCTAATTTAATCAGACATCGGCCAGGCCCACGGAGAAGAATTGGGGTCAA

AAAGAAAAGTGTATGTATTGGAAAGTTGATGAAGTGTTTTCACCTTTTCCCTTAGTGCTCTGTGCTTTCTCCTTTTTCTC

TACAATAATAATGCAGAACTCATAAAGGAAGATTATGTGTATTTGAATTTTTTTTAATCACAAACATCTTTATTTTATAA

AAGGAACATAAATATATGTTTGATTCATCAATGCAGCGCTTTAGGATGTTCCGATATCTTGTATATGAATGATGGTTTGC

TCATTTGGTCAGATTTATACGAATTGAAGAAATTTGATGGTTTTCACAACTGATGGATTTTTCCTGTTTTATGAGGGAAA

ACAAAATACAATTTAAGAAGTCAAAATTGCATGTCCAATCAAAACGTCAACTTCATATCAATATGATTTCATACCATAAA

ATCATATCGCCTATCCAAACGAGCCCTTAAAAATTGTAAACTTTTATCTGTAAAATCGATTTTCCCTTCTTCCCCATGTA

TGGCATGAACTCTCTACTGGTATAAGTAACAAATATAAAACTATATGTATTTAGATGAATATATTTAGAATTCGATACTC

TAGGATGTGAAAGCAGAATGTGCTGATTTATTGGACAAAGGTCTGAATATATTTTACTGCAAAATTTGAGGGTTTTTTCC

ATGTTCCTCTCCTATTTGGGCTATACCGATGTGTGATTCGACTAAAATGCTTGTCAATCCTTTTTTCTGATCTGCACTCT

TCGGTCCGCCCTCCATCATTATTAATTGTCACACATTCGATATGAGTTTCTTTTTGTTTTAAAAAAATGACTACTTCCGC

GTGGGTCTTTTTTTAATAATATATCATGGAATAATTAGACATTATTCTTAAAGACAAGGGATAGAGTTGATGTTGTATTT

ACTAAAGCAATCAATAGGAATGAAGCACTATCATTAATTAATAAAGCACTAATTGTTGTTTATCTACCAGTAATTAATAG

ATTAATAATGCAATAATTCAGAACTCATACAATACACATTCCAGTCTGTTTGAGCCATTGCCAACTCTAATTATTGTTTG

ATCTCCTCTCTGTACTAGAAAACACCTTGTGCCATATAGGATTCTGATCTACGACCAATCAGTTAACAATCGATCGATCT

ATCACTGAGCTACTGAGGAACAACAGGAGATTCAATAAGTTAAGATTGAAGTGAGTTCCATTGATTCATAATTTATTTTC

ATACTTCATGGAATTTTGTATCCTCTGAATATATATACCCCCTCTTCCTAATTTAATTAAAAGAAAACTATGAATTAGCT

GGGTACGAAAATTCGCATATAACTTGGTTTCCTGCGACTTTTTCTACCAAAAAATTTTCGATGGAAATATCTTCGTAGGT

Figure 8 (Cont.)

AATTATTACACGCGAATATAAAAATCCCCAAGTAAATTACCTGGGGATTTGAATTTCGCAAGTAAATTACATTCGAATTT

TCTTGCAAATAAATACTAAAAATATCCGAGAAATTTTTAGTAAAAATTCGTGAAAAAGGGAATTTTCTTACAATTTTTTT

TTTTTTGCAAAAATTCCTAGGAAATAATTTGTGAATAATCATTTTAATTCTTTTAGTTTTTAATTTCTGGATATACCAAT

TATTTTTAATAGTTTTGTCTCTGATTATTATCTTCTTATGTAATTCTTGTTATTTTATTTTACAACCCCCCACCCCTACA

CACATGTTTACACCCTTAAATGCTCAACACAATTAATTGCACAGCCACTCAGAAACCAAAGAAACCACTGCCCAAACATT

CATTTAGCTTTAACTTTCGTTCTACCAAATATAAATGTTAAATTGTTAATGTACTCATTCGATGTGGTACAAAGATAGCA

AGGGAATTATTCCAAATTTTTTTAGTACTAATAAAAATATGACACAACTTTAAATATACTTTACGTATTTTATCCACGTT

CTTTAATCAAAAAGAGATTATTCTTTTAGAATATATATATATATATATATATATATATATATATATATATATATATATAT

ATATATATATATTTTGTAATAATAACATACGCAGTAAAATTTTACTTAGCGGGGTCTGAAGAGGATAGTGTGTACGCACA

CCTTAACACTAGCTCGTAGAGATAGATATATTGTTTTCGAAAGACCTCAGCTCAAGTGCATCAAACCCAAATAAAAGAAG

AATAAATCAATGAAAACAAATAACTATTAATAAGAAAAGTAGTGTAAAGTCTATAAGAAAGAACCTCTTAAAGAAATTGA

CACAAATTACTTAATAAGATGAATATAATTTAGGTATTTGAAAAAGTATCTATTTTTCAAAACTTTAAATAACATGATGT

TATTCCAAATTTTTATAAACATTTTGGCCTCATATATAATAGAAATTTCTGTACAAATAAAACTATAAAATGATAATTTA

AATAATTTATAAGTTTAAATAACATGATGTTATTCCAACTCGAATTATTGTTTGATCTCCTCACCCATCTTTATGTACCA

GACAACACCAGCTCGTACCACATATAAGATTTGGATCTACGATCAATCAGTTAACAATAGACCGATCTATCGCTGAGCTA

CTGAGGAATAACAAAAGATTTGATAAGTTAAGATTGAGGTACGTTCCATTCATTCATTATTTATTTTCATACTTCATGAA

TCTATATACTTTCTCTTCCCAATTTAAGTGTCTTAGTTTGATTAGACACAAAGTATAAGAAATAAAGACTTGATTCTTGT

GATATTAAATTAAAGATGTATGTAGTCCTTTAAATCTTATGATCATAAACTTGTCCTGTGGAATGTTAGAATTGAAAATT

TACTAAATATAGAAAGCGACACTCATTCCTGTTGGATACACTTACACAAGTTCATCCAGCTTTTTTTGAAGTTGAAATTC

ACCAAGTCATAAAAATGAAGCTAACAATAAAAAATGTCATTCCACCAAGTCTCCTATAGTCAAGTAAACGAAAGAAGGAA

TGAAAAAGGAGAAACAAATCATACAAGACACTAGCTAGTAGCCTAGTACAGTAGACTCATACTGGTATATACATTTTTTA

GCTTTTGAGGTTGAGTTAGACTCATGTGTCATATTTTTATAAGGTATCATAACTAGATTCATACTCCTTTGGACTCATGG

TCCATGCTCCAGTTGGGTCTGTACATGAACGAGGGTGTCAAAGTTCACATTGATTGAAAAACAGACCGATAATTTACTTA

TATATATATGGACTTAAATAATCCTCCTCTAGTGAGCTATTTTAGAGATTGAGTTTGGCTCAATGCCATATCTTTAGAAT

TATTTAAATAGTTTTTCCATATTCTAATCTAATTATTACTTGACAAGTCAGTTGGAATTCTTCAATTCCATGCACAATGG

TCAACACTTTAATCAATGTCACAATCAAATATAAATGTGGGGAAGGCGTGGGAGCCCATGCGCCTTACAAGTCCTTCTTA

CATTTCTGACCCAATAATTTTTTTGAGGTAAGGCGTGGGGGTCCTGCACGCGCCTTTGCCCCTTTGGTCTCTTCCATTTT

TTTTTGCCCTTTTAGAATTTTGGCAGAAAAATAATAATTGTCCTTTAGGCTATGGACTCCAATTGTAGACAACTTTTTGTT

ATGTAGAATTTGCTCAAAACATACAACTTTTTGTTTTATAGAATCCGGTCAAATACATACAATTTGCATTCAATTTATTT

GAGTTAGAAGCTTGGAACTTGGAAGTCACTCAATTTTGGGTAATTAGCCATCATAGTCGCTCAACTTAGCCAAGTTAGCT

CCCATGATTGTTTTAGCTAGAAATACAATTTTTGGTACATATATAATGACGTGATGACTATAAATTTTTAGAATAAAATA

Figure 8 (Cont.)

TTTTTAAAAATTAAAATCAATATTTAAATTTATTTAGGACCCAATCCATCAAAACTCAACCTAATTCTTGCCACGACCAA

TTTAATGAGTTGACTATATAAAAAATTTCTTTAAACAAACTTTATTTCTCCTTTTTCCACTTGTGATTTCTCCATCACAT

GATATATCTTCTCTTTCTCTTTCAAATATGTAAATTTTCCATTTTTTTATTGTTCTTGTTCTATCAGTCAAATCATTCAT

TGCGAAAGATTACCAAAATGAATCGAGTTCTATATATTACATGGATAGATAGGTTGAGAAAAAAGTTTATTGTTTAAACG

GTTGTTGCACTACTGAAAAATTAGGTGAATAAGATCATTTTTGTATTTGAGAAGTCACTAGTTTTTTTTTGTTATTTCAT

TCATAAGGTCATTCAAGTTTAAAAGTAATACATCCGGTCACTTTTAATGACATAATATTTGTAAGTCATCTTCTTCTTGA

ATTATTTTTATCCCTATATATAGAGAGTTGATTTTTCTTTATTGAAGAAAATTAGAATCAAGAAGAAAGGTAATTTTCTG

AGATAATAACAATTAGTTGAGTGATCATATGAAAAGAGTAATTATGCATTGTTTGCAAGATGAAATGGTACATAAGATGT

ATAATCTTTCACAAGTATTAACATAGCTTCAAACACTAGATATTGAAAGACATGAATAAAAATGTTGCTCAAAATTCTAC

CTCGTCTCCTTTTCAACACCTCCACTCGCCTTAGTTTCACACCTACAAACCAATGCATCTGTAGGTCGACACAAGACATG

TCACACCATCTCCAGCGCACGTCTCTTATTATATTATCAATGCTACTTGCACTTCTAGCGAATATATATGGATTATTTTT

AATTTATTTAATATTATATGATCGCATATCCATCTTAGCAGTTGGTCAAATTTATGTGGTCTAACCTTGCAAAAGTCACC

ATCAGGCAAGATTTCAATCAACTTTGCCCCTGCTGAGAAGAATTCTCGTCCGAGAGGACTATAGGGGACAATCCCTATGC

TATGGTCAAAGAAATCAAAAACTGCTACTCTTGAACTCAAATCTAAAATAAAAAATGTAGAAAGGAAAACACTTCTTATT

ATTTAGATACAAAAATTACATACTTTCTTTTAACAGATGCAGTGTCCCAGCTAGCTTGCACGAACCTCAACCATTCCAAG

GGGTACCTGCAATCTCTCACTGGCTACCTGCATAGGTACCTGCAACTCTATCCACCAAAACTTAGATAGCTAGGAAGACA

TCATCTAATTTATGCATTAACTACCATTTGAACCTGAAACCTCATGGTTCTCGACCCCTATCATCCACAACTAGCCAAAT

ACATATCACTTGTCAAACCCCTACTCAGCTTTCCAGGAGGACAATGGTGGCGCGCGTCTCTGAATTTATCCAACAAAATA

AGATTTACCAGTGTGAATTATAAGACTCTAAATAAGTAGAACTGATTTATTTGCAGTAAGAACGACAATGTGATTAATAA

AGGACAATGTGAAAGTTCACGTAGCCAATTAATTAGTTCTCTGTTGCCAACTGTCCTCTCCTTCCACACACTTTGATTAA

TCATTGGGAATAGATACTAACCTTCCAATAAAGTAGTTGTCTCTCTGCATATATCATAAGCCATGTTATTTCATTAAATA

ATGCAACCATTGACTTTGAAAGCCAATAGGAATGCATATTAACCTGACAATATATTAGCTATCTAAAAATTAACATGATA

ATTAAACACAATAATTATTCATAATACAACCATTGACTTTTTTGTAGGATGTAGATCCAGTCCTTTGGTTAACCATAATT

ATTCATCCACTAATCTTGTTAAGAGTATGACACAAACAACATTTCCTCATTGTTCTAAGTTAATTATGCTCATATTAATC

TTTTCTTGTTAGCTTAATCCTACTCCAATCTTTATCAGGTATTTTTCAATAAATATTTTTCTAGATCTCCCTTTGAATTT

TTATCCCTTTTTAAGTGGAATCTGCTTTATGTATAAGTTACTAGTTTTTAGGAACGTGTGTTGCACGTTATCCCCCAATT

AATATAAAATTTCTACATTTTAAAAAAGTTTTAACTTATGAAATAGAAAATATTAACATCAAAATATTGCAGATTTTACT

ATTTAAATCTATTCATTAAAAACACAATTAGTGGGACGATATAATAGCCTCTGGCCCTCTGATAGTATGCAAGAGAATTC

TTGCTCTAATTTTAATAAATGCATGTAAAAATATTTAAAAAATTTACAAAAGAAAAATATGAAGAAAGATATCTTTTTAC

AAAACCCCAAATAGGATTGTTTGTTTAGATTTAAAAATGCTATATCAGATTAAGTGAAATATAAAGTTAATTGCACTACC

TAATAAAATATTTCTTTTTTCTCTGCCAAGCAAGCATTTTATGTAAATATGATATTTGAATGTTAAAGAAAAAGATACAT

Figure 8 (Cont.)

TTTCATTTCACAAAAAATAAAATACCTCTCAATTCTATAATCCAAATGAATTAAAAAATAAATGGTTAATTATGAAGTAG

TACAAGTATTATGCATACAACTACATAGATAATTTAAATTCAACAAATTCTCCTTATATCATTTTGATGCCTCAACAACC

ACAAAGTCATAACTTGAAAAGTATTCACCAGACAATAAATTTTTAACTCCTATCTTATGGATCGTTTTTTTAAAATCTGA

AGTACTTCATCCATGCACAAAGTATTGCATAAATGTGTTATATCCAGTACAACAGTGCCTGTTGTTATGTTAAAATAAAA

ATATGAGCACAGTTGTGCCTAAATAAAGCTGATACACAATAAAGAAACAAAAATTTTGAAATAGATGCATGGAAAGAAAT

ACAAGTTTGCAATTTGTCAATTAAATAAGGATTAGACGGTAGAAACAACCACACAACAATGTGCATAGAAATAGTTAGTT

GCAATATGTGTACCGTCAAATGATAATATGACGATTAAAGTTAATTTCTTGTTCGATCGTGGTATTCAATAAAAAGTCCA

AAGTTACTTTACATAAACTTGTCGCAAGCAGTACCATGTGAAATATTTTGTTACTTACCTTTGTTTCTTTTAACCAAATG

TGCAATTTGAGCATCATGGCGGAGAAGTTGGTTAGCAGTAAACCTCTTGCAATTATTTGGTAATTGATAAATATCATGAA

AAGGAACAATAGAGGATATATATCACTAATAACAATTAGCAATAACTGGGCAAAACAAATTCTCACCAAAAAATAAGAGC

CAACGTTTCATATGAAAGGAGACGAAAAGGAAAAGTTGATGAAGAGTTTCTTGGTAACTGCTGTCCTTTAACATTATTAT

TATTATGAGATTGTGAAATAGACTTTAATTTTCATTTTCTCCAAATTTCAGATTATTTGAACTCAGACTTATTACTAAAA

ATATATACATCTATAAATATAAATATGGTGATTAAGATTATTTAAGTAATGAGTACATTGATATTGCTGGCCAAAAGGAT

ATTTCCTTAAAATATTTATATTTAATCAAATTTAAATTTAGTAGAAGGACAAAATGGTAATTCAACTTTTCACTTTGGAG

CTTCCCACTAATAATAATAATAATAATAATAATATATATATATATATATATATATATATATATATATATATATATATATA

TATATATATATATATGATCAACAACTCTTTTTCTAGGATTGGATCAGAACTTGGAGATACAAAAAGGAAAAAGAAGATCG

ATACTCAACTACTCGTCACACTCGAAAATTGTAAGATATGAGTATATATTAACTTGCTATTGCTTTCAAAAATCTCAAAG

TTCTTAAATTGATACAACAACTGAGTTATTAATTCATTTTACCAATAAACTTCATGGTTCCAAAACTACAAATATTGTGA

TAATAAAAAATGGATATCACACATAATAATTAGTTTTTGCTCTGTTGAACCAGTTAAAGAAGTGTTTTATTTTTGTTTTC

CTCTTTAATTTTCTATTTTATTTTATTTTTTAAAAAAGTGATCAACAGCAGATGGCTGGTTATATGTCTTTATAGATACA

AATTGGGGGTAGGGGAATTGAACCGTCATAAGGTGAAAGTTGTGATATTCAACCGACTGAGCGACTAATCGTGCTATCCT

TCTGCACACACTTTTTTTAATTAATCATTGGGAATGCATTAGTTGTTTCTTTGTACTAATAATTAATAGAGAAAAAGCTC

AAATATGTCATCCAACTTTGAGAAGAAAAAAACCCTCATTTAATAGTTGGGCATGTCATTGCCATTACATAAATGACCCA

TTATGCCATTGATTTTTAACAGTCAGGACTTATGTTTTGCAACACTATTTTTTTCCATCTGGCTTCTTATTAGAGGTCCA

TGTCACCAAAATTAGACTAGTCGAAAAGTAAGTTCAAATATGCCACTGAACTGTAACAAGATGTTCATCTATGTCATTCA

TTAACAGTTGGATTCAACAGCAGATGGCTGGTTATATGTTTTTATAGATACAAATCGGGGGTAGGGATTTGAACTATCAT

AAGGTGAAAATTCTGATATCCAACCAACTGAGCGACTAATCGTACTATCCTTCCCCCCACACATTTTTTTTATTATTAAT

CATTGGGTATGCATTAGTTGTTTCTCTGTACTAGTAATTAATAGGGAAAAAATTAGCTAAATGATGTCATCCAACTTTGA

GGGGAAAAAAACCTCATTTATGTCATCCATTAATAGTTGGGTTCAATCACATGCCTTTGTCATAACAGAAATGACCCATT

ATGCCATTATTTTTTAATATTCAGATTTTGTGGTTTTGCAACACCATTTTTCCATATGGCCTCTTATTAGAGGTCCACGT

CACCAAAATGAAACTGGTCAAAAAAAAGTTCAAATATGCCATTGAACTGTGACAAAATGTTCATATATGGCATTCGTTAA

Figure 8 (Cont.)

TAGTTGGATTCAACCATGTCACTGCAGTTTAATTTGGAATTATAATCCAACCCATTAACACCATACCCGATCCACCATAA

CCCATTTCCCTTTTATTTCTCCTACAAACTCTTAGATCCAAAATTTCTCCCATTTTAATGATGAATTTATATGTCAGTTT

CTTGTCAATTGATCAATTTAAGTGTTTGGGGAGAAATAAAAAGGGAAATAGGTTAGGGTGGGTCGAGTGTGATGTTATGG

GTCGGGTTTTAATTTCAAATTTAATTTAATTAGGTTGGTTTATATTGGCACGTGGACCTCTAATAAGAGACCACGTGAAA

AAAAATTAATTTTGCGAGATCATGAAACCTGACCATTAAAAAGTAGTATGAATGGGTCCCTTCTGTAACGACAATGGAAT

GGTTGAGCCCAATAATTAACAGATGGCATAGATAAACCTTTTTTCAAAATTTGATGCATATTTGAACTTTTTTTATCAGT

TTAATTTTGGTAATGTGGACCTCTAATAAGAGACCACGTGGAAAGAACGATTTTGCTAACCATCAAACCAGCTACCTGTT

AAAAAATAATGGCACGAATGGACCATTTCTGTAAAGCAGCGGCATGATTGAGCCCAACTATTAACGGGAGGCACATCAAC

AAGCATTTTCCCGATGTTTGATGGCAAATTTTAACTCTTTTACATTATTGTTAACTCAAACACAATTTTAAAGAAATTTT

ATGTGATTTTTTAATAGTTCATATCTAGGCACGTGCAACGATACTACTATATATTATAATACCTAAGTGTTAGTTCAAGC

AAGTATTGTGAACATAAAAGCTACGACAATTGTAAGGAAAATGATTCCCTTTTATAAGTGAGGAAAATCATTTCCCCCCT

TTTAGATGAAACTTGTTTTAATTTCTCGACTTCTATCATAGTTTAGACACACATTAGATGAGCTTGAGATCTAAAAAATA

AGCAATTTTAAGTTGATGTTTCATTTTCCATTTCTATATGTTAAGTTAGTCGGAAGAATAATTATAATGACCATCTTGTC

AGGGCCAAGCTTTCGTGATATGCATCGTCGAGCTCAAAAGTGTAGTGAACTTGTGTTATGTATTGTAACTTTTTTTTTA

CTTTCGTCTCTTATTTGGGCAATTCCTGTGTGTGATTCAACTAAGATGTTTGTCAATCCTTTTCTTTGACCTACTCTTAT

CGGTCCTCCCTCCTTCATTAATGTCACACATTTGATATTAGTTTCTTTTTGTTTAAAGAAAATGACTATTAGTTGAGTGA

AATGTGTCTGAGATGATATGCACTATTTGAATTAGATGAAATGGTATATAAACTGTATTATCTTTCATAAGAATTAACGT

AGCTAAAAACACTAGATATTGAAATACATGAATAAAAATGTTGTTAATGAACCTAATTCCAAGAGTTGGTGAACTTGCAG

GAAATTTTCAAGAGAAGATGGCTGAAAATGAAATTGAGGAAATGTTAGATCACCTAAGAAGGATCAAGAGTGAACGTGAT

CTGTCTAGCGCCAGGATTGAAAAAATTAAGAAACTTGAAATAGCGCTAAGAGTTTTGAGAACCTTTATAAAGTGTCATCA

TGTTCTTTTTCGTGATTCCTTAGTCAAACACAAAAAGAATGCCAAATTGACTATGGCAATGCTTCACCAGGTATTGGATG

GGATTCCAGATGAATGTAAAGCTAACCTTAATCTGGAAAGGCTAGAATCACATTTGTTGGAATTCATGGAACGTGATACC

ATTTTAAATAATAATTATGAGTTGAATGATCTTGATCTTGATCTTGATCTGTCAGAATGTATGGATTGCCTCGAAAAGAA

TCTAAATGATACTGATACTCTGTCTGGAATGTGTTAGGTCTGACCCTTCTGAAGAAAACCATGAAATACTCAGATTTTTA

AAGGAACTGAAAGTTGTTCAAAAGAAACTGAGATTTTTGTCATATTTATATGCCACAGAGATAAATGGTTACGTCAACCA

TGAGAAGCTGGGATGTTTGGAGACTCGAATTCAGTTCATGGCTAACAATGTGGGACATTTTTGTCTTGCTTTTTCTGATA

TTATAAATGGTATTGATGAGGATGAGGCTAATGAAATCTTTAATACACCTCCTTATCTATTATTCTTGATTGTGTTAGTG

GAGCTGGAAATGAAGAAGATTTTTCAGAGTGAACTAAAGGATTCAAAGTTTACTCATTCAAGAACTTTCAAGGACAAGAA

ATTACCAAAAGGATTTTCTCATCATCTCCACAAACTATTGATGTATCTCAGAAAAGAAAAGCTCGAGAACTTTCTTGATG

ATGTCTCTGCTCAAAATATTGATGTGGCAATAGAGTTCTTGTTGGTCTTCCTTGATGCTGATGTGTCAAATCATGTTATT

AATGGTAACTGGTTGAATGAGGTTATGGAAAAAGTTGGAGCTATAGCAGGTGATGTTCTATATGTCATGGAAAAACTTCT

Figure 8 (Cont.)

TCCTAGCTCTATAAACAGAGATGACACTAGCAAAATAAATCTTTGCTCGTTACAAATATTGGAGAAAACTAAAGATCTGA

AGGCACAAGTGGAAACTTACTACAAATCCTTGAAATTTACTCCATCTCAGTTCTCCACCTTTTGTGGATTGAGCTATCTG

GATTCTCTTTTATGGAAATTGAATGAGATGTCGAAATCTAAATCTGATTTAGATTTCTTGATGAAACCTCTTTTTGGTAA

TTTGGAGAAAGAGCTATCAAGTCATATATCCATTTTAGAGAAGGAGCTCTCATCTTTATCATCCATTTTCAGAGATGTTC

TAAAGGTGCACCATGAACATAAAATTCCTAAAAATCTCCAAAGACGTACCATCAATTTGGCATATGAAGCTGAGTTTGCC

ATTGACTCTATTCAGTATAATGCTTTTTTGCATATTTTTTGCTCACTTCCTACAATCTTAAAAGAGATCAAGCACATTAA

TGCACAGGTGACTGAGATGTGGTCAGCAGACGTTGCTCTTAAGCCTTGCTATGTGGTAGCACTATTTAAACACCTGCCAA

CTCAACATAACAATCCAGTGATTGATGAGGAGATAGTGGGTTTTGGGAAAGACACAGAAAAAATGATTCAGTGTTTGATT

AGAGGTACAAATGAGCTAGACGTCGTCCCAATTGTAGGCATGGGGGGACAAGGGAAAACGACAATTGCTAGAAAGGTGTA

CAATAGTGACAACATTGTTTCTCATTTTGATGTTCGAGCATGGTGCATCGTTTCCCAAACATATAACCGGAGAACGCTAT

TACAAGAGATTTTTAGTCAAGTTACCGGTTCCAAGGACAAGGGGGATAAGGATGACATCCTTGCTGACGAGTTGAGGAAA

ATCTTAATGGGCAAGAGATATCTCATTGTATTGGATGATATGTGGGATTGTATGGCATGGGATGACTTGAGGCTTTGTTT

TCCAGATGTTGGAAATAGAAGCAGAATCGTAGTAACAACTCGACTTGAGAAAGTGGGTGAGAAAGTCAAGTACTACACTG

ATCCCCGGGTACC

Figure 8 (Cont.)

AAAACTTTCACGCACCCATAGGAAGTGAAAAACACTTATTTTGTCATATCAGCATTTTGTATTTAATAGGTAATTTTTT
AAACAATTTAAGTGTTCAATAGGTAATAGTCCTAGTTAAGATGTCTAACTGAAATATACAAATAACTTTTAAGGAATC
GTGAATGACTTAAGCCTAATTTAATTGGTAAATATGTGTTATCCCGAAAGATGTATGGATGAATTATCACCACTACTT
TTTTTAATCCCTGTTTGAGATCTCGATGACTATTCTTAGTCTAATTGTTCTGACATTATTTGGTCAATAAAGCATGTGA
ATACTAGTCTAATACATGAATTTCAATCTATTTTAAAGAAGGAGACAGCATTAATCTTACACCTACCACCTAAATCAA
CTTGCTGATACAACTTGCCTTTTTCTAAATATTAAATAATATCTGACTCATAAGTTAATAATTTATATATATAAAAAAA
GGAGTCATCATTTTAAATTTATAGAAATACTCATATTCTATTTGAATGGATTGTCCGTGCCAAGTGAAAATATTAACT
TAAAGAGTAATTATTTGTTACTATTATTATTGACTAGTGGATCTTTATAAATTTATGTGCATTTGAAAGTTTGTAATCG
TGAATATTTATTTATAAAAGAAACATGAAAATATGTAATTCATCAATGCGATGCTTTAGAATATTTTGATATCTTATTT
ACAAATGATGATTTACTCATTCGGTAAGATTGCTTAAGAATTAGATAACTTTTGATAGTTTTCACAACTTGAGAATTT
TCATATTTATGAGAAAAAATAACTTCATGTCCGACCCAATACCCCTTAATTATATGCTAAACAAATATCAAAATAGTT
CATAGTTTAAGTATGAAATTAGCAAATCGGACATAATTTTGGGGGATTTTCCTAAGGAGTCGTTTGGCGTGAGGTAT
GAGGTATAAAAATTT*T*GGAATAAAATATAGGATTATTTTATTATGTATTTGATTGGAGGTACTAGATAGTCCTTTGAT
TATTTATCCCAATATTTATACTTTAGTGATGGAATAAGTTATTTCATATACATGTTAAATAACTTATTGTGAGATAATT
ACTCTCAAAATAACTTATTCTCGACCAAACGACCCTTAAAAAAAGGACTAAGTAATATAGTTGTATTATTGAGGCACT
TTACAGCTACCACCTAAAGCAACTTGCTACTACAATTCATCTCTTGTTAGGTATAAGAATTATTAGAGAGACAGAAG
AACTCTCTTCCTTCAAACCTTCAAACTTCCATTCATTTTATTTCAATGAATTTTTTTCTTATATCACCTATTGCGTAAAC
TTGGAAATATATCTTTGTTGGAATCCAAATCTGAGAAATTGAAGATTCTTGTCAACTAACTGTAAGTCATCTTCTTCA
TGAATTACTTTTTTCCCATAGATACAGAATTAGAGAGTTGATTTCTCAAATGGTTCACTCAACTATTAGTTAGTATCT
CATAAAATTGAAAATGTAAGAAAGACGATTTTCTCAGATAATAATTAGTTAAGTGACATTTGACAATATGAAAATGGT
ACATAAGATGTATAACTTTTCACAAGCATTAACATAGCTTCAAACACTAGATATTGAAAGACATGAACCTAATTCCAT
GAGTTGGTGAACTTGCAGGAATTTTTCTACAAAAAATGAATGAAAATGAAATTGAGGAAATGTTAGATCACCT
AAGAAGGATCAAAATTGAAGGTAACCTGGATTTCTTCAAGATTCGTCGTATTGGGGATCTTGATATTGTGC
TAAGAGTTTTTAGAACCTTTATAAAGTATCATGTTCTTTTACCTGATTGTTTTGTCAAACTCACAATGAATG
CCGAATGGACTGTGGAAATGCTTCACCGGGTATTTGATGGGATATCAGATGAATGTAAAACTAACCTTAA
TTTGGAAAGGCTAGAATCACATTTGTTGGAATTCTTTGAAGGTAACTCCAGTTTAAGTTACAATTATGAGT
TGAATGATTTTGATCTGTCGAAATATATGGATTGTCTGGAAAAAATTCTAAATGATGTACTAATGATGTTC
CTGGAAAAGGGTAGGTCCTGTTATCCCATAGAAAAACTTGCAATACAGCTATCTATAAAGAAACTGAAAA
TTGTTCAAAAGAAAATGATATTTTTGAGATACATATATACCACAGAGATAAATGGTAACGTCAACTATGA
GAAGCTGGAATGTTTGGAGACTCGAATTCAGTTCATTGCTAACACTGTGGGACAATTTTGTTTGGCCGTAT
TAGATTATGTTGCTGATATTGAATTTAGTGATAATAATGATATCTTTAATATACCTCCGTATCTATTATCAT
TGATTGTGTTTGTGGAGCTGGAAATGAAGAAGATTTTTCATGGTGAACTAAAGGTGTCAAAGTTTACTCA
ATCAAAAACTTTCAAGGACAAGAAATTACCAAAAGAATTTTCAGATCTTCTCCAATATCTGTTGATGTATC
TCAGAAACGAAAAACTCGAGAACTTTCCTAATAATATCTCTGCTCAAAATATTGATGTGGCAATAGAATTC
TTGTTGGTTTTCCTTGATGCTGATGTGTCAAATCACGTTATTAATGGTAACTGGTTGAATGAGGTCTTGTT
AAAGGTTGGAGCTATAGCGGGTGATATTCTATATGTAATTCAAAAGCTTCTTCCTAGATCTATAAACAAAG
ATGACACTAGCAAAATAAGTTTTTGCTCGATACAGATATTGGAGAAGACTAAAGATCTGAAGGCACAAGT
TGAGACGTACTACAAATCCTTAAAATTTACTCCATCTCAGTTCCCCACCTTTGGTGGATTGAGCTTTCTGGA
TTCTCTTTTAAGGAAACTGAATGAGATGTCGAAATCTAAGTCTGGTTTAGATTTCCTGATGAAACCTCTTT
TAGGGAATTTGGAGAAAGAGTTATCATCTCTTACATCCATTTTAGAGAAGGAGCTATCATCCATTTTCAGA
GATGTCGTGCACCACGAACATAAAATTCCTAAAGATCTTCAGAGACGTACCATCAATTTGGCATATGAGG
CTGAGGTTGCCATTGACTCTATTCTTGCTCAGTATAATGCTTTTTTGCATATTTTTTGCTCACTTCCTACAAT
TTTAAAAGAGATCAAGCAAATTAATGCAGAGGTGACTGAGATGTGGTCAGCAAACATTCCTCTTAATCCT
CGCTACGTGGCTGCTCCATTTAAACATCTGCCAGCTCGACATAGCAATCTTGTGACTGATGAGGAGGTAGT
GGGTTTTGAGAATAAAGCAGAAAAACTAATTGGTTATCTGATTAGAGGTACAAATGAGCTAGACGTCATC
CCAATTGTAGGCATGGGGGGACAAGGGAAAACGACAATTGCTAGAAAGTTGTACAATAATGACATCATTG
TTTCTCGCTTTAATGTTCGAGCATGGTGCATCATTTCTCAAACATATAGCCGAAGAGAGCTATTACAAGAG
ATTTTCAGTCAAGTTACGGGCTCCAAGGACAAGGAAGATGAGGTAGGCAAACTTGCTGACAGGTTGAGG
AAAAGCCTAATGGGAAAGAGATATCTCATTGTATTGGATGATATGTGGGATTGTATGGTATGGGATGACT
TAAGGCTTTCTTTTCCAGATGATGGAATCAGAAGTAGAATAGTCGTAACAACTCGACTTGAAGAAGTGGG
TAAGCAAGTCAAGAACCATACTGATCCTTATTCTCTTCCATTCCTCACAACAAAAGAGAGTTGCCAATTGC
TGCAGAAAAAAGTGTTTCAAAAGGAAGATTGCCCGCCTGAACTACAATATGTGAGTCAAGCAGTTGCAGA
AAAATGCAAAGGACTGCCCCTAGTGGTTGTCTTGGTAGCTGGAATAATCAAAAAAAGGAAAATGGAAGA
ATCTTGGTGGAATGAGGTGAAAGATGCTTTATTTGACTATCTTGACAGTGAGTTCGAAGAATACAGTCTA
GCGACTATGCAGTTGAGTTTTGATAACCTAGCTGATTGTTTaAAGCCTTGTCTTCTTTATATGGGGATGTTT
CTGGAGGACGCAAGAATTCCAGTGTCTAAATTGATAAGCTTATGGATTGCTGAAGGATTCGTGGAGAACA
CTGAATCTGGGAGATTAATGGAAGAGGAAGCTGAAGGTTACTTGATGGATCTCATTAGCAGTAACGTGGT
AATTGTTTCAAAGAAAGGTTATAATGGTAAAGTCAAATGCTGCCAGGTTCATGATGTTGTGCATCACTTTT
GCTTGAAGAAGAGTAGAGAAGAAAAGTTTATGCTTGCAGTGAAGGGTCAATATATCCAGTTTCAACCGTT
GGATTGGAAGGGAAGTCGAGTGAGCTTCAGTTTCAGTGAAGAGCTTTCCAAGTTTGCATCTCTGGTTTCC
AAAACACAGAAGCCTTTCCACCAACACTTGAGGTCTCTGATAACGGCTAATGGTGGAGAATCTATTGATG
TGATTCCCGTCTGTCAGATTAATGAATTGCGACTTCTTAAGGTCTTGGATTTGAGTTCTTATTATGTGGAG
TCTTTGTGGTTAGCTAGATTAAACCCACTTAATCAGCTGAAGTACCTCGCAGTTTGGGCAGGTACTTTCTA

Figure 10

TTTTGATCCACAATCACATCTGCCCCATATAGAAACTTTAATTGTGACGAGTTGTTTTTATGGTGTACGGTT
ACCAGTGTCTTTTTGGGAAATGGAAAAATTAAGGCATGTTCATTTTGCTGGCGCTGGTTTTGCTATGCAGG
GACTCTTTGAAGGATCCTCTAAATTGGAAAATTTGAGGATATTAAAGAAAATTGAGGAATTTCCAATTGAT
AGGCTGGATGTGTTATCAAGGAGGTGTCCTAATCTTCAACAACTTCAAATCACATTTGAGGATGATGTAG
AGCCTTTTTGTCCCAAATTGGAGAGTCTTACCCAGCTTCAAGAACTTCAACTTTCCTTTGTGCATCCCCGCA
TTCTATCCGGGTTACAGTTGCCTTCAAATTTAAACAAATTGGTACTTAAAGGAATTCATATGGAAAGTGCT
ATTTCCTTCATTGCGGAACTACCAAGCCTGGAGTATCTCCAATTACTAGATGTGTGTTTTCCTCAATCAGA
AGAGTGGTGCCTTGGAGATATCACGTTCCATAAACTTAAGTTGTTGAAACTGGTGCAGTTAAATATCTCAA
AGTGGGATGCCTCGGAGGAATCATTTCCCTTGCTTGAAACACTTGTTATAAAAAAGTGTGATGACCTTGA
GGAGATCCCACTTAGCTTTGCTGATATTCCATCATTGAAACAGATTAAGTTGATTGGGTCTTGGAAAGTAT
CTATGGAGGCTTCAGCTGTGAGAATTAAGGAAGAAGTCGAAGAGATTGAAGGATGTGACCGTATAGACC
TCGTAAGAAGAAGTCGAAGAGATTGAAAGATGTGACCGTATAGACCTTGTCAAAGAATACTGAAGTCTATTTTG
TTGCTAGCTCATTCTGTTATTGTAACACTAGTAGTGTTTGCTATGTTTGTTTTGATTGATCAACTCTTTTTTATGTATG
ATATGATTGGAGACAAATATACATCAGATCGTCTTTCACTAATTTCGTGTTTTTATGCAGCTTTATAATTTTGACCAAT
TTCTCTCCACTTACATCTTCATAGCTCAATACACATCAACCATGTTGTTGTTGTTGTTGTTGTTGAGTACTTCTTGATT
TTCTAATTCGATGAACATCCGAAAAATTTTAAGGTTAAACTGCTTCTTGTTGCTGTAGGTGCAATGTTGAAGGATCTC
TTTATTATGTGTTCAGGTGCCTCTTTTAGAAGTTGAAATTCATACAGAATGAAGCTAATAAATTTGTTCTTGTCATTC
ATCGATCATTTGAACTTTGCAACATATGAACTTAAGATATAGTAAAAATATAGTATGACATTCGAGTCCCCTCCGAAT
ACAGAGTCGTCTATGTTAGGGAGCGTTTCACCCCCAATGTGGGACTTTATTACGTCGTGAATCCATTGTATCGGGC
TCCAATGTGGGTACCGGACATTGGGTGGAAACAAAAAAATGTATATAGTACGACATGAAATGAATAAATAAGGGCA
TTTGACCCTTAAGAACCAAAAAAATCAATCTTTTGTATTATGATTGGCCCTGTTCTGAGAACAGACTCCATTCACAAG
ATCTATGGAAGAATTATCACCACTCCTTTTTTATCCTTGTTTGATTTATGACATATGATTTATCCTTTTTTGAATTATGT
TTTTTTAAAAAAATATAAAAACTTATTCATAAGTTTATATTTTGTAAAAAAGAACAAATCATTATTTTCAGTTTTACAAA
AATAAACTCATGTTCGACGTGAATAAATTGTCCGTCGTATCATGTGAAAGAATTACTAATTACTACTATTGTTGACTA
GTGGATCTTTATAAGTTTATGTACATTTGAAAGTTAAAAGAAACATAAAGATATATAATTCATCGATGCGATGCTTTA
GATATTATGATATCTTGTTAACGAAATGATTTACTCATTTGGTAAAATTGCATAAGAATTGAATTTCAAAGTTTTCACA
ACTTGTGCATTTTCATATTTATTAGAAAAAATATAACTTCATGTCCGACCCAATACCCAACCATAAAATTCCTTAATTA
TATGCTAAGCAAATATCATATAAGTGCATAATTTAACTATGAAACTGCCAAACCAAATAAAATTTTGGGGGATTTTCC
TAAAGAGTCATTTGGTGTGAAGTATGAGATATAATAATTTTGGGATAAAATGCAGAATTATTTTATCTTGTGTTTGGT
TGGAGCCATATTTGGTAGTCCTCCGATTATGTATCCCATATCATAGTGATGGAATATATAAATTATGATCACATATAC
ATGATCAAGTAACTTATTTCGCGATAATTAATCCCGAAATAACTTGCTCCAACCAAACAACCCCTAAAGAAAAAGAC
AAATAATATGGGTGTATTATTGAGTCACTTTACAGCTACCGACTTAATTCATCTCTTGTT

Figure 10 (Cont.)

CC

MNENEIEEMLDHLRRIKIEGNLDFFKIRRIGDLDIVLRVFRTFIKYHVLLPDCFVKLTMNAEW
TVEMLHRVFDGISDECKTNLNLERLESHLLEFFEGNSSLSYNYELNDFDLSKYMDCLEKILND
VLMMFLEKGRSCYPIEKLAIQLSIKKLKIVQKKMIFLRYIYTTEINGNVNYEKLECLETRIQF
IANTVGQFCLAVLDYVADIEFSDNNDIFNIPPYLLSLIVFVELEMKKIFHGELKVSKFTQSKT
FKDKKLPKEFSDLLQYLLMYLRNEKLENFPNNISAQNIDVAIEFLLVFLDADVSNHVINGNWL
NEVLLKVGAIAGDILYVIQKLLPRSINKDDTSKISFCSIQILEKTKDLKAQVETYYKSLKFTP
SQFPTFGGLSFLDSLLRKLNEMSKSKSGLDFLMKPLLGNLEKELSSLTSILEKELSSIFRDVV
HHEHKIPKDLQRRTINLAYEAEVAIDSILAQYNAFLHIFCSLPTILKEIKQINAEVTEMWSAN
IPLNPRYVAAPFKHLPARHSNLVTDEEVVG

NB-ARC

FENKAEKLIGYLIRGTNELDVIPIVGMGGQGKTTIARKLYNNDIIVSRFNVRAWCIISQTYSR
RELLQEIFSQVTGSKDKEDEVGKLADRLRKSLMGKRYLIVLDDMWDCMVWDDLRLSFPDDGIR
SRIVVTTRLEEVGKQVKNHTDPYSLPFLTTKESCQLLQKKVFQKEDCPPELQYVSQAVAEKCK
GLPLVVVLVAGIIKKRKMEESWWNEVKDALFDYLDSEFEEYSLATMQLSFDNLADCLKPCLLY
MGMFLEDARIPVSKLISLWIAEGFVENTESGRLMEEEAEGYLMDLISSNVVIVSKKGYNGKVK
CCQVHDVVHHFCLKKSREEKFMLAVKGQYIQFQPLDWKGSRVSFSF

LRR

SEELSKFASLVSKTQKPFHQHLRS
LITANGGESIDVIPVCQ
INELRLLKVLDLSSYYVESLWLAR
LNPLNQLKYLAVWAGTFYFDP
QSHLPHIETLIVTSCFYGVRLPVSFWE
MEKLRHVHFAGAGFAMQGLFEGSSKLEN
LRILKKIEEFPIDRLDVLSRRCPNLQQLQITFEDDVEPFCPK
LESLTQLQELQLSFVHPRILSG
LQLPSNLNKLVLKGIHMESAISFIAE
LPSLEYLQLLDVCFPQSEEWCLGDIT
FHKLKLLKLVQLNISKWDAS
EESFPLLETLVIKKCDDLEEIPLS
FADIPSLKQIKLIGSWKVSMEASAVRIKEEVEEIEGCDRIDLVRRSRRD

Figure 11

SEQUENCE LISTING

```
<160> NUMBER OF SEQ ID NOS: 40

<210> SEQ ID NO 1
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(11)
<223> OTHER INFORMATION: I
<220> FEATURE:
<221> NAME/KEY: misc_feature
<222> LOCATION: (22)..(22)
<223> OTHER INFORMATION: I

<400> SEQUENCE: 1

yytkrthgtm ntkgatgayr tntgg                                           25


<210> SEQ ID NO 2
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: I
<220> FEATURE:
<221> NAME/KEY: misc_feature
<222> LOCATION: (15)..(15)
<223> OTHER INFORMATION: I
<220> FEATURE:
<221> NAME/KEY: misc_feature
<222> LOCATION: (21)..(21)
<223> OTHER INFORMATION: I
```

<400> SEQUENCE: 2
gcnarwgtwg tyttnccyra ncc 23

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gtaacaagtc atgtatgcga c 21

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
gccaaatagt attgtcaagc tc 22

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
rragattcag ccatkgarat taagaaa 27

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
agtctccaaa cattcctgct tctc 24

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ggagtcaaag tttgctcaca tc 22

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
caccctcaac ccccatatc 19

<210> SEQ ID NO 9

<211> LENGTH: 20
<212> TYPE: DNA
<213> ORGANISM: Artificial Sequence
<220> FEATURE:
<223> OTHER INFORMATION: primer

<400> SEQUENCE: 9
tgaatggact ggtgatctgc 20

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ttggaaagaa ttggcttttg a 21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccaccgtatg ctccgccgtc 20

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
gttccactta gccttgtctt gctca 25

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cccgaaagta tagatcccat 20

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
taatgggatc tatactt 17

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
actcgattct caacccgaaa gtatagatcc ca 32

<210> SEQ ID NO 16
<211> LENGTH: 14
<212> TYPE: DNA
<213> ORGANISM: Artificial Sequence
<220> FEATURE:
<223> OTHER INFORMATION: primer

<400> SEQUENCE: 16
tgggatctat actt 14

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
actcgattct caacccgaaa g 21

<210> SEQ ID NO 18
<211> LENGTH: 34
<212> TYPE: DNA
<213> ORGANISM: Artificial Sequence
<220> FEATURE:
<223> OTHER INFORMATION: primer

<400> SEQUENCE: 18
catgcccggg caaaactttc acgcacccat agga 34

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19
gcacctgcag gaacaagaga tgaattaagt cggtagc 37

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
catgcccggg ctttgtatta tgattggccc tgttctga 38

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
gcacctgcag gctgcgagta ttggtggctg acat 34

<210> SEQ ID NO 22
<211> LENGTH: 32
<212> TYPE: DNA

<213> ORGANISM: Artificial Sequence
<220> FEATURE:
<223> OTHER INFORMATION: primer

<400> SEQUENCE: 22
catgcccggg ccaacaatgc ggcgctttag ga 32

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
gcacctgcag gtggtgcact tgcctggact tta 33

<210> SEQ ID NO 24
<211> LENGTH: 35
<212> TYPE: DNA
<213> ORGANISM: Artificial Sequence
<220> FEATURE:
<223> OTHER INFORMATION: primer

<400> SEQUENCE: 24
catgcccggg ccctccattt tccattaagt cttgc 35

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
gcacctgcag gaatggtttc atcaatgaat ctttc 35

<210> SEQ ID NO 26
<211> LENGTH: 39
<212> TYPE: DNA
<213> ORGANISM: Artificial Sequence
<220> FEATURE:
<223> OTHER INFORMATION: primer

<400> SEQUENCE: 26
catggcgcgc ctattaaaca ggaaacacaa aagcagtca 39

<210> SEQ ID NO 27
<211> LENGTH: 38
<212> TYPE: DNA
<213> ORGANISM: Artificial Sequence
<220> FEATURE:
<223> OTHER INFORMATION: primer

<400> SEQUENCE: 27
catgcccggg cttccttgca aaaatctcac tcactatg 38

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
catgcccggg ccacctaact gatttgcttc 30

<210> SEQ ID NO 29
<211> LENGTH: 33
<212> TYPE: DNA
<213> ORGANISM: Artificial Sequence
<220> FEATURE:
<223> OTHER INFORMATION: primer

<400> SEQUENCE: 29
gcacctgcag gtcaaactaa gacacttaaa tta 33

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
gcacctgcag gtcttgtggt tgtcttggta gcaggag 37

<210> SEQ ID NO 31
<211> LENGTH: 36
<212> TYPE: DNA
<213> ORGANISM: Artificial Sequence
<220> FEATURE:
<223> OTHER INFORMATION: primer

<400> SEQUENCE: 31
catgcccggg cgtagagaaa aaggagaaag cacaga 36

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
ctggatttct tcaagattcg tcgt 24

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
ttcaatctct tcgacttctt cttacg 26

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
aaaactttca cgcacccata gga 23

<210> SEQ ID NO 35
<211> LENGTH: 29
<212> TYPE: DNA
<213> ORGANISM: Artificial Sequence
<220> FEATURE:

-continued

```
<223> OTHER INFORMATION: primer

<400> SEQUENCE: 35

agtaaacttt gacaccttta gttcaccat                                     29


<210> SEQ ID NO 36
<211> LENGTH: 7011
<212> TYPE: DNA
<213> ORGANISM: Solanum tuberosum
<220> FEATURE:
<221> NAME/KEY: CDS
<222> LOCATION: (1680)..(5417)

<400> SEQUENCE: 36

aaaactttca cgcacccata ggaagtgaaa aacacttatt ttgtcatatc agcattttgt     60

atttaatagg taatttttta aacaatttaa gtgttcaata ggtaatagtc ctagttaaga    120

tgtctaactg aaatatacaa ataactttta aggaatcgtg aatgacttaa gcctaattta    180

attggtaaat atgtgttatc ccgaaagatg tatggatgaa ttatcaccac tacttttttt    240

aatccctgtt tgagatctcg atgactattc ttagtctaat tgttctgaca ttatttggtc    300

aataaagcat gtgaatacta gtctaataca tgaatttcaa tctattttaa agaaggagac    360

agcattaatc ttacacctac cacctaaatc aacttgctga tacaacttgc ctttttctaa    420

atattaaata atatctgact cataagttaa taatttatat atataaaaaa aggagtcatc    480

attttaaatt tatagaaata ctcatattct atttgaatgg attgtccgtg ccaagtgaaa    540

atattaactt aaagagtaat tatttgttac tattattatt gactagtgga tctttataaa    600

tttatgtgca tttgaaagtt tgtaatcgtg aatatttatt tataaaagaa acatgaaaat    660

atgtaattca tcaatgcgat gctttagaat attttgatat cttatttaca aatgatgatt    720

tactcattcg gtaagattgc ttaagaatta gataactttt gatagtttc acaacttgag    780

aattttcata tttatgagaa aaaataactt catgtccgac ccaataccc ttaattatat    840

gctaaacaaa tatcaaaata gttcatagtt taagtatgaa attagcaaat cggacataat    900

tttgggggat tttcctaagg agtcgtttgg cgtgaggtat gaggtataaa aattttggaa    960

taaaatatag gattatttta ttatgtattt gattggaggt actagatagt cctttgatta   1020

tttatcccaa tatttatact ttagtgatgg aataagttat ttcatataca tgttaaataa   1080

cttattgtga gataattact ctcaaaataa cttattctcg accaaacgac ccttaaaaaa   1140

aggactaagt aatatagttg tattattgag gcactttaca gctaccacct aaagcaactt   1200

gctactacaa ttcatctctt gttaggtata agaattatta gagagacaga agaactctct   1260

tccttcaaac cttcaaactt ccattcattt tatttcaatg aattttttc ttatatcacc   1320

tattgcgtaa acttggaaat atatctttgt tggaatccaa atctgagaaa ttgaagattc   1380

ttgtcaacta actgtaagtc atcttcttca tgaattactt ttttcccata gatacagaat   1440

tagagagttg atttctcaaa tggttcactc aactattagt tagtatctca taaaattgaa   1500

aatgtaagaa agacgatttt ctcagataat aattagttaa gtgacatttg acaatatgaa   1560

aatggtacat aagatgtata acttttcaca agcattaaca tagcttcaaa cactagatat   1620

tgaaagacat gaacctaatt ccatgagttg gtgaacttgc aggaattttt ctacaaaaa    1679

atg aat gaa aat gaa att gag gaa atg tta gat cac cta aga agg atc     1727
Met Asn Glu Asn Glu Ile Glu Glu Met Leu Asp His Leu Arg Arg Ile
1               5                   10                  15

aaa att gaa ggt aac ctg gat ttc ttc aag att cgt cgt att ggg gat     1775
Lys Ile Glu Gly Asn Leu Asp Phe Phe Lys Ile Arg Arg Ile Gly Asp
```

-continued

```
            20                  25                  30

ctt gat att gtg cta aga gtt ttt aga acc ttt ata aag tat cat gtt      1823
Leu Asp Ile Val Leu Arg Val Phe Arg Thr Phe Ile Lys Tyr His Val
        35                  40                  45

ctt tta cct gat tgt ttt gtc aaa ctc aca atg aat gcc gaa tgg act      1871
Leu Leu Pro Asp Cys Phe Val Lys Leu Thr Met Asn Ala Glu Trp Thr
    50                  55                  60

gtg gaa atg ctt cac cgg gta ttt gat ggg ata tca gat gaa tgt aaa      1919
Val Glu Met Leu His Arg Val Phe Asp Gly Ile Ser Asp Glu Cys Lys
65                  70                  75                  80

act aac ctt aat ttg gaa agg cta gaa tca cat ttg ttg gaa ttc ttt      1967
Thr Asn Leu Asn Leu Glu Arg Leu Glu Ser His Leu Leu Glu Phe Phe
                85                  90                  95

gaa ggt aac tcc agt tta agt tac aat tat gag ttg aat gat ttt gat      2015
Glu Gly Asn Ser Ser Leu Ser Tyr Asn Tyr Glu Leu Asn Asp Phe Asp
            100                 105                 110

ctg tcg aaa tat atg gat tgt ctg gaa aaa att cta aat gat gta cta      2063
Leu Ser Lys Tyr Met Asp Cys Leu Glu Lys Ile Leu Asn Asp Val Leu
        115                 120                 125

atg atg ttc ctg gaa aag ggt agg tcc tgt tat ccc ata gaa aaa ctt      2111
Met Met Phe Leu Glu Lys Gly Arg Ser Cys Tyr Pro Ile Glu Lys Leu
    130                 135                 140

gca ata cag cta tct ata aag aaa ctg aaa att gtt caa aag aaa atg      2159
Ala Ile Gln Leu Ser Ile Lys Lys Leu Lys Ile Val Gln Lys Lys Met
145                 150                 155                 160

ata ttt ttg aga tac ata tat acc aca gag ata aat ggt aac gtc aac      2207
Ile Phe Leu Arg Tyr Ile Tyr Thr Thr Glu Ile Asn Gly Asn Val Asn
                165                 170                 175

tat gag aag ctg gaa tgt ttg gag act cga att cag ttc att gct aac      2255
Tyr Glu Lys Leu Glu Cys Leu Glu Thr Arg Ile Gln Phe Ile Ala Asn
            180                 185                 190

act gtg gga caa ttt tgt ttg gcc gta tta gat tat gtt gct gat att      2303
Thr Val Gly Gln Phe Cys Leu Ala Val Leu Asp Tyr Val Ala Asp Ile
        195                 200                 205

gaa ttt agt gat aat aat gat atc ttt aat ata cct ccg tat cta tta      2351
Glu Phe Ser Asp Asn Asn Asp Ile Phe Asn Ile Pro Pro Tyr Leu Leu
    210                 215                 220

tca ttg att gtg ttt gtg gag ctg gaa atg aag aag att ttt cat ggt      2399
Ser Leu Ile Val Phe Val Glu Leu Glu Met Lys Lys Ile Phe His Gly
225                 230                 235                 240

gaa cta aag gtg tca aag ttt act caa tca aaa act ttc aag gac aag      2447
Glu Leu Lys Val Ser Lys Phe Thr Gln Ser Lys Thr Phe Lys Asp Lys
                245                 250                 255

aaa tta cca aaa gaa ttt tca gat ctt ctc caa tat ctg ttg atg tat      2495
Lys Leu Pro Lys Glu Phe Ser Asp Leu Leu Gln Tyr Leu Leu Met Tyr
            260                 265                 270

ctc aga aac gaa aaa ctc gag aac ttt cct aat aat atc tct gct caa      2543
Leu Arg Asn Glu Lys Leu Glu Asn Phe Pro Asn Asn Ile Ser Ala Gln
        275                 280                 285

aat att gat gtg gca ata gaa ttc ttg ttg gtt ttc ctt gat gct gat      2591
Asn Ile Asp Val Ala Ile Glu Phe Leu Leu Val Phe Leu Asp Ala Asp
    290                 295                 300

gtg tca aat cac gtt att aat ggt aac tgg ttg aat gag gtc ttg tta      2639
Val Ser Asn His Val Ile Asn Gly Asn Trp Leu Asn Glu Val Leu Leu
305                 310                 315                 320

aag gtt gga gct ata gcg ggt gat att cta tat gta att caa aag ctt      2687
Lys Val Gly Ala Ile Ala Gly Asp Ile Leu Tyr Val Ile Gln Lys Leu
                325                 330                 335

ctt cct aga tct ata aac aaa gat gac act agc aaa ata agt ttt tgc      2735
```

-continued

```
Leu Pro Arg Ser Ile Asn Lys Asp Asp Thr Ser Lys Ile Ser Phe Cys
            340                 345                 350

tcg ata cag ata ttg gag aag act aaa gat ctg aag gca caa gtt gag      2783
Ser Ile Gln Ile Leu Glu Lys Thr Lys Asp Leu Lys Ala Gln Val Glu
        355                 360                 365

acg tac tac aaa tcc tta aaa ttt act cca tct cag ttc ccc acc ttt      2831
Thr Tyr Tyr Lys Ser Leu Lys Phe Thr Pro Ser Gln Phe Pro Thr Phe
    370                 375                 380

ggt gga ttg agc ttt ctg gat tct ctt tta agg aaa ctg aat gag atg      2879
Gly Gly Leu Ser Phe Leu Asp Ser Leu Leu Arg Lys Leu Asn Glu Met
385                 390                 395                 400

tcg aaa tct aag tct ggt tta gat ttc ctg atg aaa cct ctt tta ggg      2927
Ser Lys Ser Lys Ser Gly Leu Asp Phe Leu Met Lys Pro Leu Leu Gly
                405                 410                 415

aat ttg gag aaa gag tta tca tct ctt aca tcc att tta gag aag gag      2975
Asn Leu Glu Lys Glu Leu Ser Ser Leu Thr Ser Ile Leu Glu Lys Glu
            420                 425                 430

cta tca tcc att ttc aga gat gtc gtg cac cac gaa cat aaa att cct      3023
Leu Ser Ser Ile Phe Arg Asp Val Val His His Glu His Lys Ile Pro
        435                 440                 445

aaa gat ctt cag aga cgt acc atc aat ttg gca tat gag gct gag gtt      3071
Lys Asp Leu Gln Arg Arg Thr Ile Asn Leu Ala Tyr Glu Ala Glu Val
    450                 455                 460

gcc att gac tct att ctt gct cag tat aat gct ttt ttg cat att ttt      3119
Ala Ile Asp Ser Ile Leu Ala Gln Tyr Asn Ala Phe Leu His Ile Phe
465                 470                 475                 480

tgc tca ctt cct aca att tta aaa gag atc aag caa att aat gca gag      3167
Cys Ser Leu Pro Thr Ile Leu Lys Glu Ile Lys Gln Ile Asn Ala Glu
                485                 490                 495

gtg act gag atg tgg tca gca aac att cct ctt aat cct cgc tac gtg      3215
Val Thr Glu Met Trp Ser Ala Asn Ile Pro Leu Asn Pro Arg Tyr Val
            500                 505                 510

gct gct cca ttt aaa cat ctg cca gct cga cat agc aat ctt gtg act      3263
Ala Ala Pro Phe Lys His Leu Pro Ala Arg His Ser Asn Leu Val Thr
        515                 520                 525

gat gag gag gta gtg ggt ttt gag aat aaa gca gaa aaa cta att ggt      3311
Asp Glu Glu Val Val Gly Phe Glu Asn Lys Ala Glu Lys Leu Ile Gly
    530                 535                 540

tat ctg att aga ggt aca aat gag cta gac gtc atc cca att gta ggc      3359
Tyr Leu Ile Arg Gly Thr Asn Glu Leu Asp Val Ile Pro Ile Val Gly
545                 550                 555                 560

atg ggg gga caa ggg aaa acg aca att gct aga aag ttg tac aat aat      3407
Met Gly Gly Gln Gly Lys Thr Thr Ile Ala Arg Lys Leu Tyr Asn Asn
                565                 570                 575

gac atc att gtt tct cgc ttt aat gtt cga gca tgg tgc atc att tct      3455
Asp Ile Ile Val Ser Arg Phe Asn Val Arg Ala Trp Cys Ile Ile Ser
            580                 585                 590

caa aca tat agc cga aga gag cta tta caa gag att ttc agt caa gtt      3503
Gln Thr Tyr Ser Arg Arg Glu Leu Leu Gln Glu Ile Phe Ser Gln Val
        595                 600                 605

acg ggc tcc aag gac aag gaa gat gag gta ggc aaa ctt gct gac agg      3551
Thr Gly Ser Lys Asp Lys Glu Asp Glu Val Gly Lys Leu Ala Asp Arg
    610                 615                 620

ttg agg aaa agc cta atg gga aag aga tat ctc att gta ttg gat gat      3599
Leu Arg Lys Ser Leu Met Gly Lys Arg Tyr Leu Ile Val Leu Asp Asp
625                 630                 635                 640

atg tgg gat tgt atg gta tgg gat gac tta agg ctt tct ttt cca gat      3647
Met Trp Asp Cys Met Val Trp Asp Asp Leu Arg Leu Ser Phe Pro Asp
                645                 650                 655
```

-continued

```
gat gga atc aga agt aga ata gtc gta aca act cga ctt gaa gaa gtg     3695
Asp Gly Ile Arg Ser Arg Ile Val Val Thr Thr Arg Leu Glu Glu Val
            660                 665                 670

ggt aag caa gtc aag aac cat act gat cct tat tct ctt cca ttc ctc     3743
Gly Lys Gln Val Lys Asn His Thr Asp Pro Tyr Ser Leu Pro Phe Leu
        675                 680                 685

aca aca aaa gag agt tgc caa ttg ctg cag aaa aaa gtg ttt caa aag     3791
Thr Thr Lys Glu Ser Cys Gln Leu Leu Gln Lys Lys Val Phe Gln Lys
    690                 695                 700

gaa gat tgc ccg cct gaa cta caa tat gtg agt caa gca gtt gca gaa     3839
Glu Asp Cys Pro Pro Glu Leu Gln Tyr Val Ser Gln Ala Val Ala Glu
705                 710                 715                 720

aaa tgc aaa gga ctg ccc cta gtg gtt gtc ttg gta gct gga ata atc     3887
Lys Cys Lys Gly Leu Pro Leu Val Val Val Leu Val Ala Gly Ile Ile
                725                 730                 735

aaa aaa agg aaa atg gaa gaa tct tgg tgg aat gag gtg aaa gat gct     3935
Lys Lys Arg Lys Met Glu Glu Ser Trp Trp Asn Glu Val Lys Asp Ala
            740                 745                 750

tta ttt gac tat ctt gac agt gag ttc gaa gaa tac agt cta gcg act     3983
Leu Phe Asp Tyr Leu Asp Ser Glu Phe Glu Glu Tyr Ser Leu Ala Thr
        755                 760                 765

atg cag ttg agt ttt gat aac cta gct gat tgt tta aag cct tgt ctt     4031
Met Gln Leu Ser Phe Asp Asn Leu Ala Asp Cys Leu Lys Pro Cys Leu
    770                 775                 780

ctt tat atg ggg atg ttt ctg gag gac gca aga att cca gtg tct aaa     4079
Leu Tyr Met Gly Met Phe Leu Glu Asp Ala Arg Ile Pro Val Ser Lys
785                 790                 795                 800

ttg ata agc tta tgg att gct gaa gga ttc gtg gag aac act gaa tct     4127
Leu Ile Ser Leu Trp Ile Ala Glu Gly Phe Val Glu Asn Thr Glu Ser
                805                 810                 815

ggg aga tta atg gaa gag gaa gct gaa ggt tac ttg atg gat ctc att     4175
Gly Arg Leu Met Glu Glu Glu Ala Glu Gly Tyr Leu Met Asp Leu Ile
            820                 825                 830

agc agt aac gtg gta att gtt tca aag aaa ggt tat aat ggt aaa gtc     4223
Ser Ser Asn Val Val Ile Val Ser Lys Lys Gly Tyr Asn Gly Lys Val
        835                 840                 845

aaa tgc tgc cag gtt cat gat gtt gtg cat cac ttt tgc ttg aag aag     4271
Lys Cys Cys Gln Val His Asp Val Val His His Phe Cys Leu Lys Lys
    850                 855                 860

agt aga gaa gaa aag ttt atg ctt gca gtg aag ggt caa tat atc cag     4319
Ser Arg Glu Glu Lys Phe Met Leu Ala Val Lys Gly Gln Tyr Ile Gln
865                 870                 875                 880

ttt caa ccg ttg gat tgg aag gga agt cga gtg agc ttc agt ttc agt     4367
Phe Gln Pro Leu Asp Trp Lys Gly Ser Arg Val Ser Phe Ser Phe Ser
                885                 890                 895

gaa gag ctt tcc aag ttt gca tct ctg gtt tcc aaa aca cag aag cct     4415
Glu Glu Leu Ser Lys Phe Ala Ser Leu Val Ser Lys Thr Gln Lys Pro
            900                 905                 910

ttc cac caa cac ttg agg tct ctg ata acg gct aat ggt gga gaa tct     4463
Phe His Gln His Leu Arg Ser Leu Ile Thr Ala Asn Gly Gly Glu Ser
        915                 920                 925

att gat gtg att ccc gtc tgt cag att aat gaa ttg cga ctt ctt aag     4511
Ile Asp Val Ile Pro Val Cys Gln Ile Asn Glu Leu Arg Leu Leu Lys
    930                 935                 940

gtc ttg gat ttg agt tct tat tat gtg gag tct ttg tgg tta gct aga     4559
Val Leu Asp Leu Ser Ser Tyr Tyr Val Glu Ser Leu Trp Leu Ala Arg
945                 950                 955                 960

tta aac cca ctt aat cag ctg aag tac ctc gca gtt tgg gca ggt act     4607
Leu Asn Pro Leu Asn Gln Leu Lys Tyr Leu Ala Val Trp Ala Gly Thr
                965                 970                 975
```

```
ttc tat ttt gat cca caa tca cat ctg ccc cat ata gaa act tta att     4655
Phe Tyr Phe Asp Pro Gln Ser His Leu Pro His Ile Glu Thr Leu Ile
            980                 985                 990

gtg acg agt tgt ttt tat ggt gta  cgg tta cca gtg tct  ttt tgg gaa   4703
Val Thr Ser Cys Phe Tyr Gly Val  Arg Leu Pro Val Ser  Phe Trp Glu
        995                 1000                 1005

atg gaa  aaa tta agg cat gtt  cat ttt gct ggc gct  ggt ttt gct     4748
Met Glu  Lys Leu Arg His Val  His Phe Ala Gly Ala  Gly Phe Ala
    1010                 1015                 1020

atg cag  gga ctc ttt gaa gga  tcc tct aaa ttg gaa  aat ttg agg     4793
Met Gln  Gly Leu Phe Glu Gly  Ser Ser Lys Leu Glu  Asn Leu Arg
    1025                 1030                 1035

ata tta  aag aaa att gag gaa  ttt cca att gat agg  ctg gat gtg     4838
Ile Leu  Lys Lys Ile Glu Glu  Phe Pro Ile Asp Arg  Leu Asp Val
    1040                 1045                 1050

tta tca  agg agg tgt cct aat  ctt caa caa ctt caa  atc aca ttt     4883
Leu Ser  Arg Arg Cys Pro Asn  Leu Gln Gln Leu Gln  Ile Thr Phe
    1055                 1060                 1065

gag gat  gat gta gag cct ttt  tgt ccc aaa ttg gag  agt ctt acc     4928
Glu Asp  Asp Val Glu Pro Phe  Cys Pro Lys Leu Glu  Ser Leu Thr
    1070                 1075                 1080

cag ctt  caa gaa ctt caa ctt  tcc ttt gtg cat ccc  cgc att cta     4973
Gln Leu  Gln Glu Leu Gln Leu  Ser Phe Val His Pro  Arg Ile Leu
    1085                 1090                 1095

tcc ggg  tta cag ttg cct tca  aat tta aac aaa ttg  gta ctt aaa     5018
Ser Gly  Leu Gln Leu Pro Ser  Asn Leu Asn Lys Leu  Val Leu Lys
    1100                 1105                 1110

gga att  cat atg gaa agt gct  att tcc ttc att gcg  gaa cta cca     5063
Gly Ile  His Met Glu Ser Ala  Ile Ser Phe Ile Ala  Glu Leu Pro
    1115                 1120                 1125

agc ctg  gag tat ctc caa tta  cta gat gtg tgt ttt  cct caa tca     5108
Ser Leu  Glu Tyr Leu Gln Leu  Leu Asp Val Cys Phe  Pro Gln Ser
    1130                 1135                 1140

gaa gag  tgg tgc ctt gga gat  atc acg ttc cat aaa  ctt aag ttg     5153
Glu Glu  Trp Cys Leu Gly Asp  Ile Thr Phe His Lys  Leu Lys Leu
    1145                 1150                 1155

ttg aaa  ctg gtg cag tta aat  atc tca aag tgg gat  gcc tcg gag     5198
Leu Lys  Leu Val Gln Leu Asn  Ile Ser Lys Trp Asp  Ala Ser Glu
    1160                 1165                 1170

gaa tca  ttt ccc ttg ctt gaa  aca ctt gtt ata aaa  aag tgt gat     5243
Glu Ser  Phe Pro Leu Leu Glu  Thr Leu Val Ile Lys  Lys Cys Asp
    1175                 1180                 1185

gac ctt  gag gag atc cca ctt  agc ttt gct gat att  cca tca ttg     5288
Asp Leu  Glu Glu Ile Pro Leu  Ser Phe Ala Asp Ile  Pro Ser Leu
    1190                 1195                 1200

aaa cag  att aag ttg att ggg  tct tgg aaa gta tct  atg gag gct     5333
Lys Gln  Ile Lys Leu Ile Gly  Ser Trp Lys Val Ser  Met Glu Ala
    1205                 1210                 1215

tca gct  gtg aga att aag gaa  gaa gtc gaa gag att  gaa gga tgt     5378
Ser Ala  Val Arg Ile Lys Glu  Glu Val Glu Glu Ile  Glu Gly Cys
    1220                 1225                 1230

gac cgt  ata gac ctc gta aga  aga agt cga aga gat  tga aagatgtgac  5427
Asp Arg  Ile Asp Leu Val Arg  Arg Ser Arg Arg Asp
    1235                 1240                 1245

cgtatagacc ttgtcaaaga atactgaagt ctattttgtt gctagctcat tctgttattg  5487

taacactagt agtgtttgct atgtttgttt tgattgatca actctttttt atgtatgata  5547

tgattggaga caaatataca tcagatcgtc tttcactaat ttcgtgtttt tatgcagctt  5607
```

-continued

```
tataatttg accaatttct ctccacttac atcttcatag ctcaatacac atcaaccatg   5667

ttgttgttgt tgttgttgtt gagtacttct tgattttcta attcgatgaa catccgaaaa   5727

attttaaggt taaactgctt cttgttgctg taggtgcaat gttgaaggat ctctttatta   5787

tgtgttcagg tgcctctttt agaagttgaa attcatacag aatgaagcta ataaatttgt   5847

tcttgtcatt catcgatcat ttgaactttg caacatatga acttaagata tagtaaaaat   5907

atagtatgac attcgagtcc cctccgaata cagagtcgtc tatgttaggg agcgtttcac   5967

ccccaatgtg ggactttatt acgtcgtgaa tccattgtat cgggctccaa tgtgggtacc   6027

ggacattggg tggaaacaaa aaatgtata tagtacgaca tgaaatgaat aaataagggc   6087

atttgaccct taagaaccaa aaaaatcaat cttttgtatt atgattggcc ctgttctgag   6147

aacagactcc attcacaaga tctatggaag aattatcacc actccttttt tatccttgtt   6207

tgatttatga catatgattt atcctttttt gaattatgtt tttttaaaaa aatataaaaa   6267

cttattcata agtttatatt ttgtaaaaaa gaacaaatca ttattttcag ttttacaaaa   6327

ataaactcat gttcgacgtg aataaattgt ccgtcgtatc atgtgaaaga attactaatt   6387

actactattg ttgactagtg gatctttata agtttatgta catttgaaag ttaaaagaaa   6447

cataaagata tataattcat cgatgcgatg ctttagatat tatgatatct tgttaacgaa   6507

atgatttact catttggtaa aattgcataa gaattgaatt tcaaagtttt cacaacttgt   6567

gcattttcat atttattaga aaaaatataa cttcatgtcc gacccaatac ccaaccataa   6627

aattccttaa ttatatgcta agcaaatatc atataagtgc ataatttaac tatgaaactg   6687

ccaaaccaaa taaaatttg ggggattttc ctaaagagtc atttggtgtg aagtatgaga   6747

tataataatt ttgggataaa atgcagaatt attttatctt gtgtttggtt ggagccatat   6807

ttggtagtcc tccgattatg tatcccatat catagtgatg gaatatataa attatgatca   6867

catatacatg atcaagtaac ttatttcgcg ataattaatc ccgaaataac ttgctccaac   6927

caaacaaccc ctaaagaaaa agacaaataa tatgggtgta ttattgagtc actttacagc   6987

taccgactta attcatctct tgtt                                          7011
```

<210> SEQ ID NO 37
<211> LENGTH: 1245
<212> TYPE: PRT
<213> ORGANISM: Solanum tuberosum

<400> SEQUENCE: 37

```
Met Asn Glu Asn Glu Ile Glu Glu Met Leu Asp His Leu Arg Arg Ile
1               5                   10                  15

Lys Ile Glu Gly Asn Leu Asp Phe Phe Lys Ile Arg Arg Ile Gly Asp
            20                  25                  30

Leu Asp Ile Val Leu Arg Val Phe Arg Thr Phe Ile Lys Tyr His Val
        35                  40                  45

Leu Leu Pro Asp Cys Phe Val Lys Leu Thr Met Asn Ala Glu Trp Thr
    50                  55                  60

Val Glu Met Leu His Arg Val Phe Asp Gly Ile Ser Asp Glu Cys Lys
65                  70                  75                  80

Thr Asn Leu Asn Leu Glu Arg Leu Glu Ser His Leu Leu Glu Phe Phe
                85                  90                  95

Glu Gly Asn Ser Ser Leu Ser Tyr Asn Tyr Glu Leu Asn Asp Phe Asp
            100                 105                 110

Leu Ser Lys Tyr Met Asp Cys Leu Glu Lys Ile Leu Asn Asp Val Leu
        115                 120                 125
```

-continued

```
Met Met Phe Leu Glu Lys Gly Arg Ser Cys Tyr Pro Ile Glu Lys Leu
    130                 135                 140

Ala Ile Gln Leu Ser Ile Lys Lys Leu Lys Ile Val Gln Lys Lys Met
145                 150                 155                 160

Ile Phe Leu Arg Tyr Ile Tyr Thr Thr Glu Ile Asn Gly Asn Val Asn
                165                 170                 175

Tyr Glu Lys Leu Glu Cys Leu Glu Thr Arg Ile Gln Phe Ile Ala Asn
            180                 185                 190

Thr Val Gly Gln Phe Cys Leu Ala Val Leu Asp Tyr Val Ala Asp Ile
        195                 200                 205

Glu Phe Ser Asp Asn Asn Asp Ile Phe Asn Ile Pro Pro Tyr Leu Leu
    210                 215                 220

Ser Leu Ile Val Phe Val Glu Leu Glu Met Lys Lys Ile Phe His Gly
225                 230                 235                 240

Glu Leu Lys Val Ser Lys Phe Thr Gln Ser Lys Thr Phe Lys Asp Lys
                245                 250                 255

Lys Leu Pro Lys Glu Phe Ser Asp Leu Leu Gln Tyr Leu Leu Met Tyr
            260                 265                 270

Leu Arg Asn Glu Lys Leu Glu Asn Phe Pro Asn Asn Ile Ser Ala Gln
        275                 280                 285

Asn Ile Asp Val Ala Ile Glu Phe Leu Leu Val Phe Leu Asp Ala Asp
    290                 295                 300

Val Ser Asn His Val Ile Asn Gly Asn Trp Leu Asn Glu Val Leu Leu
305                 310                 315                 320

Lys Val Gly Ala Ile Ala Gly Asp Ile Leu Tyr Val Ile Gln Lys Leu
                325                 330                 335

Leu Pro Arg Ser Ile Asn Lys Asp Asp Thr Ser Lys Ile Ser Phe Cys
            340                 345                 350

Ser Ile Gln Ile Leu Glu Lys Thr Lys Asp Leu Lys Ala Gln Val Glu
        355                 360                 365

Thr Tyr Tyr Lys Ser Leu Lys Phe Thr Pro Ser Gln Phe Pro Thr Phe
    370                 375                 380

Gly Gly Leu Ser Phe Leu Asp Ser Leu Leu Arg Lys Leu Asn Glu Met
385                 390                 395                 400

Ser Lys Ser Lys Ser Gly Leu Asp Phe Leu Met Lys Pro Leu Leu Gly
                405                 410                 415

Asn Leu Glu Lys Glu Leu Ser Ser Leu Thr Ser Ile Leu Glu Lys Glu
            420                 425                 430

Leu Ser Ser Ile Phe Arg Asp Val Val His His Glu His Lys Ile Pro
        435                 440                 445

Lys Asp Leu Gln Arg Arg Thr Ile Asn Leu Ala Tyr Glu Ala Glu Val
    450                 455                 460

Ala Ile Asp Ser Ile Leu Ala Gln Tyr Asn Ala Phe Leu His Ile Phe
465                 470                 475                 480

Cys Ser Leu Pro Thr Ile Leu Lys Glu Ile Lys Gln Ile Asn Ala Glu
                485                 490                 495

Val Thr Glu Met Trp Ser Ala Asn Ile Pro Leu Asn Pro Arg Tyr Val
            500                 505                 510

Ala Ala Pro Phe Lys His Leu Pro Ala Arg His Ser Asn Leu Val Thr
        515                 520                 525

Asp Glu Glu Val Val Gly Phe Glu Asn Lys Ala Glu Lys Leu Ile Gly
    530                 535                 540
```

-continued

```
Tyr Leu Ile Arg Gly Thr Asn Glu Leu Asp Val Ile Pro Ile Val Gly
545                 550                 555                 560

Met Gly Gly Gln Gly Lys Thr Thr Ile Ala Arg Lys Leu Tyr Asn Asn
                565                 570                 575

Asp Ile Ile Val Ser Arg Phe Asn Val Arg Ala Trp Cys Ile Ile Ser
            580                 585                 590

Gln Thr Tyr Ser Arg Arg Glu Leu Leu Gln Glu Ile Phe Ser Gln Val
        595                 600                 605

Thr Gly Ser Lys Asp Lys Glu Asp Glu Val Gly Lys Leu Ala Asp Arg
    610                 615                 620

Leu Arg Lys Ser Leu Met Gly Lys Arg Tyr Leu Ile Val Leu Asp Asp
625                 630                 635                 640

Met Trp Asp Cys Met Val Trp Asp Asp Leu Arg Leu Ser Phe Pro Asp
                645                 650                 655

Asp Gly Ile Arg Ser Arg Ile Val Val Thr Thr Arg Leu Glu Glu Val
            660                 665                 670

Gly Lys Gln Val Lys Asn His Thr Asp Pro Tyr Ser Leu Pro Phe Leu
        675                 680                 685

Thr Thr Lys Glu Ser Cys Gln Leu Leu Gln Lys Lys Val Phe Gln Lys
    690                 695                 700

Glu Asp Cys Pro Pro Glu Leu Gln Tyr Val Ser Gln Ala Val Ala Glu
705                 710                 715                 720

Lys Cys Lys Gly Leu Pro Leu Val Val Val Leu Val Ala Gly Ile Ile
                725                 730                 735

Lys Lys Arg Lys Met Glu Glu Ser Trp Trp Asn Glu Val Lys Asp Ala
            740                 745                 750

Leu Phe Asp Tyr Leu Asp Ser Glu Phe Glu Glu Tyr Ser Leu Ala Thr
        755                 760                 765

Met Gln Leu Ser Phe Asp Asn Leu Ala Asp Cys Leu Lys Pro Cys Leu
    770                 775                 780

Leu Tyr Met Gly Met Phe Leu Glu Asp Ala Arg Ile Pro Val Ser Lys
785                 790                 795                 800

Leu Ile Ser Leu Trp Ile Ala Glu Gly Phe Val Glu Asn Thr Glu Ser
                805                 810                 815

Gly Arg Leu Met Glu Glu Glu Ala Glu Gly Tyr Leu Met Asp Leu Ile
            820                 825                 830

Ser Ser Asn Val Val Ile Val Ser Lys Lys Gly Tyr Asn Gly Lys Val
        835                 840                 845

Lys Cys Cys Gln Val His Asp Val Val His His Phe Cys Leu Lys Lys
    850                 855                 860

Ser Arg Glu Glu Lys Phe Met Leu Ala Val Lys Gly Gln Tyr Ile Gln
865                 870                 875                 880

Phe Gln Pro Leu Asp Trp Lys Gly Ser Arg Val Ser Phe Ser Phe Ser
                885                 890                 895

Glu Glu Leu Ser Lys Phe Ala Ser Leu Val Ser Lys Thr Gln Lys Pro
            900                 905                 910

Phe His Gln His Leu Arg Ser Leu Ile Thr Ala Asn Gly Gly Glu Ser
        915                 920                 925

Ile Asp Val Ile Pro Val Cys Gln Ile Asn Glu Leu Arg Leu Leu Lys
    930                 935                 940

Val Leu Asp Leu Ser Ser Tyr Tyr Val Glu Ser Leu Trp Leu Ala Arg
945                 950                 955                 960

Leu Asn Pro Leu Asn Gln Leu Lys Tyr Leu Ala Val Trp Ala Gly Thr
```

-continued

```
                965                 970                 975

Phe Tyr Phe Asp Pro Gln Ser His Leu Pro His Ile Glu Thr Leu Ile
            980                 985                 990

Val Thr Ser Cys Phe Tyr Gly Val  Arg Leu Pro Val Ser  Phe Trp Glu
        995                 1000                1005

Met Glu  Lys Leu Arg His Val  His Phe Ala Gly Ala  Gly Phe Ala
    1010                 1015                 1020

Met Gln  Gly Leu Phe Glu Gly  Ser Ser Lys Leu Glu  Asn Leu Arg
    1025                 1030                 1035

Ile Leu  Lys Lys Ile Glu Glu  Phe Pro Ile Asp Arg  Leu Asp Val
    1040                 1045                 1050

Leu Ser  Arg Arg Cys Pro Asn  Leu Gln Gln Leu Gln  Ile Thr Phe
    1055                 1060                 1065

Glu Asp  Asp Val Glu Pro Phe  Cys Pro Lys Leu Glu  Ser Leu Thr
    1070                 1075                 1080

Gln Leu  Gln Glu Leu Gln Leu  Ser Phe Val His Pro  Arg Ile Leu
    1085                 1090                 1095

Ser Gly  Leu Gln Leu Pro Ser  Asn Leu Asn Lys Leu  Val Leu Lys
    1100                 1105                 1110

Gly Ile  His Met Glu Ser Ala  Ile Ser Phe Ile Ala  Glu Leu Pro
    1115                 1120                 1125

Ser Leu  Glu Tyr Leu Gln Leu  Leu Asp Val Cys Phe  Pro Gln Ser
    1130                 1135                 1140

Glu Glu  Trp Cys Leu Gly Asp  Ile Thr Phe His Lys  Leu Lys Leu
    1145                 1150                 1155

Leu Lys  Leu Val Gln Leu Asn  Ile Ser Lys Trp Asp  Ala Ser Glu
    1160                 1165                 1170

Glu Ser  Phe Pro Leu Leu Glu  Thr Leu Val Ile Lys  Lys Cys Asp
    1175                 1180                 1185

Asp Leu  Glu Glu Ile Pro Leu  Ser Phe Ala Asp Ile  Pro Ser Leu
    1190                 1195                 1200

Lys Gln  Ile Lys Leu Ile Gly  Ser Trp Lys Val Ser  Met Glu Ala
    1205                 1210                 1215

Ser Ala  Val Arg Ile Lys Glu  Glu Val Glu Glu Ile  Glu Gly Cys
    1220                 1225                 1230

Asp Arg  Ile Asp Leu Val Arg  Arg Ser Arg Arg Asp
    1235                 1240                 1245
```

<210> SEQ ID NO 38
<211> LENGTH: 174573
<212> TYPE: DNA
<213> ORGANISM: Solanum tuberosum

<400> SEQUENCE: 38

```
ctattattta ttgctaccag tagtacagct tccagggaat acagaaactt ctctatgacc      60

tctaaaaaga agttaaacag aatgccaact aaaattatga ttaaggagga taaatagaga     120

atgttgtgac atacacagac aaggacgcca aaaagcaact ttcaggaaaa ttcaaaacaa     180

aaatgagttg atctccaaga tagttctcaa gacattcaag ttcacaccat cgctctttct     240

ttcagcatgc ctctaggctc taaaattcca attaatatga ttgattcagt atttaattgt     300

tttcaacata gaattgaata caaaagctgc acccagcttc caaagctaca tcactgccaa     360

tatcttgacc attcgtatta ctgattaaca caatactgat caagacccat gagaaacagg     420

gtaaaaagaa cagaatacag tgtcaaccac tgttctcatt aaattaacta tgttggagca     480
```

```
ctgatacatg aatcaatctc tcttcttcct gtaagtgcta taaacttatc cctaaataat    540
aacagagggc atttacagat caaattagac ccatcataag cctctttaag tatcacggta    600
ctcctaacac ctttattagt gatgtagaat atactgtgtt gtttgattaa gcaaagcaaa    660
agtctagctg gtaaccgtaa ctcggaatga aatgcatcta tttgagcaga tgtcaacctc    720
ttttccatag tcaaactgag gagctcgtga agcactgcga ctactctctt ttgagctttg    780
ggatcagcaa gttcaaatct tttagcattc aagtatggag aagggaactc catcttctgc    840
catttctgaa cttccttaag gtagttcata ttcggcctaa atcctgcagg ataatgcatt    900
tgaaacgaga agggaccgaa atagtttcca tctttcaata ctctaacctt ctcttttgaa    960
gtcaggaccc cttcacacgc caacctttcc tcccgggcag tgacagctag aaaagaatcc   1020
caattttcca actgaaggga agttcttcca ttcacgtctt tcactgagaa aaattgtggg   1080
tattttggaa tcagcgactg cctgaagtca ttaggcaagc ccaaatcatt ctcaatcagt   1140
tgaatggttt ccagtggcaa cgtgcaatca accgacaaca ttaacaactt ccttagattc   1200
ttgaccaaaa taggttccat ttgcgctctt gcttcatctt cttctagtgc tattttatca   1260
gccttttcag tcagcataac catcggtgga gttccattac caccggtgac acggaatatc   1320
gtaggatatt tctcaataat acccatgaaa ttccactttt gcacaaatcc aacttctttc   1380
tcaaggtctc taagaaggac gcattgtttt ctctgtgatt gaattatgga ttttaagcgt   1440
aaaatcaatg atggtttctt ctgaagctcc atgactctgt ctagatcatt tactctatag   1500
tacattttct tcttaggtct cctccctcca ctggttttga acataatttg aacccacata   1560
tgccctactc ccagagatgg caatggatgg cacaatcttt gccttccatt gactgtaaac   1620
cattttcgag gctcaattag cgagaagacc atcacattta tgcatctgga aaagaacaga   1680
gatgtgcgca atttagctaa aacaattgaa gtgtagtaag attttggaga aaagagttgt   1740
ttccccttaa aacaaaaact acaaacagag gcatatcaag aatttgaagt ttgtgggtcc   1800
aagcccaatg gatggtgacc aacgaattcg aacccttgac caagagggca acaaagctta   1860
aaagattaca tttttaccca ctacccaaca tccccaagcc gtttctctta ctggattttt   1920
caatactccg cgcaaaattt actatgttct tgggaacccc ctccaatacc ctaaattccc   1980
cccccccccc cctgagtcta caaacaggaa atgatataga cagagtcatt gagcttggac   2040
tatatatgac caaaaaaagg acaaattttt ctcgactgct actacttata cgcagattag   2100
tgctacacta taagaacatc atgctttaaa tttgtgaaaa aaaataaaga aatgaagtaa   2160
tacaatagag ttgcagctct tcgataaatg ggaacaaata catcattaaa cacaaaaaaa   2220
aaattcactg gaattcatgg tttactaaat atactcaaat tgcaagtaaa ttaaaagggc   2280
ttcggtcaaa ttaaatagtg attgaagaga caaggagaaa cttacaagac ggtgtggagc   2340
gcagcagagc agtaagacga atgaaaatgg cttatttgtt tttcaggttc aactttgcct   2400
tttataataa tcataatcta aaattaagaa ggggtaaaat tggaatttta ttttaatttt   2460
caaattgaag ggccaaaaac ttttttcttc gactccaatt ttataaagtt aaaaaaataaa   2520
taaaaaatat ttgaaattta tgataaaaaa tttacttaaa tatgtagagt tagagtattt   2580
tgagccgttg atctattaaa tacaagtgca tctatgagcc aatttgctaa tattaagatt   2640
taatgaaaga tagaaagatt gtttttgaaa gaatgaaaaa gaaaatatga tagtgaaaaa   2700
aatataacta attaggaaag caaggtgaaa attaaaagaa ggtcaaagtc atatgtagcc   2760
cctcaaagtt gtcttcatta ttcatttaga cacctcaact acacctagta cctattgaac   2820
```

-continued

```
acctctacca ccccagattt gaaccatcta agcatttttt tttatcactt ttcataaact   2880
gtgtggcgcg tgtatttaac ctccccacgt gtatccgacg tgtatagaat gaccatttaa   2940
caactaccac gtgtatccga cgtgtatttg taaatgtctt aattggggaa gattcctaaa   3000
tcgttaaaat tgacagaaca cttctctctc tctttgcgat tttttcccaa ttgaagctct   3060
ccatcttcgc gatttcctcc agattgaagt tggattcgtc ttgttcgtgt tacaatcttg   3120
aagatttcct tgtgtaagtt aggattgtta atgattttta catgctttgt taaatgaatt   3180
ccaaaaaagc tagggttttg taaaaatata gggtttgtga tttttgcgaa tattctgtcc   3240
cttctttact attacccaaa aaatatgctt taaaactttg gtttttagtt gttgtatatg   3300
ttatatgagt atattccgtt atcttaagct agggtttgtt tgatattttg tagggctaac   3360
aattgaccat ggaggagagc cttatattta caaagattta ccatggtgga atcttatccg   3420
agatatttgt ccttacttat gttggaaact gtgtgtctgc actcaggtat attattaagg   3480
accacttttc cattttggaa ctactgtatt atactaaaga attagggtat gaaactgtta   3540
gaggctttta tgtgaaggat ttattgaata aaaaatgggt cctaattaca actgaccaac   3600
atctcctaca cctaattaaa gacttaaaat atgaggacac ttttgaagta tttgtctgtc   3660
atgtattaga tgaaccttac ttgacactga gggacctaga ggctatctaa ctaatgttgg   3720
tggtgaaggt gttgatgttg accttggtga agagggtgag actgttaact taggtggaga   3780
aggtgaggtt gttgacctaa gtggagaagg tgaggctgtt aaccttggta gtgagggtgt   3840
tgatgttaac attggtgaag agggtgtgga tgataaccta ggtagagatg gtgtggatga   3900
taacctaggt ggagaaggtg aatctgattt tttgagtagt gattcagatc tagatatacc   3960
ttcagaagat ggttcagata ttgatgaaga gttgagagct tttagacaag aaagaagaaa   4020
caaaaaacag agaaacaagg ctactgaatt tgaagaaata ccagttggag aggctggtgg   4080
tatagataga ggctttgagg atattgaaaa aaataaaaca gacaaatata caggaaaatt   4140
aggtggagat gaggattata ttgatagctc tgactgttgg agtgatgata gtgatgaaca   4200
actaaatatg gatgctgtta ggggagtaga tatacctact agaaggagaa gcaaaaaagt   4260
taggtatgat gaagattgtg aagtttcaat atttgagctt ggaatggtct ttgagggtgc   4320
aaatcagttc aggaaagcag tggcagatta tgctgtagag tacatgaggc agataaagtt   4380
aagacctaat gaaaaacata gagtgaaggt gaagtgcaaa aatgctaact gtaagtggtt   4440
gttatatgct tccattgaca gggactcagg tgatttcatt gtgaagaact atcatcctgt   4500
tcacaagtgt attccattaa acaggaacaa gttgtgtaat tcaaagttaa ttgctagaaa   4560
gtttaaggac aaaattgtat ctcaaccata cataaggatt tgagaaattc aagatttggt   4620
tagaaagaca ttgggtcttt atgttggtaa gactctttgt tacagggcta aacagaggat   4680
tatgaaggaa aacaacatgg gtgattggaa tgtggaattt gccagattat gtgtgtaatg   4740
accctaaagg tcatttttgg aaattttcat aaaatgaccg ttttacccct cccgatagtt   4800
gccccgagtc ctaattgttg tattttcgaa gttggtttgg aggaaaattg atgaaaagtt   4860
gagtttttgg aaagttgagt ttttaagagt taaagtttgg ttaaaagtgc tatttcgagt   4920
catttggagt ttcgaaactc gaattggatt ttcgttgatt ccagcagttt tagaatgtcg   4980
aaacatgtct atgagaattt acggagtcga atttggagtt aaaacgaaga tttgaggtcc   5040
taagttgcaa aaattgtgaa attttgatca agagttgact ttggtcaaca aacgaggttc   5100
cggtgctcga aatggaatcc cgagggcacc gttggattca gggggtgatt ctaagtctag   5160
aatgagtctt ggttaaattt ttagaggccc cgagtgcgtt tcgagttttt gagcctaaag   5220
```

-continued

```
ttagtttctt gacgccttat cggataccgg gtcaaggaga cctcgaattc aaattccgac   5280
gatttcattg agtccgaaat gtcattttca agctagtagc atatttggtt tgtgttcggg   5340
aagtgccaaa tgaattttgg gtgagctttt aagcttcttg gatgctttga cactatttca   5400
gcaaattgtg gcaactaaag ggttcattat taggtttaaa ggtcgaaatt tttttccgaa   5460
ggttctgaaa ttttgagcat gaattatagg actttctgca aattttggtg cattttcgct   5520
aacctgagat tggactttta tcgcaaataa gaaataattg tttacagagt agaaatgata   5580
tttgactggg caaagagcat gaaattgagc tccgattgaa cgagcaggtc cgtatcatta   5640
tttaagacat ttacaaaaaa gaatcgggtc atttcactat cgtatgagga aattacggcc   5700
tttttagtga aagattaact gctgtttttc tggtgcataa cagccatgta ctgttataaa   5760
aatctcagac tgtgttcatt tggtattttg agcatatcgg gagttctaga gatcggaatg   5820
gagtgattct tacgggtctc ttcttgaatt aatatgaggg ttagtattca atcttcaatt   5880
cgacattttc tcataatttc tttatctggt tttttttcct atccgtaaat ctcttgggaa   5940
aaattggggt tttatcgatt tggactccct ttttgatgaa aaaggtatat ttacaatcct   6000
tatgttatgg gtaaactgat tttaacataa aattattgat tcatcgatta ttttcatcat   6060
attaaccgcg tacaatttaa actttcccgg taaagttaaa gtttgataaa ttgagaattt   6120
caaggtcgat cttaactcca tttttgatga aatttcatat ttgaacttat ctaagcatgg   6180
gtaagatgtt tttcaagaga tatttcattt tcgagtcggg gtttcggatc cgaatatttt   6240
aggcttcttc aagaacgtgg attttccttc aaattgagtt tgtgaattga tttcaactcc   6300
gttttcaaat tgggtttcac cattagtttc caaatactgt aaggatcatt ttacataaaa   6360
aaatttccat atttgggtat cattttctgg tatgagactt ttggaccttt ttgccctttt   6420
cccctaaatt tcttgatttt ggtgtcattg gactcgaatt gtgattgtga ataattgttt   6480
gaatagattg tcgtgatccg gattatactc gaaaaggaaa ggctcaagtc aagtaacttt   6540
tggagttcgt ttcaaggcaa gtggctttca aactttgtaa aactcttaga ctacgcatga   6600
ctactttcct aattgtgttg gggagtaatg ggtattgagg atgagtttta tttgttgatt   6660
gaaattgttg taaatgaaag atggggaata aaacgagcta aatgtgttat atgtgacttg   6720
aatttgttaa ataagtcatg tgataactga tattgagggg atagaagagc atgagtaggc   6780
tatgattgat acagacattg atgttgtgac atatgatgtg taatactatg atgtggtcgt   6840
gatatggttg tgattgagac aggtgatgtg taatactgtg atgtggtcgt gatttggttg   6900
tgattgagac atgtgatgtg taatactatg atgtggtcgt gatatggttg tgattgagac   6960
agatgatgtg taatactatg atgtgatcgt gatatgattg tgattgatga catgtgcata   7020
ttcattattc atcccatgtg tgaactatct gttgcatgag ttctgagaca ctgatatgag   7080
gatggatgga tatgagacat agttgagact agctccggct agcgatttgg atgccgatgg   7140
gatctggttc cggcggtgat acatggtcca tgtgtggccc ccatgggttc tgatttgagt   7200
attcagcgcg gactgattac gtcaacagat gtgtatcgta ggacaaacat gcatcatgac   7260
atcattattg cattttgcat cgcatttgcc ttatctttgt ctgtgatgtg tggattgtat   7320
cggtttaccc ttcttatgtg gaatttgatc tacttgctct tatttgttga tctgaggttg   7380
atgaggatat actgttggtt ctggctgttg aatatgatct gcttagtata ggttggttgg   7440
tttgctgcta gattgaagtt tcggtggttt ggttgggatt gaaatgagtt gtttgtagct   7500
gctagttttg cttagtttag agttacttgc gagtacctgt ggtttttgat actcaccctt   7560
```

-continued

```
gcttctacac aattgtgtag gttgacagct ctctctcaga ttcggcttag tagtttcttt   7620
agcagattga gcttcgggac atactcgaga ggtagcggtt cattccagac gtgcccttga   7680
gttatcttta ctttcagttt tgttctattt gagaactata ctctgagact tgtatatttt   7740
tattcgaatt ctgtatttag aggtttgtac atgtgacaac caaattctgg gtagtgttga   7800
gtcttaatta aagtctttcg cttatttatt atcttttatt ctcgtatttc tacttctcta   7860
tcgttgtggt tgggttaggc tgatgtgtcc ggtgggaaat ggatacgtgc catcacatcc   7920
ggatttgggg tgtgacaatg tgactatgca gatatgatca aacaaaccaa tcctggaagc   7980
tcttgtcggg taaaaattga taaggaaact gaaccaggaa agaacctttt tgtgtatttt   8040
tatgtgtgct ttcatgcatt taagcaagga tggttggagg ggtgtaggaa tataattgga   8100
gttgatggtt gttttcttaa gggagcttgt aaaggtgagc tactagttac tgttggaaag   8160
aatgggaaca atcaaatgta tcccattgcc tgggaagttg tagatacaga aacaaacata   8220
gttggagctg gttcataagg tatttaattg ctgatctaaa cttgggaagt ggtgaaggtt   8280
tgactgtaat gtcagatatg caaaaggtat tgattataca atttttatat tttagtttaa   8340
tttgatcttt acttcttcaa ttacttattt tgtacatatt ttttgttagg gacttattcc   8400
tgtcttgtca gagttgttac caaatgctga gaaaaggatg tgtgctagac atatatggag   8460
taactggcat gtgaactgga aaggagaaga aagaaggaaa cagttttgga gatgctcaaa   8520
ggcctccttt gaagtcaagt ttggagaaga agttcatgca atgtcaaagc taggtaagaa   8580
ggaaataaca gaggacttgc tacattatga tcccagaaat tagtctaggg ccttttttcca   8640
aactcactcc aagtgtgatg ttgtagaaaa taacatgtgt gagactttca attcctggat   8700
cttagctgct agacataaat caattattac catgttagaa gatattaggc ataaaatgat   8760
gaacaaacat atagacatga tcaaatttgc tgaaacatgg atatcagaca ttgcacctat   8820
ggcaagggca atactagaaa gaaacgagga gtattcaaat aattgtaatg ttcaatggaa   8880
tgggttgaat gattttgaga ttagtgaagg gaatattcat ttgttgttga cttggagaag   8940
aaacattgtg actgtaggtt gtggatgttg agaggtattc cttaccctca tgctatttgt   9000
gcttattatt acttgaatca agatcctgat caacatgtag agcactggta taagaaggaa   9060
acatttctca aggcttacat ccattttatc caacctattc ccaatatgag gatgtggcct   9120
gaaactacaa atccatcaat agagcctcca aaaccaagaa aaatgccagg cagacctggc   9180
aagaagagaa gaaagagtaa ggatgagcca aaaaaatggg ggaaactttc aagaaaagga   9240
gtaaagatga catgtaccat atgcaagaaa actggtcata acaaagctgt gtgtgcaaga   9300
gtaagtaata cttcatattc acatttgtaa attgcttaaa gtttatatat attataatca   9360
tatattttat tttgtggtga catagtatac gagggggagc acttctcaac ctacaagtca   9420
aggaaattca agccaacaaa gttattctca aacaggagta agatttgatt tacatattca   9480
tttgcattaa ttttcatcgt ataagttatt catatctcct tatttttgtt caataggtta   9540
gaacacaatc aagttaacaa agttctgttt gcgctgatac cactgttgtg ccaagaacta   9600
ctcaaacaac agtaagatta gatttaataa ttcatttaca ttttctgatt gatctacaag   9660
ttattcatat atccttattt ctgctatata gtctacaatg ggaggtccat cgcattctac   9720
tttcagaacc acatatgcaa ctacataatc aagtcaacca agttctattt gtgctgacac   9780
agaatctgtg ccaagacgtc ctcaaaatag ggttcaagtt gggactggaa gaggattggg   9840
aagaaaaaaa gctaatgcaa gagtgatagt tcttctagtc aattgccacc tttatcaggt   9900
cacaaaagac cgtacaattc tgcctcattt gctgctgctg ctactggagg taacagaagg   9960
```

```
cttgcaactg gttttggtgt ttactctaat cctactactg gagcccaagt atttaatgta  10020
tgtttactct gttttggtgt atattctgat agctatatta tgatcttacc ttatcttaca  10080
ctttctttct tatattacag cctggtacat caagtgagaa gattctacat gggccaacaa  10140
aattgaagag tgcttcacca accaatatag acattgtctt taaacctcgt ggcctaaaat  10200
ggaagggaaa agatgcagtc agcacctcac agttgcaaca aatgaaagca aacaggaaaa  10260
actaaaagta gttcatttgg aaagttgtta tgattttggc ccatgttaaa agggtcttca  10320
acaagctact ctttagttta ttttgaacac tcgtgtgatg tatttttgaa ccatgccttt  10380
gtgttagcaa gactatgtat ttttgaacca tgcaagacaa tagtttttta ttacctctca  10440
atgcatttgt gttatgtatt tttcaaccat gactttgtgt tatgtatttt ccagccatgc  10500
atttgtgtta ttagctcagt ttttgaacaa caactacaca gggcaagtcg atcccagaac  10560
taatttcaga acacagggca agttagaaca cagggcaagt tagaaaacag aggcaagtta  10620
taaaagagaa actgatcaat tcacactaga agttacaaaa gagacactga tcaattcaca  10680
ttcaaacttc caatttgata taaaatatga acttaacaga ccaattaagt acaacactaa  10740
ttacgtgaaa taacttccta actattgcaa aactaaacaa ttaagtacta caattttgaa  10800
ctacacaata ttaaagaacc attttatagt tagcagacaa agagaaacaa tcacaactcg  10860
attaaatttg acattttccc aatccctttg gagtttaact tccttgagct tcttgttcaa  10920
taccatcatc ttctcttcat tttcattcaa ttgaaatttc aaaaaatccc tttcttcttc  10980
aagctctttc acttttctct ttagttgatc aatcggatta tgaccatcta tgaatctatt  11040
cattaaggat gattcatcaa tattttcaag tgacggatca atccatctaa aatagccaca  11100
tccaccattt tcctacaaac cacataacag taataaatat acaaaaatgt tgatttttca  11160
aataatacaa taatagtagt ttttgttcaa ataactacaa acctttgatg ctttgcatcc  11220
aaaaaatcga caacctgggt tcaatggagt cctcgaagtt ttcagtcgac aatagtaacc  11280
acacttacat acatcgactt cctcgatatt cactgaactt tgtgacattt gataaaacac  11340
aactgattta gaagagagaa acgttggata tttagaggaa gaagagagaa ttggggatta  11400
gggttctaaa atgtatttgg gggaagaaga agattttaat gttaaaatat ccaagttaac  11460
gttggatgtc ttaaatgcag ggtaaaaaat gggagaaaaa acaattcacg cgcccgattt  11520
gcgtgaatca caaacgattt gccatgtagg caaaaaatgc ttagatggtt caaatctggg  11580
gtggtagagg tgttcaatag gtactaggtg tagttgaggt gtctaaatga ataatgagga  11640
caactttgag gggctacaga tgactttggc cttaaatgaa tttgaatcat aaatcttttt  11700
tgagaagatt gcaagtatta catatacaac attaattgtg cttgatatat ttacaaaaag  11760
gaatctaatt ttaacctgat ttaagtctct acatgataaa ataatgagca actttcacat  11820
atagcaaaca taaaaatcat atttgtatgt tatagctata gtttgtataa ttgcgctcca  11880
taacaaattt tatgtttgct attgaacttt tgatttgtat aattcgctac aaacatccaa  11940
ttttatacaa attgttcagt tttgtataaa ttcatttata cattgtaatt tgtataataa  12000
aatctgtatt tatataatta taagtgtata ggacgaaaat atatttattt gtatttgtat  12060
atacactttt ctctcgcttt atacaaacac aaacgcattt tatacatttt ataccgaaat  12120
gtataaaatg actaattgta taccgaaaat ggctaattgt atatgacaaa aaacatggat  12180
gtttgctgct aattacaatt aaaataagct atggctataa catttaattt aaattaatag  12240
tttgctattt catacaattt tccctaaatt aattcatctt taccaacaaa agtatataga  12300
```

atttttgcc ttttatcatc tctatagaac tgactgactc tatctttaaa gcatcttgca 12360
tgttctcttt ccaaatggtt attggctctt caaaattaac tttggctggc aacatgaata 12420
tgacaacatt tttgaagaat ccaagcaaca taagttctct gccacttgtg ctcttttggc 12480
atgcccttct gtaccagatg tcttcaggta ttgtgttttc aagcctaaac cttatgcctt 12540
catttgagaa gcagaaattg tgttatggga accaaaagaa acacaatgaa ctgacccttg 12600
agaaaactta tccagccact ctatggttgt ctcctcgatc ccaagcaccg aagcagtctg 12660
ttgcaaaatc tacttttgta actgagacat tggaaaaaaa aactatttaa gaaatattcc 12720
atgaatgaat gattttggtt tcatgaagtt tttcttaatt ttaaacatat aacacagtgc 12780
acataatgtt acatgaatga atgaatgatt ttgcacttac cataattgaa atattcatac 12840
ttgttaagga cttggaggct atcacatcct gtaatctctt ccacttggtt tttaatattg 12900
aaagctgaaa gcttaagtga ctcatcgcag caaatcaatt taatcaactt cagtgttggg 12960
atatccacga agctacaagg gatctgaccg cactgaatta tgcaattgtt tataattagt 13020
tgctcaagca cggggaaaga ttcttctgag gagcgccatt ctgtcacgag aacattctgt 13080
aagttcaagt atttgagtgc tcgaaactca taatcactga catcccaaca tatgctatat 13140
ccagcctgcc catatctatc ttcagacttg aagtatactt cacgtagttt gagactctca 13200
aggtttcgta gtcttgcaag ttgtgaaaca actttttcag ttaggcaaag tctatcaagt 13260
gacaaatcct tcagatttga agggaagaca acacatctgg cccgtcctat ggatttgtag 13320
cctgaaatcg cgcgtgagaa acacagttcg agagatagaa gtgggagttc ttcaagattc 13380
ggcatatcaa cttcataacc tggttcaata aagtggaggt tgagttgttc aatatttggg 13440
aatctccacc agaactccgg agtcttatca accaagtata tacgacactt cccaaaagtc 13500
ttcaagtttg gtaacacagt ttctgaagat tcttcgaaaa gtgctcgatc attgtcttcc 13560
catttgaagg aaaaatcctg tatatccaca tgtcttagct tctgcatttt ccaaatagaa 13620
ggtgatgtct caaagcaccc cgaaagttta tcatcatttc ccaccacctg caaagtttgt 13680
agatcatgta ggtgtgatac ccactggaaa tcaaattctt gggtacgaat tgcaagatac 13740
ctcaagtgag ttactacttg cactgccgta acccaagaac atctttccaa gttgacatcc 13800
aacaaatgca atacccgaat aaatcttaag ttcttaagta cactgaaaag acgtatccca 13860
tcacccagag aggaatgtgg attatcaatg aactcactat acctagcatt acattgatca 13920
acaaactccc attccttcaa gcctgccaac attggaaact tatccaataa cttttcatac 13980
tgcaacaaat gtttaacaag atcgtcatgg atatacttgc gacgtgaccg aggttcctct 14040
gcaagtcggt acagcataaa attttcttcc tgaggttcct ttgcaagttg gtactgcata 14100
aacttttctt ttgcaagttt tctcatgcaa aactcatgca ctacatcatg aacagtgcag 14160
tactcgatct caccattatc ttctctcctt ccagaaacaa ttactaggct ttttttcact 14220
agttcattca agcaaatttt agatgcttcc tccacgttct ctaagcccat gttttgtaca 14280
aaattttcag ctatccaaaa ctttagcaaa ttggacactg gaaatttgta gtcttctgga 14340
aacaatccca tgtaaagaag gcaaaacttt aaatggtctt ccaaataatc aaaacttgat 14400
tctaatatct tcatgttttt ctcttctaaa acacgggacc ttaaatcttt tgcgatcgca 14460
agccataaag aggcttccct tttctttgca ataattccag caatcaaaac gatcacaagt 14520
ggtaatccct tgcagctttc agcaactcgt aatcctgtgt tgagtagctc tgggggacaa 14580
atctctcatt gaaatacttt cttttgaagt aagtcccagc tctcatcaac cgtgagaaat 14640
cgaagaaaat atggatcact gtggtgctta agctgcctgg ccacttcttc atctcgagtt 14700
gttagcacta ctctgcttcc attttcatca tctgggaaag atagctgcaa ctcttcccaa 14760
gcctcaactt cccatatatc atctaaaaca atgaggtatc tcttgttcat tagactcttg 14820
cgcaacttgt caggcatgtc ttcatttcgt ataccatcca cactgcctaa aacttgttta 14880
agaatctcag agcacatctt cctcaaatta tattcttttg aaatagaaca ccatgcttga 14940
acgtcaaagt gtttatccac gcttggatga gtgaacacct ttttagccaa agttgttttg 15000
cctagtccag gcattccaac aatcgagaca acgtctagtt cctcggtaca tccagtcaat 15060
ttctgtatta tactttccgc atcttcctca aaaccaacta tttcctcatc aattgatgga 15120
aaactacgag aaggggttct ttcactgctc agaacgttct ccatgctaat tatactttcc 15180
gcatcttcct caaaaccaaa tatgtcctca tcaattgatg gacaactagg agaaggggtt 15240
ctttcactgc tcagaacgtt ctccatgcca aatatacttt ccgcatcttc ctcaaaatca 15300
agttttaact tatcaattga tggaaaacta cgaaaagacg ttctttcact gctcagaacg 15360
ttctccatgc caattatact ttccgcatct tccccaaaat caaatattaa ctcatcaatt 15420
gatggaaaac tacgaaaagg ggttctttca ctgctcagaa cgttctccat gccaattata 15480
ctttccgcat cttcctcaaa accaaatatt tcctcatcaa ttgatggaaa actaggagaa 15540
ggggttcttt cactgctcag aacattctcc atgccaatta tactttccgc atcttcctca 15600
aaaccaacta tttcctcatc aattgatgga aaactacgag aaggggttct ttcactgctc 15660
agaacgttct ccatgccaat tactgcagtt aggagtaaat ataactatgt tacaactgat 15720
tgcacaatcg cttagaatta tttagattgc caaacaagtc aaaattcaac aatctattca 15780
tagtttccta gaaaagatca tttcctagag ggaatactga aagtcaatct tctcttggat 15840
actatttaga gttaatagta aaaataaaac acctaaaata tcactttttc gtgacctcaa 15900
agttatagtc ttttagcaaa ttttaactct ctttgtatta acacactcca tttttaagct 15960
ttcctattct tgaaaccact ttcctcaaac tacctaccaa caaaaatatt gaaagggtgc 16020
gtgtcagatc cttcagatat agtactccct ccatctcatt gtatgtggca accttttctt 16080
tttagtttat ctaacaaaga atgtcacctt actactacta gaaacaattt aactttaaaa 16140
tttctcttta cctactaaat aatttacaac cacacaaata tctaaagatt atttaagacc 16200
tcaagtttca aaagtcttca tttttctctt aaatacttg tcaagtcaaa cggtgacaca 16260
taaaatgaga tggagggagt atatttttaa ggatcccaca gggtttctct agagtccgag 16320
catcattgct agctacttac tcttagtaca gttaagttta tatagccaaa aaatatggat 16380
aaaatccaag ttaccttgct atatctggtg tgacattttt ggaaagaaaa aaaaattcat 16440
aatcagaagt tcagaacata aactacatga tcttctcaaa taagacacaa aaatgttaac 16500
ttatgataaa tgataaatat agacaaaata tatatacata aaaaaacagg aacctaagaa 16560
gaaatctgac cttcaattat gagagagaag cggcagcttc ttataactta aaaggatttg 16620
gaatatgaaa gcatatggtg aatgaaggag tgataatata gtaattaatc gttgagtggg 16680
agtgagaaaa agacaaaaat ggtcccttat atttaatggt aagcttaaaa tagtccgtta 16740
agtatgcact aattaatagt tttgagggtg ggcatggtat ggtatggtta atgttttgtt 16800
attgtaattt cgattttcgg ttttaaaaac atttaatcat tatcatatca atttaattta 16860
gtatggttcg gtattttaaa gtttggtttc gatagtttgt tcaacttcga ctaatatata 16920
ttcgtataat agagtattat gactttgaca attaaaaaaa gatcttaatt gtatcatact 16980
aacacattac acatgtaaaa atatatattc aaaataaagt acaaacagcc ccttttgcta 17040

-continued

```
atcaattaca tttcaatcaa aatagagtag tcaaagtttc aacttctaaa catttagttt  17100
atacaaatac tagattgcat atttgttagt attttaataa tatatttata cttcgatgtg  17160
gtatttgata tttcggtatg ttattttttta aatacaaaat accataccag atactaaaaa  17220
aaagtatacc atataccata tcaaatatca taatactgaa atcacggtat taaaattttc  17280
gatatattat aataattgga tatataccat atcaagccca cccctagttt tgatcattta  17340
agtaatttgt cacaagttag caaacatgat ctgttatgct tgaaggttca aaataatttc  17400
ttttaagtat gcacttaaca attgtggtac cttaaattta caaaaaaatt aacaggaagt  17460
ttattttcgc tagattctcg gctcaagaac aagtaaatat gtgaagaagt tgttgagaat  17520
aaaactaatt aacaaaagtg tgatgttcac atatttcgat ataatatcag agtagtcaaa  17580
gatcctgaaa ttgaatctta ccatcactat attaaaaaaa atcacttatt tgacccataa  17640
aaaagatcgt gaaatcaaat atcaccttca ctatatataa tgaaaaagaa tcaagtttcc  17700
acatgcaaaa tgggtaaaga cttgtttttt tctttttttgg atatagagag atagtagata  17760
caaagacata taagctatgt atagacacat taattaaaga gcaattgtat gttacatctt  17820
gaaagaacaa agagctcagc tgaccataat tttcaagtaa ttccccaaaa attcataaat  17880
gtgtaacttt gtcagaattt aaaaaataaa agaaggcaga ttctcaattg gagcagtaag  17940
aataggaaga aatttgaaac ttacattgaa atgagaaaga aaaccagagg tacgtagtac  18000
tgcagtgcta attcctctat gtttattgaa gttcgaataa atttgaattt atgtccacaa  18060
aaataacaaa gtcaatttca gatctgaagc tcaaattgaa gaagaaaaag aatctttgtt  18120
tggtgcacat atgagtggtc acttggaaag agcaggcaat aagcaagtta aatattcaca  18180
gtttattgaa aaaaaacaaa aaacaagcaa gttgaatgaa ggaagaatat acttcgaact  18240
ttcaacaaag gcgggctctt tccagcgatt gtatgccaaa ttcactatgt gagtcttaac  18300
gtattcttta attttgtaat attaaaaaat tgtggggaaa aaaaaatctt ttttaagcaa  18360
actaaaaaaa tatatatcaa aacaaataga ttggaagtga aggagtgtaa ttttgagtct  18420
attctttgac tccacttgga aattcttaca aaataatcga ttgaatatat atcaaagata  18480
actagatcaa gtgtttgaat aaaatcttca agatatataa caacttaatt tgctcataag  18540
atttcgtcca catgaaagct gactcattaa tttcgaagca tgtttcaata aatagttcat  18600
aatagttcaa ataaaaaata caaacacttg atagttcaaa tagaaaactc gaaaaaagat  18660
aaatatttca actgtgtttt tacaccatta tctctaaatc aaataagaca gaacttggag  18720
actttcacat cctgtgatgt cttctacttc tttaatgttc agagctgaat cctcaagtga  18780
cttcgtgcat ctcctcaatt taatcaacat ctgctatatt tttcatccca gaagcaacag  18840
cggagccatg gtttttacca aggagtttca aaatatgaaa aaataaacac atgaagaaat  18900
caaagtaatt acacatctac tatatataaa caatataact ttttgtcgaa gatgattcag  18960
atgaacccct gactctacat ggatcctccc ccgcccagaa gcaaccatca tcgtccttga  19020
actcgaagaa tgctccatta agtctctcaa ggaatctcac ctggagaatt cttgatatac  19080
tgtggatgaa aacagaatat tagcagtaaa taagagagtg agtccacgat gctacgaact  19140
agccaagcag ctcaccctga tatctccaag caaactctaa actcagtcat gacagccact  19200
atcacgggta tacattactg tacaaaaaat gcaataagtg tagtatgagt acaaaatata  19260
acgtgtattc aacaagtatc attgatagta atgagggttg gtctttcaaa tgcttgtgtt  19320
ccatcctgat tagcatatgt gatctcaaca gacatagaat aacaacatag aagtatatct  19380
aaccgaacat tgttataaaa aaaatacaca aaaccaacct acagagaaga tatgcacaga  19440
```

```
ttcaacccaa caactaaata aaatgcgcga ataagagtta tgatgcgata taagtaaagc  19500
tgattcttta ccacaattgt gtcaaccaat cccaggtaaa acaaccctac gcgatcacca  19560
ctcctcctcc catgatcaca aagcacaaaa acctgatgca ctagtaaaaa aaaatctggt  19620
gcaactgaaa taggatatta gcacccaaaa ggccaaatct cactgaacct ctcgagttgc  19680
agtgcaaaca tatgtacaag ttcaaactca tcctatgaac ctactcaaat cttgaattcg  19740
agcccgtctc atcacaacat tgacttcggt tctaacattc caaaattcat ctgagcctct  19800
tggaacccat gccccccata cccacaagtc ataaaacacc aaatgaacat actgaaagtc  19860
tcaaataggg gaaagggatt ctaaaactca aaacgaacta ataggtcatt acaaacatgg  19920
gaacataagt catttgcaac ctcaagtcaa aaggcggcag tgagctacgg ttgttttctt  19980
gatcccaaac actgaagcat tctgctgcaa aatctgcatc tgcatatcct ataaagaaag  20040
aaagaaaaat agagagaaaa atcaaaatgt tacctgaatg aattattttt tacctaaata  20100
aagtttctct caagtccaaa cagttttctg gaatactatc catggttaaa cgggcactta  20160
atgatatagc ttactgtctg gttgatactg aatatgaagt tggagactat cacatcctgc  20220
gatctcttcc acttcatttt taatgttgaa agctgacttc tcaagtgagt agttgcagcc  20280
aatcaactta atcaacttca atgtcgggat atccacaaag ctagaaggga tctgatcaca  20340
ctgaattgtg catttgttta taattaattt ctccagcaca gggaaggatg actctgagga  20400
gcgccattct gtcacgagaa tattctgtaa aagcaagtat ttgagtgcta ggaactcata  20460
atcactgaca tcccaacata tgctatatcc agcctgcctg aatctacttt ccggcttaaa  20520
gtatatatta cgtagtttga gactttcaag gtttcgcaga cttgcaagtt gtgaaaaagc  20580
ttcttctgtt aggcaaagtc tatcaaggga caaatccttt agatttgaag ggaagacaac  20640
acagcgggcc tgtccaatgg atttgtagcc tgaaatcggg cgtgaaaaac acagttcgag  20700
agattgaagt gggagttctt caagattagg catatcaact tcataacctg gttcaataaa  20760
gtggagcttg agttgttcaa tatttggaaa tctccaccag aactccggag tcttatcagc  20820
caagtatata cgacactttc caaaagtctt caaatctggt aacaaagttg atgaagattc  20880
ttcgaacagt gctcgatcat tgtcttccca tttgaaggaa aaatcctgta tatccacatg  20940
tcttagcttc ttcattttcc aaatagaagg ggatgtctcg aaacgccttg aaaaatcact  21000
attccccacc acctgcaaag tttgtagata gtgtaggtgt gatacccact ggaaatcaaa  21060
ttcttgggta caaattgcaa gatatctcaa gtgagttact gcttgcactg ctgtagtcca  21120
agaacgtctt tccaaacaga catctgacaa atgcaacacc cgaataaatc ttaagttatc  21180
gagtaaagga aaagtctttt cccaaacacg ggactttgga tgagcaataa acttaagaaa  21240
cctatcatga cattgagcaa aagactctcc ttccttcaag cctgccaaca ttggaatcct  21300
atccaatgat tttgtatact gcaacaattg gtgaacaaga tcatcatgga taaacctaat  21360
atattggggt tcctttgaag gccggtactg cataaacttt tcttttgtaa gtttcctcat  21420
gcaaaactca tgcactacat catgaacagt gcagtactct atctcaccat tatcttctct  21480
ccttcgagaa ataattacta agcttctgtt cactagatca ttcaagcaaa ttttagatgc  21540
ttcttcaacg ttctctgtgt ccacgctgtg tataaaattt tctgctatcc acaagtttag  21600
caaattgaat actggaaatt gatggtcttc tggaaacaat cccatgtaaa gcaggcaaga  21660
ctttaaatgg tcctccaaat ggtcataact tgattctatt atcttcatgc tttgctcttc  21720
taaaacatgg gaactcaaat cttctgcgaa cccaagccac aaagaggctt ccctttgctt  21780
```

```
tgcaataatt ccagcaatca aaacgatcac aagaggtaat cccttgcagt tttgagcaac  21840
ttgtaatcct gttttaagta gctctggggg acaaatctct ccttgaaata ctttcttctg  21900
aagcaagtcc cagctctcat ccacggtgag aaatcgaaga aaatatggat cactgtggtg  21960
cttaagctgc ctagccactt cctcatctcg agttgttagc actactctgc ttccattttc  22020
atcatccggg aacgataagt gcaactcttc ccaagcctca acttcccata tatcatctaa  22080
aacaatgagg tatctcttgt gcattagact cttgcgcaac ttgtcaggca agtcttcaga  22140
tgggctatca tccatattgc ctacaacttg tttaagaatc tctaagaaca ccttcctcaa  22200
attatattct tttgaaatag agcaccgtga tcgaacgtca aagtgtttat caacacaatg  22260
atgagtgaaa accattgtag ccaaagttgt tttgcctagt ccaggaattc caacaattga  22320
gtcaatgtct agttccttcg ttcctcccgt caattgttta attatgttat cagcattttc  22380
cttaaaacca accacttcct catcaattga ggtggaagtt ctttcaccct tcagaacgtt  22440
taccatgtca gttatcttga tctctttact gctggtagaa gtagaaataa ctatattaga  22500
actgattgct cgtcctagaa taaatagatt ggcaaataaa ttaaagttaa ctaatctact  22560
aggtctatca aataatcagg tccatttatg taacggtagg ggtatatgtg agccactttt  22620
gtaacgaggg atatatcatc tctaaatcgc aaagttgagg ggggatatga gacccttttc  22680
ccttcttttt tttggggtat aagctatata taggcacaca ttatagctta gtgcattcat  22740
cttcttcttt tcttaacatg aatgtagcag aactctttta tgctacatct tggaagaaca  22800
aatagctcag ctgaccataa ttttgaaggt cttcacctaa tactccctca gttcactttt  22860
acttgtccac tattccaaaa atagaattta atttttattt gtcaattcta acatataaaa  22920
aaaagacgat tttttcccat gttttaacat ggagtattaa ttacttattt ccctaatcat  22980
tttccaagac ttaatattgt aaaaatactc atatgagtca tatcaattat tgtttcttaa  23040
gcatctgcaa agtccaaagt ggacaagtaa aaataaaccg aataggtaat ttcttttccc  23100
aaaatttcag gactttgtaa cttctgatag aatttcaaaa accaaaaaag acacgctctg  23160
cataaaattt ataaacaatt gccgaaagat tcgtaaattc aaacttacat tctcaaatga  23220
gtagaaaacc agaggtacgt agtactgcaa tgctaattcc tggatgcttc tttcacttct  23280
ttactccaat taaatttgga tttgtactcg taacaaaggc gatttcatat ctgaagctca  23340
aagttgttga agaagaagaa tagtgtttgt tcttctacga taccaatgtg tatggaattt  23400
ggaaaatact ttttcacttt caacaaaggc tgacgctata tattctttcc cttttttgaa  23460
atgaaataaa agttccacta gtaatattat aagtttttat ggtatacact agatctttaa  23520
ttaaatccat gtgagggatc ttttttttt tttatgtcca gatcaacttg catgcacctt  23580
aactaattcc acgaaatact ttatacttgt cacctctcac caacaactca actaatttca  23640
tagggtattt gttacctccc accatcaata gataccaaat aaatttgtac accaagatta  23700
ggacaaatag gaagaaatcg cctagtgatt ttgtctatgt aataatttga acctcgtttt  23760
ggaattcaca caatgtccaa aagagtccca aaaaggagta tcaaaaggtt aacatctgct  23820
aatcatcata tcatattata tatatatata tatatatata tatgtaatga ccctaaaggt  23880
catttttgga aattttcata aaatgaccgt tttacccctc ccgatagttg ccccgagtcc  23940
taattgttgt atttttgaag ttggtttgaa ggaaaattga tgaaaagttg agtttttgga  24000
aagttgagtt cttaagagtt aaagtttggt taaaagtgct atttcgagtc atttggagtt  24060
tcgagactcg aatcgaattt ccgtcgattc cagtagtttt agaatgtcga aacaggtcta  24120
tgggaattta cggagtcgaa tttggagtta aaacgaagat ttgagatcct aagttgcaaa  24180
```

-continued

```
aattgtgaaa ttttgatcaa gagttgactt tggtcaacaa acgaggtttc ggtgctcgaa  24240
atggaatttt gagggcaccg ttggattcag ggggggattc taagtctaga atgagtcttg  24300
gttgaatttt tagaggcccc gagtgcgttt tgagtttttg agcctaaagt tagtttcttg  24360
acgccttatc ggataccggg tcaaggagac ctcgaattca aattccgacg atttcattga  24420
gtccgaaatg tcattttcaa gctagtagca tatttggttt gtgttcggga agtgccaaat  24480
gagttttgag tgaagctttc ttcttggatg ctttgacact atttcagcaa attgtggcaa  24540
ctaaagggtt cattattagt tttaaaggtc gaaaaattat tccgaagatt ctgaaatttt  24600
gagcatgaat tataagactt atctgcaaat tttggtgcat tttcgctaac ccgagattga  24660
acttttatcg caaataagaa ataattgttt accgagtaga aatgatattt gactgagcaa  24720
acgagcatga aattgagctc cgattgaacg agcaggtccg tatcattatt taagacattt  24780
acaaaaaaga atcgggtcat ttcactatcg tatgaggaaa ttacggcctt tttagtgaaa  24840
gattaactgc tgtttttttg gtgcataaca gccatgtact gctataaaaa tctcaaactg  24900
tgttcatttg gtattttgag catatcggga gttctagaga tcggaatgga gtgattgttc  24960
cggttttctt cttgaattaa tatgaaggtt agtattgaat cttcaattcg acattttctc  25020
ataatttctt tatctggttt ttttttccta tccgtaaatc tcttgggaaa atttggggtt  25080
ttatcgattt ggactccctt tttgatgaaa aaggtatatt tacgatcctt atgttatggg  25140
taaactgatt ttaacataaa attattaatt catcaattat tttcatcata ttaaccgcgt  25200
acaatttgga ctttcctggt aaagttaaag tttgataaat tgagaatttc aaggcgattt  25260
taactccgtt ttttatgaaa tttcatattt gaacttatct aagcatgcgt aagatgtttt  25320
tcaagagata tttcattttc gagtcagggt ttcggatccg aatattttag gcttcttcaa  25380
gaacgtggat tttccttcaa attgagtttg tgaattgatt tcaactcctt tttcaaattg  25440
gttttcacca ttagcttcca aatactttaa ggatcatttt acatcaaaaa tttccaaatt  25500
tgggtatcgt tttccggtat gagacttttg gaccgttttg cccttttccc ctaaatttct  25560
tgattttggt gtcattggac tcgaattgtg attgtgaata attttttgaa tagattatcg  25620
tgatctggat tatactcgaa aaggaaaggc tcaagtcaag taacttttgg aggtcgtttt  25680
aaggcaagtg acttccaaac tttgtaaaac tcttagatta cgcatgacta ctttccaaat  25740
tgtgttgggg agtaatgggg attgaggatg gattttactt gttgattaaa attattgtaa  25800
atgaaagatg gggaataaaa cgagctaaat gtgttatatg tgacttgaat ttgttgaata  25860
agtcatgtga taactgatat tgaggggata aaagagcatg agtaggctat gattgataca  25920
aacattgtga ttgagacagg tgatgtgtaa tactatgatg tggtcgtgat atggttgtga  25980
ttgagacagg tgatgtgtaa tactatgatg tggtcgtgat atggttgtga ttgagacatg  26040
tgatgtgtaa taatatgatg tggtcgtgat atggttgtga ttgagacatg tgatgtgtaa  26100
tactatgatg tggtcgtaat atggttgtga ttgagacagg tgatgtgtaa tactatgatg  26160
tggtcgtgat atggttgtga ttgagacaga tgatgtgtaa tactatgatg tgatcgtgat  26220
atgattgtga ttgatgacat gtgcatattc attattcatc ccatgtgtga actatctgtt  26280
gcatgagttc tgagacactg atatgaggat ggatggatat gagacacagt tgagactagc  26340
tccggctaga gatatatgag atggactagc tccggctagc gatttggatg ccgatgggat  26400
ctggttccgg cggtgataca tggtctatgt gtggcccccca tgggttatga tttgagtatt  26460
cagcgcggac tgattacgtc aacagatgtg tatcatagga cagacatgca tcacgactac  26520
```

-continued

```
atgacatcat tattgcattt tgcatcgcat ttgccttatc tttgtctgtg atgtgtggat  26580
tgtatcggtt taccccttctt atgtggaatt tgatctactt gctcttattt gttgatctga  26640
ggttgatgag gatatactgt tggttctggc tgttgaatat gatctgttta gtatatgttg  26700
gttggtttgc tgttagattg aagtttcggt ggttcgattg ggattgaaat gagttgtttg  26760
tagctgctag ttttgcttag tttagagtta cttgcgagta tctgtggttt tcggtactca  26820
cccttgcttc tacacaattg tgtaggttga cagctctctc tcagattcgg cttagtagtt  26880
tctttagcag attgagcttc ggaacatact cgagaggtag cggttcattc cagacgtgcc  26940
cttgagttat ctttactttc agttttgttc tattcgagaa ctatactctg agacttgtat  27000
atttttattc gaattctgta tttagaggtt tgtacatgtg acaaccaaat tctgggtagt  27060
gttgagtctt aattaaagtc tttcgcttat ttattatcgt ttattattgt atttctactt  27120
ctttatcgtt gtggtctggt taggctgacg tgtccggtgg gaagtggaca cgtgtcatca  27180
catccggatt tggggtgtga caatatatat aatagagaac cttaggcttg tctacgtgtc  27240
gacaccacaa accaaaattc tcttttaatt tatttattta taaaattagt cttctctttt  27300
atgaaaagtt gcgactttaa tgaagagttg tgacttttat gaaaaattgt gatttttatg  27360
aagagttgcg actttaatga agagttgcga cttttatgaa aagttatgac ttttatgaaa  27420
ggttgtgaca tttccgaagt gttgtaactt ttccaaatag ttgtaacatt tttgataagg  27480
cacaataaac atttgtccac tttacccttt gttgtcaata aatagaggga tttcctctca  27540
ttttaacaca actaaaattc tgaacctctt cttcttcttc ttcttcttcc caattaaata  27600
tttgtatact ttgatcatgt tgagtggctc actgacacta ttgtttatgt tacagatcat  27660
ggtatatatt tttacaatca ttaatttata atttatgctt atgttattaa gctaaatgat  27720
aagatgtaat aattttcatt tttctttaca ttattaatgt ttgttactat gtaattttgt  27780
atgtaagata atatagtgtt ttagttttaa tgtctgatat gttttaagta ttattttata  27840
aattttgtga tattaaattc tcacacgaaa cgcgggttat tttactagta tatatataaa  27900
agagaacctc aggcccgcct acgtggcgtc accaaaatcc aggattccct tttaatttat  27960
ttatttccaa aattagtctt cccctttttat gaaaagttgc gacttttatg aaaagttgcg  28020
acttttatga aaaattgtga cttttatgaa gagttgcgac tttttgaag aattgcgact  28080
tttttgaaga gttgtgactt ttttgaagag ttgcgacttt tatgaaaagt tgtgaccttt  28140
ccgaaagagt tgtgaccttt ctgataagac acaataaata tttgttcaca ctactctttg  28200
ttgcttataa atatagagat tttctctcat tttaaaacaa caaaattttt gtactacttc  28260
ttcttttact cctgttcagt gactcacttc accattgttt tttgtatcaa tacaatgatg  28320
aatagaatcg ttatatcctg agaggatcta ttcctttaaa tctcggatac tgaaggggaa  28380
taattttcct aagggtacac aatgcattta gtgggctcaa ttttttcctt tctgtttcat  28440
tctattgtta catatcttga tttttttttca cagtcattaa tttatgctta ttttattaat  28500
tattattttt gagtatatct tttaaaattt gttgtttatg tttcttcaaa gttattatta  28560
taagtatttg ttagtacatg ttaaataaca cacgttaatt gagtattcat gcaagttttc  28620
tctactaaaa ctgttgaaag tagagtaaaa gaattcctta aagatctgta ctaccatatc  28680
ttgaagacaa aattcaaatt tgatatgtca ttgtaaacac ataaagatct taaaaatttt  28740
atcgcacctt gatgtgcaaa gtgaaccagg aaaagaagac aaaaattaat aaacttttga  28800
cataagttca aggatgtgtc ggatgaccta tagaggaaaa tgactagact gcaacatctt  28860
ttaatcccaa agaaatagat aactacataa taaattaatt gctcatattt aatatgaagt  28920
```

aaggacaaat ttctcaagtt tactgcaagt tgtaaatatt tttcttgaag taatagacgt 28980
gttttcgaca ctgtgtggaa tagaagtgta gttcaaattg aactttatca ctctggtgtg 29040
ttaattttta aaaaacaact agacaaattg aatagttttg tgtaatattt tttcctttca 29100
agtatatata atgagttgaa ttgttgtcca atatgataca ttttccattt aatattcatt 29160
ttaataatta cttacgatac atttaaatgg gaatttcaaa atgatatatg taaaacaaaa 29220
gatagtgctg aactttctac acgctagaat tagaatattt gtttactttt ttcaatcttt 29280
tacaatttat ttatctctac accaacaatt atttatttat tagaatattt aatactacca 29340
gtttatgcat ttgattcctc aaaaatgtcg aatagtaaca cttcctagaa gcaaaataaa 29400
aaataaaaaa atcaaattaa agatgattga ttgaaagata aatgataaaa tgttataatt 29460
atcacttcct ttgtagtgtt ttacttaaaa tggctaatat gttataagta ttattttata 29520
aatttcgtaa cattatatat ataaaagaat gttttagtgg caacattcgt cgctgctaat 29580
acattaatag tcgctactaa aagaatactt tagtggcaac attagtcgct gctaatgcat 29640
taatagtcgc tactaaaaga atactttagt ggcaacatta gtcgctgcta atacattaat 29700
agtcgctact aaaagaatac tttagtggca acattcgtcg ctgctaatgc ctataatagt 29760
cgccactaaa aatatgtttt agtggcacca tcagtcgctg ctaatgctta taatagtcgc 29820
caccaaaagt atgttttagt ggcaacatta gtcgctgcta atgcctataa tagtcgccac 29880
taatagtttg ttttagtgac aagattaatc tccgctaata cctataatag tcgctactaa 29940
aagattgttt tagtggcaac attagacact gccaatgcct ataatgccac cactaaaaga 30000
atgttttagt agcaaaatca gtcgctgcta atatcgataa tagtctccac caatagtttg 30060
ttttagtgac gagagctcac ttggacaaaa ctttcgtcct tttaatgttt ttctttttt 30120
ccttctcatt caattcttct aaatattttt tgtgtgagtt attactattt tcggcaagct 30180
taatttgaag aatatgaaac aaaacattct ctgaataaaa ataatatctt aagctacaaa 30240
agatatgtct attaacattg ttgtccttta tgtcctaagt tattgctgaa catttgaatt 30300
atctaggtta gactcatttt taatgttttt aatgttcgaa aatatttctt tagcatgagt 30360
ctagaattca acattttgat ctacttgtac tttcataatg caactagaag ggctttcaaa 30420
gcagcatttt aataaagaat gaatttctaa aagagtcaac aatattattt tgctgttgtt 30480
tcaaattaat ttttctcctt ctataaattt tgttagagta gcaaagtaac aataacgaaa 30540
agtagtgaac gtttgacctc accaaataga tagtctctaa aaaaaattat ttatgttgtt 30600
gtggtgtaca tttttaacgg tcttaacgta tttataacta atattgatta tcgaaaattt 30660
ttacataatt ttttttccac aaggagttat tctaaccata aaattatctg attctatatt 30720
tttcatgtac aaaaaaataa aaaattatgt ttaattgcta cataaaaaca tcacttaatt 30780
ttaacaacac aattatatca tcaaacatat attatgataa attatgtaaa agataaaaat 30840
gattagatct caaaatattt ttaatcattc aacatatatt tacaattctt taaatatgtg 30900
ataatgtcaa atcatttaat ttctgttgaa atgtttttaa aacctactaa aatttactct 30960
ttttttcttt ataacagtcg attattgaaa aagttgttca aaagtttaga aagattattt 31020
atgcccgcgc aaagcgcagg taaattacct agtacaaaaa taaattggaa cttctctact 31080
atttgtaaat ggtaaaacaa aaaatgggaa ttatttacta ttgaaagtaa ttcaatgagt 31140
tacaacattc tccttgtttt gtgattcttg tgatgttaca taattaatca attgaatgat 31200
tgaatataca tagagagaag gatagtgaag tattcctttg gaaaacttca aactctattt 31260
acaacttttg cagcatgaaa cataccaatg gcttgtgctt tgtcaccttt atattcttca 31320
aaagctttat caagcacttc ctagacgcgc ttcagccatt tgttttgatt catcgcaatt 31380
ggtccaaagg tctttcaatt cgcgtctcac tgcccccagt accacacaag ttcctagacg 31440
ataaaggttt taaaacgatg aaaaaactaa acaacaattt caattaagtg gtcatcaatt 31500
tcgtcatacc taatgtgcat ggcacgagat acaggagagc aggttgacca tgtccattca 31560
tcaaaaacaa gccgacataa gtaatgcaaa gacctgcacg gattttaggt tgattaaggc 31620
gaggaatgaa cgaaatgcag cattagaaaa gagaaaaagg agggagaaag tacaagaatt 31680
aaaaagaaac acggaaagaa agaaactcag aaagaatgat agataatcaa catgattcac 31740
acgtaaaaat caaaactaac atatgtggcg caaaaaacaa tttccataga tgtgcagaat 31800
cataagcaga ggttttatta gaataattag aagcattgaa cgaaagaatt gtacattgga 31860
gcgataatct caaaatgatt ttcaattatg aaatgaggct atttctcaat tttacccgtt 31920
tttgtggtct caaacaacta agagcagcag taatgtatta agacaaaacg gatatgaaat 31980
aacacaccaa caacaaaata cccagtataa tcacacaagt ggagtttgga taagaaataa 32040
catagtaaga gcatataaaa gcagaaagaa caaaaagaac tacatataaa ataaaaaata 32100
agaaggaaga aacaaaagag aggtacccac cagttccata accaatcatc agccaaagga 32160
agtatccatt tagtaccccc ttctttttag cttcatcaaa tctgcaaaaa agatcgagaa 32220
agagatcaac aagaggtcca aatgggataa atcagaagtc aaaactaaat cgccatcatt 32280
ctgtagaaag aacgagtgaa tttagacaaa ctgggccgct aagttgattt gaaaacatcc 32340
tctactgaat cccacaaata tttatccaat ttttgttttc ccatttttta accattgtca 32400
tcggaatgat ttgtaacact tgtaaactgg aataattaga gatgtttgca taacaaataa 32460
gaatttgcat tgaaacctag agcttcatat atcaaaacat tcatgactaa attcatatat 32520
actcactgtc cttgtagatg cctataagaa gaatatcttt aagaacaaag gtagagaagt 32580
aagtgaaata gaagtttctt atcatttaat cgaggtgatg tgctaatctt tacatttcta 32640
aaagagagca acaattatct ttgcaagatg actgaagagc aaaaatacct gtatgtaaag 32700
caaattagca aaccagggaa gagaatatcc ccaaagccaa gcatatcaaa tcctttataa 32760
ggatctgtta atttaggaac tctcagaagc atcgggattg attctccacc agctttctta 32820
cctttagcaa cctacaagag aggccaaatc caaccacccg aaaaattaga gacagatact 32880
gaagagctaa attatcttct ggtaagaagt gcgtggcaag aagcgagttt aacccaactt 32940
aataatgaaa ggatccagtt ttgagcacgt aaatgtaatt aacatatacc aagaaaaaaa 33000
cattgaaacc atcaaaagat aaaagatgca tgtgtgcaca tttaaatcat acaggtacat 33060
ctttatgttt taaacaatcc ggagcagctt cattataatc attacctagt tcctgtgcaa 33120
aacaatcaaa taattttgtt gcattttgtt aatgttccac aatccacaac gacaagataa 33180
atatccaaaa gtgttcaata aggttattta gctgctacta ctttgaaggt gtgcatttat 33240
gcatgttgca ggaaggcaat gacatcagag taaaagaaaa ttttaatgcc caacattagt 33300
ggcatatttt gaaagaacag aaaccaagta gagggaagtt ctccttccta tctaccttat 33360
aaaatggaac tagaaaaaga ctgaaacttc atacagacag gtggtataac accacctgcc 33420
tgtaaagggg aacaattttt aattttctag agatcaaaga ccaaaaaggc ttcatgctga 33480
aaatattaag aggaagaaaa ctgggaagag ataatagcat tcttaccaag ttaatacaaa 33540
taaattacaa gatacacctg tatataggtg tgaaatccat ataattaagt gtgagtataa 33600
taaataaaac atggtgtatt aatgcaaagc cgaacacatt cattatgttc ataccttcca 33660
ttgccaacct ctggcttcta aaaagtacca ttctcaaaac taaaaacaat aaaaatttaa 33720
attaacttaa ctttcttcat ttcttataca aatctttatt tagacatcta actcatgata 33780
tgatttgaca aaatatctac atcagcagta cagcttaaaa ttgtaactaa agagaaaact 33840
tactgaaatc ataacactgt catggaatat agcaggagat aggaaaaccc agaagatgtc 33900
atagacaaac gcgcagcaga gaagcactgt agcaacctaa aagagaaagg aaatgacaga 33960
aatgaaaggt atattagtag acataggtaa agcaaaacaa gaaatcaact atgttcactg 34020
gtgaatttta aaagctataa acacaccttt atattaggca attgagccaa ctgcagaaca 34080
gtgatcatca aagcaatccc ctggcgaaaa aaaattttca tttactttta acagttttca 34140
gctggagtaa gtatctagaa gagtgaaact tggtgataag gatgcataaa accaactaaa 34200
tatccaactg caaataaagg tctatcacac aaacagtttt tcagttaagg aggagattat 34260
aaaattagct tacaagaatg tcttggccaa cccaagagta tgattctttc ctgtttattg 34320
cccagaagat ggcgaatccc acacaaagtg ttaggacaac tagagacaga atagcgacct 34380
ccccaacaag cggcaaattc aatgttttct ttccacaacc tctaaatttg ctgcttaaaa 34440
gattgtatga agcatagtta aggatctaat cagaaattct gtacataata tgaaatagac 34500
ataatgggtc aatacatcat accttagtat gagcgtcact atacagttat gcagtccctg 34560
gaaagaaaca aaaagttaaa caataaaaat tcaacaacca gaaaaaatgt tgaccaaatg 34620
caaaccagaa ttagttttgc tccaaaacgt agaaagtgca tatgttgcac aaatcaagcg 34680
taatcaaaag tagtcagaat ttaggtaagt aacctcccaa gcaccatatg gacttgcgca 34740
tatcaactaa cagaaaatgg aagctaacta aagcatatgg atttgtaagt ccacatatta 34800
atcacaatta caatattgca tctataagca gatggaaagg ttaacctttc agaagattat 34860
ggaaggcaca attatcatgg aaaatgcatt tatgactcaa aaagttggct aaaatctact 34920
gttcctacga tctaaagtta gaatcataga taacataagg tctttgatgc agccagtata 34980
ttaagcctta agcctaatac acctcatcag ctggtgtatt cccttgactt ggcggttaag 35040
aaagcatagc tccatgacaa tgttacccat aatgatcccc taccattaat gagcttgatg 35100
agtgcaagta caatattatt agagggccac taaaaagata atatgaaaga acaatatact 35160
aggcacagct gatgtgtttc aaataactac aactacaaag ctactaattc acttcgcatg 35220
cccaaaagga aatttggcct ggtgattaag agtcttatag aggaaaattc aacaattcca 35280
cagaaatgca tgaattttgc atatcaagaa acatttaaca tttgtagcac aattcaagag 35340
tcaaatgatt gatttgaacc attaaactga tgggcattaa ttttaactat tttaaccttg 35400
taatctggca caagtgaata gaaaaggtaa tccactcatg tgagtgcctt ttttctagta 35460
aaatgtaaac caagtacatc tccatggcaa gtgggtgggc ctacgtagga tgttgtccca 35520
gtgtgttatg ccaaaatgtt agagagctga acactggacg ataacccttt aatgatcaat 35580
ttggactttt tggttggaaa acattataaa acctttcgaa ggagaggaaa acctttaaat 35640
aattctaagt ttatatctat ttccaagctc tacgttttaa gttcgggaag caatgattac 35700
tagtgaagac ttgagagttc cctagatatg aagaaaaagt tgttttgatc atctactttg 35760
ttaatcatca tggtatgtga ttgtatccat catccaggag ctagcactcc ctgtcccaga 35820
agcttctttg aatattttta tcaggggtct aaggcaggga gtgggagcat gacaaaagat 35880
ttgtccactt gaatgctaga ttagaccagc tctgaaacag ttactaccga agcacaaagt 35940
tgtatcattt tcctgagtag ttttagatta gcaggaaaaa ctactataaa cacggcatgg 36000

-continued

```
aaaatattgc aaggaggaat attatagttc agtaacataa taattcaaaa aatacatcaa  36060
aatatatatt attaggcatt gacaaacaca ttttttctaa aaatctttag acattatatt  36120
ccattttctt tgcatactat acgaacagat gcatgatatc attatcttgc tcatctgtca  36180
gatactacat gcatggcccc aacttataaa ctaattcaac aataaagcat aaataagcag  36240
tgccatgaaa tgagacttag acgaaagaag aaggagaaag aacgaacttg aatacctcga  36300
ttccaccgat acagaaaagc aatatcagca gccagacaaa ccatgtggac atgaaaaagt  36360
aaagcagcac cagaaatgtg gatgctgaga tgacaaatcc aatagcagtc catgcagtaa  36420
tgtgcagaat ttcactatca tcctcctcct tgacggtcat atcatcatcc tgtaaggaga  36480
gcatacactt tttaagacat tacagctatt aatcaagcaa ggcatcattg ggtgttatca  36540
atatttgaca caagaactag aagtaggaaa accaagaaag acatgttcac aatacgctca  36600
taacattcaa atacaaatca tagatataaa tagatcactc gttcaactat atttaaatca  36660
gatcaactaa ggtcatatat gaatcttcag ttccattccc cgctctattc ggggatattt  36720
cactccaata ctagataatt tgtattttaa cacaaacaag gagttccgca aaattagtgt  36780
gttaaggtat gataagattt atattgatta gggtttattt aattttatta gcttgattag  36840
ggattaaatc agattatatc tgatttcaat atagcaattt tcaaaattac acaccttgcg  36900
acacttttga gaatattagg tcttctaaca ctacaccatt tctacccagt cgatatattg  36960
tagctccacc aaccaaacag gccttcatta tgtgagtctt gtcaccacaa aattgtcgac  37020
agtttttgag atcctccaaa ctgggaaaga cctctccaat ttcttctctg gataaatatg  37080
tctctcacac acctttacct ttgccgttaa gggaaaagga tctatagaac aagccatctc  37140
ctcgatgtca aaagtttttc catcaatctg gtggccaagt atacttagaa agcccattct  37200
attccattcc ttttaaattc ttgacttact ggatccagtt tagcttcagc atacctcttt  37260
tttcgctgga gatgctttgt aggtgacacc ctattagtgg tatggaaggg aaaaatgtaa  37320
gcagtgcact ggtcaagaac taaagtatcc aaaggaagta tgtatcaagg ataaattatt  37380
tggaaaaggg cagagtagtg aaaagattac acagacatat caaccttggt caattcagat  37440
gtatgttaac ttctggggca gctcttgtga cgcaggcagc taagttttga aagaccaaca  37500
actattacca attatgttac ctaaaatcca acagccagag taaactaaat ttactacatt  37560
atcatcaaga tgcagtgctg aaaagctaag acaaatagcc caaacaaaat caatgttgac  37620
aatgctacta gctgaattta aaagaatata agaagctgag catgtcaagt ttgagattgt  37680
atcagacagc ttattttttt atttttttgt gtgtgtgtgg gggggggggg ggaggctctt  37740
gtgatagttc atagttgtca ctttccttag attgagtaaa ctttttccaa agagctgcac  37800
aaatgattgt tccaacagcc atcaaccata tgaaagacac cgagtagtcc acaatagggc  37860
gatctggcga atataacagc agctccactg gattaagaaa aggattccat atgtcaaaag  37920
tattccaagt gaaataaaac aaacaacaag aaataagaag atcagaacaa aagatatgca  37980
tcaattagag agtcactata attgtttgca aataaaaagg ccatttgatg ttagccaaca  38040
ctgcgtttaa gtccacattc tcatcagcta ccactgacat tttgaagaga aaatcaatct  38100
ccgatcttca atcttcgttg catcacacta aaccttcatc ccaaactcat tgcttaactg  38160
ttttttcaaa gtatcaacct gacatgcctt ttgcggtgaa gacacatcat cgagatccaa  38220
ccataaatag atgaagaatc atctaaaagc tttctatgaa cacacaaatg gcatacggtt  38280
cctacagaat acacccaata atatatgcaa caaggaccta ttgtttgcac caaaagttaa  38340
ccagcaagaa gtgggattac atctcaatga tatataataa atctattttc atacttcaaa  38400
```

```
agcactcatt aaaatgaatt ataatgcatg taatatagaa aaagtagatt acaacacaag  38460
ctaatcaaca tcttgacaac caaaattaga atctaaaaga aagctaacct ttataaaaac  38520
atctaagcaa tacatatgag gccagggctt acctttcttt cctgaattga tgtatttatc  38580
aataatatct gccccctctt ttgaaattga aacaacagga atggttacat ttgatatggt  38640
agaattatta ggacaagcaa tatccagagg acctaaataa atgcaagaaa aagcagcgtc  38700
atatcagaaa gagatgaagg gaaacatata aaacagacct tgagacctaa gatgacaatg  38760
tgagtcaggg ttacaacctc cttcattatt tattagcaca acacctcctg cacctccttc  38820
ttgggcaacc gtggccttgg ttataaattc acattcaccg cgacgagcta gtgcaataga  38880
gcctgataac tagaacaaat gatatttctg cattattaat gtataacaaa caacaccact  38940
attattttct ttttatagga cattctcgag cctattttta caacagccaa acagatatag  39000
caaatttaga cttctttggt attcaaagta aaatcagttt gtaatagtta acttctggta  39060
gatcctagtg gtaacccttt cagatcattt tacaattcaa aattcctcca ccactactat  39120
ttggttccac ttctgaaaag taccatgaaa aggatatttt tcctctaaaa taccagttgt  39180
atttgtatcg ctaaaaataa cacaagatcg aagaaagaaa aaactaacag aattactaag  39240
actcacaaat tgctaatata attgatattt ttgcaattgg ggtaatatat ggttattttt  39300
agcaagaact taaaagtata gctgatcaca caaatagttt aaaataaaat cttgaaagtt  39360
gaaaatgaag tcatgtagtc ttttgtaaat gaaacaaaaa aagaagaaaa agatctaaat  39420
tttggaagat gatgtaaaca atgattatca cttgaaaaac ttataaacaa tttaagcaat  39480
agcttatatg aagatgagtt gctgtacaga gaggggtgag ggtgttgaca agactcacga  39540
cagaacaaaa ggttgttcag taagtattta actatttatc tagtatgtgt ttagttcatc  39600
aaattaatca aaaagaagaa ggaaagattg tggctacttt tgagctatca agagatcatt  39660
ccttcaccac cctgtacata gtgctacatc atcctcaacc tatctccatt tctactcttt  39720
tctcctattt caaccctcca ctgcaatcca ccagaaaaaa gtatctttcc attttcacga  39780
gtgaaactta ctcttaagtt ttcttatatg ctgaaaataa gttgttctat gcagagtaag  39840
tttgaattac tttaacttcc tgatagaaga cagagatggt caatggctta acatgtagat  39900
gttttcacct aaactatatt aaaaaaaaaa aattgtttct tcacttctcc ttgatataaa  39960
tgagattggt tcacaattcg gctccttaaa tcttttcaac cttgctgaga tttgcatcaa  40020
ttcttcactc ttaaagcagg acttggctca taaagaagta tgaattctat tgttttcaaa  40080
tattcgcaag ttaacaaatg agagatggaa gatcatcaag aaagatcaaa agaaccgaaa  40140
ttgggccacg aaagaattat gactattatt taatcaacca gcaacacagt tttgtttcgg  40200
atatccacct aaaagtaaag gtgtgtaagg aatgtggagt aaatacctta gtggaggaag  40260
cagaacagcc attcaaaggt tgtgtataaa cagcacgcaa cctggaggca cgtttagtat  40320
cagtgggtaa tacagaccca aatgccgcac tcaagccaac tattgaatct tcttcaccac  40380
cattaaccca caacttcacc agcatcttta acaaaagaaa ggaaaagatg attagcaccg  40440
gtaagtttct atatgtgcag aacagaatga aaatagagaa tacttcaagt ccagttaaga  40500
ctaaacatca actaacatgg atattgtggt aaaatactca tttcaatcat tgtttcttaa  40560
agggcatgca aagtccaaaa tcgacaagta aaagtgaacg gagggagtat aataaatgct  40620
aaataaatcc ttgtatagta atcttataac acacacacac acaccacaca ccagaacctc  40680
aaattaaact tttttatgga gtggtgtctg agctaacttg cccacacctc aactattcca  40740
```

```
ccgagtaact ctgccacccc ggcacagaat caaaacataa tatatcaaat aactccattt  40800
cataacaaat tccaccaaat gcatgaaccc aatcctcacc atttcaaatc atcttattag  40860
cattacccaa aaaagattgc ttttttaatg ataatcgcag tgtccaggcc agctcaacta  40920
attccacgag atacgtacca cctcccacca acatgtccat accaaacaaa gattcttaac  40980
tattgaaacc cctcaagaga aaacaacaaa aaaatccata accccatcat aactttccac  41040
ataatcaaga aatgacaata tcaaataaga aaatctacaa aacccataaa agactacatt  41100
tttaacacaa tttccaccca aaaaacaaac cccataattt attttctcta cacaagaaaa  41160
gggttgaata catttaccat attgatttca ttgctgcaag agctatgtgc cttggtagga  41220
gcagaatgtg ctattgatga tacatttaga agaaaaacaa aaatagatag tccaataaaa  41280
cgccatgaaa atgccataat tatttattca atgttgattc ctcccttttt cttcctcaat  41340
attttcccca attcttgcgc tatattttct tcgcctattt ctgcattgaa ttttttttt  41400
tctttctttc aggggaatga aggaagaaag gaattttctt tccgatgaag aagtaaacaa  41460
acttttaatg attaataaat ctcaaattaa attaattaat taaaaaattt aattatgaat  41520
tggtaaaaaa tccaactcat attaatatag tgtgaaattt atgatttgtt gcatttataa  41580
aaaaaattta aaaaaaagat aaatatgaat ttatttcatt ataaactttt atactgatga  41640
gttaaaaata aagttaataa aaatgtaatt gtgtgtaata attacaaaaa ataaaagact  41700
agaagatgaa aataagagac aggaaaagaa aaataatatt aaaagactaa tatatatttg  41760
acaaacggaa aataaaagag caatataaat agctactaaa gtatttgatt acacaatgta  41820
attttcacct ttccattcaa attaagatag tgtaattata ttgcaccctc tcaattgtat  41880
tcaatatatc atattgatcc agtaattact tagctaaata tatacatatt aattatgtaa  41940
ttacacataa gtttgatttt taggtgtttt tcaaaatatg attttagtaa atgtgatttt  42000
cgtttctaaa atagagtaga agttcaggtt ttttatttag tttttttca aaatcttttt  42060
tttgggagca aactcttgtg gaggaaaaag aggcatttga ctagtaggat tcgcctaagt  42120
gaattttgat tctctatgaa ttttttcaaa gaataaataa gagtcaatcc aaaattcaat  42180
ttatgcctat gcttatcgat ctttcttgat ggatgtaaag ttatagtgaa ttctccaaat  42240
tagagtcaga agttgagggg gaaccacact tccacctttc agttcaaagc tgcttttttc  42300
tttatcatat atcgcattag aaagtgataa taagaatgac tttgacatac ttgtttatag  42360
caagtaatct aactcgaagg ctctgcccct aaccttaaaa aatcgcatgt gcatgtctcc  42420
cgtatacggt tcaagtggca aaagcatttt ctttgcgcta aatttgaact aatgatatgt  42480
tagacaatct tttaccttaa taaacttatg agatatgcat atcacatttc tttcatgtgt  42540
tttacatatt atttgaattt ccacaaaaaa aaacatattt tttaaagtca aaagcgcaca  42600
gtttttttga aaatatctaa tatatgccct taattgtgga agagcgataa atttataaaa  42660
gaaaaattca aaaagatacc aaaatctcac atattataca tagggtttca aatgtgatat  42720
acaaattttt aatcttattt atcattaaac taaaatctgt ttcttttta tcaaaaattc  42780
aagaaaatgt atgagtaaat taaattattt tttccataat ttcgcaatac aattttcctt  42840
tgaaaaggat tcaattgaac tcatttgact ctctttagct ctattatatt tgtaatcact  42900
agttttgatt cacattctga aaataaatat gttctttaat tagacattta caatatgaat  42960
ataaaccaat aaaattattg aatattaaat attgaatagt taaaaataaa ataaaattta  43020
gcaatacact taatcctaga tattctaaaa aaaacgtatt tattatactc ctagtgggat  43080
accatactca aaccactaag atccaaatgg attatacttt taaaatggaa gatataattt  43140
```

```
aaaaaatgca ctaaacatta tgtggaatcc tccccatggt atcaacaaag tgaggacaca  43200
aggaagtcaa ctcatgataa tttatgtctt taaatttgtt tagttgactt tattttttga  43260
tattcatatt gaagctttga ttaatttaaa ttcgtgctac ataaagttat ataaaggaaa  43320
atattatcta actagatgtt ttttattatc taactagatg ttttttacat tttaatggaa  43380
aaatcttatt gttaattaac ttgtcttgat attgtttaat tagaatgaag tgtttgttac  43440
atgttaattt acaattagtg accgtgaaaa gaaaagatgt gaattgtcat tattattagt  43500
agaattacaa aaagaataaa gactttttaa acattccttg tacaactcaa ataaaattat  43560
tagtggaaaa tattgaagaa atattcaaat ttttgactag acaatataaa gtcaaaaggc  43620
ttgttccata atgaaatctg aaattaattt aatttttcag catttccatt atatcattta  43680
tttatttaag cactcaattt attaattgat attgaaagca aaaagtttaa tacacgttca  43740
aattatggtt gttaagaact taagataact aactattata acaaatctct aaaaatatta  43800
taagtatcta tttttcctat atgttgtgct ttgtttcaga ctctttaaaa atattatgaa  43860
tatatttgtt tcagttcctt aacacatatt tatcgacatt gctaaagagt tcgatcacat  43920
tgatttttac ctctaaaact tacctacaac aatattttgc ctaacaattt tatgtcttct  43980
tttttgttaa atatttacaa tgttctctcg tggaaattta agtttttgtt ggacttaaat  44040
aattatactg aaaaaaaata attccttaat tttcatggtc aatgaattgt ggccgctcac  44100
ctttgttgat aaactatttt taaagagttt aattattttg atcataatca atgtataaag  44160
tttatttatt atcatattaa gttctcttat agtatagtaa taaataaaaa attcaaataa  44220
tcctagtatg ataatatgca tatgtaataa tacacaatat aatatgaaat aaagtaaatg  44280
aatatgaaaa aattcattga atgagacaat gtcgactgct gagaaattga ttgttctgaa  44340
aataataata atattgtgat gaaaatagtt gaacagtatg gagtagatta tatttcacca  44400
tctatacaaa ttgaaacagt attattaaat aagaagggtc actaaaattt gagttgtaat  44460
acacaaatta ttttaaaatt ttgtattata tggaaatatc ttatacctga atcttctcga  44520
tgtcttcttc ccataattaa attatagaat ataatactac taaaataaag ctttgcgtga  44580
taatggcaaa ttaaaaaaat aaaaaaatta atatcttaaa aatatttact atgtaacttt  44640
taaggatatt atagcttgtt tggttaggat tttattagat ttgaagtgct tatttgtttt  44700
agaacataaa taacttattt ttaaaaaggg ttagttcata tatttggtcc ctcaattatg  44760
gatataatat atctcattaa tcatttttttc cctttaaatc tcaattaaca taatataact  44820
aatgaacact ttatagggca atttttattt tattatttta ttttttatca tataataaaa  44880
gtgaatgtgc atattgtatt gtaagcataa tgtcatatga tactgtcatt gttgttgcca  44940
ttacagagtc atgtctcaat aactgatttt gtagtttggc agactacata gctttctgat  45000
ttttcttatc tatatttttc tattaaaata ttttttatat ttatttcata attgcaattc  45060
aattttctta tacataattt actgcagaca tgcaccggtg gaatatgata tttaaaatat  45120
tagttggtaa acttttaatc aagttgttgc tatcttacga caatatttga taacttagac  45180
atatgaaagt gtatattaaa taataaatac atgatacatg tttactatat atatataaaa  45240
ttagcactcg accgtagtta acttatgttc catgccaaaa acctaacaat tgtagcttta  45300
gtttatctaa tcttgtttta tttataggtc gatataattc attattttgg ctcaaacctt  45360
atatttttgt taaaaaatta tttaatatat tcaaaacaag caataaagat tatggtccgc  45420
acttatacgg aaaaggtaaa agataaatgt catcttctcg taattcgtac ttgtattgaa  45480
```

```
aaggtcaaat tatgataagc caatcaacat tacctaactc ttcttacttc agttcatcac  45540
ttaatcatgg taaattaaca ttgttaactt aaatgatgtt ttacaaaagt aggggtgaag  45600
ctactattat aattacgata aattcgacgc aaattcttta tattatttag gaaaactata  45660
attcaaaatt gataaactaa aacctttgaa tatcttttta taaattgcat acagtcttgc  45720
caaataagct aataaagctt ggtacaatgc caatatacaa tcaacaaaga atagaaagga  45780
gaaaaagcac tatcccaaat atatataatc cacaaagtgt tgcactatac ccatgcacat  45840
aaagtttatt caacttacaa atgcaatatg cactattgag tataataaat gaaaagtgca  45900
aaactaagga tttgcttcta gaaactttac ccacaaaaag gcatgatgaa tggataatgc  45960
actttaaact tttgaaacac ttgaacattg agaatgaaat aacaataaac taggataatt  46020
tttttgttaa gtatttttat attaatatat aggtgagcgt tatattagtt aaataatagt  46080
tataactagg ggtgtacaag tcaaattgta aagtcaaacc gaattgacga accaaattaa  46140
accgaaaaaa aaactgatgt gtgatttggt ttggttggtt tggcagttga aaaaaaaaaa  46200
ccgaccactc ttgatttggt ttgatattaa aaaaaaagtc aaattgaact caaatcaaac  46260
cgacaatata tatatatata tattatttgt tttatttata gataaaaata ttatttataa  46320
tctactttgt taatatattt ttagttagtt tatagttttc aatgtttata tattttattt  46380
caaattttgg gcatgtaaaa tttgtaaata tttattttgt attaatatct gaagttacaa  46440
ttatattgtt atagtttttc aaattcgaag ttaacaattt actttgtaaa tattttattt  46500
tgtattcagt ttgactataa cctttaatct tattaatgta acataatgaa cattgatatt  46560
tcaaaaaaaa tattttgtat tcatgtgaat tttaccgtct tttcgaaatt tctattcatt  46620
taacattttt taggtttagc ttataacacg ggtaagtgaa aatatatttg atctcttttt  46680
caagcaccgt atagttgtaa aaaccgacta aagccaaaac caaaaaaacc aactttatgt  46740
gttttgattt ggtttttaga tttaataagc cgacataatt ggtttatgtt ttttttaatg  46800
gaaaatcaaa ccaaatcgac ttatgtacac ccctagttat aacaattcaa tggtagaaat  46860
tcacaagaat gtatctagac atatattttg gtaagcgtca ctttggactt tctttggtaa  46920
gctcaaaaga catgcatgta tacttcgctt ggagggggaa atgtacatat actcgatttt  46980
aatgtcccta ttaaaattat attttgagtt tataaattct ttttcatatt tatcaattat  47040
tatttcacga taactttaca tatatgatgt ctgaattttc atatggatga aattcagaca  47100
tttttagtta gagtttttaa aaatattttt ctttcgtgat atttaattga aaattagttt  47160
atttcgtaca aatccttctt cagaatttga agccaacctc atatttggaa gaaatgttaa  47220
ataatgtata gtaatttttt tctttaaaat gatttcttac taaaattttc ttttaaagac  47280
attttttcct aaattagtaa ttttctccca aatacatttg actttcaaaa gggcttttca  47340
cacaaaggaa aaaagcattc atcatgatga cacaagcctg aaatcatcat atattaatat  47400
ccatatacta aaatccaaat aataaattaa aataacaata aaaaaattag ctgtcttttt  47460
caatattcaa cttacagagt tccctcaatt tgaaccccat tttcaatatt ctaaaaattt  47520
tcatataaat agggaaacat agtttacaag atacacacaa aaataataat caagaattgt  47580
tatatgagag ctatttctga aatattttta gtgaattttt ccccatttgt tagaaataat  47640
ttttttttcaa gaaagcctat tttttttcta ttagaaatat tactatgtct gaatcaagtc  47700
aatatgattc ttgttttgat agaccaagat tggtgattaa gaaagtttta gctaaacctc  47760
aaagtgaagg gaatggagct gttgttagaa gaagcattgg aaggtattaa aatttaggat  47820
ttttatattt ttcacatttt ctttttgttg attttaagtt ttgtttctaa attttatgac  47880
```

-continued tttttgtca tttgggtatt tttcattttt caatttggac aataaaagaa gtaactttaa 47940
taggaaattg tgttttgaaa ctttggcctt gatgtgtttt cttgatttcc ttattggaaa 48000
gtctctgtct taatgtgatt tctttctatt tgtcaagtct ggatgaatag agttacctag 48060
tacctgttat tggtgggagt tgacaggtat ctagtgtaat tagttgaggt gcggaaaagc 48120
tgccaagaaa ccacaattat caaaaagaaa aaaagtatct gtctttatga ttttttctat 48180
agtcttgttg ctaattgaat gtggggtttt tgttttaaaa atttgatctt gcaggcatga 48240
attgaggaat cttgatcctt tcctcatgtt ggatgaattt tcaggtactg ttttgagtaa 48300
tgttgcttgg accctccaaa aatgttgttg cacatgtgtg agattctcca aaaaagcata 48360
gcttttggag gatcaacaca cacgacaata tttttgaaga gtttgagcaa cataagtctt 48420
gaacatctaa ctggaatgtg ttgattattt tattttttg agccaagtga agttgatata 48480
gtactgtttt attgtttcag tttctgctcc tgctggtttt cctgatcatc cacacagagg 48540
ttttgagaca gtaacttaca tgttagaggt aaaaaaatta tgttgcctaa ttcaatccaa 48600
tataacagta aggagaaagg gccgacgaag ggtggaaaat ggaaggccat ttcttgttcc 48660
ctgaggccgt gtgtgtgcca tgaccaaaca cccatttgat gctctttaac ctccccatta 48720
ggatggctcc gttgtattgg tatccgaatc atccaacaaa gtataagcag caaagcacca 48780
aatggcattc cttgttgaat tgtactgagg cggatgtagt gtttacttga acccaatatt 48840
tttgacacaa aacataaata aacgcacatc aaaatcttaa ctcatgattt caaaagtaaa 48900
acgggcacag aagacgtgat aatgctaatg ttgtgttttc atttccttag ggagctttta 48960
ctcatcaaga ttttgctggt cacaagggca caatcaatac tggtgatgtg caggtataga 49020
atattcagct cttagcattt ttacttacaa gctatgttgc tcggatcctc caaaaatgca 49080
taacttttgg aatatccgac acacgttcaa tagtattttt gaagaatccg agcagcatag 49140
cttacaagaa cagaagagat attttggttg ctgatatatg tttcttattg tggatgatat 49200
tgcagtggat gacagcagga agaggtataa ttcactcaga aatgcctgca ggagaaggca 49260
gtcaaaaggg gttgcaactt tggataaatc tttcttctaa ggacaaaatg taagttatag 49320
tcatttacat cattagaagc tttcagtctt atcactcctt ttgacctatg ttgctcgtac 49380
tctttgaaaa tgctggcaca ctcgtttcag atcctccata aatgcgctat tatttggaga 49440
atctgacacg cacctgttga catttttaaa gagtacgagc aacacaactt ttgacctgac 49500
cccatataga tactttacac accaccactt tattgtactt ggctctagca tatagtagta 49560
aaaaatttta atgttagctc ttatctactt tttttgtggg gcaggggggg tgttaggagt 49620
gtactaatat gcagtataaa aatcacctct gtttctgctg tgttttgcta agcttaatca 49680
ttcacttttg actaagttct caaaattttg gacattttat gatgtgatat tctagaaatc 49740
aagatttagt ttgaaccaat attttcccat gttcaagttt atagcccaaa acgaagactt 49800
tgtggcgaac acacgtttga tattggattg cttttccttt ttcaattctt attaagttca 49860
aagttcaact gcaggattga gccaaggtat caagaactgc tgaaagaaga cataccaaga 49920
gcagtgaaca atggtgttga agtaaaagtt atagcaggtg aagcgatggg tgtccaatcc 49980
ccggtttaca cacgaacgcc tacaatgtac ctcgatttca ccctacaacc aacagcttac 50040
tatcatcaag ccatccccga gtcttggaat gcgtttgtgt atatagttga aggagaagga 50100
gtctttggaa ttccgaattc aggtcctgta tcagctcacc attgtttggt tttaggccct 50160
ggagagggac ttagtgtatg gaacaagtct tcaaagccat taagatttgt tcttttaggt 50220

```
ggacaacctc ttaatgagcc tgttgttcaa catggtccat ttgtgatgaa ctcacaagat  50280
gaaattgatc aaacttttga ggattatcaa tattgcaaga atggttttga gaatgctaga  50340
tactggaggt cagggcactg aagaaataga gctgaaacaa taatacaagc tatgttggtc  50400
ggaatcttta aaagtgcata taggtgtgtg tgttggatcc ttcaaaagta gtgtattttt  50460
tggaggattc gacattggtg tggcaacatt ttaggagagt acgagcaaca tagactatta  50520
gcctcaaaat gcaccttttt tatgtttctt tttttctttt cataaatata tccctagtaa  50580
agaaataatg gtcaacttta tcttgattta tcatttgaaa attgcttagg ttattgttat  50640
ttattcttat tttcagtgtg gggtttaata gcatatttgg tcccttgatt atcaaaaaat  50700
tccagttttc ttccttgtga tatctcactg acatttacca tacaattact ttgaaacgtg  50760
cacgtttgat cactttgctt atgaatactc acaaaatttc aacacttatt aaccatatgt  50820
taagttaagc ttgtataaaa acacacacat tctaattaat tgaagattaa atatgttgag  50880
tcattctata tcacaagaat aaaaaatatt atttatcaat tattgaagga ttaatgctat  50940
tctcccttca atgttgatag gtcgtgatca aaaagttgat tgttatttct ttttcttata  51000
gtgaatattg attctgaatc tatgataata tcttcttgga tattgatata gtggtggtgg  51060
tggggtaaga ttctttgttg ttagttggtt tctctctttc ttttcctgtt tcccttaggt  51120
gttcagtaat tattttggag tttgattaat tcaaagtcat gttgaaagca tgcactattg  51180
aatatgactt catatcctga gcttgaacct aagatctcta attaagatta tcggaatagt  51240
tactgcttga tcacaacaag tttttattga caagttttaa atatgggaac ctctcataat  51300
gttgctagaa ctaagagtgt tggtgaggat gaaaggaatc attttacata atttggtgag  51360
aaaaggatgt ttgctcagtt tctagaagat gttgatatgc acagtttact gataagatga  51420
ccttgacaga ctatactgtc tttgttcttt tagaatgttt tagttttgga gttgttgagt  51480
tgcatcacta atgcatgtta taatcagctc tcccaaaaag caaacaattt cttttcgttt  51540
ctcacccagt gtctaatacc tgtattaaag cccaactaaa acatttacat cagaaagtcc  51600
catattgtga gtacactact ccctaacaaa ggtgattcca tacactcgag ttcaaaagct  51660
ctgattgaat atgaaatagt atttatcact cactctacca caacatttgt tggtaaaaag  51720
tggcaacaat tgaacaatca agaatgacaa atacataaag cagcacacag agttacattg  51780
gtaaaagaaa catttttaat ttcagctgcc atatagaata taaatatcaa gttcctgacc  51840
attacaaaag tactccatcc attaacaaat caataaacag taacaccaac aaaaataatt  51900
taatgaacca ttcttgtaaa acttaagggg aatcaagaaa acataacatg aatcacctag  51960
aacaacaaga gtagccctgc ttttgtttcg atccatcggt accatcrttg accaggttaa  52020
ctctgttgac agataattct gctttataag aatcggaatt caaaaccttt ctactaacac  52080
tattatagat ctctcgaatc acaatctcga aagccttgtt tacgtttgtt gaatcgaggg  52140
cagatgtctc catgaagaac atcccttctg attctgccag gcttttgcct tcttctacgc  52200
tcacagctct tatgttctcc aagtcacatt tgtttcccac gagcatcctt gctaccgttg  52260
tatcagaatg agctgcatgt aaatggttgt ttcagttata gaacgattgg gagtatgaag  52320
aacatataga acaccaccgt aacatgtaat ttgaacacct aatatacaac ggtataaata  52380
aaagttggga ttctcgacag cagaaagtat cattccaaga aaaaatgtga ataaataagc  52440
tcgtgaatgc aaagtttaag tacagcacct gcacatataa agagtctgta aaccttaata  52500
ttactaccta tatttccttc aaaagtatgt atctgaattt tctcaagttg ttattagcaa  52560
cgtcattgtc tcctttcatg aggaagaaaa atgctgcacc ttattaacac tgacttcgat  52620
```

tttgatgaca taatcctctg ctcatttcat cccgtgatta aatgaagctt ctggagtaca 52680
aacctcattt gtggttttat atgctgcaaa tgttaacatt ctatttatcg catttccctg 52740
gccctgggct ctttaatgcc cttaactcaa gctaaaatct tctacttggg caaacggcct 52800
tgtatctggc ccactcattt tgatagatca agagttaata ctcctctatt ttatggacat 52860
taagttctaa aagttttcaa ctttggaaac agtgagcaca aagtcattca ttttcaagat 52920
tcaaatgata tttgcaagac aagaacagat ttgaataaca aaataaggtc gtgcaagtat 52980
cacatagcag ctcacggctc aaagcaacac atatacattc ccgtccagcc aaaagttagt 53040
tagctaaggg cttaatagag agactaccta agttataaat atggcaccac ttaacatcaa 53100
aagaatctca gagatttttt atcaatcccc gagactcctt agtctaccat aatgccatac 53160
gtaggtaagc caggcagttg gtcctaatta ttttcacaat caagcaaata aaacagattc 53220
catataagta tgatctgttg acaagttcat ttagattggc ttttcggaga aagaaaagca 53280
tgacttgatt tccaattcct aatatacatc caattgacag tctgtctaat tcgttcttat 53340
cataggttcc caactgcatc tagacaaaat tgagcataac agctacattg gcatatatac 53400
cgctttcttg gccattgctt caagtaacaa tgatccataa tcaagactca aggtttttct 53460
agctaacatt accatttgtt tttatgcctg gtaagtagtt tttcactaaa aagattgaat 53520
tagacttgat agcaactgta aaatcttact ttattcagtc aaagagaaaa gtgataggaa 53580
ccaaatccac agaagaagaa aaaaagcaaa ggacaagatt caaaaaatat aaattcaaca 53640
cattcattat tcaattctgg aaaaactcaa ttaaaattac ccttatggct tattccatca 53700
tcctaaatag ttaaagtagc caagactttt cggatctaca agatatctta catacttata 53760
agttataatc aagaaccaag aatgtggaag tcaaattcca gaatcgccat catatcataa 53820
caccatcaaa tctcaaaaac tgaacttcat actaccaacc tcaatatatc tcaaaaaggt 53880
gagaaccttt gtattaaact ttgatgggaa ctcaacatat gccaaaacca agttgaaaag 53940
tgggaattca acatgaacca aaaccaagtt taaatttttt tgtagcaaca gagacatatg 54000
aatacaacaa tcagatctcg actcacttgt caatttatcc aataactaat tataaacaaa 54060
atgaataatg tagaagtcaa atcaaaagaa ctaccattct atcataacac catcaattct 54120
aaaaaaacta gactttacag ccaatccacc aaaaaggtga gaactttctg tgcacaaaga 54180
aaagataatg cataaagctt agatgacaat tcaacataaa ccaaaaccaa gtctagaaaa 54240
agagaagaat tttagcaaca gatgccaaat ctaagaatta ccattatatc atagcacaat 54300
caaaatctca agaactaaac tttatagcca atccaccaaa acctcactat atttcaaaaa 54360
ggtgaaaact ttttcttgca caaagaaaaa gatatgcata aaactttgat gggaattcaa 54420
cataaaccaa aaccaagcta aacaaagaaa agactactag caacataaac aagaatgtag 54480
aagtcaaatc taagaattac cattctatcc taacaccatc aaatctaaaa aaaactaaac 54540
tttacagcca atccaccaaa aaggtgagaa atttctatac acaaaccaaa gacaatgcat 54600
aaaacttgga tgggaattca acataaacca aaaccaagct aaacaaaaga attttttcag 54660
caacataaac aagaatgtag aattcaaatc taagaattac tattccatca taacatcatc 54720
aaatctcaaa agactaaact caagccaatc caccaaaaaa ggtgagaact ttcaatgcac 54780
aaaccaaaac taatataaga attcaacata aaccaaaacc aacttataaa aaagagaact 54840
tttagcaaaa aagatacata cttttgagtt catcaagcca acgagggatg ctatcaaaag 54900
ttgtccttct tgaaatatca taaacaacaa gagcaccaaa agcaccacga taataagcag 54960

```
aagtcacagc tctaaacctt tcttgtccag cagtatccca aatctgagct ttaacttctt  55020
ttccatcaat ttcaagagtt tgggtctgaa actcaactcc aatagttgct tttgaatgca  55080
aattaaactc atttcttgca taacgtgtaa gcaaattaga tttcccaact gcagaatcac  55140
caatgattac aatcttgaaa aggtactcct caccctcatc atctgaagag tccatttggt  55200
gaaaaattga aacttttta tgtttagaga gagaaagaat tggaaaatgg tgatctagag  55260
agagaggggg aaaggagtgt tggggttttg tgcaaagaag taatggtggc agagctggca  55320
aagattatac agagaatttg aaagaagtgg tcttgctgga tttttatttt ttgttatttt  55380
gtttttatt gtttttttaa taaaataaaa tcataagtgg gtgttctttt ttaggtaaat  55440
aaaaaggaat atataataat tatataacct tttgtttgaa aagaaaacag gcggttgaag  55500
acttggagtc taatagtttt tttattaaaa aaataacttt ttatgataac cttttgcctt  55560
tttccttctt tttattggtg taatccttgt gatatatatg atttaacata tttaaattat  55620
tcaatataag aaattatgtg ttcatagttt ttttaggtaa gaaatatgtt aactttgagc  55680
tatttttaga agtacattat gtactcacaa attaaaaaaa tttcgttttg actataaatt  55740
ttaggagtat tcacttttat ttacaaaata catatctaaa catatcttta catttcaaac  55800
agtactattt ttcaacataa cttcaaaagt tttttttttt ctttcaattt atggctaaac  55860
gttagcaaag ttacaccaca agcttagtat aatacttggg ttattaaata tgatagaaca  55920
attaatagtt ctaaagattt gaatgaagaa aagagaaaaa aaaatggcat gtttcaagta  55980
attacaagtt aaattatata tattatcact ctcaaaaatt aaaattcgaa tatatcaata  56040
attgagagat caaaattgtt agtattggct atttcttttt ttaggggaac aataaaagtt  56100
tctcacattt gcatagaaaa agactccata tgatgtgaga aagacttaac ttcgaattgc  56160
cagtggggtg ggggtggggt gttgtacaag aagtgatggc aaagctggca aagataggta  56220
cagataattt tgttaagaag tggtgttgct ggattttatt aattttcctt ttctaggatg  56280
attttataaa tggaagaata atagtcaatt tgttctattg tcttaagcag aatatttttg  56340
caagactaat ggtaaaagta cacaccatcc tgcttttttt ggataattaa acggtaaatt  56400
gtttaattct tatgtgaatt tgaacatcaa tttctcttta taaaaaaatt caagctaata  56460
taaagtgcat gaaattagtt cttgagtcgg ttatgattaa aactcatgga ggaccacatt  56520
gactcaataa ttgagaaatg attgtaaaaa atcacatgga ccatgttttt catggacatc  56580
cactccctat aatatgataa tattgtcatt acattttcaa tgaatgatcc aaacaaaaaa  56640
ataagatatt gttcaagaag tgaatatatt tttccactat ggctacaaga attaccatca  56700
attttgaaga aataaaggat ttaaatacca cttcatccaa cacactacat ttgttgaaag  56760
gaaaaaaagg actattaaga gaacttatgt tgctcgaact attaaaaata tcaacgggtg  56820
caagtcagat cttccatgtg cattttttaa agaagcttat acgagatacg acggtctttt  56880
tggatagtcc tgacatgaaa attgaatctt gatccaaaca aaagagacaa gatataattc  56940
aagaattcaa cataaattac aaccaataca atcttgaaca aatgaaggaa atgaacaact  57000
aatataactt caatcaacac acatcacatt tcaaatgaaa acaaagacta aaacaacttg  57060
aaatcataac atttataaga aaactaatga atattgtact agtttatagg ctaattttga  57120
tgaagcatat aagatgtaac tctgtttact catttagaac accattgcct tgacctttca  57180
aatccattct ttccaagttg ataatcttga taagcctgca taatctcact cttagtgttc  57240
ataacaaatg gaccatactg cacgacaggc tcgttaatcg gttgccctcc tatcagaaca  57300
aacctcaatg gttttgaaga tttgttccac acacttaggc cttcaccagg gcctaaaacc  57360
```

```
aagcaatggt gagctggtgt agtagttgaa tccgaagaac caaacgcctc ttctccttca  57420
actatgtaga tgaaggcatt ccaggtctcg gggatctgtt ggtgatggtc agaacctggt  57480
tttagggtga agtcaaggta cattgtaggc gttcgtgtga aaacttggga ttttatgccc  57540
atggattccc ctgctaaaat agtaaccgaa acgccatctt tttccacttt tggtatatct  57600
tggtgtagca attcttgata ccttggctca atcctgcatc atggacggat aaaaggaggg  57660
aagttacaaa aacggggcaa tgaaggctcg tgaagtagac aacaagcagc aagacaagga  57720
tcattagttg ttgtgtctat tgcatggtgt agcctcacac attgaaggct ggttagttga  57780
acaccctttg tcgactcgta gagtcaaacc atactttaat acatatatat tagatcttaa  57840
acgcctaaat tttatgaatt ttgatcaaag tacatgtaac aggaatatgt tctaaaatga  57900
aatagattgt tcaaacacta tatttttta agccaaagtc aagattgaat caatgtaact  57960
tacattttgt ccttggaaga tagatttatc caaagttgca accccttatg agtacctggt  58020
ccagcaggca tttctgaatg aactatacct cttcctgctg tcatccactg cattaaacca  58080
aatggaaaat cataaacaca cttaaatttc ataaattcga tatccggtcg catcatgaag  58140
tccactttag gaggtaacac actccttttc aaatgtgact acatttacaa gccttgaact  58200
cgagacctct aattaaggac gaaataatac ttactattct accaccatga attttgatgg  58260
taaacattaa ttggttacat tagtaaaatg agtagctaac aatctatcac atgttatata  58320
acgctgatac tattaaaaat ctttacactg tcagtgcaca taacttaaat acttaagagg  58380
tatatatggt ggtgttgtta gcaaacacat tacctgcaca tcaccagtcc tgattgtacc  58440
cttgcgacca gcaaaatctt gatgagtaaa agctccctaa aattaaacac cacaaaatta  58500
cattagaatt ttcaatctcc ataatccata caccaacaca gagtttaact tatatacatc  58560
accaatacct gatagtatat atcaattttt tttgtcgatg tacaaaagtt aaactttcta  58620
cccaaaaaaa ggaaaataaa atgaattttt acctgcaaca tataagtgac ggtctcaaaa  58680
cctctgtgtg gatggtcagg aaatccagca ggtggtgaaa ctgcaagaag ccaaaaataa  58740
catagctttc taattagtca aaaataaaaa taaaattcac aaaataatat actaaaagaa  58800
taaaataaaa gaaaaaatta ccattaaact catctaacat gaggaatgga tcaagattct  58860
gcaattcagg cctgatcaaa ttccaaattt cataacaaat atatataaaa aaaaaacaat  58920
cagtattcga ttcgtattgc tgacaaaagt atgatattta attggagaag agtaaaaacg  58980
tcgttagaga tttctcgatt atcaaaacat aaaaaatcaa gaaaaaggaa ggaagtaccc  59040
aaaaataatt accttccaat gcttcttcta acaatagcac catcaccttc attttgagct  59100
ctagccaaaa ctttcttaac aaccaatctt ggtctactaa aaatagagga catagacatt  59160
ttgatgtttt taatgtttgt ttcagctaaa tttatttttt gtttgttgtg ttttcttttg  59220
attgtgctaa tgtggctatt tataggcaat ttattcttga ggattcatat tcattgaata  59280
ttgatgacga aatatattac atattatttt cgtgtgttga atagaagttt caagtggggc  59340
ctacttaatt ttttttttg atgatttcat gctgatgtta ttatgacgtg gtttcttatt  59400
aaaaaaatta tttggataaa aaatgaggaa tatactatcg tatgaatttg tagagttaat  59460
tgactaaaaa gaaaaataag ttaaaagaat aaataagata aatactagaa ttattagata  59520
ttaaagaatt caaaataata ttaaatatgc atgaattata gattgaataa ctaaaatgga  59580
aaataagtta aaagaataaa taagatacta gaattattgg atattaaaga gttcaaagaa  59640
tactaaaact atcatactta ggatttgaac ttttgacgta aaataatctt ttgactcatt  59700
```

-continued

```
ttgttgtaat actaaaagta tcttttgata taaaaaaaga ttctaccatt tatatgtaat  59760
cgaagcatat attatggagt agttttttta atgaggaatt caataatata tacctagttc  59820
ctctaatttc atgagttaac tcttaaatat ttaaggattc aaattaatac taaaaatgtc  59880
atacttatga tttgaagttt tgacgtaaaa atctcataaa aggtagaagg taaattttaa  59940
gtaccattta tacgtaacaa aatgaaactt cttttggcaa gaaattcaat tatatatctt  60000
gccaactacc tttcctttgt gatttcacaa gttaccaata aaaattgtga ttgaatcaat  60060
agaatttcct cattttaaaa agttttaaat ttaaagtcaa tatatatata aaagaattac  60120
attaaaaatt aaattgtttt ccttaaataa ctttacgtga tataaattca aaaattaatt  60180
aaataaaatt ttatataaat atgaaacatt aggtggagga ggatgttact tttgaattga  60240
atgtttatac ataattattt aagaaagaaa catctagcaa cttcaaaaat caaaagagaa  60300
acaatgtttg gtagttgtcg gcatgtaaac tttgtttatt tttgctgcct ttgattcgtt  60360
gaccgttgac gtgaccaata tctattcaaa aattataaaa ataataatat tataaatttt  60420
tattttttta tatatgataa aaaaatatac atcgtaaaac gttaataaaa gtttttatca  60480
tttgtctcta aaatagaaaa ccataacaac taaaagaaac gaaaaaaataa tattgaataa  60540
tatacaattt atttattttt attgatgtac aaaaattaaa atgttcactg atccaaaaaa  60600
gattcaaaaa aaattgtatt tgatttagta ataataagac aaatcatttg ttcataaata  60660
ctttatactc atcccgtgtt agaagcaaaa cttaattcat gaacttaaga atcacaattt  60720
atgttttaca tattattttc attgtatttg atttacaaga tattttataa cttttatttt  60780
atagataaaa atttattaaa aattttagaa caacttatgt ccgtggacaa tatttaacac  60840
catgtccttg ttctaattta taattctctt tcagtttgca aatcttaact ttaactaaat  60900
ttaaattttt aatcgataga aaatactagt cataaaagga taaaaatatc tttacccata  60960
catatagatg tataatgaag ataagtgtta aaagagattt tttgattgaa ataattcatt  61020
atttaatatt ttattgtaaa aaaagtcact aaaaataagt acgaaaataa ctttaataaa  61080
aacaatttga agaaaatttt cattatttgt taaccttcat gccctatcaa acaatacaaa  61140
aagactatgt tttcttttaa tttttcattt ttttacacat ctaatataaa catcctttca  61200
atagcgtata gacattattt cattcttcaa caaataaaca ctatcaacta acaaataaac  61260
gtataaaacg ttaccagtaa taacaaattc aaaactcatt actctcatct cgactttaat  61320
gtaagttaaa taaatttaag atcagactct aaaaccgtta caattccaaa aaaaactaaa  61380
aaatgataaa atatccacaa aatacttatg gtgggtccca acttaaaaac ttttaattac  61440
ttatgtccca ctagcctttg acttaaaaaa atctcaaata attgaatcaa caatcccaaa  61500
aaaatcccaa aaaattctct aaaccaaata tttcaatggc gaaaaaagca gtgttaattg  61560
gaatcaatta tccaggaaca aaagcagaac ttagaggttg tattaacgat gttaatcgaa  61620
tgtacaattg tttacttaat cgtttcggat ttgctgagga agacattact gttcttatag  61680
atactgatga ttcttacaca caaccaacag gacggaatat acgtaaagct ttatcggatc  61740
ttgttggatc tgctgaatca ggggattgtt tgtttgtgca ttatagtgga catgggacta  61800
ggttacctgc tgaaacgggt gaagaagatg atactggttt tgacgagtgt attgttcctt  61860
gtgatatgaa tcttattaca ggtaattcta catttttttt atttaaagca cttttttttta  61920
aggatttgga gtaggggaaa tggggcgggg attatgaagt ggggaattgg aaattcaggt  61980
agctggtgag ctactgagat tgtacttgat ctatatgatg ggtttgttcc aagattgttt  62040
ttttttcttt tgtgtttgtt gaatttgttg gggagttagt tggtttgatc taaatgatgg  62100
```

gtttgttcca aaaattgttt ttttttgtgt ggtatgcatt ttaatgcagc tatttgagca 62160
tttctttgat caaaattagg aattgagtag tcaggtagct aatcaactga gctagtaaga 62220
gtgtacttga tctaaatcat gagtttgttc ccaaaaaaat gttgtttttt tttgtgtgtg 62280
tgttgaattt attggggtt aagttgtatt gctttgatct aaatcatggg tttgttccaa 62340
aatttggttt tttgtgttgt gggttgaatt ttataggtag ttacttgtat tgctttgatc 62400
taaatcatgg atttgctcca agatttgctt ttttggtgtt ctgtgttgag tactacttgt 62460
atgctttggt ctatagatca tgggtgtctt ccaaaatttg tttttttttt tgtgttgtgt 62520
catgtgtgtg tgatatgagt tttattgcag gtacttctat tgctttgatc taaattatgg 62580
atttgctcca aattttgctt tttgtttgtt ttggtttggg ggttgggggg tagagttgat 62640
gtggtaaggg atctaggaga ttgagatctt gaaatggttt tcttaaaaaa tgatcttgaa 62700
aggttgagtt gatctgtttt gatgataatt caggtggatt gaagatataa ggagatttgt 62760
aaaacgagga aatgggattt tagaaatgag aatttgggtt tctagagtaa ttcaaatagt 62820
tgaatggggg acgaggaaca gttggaaaaa aagagggagt atagtttaca gcattgtgat 62880
atgaatctca tttacaggaa cttaactatt tccttgagct taatcatggg ttgttccaaa 62940
atttgttttt tttcttcgtg tgtgtgattt gtagattggt atgagattga gatcatcata 63000
tagaatattg tgtaaaaaag gatcttgaaa gtgcttagtt gatctgtttt gatgattatt 63060
gagacggatc ccgagtttta gggagatttg tgaaatgggg aaccaggatt tagaaatgag 63120
aatttggaac cagagctatt aaaattgttg aatgggagat cagaaaaagt tggcaaaaaa 63180
gaggagaata gtcatgatcc cacaagtggg gtcttgaaag ggtaggatgt acgcaaacct 63240
tacccttgat ttccgacact cggctataga atttattacc tcttggtttt ataatattgg 63300
aaaagtaaca ggcaatttaa tattgaactg ttggacgtgt tgtttcatcc ttgatcagat 63360
gatgatttta gagagctcgt tgacaaagtt cctgaaggtt gccggatcac aattgtatct 63420
gactcatgcc acagtggagg cctcattgac aaagctaaag agcagatagg ggagagccac 63480
aagcaaggtg atgacgatga aggccatgga tctggttttg gattcaagaa tttcttacgt 63540
cgaaatgttg aagatgcatt tgaatcccgg ggtatccaca ttccacgtcg ccaccatcgc 63600
cgtgaggaag aagaggagaa ctttgctgag agtagtgtga ttgagacgga agacggtgat 63660
caagttcatg tgaagagcaa gtccttacct ctttccactc tcatcgagat acttaagcag 63720
aaaaccggta aggatgacat tgatgttggg aaacttaggc caacactctt tgacgtcttt 63780
ggtgaagatg caagtcctaa ggtgaagaag ttcatgaagg tcatttttaa caagctacaa 63840
aagaataacg agcagggtgg aggtggtggg ttcatgggta tggttggtaa cttggctcaa 63900
gagtttctga aacagaaact tgatgaaaat gatgagagct atgcgaaacc ggccatggaa 63960
acacacgttg aaggtaagca ggaagtttat gccggttcag gtaatagagg tcttccagac 64020
agtggcattc tcgtcagtgg gtgccaaaca gaccaaacat ctgcagatgc caccccctgca 64080
ggcggagatt cttatggtgc tctaagcaac gcaattcagg aaatcctagc tgaatcagat 64140
ggtccagtca ccaatgagga acttgttagc aaggctagga aaaagatgca gaaacaaggc 64200
ttcacacaac gtccaggcct ctactgcgat gatcatcacg ttgatgctcc ttttgtttgt 64260
tgattctgct gtgctatgcc ttctcgagta gctgttgaaa atacgactgt gaagttaacg 64320
aggtgttata taactacatc cttttgtgta tttgtgtgat tgtttgtgct tatgttggag 64380
tagctcttct actctggtgt tgcagaagaa ccattctcca tcatgtgaat gtgtatttgg 64440

```
ctctgttttt ttttcctttt aaatttggtc agagaataag gtattaaaga accacagttt  64500
tcggtattgt tttggatatt tgaaagttta atctggagaa cttgtcttgt atactgaata  64560
tactgaatgt gttataattt aatgcaactg aatgtataaa tttcttatca tgtgccatca  64620
taagaattga cctttgtctt gtgaaactag ggaacagaac gaaaggagga gctgaatttc  64680
aaaattttgg tttacataag aaaatattca cctgaattgc actttcatat tacatcttgg  64740
atatatatag taatcaagta caacaaattc ttgcacgcat aacacaatat cgcaatgcat  64800
gtaaacaata ttactcgcgc tagaactcag atatggttat ttaaatttca aagagatttc  64860
actcattcga taacagtcat tcttcaaatt ttacttgtac aagtttcaaa gatatatatc  64920
aataactcca gttgtgtcca tgactccatt ccaaagcttt atccacttgg aaaagtagaa  64980
gtaccaaact aaagcaacaa aattagctaa gccgcgatct acttatgttc cttctttggt  65040
tcaatatcac ttggatttgg gactggttga attctttggt aaggtttcct tgtcaatgtt  65100
tcacccttca gagctgcaac atatctgtca tttgtgttct cctttctctg cagttcgcca  65160
aggtactcag ccaacctctc tttattaact ttacccatca tctgttacaa aaatcaaaac  65220
aatgtatgtt taggaattca acaatcgtaa gtcaaagtac taagctataa aagaaagcca  65280
atgaaaccag aagaaaccac tgtgagtcca tttttttat ctactgtaaa gctttatcta  65340
cttagctctt cataaaaaaa agcaaagtcg atgttctttc aaacagcaaa tgactgaaca  65400
agatagagaa gtgaacatta tagctatttg tagttcccat agacagcagg tggccgattt  65460
catcaaaggt gtaaaccaaa gttacgtgga agtgctcaca actctgtttt agtttttaac  65520
aaagacaaga cataaatggg tatattcaaa tgctgtgttc atcttcacct acaatatatc  65580
attcaaaacc aaactagaaa aagagaaggg ccatttgtaa tatgaaagaa aagggtctga  65640
aattaagctt tattctcact aaaatagtcc tgctcggcag tcaagccact tcactcaata  65700
gaggttcttt ggggacttaa agaacttagt tgtccttcct ttccaattta caagttccaa  65760
aaatacaagc tggaattgtt atccttatct atctatttgc cttctcaaca attctctgct  65820
cttgccaaca ttccgatgct ccatttactc accctggcat ggtccaagca cccaaaggca  65880
agccaaggta gatagtgatg gattcttcca ccttacggcc caaaatgctg gtagaatctg  65940
tacgttaaaa ggtaataaca ttcgagtcgt ttacagctta acatgcacaa gtcaatatat  66000
ttaacccatg ctctcaagta gctttagcaa gaaaggccag ctaacatggt catatgcctt  66060
gaagtctaat ttgcacattg ccccagcatc agtaaacttt atcttggact ccaactctct  66120
aagctcatat tagctactag cactcccaca aagaaaaagg attttgtgat ttagatacca  66180
atttgtctat tattgccctc aaccttccat tgaggatttt ggcaataatc ttgtaactat  66240
tgccaaatag aatagaggtc aaaagactct aatcaacacc ctttcctctt cagggattat  66300
agcaataaaa atcacattta ggcttctatc tagtttctcc accttaagaa aatacttgaa  66360
gctggtcttt gaatcttcct taatgattgg tcaagaaaaa aatgataggt caacatattc  66420
aacaaaaagc ccttggtgaa actattgaat tccagagact tcgtttcgta cactgcttag  66480
atagcaagcc atacattttc tcagtgaaag gtctttcaac tcagtcctct tctgctccac  66540
ttataatgta ttccccagtt cctcaacata ccattcatgc cttcacttct ttgtctctct  66600
gaacaaattc ttgtagaatt tcaggatcaa cattttaata tttgttttga ctacaactta  66660
gaaaatacac ctgacaatct aatatcttaa actccctgat ctgtcatatg gtgtctcata  66720
aaacatacag aggaacctat caataaataa ataaatatag aggaggtgtt ccaaccaaat  66780
tctcagaagt aattcaattc ctttacactc ttcgttctct atctaccaag actagctatc  66840
```

gattgctatt ttctataagt taaatatcaa tcactttatc tacactaaaa aataaagctc 66900
caaacatcat tttcttttta aaggtaacaa gtacatcaaa caacaagaaa cattatcaaa 66960
tgatactgcc aggttacctt tcattttcat agatcaaaaa gcacaatcat cacagcagaa 67020
tgtacaatag acatgaggtg catactgatc tcgccatatg aaagtttgct ccagatatac 67080
cattactatt aacagagcat ctttcaaagg cctttgctta gctaactgtt atgaaagatg 67140
ttctggtaat aacagtcagc taggcaaagg cgaaagggag tacaatacag aataagaacc 67200
aacaacacaa atcaatatgc gtacaatcat aacagcagaa gctacaacac atatgaatca 67260
ataagcatct ggtaaaaaca attctactag gtgaggggac tctaaaacac attagaaaat 67320
gataacaaca aggcaattct tggtataatc atcacagcag aatgtacaac acatgtgaaa 67380
cagatacact catcctacca gattgaagat gctcctgcaa taacactcag ctaagtagca 67440
gccaaaggaa gtcaaagcaa agaatgattt ttctttcctt cgaggctcca gggtaaagat 67500 acattttttta cgaaaaattg ttaaaaaaat tcagtttatg ttagcaaaaa ccatgttccc 67560
ttctttttct gatattttta taatggatta gtttaatgaa taacaacgaa tcaactgatt 67620
gatggtctat ctcttttaga ctatagttaa tggatattct taaatcataa ttgtaattat 67680
atagactatg attccatacc agaaattttt taaacaatac acaataagaa ccaataatac 67740
caagtcaatt tacgtataat cataactgta gaagctacat cacatacgaa tcagttattc 67800
atctggtaat aacaatacta ctagaaaaga agactctaat acacattagg aaatattaat 67860
gacagcagaa tttccatcca atcattaaac cacaatatac aacacatata aagcagatac 67920
tcatccgtcc ataacagtta gctaggcaaa aacaaaggcc aaacggagta caacacacaa 67980
taagccaagt aaatttacat acaaccaaaa ctgcagaagc tacaacactt atgaatcaga 68040
tactcatctg gtaataacaa tactacttgg tgaagggact ctatgttaat atcaaagcaa 68100
tttcacgtag cagaagctac aatacttatg aatcagatac ttatttggca attacaatac 68160
tattaggcga ttgataatcc taagcaattt cccgtataaa acagcagaag gtacaacata 68220
catgagcaca aactgatcta gttttagcaa tatgagtatt cgaaggggaa gtgaacatac 68280
tagggtttcg gggcgagcgt tcttccggag tttggcttca agttcaggac tgcgagtatt 68340
ggtggctgac ataacgcaga aaccaataat ccccggaatg acgccgcaaa cggtggcgaa 68400
tccgatgaag aacggcttcg attccttcgt tctcctcact aaccaccgcc atgttccact 68460
cttctcccac agaatcgaca tcgacttttc tgatgattct ctcaacactt ttcttctgct 68520
attttctaga gtagaacagt gcaagggaga aataaaaatg acaaaaatgg ctccttatat 68580
ttgcggaaca ttcaaaatag tccttaagta tgaattgatt gacaaaagtt aagatccaag 68640
tatatttagt aatttatatt ttatatttat aaataaattt gaaggaaata atgcaaaaaa 68700
gaaagatttt tgtaatttta aacatcaaga aatctttaaa aaaacaataa aaagaacaaa 68760
ctatatagag taaaaaatat caaaaattgc actttaaaaa aggtatataa ttttgatttc 68820
gatctatctt aagtggacta gaattgatat cttaataccg attctttggt ccaaagcgga 68880
cagctcagga gtgaaatgat tgtgtgtatt agttgaacca cgaaccaact acccatagaa 68940
gaaaattatg ttctaaaaag gatggttttt ttttaataaa aagagaattc tttgaactag 69000
tttgcctaca attttacact catttgttag tacatttcat tgttagtgaa tctcctatat 69060
ggctttatac caaaggaaac agagaagaat ctgtccaaac tttggaaaat attgcatctc 69120
cagcaacaag aagcagtaaa tttaaccttg agctttttcg gatcgttcat cgaattagaa 69180

-continued

```
aatcaagaac tactcaacaa caacaacaac atggttgatg tgtattgagc tatcaagatg  69240
ttaatggaga gaaattggtc aaaagtataa agctgcataa aaacaagaaa tcagtgacag  69300
accaactgat atatatttgt ctccaatcat acataaaaag agtttatcaa tgaaaacaaa  69360
catagaaaat agtagtagtg ttacaataaa agagaaatgg gctagacttc agtatgagca  69420
tggctgcaac aattagctat taaaacctca ctaatctgac tattctttga cgaggtgtat  69480
acgattacat ccttcaatct cttcgatctc ttccttaatt ctcacagctg aatcctccag  69540
agattctttc caggacccaa tcaatttaat ctgtttcaat gatggattat cagcaaagct  69600
aagtgggatc tcctctaggt caccacactt ttttataaca agtgtttcaa gcaagggaaa  69660
tgattcctcc gaggcatccc accttgagat acctaactgc accaatttca acaacttaag  69720
tttatgaaac ctgatatctc caaggcacca ctcttctgat tgaggaaaac acacgtcctg  69780
taattggaga tactccaggc ttggtagttc cgcaatgaag gaaatagcac tttcaatatg  69840
aattccttta agtaccagct tgtttaaatt tgaaggcacc tgtaacccgg atagaatgcg  69900
gggatgcaca aaggaaagtt gaagttcttg aagctgggta agattctcca atttgggaca  69960
aaaaggctct gcagaatctt catcatcctc aagtgtgatt tgaagttgtt gaagattagg  70020
acacctcttt gataacacat ccagactatc aatcggaaat ccaacaattt tctttaatat  70080
cctcaaattt tctaatttag aggatccttc aaagagcccc tgcttatcaa aaactgccca  70140
accaaaatga gcatgcctta atttttccat ttccaaaaaa gacactggta accgtacacc  70200
ataaggaaaa ttcctcacaa ttaaagtttc tatatggggc agatgtgttc ctggatcaaa  70260
atagaattta tctgcccaaa ctgcgaggta cttcagctga tttagtggtt tgaatgtagc  70320
aaacgacaaa aactccacag tataagaaat caaatccaag actttaagaa gtcgcaattc  70380
agtaatctga cagaagggaa tcacatcaat agattctcca ccattagccg ttatcagaga  70440
cctcaagtgt tggtggaaag gcttctgtgt tttggaaacc agagatgcaa acttggaaag  70500
ctcttcactg aaactgaagc tcactcgact tcccttccaa tccaacggtt gaaactggat  70560
atattgaccc ttcactgcaa gcataaactt ttcttctcta ctcttcttca agcaaaagtg  70620
atgcacaaca tcatgaacct ggcagcattt gactttacca ttataacctt tctttgaaac  70680
aattaccacg ttactgctaa tgagatccat caagtaacct tcagcttcct cttccattaa  70740
tctcccagat tcagtgttct ccacgaatcc ttcagcaatc cataaactta tcaatttaga  70800
tgctggaatt cttgcgtcct ccgaaaacat ccccatataa agaagacaag gctttaaaca  70860
atcgggtaag ttatcaaaac tcaactgcat agtcgccaga ctatattctt cgaactcact  70920
gtcaagatag tcaaataaag catctttcac ctcattccac caagattctt ccattttcct  70980
tttttgatt attccagcta ccaagacaac cactaggggg agtcctttgc atttttctgc  71040
aactgcttga ctcacatatt gtagttcagg cgggcaatct tccttttgaa acactttttt  71100
ctgcaacaat tggcaactct cttctgttgt gaggaatgga agagaataag gatcagtatg  71160
gtacttgact tgcttaccca cttcttcaag tcgagttgtt acgactattc tgcttctcat  71220
tccaacatct ggaaaagaaa gccttaagtc atcccatgcc atacaatccc acatatcatc  71280
caatacaatg agatatctct ttcccattaa ttttctcctc aacatgtcgg caagaacgtc  71340
aaccgtatct tccttgtgtt tggaacctgt aacttgacta aaaatatctt gtaatagctc  71400
tctccgatta tatgtttgag aaatgatgca ccatgctcga acatcaaagc gagaaacaat  71460
gatgtcatta ttgtacagct ttctagcaat tgtcgttttc ccttgtcccc ccatgcctac  71520
aattgggacg acgtctagct catttgtacc tctaatcaga taatcaatta gttcttctgc  71580
```

-continued

```
tttattctca aaaccgacta cctcctcatc agtcacagga ttgctatgtc gagctggcag  71640
atgtttaaat ggagcagcca cgtagtgagg attaaaagga atgtccgctg accacatctc  71700
agtcacctct gcattaattt gcttgatctc ttttaaaatt gtaggaagtg agcaaaaaat  71760
atgcaaaaaa gcattatact gagcaagaat agaatcaacg gcaacctcag cctcatatgc  71820
caaattgatg gtacgtctct gaagatcttt aggaatttta tgttcgtggt gcacgatatc  71880
tctgaaaatg gatgatagct ccttctctaa aatggatgta agagatgata actctttctc  71940
caaattccct aaaagaggtt tcatcaagaa atctaaacca gacttagatt tcgacatctc  72000
attcagtttc tttaaaagag aatccagaaa gctcaatcca ccaaaggtgg ggaattgaga  72060
tggagtaaat tttaaggatt tgtagtacgt ctcaacttgt gccttcagat ctttagtctt  72120
ctccaatatc tgtatcgagc aaagacttat tttgctagtg tcatctttgt ttatagatct  72180
aggaacaagc ttttgaatta catatagaac atcacccgct atagctccaa cctttaacaa  72240
gacctcattc aaccagttac cattaataac gtgatttgac acatcagcat caaggaaaac  72300
caacaagaat tctattgcca catcaatatt ttgagcagag atattattag gaaagttctc  72360
gagtttttg tttctgagat acatcaacag attgcagaga tgatgtgaaa attcttttgg  72420
taatttcttg tccttaaaag tttttgattg agtaaacttt gaagccatta gttcaccatg  72480
aaaaatcttc ttcatttcca actccgcaaa cacaatcaat gataatagat aaggaggttt  72540
actaaagatg tcattttctt cattaacttc acgttcagta acataatcta atacggccaa  72600
acaatattgt cttacattgt tagtcatgaa ctgaattcga gtctccaaac attccagctt  72660
ctcatagtcg acataaccat ttatctctgt ggcatatatg tatttcaaaa atctcatttt  72720
cttttgaaca attttcagtt cctttataga tcgatgtatt gcaagttttt ttttggaatg  72780
gcaggaccta cccttttgca agaacatcat cagtacatca tttagaattt tttccagaca  72840
atccatatat ttcgacagat caaaatcatt caactcataa ttgtaactta aactggtatt  72900
accttgaaag aattccaaca aatgtgattc tagcctttcc agattaaggt tagttttaca  72960
ttcatctgga atcctatgca atacccggtg aagtatttcc ccagtcaatt tggcactctt  73020
tgtgagttcc accaaggaat caggcaaaag aacatcatga tactttataa aggttctaaa  73080
aactcttagc accatttcaa gttccttaat tcgcaatatc tcgaaccaat ccagattacc  73140
tccactcttg atccttctca ggtggtctaa catttcctca atttcatttt cagccatttc  73200
tgtagaaaaa ttcctgcaag ttcaccaact tttggaatta ggttcttgaa gccatcttaa  73260
tgcttttgaa aagttataaa tatttacaat tttacatctt atttaccctt ttcgtattgt  73320
catttaacta acaattatta tcgcataaaa tcgtcttttt tcttgttgtc atttatgaga  73380
tagtaactat tagttgagtg gaccatttga gaaatcaact ctctaattat gtatctatgg  73440
gaaaaagatg acttaccgtt agttaacaag tatcttcaat ttctgatcca atcataaaag  73500
ggagcaatag agaaaaacaa acattataag gtaaaccaga gagtaataat tctcagattt  73560
ggattccaac aaagatatat ttccaagttt acataatagg tgaaacaaga aaaaatttat  73620
tgaaataaaa tggatgaagg tttgaaggaa gaaggaagag tcttcttctc tctctataat  73680
atttcttata cctaacaaga gatgaattaa gtcggtagct gtaaagtgac tcaataatac  73740
acccatatta tttgtctttt tctttagggg ttgtttggtt ggagcaagtt atttcgggat  73800
taattatcgc gaaataagtt acttgatcat gtatatgtga tcataattta tatattccat  73860
cactatgata tgggatacat aatcggagga ctaccaaata tggctccaac caaacacaag  73920
```

-continued

```
ataaaataat tctgcatttt atcccaaaat tattatatct catacttcac accaaatgac  73980
tctttaggaa aatcccccaa aattttattt ggtttggcag tttcatagtt aaattatgca  74040
cttatatgat atttgcttag catataatta aggaatttta tggttgggta ttgggtcgga  74100
catgaagtta tattttttct aataaatatg aaaatgcaca agttgtgaaa actttgaaat  74160
tcaattctta tgcaatttta ccaaatgagt aaatcatttc gttaacaaga tatcataata  74220
tctaaagcat cgcatcgatg aattatatat ctttatgttt cttttaactt tcaaatgtac  74280
ataaacttat aaagatccac tagtcaacaa tagtagtaat tagtaattct ttcacatgat  74340
acgacggaca atttattcac gtcgaacatg agtttatttt tgtaaaactg aaaataatga  74400
tttgttcttt tttacaaaat ataaacttat gaataagttt ttatattttt ttaaaaaaac  74460
ataattcaaa aaaggataaa tcatatgtca taaatcaaac aaggataaaa aaggagtggt  74520
gataattctt ccatagatct tgtgaatgga gtctgttctc agaacagggc caatcataat  74580
acaaaagatt gatttttttg gttcttaagg gtcaaatgcc cttatttatt catttcatgt  74640
cgtactatat acattttttt gtttccaccc aatgtccggt acccacattg gagcccgata  74700
caatggattc acgacgtaat aaagtcccac attgggggtg aaacgctccc taacatagac  74760
gactctgtat tcggagggga ctcgaatgtc atactatatt tttactatat cttaagttca  74820
tatgttgcaa agttcaaatg atcgatgaat gacaagaaca aatttattag cttcattctg  74880
tatgaatttc aacttctaaa agaggcacct gaacacataa taaagagatc cttcaacatt  74940
gcacctacag caacaagaag cagtttaacc ttaaaatttt tcggatgttc atcgaattag  75000
aaaatcaaga agtactcaac aacaacaaca acaacaacat ggttgatgtg tattgagcta  75060
tgaagatgta agtggagaga aattggtcaa aattataaag ctgcataaaa acacgaaatt  75120
agtgaaagac gatctgatgt atatttgtct ccaatcatat catacataaa aaagagttga  75180
tcaatcaaaa caaacatagc aaacactact agtgttacaa taacagaatg agctagcaac  75240
aaaatagact tcagtattct ttgacaaggt ctatacggtc acatctttca atctcttcga  75300
cttcttctta cgaggtctat acggtcacat ccttcaatct cttcgacttc ttccttaatt  75360
ctcacagctg aagcctccat agatactttc caagacccaa tcaacttaat ctgtttcaat  75420
gatggaatat cagcaaagct aagtgggatc tcctcaaggt catcacactt ttttataaca  75480
agtgtttcaa gcaagggaaa tgattcctcc gaggcatccc actttgagat atttaactgc  75540
accagtttca acaacttaag tttatggaac gtgatatctc caaggcacca ctcttctgat  75600
tgaggaaaac acacatctag taattggaga tactccaggc ttggtagttc cgcaatgaag  75660
gaaatagcac tttccatatg aattccttta agtaccaatt tgtttaaatt tgaaggcaac  75720
tgtaacccgg atagaatgcg gggatgcaca aaggaaagtt gaagttcttg aagctgggta  75780
agactctcca atttgggaca aaaaggctct acatcatcct caaatgtgat ttgaagttgt  75840
tgaagattag gacacctcct tgataacaca tccagcctat caattggaaa ttcctcaatt  75900
ttctttaata tcctcaaatt ttccaattta gaggatcctt caaagagtcc ctgcatagca  75960
aaaccagcgc cagcaaaatg aacatgcctt aatttttcca tttcccaaaa agacactggt  76020
aaccgtacac cataaaaaca actcgtcaca attaaagttt ctatatgggg cagatgtgat  76080
tgtggatcaa aatagaaagt acctgcccaa actgcgaggt acttcagctg attaagtggg  76140
tttaatctag ctaaccacaa agactccaca taataagaac tcaaatccaa gaccttaaga  76200
agtcgcaatt cattaatctg acagacggga atcacatcaa tagattctcc accattagcc  76260
gttatcagag acctcaagtg ttggtggaaa ggcttctgtg ttttggaaac cagagatgca  76320
```

aacttggaaa gctcttcact gaaactgaag ctcactcgac ttcccttcca atccaacggt 76380
tgaaactgga tatattgacc cttcactgca agcataaact tttcttctct actcttcttc 76440
aagcaaaagt gatgcacaac atcatgaacc tggcagcatt tgactttacc attataacct 76500
ttctttgaaa caattaccac gttactgcta atgagatcca tcaagtaacc ttcagcttcc 76560
tcttccatta atctcccaga ttcagtgttc tccacgaatc cttcagcaat ccataagctt 76620
atcaatttag acactggaat tcttgcgtcc tccagaaaca tccccatata aagaagacaa 76680
ggctttaaac aatcagctag gttatcaaaa ctcaactgca tagtcgctag actgtattct 76740
tcgaactcac tgtcaagata gtcaaataaa gcatctttca cctcattcca ccaagattct 76800
tccattttcc ttttttgat tattccagct accaagacaa ccactagggg cagtcctttg 76860
catttttctg caactgcttg actcacatat tgtagttcag gcgggcaatc ttccttttga 76920
aacacttttt tctgcagcaa ttggcaactc tcttttgttg tgaggaatgg aagagaataa 76980
ggatcagtat ggttcttgac ttgcttaccc acttcttcaa gtcgagttgt tacgactatt 77040
ctacttctga ttccatcatc tggaaaagaa agccttaagt catcccatac catacaatcc 77100
cacatatcat ccaatacaat gagatatctc tttcccatta ggcttttcct caacctgtca 77160
gcaagtttgc ctacctcatc ttccttgtcc ttggagcccg taacttgact gaaaatctct 77220
tgtaatagct ctcttcggct atatgtttga gaaatgatgc accatgctcg aacattaaag 77280
cgagaaacaa tgatgtcatt attgtacaac tttctagcaa ttgtcgtttt cccttgtccc 77340
cccatgccta caattgggat gacgtctagc tcatttgtac ctctaatcag ataaccaatt 77400
agtttttctg ctttattctc aaaacccact acctcctcat cagtcacaag attgctatgt 77460
cgagctggca gatgtttaaa tggagcagcc acgtagcgag gattaagagg aatgtttgct 77520
gaccacatct cagtcacctc tgcattaatt tgcttgatct cttttaaaat tgtaggaagt 77580
gagcaaaaaa tatgcaaaaa agcattatac tgagcaagaa tagagtcaat ggcaacctca 77640
gcctcatatg ccaaattgat ggtacgtctc tgaagatctt taggaatttt atgttcgtgg 77700
tgcacgacat ctctgaaaat ggatgatagc tccttctcta aaatggatgt aagagatgat 77760
aactctttct ccaaattccc taaaagaggt ttcatcagga aatctaaacc agacttagat 77820
ttcgacatct cattcagttt ccttaaaaga gaatccagaa agctcaatcc accaaaggtg 77880
gggaactgag atggagtaaa ttttaaggat ttgtagtacg tctcaacttg tgccttcaga 77940
tctttagtct tctccaatat ctgtatcgag caaaaactta ttttgctagt gtcatctttg 78000
tttatagatc taggaagaag cttttgaatt acatatagaa tatcacccgc tatagctcca 78060
acctttaaca agacctcatt caaccagtta ccattaataa cgtgatttga cacatcagca 78120
tcaaggaaaa ccaacaagaa ttctattgcc acatcaatat tttgagcaga gatattatta 78180
ggaaagttct cgagtttttc gtttctgaga tacatcaaca gatattggag aagatctgaa 78240
aattcttttg gtaatttctt gtccttgaaa gtttttgatt gagtaaactt tgacaccttt 78300
agttcaccat gaaaaatctt cttcatttcc agctccacaa acacaatcaa tgataataga 78360
tacggaggta tattaaagat atcattatta tcactaaatt caatatcagc aacataatct 78420
aatacggcca aacaaaattg tcccacagtg ttagcaatga actgaattcg agtctccaaa 78480
cattccagct tctcatagtt gacgttacca tttatctctg tggtatatat gtatctcaaa 78540
aatatcattt tcttttgaac aattttcagt ttctttatag atagctgtat tgcaagtttt 78600
tctatgggat aacaggacct accctttcc aggaacatca ttagtacatc atttagaatt 78660

-continued

```
ttttccagac aatccatata tttcgacaga tcaaaatcat tcaactcata attgtaactt  78720
aaactggagt taccttcaaa gaattccaac aaatgtgatt ctagcctttc caaattaagg  78780
ttagttttac attcatctga tatcccatca aatacccggt gaagcatttc cacagtccat  78840
tcggcattca ttgtgagttt gacaaaacaa tcaggtaaaa gaacatgata ctttataaag  78900
gttctaaaaa ctcttagcac aatatcaaga tccccaatac gacgaatctt gaagaaatcc  78960
aggttacctt caattttgat ccttcttagg tgatctaaca tttcctcaat ttcattttca  79020
ttcatttttt gtagaaaaat tcctgcaagt tcaccaactc atggaattag gttcatgtct  79080
ttcaatatct agtgtttgaa gctatgttaa tgcttgtgaa aagttataca tcttatgtac  79140
cattttcata ttgtcaaatg tcacttaact aattattatc tgagaaaatc gtctttctta  79200
cattttcaat tttatgagat actaactaat agttgagtga accatttgag aaatcaactc  79260
tctaattctg tatctatggg aaaaaagtaa ttcatgaaga agatgactta cagttagttg  79320
acaagaatct tcaatttctc agatttggat tccaacaaag atatatttcc aagtttacgc  79380
aataggtgat ataagaaaaa aattcattga aataaaatga atggaagttt gaaggtttga  79440
aggaagagag ttcttctgtc tctctaataa ttcttatacc taacaagaga tgaattgtag  79500
tagcaagttg ctttaggtgg tagctgtaaa gtgcctcaat aatacaacta tattacttag  79560
tcctttttt aagggtcgtt tggtcgagaa taagttattt tgagagtaat tatctcacaa  79620
taagttattt aacatgtata tgaaataact tattccatca ctaaagtata aatattggga  79680
taaataatca aaggactatc tagtacctcc aatcaaatac ataataaaat aatcctatat  79740
tttattccaa aatttttata cctcatacct cacgccaaac gactccttag gaaaatcccc  79800
caaaattatg tccgatttgc taatttcata cttaaactat gaactatttt gatatttgtt  79860
tagcatataa ttaaggggta ttgggtcgga catgaagtta tttttctca taaatatgaa  79920
aattctcaag ttgtgaaaac tatcaaaagt tatctaattc ttaagcaatc ttaccgaatg  79980
agtaaatcat catttgtaaa taagatatca aaatattcta aagcatcgca ttgatgaatt  80040
acatattttc atgtttcttt tataaataaa tattcacgat tacaaacttt caaatgcaca  80100
taaatttata aagatccact agtcaataat aatagtaaca aataattact ctttaagtta  80160
atattttcac ttggcacgga caatccattc aaatagaata tgagtatttc tataaattta  80220
aaatgatgac tcctttttt atatatataa attattaact tatgagtcag atattattta  80280
atatttagaa aaaggcaagt tgtatcagca agttgattta ggtggtaggt gtaagattaa  80340
tgctgtctcc ttctttaaaa tagattgaaa ttcatgtatt agactagtat tcacatgctt  80400
tattgaccaa ataatgtcag aacaattaga ctaagaatag tcatcgagat ctcaaacagg  80460
gattaaaaaa agtagtggtg ataattcatc catacatctt tcgggataac acatatttac  80520
caattaaatt aggcttaagt cattcacgat tccttaaaag ttatttgtat atttcagtta  80580
gacatcttaa ctaggactat tacctattga acacttaaat tgtttaaaaa attacctatt  80640
aaatacaaaa tgctgatatg acaaaataag tgtttttcac ttcctatggg tgcgtgaaag  80700
tttttgaaat actgttttat ttttattttt tccaaaaaaa cttacacttt ttcttcttta  80760
agtgacactt ggcatttaaa taaactaaaa taattttta atattttta aaaaaaattc  80820
ttaattcaaa aaagaaagag cacccctacc cttcaagtca tcttcttctc taaatttaaa  80880
ttttcaaaga caactaaaga atcttcattt tttttgtttt tgtttttgtt tttccatttc  80940
ttttcaatat tcgtaaaaaa aattgaatca agtaactgaa tttgcaagaa agataatgaa  81000
agtagatttt tgaacattgg gataaaaaaa gtaagtcgac gctccatctc cattttcggt  81060
```

-continued

```
caccttcaaa taaatattac cattccgaga aaattgtaaa ttcactaaac ttatcaaaaa  81120
caatatcaaa taattcgcta aattaattta ggtcctcttg atttctcctt acaatcaatt  81180
tcaagatgat taaccattag catacttcct ttattcatca ctcttgtacc aactctttga  81240
atatctttct ctatcatgta ttaggaatga aaaataattt tcgataaatt aatttgggtc  81300
ctttcgattt ttctttgcaa tcaattttcg gatgagtaac tattgacaaa cttcttcatc  81360
actattgtat caatctcttt gaatattttt ctctcacaca tattaggaat acaaaatatt  81420
ttttttaaaa aattgaatct gcaagtaatt tgcagtgaag gtttttgtgg tttgagaaaa  81480
aaaattgatg agaagaagat gaagaacaaa ggggggttgg gtagggtggg gttaagtaaa  81540
atgggttgtc atttcattta ttttttttatt aagaaataga tataaaattt atttgaaata  81600
attttcattc tttttaacat aaaaaaaaat aaaaatctat agttgttggg gtcaagtgac  81660
acatgtcatc ttttaattag ttattttagc cacgtcatag caagtgtatc acacacactt  81720
taacttttttt actgattatc aaaaaaggtc taataggaac aggttttaga tagataaaag  81780
tgttcaatag gtactagtcc tagttgaagt gtttaagtga attatgcgga caactttaag  81840
gggccgcaga tgacttaagc cattagatta tgatcgaaat tccatagaca caccttaact  81900
aaatcagggg cgtaggcaca tgtatgtcag ggtgtccaat tggacatcct tagttggaaa  81960
aaatttcgca tatacaagta aaatgataca cgaaatgatt aaataatata ttttggacac  82020
ccttgacata ataggttgtt atagcctagt gatttaagat gtcttgaatg tgtgtttata  82080
catctttaat gagtcagtgt ttgtgtgttc aaatctcact tgcaacaatt tttttccctt  82140
tttaaaaaga acttttgttg tttaattttt agaccctctt cgtgaaattt ctagctccga  82200
cattgaacta aaactaaggt cctattatcc cctgaactca tttttttgat aattttgtac  82260
acattttagc ttggcatatg cactccgtga ctccacacaa ttgaggtgcg tgggagatat  82320
tttaatgcca caagccaaaa tgatgtacaa aattaaaaaa aaacatgggt tcaggagtaa  82380
taggacatta gtctagttaa gttgtgtctc tgagattttg gtcatagtct agggaggtat  82440
ttgtaccttt tttccctaca tcttccttgt aaatggaatg tgttaccaat gagggtcata  82500
gtggagtgat tagtattcct tcgtccttaa ccagatgcct tggattcgaa tccccccttga  82560
tacataatcg tctttgttaa ggagcgtttt cccgtatact aagtatgtta ttgttattgt  82620
atcgatagag acaaccagat ggttcgaaac cactaaaaat caccatcttc agataaaaga  82680
aatattagat gattataaga aaatcctgat atgggcatat gaacacataa aataaggcca  82740
taaagagatt tactctagaa accaatttag acaagcaaaa catatatatc tggcttacca  82800
taaacatgac caaaaagttt cttaattaat ttccaggacc tgagcctaaa tatattctct  82860
ttgtatcaaa caagaaatcc tactgaattt attttcttct cagaactaaa aatgccttct  82920
ccacttggcc tccaaaagag ccttccatat cacaacttga tcccaaagtt gatgagaagc  82980
aagctatata ttacgaacat tgaagttcaa cgtgttaatt tccctgaaag tacaatcgtc  83040
aaattaatct ttttattagc taagaaatga attccagcta actgtctgta gttgtgtaac  83100
aagtatcaca atttgatcaa tcttgacgct attcagattg cttacactct tcatccttct  83160
tagctgatct aacatatcct caatgtcgtt tcgagccatc tttcgtagaa aattcctgcg  83220
agttcaacaa acacttggaa tattaatttc attaattatg agcaacattt ctattcgtgt  83280
ctttcaatat ctgccacagg aacatgatct ttattatagg ataagaagtt taaagtcgta  83340
catttttagg aggtcaatca ttatgtgatt agtaaaaaaa tgagagaact gtagagaata  83400
```

-continued

```
gcagaagaaa tgtataattg ggagaccttc tactagccaa taattcgagt tttcaataga  83460
ctggaattat gaagtctcta ttattttata tatatatata tatatatata tatatatata  83520
tatatatata tatatatact ctatgataca gaaaaaggag gagagagcag agtacatatg  83580
tacatataag ggaaaaggag aaataataat cctcatcaag actttatagc cacaaacttt  83640
ttgacccccc aaatcttccc tgtgggtctg gcctatgttt aaaaattaga atataggagg  83700
accattttat aacttaataa tcatggaatt aagtaagcgt tacgaaaatt tagcaactca  83760
ggtcgaaaat tcaaatcatg ttttcttgaa aagattgaaa tttgaaatta atctcaaatc  83820
taaactttga tttggaatca tatcttcata ttacatattc aaatgtgagt tcaagtttaa  83880
atatgtccag cttgtaataa ttttatcaac ctaacataga cattgacaat cgtgagattt  83940
ctagaagatt agaagaaaaa acaaccttga aagagaataa gtacatttca ataagaaaag  84000
aagttttagt agctcgattt tatcgactaa ctgaattctc attttattga tgaggatcac  84060
atttcattcc atcattccaa aagaaaaaac ctcaaatggt taattattga attttcaatt  84120
tgttagttat ctaaactctt tcacgaggat ccaatttcat tctctgaagt tcttcagatt  84180
tttggtaaaa ttcaattcat ttcagaaaaa aaataatctt aaattcttaa aaaattgaca  84240
catatggtaa aaattcgatc catttcaaag aaatatacta tatttatgta tacaacaccc  84300
actatataca gctatatagt gttggaaaac aaaaacgtag agaattattc attcatcaac  84360
aaagtatatc cacacacgcc aacatatata tacaagtcct atatatcaca aaagtgaaaa  84420
taaaagttga acaaaacact agacgatatc cgacttcgct agccaaaacg ctagcgaaaa  84480
cgaaatgaac atatgagcaa tcgaacatga aaacgagatg aacatatgag caatcgaacg  84540
cgacttcgct gtcggagctt aaacaaaaac tctagggaca gattcgatag gtttacaatg  84600
aacttctcta aggagagtgc gaatgccttt gcctccagca ttagcaagtg ggtgaattcc  84660
atgggcagga ccttccatgt atgccctctt ctccctttct tcatcaaatg acgcaccaaa  84720
acgtttctcc acatctacat caaattttaa aaacctcgta aaaaacgcta tgttaaataa  84780
acatactatt aagactaaga cataatccta aacacccaaa ttcatgtaag atagatcaaa  84840
tagtcaacca actaaactat taaaattctc cgaagaaaag tgactcaaaa ctactcaaca  84900
ccaaattcat gtatcacaca ctaatatccc ttccaaatct atccgaaaga ggtttaaaac  84960
ggaaaaggga aatagggagg cgattacaac gtgaaaaatt aaatcctcac caataagata  85020
gatcaaataa tcaaccaact gaactattga ggttttccta attaagaaag ggtcatttaa  85080
aatttaactt aaaatttttt catgctactc ctagttagac aatttacaac tctattagat  85140
gattttctaa ctaaataatc gtctatgact tgtttcagac cacaaagttt ttttgagctg  85200
tgtgtctagc aaacggagct actcctattg ggacggtagg tattaattaa tgctttatac  85260
tagcaaccta tataattata acgagttcaa gttctataca attagattat attatcactt  85320
caaaagtaat taataacatg tatcaatcat aatatgataa gtaatttttg tgtaccttga  85380
gcaaggttct gatcgagttg accatctcta gtaagcgcca tcataacttg aggaattccc  85440
aaaggaagtg tatcacctct atcaacctgc cagaaatgta tcactttgcc ataagttttc  85500
acggtttttt catgatcttg tcgttgaatc gggcctggaa caccgggcat gaacaggaca  85560
ccgcttttca cctcgtacaa agatgttgat gaattttatt gataggacca aatccttgaa  85620
tggtagctgt tgcagtctca agaattgctg ttcctgtttg cgtaggttca cctggaacat  85680
ctggatgagt cgatacattt attccttcca tttttttcc tttcaaaaat ctcaaataaa  85740
ttcagaattc gaaattatag taaagtattt tgttgtggtg atctgttaac ttatttttgg  85800
```

```
cctagaaaga agaggcagct agcttataga taggaatatg actagcatgc agactaacac  85860
gtggcacgac acgtggcgat acaactggtt acgtggcagt acaggtgtct tttgtttggg  85920
taatttgaaa gctgactcct tatactccta ctcatgactt gttctctaac ttgtgtgaca  85980
aatgtttttt tttaatgagc tctgatgtgt gacgttcaga caaatatgtt attaatttac  86040
ttgttttgag tataatttat attttaaaat tttataattt atattaaata atatatttac  86100
tttcttcata gattggaaag ttgcgatgta ttcggaagcg gctcccctcc tgtatacatc  86160
ttaatccatc actttagtag caaaattgca cacctaatgt aattcaaatt tgataaaatt  86220
tagtaatttt ctcaaatgtt gctttgcttt cctacaactt gtcatgtcaa ttttcatctt  86280
cttgagatgg taaggtttgt tgttgccaaa atctttttgg gccaagccca tcaacattcc  86340
aatgtccaat tctgactaag caagcccaat acgagatgac atacttgtaa caaaccccaa  86400
tattcacatc cctagctatc gatgtggaaa ttctcaacat gagaacggat gttaattcac  86460
acctctttgc ataaggtagc tctgccattg ccaccaacac aaatacatga caccatcaca  86520
atatatcatc ctgataaaat gcgcacatcg tagaacctta acaattatga gacgttagga  86580
tggtaaaaaa aaaagaatgt attcatcgat ctttctatcg atgtgagaac tcatcattaa  86640
gtgcagagtt atttaatttt gtaaataatg atatagtttt aataagtaaa ttttcagtta  86700
cgtattacga tgccaaaacc tacctatgac cacatttaat tgttcttttt aatattggca  86760
ccaacttttc ttacattaag ccatataagt atgaaacaac ttgggcagct tcacgatcct  86820
taacgcattt ccaactgaaa tagaagaaac caaatcaagg gtgtgtttgg cttggagaaa  86880
aaaaaaacaa ttccatcttt ggttcaaatt ttttgaaaaa tactttctct aaaaaaaata  86940
ttagtccaat gcacaaagaa aaaaaaacaa gattcacgaa taatattcca cattgatgat  87000
ttgctctctg cctttcagca caaactatcc caccccataa cgccctgacg acccaacact  87060
ttaccaccca ccctccagtc ctccatcgat ccacaacata gtgttcgcca aaattaatta  87120
tacactaata tttttgggac aatatttttt gttacgtacc aaaacacgaa gaatattttt  87180
cttcaaccaa atacacccta agaagtagct aaaactaata acgtgactcc aaatcaaagc  87240
ttgcatgaaa aatctaagcc ttgcatttca cgtgcctctc tcaaacgact cttattatta  87300
aattgaaaat tttcgattat caaatacaca acaactaaaa aaagagatta tattcccaaa  87360
aaaaaaaaaa tcatcaatga actctcaaga aattcaacca tcaaattcta cacaaattca  87420
aagtgttgaa atatcaattc aaaatctcat aaaaaattgg gacaaaaagc aaagatggaa  87480
tttctttatc atgaatcctt cacaacaacc aacaaaacaa caatggagaa caaatttaac  87540
aaagttttta gaatccatac ctcttagaat tttcaccatt gtgttactca taattgatct  87600
tgttttcaca agttttgagc tctcttcatc tttgatatcc tgcccgcaaa atcggaacgc  87660
gataaatcaa gaaacggaag aggtttggta ccattgggca ggtaatatta gatagtttgt  87720
aatatatatg aagtaacatt ttcttgtatc aaaaggaaaa aaatgagttt gaaagccttt  87780
atattttaat cttattagtt acaaactatt tagcgacaaa ttttatagct aattcatgtt  87840
ttttacgata gagatatatg tagctttgtt gtttcctaac ttgaaaattg tgatatttaa  87900
aacatagtca caatttacaa ttgtatttaa attttagtta cttttcttct ttcttcttct  87960
tgattttcct tgttgttggc ccttataaat acatatacaa catttctact aaagatatta  88020
tttttgatgc ttcaaagctt taaatcaatt ccatctttct attttccgaa caggtatagg  88080
gatcttggga ttgttatttc tgaagagtgt aggccttgtt gtaggtctag ggtacgcatt  88140
```

```
ttttcgaaga ccagggtact tgctagatgg catagttatt atggtggcat tatttttgga  88200
agcatatttg gaaaaaaatg gaggcggatt acttgttgtt gttagcttat ggagagttgt  88260
tagagttgtt gaaagtgctt ttgagttaag tgatgaagca attgaagcac aaattgaaga  88320
aattgtttgt caatttgaag aattgaaaga agaaaataaa agattgatgg atagtgttgt  88380
tgagaaagat aaacaaattg aaatacttca acaagaattg gatcaataca aaaaatcaac  88440
ttactagaga tgcaactaga attttatctt gtttttaggt actattttta taatttatat  88500
atatatatat atatataaaa tcaatcaatc gatagaaact tttaagttat ctgaacaagt  88560
aataattcat attaaaattt tcccaaaaag cagattgaac atgaaaaata agttcatatt  88620
aagtatgggt ccaacatcaa ttgatacttc ttgatcttag gcatattttc attttaattg  88680
aggattcttg taataaaata tataaatatc gagcatgaat aacctacatg tcatgttggt  88740
accccaagtg gcataaattg tcaaaactgt gcagtttatt gcccactgaa tgaataaaga  88800
gctggtccat atatattaag aacctgttta atttggcctt tgattccatt ccctttgttt  88860
gctttttttcc ctgcaaaagt ttttagcttt tggtasaagt gtagtgacca atcagaggaa  88920
acttttctta ttcaccaatt aaaactatat gataaattaa taacaagctt ttgaaatgta  88980
attcttattt ttagagttta ggataaaaaa ggagtatatg atttaaaata tctcattttt  89040
tcaaatttta tacctgaact atctgtatgc tasttttcta tttgaattat cacktaagct  89100
tgaatcwctt ttctattgaa atatcatcat tgttcgggag caactgatag ttgtggtttg  89160
ttttgataaa tagttgatga tagtttaggt gaatactcgc acaccgaata gttaagatat  89220
aaaactcgaa aaaatcaaaa tactatagtt gtgttttgac cctttactct tcttcttttt  89280
ttaatgtgaa actcaatgga tctttactta cttttataaa acaaaactta tacactacgc  89340
atggatgaat ttagaagttt aaatacagat tcaattgaac ccaatagttt ttgtataaac  89400
gatacatttg tgtgaagaat ttcattaaat atatattcat attagattta aagctcaatt  89460
attattattt gaagtcgtta ttctataatt ttaaacccat aaaattaaaa tcatgactcg  89520
ccttaatcat cacatattaa tcaaaaccac tcgcgttaat taattatgtg gatataatat  89580
ccattgtttt aacctaatat ataatcttaa atatgaactt tttatatata aaagattgat  89640
ttcttttgta attgtgggga aaagggagga agttataagc aacttgtaaa ttaatataat  89700
tgaaccctag tttgcctatc atccatctat tcattcgagg tgggaataaa aaataaaaaa  89760
attaaaacct tcttttatta aaaaaatata accttacaat tatagtagtc atattcttaa  89820
agggaaaagg gtgcaacttg tgcaattttt agtacactta attaggtcat atacatgcat  89880
ctagttgttg aatcgatgtg agagttgaaa taaattatta ttaagagaga atagtgggaa  89940
aagggttgaa atttgtgtaa tttagaaccc ttatttgtac catgtagcta ttcaatcgac  90000
gtaagagtca gaaaattgtg ataacagtca gacgacactc caaaaaaataa aaatatataa  90060
gggtacaact tggatgattt aatttttttaa attttaaatc gtctagtcat tgaactcgag  90120
tttgtataaa agaatgattt gtacttacgt atagtgatat aggtcatcaa ctgtcaatta  90180
taatatagaa tattctattt ttttttattt gaatgaaaca agaagattta aatgaaggat  90240
attcttttta ccaataatat aagctagaat tagtaagttt ctatgataag caattaatgt  90300
tttttttttct tcttctttttc taatctctgt gggcatattt atgagagtaa gggtatgttt  90360
ggcctgttga agtttggtaa ttgagtattt aaggttcaaa aattcaaata aagttagcat  90420
atgactttct ggagtatact tttttctaaa ttataaacta tagtgtttaa atttatgtat  90480
aaaaaaaaata ttagtgttca aataaggtaa gcataggact ttttgagata gactaataaa  90540
```

```
tatttttca gaaaaaataa taattttcac actaggaaat gtcaatatct aaaataataa 90600
taaaaatact ggacatggtc aatacaaata taatacacag gacatactat gttctaggag 90660
aagtgcatat gaacatgaaa aagaaagaac tattcaatat gaaaaaataa aagataatta 90720
atcttctaat tatttatcaa ggaagtaatc aaagtgtcat atataattat tagtagaatc 90780
ctaaaattta caaatgatga ttttttaat tatgaaaaat agtttagtga ctttatatta 90840
cttatattaa atagaatatt tcttaaatca caaaagttat actttctcta attcacttta 90900
tttgtcgtat tttattttgt acacaatatt aattaaagga ttatttgact aaattagctt 90960
tgtttattac tccttttaat ttaatatata cttccctctt tgtaaagtag caatatgcat 91020
gcacacttat taacctactt gtatatatgc catcaaaaca cttaattaat gggaccaatt 91080
catttctcga ccaataatat cataacttcg acattataat actctcttcg tattaattta 91140
tgagacatct ttcaaatttc aaatgttaaa taattttttt aatcactagc tttttatatg 91200
tcttataaat atttaaatca ttaataaaaa gataattact ataatactat ttctacaaat 91260
ccttgtggaa tacaacaaac ttctcgtgac ttgagtatat atacgtgcaa ttgctagtat 91320
agtactatat agtgttgctt cacatgcatt gtacaggatg ctttgacaca ccacattgag 91380
cagcaagttg aacaatatgg attgaggccg ggtcaggcct gcacctgttc ggatcgaccc 91440
ggtgaggacc cgccaaatga aacaaccaat gtagaagagg aaggggccgg ttaattaggc 91500
aaagtatgtg tctgtggaga gtagattgta tgaatagacc ttcgttacaa aatgaatatt 91560
atgatcaaag caggatgaca agaaaatatg acaactgaat aggaagatac aagcaaatgt 91620
agtaagagtt cgatagtata cacataaaag aataagaaac tacatgatta ctaaatacta 91680
ctactaaaag cgagaagagg gaaggagaag actggcccca cgtctcccat acatatagta 91740
cgagaatact tggatatcta ctaactttct actttaatca tcgatctcca gactttccta 91800
tcttgatact agctatgatc acctcgatcc ctttagttct ttttcaacct acttttacat 91860
cccctagctc ctactatagt caacctctca taccatctac ccgatgtatc tgcacactcc 91920
atatttacat gtttgaacca tctcactctc atttccctta ttttgattgt cgcaaaagcc 91980
actcacatat tttccctgta taactttatt cctaatcata ttcctcatag tatgcccaca 92040
cgaccactct tctaaacgtg gatattcttg actagctagc cacccctctt cccaatacaa 92100
caatgtcgat ctaaccacta ttctgtaact tacctttaaa actctactac atattcttat 92160
cacacaaaac ataccacatc gtgatccatc tcctcgttct cttgaattat gaattcaaaa 92220
tacttggata tctactaatt ttctacctaa aagtgagaag agggaaggag aagactggcc 92280
ccacctctct cccatacatt tagtacgaca atataacttg gatatctact aactttctac 92340
cttaatcttc gatctccaaa ctttcctatg ttggtacaag ctataatcac ctccctttag 92400
ttcctttaat ttcaacctac ttttacatcc actaactcct gctatagtca acttctcatc 92460
ccacctaccc gacatatctg cacactccat cttcacatgt ttgaaccatc tcaatctcac 92520
ttctctcatt ttgattgtca caaaagccat tcacatattt cccccatata actttattcc 92580
taatcatatc cctcataata tgcccacacc ccatctttcc ccgtataact ttattcctaa 92640
tcatattcct catagtatgc ccacacgacc actcttctaa acgtgggtat tcttgactag 92700
ctagccaccc ctcttcccaa tacaacaatg tcgatctaac cactattctg taacttacct 92760
ttaaaactct actacatatt cttatcacac aaaacatacc acattgtgat ccatctcctc 92820
gttctcttga attatgaatt caaaatactt aaaacttcct ctctttgaaa taactcatgc 92880
```

```
atcatttttc atgaattacg ttattaaact tacactctag ataaaaataa taattcacga  92940
catgatctaa taacgacaac gtgccacgta aattgaaaca gataaattat aaatataata  93000
atttagtagg ataggatgta gtacacattg tatattaatt ttctattaaa aaaaaagaag  93060
gtaaagacaa aatcacaaaa acaacaaaac cccattggct gatccactct ctttctcaca  93120
agacttttca tcaaacaagt gtagcacttt ttcatttttt ttattcccaa cttgctcttc  93180
cctcttaccc cctcacccca cccacccacc tctctctcta ttaagttctc cacctccaaa  93240
tcttaacaat ccaattcaaa acaattctca aatgtatcca tcatcaacat cttcttcatc  93300
acaaggttca atgagccaca ccagcaccac cgctggcggc ggtggcggtc tcactcgcta  93360
cggttcagct ccgggatcat ttttaactac agcagttgaa tccgtcgtta acggtaatca  93420
cgagttcgct tctcatggat ctcatcactc aaaccttggt ccttcacggt ttttcccgtc  93480
caatttagca tctaattcgt taaattctga atctacaagc aaagcgaagg aacaatcgaa  93540
tttacagagg tcaattggtt tcaacgactt aacaatcggc ggcggcggcg gaggtttgcc  93600
gacgacttca accacgccgt tggttcgaca tagtagctca ccggcgaggt ttcttaatca  93660
acttgctact gctgcaggtg atactggtaa gttttcaact ttcctttttt cctaattgaa  93720
atgtgaaatg acgaatttga ccttcctgta tatgattcct tctgtttgct tttttttttt  93780
cccctgctaa agtcttcagc ttttggtaac tttttaacca atcagagcag actttgctaa  93840
ttgactaatc acaaccgact ttgcataaat taacaaactt tgaaatgtgt tttacatttt  93900
taagtattcc tttggttata tcttctagaa acaaaattta agaaagaaat aatttttttct  93960
ttttccatgc ttaaacatgt taggacaatt ccatagttat tcgagtatat cacattacta  94020
agggtgaaat gagaagttcg aaattcaaaa aatcaatttt gttgaaatag actaaacata  94080
taagagtgtc gtacaagacg gagtcttagt tttatactag tcaaattcag ttaagatgct  94140
agttgtgtag taaatgatta aaatttgacg atggataaat tagaaccacg agttcatgag  94200
ttcaagttgt ggaaacaatc tattacagaa atgcaaggta aaattatgcg caataaactc  94260
ttgtgaccct gacatagcag aagcttaatt agtgcatcga gctaccttta aaaaaaattg  94320
taattagcta tagatgaaaa gagaaagtag gtttcttgca gatagaacca attaatggag  94380
gattaactta tattgattat cattggacta tattaacttc ttaatgaatt gtcatgagat  94440
tagagtacaa aagtaagatt tacttatgtc acaattagac gttataaact gactagttga  94500
gcacttaaac ataattaatt actcaaaaaa ggacacataa aagagtaagt ggggaaagat  94560
gcttagagtt attgaatttg tcttatctaa ttatctaatt acatacaaca agttgctaaa  94620
aagaattacc aaaagattaa aagagagcta tgcaaatgct aaagatatac ttggtactca  94680
aagaatcttt aatacctcct tacaacttgc aaattctttt tttttctttt ccttccatat  94740
gattagtact tttaacattt aaacttagaa gtacttcatt tgtctcactt catgtagtta  94800
ctaaattggt gagttaaaaa ggaattcttt aaatattttg aattatgaat tattgaaatt  94860
atagtacata tcaagtaatt tttaaatatg taaaaaaatt atttttaatt tttttaaaat  94920
tatgtgtcca tcaaatattg aatcatctca cataaaaaag tatatcatat cgaccaaaag  94980
tttagctagt tctacttttc ctatggtgag tgtcattttt gtgtctattc tttgtatctg  95040
tctacgataa taacaataac atacttaaca taatcttata actgaagtct cgaaagaaca  95100
gagtgtacat atattttatg tctattttgt agaaattaaa aggctgtttc ccatagactc  95160
tcgacttaaa taaaacattt taaaaacagt ttgatttttt tttatctgtc taccttctac  95220
aatttccaac aaaactttcc aatcttgaca aagatgtcaa aaccagattt cagacttcag  95280
```

tagttcgtgt ttgtaaattg aatccatagt ataattcaag gattatactc catctcatcc 95340
caattatcat tcgtttggca agttgaagtt atttaaaagt attattcatt ttaggaaaaa 95400
acaaagaagt gattttgcta atccatccgt tccaatttat gtgtcataat ttgattttgt 95460
acaaactttt gaaaaaaaag taaatacttc taaaagtttt ggttttaaac atcccaaaac 95520
atatatgtga cttttataag acgtgtatac cataaaagct tcagattaaa aacatgtcat 95580
tatttctgaa acatataaaa aagaacctga tagttttggc caaaattata tatttatctt 95640
gaaaaattca ttcaacataa ataaattctt gtttacaacc aacttaatga tttagaattc 95700
gaaagttata tacttcaaat atagttaatt agtataaaaa gtagagggga acaatcttgg 95760
gttagcttag agtaaatgga attagtttcc taaattagaa ggtatataac gtaagcagcc 95820
gcaaattatt attgtttttt cttaaacaaa ataacttatc catcaatagg gcaaattagg 95880
agattagtgg agctaattgt cagtatttct taatcctgtc tcaactctta gtgacatgta 95940
aaggtgggtt ccacatttgg ggaaagtgaa tgcatgtgtg tctgctaagt ttccaatcgc 96000
ccacaacatt tggctaatga aaccactggt attaattaat tactcattaa tcatggtgga 96060
tccttcttta agatagaatc tcattagcac taattaatat atattttttt aaagtttttg 96120
gaggtaggat ttgggggttg gtttggggtg ggggtagaag ggagttagat gcaacttgtg 96180
caatttgaca ctcttgagct tataaacaat aatatattca gtataattgt gaggtttgaa 96240
gacgataaag tgtgtgtaca actttaaaaa gttattttca atagatcctg acacgataca 96300
tctaagttta tatatcaaac aaatttgtta ccttttagtt ttttataact attattattt 96360
aaaccaactt gcatgtatct aattaattac atatctagtt aattatataa gagtatttgt 96420
tacctcatgt caacacatac aacaacatac ctaacaatta caaagtaaat ttttactagt 96480
agagtttaga tagggtgaaa tgtatgtagg tcttattgaa atagaaatgt tataagagtt 96540
aaattttaat tctttttagt ctaaggagta aggggtttga tcttagtggt aaaagtataa 96600
cgtgcgatat gttaagtgta gatcatgaaa ttttgcctca ggtaaaattt tttatattca 96660
agtggagaag atcagaaaga tgaattcatt atcctttgaa ttgtgaatca tgcatcactg 96720
atccttgttg ttttcgattt aaaaaaaata tttgaccttt gtattaatat aattaatggt 96780
gcctagatcc ttagaagcag ggaagggaga aggaatgata ctacttgtgt gaattaattt 96840
gatatgaggt gggagacaga aaggctatgc ttttattgtc aactatcaaa aactctacaa 96900
ctcattttgg tcgatttaat taagttgctt gaacttttca aaattgttgt tgtatccgtg 96960
tcagattctt taaaaatgta ctattttaaa gatctgacac ataccccttct acatttttga 97020
agaatccgag caatatagaa atagattctg ctttcatcta aaaatgtggt ttaatctatg 97080
attttttgcc aacaatatat gttgatttgg aataggacat acaatgtgtg tatgttttga 97140
cctcgaaata aggcaattta ttctctatta attttttttta ataattataa tctactctag 97200
gttaggttta ggtctgctat tagaccttta atcgttgtat tagtttctta agttaatgtg 97260
tgtatgaact aagtcatgtt cattatgtca cacaaacttg aatgagtcaa taaagtggtg 97320
ttggggttcc tttattcatt ttttccactt gtagaaattg atacattaga ggttggtgtg 97380
cttcttgagc acgagtctat tccattagtt atgttgtagt tttctcttct tcaacccaaa 97440
taaaatagta ataaataaat aaattaaaca agtacaactt gggatatatt actcgttttg 97500
ttccatttta tatagcttca tttcttttaa atttattcct ataataataa taataataac 97560
aaaaacatat aagtgtaatt ccacaaataa ggtctaggga ggataagatg taccagactt 97620

```
tacccctacc tttgtgggat agtgaaactt taggctaaaa aaaattattt gaagtaagat  97680
cgtaagaaaa atatttttaa cgaaatatca agatacaaaa tattttataa ctgtatagta  97740
atgtaataga caaaattgaa gaacttttag gggccaaaaa atgttttgtg gtctttgtat  97800
tttatacgag tattgtacaa gtagagatat aagtggccat tttcgaatta ttaagtagct  97860
ttatagaaca agttgtcact tgggccccaa tgagcaatat agatattatt attttcttgt  97920
ttccttaatc ataatcttag caagaatctc cttattggag gaagtgagca tttttttttg  97980
gtggggtcca aactttcaaa tagcaagttg acattatata aaattctact aaagtaccaa  98040
ctagccaata aaataatgaa taaagaaaag ggaaggggtt ttgtcccttt atttaattga  98100
tggtgattgt gcctacgatt ctttgaatcc atttttactt attttgaggt caagatgcat  98160
tcaccaaaca gctcctaaaa ttccatgact ggtgagttat cacgtgcatg ggtatttact  98220
tgacccgtta ttcccacttg ctctatccat tattatcatc atatatatat aatttatatc  98280
ttagccgcca cctaaaacca gcccaatgtt tttgagtgct ttactagttt tacaataatt  98340
gatgtttttt taccagactc ctttttctcc ccttctaaga tattttctga aacttttatg  98400
gtcaactgtt tagcagatga tcctattttt atttgttctt gtaatttatg aaccttctag  98460
atagtaaatt gaaaatctta taagaaatga cttgcttatg atcttaaatt ttgtagacat  98520
taaacaaact taaatgtttt gttagtttca caggttatat tttcacaact tctgaaaata  98580
gtgataaaat ttaaatgatg acttatataa aaaaattatt taaatctagg acttttacat  98640
ttactgttca cattctgttc tgtcgagtgg tcaaatgaag gggtttaagc accataaggt  98700
cctaggttca gttcctaaca aagacaaaac actaggtaat tttttccccc atatatccca  98760
tgaaatggag ctttagtaga tcagttcgtt ttgagcagag ggtctaccgg aaacaacctc  98820
tctacctaac aaggtagggt aaggtctgtg tatatcttgt tgtcgttggt tttatctttt  98880
gtttgagtag taatattcta agttgctcgg actctccaaa aatgatgcgc acccgtgtgg  98940
gatccttcaa aaatacacta tttttggagg atccgacacg cacctgtcaa cattttgaaa  99000
gagtccgagc aacataggta atattcatac ctagtcaaac aaagacttca atttagttat  99060
cgaatgaaag tcgaacaatt tgatgtggaa aagagaatct ctttatgtta tgtctgtgat  99120
atcctttaat tttgtcaaag aagatcttaa tatatagagc caaatgaaac caaatacttt  99180
tccatggaga ctacaagggt cacactagaa ctatcagctt ttgtggtgac atttttgagt  99240
cacacccacg aaaagattca tatctaatat attgtaaaga ttttaatttg gtaaaaaaga  99300
cctcgttacc ataactcgta atataattct agtttgactt gacgttagga ttttcagttt  99360
caatggggag aggaagctat aactcaaaag gcggtggaga tagtggccgg ggaataacaa  99420
ggctgaactc tcagctcagc ttcactaggc aagaagctct ctctcaaata gcagaggaaa  99480
atgaggatat tgaagggacc agtatagcca atggccacag aaagtcaaca cattcttatg  99540
ccagtgcaag tagtttcgca atgggttctt gggaagataa caactctata atgttctctg  99600
tcacacctag caaacgagcc aagcagatta gcaatgacat ggtcaatggg ctcgatgatg  99660
gggaaactca ggtaatataa ctgaaatttt gtgaaagtat gtttctctgg agaaattgta  99720
tttttagttg caagtgttca agggtcatgt tttctttatc ctgaattctg gagttgtgca  99780
tgtgatatgc ctaactttaa caacatttat gtgaaaaaat gagatgtcat tttaatgatg  99840
ttagccttct agatgaaaaa atgtcttgtg ctttgatttg gtgacccttc aaaaagctga  99900
cgatttgttt tttctcttgc attcttttat tcctaattcc ctacctttct tctttcttcc  99960
agctaatatg aacttgacag tcactatcag aaaacacata aaccttcact gtttgacgtc 100020
```

-continued

```
tgtgttttca acatgtcaac ggcgatagat atacttcctc tgcatttttc cccttaacaa 100080
ccttactact acattctgta tgtgtttgtt ttctttctgc agaagaatgt aaattaaaac 100140
agacaaaata atccatgttg gcatactcaa tcatgtttct cgtgcgcaac tctcgcaaat 100200
attgatgaaa actgcatttt tgtttcttgt gagaggatga actgatgttt tacatttttg 100260
aatcattttc agtttcagtt tggcttgtct cagacagcac tagaaatggc atctatggat 100320
agattgctgc acatccccga ggattctgtt ccttgcaaaa ttcgtgccaa gcgtggttgt 100380
gctactcatc ctcgcagcat tgcagaaagg gtaatcttca tatttcttaa gtcattcctt 100440
tactcttggc ccttataatg aacaaagaaa taaaaatcca attgaacttt atcaatttat 100500
ttttcccttg ctccgtttca ttttatatgg ctttgattga gaatgacgtt caagatacta 100560
tctgaagctg atgcaatttg tccagccact gattttaaat ggcaattttt ccattatgta 100620
acactagatg tagttatcaa catgtagtag ttgcggcatt tgaaatactt ttcctcaaaa 100680
tttggatcat catagctatg ttttgttttt tctaatacgt gataatgaac attcttttct 100740
tttcttttct tttcttatct tatgcaggaa agaagaacca gaattagtgg gaaactaaag 100800
aagttacaag atcttgttcc aaacatggac aaggtatagt ttgctcattt cacattaact 100860
tttgtgtgag agaagagtat cacgagaaat gtctttatgg tgttggaggg ggatgagtgt 100920
cattaagttt taagccgaac ttgcagtata gctctgcaat tataaattat agctatctat 100980
gaagtgcttc atatactata actctgtaat catgtttgct tggaacaaag aaaattagct 101040
attggaagtg gcgtgctatt caattggata attgttactt gacgtgctaa aatgctgtta 101100
aaccatcaat ttattgaata tttatagatt tgtgtaaaca aaaaattagt ctttcagtaa 101160
tcttgattgt atgctttctt ttcttatgtt ccacttcaca atattttctc agttggcact 101220
tattgcaaca tgcttgagct gcaaatttta tcgcagcaaa cgagctacac tccaatatta 101280
acaatatttc cttgtttgtt tttgcagcaa acgagctacg ctgacatgct ggatctagca 101340
gtgcagcaca ttcgaaccct tcaagatcag gttcaggtgg gtgattaaat tgatcaacct 101400
tactgctttg cagctttacg taatctatca tgctgcatgc acctaggtac aaaattaaaa 101460
tacttatact ctgttgctca gactcttcaa tgatactgtt ggatgtgtta gattttatcc 101520
tccaaaagct atgcattttt ggaggatcag acactagtac aacaattttg gcccgagcaa 101580
cacatcttat attctcacat gatgtttaca ccaaaccgaa taatataacc ttaatgtttt 101640
tgggatagat aatgtctaat atattttgca aaaaaaatga taaattttct agccccacct 101700
ttatagctgt gattgaagta gtagaaacat atttttcaca ttttcttttt cttatgcaga 101760
atctgaatac agaacttgaa aactgcaaat gtggatgtaa gaaatcaagt caataacaaa 101820
atggaaggaa gcactttagc tgaagatcga cttaaaagga tttttgtcac catgattttg 101880
cctcttagaa actcaaattt gtacataagg aagtaaattt catactagtt ttttaaagct 101940
aaaaggcgaa ctcttctttt tttttttttg tttttttttcc ttttccagtt agaagactac 102000
gtatatgatt gttttggatt atttgtagtt tttttttttc catctaacat ttacattttt 102060
aatttagttt tgagtttatt ttggttgagg atcataaagc taattgatga tgttgtacaa 102120
caactttctc tatttcattt ttatgtaaaa tgagtgggta agacattttc ttgctttctg 102180
ttatgttctt cttggaaaac gaccatttac aattttaaaa taagaaaagt aaatctactc 102240
tacaaggatt tcattgtttt atttatcgaa ctgatcattt tctgtgaaaa aaactcattt 102300
aattaatata acgtttgtat tgagccacaa aatcgatatt tcccttctta cccatgtata 102360
```

tcatgaatat atgtgattca acaatgcggc gctttaggat atttcgatat tttgtttatg 102420
aacgatgatt tgctcattcg gtaagattgc ataagaattg ggggattttt tttatatcaa 102480
tgtgatttcg tatcgtatat ccaaacaaaa tttcaacttc atatcaatat gatttcatat 102540
cgcatatcca aatggggccc caaatttgta aaaaaaaatt attgtacttg ttctattaat 102600
caaatctttc attgtgaaag atgagcaaaa tgaattgagc ttgaatagtt aagttgaata 102660
aaagttcatt gttgaactat tgaaaaaata ggtgaataag gtcatttgaa aagtcagtaa 102720
ttttttgtta tttcactcaa aaagtcattc aagttcaaaa ataattctct gtcggaatct 102780
gaatatgaga attattactc tcatgtttac ctcataataa tctgctttca attttaatta 102840
tgattgaatc agaaaattga agatactaaa caggcataac agaagacaaa agttccaagt 102900
tggtttcact tgttaactaa ctgtaagtta tcttcttcat gaattacttt tacctattga 102960
tacaaaatta gggagttgat ttcttaaatg gtccactcaa ctaatagtta ttatattagg 103020
aagccagttt ctttgttgac gaaaattgga attaaaaaaa gaaagtctga gataataatt 103080
actccctccg tcccatttta tgtggcaaca tttgaccggg cacggagttt aagaaataaa 103140
tgaaaacttt gaaatgttta ccaaattgac ccttcaaaaa atagtcatat taaaaaatag 103200
acttactttt ctctctcctc ataagtgtat aattaagtgg gatcaataag ggtaaaagag 103260
gaattgtacc tttaagtact taccatataa gaaaatgtga cattcttttt gggactcata 103320
tgtgaaagag ttctcaaaag cttgaaaatc taaaaatcga ttttgtgaac ctatgaccct 103380
aaaacccaaa caatgaactt gatccttcaa cacgcaatta caacttcaag caaacttcag 103440
cacactttga aactggagtt ccaaagtccg aacaacaact caaaagagaa caatggaaga 103500
attatatttg attttctttt tgtgataggg ataaacaagg aaaaacaaca ttattgagag 103560
gaaggtattt ttgcaatgtt ggactgccat gtcagttcta atggcaaaga taacgtttta 103620
aggatgtttg tgacataatt aaaaggtata tataagctat ttcaaatagt ttaagagtaa 103680
ttttgaccat tttccgtata atatattata tatggaataa gacataattc tcaaagacaa 103740
tgatagagtt gatggacgtt tttactaaag caatcaatag caacgaagca ctatcattaa 103800
ttaataaagc actaattgtt gtttgcctac cattaattaa taaattaata atgcaataat 103860
tcagaactca tacaatacac atttcactat gtttgtgcca ttgcaaactc taattattgt 103920
ttgatctcat ttcccatctc tatgtactag atatagacaa caccttgtaa catagattc 103980 ggctatacaa tcaatcagtt aacaatcgat tgatctacta ttgagctatt gaggaataac 104040
aagagattcg ataagttaag attaaggtga gttccattga ttcataattt attttcatac 104100
taaaggaaat ttttatcctc taaatctata tgtccccccct ttccaattta agtgcttgag 104160
tttgaccagt ggaagaggtt tggcttgttt ctctttggga taagggtcta aaaaataccc 104220
caactttggt cggatttgct gttgcgatac taaactttca tgagaaccta ttacctccct 104280
agactattta ataccgtatt ttaaacatat atatttgtcc acgtgacata aaaaataatg 104340
caaaattata aatagtaatg tgtccatgtg ggcacatata tacctttaaa atacactatc 104400
aggggataaa aaatacggta ttaaatagtc tagggaggta ataggtcctt atgaaagttt 104460
agtatcgcaa caacaaatcc gaccaaagtt gaagtatttt tcagaccctt atccctttct 104520 ctttttctg tatgtttcat atggtcttcc actgtaatgc cctatataag tatcatcact 104580
tgcgtttgta gcttggtggt tgttttcccc tttaatttc tataatcctt tcatctaaca 104640
ccttctatgc aaatatctca ccaagtccct cattgttctt tctattaatt atatttgtaa 104700
caagttaggt acatatgact tgtatgcact agcttgagga gagtgttaga ataggaatag 104760
gagcacgaat aatatataca attctactta gaataagaat aaaaatagta tacaatgtag 104820
tgtcctagtt ggaaaaagag tcgaacataa taggtctctt gaggcattac taatatcatg 104880
cctttttca ctgtcatgaa aattcccagt cgcacccttt tcactacatg gagaattatt 104940
ttgactagtc gaggaaagag ttcgactact agttgaattt ttgtgtgcaa ccagtgtcca 105000
gtttttagtt gcattcttgt tttcaacttg caaaacatgc tgcccagaat tttcagcatc 105060
ttcaacatca gatgtatcca ttagtttttg tcttgaatcc attaattttt gccctgaacc 105120
aactcgcggt gcatcaaccc taacttttgg tgtccccctg cgtttttagt tgcattagac 105180
atcaaagtca gcccaacttc ttttgattgc acctcattag tagcagcccg ttggttattg 105240
caatcacctt tatttttggt agttgtttga acaccaatat tacttgtatc aacatccatt 105300
gagtcaacac gattttgctc agaagtggca gcaaccaatt gtcgatctaa agaagtagct 105360
ttactttgat cgatatccac aatctttctt ttttcattta gtatttctct cgcatcacct 105420
tgatactttt ccttatcgat agtacctttt aaagcaactt caatggtatc atcaatttgt 105480
ttgttatttt gatttctttt cgagatcaaa cgacaactat cttcattgtg accttggtgc 105540
ttacaataat tgcaatacaa aggtagatta tcatatacaa tctcttgatt ttttttagat 105600
aatactactt ttgtcctaat ttatgtgtca catttcattt tttagagtca aatagtttaa 105660
gtttgatcga gaatttgccc atggaatctt caaatttttt aaaatgaaaa tatacatatt 105720
tgtaaactat gtcaaaagta ttataagtca caataattga caattcaaaa tatttaaaag 105780
atatatggaa aatttatgat caaagataga cttgtttgaa tctcgaaatc taaaaatatg 105840
tcacataaaa tgagagcgga agtaattatt agttgagtga ccatatgaaa agggtaaata 105900
ggcactgttt gtaagacaaa atggtatata taagggtaaa tagacactga cacactgttt 105960
gtaagacaaa atggtacaaa attgctctta atgaaactta ttccaagagt tggtgaactt 106020
gcaggaattt ttctactgaa gatggctcaa aatgaaatta aggaaatttt agatcacctg 106080
agaaagatta agagtggagg taatctggat agcatcaaga ttgctcaaat tgaagtactt 106140
gaaattgtgg taatgtatca taattttctt ttgcctgatt ccagagacat aatcatacag 106200
aaggccaatt ggattgtgaa aatgcatcgg tgggtattag atagaattcc agttccagat 106260
gaatgtaaaa ctaaccttaa tctaggaagg ttattttcac atttgttcaa attctttgaa 106320
ggtaaaacca atttaagtta caattatgag ttgaaagatt ttgatctgtc gaaatatatg 106380
gatttccttg gaaagactct taatgatgta ctgatggttt tattggagga agaggttagg 106440
tatgaccctc ctgaggaaaa ccttgaaatg cacgtattta taaagcaact gaaaattgtt 106500
caaaagaaaa tgaaattttt gagacactta tatgacacag agataaatgg ttacatcaac 106560
catgagaagc tggaatgttt ggagactcga attcagttca tggctaacaa tgtgggacaa 106620
ctctgtattg ctgtttcagt tattcttttt tctgattttg tagatgatac aaatgagggt 106680
gaggttgaca gatatgacac gtataagtat tatatcttcg ataaatctcc atatgtatta 106740
tgcttgattg tgttagtgga gctggaaatg aagaagattt ttctcagtga actaaaggct 106800
tccaagttta ctcaatcaag aactttcaaa gataagaaat taccaaaaga attttctcat 106860
catctccata gtctgctgat gtatctcaga aacaaaaagc tcgagaactt tcctaataat 106920
aaatcttctc aaaatattga tgtagcaata gagttcttgt tggttttcct tgatgctgat 106980
gtggcaaatc atgtaattaa cggtaactgg ttgaatgagg ttatggaaaa ggttttagat 107040
atagcgggtg atgttctata tgtaattcac aagcttctgc ctagctctat aaacaaagat 107100

-continued gacaatagca aaataagtct ttgctcgata cagatattgg agaaaaccaa agatctgaag 107160
gcacaagtgg agacgtacta taaatccttc aaattcactc catctcagtt ttccactgtt 107220
ggtggatgga gctttctgga ttctctgata cggaaactga atgagatatc gaaatctaaa 107280
tctggtttag atttcctgat gaaacctctt ttggagaatt tggagaaaga gctatcagct 107340
cttgcatcca ttttagagaa ggatctgtca tctttatcat ccattttcag agatgtcgcc 107400
aaggtgcacc atgaacatga aattcttcaa gatgttcaca ggcgtactat caatttggca 107460
tatgaagctg aagttgccat tgactctatt cttgctcact ataatgtttt ttggcatatt 107520
ttttgctcac ttcctacaat attaaaagag atcaaacaaa ttaatgcgaa ggtgactgag 107580
atatggtcag cagacgttgc tcttaaacct tgctatgtgg tagcaccatt taaacatctg 107640
ccaactctag atagcaatcc agtaactgat gatgagatag tggattttgg gaattacaca 107700
gaaaaaatga ttcagtatct gattagaggt aaaaatgagc tagacgtcat cccaattgta 107760
ggcatggggg gacaagggaa aacgacaatt gctagaaagg tttacaatag tgacaacact 107820
gtttctcatt ttgatgttcg agcatggtgc atcgtttccc aaacatataa ccggagaaag 107880
ctattacaag agattttgag tcaagttacc ggttccaagg acaagggaga taaggatgac 107940
atccttgctg atgagttgag gaaaagctta atgggcaaga gatatcttat tgtattggat 108000
gatatgtggg attgtatggc atgggatgac ttaaggcttt cttttccaga tgttggaaat 108060
agaagcagaa tcgtagtaac aactcgactt gagaaagtgg gtgagaaagt caagtactac 108120
actgatcctt attttcttcc attcttcaca acagaagaga gttgcaaatt attgcagaaa 108180
aaagtgtttc caaaggaaga ttgcccgctt gaactacaag atgtaagcca agcagttgca 108240
gaaaaatgca aaggattgcc tctggtggtt gtcttggtag ctggaataat caaaaaaagg 108300
aaaatggatg aatcttggtg gaatgaggtg aaagatgctc tctttgacta tcttgatcgt 108360
gagtcagatg aatatagtct ggcgactatg caattgagtt ttgataactt accccatcgt 108420
ttaaagcctt gtcttcttta tatggggatg tttccggagg atgcaagaat tccagtgtct 108480
aaattagtaa gtttatggat agcggaagaa ttcgtggtga acattgaatc tgctgaagat 108540
tacctgatgg atctcattag ctgtaacatg gtaatggttt caaagaaaga atataacggt 108600
aaggttaaat actgtcaggt tcatgatgta gtgcttcact tttgcttgga gaagagtaga 108660
gaagaaaagt ttatgttggc agtgaagggg cattatagcc agtttcaacc ttttgattgg 108720
aatgaaagtc gagtgaactt ccatttgagt gaagagcatt ccaaatttgc atctctggga 108780
tccaaaacac ggaagccttt ccaccaaccg ttgaggtcac tgataacgaa ccaaaaatct 108840
tttcatggga ttcccttaag gtcttggatt cataagatgc ggcttcttaa ggtcttggat 108900
ttgagttccc atgaagtgtg ttatttgttt tcagatacat tgaaaacact aaatcacctg 108960
aagtaccttg cagtttcagc agagagattc tattttcatc cagaatcaca tctgccccat 109020
cttgaaactt taattgtgaa gaataattgg acaaatacag tagtgttacc atcatcttta 109080
tgggaaatgg aaaaattaag gcatgttgag attaggaaag ctgaatttga taagcagggg 109140
ctctttgaag gatcctctaa attggaaaat ttgaggatat taaagaatat tgttaccttt 109200
ccaattgata gggtggatgt gttatcaagg aggtgtccta atcttcaaca acttctcgtc 109260
gaatttgatg gacattctgc agattatttt catctcacat tggagaatct tacccagctt 109320
caaatacttg acctttcctt taagggaccc cacattgtat ctgggttaca attgccttca 109380
actttaaaca agttggtact aagaaggact ggtataggaa acctgatttc cttcattgcg 109440
ggactaccaa acctggagta tctccaatta cacaaccagg atcgtgttca aatcagagat 109500
tggtgtcttg gagatatcac gttccataac cttaagttct tgaaattggc gtggttagaa 109560
atctcaaggt ggaatgcctc ggaggaatcc tttcccctgc ttgaaacact tgttatggaa 109620
gagtgtgacg acctcgagga gatccccctt agctttgcag atattccaac actgaaacaa 109680
attaagttga ttaggtgtga gaacaaatct ctggaggatt cagctgtgag gattaagaaa 109740
gatgttgaag agaatgaagg aaacgaccgt attgacctca ttatcaaagt aagtagcaac 109800
aaactcctat gttctgtttt tgagtatcta tatgcatcta atgtgcaaac aatatgttta 109860
atacaggata ggtgaggaaa tccaaagcag ctgtgagtaa agtatgtact tgtcacgaca 109920
acatggtagt ctttcagttt cttttcttgt tcctttatgt ttttttcggg ataaaatgct 109980
tgctttctct taattgctcc atgtcgatct caaagtaatg aggatgtgtt tgaatttgac 110040
aattgctcag aaaactgcag caaaagcaca aacagcatgg accgaggtca ctcttagcaa 110100
attgttgtaa ccatgctcat gctggagtct attagccaga acacccatcc ttgtgacact 110160
actactgatt gctaagggat tttttattgt tcgacataga cgactcattc ctactgggaa 110220
gggaaggatt atgccttgat tctctttttc cagtatgttt cagatgctct tccactgtga 110280
tgccctatat aaatatcatc acttgctttt gtaacttggt ggttgttttc cccttttatt 110340
ttctataact agtttcagga cacgtgcatt gcacatatat cccatgtgaa tttttatatg 110400
atcccttcat cttttgtatc ttgatggctg tagcttgaaa gctccgacag tatagcgtat 110460
gtgttcatca gtcacctcag agatgaaacc accatcagct aactcctcaa acttcacctt 110520
cctaagtgat ttttttttgtt attaacgtgc acaaaactct gttttccaac aatataattg 110580
gaaactttcg aaagcattgt catatatact aacacgtcca tcagtcacga gtggtgatca 110640
tgattcggtg gccttttctg tctctgggga aaacattcat gacggaatcc acaacgtctg 110700
tcatccaagc atcatccaac atgataagac atttacctcc tttgtcaatg aattcacata 110760
ttctgtagtg agtttgttga acactttcag aatactaaga aagaccccga atatcaggaa 110820
atactcaaag gaaacctgag ggcctttaaa gatttttatt gcccatgtcg acttttaaag 110880
tccaggcaag tgcaccacag ggataagtac aagcaaggag ggctaaacgt catctctagg 110940
gaggtaaatc attggttcct tcagcaagtc atttgatcat tatttttgtt gaggataaga 111000
actatatatt acccatatat ttgaccttac gtcttctatt aaacattttc ccatttcatt 111060
tcaataaact tatttctagt ttcacctaat agtgatctca taaatatatc tttattggaa 111120
tccaaatctg aaatctttgg tttacgaaat aggagtgcct aaaaatcctt gagtacgtga 111180
aattacatag taaaatcact caacttagga gttatttgat gtgaggtgaa cgatataata 111240
agttgttcgg aaatcatccc atttgattcc attatttttt ttaaaaaagg catatatgtg 111300
gcaattttcg ctttgtgcag ataagataac tagggaataa tgaaaaaaaa tgagtaacac 111360
aagacactag tacagtaaac atggggtcaa caagtctatg cattattttt cttctttaac 111420
cttctatgtt acacatgcaa aactaatttt aagtatagaa atcatttact cgatatagat 111480
attcgagaaa actaaagatc cgaaggtaaa agtgaagacg tactacaaat ccttaaagtt 111540
cagtacatct caatttttca atattgttac tttgagtcgt ttgttggtct atatcactaa 111600
taacaatatc aaattacatc agaaatgatc tatagtgaca attaattaac gacaatagat 111660
taactgttga aaatatgtat ttttagaggc aataaacaat ctttgtaact gtctctaaag 111720
ccaatagcga cattagatct aaggataatt aactaatgtc ggtaaaagct ttatcactat 111780
ttactgccgc taatagatgt ttttgttgta gacttgtagt gatcatcatc tttatattcc 111840

-continued atgaataaaa aatttggttg gtaagagtaa ttattatatt tgatataaat ggtctaattt 111900
tggtaaaaaa taataatatc aattataaat tttgtttaaa tatgaaataa atgattggta 111960
gatataaaat aatttatttt taacaaaata taaacttgtt agttaatttt tgtatattaa 112020
aaatgtgaaa tcatgatacg aaatttccaa atcaagattt ttggaaaatt tgagatttca 112080
tctcattatt taaaatcatg agataaaatt atatgttcaa atgttgattt caattcatta 112140
tttgatgaaa tcacatgttt aaacacctac ttaaataaag ctccgctaat gagccaattt 112200
taaaaattga gttaggcctt aagtgtcatg tgatacaaat gaaatttcaa aagtcaatct 112260 tttttttat aaattctttt tgatatttaa gttatcaatt attgtgattt ataatatatt 112320
taattttatg tattttatat aatatctcta tctctttatc ccaatttatg tgttatagat 112380
gaaattttga gagttaacaa aatcttttta tatattttca aatattttga agatattaat 112440
tattatgatt tataatatat ataaagtgat aaaagacaat tttttttaaa aaagaaaact 112500
ttaaattgcc aaactaaccc tggctacaag catgcatgtt gaaacttgag aagttattca 112560
aaattttatt tcttctatcc taatttatgt gacattaata aaattttaga gtgtcgataa 112620 tttttaata ctatttttaa atattagtaa tgaacaatca tattatcatt taaatttagc 112680
cttagtactg aaatatgaaa tattaaattt tattctacat gatctcaaac acaataacaa 112740
agaaagccta aaataactac aaatgaatac taaatatgtc tccaaaaaaa aaatgaatac 112800
taaatattat tgatgggacg tgtgggtctg agtaagtgct aacatcaaca cttttatgcc 112860
tttaaggcat tgaaaaaagc ctcatatttc aatatattta ccaatatgta ccggttgatt 112920
tcttgtaaaa aggtacaaaa gaaggggcaa ataaagcttt gaaaaagtac tgcattatca 112980
acaaaaggac acaataggaa ttagagggaa aaaatcatga aacgcacaat tcgcaaagca 113040
aattgtataa gcattcacag caaagtataa agcagaatta gatagtaact tatcaaagta 113100
tccttgtcta ggaagcaagc atgttgacga acagttatca ggaaacaaag tcatccacag 113160
attgctaaca aaaaaaaaaa ttggataaaa cttcaaggag tattttatga gaaatatgag 113220
aagtgaggag aatttgatca aagagagaaa acatagcaat tgttctttaa agttctacgg 113280
aacaaaatga agaagtgtat gtttgaaagc cacgtggaat atggataatg ctctaaatta 113340
cttatttgat aggaagacta atataccctt aggtgagaat ttatttccaa gaagctaaca 113400
tgttgatact gagctgcttc tcatgcttct ataatagtag aataataatc taatcaaaca 113460
taggaggaaa atttgggctc aaaaagtctt ttgcacattc tgtaattatt atttttatca 113520
tttattgtaa aagagcattg taaagtactt gacaagtgac tctgttattg cttgataagt 113580
cacctcatag gccccatttg catgtgtgat tgctttattc atttgtattt tcccctttaa 113640
tttctaagca gcacctgcaa aatgttagca atatgtgttt aaaaatcaga attactgatt 113700
tcaataaact ttgcagaatc acgaagtaac taaagtttaa taaaccagta agaataaaag 113760
aacataaatt aattgacaaa actaaaatct gtaaaaaacg taccacaatc tgaaaaaaca 113820
gaatcagaaa aagatcaagc ccactgaatg cacagtattc ccttaaggaa attattcccc 113880
tctagtattc gaggtttgat ttggaatatg tccacccaga atagaatgat ctcaatcacc 113940
agtgtattga tacccaaaac tctggtgtca gcgaaccact ttacagcagt aaagtacacg 114000
aaaatttttt gtgcaaaaga agaagaagaa atcagaaaaa ttcattagga ataagtccga 114060
ggaatcaatg tatttatagg gaagaggaac tggttccgaa aggttgtaat cctttcagaa 114120
tccacacgac cattcatgaa agtttgcaac ctttcaaacg gtcatggctg tttctgaaag 114180
ttgcaacctt ttagaacagt cacttccaac ggtgaaaaat tcaaataaaa tgggaaagat 114240
ttaaattaaa cggatcgcgc gtggatccga gtcgggtcgg atcaattaac taattaattg 114300
aatcggttaa ttaactaatt aaaacgttgg tcatttaatt taattaattc aataaataat 114360
taacaaattt tgtccaaaaa ataatctctt gatcattttc cgaagctgaa gccgagcgag 114420
cgacgacggc acgagggagg tccctctttc caacccttt aacaattaat aggagtgttt 114480
ctatatttaa actctcatat ttttctttcc accacagatg agggacaaat gccttttcaa 114540
taaagcataa aaagactttt caagttctca actcttcaag ttcccaactt ttcaagttcc 114600
tctcttctca tctttcctcc attttccatt aagtcttgct acatacccaa cacaaaattc 114660
atttaaggaa atacctactg aagttatttt ctggttgaat ataacacctt tcattaatca 114720
tcaactaaca aacataatat tttagcagta taaaatacta aaggtaaatt aaatatatat 114780
ggaagaaaac ttcaatagtg actttagtga gatcaatact tggatgaccg tatagggaat 114840
taactcatat tcgaaaacta aactgatgga tttgtttaca aagagtatta cctcaggaaa 114900
tgttcgaatc tctcaagcaa taaagtggag ttcgattcaa aatgccaaat ggtgtttgaa 114960
aagatagcgt tttaattcat ggcctttcat ttacttgaca agttacctca tggtccattt 115020
gcctgcttga agaataacaa aaagtagagt tcttttgtac caatattgtc tcatgggtca 115080
tattcatgat taaagtttag aaggtaacaa cttcaaaaat agcattaaat aaatgttcca 115140
tttaatttgt tataactaac atttatgtct ctaaatatgc actatatatc tttcttttca 115200
cttaaaagtt tgcgtttaga tatacggtat gattaaagtc atgatttcaa atcaatattt 115260
aaacatgcgc ttttgaatta tgatttcaaa tcccaaattc ttcaaaagag aatgacttgg 115320
aatttaaatt atattaaata taaaatttga tacataatta agtttatatt ttttttaaa 115380 aaaaaagatt catcatttta aattttgcat aaaaaaactc atgtttgtcg tgaatagatt 115440
gttcgtacaa tgcaaaatga ttgcatgaat agctagttac tgctattgga gatagtggat 115500
ttttataaga ttatatgtat ttgataatca caaacatcta tttatgaaag gaacatgaag 115560
atatatgatt cattaatgtg gcactttagg atattccgat atcttattta tgaatgatag 115620
tttgctcatt tggtaagaat gcatattttt gagtaaattt gaagattttc acagcttgtt 115680
ggtttttcat gtttatgcaa aaaatacaat ttaagaaatt aaaattgcat gtccaatcaa 115740
aacttcaact ttatatcaat atgactccct accataattt catattgcct ctctagctaa 115800
acgaacccca aatttgtaat tttttatgtt ttatcgtact tgttctatca ttcaaatctt 115860
tcatggggaa agatcaacaa aatggattga gttctacaca ttacatgcat agtaaggttg 115920
aacaagaaat tcattgttta gacggttgtt gaactatata taatttaggg ggattttagt 115980
gtattttcct agaaaaagac aaataatata cctcctttgt cccattttat gtggcacatt 116040
ttctttttaa gtccgtccca aaaagaatgt caacttacta taattagaaa taatttcact 116100
tcaaatctta atgaaatgat ttataaccac aaaattcaaa agtctttttt aaaaatagtg 116160
tattaagtca aacggtgcaa cataaaatga gatggaaaga gtagctgtat tattaagcta 116220
cgttacagat accacctaaa acaacttgct agtactacaa ttcatctctt ccttcttcct 116280
ttaaaccctc ctccatttca tttcaataaa cttcctccaa tttctttgtt ggaacataat 116340
ccagatctga gaattataac tcttttttta cctcataata tttgtttttt ctcttgatga 116400
aacctgcttt caatattaat tatcatctct tttgctcctt tttatgattg gatcacaaaa 116460
ttgaagatat taaagaggta taagagaaga cagaattaca agttggtttc attgtaagtc 116520
atcttcttca tgaatgactt ttttcctatg gatagaaagt tgatttctca aacagtccac 116580
tcaactaatt gttactagta tattagctag aaagcccttt ttttttgttg taaaaatgtg 116640
atttttcttc tatgcattgt ttaattttat acaagttaaa tgtttattta tgcacatcca 116700
aagttagagg gcatgaatat caagttaaag aatatatgta tgtattatgc ctccaacaaa 116760
tccttgaagt tctgtattcc atctcagttt ttcaacattg ttaattactt tgagtcgttt 116820
gttttcaata tcattgataa ctatatcatc atgtttatat ttcataaata aaaaatttgg 116880
ttggtaagag taatggttat atctgatata gatggttcaa aggttggtaa gaataataat 116940
atcgattata aattttgttt atacatgaaa taattaagtg attgatagat ataaatgact 117000
tttttcttat aaaatataaa gttatgggtc aatttttata tatgaaaaat gtgaaatcat 117060
aatatgaaat ttttaaatca aattttggaa aattttgaat ttcacctcat gagctaaagt 117120
tgcatgtcca aacattgact tcatctcatg atttcaattc acgagataaa atcgcatgtc 117180
caaacaccta cttaaataat actccccccc cccctccttc cccccatgag ccaattttaa 117240
aagttaaatt aagcctaagt attagttgat catcttacta aaattagttg tccattatta 117300
gttgttcacc ttactaaatc agaaaagtat taattaaaat tttcttatat taccctttca 117360
attaattttt taaagtattc acattcgctt ataaaatatc aagaaatttt ttaagggata 117420
aattggtaaa attatttttt tatttataat ttcttaatat gcatgcgaaa gataatttta 117480
ttaaagtaaa gactagactt cttttgtacc aatataacaa gtcgcctcat aggtcatatt 117540
cataattaca gtttaggagg taaaaaaaat ctttttaaaa ggcatctcgg cgactgagaa 117600
ccataaggtg agcgccaaaa cgctagcacc aactgcttcc acaaacatgc atgataaggg 117660
ggtgtgggga caaccaggcc accactttat ttgaaatatg agccgctaaa atttatcccc 117720
ttttgaatgt atttacccct atgaacctga tgcatacaaa acttcaaaag taatatacgt 117780
tctattttag ttgatcattt ttcacacaca tattaataat cataaataga aagataattt 117840
tgttaattca cccaaaaata attcgtagaa ttttttacaa ataaatgtga acactttcaa 117900
aaagaataaa ttacaagggt aatacacgaa aaatttaatt aatgttttct tgatttagta 117960
aggtggagtg atgaacaact aatatgagac aactattttt agtaagatgg tcaactaata 118020
tgggacgaag ggaacaatac ataaatgcat gtttctttta atttgacttc aattgatttt 118080
tatgtcttta actttgattg tacacaataa tatatcttgt ttttcacttg taagtttgcg 118140
cttggacata taatatgaac tcatgatttt aaattccaaa ctcccccccc cccctcccca 118200
aaaataaaac ataatttgga atttcaaatt atgatatcaa attttgtaaa atagaaaact 118260
tgatccataa atttatattt tgtaaaaaaa aaataggact cgtgctcaac gtgaatagat 118320
tgtccgtacc atgtgaaagg attatattaa ggaataacta gttgattaat tagtggatcg 118380
ttataagatt aatcgcattt gaaagttatt tataatcaca aatatttatt caaggagata 118440
tgtgattcat caatgcgttg ctttaagata tttttttatc ttgtttatga atgatgattt 118500
actcatttga taagattgca tacgaattgg agaaattttg ataattttca caacatgtgg 118560
cttttcatgt ttatgagaaa aaaatataac ttaagaaatt tcaattgcat atcaaacaaa 118620
atttcatctt catattaata taatttcata tcacctgtcc aaattaaaca tgccccaaat 118680
taataatttt ttactttatt gtactttatt caatttaaaa aataattcat ccgactactt 118740
tttaaggggt acctgcaatc tcaaccagct agctgttttc tcatcatttc catagtctgt 118800
tgatgtatct cagaaacaaa aagttcgaca actttcctaa ttatagcact gctcaaaata 118860
tttgtgtagc aataatagag ttcttggttg ttttccttga agctgatgtg tcaaatcatg 118920
ttattaatgg taactggttg aatgatgcta tggaaaaggt tggagctata gcgggtgatg 118980

-continued ttctatatgc aattcaaaag gttcttccta gatctataaa caaagatgac accagcaaaa 119040
tgagtctttt ctccatacat atattaaaga aaactaaaga tctgaagaca caagtggaga 119100
cgtactataa atcattaaaa ttcactccat ctcagttccc cactgttggt ggatggagct 119160
ttctggattc tcttatacgg aaactgaatg agatgtcgga atctaaatct ggtttatatt 119220
tcctgatgaa acctctcttg gggaatttgg agaaagagct atcagctttt acatccattt 119280
tagagaagga tttgtcatct ttatcatcca ttttcagaaa tgtcgccaag gtacaccatg 119340
agaatgaaat tcttcaagat cttcacaggc gtactatcaa tttggcatat gaagctgaag 119400
ttgccattga ctctattctt gctcactata atgtttttg gcatattttt ttctcacttc 119460
ctacaatctt aaaagagatc aagcaaatta atgtgcaggt gactgagatg tgttcaacag 119520
acgttgctct taagccttgc tatgtggtag caccatttaa acacctgcca actcgacata 119580
gcaatccaat gactgatgag gagatagtgg gttttgggaa tgatacagaa aaaatgattc 119640
agtatctgat aagaggtaca aatgagctag acgtcatccc aattgtaggc atggggggac 119700
aagggaaaac gacaattgct agaaagttgt acaatagtta caacattgtt tctcattttg 119760
atgttcgagc atggtgcatc atttcccaaa catataaccg gagagatcta ttacaagata 119820
tttgtagtca agttaccggt tccaaggaca agggggataa ggacaaggac aagggggaca 119880
aggacaagga caaggacaag gggggataatg atgacatcct tgctgacgag ttgaggaaaa 119940
tcttgatggg caagagatat ctcattgtat tggatgatat gtgggattgt atggcatggg 120000
atgacttaag gctttgtttt ccagatgtta gaaatagaag cagaatagta gtaacaactc 120060
gacttaagaa agtgagtgag caagacaagt accatactaa tccttattct cttccattcc 120120
tcacaaaaga agagagttgc aaattgttgc agaaaaaagt gtttcaaaag gaagattgcc 120180
cgcctgaact acaagatgtg agtcaagcag ttgcagaaaa atgcaaagga ctgcctctag 120240
tgattgtctt ggtagctgga ataatcaaaa aaaggaaaat ggaagaatct tggtggaatg 120300
aggtgaaaga tgctttattt gactgtcttg atcgtgagtc ggaagaatat agtctggtga 120360
ccatgcagtt gagttttgat aacttaccca attgtttaaa gccttgcctt ctttatatgg 120420
ggatgttttc agacgacgca agaattccag catctaaatt gataagttta tggattgctg 120480
aaggattcgt ggagaacact gaatctgctg aagagtactt gatgaatctc attagcagta 120540
acgtggttat ggtttcgaag aaagaatata acggtaagat caaatactgt caggttcatg 120600
atgtagtgct tcacttttgc ttggagaaga gtagagaaga aaagtttatg ctagctgtga 120660
agggaaatcg tagccaattt caaccttgtg attggaagga acttcgagtg agcttcaacc 120720
aaacacggaa tccaaaacac agaaaccttg tgattggaag gatagtccaa gagcatttca 120780
actttgcatc tctgagatcc aaaacatgga aaccttgtga ttggaaggaa agccaggtga 120840
gcttcaacca aacaccgaat ccaaaactcg gaaacccttgt gattggaagg aaagtcaaag 120900
agcattccaa gtttgcatct ctgggatcca aaacacggaa acctttccat caacagttga 120960
tgtcactgat aacgaacgga gaatattttg atgggattcc cctctgtcag attcataaat 121020
tgcgacttct taaggtcttg gatttgagtt cccatagagt gaattctttg tcattagcta 121080
gtttcaaacc actaaatcac ctgaagtacc ttgcagtttt tgcaactaaa tttgattttc 121140
atcccgaatc acatatgccg catcttgaaa ctttaaccgt gaataatgat tgggaaaata 121200
tagtagtgtt accaacgtct ttttgggaaa tggaaaaatt aaggtatgtt gagatcgaat 121260
atgctgaatt tgataagcaa ggggtcagtg aaggaacctc taaattggaa aatttgagga 121320

-continued tattaaagaa tatttttaga ttcccaatga tagtgtggat gtgttatcaa ggaggtgccc 121380
taatctccaa caacttcaca tcggctttgg ggactataat tattctgcgg agtctttttg 121440
tctcacattg aagaatctta gccagcttca aaaacttcgc cttacctcta agtggcgccg 121500
cactgtatct gggttacaat tgccttcaaa tttaaagatg ttggtactaa gtgggactga 121560
tataggaaac cttattgcgg gactacgaag cctggagtat ctccaattac aaaatgtgta 121620
ttttcctcct tcagaagagt ggtgccttgg agatatcacg ttccctaaac tcaaggtctt 121680
gaaactggcg gcgtcacata ttttgaggtg ggatatctca gaggaatcat ttccccagct 121740
tgaaacactt gttataagag ggtgtaagaa tctcgaggag atccccctta gctttgcaga 121800
tattccaaca ctgaaacaga ttaagttgat tcgctgcaat aaatttctgg aggattcagc 121860
tgagaggatt aagaaagatg ttgaagagaa tgaaggaaac gatcgtactg acctcattat 121920
caaagtaagt agaaacaaac tcatatgttc tgtttttgag tatctacctg catctaactt 121980
gacagcaata tgtataatac agtattatta gggtcatttg gcagctgtga atcaattatg 122040
tgcctgtaat cacaacaatg gtaaatattg tttctgtttt tttcttgttc cttcttctaa 122100
tttaatgttt gcttttgctt aattgctcca tgttgatctc aaactaacaa ggatgtattt 122160
caatttgata attgcagcaa aagtacagcc aattgttgta gccgtgctca tgctcatgta 122220
tattgtgcgc ctagtgccga catccctgtc ctttttctgt atgttttaga tgttctttta 122280
ctgtgatttc ttgttgcctt ttataaacat catgcctttg ttatgtagct ttattatttt 122340
acaacctgtc aaaacattgc ttcttgtttg tttttgtaat atagtagttg tttcccttca 122400
tcttactcct atacaaggtg aattgaaaga tgagtattcc tgaatgaaag ctgttttgat 122460
agcttagtac taaatagttt aggagcaatc cataacatac gtctcacttc ataaataagt 122520
attgagtaca cgtacaaaag ctatctatgt tgtttggact cttcaaaaat gtcttccgag 122580
tgtatattgg attgtccatt ttacattttt ggaggatccg acatgggcac aataatatct 122640
ttggagagtt tgagcatcat aagaagccaa atagataaca cttgtcaaac ctctattcag 122700
ctttctaggg aggacaatgg cagagtctcc caagttgacg acatgtatgc atgtctctca 122760
cctttgacaa catcaccaga ggtatacgat tcgagttctt tcatgtcttc cgttgtcaat 122820
tttacagata aggctcctat gttttcgttg aagttttcaa tcttcgatgc acctggtata 122880
gggcatacat catctccttg atgaagaacc catgccaatg ctaattgtga aggggtgcaa 122940
ttagattgat tttctcaaat actggcttta tgctcaaaat tctctggctt gaacctagag 123000
aaattctaca aagcaaatca gcaaataata aattaatgtt gcagtcgaaa tagaaagatt 123060
cattgatgaa accattacat agctatatat atatttcacg gagcaaaaag gttgtgccaa 123120
aaaatttatc cgttaaattg tgcgttaaat cagtcgccag atgcatctca tgaaatgttc 123180
aacgaaaggg cgagtgggaa gtttaggaga atttttcctg aacttggaat aacaactgca 123240
attataacta tgcctcaatc acaaataagt tgcaatcgac tatatgaaat cttgatttct 123300
ccacttaagt tcaactaacg tcatcatcat accaaataaa ataaaagcaa aaaataagtt 123360
aaatatataa aacaatatta gaagttctta gaaaaagact aaatcctact ctccacggct 123420
agatatctcc tatatatggt tctatgtctt ctattgtgcc atattttttt gctaagtatg 123480
catttatcct tagaaatttg taagtatttc aaaattctac ctcgtctcct tttcaacacc 123540
tccactcgcc ttagtttcac acctacaaac cagtgcatcc gtaggtcgac acaagacatg 123600
tcacaccatc tcaagcgcac aatgctactt gcacttctag cgaatatgga tcattttaaa 123660
ttttatttaa tattatatga tcgcatatcc atcttagcag ttggtcaaat tactgcatgc 123720

-continued ttggtaaaac cagattactc catgcttagt tagtgtcggc ctgtcgggca gtttaattca 123780
aagacatcag catgtccata aaccagtaga atttccagat ttcaagaaga cttaagataa 123840
ggacatccag ttgatgctct ctgtaaaaca tcaatgcaca aagaaataac aggatactaa 123900
attcaaatgc aactacaaat atccagttga tgctcactgc acattcgtat aaatgtctat 123960
taaacaggaa acacaaaagc agtcacagtt ttgatttatg tggtctaacc ttgcaaaagt 124020
caccatcagg caagatttca atcaactttg cccctgctga gaagaatcct cgtccgagag 124080
gactataggg gacaatccct atgctaaggt caaaaaaatc aaaaactgct aatcttgaac 124140
tcaaatctaa aataaaaaat gtagaaagga aaatacttgt tattatttag atacaaaaat 124200
ttcatacttt cttttaacag acacagtgtc ccagctagct tgcacgaacc tcaatcattc 124260
caaggggtac ccgcaactct atccaccaaa tattagatag ctaggaagac atcacctaat 124320
ttataccttt actatcattt gaacttgaaa cctcatggtt ctcgacccct atcatccaca 124380
actagccaaa tacatatcac tcgtcaaacc cctactcagc tttccagaag gacaatggtg 124440
acgcgcatct ctgaatttat ccaacaaaat aagatttacc agtgtcaatt ataagactct 124500
aaataagtag aactgattta tttgcagtaa gaacaacaat gtgattaata aaggacaatg 124560
tgaaagttca ggtagtcaat taattagttt tctctgtagc caactgtcct ctccttccac 124620
acactttgat taatcattaa taatagatac taaccttcca attaattagt tgtctctctg 124680
tagtatatca taagccatgt tatttcatta aataatgcaa ccattgactt tgaaagccaa 124740
tgggaatgca tattaacctg tctaaaaatt aatatgataa acccaaaaat tattcattaa 124800
ataatacaac cattgacttt tttgtaggat ttagatccag tcctttggct aaaccataat 124860
tatacatcca ctaatcttgt tagagtatat gacacaaaca tttcctcatt gttccaagtt 124920
aattatgctc atattaatct tttcttgtta gcttaatcct actccaatct ttatcaggta 124980
tttttcaata aacatttttc taatctccct atgaattttt atcctttctt atatataagt 125040
tatcaacaac tctttttcta tgattggatc agaacttgga gatacaaaaa ggcaaacgaa 125100
gatcgattga tcgactactc gtcacgcttg aaattagtaa gatatattga atgttaactt 125160
tctattgctc tccaaaatct cgaacttctt aaattgatac aacaactgag ttattaatcc 125220
attttaccaa taaacttcat ggttccaaaa ctacaaatat tgtgaatatg gttttgatgt 125280
atattaatgt agacatttat gattatcttg tatgaaacaa tatggcactt caaaacactt 125340
gtgtttttat tccttatatg gtttagataa ttaaaaaatg atatcaccca taataattag 125400
tttttgctcc gttgaaccag ttaaagaagt gttttatatt tgttttcctc tttaaatttc 125460
tatttaaaaa aaaagtgatc aacagcagat ggctggttat atgtttttat atatacaaat 125520
tgggggtagg gatttaaact taaggtgaaa attctgatat ccaaccaact gagcgactaa 125580
tcgtgctatc cttctccaca cacatttttt tttattaatc attgggtatg cattagttat 125640
ttctctgtac tagtaattaa tagggaaaaa ttcgctaaaa tatgtcatcc aactttgaga 125700
aaaaacaaac ctcatttatg tcgtccatta atagttgggt tcaatcatgc ctttgtcatt 125760
acataaatga cccattatgc cattattttt taatattcag attttgtggt tttgcaacac 125820
catttttcca tatggcctct tattagaggt ccacgtcacc aaaattaaac tggtcaaaaa 125880
aaaattcaaa tatgtcatgg aactgtgaca aacggttcta tgtcattcgt taattgttgg 125940
atccaaccat atcacagccg ttaaatttga aattaaaatc caacccatta ataccagacc 126000
cgacccaccc taacccattt ccctttttatt tctcctacaa acgcttggat ccaaaatttc 126060

-continued tcccatttta atgatgaatt tatatgtcag tttcttgtca attgatcaat ttaagggtct 126120
ggggagaaat aaaaagggaa taggttaggg tgggtcgagt gtgaatttat ggaccaggtt 126180
ttaatttcaa atttaattaa attaggttgg tttattttgg cacgtggacc tctaataaga 126240
ggccacgtga aaaaaaaaaa tttgcgaaat gatcaaacct gaccatttaa aagtagcatg 126300
aatgggtccc ttctgtaacg acaatggaat agttgagccc aattattaac agattgcata 126360
aataagacct tttttctaag tttgatggtg catttaaatt ttttttatca gtttaatttt 126420
ggtgatgctg acctctaata agagaccacg tggaaagaac gattttgcta accatcaaac 126480
cagctgcctg ttaaaaaata atggcacgaa tggaccgttt gtgtaaagca gtgacatgat 126540
tgagcgcaac tattaacggg aggcataaaa aagtcttttc ccaaagtttg atggcaaatt 126600
ttaactcttt tacattattg ttaactcaaa cacaatttaa agaattttta tgtgattttt 126660
taatagttga tatctaggca cgtgcaacga tactagtact actatattat aatacctaag 126720
tgttagtcaa agcaagtatt gtgaacataa aagctacgac aattgtatgg aatatgattc 126780
ccttttataa gtgaggaaat tcattttctc cctttttagat gaaacttgtt tcaatttctc 126840
gacttccatc acagtttaga cacacaatag atgagcttga gatctaaaaa taagcaattt 126900
taagttgatg tttcattttc catttctata tgttaagtta gtcggtagaa taattataat 126960
gaccatcttg tcagggccaa gttttcgtga tatgcatcgt ggagctcaaa agtgtagtga 127020
acttatgttc tgtattgtca cttttttttaa aaacttattt gggctattcc tatgtgtgat 127080
tcaactaaga tgcttgtcaa tccttttctt tgacctgttc ttatcggtcc accctccatc 127140
attagcgtca cacatttgat attagttttt tttgtttaaa gaaaatgact attagttgag 127200
tgaccatatg aaagttgagt gaaatgtgat tttatgagat aatatgtcac gccccgagcc 127260
tacaccctgg gcgggaccgg cacccggaga ccattcctgg ccccaagcga acccttggcc 127320
tggctttctt aactcagcgg aaacctaact caacagaata actcaatgcg atgcaatatt 127380
gcaaaacaac ttaacataaa aagtatggcc ataaggcaac ccgagtctca aaataggatg 127440
tttacatata tacatagata agagacttaa aactagctga ctgactgtct gtctgtctat 127500
gaagcctcta aaaaaaaata ctgagatgga tgttgggaca gaccccgcaa tatcctaata 127560
agacaaaact aagaacacaa agtaattgag tcctccggaa tgcaaggagg ctcaccactg 127620
actctggagt gctcagctgg atcaacgacg tacaggatgc tgatccgggg tacctgaatc 127680
tgcatcatca aacgatgcag gccaactggc atcaatacat ggaatgtacg agtatgcaag 127740
atggaaaact aagcaacaaa ggctagaagg aaatctggaa gaaactgaac aacttacctg 127800
gctcaactca acctgactga cttctttcaa tataaggcaa tttaaaacaa gtgcgatata 127860
aagaaagact gcttaaaaca tgctataaac tctgtgtgta tacaaagata caataggcct 127920
gaaatgtata tagaaataca atgaactgat gtatataaaa tacaataact gtagtgggag 127980
tttctctaac cgacaaccat cacataagag ctatagtgat gatacagcga tcgacctcac 128040
gctgccagag catcttatac ccggccaaag gtataagacc tgaactgcct aatggatcca 128100
ctagtctaat ctgaaaagga ttcatctaaa aagtatgatc cttttctacc catggtggct 128160
aacatggttc tatgggggct gtgggttctt tgaacgctcc cccaattcgg tgctcgatac 128220
tactcccaaa atgtactggc tcttatgttt ttaaaacata tttattcctg ctgatatgag 128280
ataattactc aaaaactagc ccgaaggctc ctttggaaat cttagtttcc aaccttgtct 128340
aaatgtaaaa acatttattt aaaacttctt tgggaataca tagttcccca ataactttga 128400
gaaaagaact caactttaaa ctcatgactt aacttgaaac tgagactctt actcgacttg 128460

```
aaactctata ctcttttact tgacttctaa ctatctttcc ttgaatcgga actatgaatt 128520
caagggattc gatcacatgt tgaggaggga tccttgaacg cttagacgta cttaggagtg 128580
tcggaaacaa ctataaaaca taggtataat acttggaact tgcatgagaa agtgagaaaa 128640
ggaatgggga aacttggcta aaacttcaga tttctggtga cacaggtgtg acttacggac 128700
gccatcgacg gaccgtagat ggacttacgg tccgtcctgc aggtccgtag atcgcttcag 128760
aaacttcccc agaattcatt tcagaaaatg actaagtgtt gacctacggt cctgacttac 128820
ggtccgtagg tcaggtcacg gaccgtaggt cgtgaccgta gatcgaagcc ccaaaaaccc 128880
aacttctgtt ccgattgacg gttgaccagt acggaccgtc aatcgatcta cggtccgtag 128940
gtcaggcccg tagacgggaa tcatcagccc agaaatttct gtgaaataag gatgaatcaa 129000
cttcacaagg gtcataactc tagaatcata attccctcaa catacaatag gtttcaactt 129060
aaatactcga ccccaatcat gtctcacgaa gaacaataac ttcaacaaca aattccatct 129120
tttctcaaat catagaataa acttggtgtg tgtgagggaa aggatcaacc cacacgaaaa 129180
ctcacatacc ttgataggga tcacccccga cgaaaatcca caatgatctt gttgatctcc 129240
tctttcttct cttcttcttc ttcttctcct tctccttctt ctcttcttca atctcaagaa 129300
ccctaactct ttctctttca aaatgggaca aaaatgatcc aaagatcatt ctaatacaac 129360
aatatgagct caattaaatg atttgtgaaa ggaccaaaat gcccttaaat ttccggacgg 129420
atttcccttc caactgccca acttctacaa agcataactc gctcatacga actcggaatc 129480
gagtaaactc agtggcgttg gaaagattgt tccaagggct tcgcaaccat aactggaact 129540
actcctaaat catcctgggc taggagttac gactactcaa agttggccaa aaactcattg 129600
atttccacac ttagccaatt ttttccagat tcgtcatttt ttccaaaaat gactatttcc 129660
aaatttcaag ctccttctaa gccacttcaa attgtcggat gttacataat atgcactatt 129720
tgaattagat gaaatggtac ataaaatgta ttatctttca taagcattga catagctaca 129780
aacactagat attgaaagac gtgaataaaa tgttgttgtt aatgaaccta atccaagagt 129840
tggtgaactt gcaggaagtt ttcaagagaa gatggctgaa aatgaaattg aggaaatgtt 129900
agatcacctg agaaggatca agagtggagg taatctggat agcgtcaaga ttgatgaaat 129960
tgagaggctt gaaatggcac taagagtttt gagaaccttt ataaagtatc atcatgttct 130020
ttttcgtgat tccatagtca aacacaaaaa gaatgccaaa ttgactatgg caatgcttcg 130080
ccgggtattg gatgggattc cagatgaatg taaaactaac cttaatctgg aaaggctaga 130140
atcacatttg ttggaattct tggaacgtga agccatttta aataacgatt atgagttgaa 130200
tgattttgat ctgtcgaaat atatggattg cctcggaaag aatctaaatg atgtactgat 130260
gatttcactg gaaatggtta ggtttggcct tgaaatacac ggatttataa aggaactaaa 130320
aattgttcaa aagaaactga gatttttgaa atacttatat gccacagaga taaatggtta 130380
cgtcaaccat gagaagttgg aatgtttgga gactcaaatt caattcatgg ctaacaatgt 130440
gggacaactt tgtcttttta ctttaggtta tgttgatgag gatgaggatg aggatgagga 130500
tgaggatgat atcttgaata aacctcctta tttattattc ttgattgtgt tagtggagct 130560
ggaaatgaag aagatttttc ttagtgaact aaaggcttca aagtttactc attcaagaac 130620
tttcaaggac aagaaattac caaaaggaat ttcttttcat ctccacagtc tactgatgta 130680
tatcagaaaa aaaaaagctc gagaactttc ctgataatat ctctgctcaa aatattgatg 130740
tggcaataga gttcttgttg gttttccttg aggctgatgt gtcaaatcat gttattaatg 130800
```

gtaactggtt gaatgaggtt atggaaaaag ttggagctat agcgggtgat gttctatatg 130860
tgatccaaaa gcttcttcct agctctataa acaaagatga tactagaaaa ataagtcttt 130920
actcgataca gatattggag aaaactaaag atctgaaggc acaagtggag acttactaca 130980
aatccttaaa attcactcca tctcagttcc ctactgttgg tggattgaac tttctggatt 131040
ctcttataag gaaactgaat gagatgtcga aatctgaatc tgatttaggt ttcttgatga 131100
aacctctttt aggtaatttg gagaaagagc tatctactct tatatccatt ttagagaagg 131160
agctgtcatc tttatcatca attttcagag atgtcgcaaa ggtgcaccat gaacataaaa 131220
ttcctaaaga tcttcagaga cgtactatca atttggcata tgaagctgag gttgccattg 131280
actctattct ttcacagtat aatgtttttt ggcatattct ttgctctctt cctacaatct 131340
taaaagagat cgagcaaatt aatgcgaagg tgactgagat gtggtcagca ggcatcactc 131400
ttaatccttg ctatgtggta gcaccattta aacacctgcc aactcgacat agcaatccag 131460
tgactgatga ggagatagtg ggttttggga atgacacaga aaaaatgatc cagtatctga 131520
ttagaggtac aaatgagcta gacatcatcc caattgtagg catgggggga caagggaaaa 131580
cgacaattgc tagaaaggtg tacaatagtg acaacattgt ttctcatttt gatgttcgag 131640
catggtgcat cgtttcccaa acatataacc gcagaacgcc attacaagag atttttagtc 131700
aagttactgg ttccaaggaa aagggagata aggatgacat ccttgccgac atgttgagga 131760
aaagtctaat ggtaaagaga tatctcattg tattggatga tatgtgggat tgtatggcat 131820
gggatgactt aaggcattgt ttcccagacg ttggaaatag aagcagaata atagtaacaa 131880
ctcgacttga agaattgggt aagcaagtaa agtaccgtac tgatcctcgg gtattctctt 131940
ccattcctca caacagagag acgagttgca aattactggc agaaatttta aagtgttgtc 132000
aaaaggaaga ttgtccgcct gaactacaag atgtgagtcg agcagttgca gaaaaatgca 132060
aacgactgcc tctagtgatt gtcttggtag ctggaataat aaaaaaaaga aaatggaaga 132120
atcttggtgg aatgaggtga aagattcttt atttgactat cttgattgtg attccgaaga 132180
atatagtcgg gctactatgc agttgagttt tgataactta gttgattgtt taaagccttg 132240
tcttctttat atgggaatgt ttccggagga tgcaagaatt ccagtgtcta aattgataag 132300
tttatggata gcggaagact tcgtggtgaa cattgaatct gctgaagatt acttgatgga 132360
tctcattagc agtaacgtgg taatggtttc aaagaaagaa tataacggta aggttaaata 132420
ctgtcaggtt catgatgtag tgcttcactt ttgctcggaa aagagtagag aagaaaagtt 132480
tctgcttgct gtgaagggaa atcttagcca gtttttacct tgtgatttga aggaaagtcg 132540
agtgagcttc attttgagta aagagaattc caagtttgta tctctgggat tcaaaacaca 132600
gaagcctttc caccaaccat taaggtcact gatgacaatc ggaaaatctt ctgatgagat 132660
tcccttgagt tcttggattc ataaattgcg acttcttaag gtcttggatt tgagttccca 132720
taaagtgtat tatttgtcgt cagctacatt gaaaccacta aatcacctga agtacctcgc 132780
agtttggtca gagaaattct attttcatcc agaatcagat ctgccccatc ttgaaacttt 132840
aattgtgaag acttggagta atatagtact gttaccagcg tcttttgggg aaatgggaaa 132900
tttaaggcat gttgagatcg ttgaagctaa atttgataag caggggcttt ttgaaggatc 132960
ctctaaattg gaaagtttga ggatattaaa gaatattgtt agctttccaa ttgatagggt 133020
ggatgtgtta tcaaggaggt gtcctaatct tcaacaactt cacatcgaat ttcacggggg 133080
tgatagtgat tctgcagagt ctttttgtct cacattggag aatcttaccc aacttcaaat 133140
actttgcgtt tcctttgagc ggccccacat tgtatctggg ttacaattgc cttcaaattt 133200
aaagaagttg gtactaagag ggactgatat aggaaacctg atttccttta ttgcgggact 133260
accaagccta gagtatctca aattacaaga tccctatttt cctcaatcag aaaagtggtg 133320
ccttggagat atcaagtttc ataaactcaa gttgttgaaa ctggtgaact taaagatctc 133380
aaggtggaat acctcggagg aatcctttcc ccagctcgaa acactggtta taaaaaggtg 133440
tgaccatctc aaggagatcc ctcttaactt tgcagatatt ccaacgctga aacagattaa 133500
gttgattagg tgccagaacg aatcactgaa ggattcacct gcggagatta agaaagatgt 133560
tgaagagaat gaaggaaacg accgtattga cctccttatc aaagtaagta gaaacaatct 133620
cctatgtttt gtttttaagt atctacctgc atctaactgg acaacaatat gtataataca 133680
gaattattag ggtcatctgg cagctgtgag agtcaatcat gtgcctgtaa tcacaacaat 133740
ggtatatata gtttcttgtt ccttcttcta atttaatact tgctttaact taattgctcc 133800
atgttgatct caaactaacg aggatgtatt tcaatttgat aattgttgca gccatgctca 133860
tgctcaagta tattgtgcgc ctagagctga aattcctgcc ctttttctgt atgttttaga 133920
tggtctttaa ctgtgatttc ttgttgcctt tgttatgcag ctttattatt ttacaacctg 133980
tcaaaacatt gcttcttgtt tgttttttgt aatataatag ttgtttccct tcatcttaca 134040
cctgcaaaat tcaataaagt atacaattga aagctggttg aatacaagtt tatatacctc 134100
cctattatca atcaatagaa tactgaatga aagttgtttt gatagcttag tactaaataa 134160
tttaggagca atccataaca tacgtctcac ttcataaata atcattgagt acatgtacaa 134220
aagctatcta tgttgttccg actcttcaaa aatgtcacca agtttatatt ggattttcca 134280
tagaggatcg acacatgtgc aacaatatct ttggagagtt tgagcatcag aagaagccaa 134340
atagatatca cttgtcaaat ccctattcaa ctttctagtg tggacaatgg tggagtctct 134400
gaatttatcc aagttgacga catgtataca tgtctctcac ctttgacaac atcaccagag 134460
gtatacgatt cgagttcttt catgtattcc gctgtcaatt ttatggataa ggctcctaca 134520
ttttcgttga agttttcaat cttcgtagtg cctggtatag ggcatgcatc atctccttga 134580
tgaagaaccc aagccaatgc taactgtgaa ggggtgcatc atttccttgc agctgttgtc 134640
tcgaaattca tttccaatta aagtatttca gaaattactt gttatgaaag tgtttatcat 134700
aaattgaaga agttcgtaaa atgacatcaa taaaatcgta aaacaaagag aagcaaaaat 134760
ggaagagtag catagactta acaaggtgtg tcgcacaaaa catggactga tataccaagt 134820
acaagtagta cttttggata acaacttgac tctataaact acgatcaatg aaataggatt 134880
tacctgaatc atataatgca actacttctt aaaaattaag agtgatatga gtacactaca 134940
aaaatataac tttggaacaa agatgtcaaa ccgtgacttc aattggcaac tgagtatcga 135000
tgcgatgaac ataatacata tgtcattacc aaagtgtcaa ttttctgctg aatgcttctc 135060
aaagtgagag agtctttcca ttatatagag aaaataaaga ttacacatcc ctaaagatcc 135120
gatccgccat tccctacccc taaagatcag ctatctatct ctacaaatct gctattgaat 135180
ccctctaaat ctgccttgct atccctccaa atcagctatt ctatcacaat atttattcct 135240
ttgattctac aacaaatgta tatgatcatg ctaatttata tcactgtata attacattaa 135300
tatatacaat catttagttg tccatcatgc taacacaaag taagtagaaa caaactcata 135360
tttgctgttt ttgagtatct aatatgcaaa cagtatctta attactagtc acgacaacat 135420
ggtattcttt caggtttttt tactttttcc tttatgttct ttctttttca gataagatgc 135480
ttgatttctc ttaattgctg catgtcgatc tcaaacgaac aaggatgtgt ttgaatttga 135540
caattgctta gaaaactgca gcgaaagcac taacagcatg gaccgagttc actcttagca 135600
aattgttgta atcatgctca agctggagtc tattagccaa aacacccatc cttgtgacac 135660
tatactgatt actaaggttt tttttaggga aaatgcataa gtacaccccc ttcctatgcc 135720
caaaatccct gagacacacc taacctttac taaggtccta ttacccccga acttatttta 135780
tatataattt tctacccctt ttcggcctat gtggcactat ccttgaaaaa attgtcaaca 135840
cgcgatgggc ccacaagata gtgccacgta ggctgaaaag gggtagaaaa ttatatataa 135900
aataagttca agggggtaat aggaccttag taaaggttag gtgtgtctct gagatttcgg 135960
gcataggtta ggggggtact tatgcatttt ccctttttttt tattgttcga cttagacgat 136020
tcattcctga tgggaaggga agattttttt gccttgttcc tttattttcc tatatgtttc 136080
agatggtctt ccactgtgat ttcatgatgc cctctataaa tatcatcact tgcttttgta 136140
acttggtggt tgttttcccc ttttattttc tataactagt ttcaggacgt gtgttgcaca 136200
tgtactcccc agaaaatttt tcgaactaag actcaaaccg ttcttcatag tgagtgagat 136260
ttttgcaagg aatttgaaag ttctcgagtg ttaaggtcac tatatgtagc accttaagtt 136320
ccaagaagaa tcgaagagaa aagcattcaa gtcattccta agtttttctt aagttttggg 136380
caacttcaaa tgactataaa ttttagtaca gaatgagtta ggagacccat aagatgttaa 136440
attaaagccc ttcgagtcct ctttccaacg ccaccgagtt tgatcaattc cgagctctga 136500
gtaaaaagtt atgacgattt actaacgtcg cacaaatcta gtgaggacaa tggtggagtc 136560
tctgaattta tccaagttga cgacatgtat gcatgtctct cacctttgac aacatcacca 136620
gaggtacacg attcgagttc tttcatgtct tccattgtca attttacaga taaggctcct 136680
atgttttcgt tgaagttttc aatcttcgta gtgcctgata tatatagggc atacatcatc 136740
tccttgatga agaacccatg ccaatgctaa ttgtgaaggg gtgcaattag attgattttc 136800
tcaaatactt gctttatgct caaaattctc tggcttgaac ctagggaaat tctacaaagt 136860
aaatcagcaa aataataaat taatgttgct tttaatttat ctctcttctt atcattacta 136920
caatttattg ctttttcatc tcccctcatc attactataa tttaattttt tttttaaatt 136980
agatttttta ccctctatat tttaataatt tttttaaatg aaaaatctta tttactaccc 137040
tctttattat cataactagt taacatgttc gcgcttcgcg cgatcataac aaatattttt 137100
aagacaattt cttttataaa ttagcacata ctaaaaaaag aagaaatatg atcaatactt 137160
tggtaaaagc tttaaaatgt ttatgataat tgtttcaatt tataagatac tattttcgta 137220
ttattttgta ggggtgaaaa gaatatgttt aatattttga aaaaaaaaat gctaacttaa 137280
ttttctgctt aatttttttat ttgtcgtgga tcatcaaatg aaacgtaaat aatctttcct 137340
cctcgttttt taaaagtagg aatgcttatt ttatataagg aactactgaa cttagaccct 137400
tttagatata attcttcaat atgatttgtt taacaaaaat atacttgtta ggtacgtaat 137460
ctttcataaa attctttatt tttaaaaaaa gattgtgcaa gttaaaatat gaaaaataac 137520
aaaaagcatg tcaatagtaa tacaaaggaa agaacgacta actattttct aatcaaataa 137580
aatataaata taaaaaatca taataattaa attgaaaagc aatcaatatt aatatttcaa 137640
caaacaactc gatacaaaac atatcatcat ttttatttgt tttaattatc aaagaataat 137700
tatacaaata ataaatagtg aatattttaa cttttgagga gttacaaaac tcactaaata 137760
tataattatt tagagaaaat cacaatttaa ataatgacaa aaaaaggcaa agaatgggag 137820
aaaaagaata agtaggactt ttagtatata agagttcctg ctatcgtttg tttttatatc 137880
atatcgaaat tatttataat ttttttcgtc ttcacacaaa taataaaaaa agtttatctt 137940
tatttacaca atatatttca ctaaaataat acttcaattc attttagtgt gtattttgta 138000
tgttttgttg aggtcattta tttaattact aaaaagttag aaaatagaaa aatatatttc 138060
attattttag tacaaacttt aaaaatctca agttttaata aataatactc actccctcta 138120
tttcaaaata agtgaattgt tccaagttta agagagatgt tgaaaaattc ttccattttt 138180
gccctcattt acaatgttaa ataattataa aagaaatgac cttttaaata caaaatgtgt 138240
acataacgtc atcaggaaaa taaattattt attttaaagt tatttagagc gcatagataa 138300
atgacttaat tttgagtaat tttaatatat gacgtaaatg aaagaaaaat ggaaagacgt 138360
cttaaaaaaa gagagaaaga attaagtaaa aggaaattga ggagacatgt taatttagaa 138420
aaaaatataa atagataaaa aaaattataa gtcatgagat ggatcaaccc tttaataaaa 138480
agaacaacgc aacatagtag tatttcctat taattttaaa caaaattaga gtatgtcttg 138540
ttaccaaaag cttacaacca caaataaaga aaaaaacata tgctcccatg aaaatgttct 138600
acgtgtaaat cttgaatagc tgatgtgcaa atgatagact aaaatctaaa tctattatat 138660
gttgggaaaa ctaaatgtag aggtgatgaa aagaatcgta gaaaggagtt gaggagatat 138720
gtcattattt aagtagaaaa aagtgaataa actaaggttt ttgtaattta tgagatataa 138780
ttagctgtaa taaatattat attttttttt agttatcaaa caaattaatt aatgaagaga 138840
gtaaatcatt ttttgagttt cataatcaac ttaaacaaat atcaattttc tctaaaactt 138900
aagaaaatat gttcattgta attagatatt ggcagaacaa acttggttca ttttgaaaaa 138960
tttcactaaa ttagaagaat taaatgtttt gtgaaatttg aatccaacaa taatatatat 139020
cgactaattt tacacaagtg ttaacaaata agaaacaaaa acttaatgga ggggaactca 139080
tctccttttt agttaattca aaatccacaa aagaaaaaaa tttgttatat catctaaatt 139140
agaatgaaaa aaagcagata atgctaaaca aaagatgata gaatcttgat tgagaaatta 139200
tgtcatatta acatgttata tacataatat atatcgatat aaaatatgaa ttgtatatgc 139260
aaaagacaaa agtttatata atgaaagtat caattaaagt tttctttaag caacaaaatt 139320
ataatatgtg gaagatcatg ttgcccttga tacaaaaagt gtgctttgta atataatctt 139380
gttcttgaag ggtacatatc ttgatggata aataattaat tgaaaaatta tataagcaac 139440
aataagtgca tctatatatt tgtaaattat tgaaacttct actttttcaa atcttgatga 139500
atctcccacc gtcattaaac tttcttcatt ttgatgactt gtagcaaatt aatttttgaa 139560
tctcttttgg cgaatcttac accgccttca aactttcttc ttcatcttga taaacttttg 139620
cttggcaatt gtaacacaag aagaaattct aaaacatata tctataatct tcataaaagc 139680
tgaaaaacaa aaaaaatata ttaacaatat gaagttggag aaaatataaa tggacatgca 139740
acaacaccat agatgattgt tatttataga tgagaattaa gtagaaggaa gttgaggaga 139800
cgtattattt aatttgagaa ttcaaatagg tagaggtttt tttgtaactt tcatgtgata 139860
taattatatg taatgaatat gattgatttt tttaattttt taatgattga ttaatgaaaa 139920
aaatgaatgg aaaaactcaa aaaaggaaga aaaaagataa atagctttct agaccattga 139980
gaggtgtcac atcaccttgt ttagatcttt attatatata tatagatttt tgtaattaac 140040
taagtaatac aaccttttat ataaattaaa taataaaaat aaaatattaa aaaaatattt 140100
tttcgtaatt gtaattagaa gaaggacaaa aaattaattt tttttatta ataatagaaa 140160
ttagagaggt atgaattacg aataattatt ccttgtaagt tggcatgtga agagtctttg 140220
ttgtaaatgt tttttcatta atataatatt tattgtaata aattaaataa ttgactttta 140280

-continued

```
caataaaata agtaatttaa ataaaaagaa aggccaaaaa aatgagaaaa aagataaata 140340
catatgaaga tcatagagag gtgccacatc accttgtcta tgtttctcct ttatattata 140400
ttaagttaag atttataatt attattgaag aaaaatttct tctttaaagt ttttttttta 140460
tggatctata aaatcagtaa aaataataat tcaaatacct taattgtctc tctcctcaca 140520
ttactacaaa tttttttctt aaactttttt tttttacctt ctattttaaa aaaaaaaaga 140580
ttctaaaaat aataatatta ttcatttctc ttccttatta tcataattta ttattatgct 140640
taattttgta actattctct tttactcttc taaaacgttg tagaatttat aattttaatt 140700
ttaattcaaa tgtagtaatt tcacattttg tttgtcaaag taatatccta acttagattt 140760
tttttatcg tgatttacta aattcatatt tgatttacaa attgaaagaa aaggaattga 140820
gaaactatga ttatcttaat gctttgaagg cacatgataa cttaaaaaga tgtgattatt 140880
tttctcatct caaaataatt aatatatttt gtatgcatat gctataataa taaacctttt 140940
ttttaaaaaa aaattataaa aaggattcaa ctttattgct attggcattc tgataaagtt 141000
tgtttagaaa acttttctca aatttgttat atgcattttg ataaagtata tagtgcctca 141060
aataattagt ttctttaaat actttatatt atttgtgtaa ttggggttgt acatctctca 141120
atctattctt ttttttatat aaaaaataata aaaaaattatt tatctctctt ctttattacc 141180
ctaattaatt attcttattc acaaaaaaac tcttttttct taactgttat tattcacaaa 141240
atttctcttt tttttaaaa aaaaaaatat attctcttga tccgtaaaaa taagatatct 141300
cttgattttt aaatattttt atcctttata ttttatgtta aaaaaaactc aaaagaagtt 141360
atccttttc tccttttcat gatttttaaa gatttttctt atttatattt tatgtttaaa 141420
aactcaaaaa aagttataaa tagtatctaa tttgatatat ttttaacata attatagtat 141480
tcaccttata ttatgattat aataaatatg tttaccttat tgatctctct tcttaccttt 141540
actataattt attgctttca tctcctcatc attacctata atttaatatt ttttcttaaa 141600
ttagtctttt taccttctat ttttataaat ttttaaaaga gaaaatctta tttatctctc 141660
ctccttatta tcataattta ctattattat tgaaatttgt tttcttcttt aattttttt 141720
tcttttattc tataaaataa atgaaataaa attcaaatat catatatgtc tctctcccca 141780
atccccatat tactacaatt tatcgctttt tcttaaattt ctctctctaa tatatatttt 141840
aaaaagattc taaaaaataa taatattatt catttctctt ccttattatc gtaatttatt 141900
attatgcatg gaatttctat tttttctcaa ttttatttct ttttatctat aatatttgtc 141960
aaaaaattat ctatttaacc aagaatcatt attattttt tcctcttatt cttgactttt 142020
aaaatatttt ttcttattta tgtgttatgt taaaaaaatt caaattcaaa aaaattataa 142080
aaaatattat ctaatttact ttttaatata gttgtgctca catttataat atgatattac 142140
atttcaaata ataataatat atatatttat atatacacac acacatacat atatttatat 142200
aactttttt tctatttaaa atgctatata ataaagaaga aagagagaga agtagttaaa 142260
gaaaaataaa taaaaagtaa cggttttaca tttttttcct ttcatgtgtt tatttttatt 142320
gtagttactt ccaaaaaaaa attctttcct ttttcttctt taccttcctt ttacttttta 142380
ctcaattcac tactatacat cttcttcctt ttattttgct atttcctgcc tcatctcctt 142440
atatttttt tctaattata tcacactaaa tttattcttt actattagaa aagattcact 142500
actatcttct tccttttatc ttgctatttc ctgcctcatc tccttatttt ttttgtaatt 142560
atatcacact aaatttattc tttactatta gaaaagaaaa tcaaaaaaat atttttctta 142620
taacttttca tttgtgaaaa agaaaaagaa tagaattaga gaactaatac ttcatggtgg 142680
```

catcattttt acggtttaca aattgaatgt tagaggacat tttgatgtct ttcgatcttt 142740
ggtatattga attcctaaat aggatttcat tgtacaattt tgatagatct gttgatataa 142800
ttcttgttgg cataaaatga ttaaatttgc acaggtatat tctaatgaat tcatttatat 142860
aaacaaatca aatttttaat ttacctgaaa tagtaaatct tcttgtggaa tgattcttca 142920
tttttctcaa tttacctcca tatttgaggt agtaaaactt ttcaaaaatt caatttacct 142980
gacgtagtat atcttctatt gcaataattt ttttccattt tgtcaactta cttttagatt 143040
atgtgctctc atgcgtaatt tcatttgtat aaacaaataa aaaaacttga tttacatgag 143100
gtagtaaaac ttttttcttt ttgacaataa tttttgaatt ttgttggtta cttttagttt 143160
atgtgctctc ctattttata atttataatt tttaattgat tgattgtact aagttcttga 143220
caatcgttac aactcttaat tctccattac aacaataaaa atatcatttt tattaaaact 143280
tttcattatc ctctttaaga aatatcattt atgttagatg tatttagtag attattatat 143340
taagaaatga ctaaaagagt tcaaaaaatt gagaaaaaaa taaaaataaa atggtggcca 143400
tataggcatg ccacatcaac ttttctagat tcagcttcat atatatatat agagtttatt 143460
ggtgcatgca gcaactccca agccgttggt ggcttaagtg tccctttatt ttcattcttt 143520
attcctccat tataccttgt aacatatgta actcctaagg ttattatctt cactatttag 143580
tacccccatt atcttcctat ttattcctag gaagacttct tctactataa atagtggtga 143640
tcttcatttg ttttacatat aagaaaatat agagtgcata aagtttgtta aaaaaagaga 143700
gttcttatta gttgaaggga tgtgtttttt ttgtggagct ttggactaaa ctcttgtcca 143760
tagttgttga gttatctttt gtgaataggt tgttgtatcc tggaggggac aagtaaagaa 143820
ggactactgc tggaccagtg aaaacatttg ctgcgtgggc ttgaatctcc ttaaagagag 143880
cgagatatcc gcacctcagc ttgaagagat ttatttcttc atttttattt tcaattgtaa 143940
tcttgtaatt ctgttatttt gtaatttttc actaaggact ttaagttttc actaacaatg 144000
aataattagt ttatgctctg ttgaaccaat taaagaagtg ttttattttt gttttcctct 144060
ttaaatttat ttatttttaa aaagagtgat caacagcaga tggctggtta tatgtcttta 144120
tagatacaaa tttggggtag ggagttgaac cctcataact gagcgattaa tcctgctatc 144180
cttccacaca cactttttta gattaatcac tgggaatgca ttagttgttt ctctgtacta 144240
ataattagta gagaaaaagc tcaaatatgt cattcaattt tgtgggaaaa aaaccttatt 144300
taatagtttg gctcaataat gtcattgtct ttatataaat gacccattat gccattgatt 144360
tttaacggtc agaattcatg gttttgaaac actatttttt ccatatggcc tcttattaga 144420
ggtccatgtc accaaaatta aattgattga aaaataagtt caaatatgcc attaaactat 144480
gacaagatat tcgtctatgt cattcattaa tagttggatt caaccatatt tctagtcaat 144540
tgatcaatct aagggtttgg ggataaataa aaagggaaat aggttagggt gggtccagtg 144600
tgatgttatg agtcaggttt taatttcaaa tttaattaaa ttaggtggtt tatttttgca 144660
tgtggacctc taataagagg ccacatgaaa aaaataattt tgcgaaatca tcaaatttgg 144720
ccgttaaaaa agtagcacga atgggtcctt tctatagcga caatggaatg gttgagccca 144780
attattaaca aatggtatat atgaaccttt ttccaaagtt tgatggcata ttcgaacttt 144840
tttgatcagt ttaattttag tgatgtggac ctgtaataag aggaaagaag agttttgcta 144900
agcgtcaaac ctgtatgtta aaaaataatg gcacgaatga accctttctc taatgcagtg 144960
gcatgattga gtcagccaac tattaacggg tggcataaac gagtcttttt tccaaagttc 145020
gatggcatag ttgaactctt ttacattact gttaattctt tgtttttttt aaaaataaat 145080
taatatgacc acatgggtca ggcttttatt gaattaataa aaacaactac aacttcctag 145140
aaagctaaca gtaaagaaga aacaaaaaga aaaaataaat atctggaaag tcttatgggt 145200
ctcatttctg cttaggattt gcaaggatgt ggatccatat tttgagagta tttgggatga 145260
tgtactattt caagacgtct tcttcgttgt cggtgttgtt gtaggacatc agcctagttc 145320
caaatctttg aacatcgatt gggaaatcca ctagcttctg ctaagctggt aactcctctt 145380
gacttgtact gaacattttt aatcaccatt ttcagatgta taatgaccga ctttgttctt 145440
gttgtatttc ctcttgatct agccccccatt tgttgcttgg tcttgtttag gactgtgtaa 145500
tctttctagt ttctgattct gaggattgga atttgtgatt tatccgaatt caatatcttc 145560
cgtcctttgg tggggagatc ttgaaaactg tggtaatgga ctgggttatc ttgttcaagt 145620
gcaatgcttg taatatagtc acctaactga tttgcttctc tgtatgtgtg tgtaatttcc 145680
atctgtagtt gttgcattgt attctttatt tcttccacct gttgtactaa ttcccatggc 145740
actttccaca cttcctggat gatgttcttt agtattaaag aatctcatgt ttctattctt 145800
gcattatgta tatctcttga taaacaacaa tgcactgcct tttgtgctac tatggtttct 145860
acaatcatat tggtgttttc ccctatttgt cctgcctctg catacaatag atctcctcta 145920
tcattcctta ggcagaaccc gtaagagctc aatcctggat tccctttgct tgctccatca 145980
gtatttatct ttattctgcc tgtttctggt ttcttccaat gtgtcaaaca atgatatagt 146040
cttggtctgt aattacttag cacttgtatc attgatggcc aatcttttgg aacagaggag 146100
ataccattct attatatgta gtatctcctc catgcttcct ataattcctt ctcttccata 146160
atgattgctg ggatggcttt gaaaatgctg tgggggttga ttagttgtcc accacttacg 146220
tatgacttgt tgcagttgca atccttcaat gttataacct gcacaagaag aaaactgtct 146280
ccatagctta gtagctattg gagatgttag aaaaatatgt gacatggttt ctattttatg 146340
atcctcacaa caccaacatc ttgataccac actaatttc atcctttta gattatcgtc 146400 agtaggtatt cttcctttcc atgctctcca taaaaagaaa ttaatcttta taggcaaccc 146460
tttagtccat atatagtcct gtattttctc cttcttccgt cttaattcat tccatgctga 146520
tttgactgtg aactttccat ttgaatttcc catccaccat gatgtgtcat tatctacatt 146580
gactagttgt gggctgatgt tatcaagtat atgctgcacc atatctactg ataagacttc 146640
ctgtagtttc tgcacattcc aatagccatt tgtaatgaat tgtttcactt ctacctcctc 146700
atccaataca ttttcattgt ccacgaaatg aaggcccctg cttagtccaa ttatcaaacc 146760
agaagctaga atttccagcc ttaagttgcc accaaatcaa atgttctagt tcttctctaa 146820
cttccaccat ctttttccaa acaggtgaac taccttttgc ttgagctatg acagggtgaa 146880
gtttcttgtt gtatttgttt accatatcag cactctatag tgatctagtt gtccttagat 146940
tccaccatag ttttccaaac aatgcctttg atgtatcatg tagtgatcta aaccctaagc 147000
ctccttcaat tctaggtaaa cacatagctt cccaggtaac ccaatgtttt cttttcggac 147060
ttgatgtatt accccagaag aaagttgcaa aatttttatg aatatgttct ataactcttt 147120
tagggggatt catggctgat aggagatata caggtatcga ctgcaaaaca tgtgatatca 147180
aaatatatct tcctccaaaa tataagagtt tattttgcca agacatcatc cttttcataa 147240
ctttcttcac cagatcttca aaaaatacta tcttcttcct accatagaaa atcaggcatc 147300
caaggtaagt aaaaggaaaa gtcccctttc tcatgccagt tttcttcta tcttctttaa 147360 cattactgtt aactcaaaca caattttaaa gaatttttat gtgatttttt aatagttcat 147420

-continued actcatcatc atggggtgca catacaacac gtgtgcctaa atactagtat attataatac 147480
ctaagtgtta gttaaagcaa gtattgtgaa cataaaagct acaacaattg taaagaaaat 147540
gattcccttt tataagtgag gaaaaaaaat ttcccccttt tagatgaaac ttgttttaat 147600
ttctcgactt gtatcacagt ttagacacac attagatgct catgagatct aaaaataagc 147660
aatgataatg accatcttgt cagagccaag cttttgggat atgcctcgtc gagctcaaaa 147720
gtgtagtgaa cttgtgttat gtatttgtaa cttttttttt actttcttct cctatttggg 147780
ttattcctat gtgtaatttc aactaagatt cttgccagcc taaattcttg tcaatccttt 147840
tctttgacct gctcttatcg gtccgccctc catcattagc atcacacatt gatattagtc 147900
ttcttttgtc taaagaaaat gactagtagt tgagtgacca tatgaaagtg agtgaaatgt 147960
gattatctgt gataaatatgc accatttgtt agatgaaaat ggtacataaa atatactatc 148020
tttctcaagc atcgacatat atagctacaa acactaggta tgaaagacat gaataaaaat 148080
gttgttaaat aaacctaatt ccaagagttg gtgaacttgc aggaattttt caagagaaga 148140
tggctgaaaa tgaaattgag gaaatgttaa atcacctaag aaggatcaag agtggaggta 148200
atctggatag cgccaagatt gatgaaatta agggacttga aatgacgcta agagttttga 148260
gaaccgttat aaagtatcat catgttcttt ttcgtgattc ctttgtcaaa cacaaaaaga 148320
atgccaaatc gactatggca atgcttcacc aggtattgta tgggattcca gatgaatgta 148380
aaactaacct taatctggaa aggctagaat cacatttgtt ggaattcgtg gaacgtgata 148440
ccattttaaa taataattat gagttgaatg atcgtgatct gtcagaatgt atggattgcc 148500
tcgaaaagaa tctaaatgat gtactgatac tcttcctgga aagtgctagg tctgaccctc 148560
ctgaagaaaa ccatgaaata cacagatttt taaaggaact gaaagttgtt caaaagaaac 148620
tgagattttt gacatattta tatgccacag agataaatgg ttacgtcaac catgagaagt 148680
tggaatgttt ggatactcga attcagttca tggctaacaa tgtgggacat ttttgtcttg 148740
ctttttctga tgttgtaaat gatattgatg actatgagga tgaggatgtg tataatgata 148800
tcttcaatag acctccttat ctattagtct tgattgtgtt agtggagctg gaaatgaaga 148860
agatttttct caatgaacta aaggcctcaa agtttactca ttcaagaact ttcaaggaca 148920
agaaattacc gaaaggattt tctcatcatc tccacaaact gctgatgtat ctcagaaaag 148980
aaaagctcga gaattttcct gatgatgtct ctgctcaaaa tattgatgtg gcaatagagt 149040
tcttgttggt tttccttgat gctgatttgt caaatcatgt tattaatggt aactggttga 149100
aggaggttat ggaaaaagtt gtaactatag cgggtgatgt tctatatgtg atccaaaagc 149160
ttcttcctag ctctataaac agagatgaga ctagcaaaat aagtcttttc tcgttatgga 149220
tattggaaaa aactaaagat gtgaaggcac aagtggagac ttactacaaa tccttaaaat 149280
tcactccatc tcagttttcc acctttagtg gattgagctt tctggattct ctttcaagga 149340
aacttaatga gatgacaaaa tctaaatctg gtttagattt tctgatgaaa cctcttttag 149400
gtaatttgga gaaagagcta tcatctctta catccatttt agagaaggag ctgtcatcca 149460
ttttcacaga tgtcacaaag gtgcaccatg aacataaaat tcctaaagtt cttcatagac 149520
ataccatcag tttggcatat gaatctgagg ttgccattga ctctattctt tctcagtata 149580
atgttttttt gcatattttt tgctcacttc cttcaatctt aaaagagatc aagcaaatta 149640
atgcggagtt gactgagatg tggtcagcag acgttgctct taagccttgc tatgtggtag 149700
caccatttaa acacctgcaa actcgacata gcaatccagt gactgatgag gagatagtgg 149760

-continued gttttgggaa tgacacagaa aaaatgattc agtatctgat tagaggtaca aatgagctag 149820
acgtcgtccc aattgtaggc atggggggac aagggaaaac gacaattgct agaaaggtgt 149880
acaatagtga caacattgtt tctcattttg atgttcgagc atggtgcatc atttcccaaa 149940
catataaccg gagaacgcta ttacaagaga tttttagtca agttagcggt tccaaggaca 150000
agggggataa ggatgacatc cttgctgacg agttgaggaa aatcttaatg ggcaaaagat 150060
atctcattgt attggatgat atgtgggatt gtacggcatg ggatgattta aggttttgtt 150120
ttccagacgt tggaaataga agcagaatag tagtaacaac tcgacttgag aaagtgggtg 150180
agcaagtcaa gtaccatact gatccttatt ctcttccatt cctcacaaca gaagagagtt 150240
gccaattgtt gcagagaaaa gtatttcagc aggaaggttg cccacctgaa ctacaatatg 150300
tgagtctaga aattgcaaaa aaatgcaaag gattgcctct tgtggttgtc ttggtagcag 150360
gagtaatcaa aaaaagaaaa tcggaagaat cttggtggaa tgaggttaag gatgctttat 150420
ttgactatct tgatagtgag tcagaagaat atacttgcgc gactatgcag ttgagttttg 150480
ataacttagc agattgttta aagccttgtc ttctttatat ggggatgttt caggaggatg 150540
caataattcc agtatctaaa ttaataagtc tatgggttgc agaaggattc gtgcaaaaca 150600
gtgaatctgc tgaatattac ttgatggatc tcattaacag taacgtggta atggtttcaa 150660
agagtagtta taatggaaaa gtgaaacact gtcaggttca tgatgtagtg catcactttt 150720
gcttggagga gagtagaaaa gaaaagttta tgctggcagt gaaggggaat gttgtccagt 150780
ttcaaccttt ggattggaat ggaagtagag tgagctttag tttcagtgaa aagctttcca 150840
agtctacatc tctgagatcc aaaacacaga agcctttcca ccaacacttg aggtcactga 150900
taatcagaga atattatgat gggtttccct ttaggtctag gattcataca ttgcgacttc 150960
ttaagatctt ggatttgagt tccaataaag tgagttattt gtcgacagct acattgaaac 151020
cactgaatca cctgaagtac cttgcagttt tggcaaacgt attctatttc gatccagaat 151080
catgtctgcc ccatcttgaa actttaatgg tgaatagtga taatttggat tatatagtac 151140
tgttaccagc gtctttttgg gaaatggaaa aattaaggca tgttgatatt tttagtgctg 151200
aatttgattt ggaagaggat aagcaggggc tatcctctaa attggaaaat ttgaggatat 151260
taaagaaaat tcttagattt ccaattgata ggatggatgt gttatcaagg aggtgtccta 151320
atcttcaaca acttcacatc gaattttacg gggtgatag tgattctgca gagtcttttt 151380
gtctctcatt tgagaatctt acccagcttc aatatctttt cctttacatt gagaggccca 151440
acattgtatc tgggttacaa ttgccttcaa atttaaagaa gttggtacta tgtgagactg 151500
atatagaaaa cctaggttcc ttcattccgg gactaccaag cctggagtat ctccaattat 151560
tggacccgga taaatttgtt caaaacagag attggtgcct tggagatatc acgttccata 151620
accttaagtg cttgaaactg tcgcgcttag atatctcaag gtgggatgcc tcggaagaat 151680
cctttcccca gctcgaaaca cttgtcataa aaagttgtca ccacctcaag gagatccccc 151740
ttagctttgc agatattcca acactgaagc agattaagtt gattaggtgc gagaacgaat 151800
ctctgaagga ttcagctgcg gagattaaga aagatgttga agagaatgaa ggaaacgacc 151860
gtattgacct cattatcaaa gtaagtagaa acaaactcct aaatatgttc tgtttttgag 151920
tatctaatgt tcaaacaata tgttcaatac aggattgctg aatcaagtat gtgcctgtaa 151980
ccacaacaat ggtattgttt cagttctttt taaattgatg cttgttttcc cttaattgct 152040
cttaaactca cgaggatttg tttgaatttg actactgcag caagttcatg acggcttgcg 152100
tccacacatt atcccgcaca atgaaacgtt tgccttctct gtcaatggat tcacatacta 152160
tttttggcaa ttccttcaca tccatgtctt gatattctga agtgagcaag tttcttcaag 152220
tcttttagag tactaagaaa gaccccattt agtttgtatt acgggcctac gttcaggaaa 152280
aactcaaggg aaacctgaac atctttagag attttttggt tggatgtgat cttgaaactg 152340
actctttctt ttgaaatatt gcaatttgtg gcagctattg aaatattctt tttttcacta 152400
ctgccccacg tattgtcctt ttttgttctt tcatttactt gacatttgga gactagattg 152460
tgttacgacc caaattccaa gagccgttac aaaaaaacat aatagatgtt cacactgatg 152520
ctttgcgcta ccaaatatat gtgtttttac catcaactcc aaacgtatcg ttcccttagt 152580
ctataacaat ggcatcttca cattctttac tagatttact gtgtcttaat taaaattatt 152640
taaatatctt tgtatattct aatttaatca gacatcggcc gggcccacgg agaagacttg 152700
gggtaaaaag aaaaaagtgt atgtgttgga aagttgatgg agtcttttca ccttttccct 152760
tagtgctctc tgctttctcc ttttctcttc aataataatg cagaactcat aaagaaagat 152820
tatgtgtatt tgaaattttt ttaatcacaa acattttttt tataaaagga acatgaatta 152880
ataaagcact gattgttgtt tatctaccat taattaataa attaataatg caataattca 152940
gaactcatac aatacacatt ccagtctgtt cgagccattg ccaactccaa ttattgtttg 153000
atctcctcac ccatctctct gtactagaca acaccttgtg ccatatagga ttcggatcta 153060
cgatcaatca gttaacaacc gatcgatcta ccactaagct actgaggaac aacaggaaat 153120
tcgataagtt aagattgagg tgagttccat tgattcataa tttattttca tacttcaagg 153180
aattccgtat cctctgaata tatataccc ctcttcctaa tttaagtgtc ttagtttgac 153240
gaggaattca atacacaagt cataatgaat aaagctaaca aattcttttc cgttccacca 153300
agtctatcct acagccaagt aaacgaaaga aggaatgaaa aaggagaaac aaattataca 153360
agtcacgagt acagtagact cgtattggta tataaaactt ttagtttttt agattgagtt 153420
atatctaggt gtcatatttt tctaaggtat catagcaaga tccattctcg tttggacaca 153480
tgatccatgc tccagttggg tctgaatata aacaggggtg ttatagtccc acattgattg 153540
ggaaacagag tggtaatttg cttatatgta cttaaataat cattccctaa tgagttacac 153600
tttaggggtt gagtttcgct caatgtcata tctctagaat catttaaata gtttttctat 153660
agggaaacat gttttcaata ttaattataa tcatatttgt tctttttaat gattggatca 153720
gaaaattgaa gatactaaag atgcataaga gaagaaaaaa ttacaagttg gtttcactta 153780
ttaactaact gtataagtca tcttcttcat gaatgatttt tttcctataa ttttttttttc 153840
aaatggtcca ttcaaaagaa ttagttaagt gattttatga gataataatt attagttaag 153900
tgaccatata aaaaaagata aatatacacc atttgttaga tgaaatgata catgagatgt 153960
ataatctttc acaagcatta agatattgaa agacatgaat aaaaatgttg ctcttaatga 154020
tcctaattcc aggagttgaa taacttgcag gaatttgtaa acagaaaatg gctcaaaatg 154080
aaattgagga aatgttagct aacctacgaa ggatgaagag taacggttct cagagtagcc 154140
tcaggattaa tcgaattgag aaacttgaaa tggtgctaag agttttaaga acctttataa 154200
agtgtcattg tgttcttttt tctgattcct cagtcaaact cacaaagaat gccaaatcga 154260
ttgtaagaat gcttcgaagg gtattccaag ggacttcata tatcaaagta gataagtgta 154320
gttatgagtt ggttagggaa aggcaagtac cacatttgtt ggaattcttt gaaggtaata 154380
ccaatataag ttacaattat gagttgaatg attttgatct gtcagaatgt atggattgcc 154440
ttggaaagaa tctaaatgat atgataatga tgttcttgga aagggttagg tttgaccctc 154500

-continued

```
ctgaaaaaaa ccctgcaata cacagattta taatgcaact gaaaattgtt cataagaaaa 154560
tgaaattttt gagatactta tatgccacag agataaatag ttacgttgac gatgagaagc 154620
tggaatgttt ggagactcga attcagttca tggctagcaa tgtgggacag ctttgtcttt 154680
ctgtttcagt taacgttgat gctgattttt tatataatac acataacggt gaggttgaac 154740
catatgggtg tgatatcttg aataaacctt cttatctatt atgcttgatt gtgttagtgg 154800
agctggaaat gaagaagatt tttctcaatg aactaaaggc ttcaaagttt attcaatcaa 154860
aaacattcaa ggacaagaaa tttccaaaag aattttcaca tcatctccac aggctgctga 154920
tgtatctcag aaacaaaaag ctcgagaatt ttcctgataa tatctctgct caaaatattg 154980
atgtggcaat agagttcttg ttggttttcc ttgatgctga tttgtcaaat catgttatta 155040
atggtaactg gttgaaggag gttatggaaa aagttggagc tatagcgggt gatgttctat 155100
atgtaatcca aaagcttctt cctagctcta taaacagaga tgagactagc aaaataagtc 155160
ttttctcgtt atggatattg gaaaaaacta aagatgtgaa ggcacaagtg gagacttact 155220
acaaatcctt aaaattcact ccatctcagt tttccacctt tagtggattg agctttctgg 155280
attctctttc aaggaaactt aatgagatga caaaatctaa atctggttta gatttctga 155340
tgaaacctct tttaggtaat ttggagaaag agctatcatc tcttacatcc attttagaga 155400
aggagctgtc atccattttc acagatgtca caaaggtgca ccatgaacat aaaattccta 155460
aagttcttca tagacatacc atcagtttgg catatgaatc tgaggttgcc attgactcta 155520
ttctttctca gtataatgtt tttttgcata ttttttgctc acttccttca atcttaaaag 155580
agatcaagca aattaatgcg gagttgactg agatgtggtc agcagacgtt gctcttaagc 155640
cttgctatgt ggtagcacca tttaaacacc tgcaaactcg acatagcaat ccagtgactg 155700
atgaggagat agtgggtttt gggaatgaca cagaaaaaat gattcagtat ctgattagag 155760
gtacaaatga gctagacgtc gtcccaattg taggcatggg gggacaaggg aaaacgacaa 155820
ttgctagaaa ggtgtacaat agtgacaaca ttgtttctca ttttgatgtt cgagcatggt 155880
gcatcatttc ccaaacatat aaccggagaa cgctattaca agagattttt agtcaagtta 155940
gcggttccaa ggacaaggga gacaaggatg acatccttgc tgacaagttg aggaaaatct 156000
taatgggcaa aagatatctc attgtattgg atgatatgtg ggattgtacg gcatgggatg 156060
atttaaggtt ttgttttcca gacgttggaa atagaagcag aatagtagta acaacacgac 156120
ttgagaaagt gggtgagcaa gttaagtacc atactgatcc ttattctctt ccattcctca 156180
caacagaaga gagttgccaa ttgttgcaga gaaaagtatt tcagcaggaa ggttgcccac 156240
ctgaactaca atatgtgagt ctagaaattg caaaaaaatg caaaggattg cctcttgtgg 156300
ttgtcttggt agcaggaata atcaaaaaaa gaaaatcgga agaatcttgg tggaatgagg 156360
ttaaggatgc tttatttgac tctcttgata gtgtgtcgga agaatatagt cgtgcgacta 156420
tgcagttgag ttttgataac ttagcagatt gtttaaagcc ttgtcttctt tatatgggga 156480
tgtttccaga ggatgtgaga attcgagtgt ctaaattgat aagtctatgg gttgcggaag 156540
gattcgtgca aaacagtgaa tctgctgaag attacttgat ggatctcatt aacagtaacg 156600
tggtaatggt ttcaaagaga agttataatg gaaaagtgaa atactgtcag gttcatgatg 156660
tagtgcatca cttttgcttg gaggagagta gaaaagaaaa gtttatgctg gcagtgaagg 156720
ggaatgttgt ccagtttcaa cctttggatt ggaagggaag tcgagtgagc ttcagtttca 156780
gtgaaaagct ttccaagtct acatctctga gatccaaaac acagaagcct ttccaccaac 156840
acttgaggtc actgatagga gaatattttg atgggtttcc cttaaggtct tggattcata 156900
```

```
aattgcaact tcttaaggtc ttggatttgc gttccgatgc agtgagttat ttgtcaacag 156960
ctacattgaa accactaaat cacctgaagt accttgcagt tgtggcaaag aaattctatt 157020
ttgatccaga atcacgtctg ccccatcttg aaactttaat ggtgcataat tattgggatg 157080
atacagtact gttaccagcg tctttttggg aaatggaaaa attaaggcat gttgatattt 157140
ggagagctga atttgatttg gaagaggata agcatgggct atcctctaaa ttggaaaaat 157200
tgaggatatt aaagaacatt cttagatttc caattgatag gatggatgtg ttatcaagga 157260
ggtgtcctaa tcttcaacaa cttcacatcg aattttacgg gggtgatagt gattctgcag 157320
agtctttttg tctcacattg gagaatctta cccagcttca aatacctcac ctttcctttg 157380
gggggcccca cattgtctct gggttacgat tgccttcaaa tttaaacaag ttggtactaa 157440
gtgggactcc tataaaaaat ctgatttcct tcattgcggg actaccaagc ctggagtatc 157500
tccaattact agatatgtat gttcctcaat cagaagtgtg gtgtcttaga gatatcacat 157560
tccataaact taagttgttg aaactggggt ggtcagatat ctcaaggtgg gatgcctcgg 157620
aggaatcatt tcccctgctt gaaacacttg ttataaaaaa gtgtagtaac ctagaggaga 157680
tccctcttag ctttgcagat attctaacac tgaagcagat taagttgatt tggtgcgaga 157740
agaaatctct ggaggcttca gctgtgagga ttaagaaaga tgttgaagag aatgagggaa 157800
atgaccgtat tgacctcatt atcaaagtaa gtagaaacaa actcctaaat atgttctgtt 157860
tttgagtatc taatgttcaa actatatgtt caatacagga ttggtgaatc aagtatgtgc 157920
ctgtaaccac aacaatggta ttgtttcagt ttgccttttt taattgatgc ttgttttccc 157980
ttaattgctc ttaaactcac gaggattcgt ttgaatttga ctactgcagc aagttcatga 158040
cggctagcgt ccacacataa tccagcacaa tgaaacattt gccttctctg tcaatagatt 158100
cacatactat ttttggcagt tccttcacat ccatgtcttg atattctgaa gtgagcaagt 158160
ttcttcatgt cttttagagt actaagaaag accccattta gtttgtagta cgggcctacg 158220
ttcatgaaaa actcaaagga aacctcaaca tcgttggatg tgataattca aattgactct 158280
ttcttttcgt tattattggt tttattagtc gttgtcttat aacagactct ctagctaaaa 158340
tcggagaaac aggaaacttt cttcactgag gttgaggttg tctctttgca tgacaagtta 158400
gagttgcaaa attaactcaa ctacaaaaaa aatttcttgt tgaatataag caaacctcac 158460
aaatttacaa attttcgcag catagaaaac tcgaaggttt tgataagagt cttagattta 158520
agctcatcga cataatactt tactatgcac taaaactttt gaactttgtt attgttgtat 158580
tgtccttttt tgttcttcat ttacttgaca ataggagact agattgtgtt acgacccaaa 158640
ttccaagagc cattacagaa aacataatag acgttcacac tgatgctttg cgctaccaaa 158700
tgtatgtgtt tttaaccatc aactccaaac gtattgttcc cttagtctta gcaacggcat 158760
cttcacattc tttactagat ttacatgtgt cttaaatatc tttgtatatt ctaatttaat 158820
cagacatagg ccgggcccac agagaagact tggggtctaa aagaaaagta tatgcattgg 158880
aaagttgatg gagtgttttc accttttccc ttagtgctct ctgctttctc cttttctctg 158940
caataataat gcagaactca taaaggaaga ttatgtgtat ttgaaatttt ttaatcacaa 159000
acattttttt tttataaaag gaagatgaag atatgtgtga ttcaacaatg cggcgcttta 159060
gaatgttctg atatcttgta tatgaatgat ggtttgctca tttggtaaga ttgtataaga 159120
attgaagaaa tttgatggtt ttcacaactg atggattttt catgttttat gaggggaaaa 159180
aaatacaact taaaaagtta aaattgcatg tccaatcaaa acttcaactt catatcaata 159240
```

tgatttcata ccataatttc atatagccta tccaaatgag cccttaaaaa attgtaaact 159300
tttatttgta aaatcgatct tcccttttc cccatgtatg acattaactc tctactgtag 159360
ttaaattctt tttaaaattt gtgtaagtaa caaatataaa actatatata tttagatgaa 159420
tatatttaga attcgatact ctaggatgtg aaagcagaat gtgatttatt ggacaaaggt 159480
ctgaatattt tttactgcaa aatttgagtt tttttacgtt cctctcctat ttgggctata 159540
ctgatgtgat tcgactaaaa tgcttgttag cctaaatgct tgtcaatcct tttttctgct 159600
gatctgccct cttcggtccg ccctccatca ttattgtcac acatttgtta tagtgggtct 159660
ttttttaata atatattatg gaataaagtt gatgtcgttt ttactaaagc aatcaatagg 159720
aatgaagcac tatcattaat taataaagca ctggttgttc tttacctacc attatttaat 159780
aaattaataa tgcaattatt cagaactcat acaatacaca ttccagtctg tttgagccat 159840
tgccaactct aattattgtt tgatctcctc acccatctct ctgtactaga aaacaccttg 159900
taccatatag gttttggatc tacgatcaat cagttaacaa tcgatcgatc gatctatcac 159960
tgagctactg aggaacaaca ggaaattcaa taagttaaaa ttatattgag gtgagtgttt 160020
tactcgaaaa aataaaaatg aaaatggact ttttttcgaa aaatcgatta aacttatgat 160080
ttgaagagaa atcgattttc caaaagaaac agagtcgcca cttaattttt tagtaaaaat 160140
caagaaaaaa acttaaggtt ttcaaaagat ttaatcagat aaaatcaatt gaaaataaaa 160200
gggtttggag ttcaatgtac attccgagaa ggtgttgggc cctcgaaatg tccgctaact 160260
tgcggttgac cggcgatttg actaaaaatg actttgacta aattttgaaa ttttaaccaa 160320
gtaagaaaaa ctcatttatt ataacttgca gtatagctgt gcgattataa agcatagcta 160380
tttatgaact gcttcattta ctataactct gtaaccatgt ttgcttggaa caaagaaaat 160440
tagcgaattg gaagtggcaa atggtacttc caagacttct attcaattgg ataattgtta 160500
cttgacgtgc taaaatgctg ttaaaccatc aatttattga atatttatag atttgtgtaa 160560
acaaaaaatt agtctttcag taatcttgat tgtatgcttt cttttcttat gttccacttc 160620
acaatatttt ctcagttggc acttattgca acatgcttga gctgcaaatt ttatcgcagc 160680
aaacgagcta cactccaata ttaacaatat ttccttgttt gtttttgcag caaacgagct 160740
acgctgacat gctggatcta gcagtgcagc acattcgaac ccttcaagat caggttcagg 160800
tgggtgatta aattgatcaa ccttactgct ttgcagcttt acgtaatcta tcatgctgca 160860
tgcacctagg tacaaaatta aaatacttat actctgttgc tcagactctt caatgatact 160920
gttggatgtg ttagatttta tcctccaaaa gctatgcatt tttggaggat cagacactag 160980
tacaacaatt ttggcccgag caacacatct tatattctca catgatgttt acaccaaacc 161040
gaataatata accttaatgt ttttgggata gataatgtct aatatatttt gcaaaaaaaa 161100
tgataaattt tctagcccca cctttatagc tgtgattgaa gtagtagaaa catatttttc 161160
acattttctt tttcttatgc agaatctgaa tacagaactt gaaaactgca aatgtggatg 161220
taagaaatca agtcaataac aaaatggaag gaagcacttt agctgaagat cgacttaaaa 161280
ggatttttgt caccatgatt ttgcctctta gaaactcaaa tttgtacata aggaagtaaa 161340
tttcatacta gtttttttaaa gctaaaaggc gaactcttct tttttttttt ttttttttcc 161400
tttccagtta gaagactacg tatatgattg ttttggatta tttgtagttt ttttttcca 161460 tctaacattt acatttttaa tttagttttg agtttatttt ggttgaggat cataaagcta 161520
attgatgatg ttgtacaaca actttctcta tttcattttt atgtaaaatg agtgggtaag 161580
acattttctt gctttctgtt atgttcttct tgggaaacga ccatttacaa tttgcaaaga 161640
agaaaagtaa ctctactcta caaggatttc atgtgtttta tttatcgaac tgatcatttt 161700
cattgaaaaa aagtcattta attaatataa catttgtatt gagccataaa atcgatattt 161760
cccttcttac caatgtatgt catgaatata tgtgattcat caatgtggcg ctttaggata 161820
tttcgatatt ttgtttatga acgatgattt gctcattcgg taagattgca taggaaattg 161880
actctttctt ttcgttgtta ttgctttcat tagtcgttgt ctcataacag actctctaac 161940
taacattgga gaaataggaa actttcttca ctgaggctgt ctctttgcca tgacaagtta 162000
gagttgcaaa ataaactcaa ctacaatttt tttttcttgt tgaatataag tacacctcac 162060
aaatttacaa atgtatgtgt ttttgaccat caactccaaa cgtattgttc ccttggtctt 162120
agcaacggca tctttgcttt ctttactaga tttacatgtg tcttaaaatt atttaaatat 162180
ctttttatat tctaatttaa tcagacatcg gccaggccca cggagaagaa ttggggtcaa 162240
aaagaaaagt gtatgtattg gaaagttgat gaagtgtttt caccttttcc cttagtgctc 162300
tgtgctttct cctttttctc tacaataata atgcagaact cataaaggaa gattatgtgt 162360
atttgaattt tttttaatca caaacatctt tattttataa aaggaacata aatatatgtt 162420
tgattcatca atgcagcgct ttaggatgtt ccgatatctt gtatatgaat gatggtttgc 162480
tcatttggtc agatttatac gaattgaaga aatttgatgg ttttcacaac tgatggattt 162540
ttcctgtttt atgagggaaa acaaaataca atttaagaag tcaaaattgc atgtccaatc 162600
aaaacgtcaa cttcatatca atatgatttc ataccataaa atcatatcgc ctatccaaac 162660
gagcccttaa aaattgtaaa cttttatctg taaaatcgat tttcccttct tccccatgta 162720
tggcatgaac tctctactgg tataagtaac aaatataaaa ctatatgtat ttagatgaat 162780
atatttagaa ttcgatactc taggatgtga aagcagaatg tgctgattta ttggacaaag 162840
gtctgaatat attttactgc aaaatttgag ggttttttcc atgttcctct cctatttggg 162900
ctataccgat gtgtgattcg actaaaatgc ttgtcaatcc ttttttctga tctgcactct 162960
tcggtccgcc ctccatcatt attaattgtc acacattcga tatgagtttc tttttgtttt 163020
aaaaaaatga ctacttccgc gtgggtcttt ttttaataat atatcatgga ataattagac 163080
attattctta aagacaaggg atagagttga tgttgtattt actaaagcaa tcaataggaa 163140
tgaagcacta tcattaatta ataaagcact aattgttgtt tatctaccag taattaatag 163200
attaataatg caataattca gaactcatac aatacacatt ccagtctgtt tgagccattg 163260
ccaactctaa ttattgtttg atctcctctc tgtactagaa aacaccttgt gccatatagg 163320
attctgatct acgaccaatc agttaacaat cgatcgatct atcactgagc tactgaggaa 163380
caacaggaga ttcaataagt taagattgaa gtgagttcca ttgattcata atttattttc 163440
atacttcatg gaattttgta tcctctgaat atatataccc cctcttccta atttaattaa 163500
aagaaaacta tgaattagct gggtacgaaa attcgcatat aacttggttt cctgcgactt 163560
tttctaccaa aaaattttcg atggaaatat cttcgtaggt aattattaca cgcgaatata 163620
aaaatcccca agtaaattac ctggggattt gaatttcgca agtaaattac attcgaattt 163680
tcttgcaaat aaatactaaa aatatccgag aaatttttag taaaaattcg tgaaaaaggg 163740
aattttctta caattttttt ttttttgcaa aaattcctag gaaataattt gtgaataatc 163800
attttaattc ttttagtttt taatttctgg atataccaat tatttttaat agttttgtct 163860
ctgattatta tcttcttatg taattcttgt tattttattt tacaaccccc caccccctaca 163920
cacatgttta caccccttaaa tgctcaacac aattaattgc acagccactc agaaaccaaa 163980
gaaaccactg cccaaacatt catttagctt taactttcgt tctaccaaat ataaatgtta 164040
aattgttaat gtactcattc gatgtggtac aaagatagca agggaattat tccaaatttt 164100
tttagtacta ataaaaatat gacacaactt taaatatact ttacgtattt tatccacgtt 164160
ctttaatcaa aaagagatta ttcttttaga atatatatat atatatatat atatatatat 164220
atatatatat atatatatat atatatatat attttgtaat aataacatac gcagtaaaat 164280
tttacttagc ggggtctgaa gaggatagtg tgtacgcaca ccttaacact agctcgtaga 164340
gatagatata ttgttttcga aagacctcag ctcaagtgca tcaaacccaa ataaaagaag 164400
aataaatcaa tgaaaacaaa taactattaa taagaaaagt agtgtaaagt ctataagaaa 164460
gaacctctta aagaaattga cacaaattac ttaataagat gaatataatt taggtatttg 164520
aaaaagtatc tatttttcaa aactttaaat aacatgatgt tattccaaat ttttataaac 164580
attttggcct catatataat agaaatttct gtacaaataa aactataaaa tgataattta 164640
aataatttat aagtttaaat aacatgatgt tattccaact cgaattattg tttgatctcc 164700
tcacccatct ttatgtacca gacaacacca gctcgtacca catataagat ttggatctac 164760
gatcaatcag ttaacaatag accgatctat cgctgagcta ctgaggaata acaaaagatt 164820
tgataagtta agattgaggt acgttccatt cattcattat ttattttcat acttcatgaa 164880
tctatatact ttctcttccc aatttaagtg tcttagtttg attagacaca aagtataaga 164940
aataaagact tgattcttgt gatattaaat taaagatgta tgtagtcctt taaatcttat 165000
gatcataaac ttgtcctgtg gaatgttaga attgaaaatt tactaaatat agaaagcgac 165060
actcattcct gttggataca cttacacaag ttcatccagc ttttttgaa gttgaaattc 165120
accaagtcat aaaaatgaag ctaacaataa aaaatgtcat tccaccaagt ctcctatagt 165180
caagtaaacg aaagaaggaa tgaaaaagga gaaacaaatc atacaagaca ctagctagta 165240
gcctagtaca gtagactcat actggtatat acatttttta gcttttgagg ttgagttaga 165300
ctcatgtgtc atatttttat aaggtatcat aactagattc atactccttt ggactcatgg 165360
tccatgctcc agttgggtct gtacatgaac gagggtgtca aagttcacat tgattgaaaa 165420
acagaccgat aatttactta tatatatatg gacttaaata atcctcctct agtgagctat 165480
tttagagatt gagtttggct caatgccata tctttagaat tatttaaata gtttttccat 165540
attctaatct aattattact tgacaagtca gttggaattc ttcaattcca tgcacaatgg 165600
tcaacacttt aatcaatgtc acaatcaaat ataaatgtgg ggaaggcgtg ggagcccatg 165660
cgccttacaa gtccttctta catttctgac ccaataattt ttttgaggta aggcgtgggg 165720
gtcctgcacg cgcctttgcc cctttggtct cttccatttt tttttgccct tttagaattt 165780
tggcagaaaa taataattgt cctttaggct atggactcca attgtagaca actttttgtt 165840
atgtagaatt tgctcaaaac atacaacttt ttgttttata gaatccggtc aaatacatac 165900
aatttgcatt caatttattt gagttagaag cttggaactt ggaagtcact caattttggg 165960
taattagcca tcatagtcgc tcaacttagc caagttagct cccatgattg ttttagctag 166020
aaatacaatt tttggtacat atataatgac gtgatgacta taaattttta gaataaaata 166080
tttttaaaaa ttaaaatcaa tatttaaatt tatttaggac ccaatccatc aaaactcaac 166140
ctaattcttg ccacgaccaa tttaatgagt tgactatata aaaaatttct ttaaacaaac 166200
tttatttctc ctttttccac ttgtgatttc tccatcacat gatatatctt ctctttctct 166260
ttcaaatatg taaattttcc atttttttat tgttcttgtt ctatcagtca aatcattcat 166320
tgcgaaagat taccaaaatg aatcgagttc tatatattac atggatagat aggttgagaa 166380
aaaagtttat tgtttaaacg gttgttgcac tactgaaaaa ttaggtgaat aagatcattt 166440
ttgtatttga gaagtcacta gttttttttt gttatttcat tcataaggtc attcaagttt 166500
aaaagtaata catccggtca cttttaatga cataatattt gtaagtcatc ttcttcttga 166560
attattttta tccctatata tagagagttg atttttcttt attgaagaaa attagaatca 166620
agaagaaagg taattttctg agataataac aattagttga gtgatcatat gaaaagagta 166680
attatgcatt gtttgcaaga tgaaatggta cataagatgt ataatctttc acaagtatta 166740
acatagcttc aaacactaga tattgaaaga catgaataaa aatgttgctc aaaattctac 166800
ctcgtctcct tttcaacacc tccactcgcc ttagtttcac acctacaaac caatgcatct 166860
gtaggtcgac acaagacatg tcacaccatc tccagcgcac gtctcttatt atattatcaa 166920
tgctacttgc acttctagcg aatatatatg gattattttt aatttattta atattatatg 166980
atcgcatatc catcttagca gttggtcaaa tttatgtggt ctaaccttgc aaaagtcacc 167040
atcaggcaag atttcaatca actttgcccc tgctgagaag aattctcgtc cgagaggact 167100
ataggggaca atccctatgc tatggtcaaa gaaatcaaaa actgctactc ttgaactcaa 167160
atctaaaata aaaaatgtag aaaggaaaac acttcttatt atttagatac aaaaattaca 167220
tactttcttt taacagatgc agtgtcccag ctagcttgca cgaacctcaa ccattccaag 167280
gggtacctgc aatctctcac tggctacctg cataggtacc tgcaactcta tccaccaaaa 167340
cttagatagc taggaagaca tcatctaatt tatgcattaa ctaccatttg aacctgaaac 167400
ctcatggttc tcgaccccta tcatccacaa ctagccaaat acatatcact tgtcaaaccc 167460
ctactcagct ttccaggagg acaatggtgg cgcgcgtctc tgaatttatc caacaaaata 167520
agatttacca gtgtgaatta taagactcta aataagtaga actgatttat ttgcagtaag 167580
aacgacaatg tgattaataa aggacaatgt gaaagttcac gtagccaatt aattagttct 167640
ctgttgccaa ctgtcctctc cttccacaca ctttgattaa tcattgggaa tagatactaa 167700
ccttccaata aagtagttgt ctctctgcat atatcataag ccatgttatt tcattaaata 167760
atgcaaccat tgactttgaa agccaatagg aatgcatatt aacctgacaa tatattagct 167820
atctaaaaat taacatgata attaaacaca ataattattc ataatacaac cattgacttt 167880
tttgtaggat gtagatccag tcctttggtt aaccataatt attcatccac taatcttgtt 167940
aagagtatga cacaaacaac atttcctcat tgttctaagt taattatgct catattaatc 168000
ttttcttgtt agcttaatcc tactccaatc tttatcaggt atttttcaat aaatattttt 168060
ctagatctcc ctttgaattt ttatcccttt ttaagtggaa tctgctttat gtataagtta 168120
ctagtttttta ggaacgtgtg ttgcacgtta tcccccaatt aatataaaat ttctacattt 168180
taaaaaagtt ttaacttatg aaatagaaaa tattaacatc aaaatattgc agattttact 168240
atttaaatct attcattaaa aacacaatta gtgggacgat ataatagcct ctggccctct 168300
gatagtatgc aagagaattc ttgctctaat tttaataaat gcatgtaaaa atatttaaaa 168360
aatttacaaa agaaaaatat gaagaaagat atctttttac aaaaccccaa ataggattgt 168420
ttgtttagat ttaaaaatgc tatatcagat taagtgaaat ataaagttaa ttgcactacc 168480
taataaaata tttctttttt ctctgccaag caagcatttt atgtaaatat gatatttgaa 168540
tgttaaagaa aaagatacat tttcatttca caaaaaataa aatacctctc aattctataa 168600
tccaaatgaa ttaaaaaata aatggttaat tatgaagtag tacaagtatt atgcatacaa 168660
ctacatagat aatttaaatt caacaaattc tccttatatc attttgatgc ctcaacaacc 168720
acaaagtcat aacttgaaaa gtattcacca gacaataaat ttttaactcc tatcttatgg 168780
atcgtttttt taaaatctga agtacttcat ccatgcacaa agtattgcat aaatgtgtta 168840
tatccagtac aacagtgcct gttgttatgt taaaataaaa atatgagcac agttgtgcct 168900
aaataaagct gatacacaat aaagaaacaa aaattttgaa atagatgcat ggaaagaaat 168960
acaagtttgc aatttgtcaa ttaaataagg attagacggt agaaacaacc acacaacaat 169020
gtgcatagaa atagttagtt gcaatatgtg taccgtcaaa tgataaatatg acgattaaag 169080 ttaatttctt gttcgatcgt ggtattcaat aaaaagtcca aagttacttt acataaactt 169140
gtcgcaagca gtaccatgtg aaatattttg ttacttacct ttgtttcttt taaccaaatg 169200
tgcaatttga gcatcatggc ggagaagttg gttagcagta aacctcttgc aattatttgg 169260
taattgataa atatcatgaa aaggaacaat agaggatata tatcactaat aacaattagc 169320
aataactggg caaaacaaat tctcaccaaa aaataagagc caacgtttca tatgaaagga 169380
gacgaaaagg aaaagttgat gaagagtttc ttggtaactg ctgtccttta acattattat 169440
tattatgaga ttgtgaaata gactttaatt ttcattttct ccaaatttca gattatttga 169500
actcagactt attactaaaa atatatacat ctataaatat aaatatggtg attaagatta 169560
tttaagtaat gagtacattg atattgctgg ccaaaaggat atttccttaa aatatttata 169620
tttaatcaaa tttaaattta gtagaaggac aaaatggtaa ttcaactttt cactttggag 169680
cttcccacta ataataataa taataataat aatatatata tatatatata tatatatata 169740
tatatatata tatatatata tatatatata tatatgatca acaactcttt ttctaggatt 169800
ggatcagaac ttggagatac aaaaaggaaa aagaagatcg atactcaact actcgtcaca 169860
ctcgaaaatt gtaagatatg agtatatatt aacttgctat tgctttcaaa aatctcaaag 169920
ttcttaaatt gatacaacaa ctgagttatt aattcatttt accaataaac ttcatggttc 169980
caaaactaca aatattgtga taataaaaaa tggatatcac acataataat tagtttttgc 170040
tctgttgaac cagttaaaga agtgttttat ttttgttttc ctctttaatt ttctatttta 170100
ttttattttt taaaaaagtg atcaacagca gatggctggt tatatgtctt tatagataca 170160
aattgggggt aggggaattg aaccgtcata aggtgaaagt tgtgatattc aaccgactga 170220
gcgactaatc gtgctatcct tctgcacaca cttttttaa ttaatcattg ggaatgcatt 170280
agttgtttct ttgtactaat aattaataga gaaaaagctc aaatatgtca tccaactttg 170340
agaagaaaaa aaccctcatt taatagttgg gcatgtcatt gccattacat aaatgaccca 170400
ttatgccatt gatttttaac agtcaggact tatgttttgc aacactattt ttttccatct 170460
ggcttcttat tagaggtcca tgtcaccaaa attagactag tcgaaaagta agttcaaata 170520
tgccactgaa ctgtaacaag atgttcatct atgtcattca ttaacagttg gattcaacag 170580
cagatggctg gttatatgtt tttatagata caaatcgggg gtagggattt gaactatcat 170640
aaggtgaaaa ttctgatatc caaccaactg agcgactaat cgtactatcc ttccccccac 170700
acattttttt tattattaat cattgggtat gcattagttg tttctctgta ctagtaatta 170760
atagggaaaa aattagctaa atgatgtcat ccaactttga ggggaaaaaa acctcattta 170820
tgtcatccat taatagttgg gttcaatcac atgcctttgt cataacagaa atgacccatt 170880
atgccattat tttttaatat tcagattttg tggttttgca acaccatttt tccatatggc 170940
ctcttattag aggtccacgt caccaaaatg aaactggtca aaaaaaagtt caaatatgcc 171000
attgaactgt gacaaaatgt tcatatatgg cattcgttaa tagttggatt caaccatgtc 171060
actgcagttt aatttggaat tataatccaa cccattaaca ccatacccga tccaccataa 171120
cccatttccc ttttatttct cctacaaact cttagatcca aaatttctcc cattttaatg 171180
atgaatttat atgtcagttt cttgtcaatt gatcaattta agtgtttggg gagaaataaa 171240
aagggaaata ggttagggtg ggtcgagtgt gatgttatgg gtcgggtttt aatttcaaat 171300
ttaatttaat taggttggtt tatattggca cgtggacctc taataagaga ccacgtgaaa 171360
aaaaattaat tttgcgagat catgaaacct gaccattaaa aagtagtatg aatgggtccc 171420
ttctgtaacg acaatggaat ggttgagccc aataattaac agatggcata gataaacctt 171480
ttttcaaaat ttgatgcata tttgaacttt ttttatcagt ttaattttgg taatgtggac 171540
ctctaataag agaccacgtg gaaagaacga ttttgctaac catcaaacca gctacctgtt 171600
aaaaaataat ggcacgaatg gaccatttct gtaaagcagc ggcatgattg agcccaacta 171660
ttaacgggag gcacatcaac aagcattttc ccgatgtttg atggcaaatt ttaactcttt 171720
tacattattg ttaactcaaa cacaatttta aagaaatttt atgtgatttt ttaatagttc 171780
atatctaggc acgtgcaacg atactactat atattataat acctaagtgt tagttcaagc 171840
aagtattgtg aacataaaag ctacgacaat tgtaaggaaa atgattccct tttataagtg 171900
aggaaaatca tttcccccct tttagatgaa acttgtttta atttctcgac ttctatcata 171960
gtttagacac acattagatg agcttgagat ctaaaaaata agcaatttta agttgatgtt 172020
tcattttcca tttctatatg ttaagttagt cggaagaata attataatga ccatcttgtc 172080
agggccaagc tttcgtgata tgcatcgtcg agctcaaaag tgtagtgaac ttgtgttatg 172140
tattgtaact ttttttttta ctttcgtctc ttatttgggc aattcctgtg tgtgattcaa 172200
ctaagatgtt tgtcaatcct tttctttgac ctactcttat cggtcctccc tccttcatta 172260
atgtcacaca tttgatatta gtttcttttt gtttaaagaa aatgactatt agttgagtga 172320
aatgtgtctg agatgatatg cactatttga attagatgaa atggtatata aactgtatta 172380
tctttcataa gaattaacgt agctaaaaac actagatatt gaaatacatg aataaaaatg 172440
ttgttaatga acctaattcc aagagttggt gaacttgcag gaaattttca agagaagatg 172500
gctgaaaatg aaattgagga aatgttagat cacctaagaa ggatcaagag tgaacgtgat 172560
ctgtctagcg ccaggattga aaaaattaag aaacttgaaa tagcgctaag agtttgaga 172620
acctttataa agtgtcatca tgttcttttt cgtgattcct tagtcaaaca caaaaagaat 172680
gccaaattga ctatggcaat gcttcaccag gtattggatg ggattccaga tgaatgtaaa 172740
gctaacctta atctggaaag gctagaatca catttgttgg aattcatgga acgtgatacc 172800
attttaaata ataattatga gttgaatgat cttgatcttg atcttgatct gtcagaatgt 172860
atggattgcc tcgaaaagaa tctaaatgat actgatactc tgtctggaat gtgttaggtc 172920
tgacccttct gaagaaaacc atgaaatact cagattttta aaggaactga aagttgttca 172980
aaagaaactg agatttttgt catatttata tgccacagag ataaatggtt acgtcaacca 173040
tgagaagctg ggatgtttgg agactcgaat tcagttcatg gctaacaatg tgggacattt 173100
ttgtcttgct ttttctgata ttataaatgg tattgatgag gatgaggcta atgaaatctt 173160
taatacacct ccttatctat tattcttgat tgtgttagtg gagctggaaa tgaagaagat 173220
ttttcagagt gaactaaagg attcaaagtt tactcattca agaactttca aggacaagaa 173280
attaccaaaa ggattttctc atcatctcca caaactattg atgtatctca gaaaagaaaa 173340
gctcgagaac tttcttgatg atgtctctgc tcaaaatatt gatgtggcaa tagagttctt 173400
gttggtcttc cttgatgctg atgtgtcaaa tcatgttatt aatggtaact ggttgaatga 173460

-continued

```
ggttatggaa aaagttggag ctatagcagg tgatgttcta tatgtcatgg aaaaacttct 173520

tcctagctct ataaacagag atgacactag caaaataaat ctttgctcgt tacaaatatt 173580

ggagaaaact aaagatctga aggcacaagt ggaaacttac tacaaatcct tgaaatttac 173640

tccatctcag ttctccacct tttgtggatt gagctatctg gattctcttt tatggaaatt 173700

gaatgagatg tcgaaatcta aatctgattt agatttcttg atgaaacctc tttttggtaa 173760

tttggagaaa gagctatcaa gtcatatatc cattttagag aaggagctct catctttatc 173820

atccattttc agagatgttc taaaggtgca ccatgaacat aaaattccta aaaatctcca 173880

aagacgtacc atcaatttgg catatgaagc tgagtttgcc attgactcta ttcagtataa 173940

tgcttttttg catatttttt gctcacttcc tacaatctta aaagagatca agcacattaa 174000

tgcacaggtg actgagatgt ggtcagcaga cgttgctctt aagccttgct atgtggtagc 174060

actatttaaa cacctgccaa ctcaacataa caatccagtg attgatgagg agatagtggg 174120

ttttgggaaa gacacagaaa aaatgattca gtgtttgatt agaggtacaa atgagctaga 174180

cgtcgtccca attgtaggca tggggggaca agggaaaacg acaattgcta gaaaggtgta 174240

caatagtgac aacattgttt ctcattttga tgttcgagca tggtgcatcg tttcccaaac 174300

atataaccgg agaacgctat tacaagagat ttttagtcaa gttaccggtt ccaaggacaa 174360

gggggataag gatgacatcc ttgctgacga gttgaggaaa atcttaatgg gcaagagata 174420

tctcattgta ttggatgata tgtgggattg tatggcatgg gatgacttga ggctttgttt 174480

tccagatgtt ggaaatagaa gcagaatcgt agtaacaact cgacttgaga aagtgggtga 174540

gaaagtcaag tactacactg atccccgggt acc                              174573
```

<210> SEQ ID NO 39
<211> LENGTH: 57
<212> TYPE: PRT
<213> ORGANISM: Phytophthora infestans

<400> SEQUENCE: 39

```
Met Arg Ser Ile Gln Leu Leu Ile Ile Ala Leu Val Ala Phe Leu Ala
1               5                   10                  15

Cys Cys Ser Ala Thr Pro Ala Pro Pro Gln Val Ser Leu Ser Phe Leu
            20                  25                  30

Pro Val Gln Arg Arg Ser Leu Arg Thr Asp Thr Thr Leu Asp Ser Glu
        35                  40                  45

Asp Asn Asn Glu Asp Ser Gly Glu Arg
    50                  55
```

<210> SEQ ID NO 40
<211> LENGTH: 187
<212> TYPE: PRT
<213> ORGANISM: Phytophthora infestans

<400> SEQUENCE: 40

```
Ser Val Trp Lys His Val Lys Val Arg Trp Trp Leu Glu Thr Glu Lys
1               5                   10                  15

Ser Asp Asp Phe Val Arg Lys Ala Leu Lys Leu Asn Gly Leu Asp Asp
            20                  25                  30

Thr Ala Met Lys Ala His Lys Asn Tyr Lys Tyr Tyr Ala Tyr Phe Ala
        35                  40                  45

Lys Lys Ala Glu Asp Tyr Leu Phe Asn Lys Trp Leu Arg Asn His Val
    50                  55                  60

Pro Thr Phe Glu Ala Trp Lys Ser Leu Asn Leu Gly Lys Ile Thr Lys
```

-continued

```
65                  70                  75                  80

Ala Asp Gln Leu Lys Glu Ile Ala Asn Thr Lys Asn Phe Ile Ser Tyr
                85                  90                  95

Ser Arg Phe Val Lys Gln Tyr Asp Asp Asn Val Val Ser Thr Leu Asn
            100                 105                 110

Ala Gly Tyr Asn Pro Pro Val Val Ala Val Ala Arg Gly Ala Ser Glu
        115                 120                 125

Ala Glu Ile Thr Ala Arg Thr Met Ile Met Ala Ser Ala Arg Arg Asp
    130                 135                 140

Asp Asp Val Ala Lys Val Leu Leu Gly Leu Thr Lys Pro Gly Tyr Pro
145                 150                 155                 160

Arg Arg Val Leu Asp Gly Asn Ala Leu Thr Gln His Asp Glu Tyr Lys
                165                 170                 175

Tyr Tyr Gln Leu Phe Lys Glu Ala Lys Thr Ser
            180                 185
```

R8 *PHYTOPHTHORA* RESISTANCE GENE IN POTATO

This application is a divisional of U.S. application Ser. No. 15/511,103, filed Mar. 14, 2017, which national phase entry pursuant to 35 U.S.C. § 371 of International Application No. PCT/NL2015/050646, filed Sep. 17, 2015, which claims the benefit of U.S. Provisional Application No. 62/051,361, filed Sep. 17, 2014.

This application contains a sequence listing submitted in electronic format. The file name is "2019-01-08_01190-0001-01US_seqlist_ST25," it was created on Jan. 8, 2019, and is 269,566 bytes in size.

FIELD OF THE INVENTION

The invention is related to new resistance genes to oomycete infections, in particular infections with *Phytophthora infestans* in plants, in particular potato plants. Further part of the invention are the production of transgenic plants with said resistance gene and transgenic resistant plants harbouring said genes.

BACKGROUND

Potato is the third largest global food crop after wheat and rice and it suffers from yield losses up to 16% because of infestations with late blight.

Late blight, caused by the oomycete *Phytophthora infestans*, is one of the most serious diseases in worldwide potato production. It was responsible for the Irish potato famine of the mid-19th century, resulting in the death of one million people. Although a lot of effort has been invested in controlling the pathogen, chemical control of *P. infestans* is still the main crop management strategy, but environmental safety is becoming more important and the pathogen is sometimes able to evolve resistance to the fungicide treatment. Therefore, introduction of resistance into modern potato varieties is the most durable strategy to control the disease.

The family of Solanaceae is of high economic importance and is composed of more than 3,000 species which include important crop and model plants such as potato (*Solanum tuberosum*), tomato (*Solanum lycopersicum*) and eggplant (*Solanum melongena*) (Knapp, S., 2002, J. Exp. Bot. 53:2001-2022), but also wild species occurring in very different habitats (Spooner, D. M. and Hijmans, R. J., 2001, Amer. J. Potato Res. 78:237-268). About 15,000 wild potato accessions are being maintained in large collections worldwide and the establishment of core and mini collections enables an effective use of the existing variation in gene banks while maintaining the variability, as has been proposed before (Hoekstra, R. 2009, Potato Res. 52:237-244). Plant breeders try to improve varieties by introducing new alleles, resulting in higher yields and better quality or resistance characteristics. Identifying new, promising alleles is not an easy task. In the post-genomics era, mining of a crop's (wild) gene pool for novel and superior alleles for agronomically important traits is becoming more and more feasible. Genebanks all over the world contain huge untapped resources of distinct alleles that may have potential application in crop breeding programs. The genome sequence of potato (Potato Genome Sequencing Consortium 2011) and tomato (The Tomato Genome Consortium 2012) will facilitate mining for novel alleles or paralogs of resistance (R) genes. These may be found in the largely untapped resources of crossable species within the genus *Solanum* allowing their exploitation in breeding programs. Also, insight into sequence diversity at the R gene loci in wild *Solanum* species with different resistance response against economically important diseases will result in a better understanding of the mechanism of R gene functionality and evolution but can also help to identify new alleles or paralogs with different race specificities, and develop allele-specific diagnostic markers for marker assisted breeding.

In the last century, *Solanum demissum*, which is a hexaploid Mexican species, was extensively used in breeding for late-blight resistance in potato. Initially, a series of 11 R genes derived from *S. demissum* was described. Of these, R1, R2, R3a/b, R6, and R7 have been localized on the genetic maps of potato (*Solanum tuberosum*). However, these R genes confer pathovar-specific resistance and those that were introgressed into potato varieties, mainly R1, R2, R3, R4, and R10 (Vleeshouwers, V. G. A. A. et al., 2011, Ann. Rev. Phytopathol. 49:507-531), were quickly overcome by the pathogen. Also several other wild *Solanum* species have been reported as being potential sources of resistance, many of which have been genetically characterized (Table 1). Recent efforts to identify late blight resistance have focused on major R genes conferring broad-spectrum resistance derived from diverse wild *Solanum* species. Beside *S. demissum*, other wild *Solanum* species such as *S. acaule, S. chacoense, S. berthaultii, S. brevidens, S. bulbocastanum, S. microdontum, S. sparsipilum, S. spegazzinii, S., stoloniferum, S. sucrense, S. toralapanum, S. vernei* and *S. verrucosum* have been reported as new sources for resistance to late blight (reviewed by Jansky S., 2000, Plant Breeding Rev. 19:69-155).

TABLE 1

R-genes and quantitative trait loci for late blight resistance reported for wild *Solanum* species

| Wild species | Locus type or name | Also known as | Chromosome | cloned | Reference |
|---|---|---|---|---|---|
| *S. berthaultii* | QTLs (4) | | I, III, VII and XI | | |
| | Rpi-ber | | X | | (Rauscher et al., 2006) |
| | Rpi-ber1 | | X | | (Park et al.) |
| | Rpi-ber2 | | X | | (Park et al.) |
| *S. bulbocastanum* | RB/Rpi-blb1 | RB | VIII | yes | (Song et al., 2003; van der Vossen et al., 2003) |
| | Rpi-blb2 | | VI | yes | Van der Vossen et al. 2005 |
| | Rpi-blb3 | | IV | yes | (Park et al., 2005a) |

TABLE 1-continued

R-genes and quantitative trait loci for late blight resistance reported for wild *Solanum* species

| Wild species | Locus type or name | Also known as | Chromosome | cloned | Reference |
|---|---|---|---|---|---|
| *S. caripense* | QTL (2) | | unassigned | | |
| *S. demissum* | R1 | | V | yes | (Ballvora et al., 2002) |
| | R2 | | IV | yes | (Park et al., 2005b) |
| | R3, R6, R7 | | XI | | |
| | R3a | | XI | yes | (Huang et al., 2005) |
| | R3b | | XI | | |
| | R5-R11 | | XI | | |
| | R10, R11 | | XI | | (Bradshaw et al., 2006) |
| *S. microdontum* | QTLs (3) | | IV, V and X | | (Tan et al., 2008) |
| | QTL | | Unassigned | | |
| *S. mochiquense* | Rpi-mcq1 | (Rpi-moc1) | IX | yes | |
| *S. papita* | Rpi-pta1 | | VIII | yes | (Vleeshouwers et al., 2008) |
| *S. paucissectum* | QTLs (3) | | X, XI and XII | | |
| *S. phureja* | Rpi-phu1 | | IX | | |
| *S. pinnatisectum* | Rpi-pnt1 | (Rpi1) | VII | | (Kuhl et al., 2001) |
| *S. stoloniferum* | Rpi-sto1 | | VIII | yes | (Wang et al., 2008) |
| *S. venturii* | Rpi-vnt1.1 | Rpi-phu1 | IX | yes | Foster et al. 2009 |
| | Rpi-vnt1.3 | | IX | yes | Pel et al. 2009 |
| *S. vernei* | QTLs (several) | | VI, VIII, IX | | |
| Hybrids with *S. tuberosum* | Rpi-abpt | | IV | yes | Lokosou et al. 2009 |
| | R2-like | | IV | yes | (Park et al., 2005b) |

Recently, a further R gene from *S. demissum*, which was denominated R8 was mapped in more detail (Jo, K.-R. et al., 2011, Theor. Appl. Genet. 123:1331-1340). This resistance gene has been labeled as providing a durable resistance, also because infections with *P. infestans* isolates that were derived from clonal lineage US8, which is recognized as the most common and the most aggressive genotype of *P. infestans* in the US (Fry. W. E and Goodwin, S. B., 1997, Bioscience 47:363-367), were overcome by the R8 producing plants, both in detached leaf assays and in field trials (Bisognin, D. A. et al., 2002, Euphytica 125:129-138).

In 2009, the sequence of the *P. infestans* genome of ~240 Mb size has been published (Haas B. J. et al., 2009, Nature 461:393-398). The genome of *P. infestans* revealed large complex families of effector genes encoding secreted proteins involving pathogenesis which fall into two broad categories of apoplastic effectors and cytoplasmic effectors (Dodds P. N. and Rathjen, J. P., 2010, Nat. Rev. Genet. 11:539-548). The former accumulate in the plant intercellular space (apoplast) and include secreted hydrolytic enzymes such as proteases, lipases and glycosylases, enzyme inhibitors to protect against host defence enzymes, and necrotizing toxins. The latter are translocated directly into the plant cell by specialized infection structures known as haustoria (Whisson S. C. et al., 2007, Nature 450:115-118). 563 RXLR and 196 Crinkler (CRN) cytoplasmic effectors have been revealed by annotation of the *P. infestans* genome (Haas et al. 2009). The domain structure of *P. infestans* AVR proteins shows a typical modular structure with a N-terminal (signal peptide) domain, RXLR motif (Arg-X-Leu-Arg, where X indicates any amino acid), and C-terminal effector domain that often contains conserved amino acids residues (W, Y, and L) and tandem repeats (Oliva, R. et al., 2010, Cell Microbiol. 12:705-715; Schomack, S. et al., 2010, Proc. Natl. Acad. Sci. USA 107:17421-17426; Win, J. et al., 2012, PLoS Pathogens 8(1):e1002400). The N-terminal domain plays a role in secretion and host translocation whereas the variable C-terminal domain carries the effector biochemical activity. Like RXLRs, CRNs are modular proteins. CRNs are defined by a highly conserved N-terminal, 50-amino-acid LFLAK domain and an adjacent diversified DWL domain followed by a diverse C-terminal domain (Haas et al. 2009).

The Avr genes reside in the gene sparse regions with bigger distance to their neighboring genes (Haas et al. 2009) and represent the highly variable peripheral genome. To date, a catalog of more than eight Rpi and Avr gene pairs for the potato-*P. infestans* pathosystem is available, including R1/Avr1 (Ballvora, A. et al., 2002, Plant J. 30:361-371), R2/Avr2 (Lokossou, A. A. 2010, PhD thesis, Wageningen University; Champouret, N. 2010, PhD thesis, Wageningen University), R3a/Avr3a (Huang, S. et al., 2005, Plant J. 42:251-261; Armstrong, M. R. et al., 2005, Proc. Natl. Acad. Sci. USA 102:7766-7771), R3b/Avr3b (Li, G. et al., 2011, Mol. Plant Microbe Interact. 24(10):1132-1142, R4/Avr4 (van Poppel, P. M. J. A. et al., 2008, Mol. Plant Microbe Interact. 21:1460-1470), Rpi-blb1/Avrblb1 (van der Vossen, E. A. G. et al. 2003, Plant J. 23:567-576; Vleeshouwers, V. G. G. A. et al. 2008, PLoS ONE 3:e2875), Rpi-blb2/Avrblb2 (van der Vossen, E. A. G. et al., 2005, Plant J. 44:208-222; Oh, S. K. et al., 2009, Plant Cell 21:2928-2947), and Rpi-vnt1/Avrvnt1 (Foster, S. J. et al., 2009, Mol. Plant Microbe Interact. 22:589-600; Pel, M. A. 2010, PhD thesis, Wageningen University), which have proven valuable in e.g., dissecting resistance in genetically modified plants (Zhu, S. X. et al., 2012, Transgenic Res. 21:89-99) and classical breeding material (Rietman, H. et al., 2012, Mol. Plant Microbe Interact. 25:910-919).

Field resistance against late blight, which occurs in several potato varieties has been thought to have its basis on other mechanisms than R genes, since the field resistance has a more durable nature, while R genes are quickly defeated because of the ability of *P. infestans* to quickly adapt and evolve and break through such a 'qualitative' resistance. This has led to the misguided concept of breeding for so-called 'R gene free' potato plants that carry field resistance but lack known R genes. However, the genetic basis of field resistance has remained unclear, mainly because the weak phenotypes are too difficult to follow in the genetically complex potato and because hitherto the AVR profiles of infecting *P. infestans* strains could not be determined accurately.

"Sarpo Mira" is one of the few potato cultivars that have been reported to retain resistance in the field for several years and it is a candidate for delivering durable late blight resistance (Kim, H. J. et al., 2011, Theor. Appl. Genet. 124:923-935). The cultivar was bred by the Sárvári family in Eastern Hungary. However, to our knowledge, the pedigree is not described in the literature. Most likely, prebreeding leaned on the heritage of the Russian breeders Vavilov and Bukasov. Unfortunately, the origin or genetic constituents that determine the resistance of 'Sarpo Mira' are not known, and the degree to which resistance includes previously characterized R genes could not be unambiguously determined using classical pathogen assays. To elucidate this further, Rietman, H. et al. (2012, Mol. Plant-Microbe Interact. 25(7):910-919) have found that the resistance has a highly complex genetic basis. They found that it is based on the combination of four pyramided qualitative R genes, including the 'old' R3a, R3b and R4 resistance genes (see table 1) and a newly discovered gene, labelled Rpi-Smira1, and a quantitative resistance conferred by a novel gene, Rpi-Smira2. While the qualitative resistance matched responses to avirulence (AVR)3a (PITG_14371), AVR3b (PITG_18215), AVR4 (PITG_07387) and AVRSmira1 (PITG_07750) RXLR effectors, which was overcome by particular *P. infestans* strains, the quantitative resistance surprisingly appeared to be corresponding to responses to the RXLR effector AvrSmira2 (PITG_07758) and was only detectable under field conditions. However, Rietman et al. did not elucidate the molecular nature of the Rpi-Smira2 gene or its location on the genome of the 'Sarpo Mira' variety. Further, they argue that the quantitative resistance is only effective in combination with a qualitative resistance, and that in the case of 'Sarpo Mira' the five resistance genes act in concert to provide the durable field resistance.

Accordingly, there still lacks a gene that is able to provide field resistance against late blight and methods to provide such a durable resistance to plants.

SUMMARY OF THE INVENTION

The inventors now have found the R8 gene from *Solanum demissum* and show that it is the same gene as the putative Rpi-Smira2 gene found in potato variety 'Sarpo Mira'.

LEGEND TO THE FIGURES

FIG. 1. Positions of NBS profiling markers and R gene homologs on chromosome IX.

Markers in large font indicate the NBS profiling markers that were linked to R8. Potato genome sequences, the tomato genome sequences and the marker sequence database from the SGN were searched using the NBS5a6H and NBS1M by BLAST analysis. The bars on the left indicate *S. phureja* scaffolds (PGSC v3). In the middle are the tomato EXPEN 2000 genetic map and the tomato SL2.40 Ch9 physical map (SGN). On the right positions of tomato genome sequences with homology to R genes are shown. Horizontal and diagonal lines indicate corresponding marker positions in the different maps.

Figure 2:
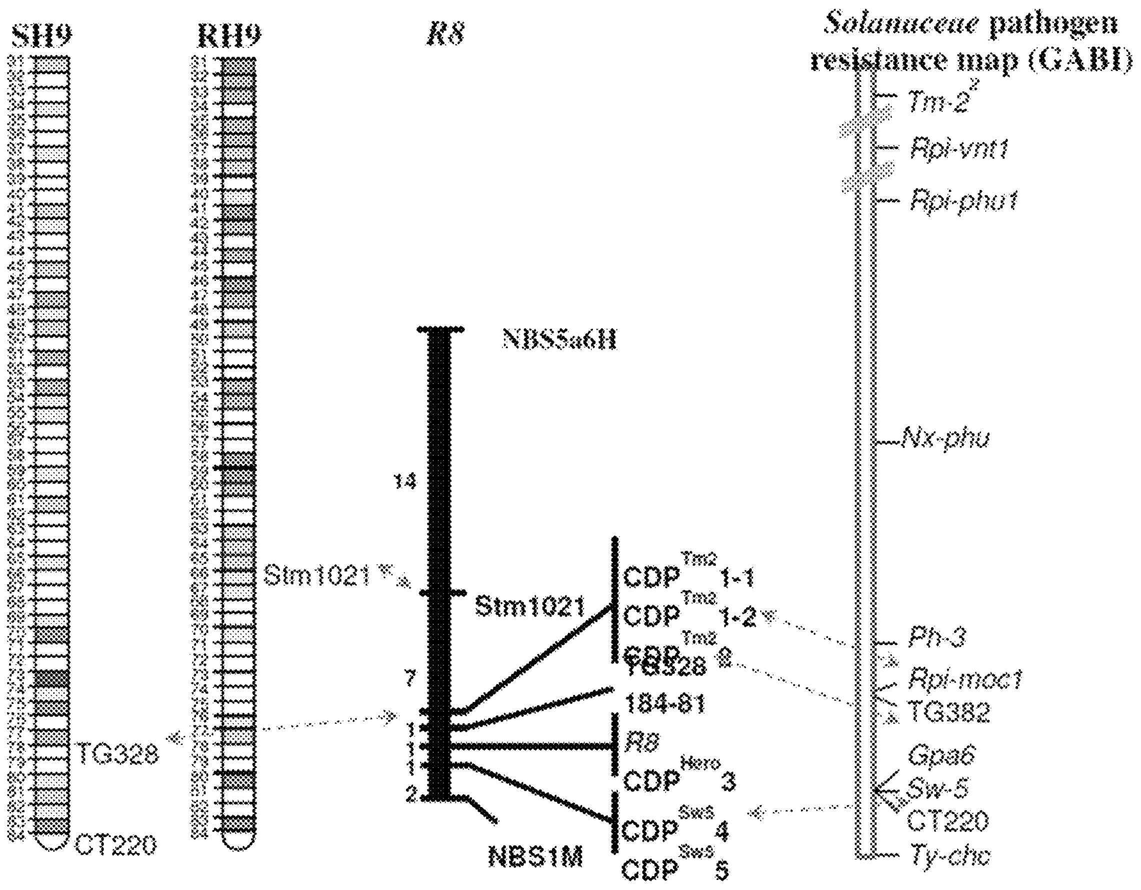

FIG. 2. Comparison of different genetic maps of chromosome IX. From left to right the potato SHxRH map (Van Os et al. 2006), the R8 map produced in this study and the combined Solanaceae pathogen resistance map as extracted from the GABI website (May 20, 2011). Only the long arms of chromosome IX are shown. The dotted arrows indicate relative positions of studied markers shared between the different maps.

Figure 3:
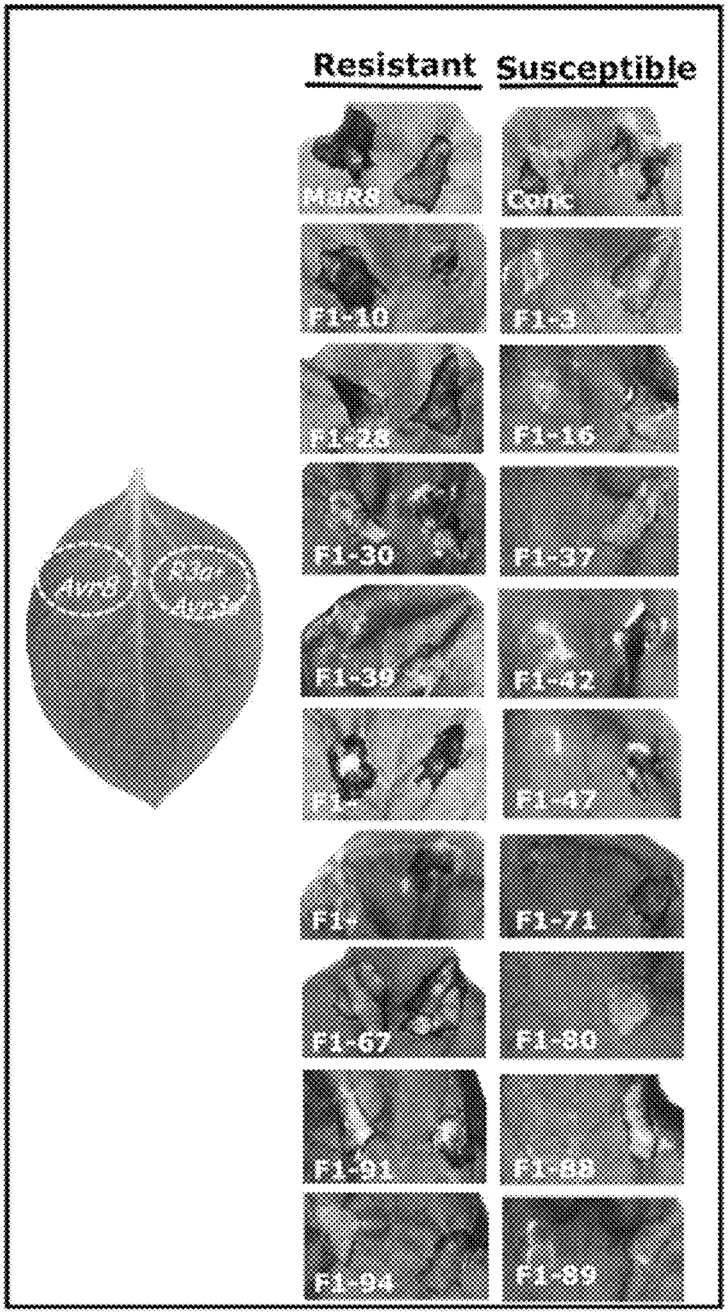

FIG. 3. Agroinfiltration assay for parents MaR8 and cv Concurrent and nine resistant and nine susceptible progeny. R-Avr interactions were validated by co-segregation of responses to the effector AVR8 with resistance to *P. infestans* isolate IPO-C in F1 population (MaR8 x Concurrent). Avr8 was transiently expressed (left side) in MaR8, Concurrent and F1 progeny plants by agroinfiltration. A 1:1 mixture of R3a and Avr3a was infiltrated as positive controls (right side).

Figure 4A:
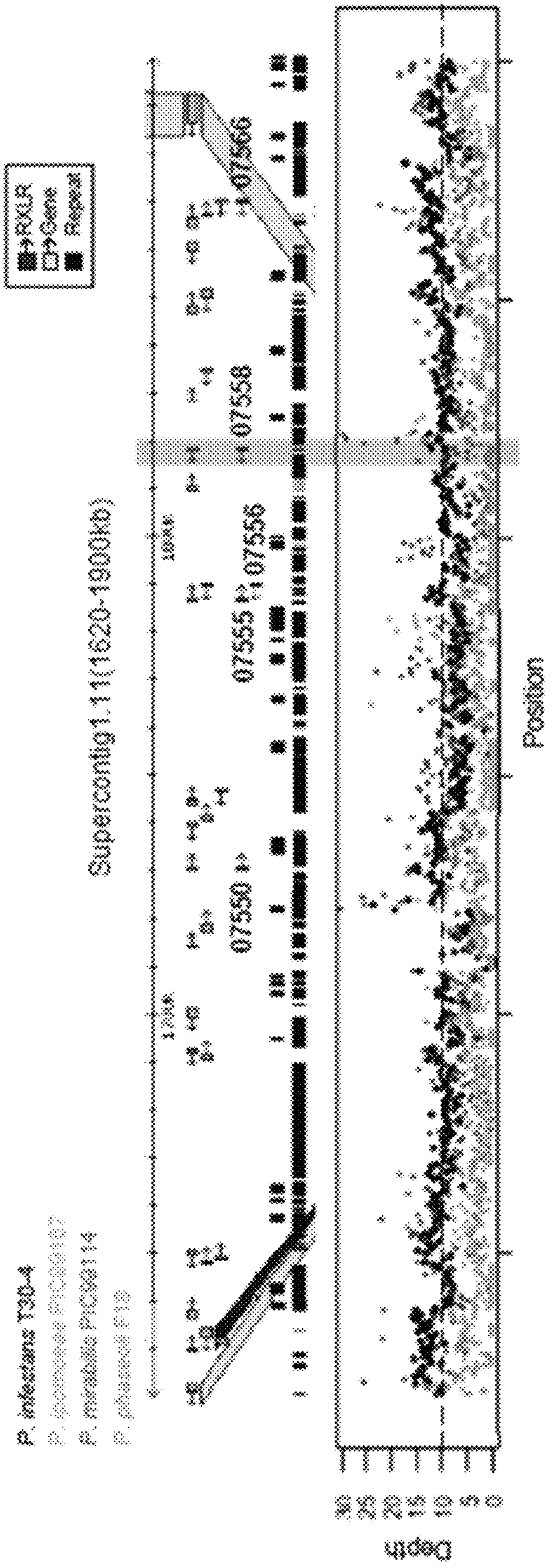
Figure 4B:
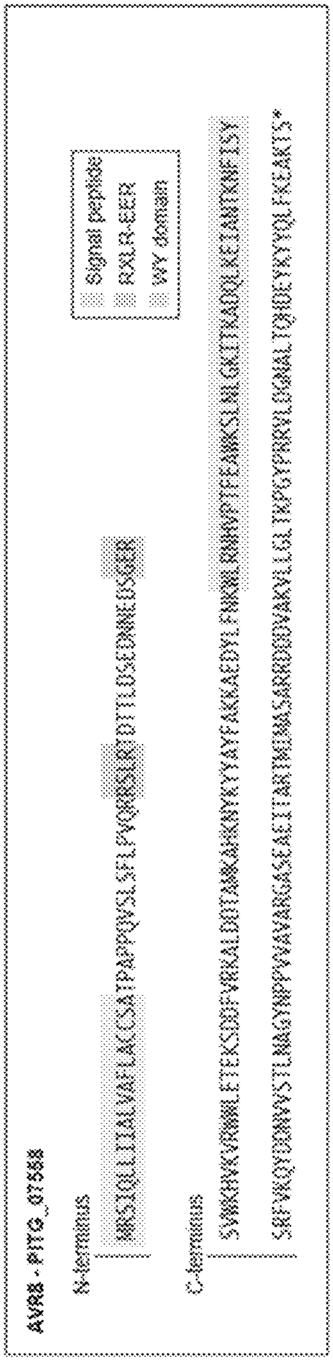
Figure 4C:
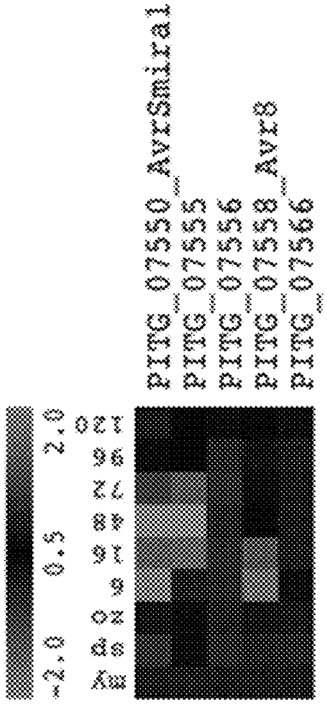

FIG. 4. Avr8 effector features. A. Avr8-containing genomic region. The 1620-1900 kb of genomic region in supercontig 1.11 was shown. This region includes Avr-Smira1 (PITG_07550), PITG_07555, PITG_07556, PITG_07566. The Avr8 gene is present in *P. infestans* and *P. mirabilis* but not in *P. ipomoeae* and *P. phaseoli*. B. The Avr8 gene is a single copy gene and encodes a secreted protein with a signal peptide followed by a typical RXLR motif and most likely an EER-like motif at the N-terminal (SEQ ID NO: 39) and a WY domain at the C-terminal effector region (SEQ ID NO: 40). C. A heat map showing expression levels of five RXLRs including the Avr8 gene from a time course infection on potato (6 to 120 hpi). Out of these RXLR effectors, PITG_07550, PITG_07555, PITG_07556, PITG_07566, Avr8 (PITG_07558) is the only one specifically induced at 6/16 hpi. my; mycelia, sp; sporangia, zo; zoospores. Gene induction is relative to mycelia as previously reported by Raffaele et al. (2010b). The gene expression values are from the reference genome strain T30-4 (Haas et al. 2009).

Figure 5:
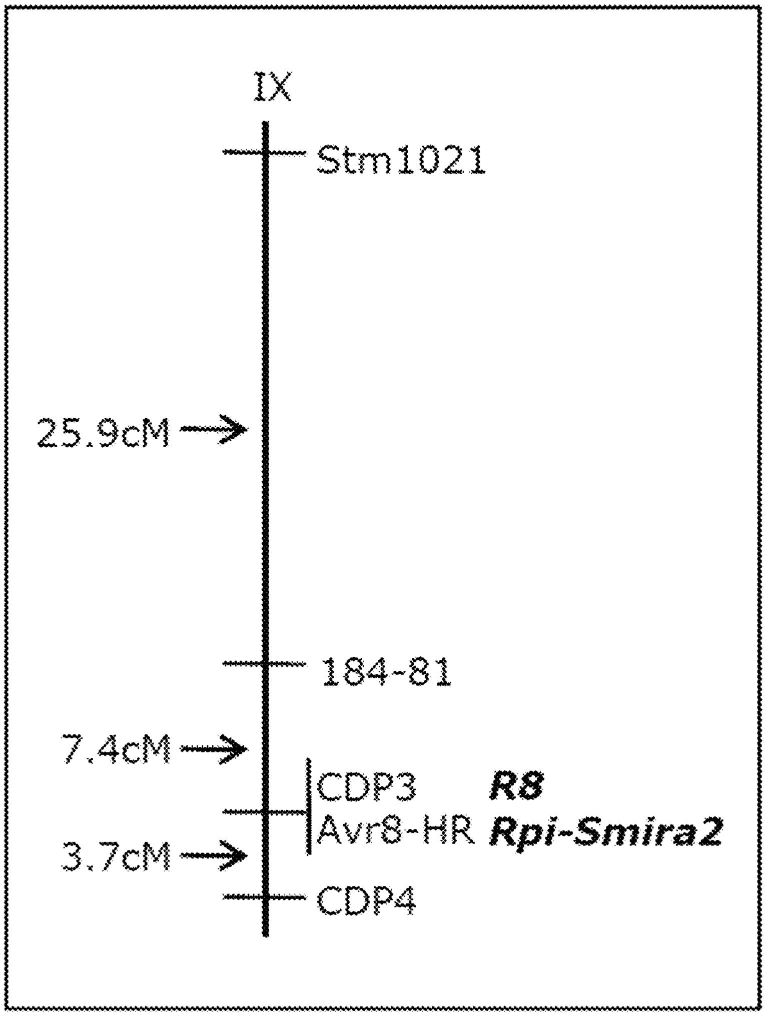

FIG. 5. Rpi-Smira2 resides in R8 locus on chromosome IX. The quantitative resistance conferred by Rpi-Smira2 in cv. Sarpo Mira based on AVR8 responsiveness (AVR8-HR) mapped between R8 flanking markers 184-81 and CDP4 where R8 was also localized (Jo et al. 2011). The map distances were calculated based on the frequency of the recombination between markers.

Figure 6:
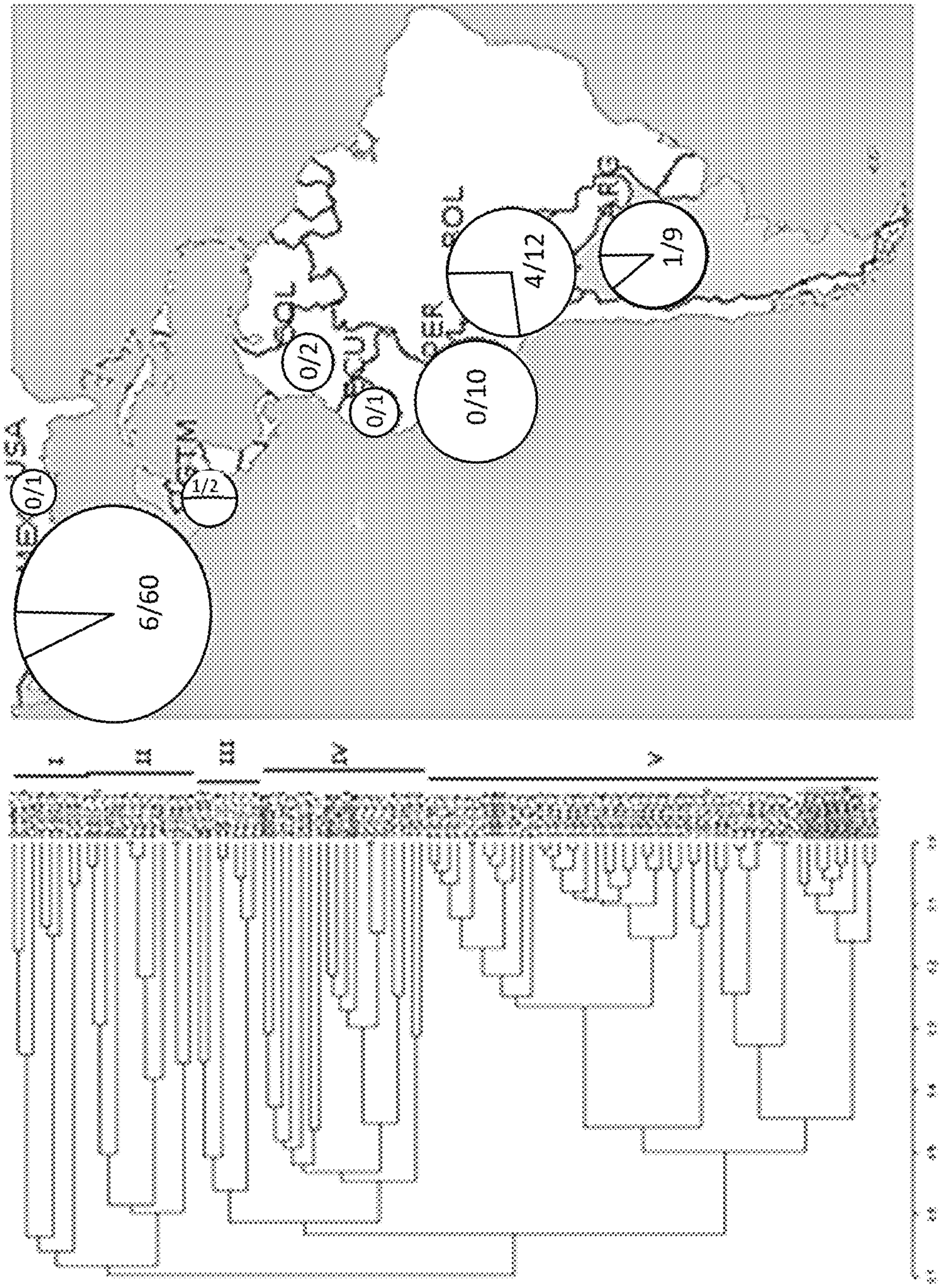

FIG. 6. AVR8-responding *Solanum* germplasm accessions are distributed both in Central and South America. The phylogenetic tree was assembled using the AFLP fingerprinting data generated by Jacobs et al. (2008). All fingerprints can be obtained from SolRgene database website. Some genotypes, e.g., TUQ299-4 (previously named DMS299-4), DMS585-7, and CHN544-2 (previously named STO554-2), were not included in the phylogenetic tree because these are not available in SolRgene database. Genotypes in red color respond to Avr8. At the right side is a geographical overview of Avr8-responding *Solanum* species. The bubble size represents number of genotypes tested, and red sector the number of AVR8 responding genotypes. DMS; *S. demissum*, TAR; *S. tarijense*, GIG; *S. microdontum gigantophyllum*, USA; United States, MEX; Mexico, GTM; Guatemala, COL; Colombia, ECU; Ecuador, PER; Peru, BOL; Bolivia, ARG; Argentina. The unclassified *Solanum*, previously named *S. astleyi* and *S. ugentii* were not included.

Figure 7:
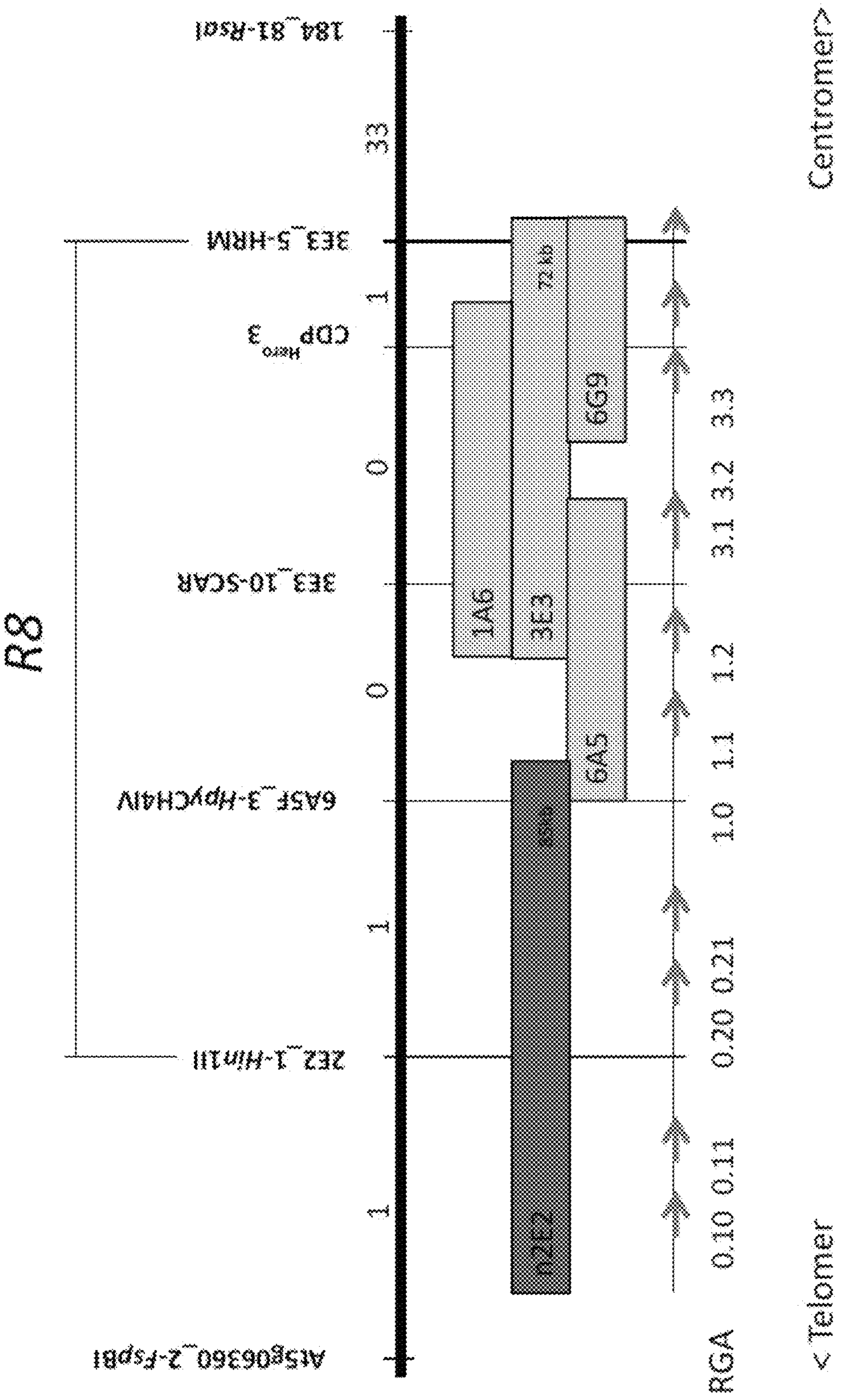

FIG. 7. Genetic and Physical map of R8 on the bottom end of chromosome 9. The upper part of this figure represents a genetic map. Markers of different origin were mapped in a F1 recombinant population (R8*C) of 1670 individuals and their relative positions are indicated by vertical lines. The number of recombinants between the markers are indicated by numbers between the vertical lines. The horizontal line marked by R8 indicates the genetic mapping interval for R8. The lower part of this figure represents a physical map. Using molecular markers BAC clones were identified from BAC libraries derived from MaR8. The grey bars represent the individual BAC clones. Vertical lines indicate the connection between physical and genetic maps. The arrows on the bottom line indicate the position and orientations of resistance gene analogs (RGAs) on the physical map, which are labeled as RGA0.10-RGA3.3.

FIG. 8: Nucleotide sequence of the 170 kb BAC contig (SEQ ID NO: 38).

FIG. 9. R8 complementation analysis. A. Transgenic Desiree events, transformed with resistance gene analogs (RGAs) show different phenotypes after inoculation of whole plants with IPO-C, ranging from full resistance (R), to intermediate resistance (IR), to susceptible (S). B. Co-expression of RGA0.20, and not of any of the other RGAs (RGA0.21 is here provided as an example), with different concentrations (OD=1, 0.5, or 0.25) of Avr8 in *N. benthamiana* results in a HR response.

FIG. 10. The nucleotide sequence of the R8 gene (SEQ ID NO: 36). The coding sequence is in bold. Start and stopcodons are underlined. The coding sequence is preceded by the 5'UTR region and followed by the 3'UTR sequence. A Thymine at position -723 in the 5'UTR of R8 differred from Rpi-smira2 which had a Cytosine residue at this position. This SNP is underlined and in Italics.

FIG. 11. Amino acid sequence architecture of the R8 protein (SEQ ID NO: 37). Coiled coil (CC), Nucleotide binding Apaf-1 R gene and CED4 homology (NB-ARC), and leucine rich repeat (LRR) regions can be distinguished. Conserved residues are in underlined red font.

Figure 12:
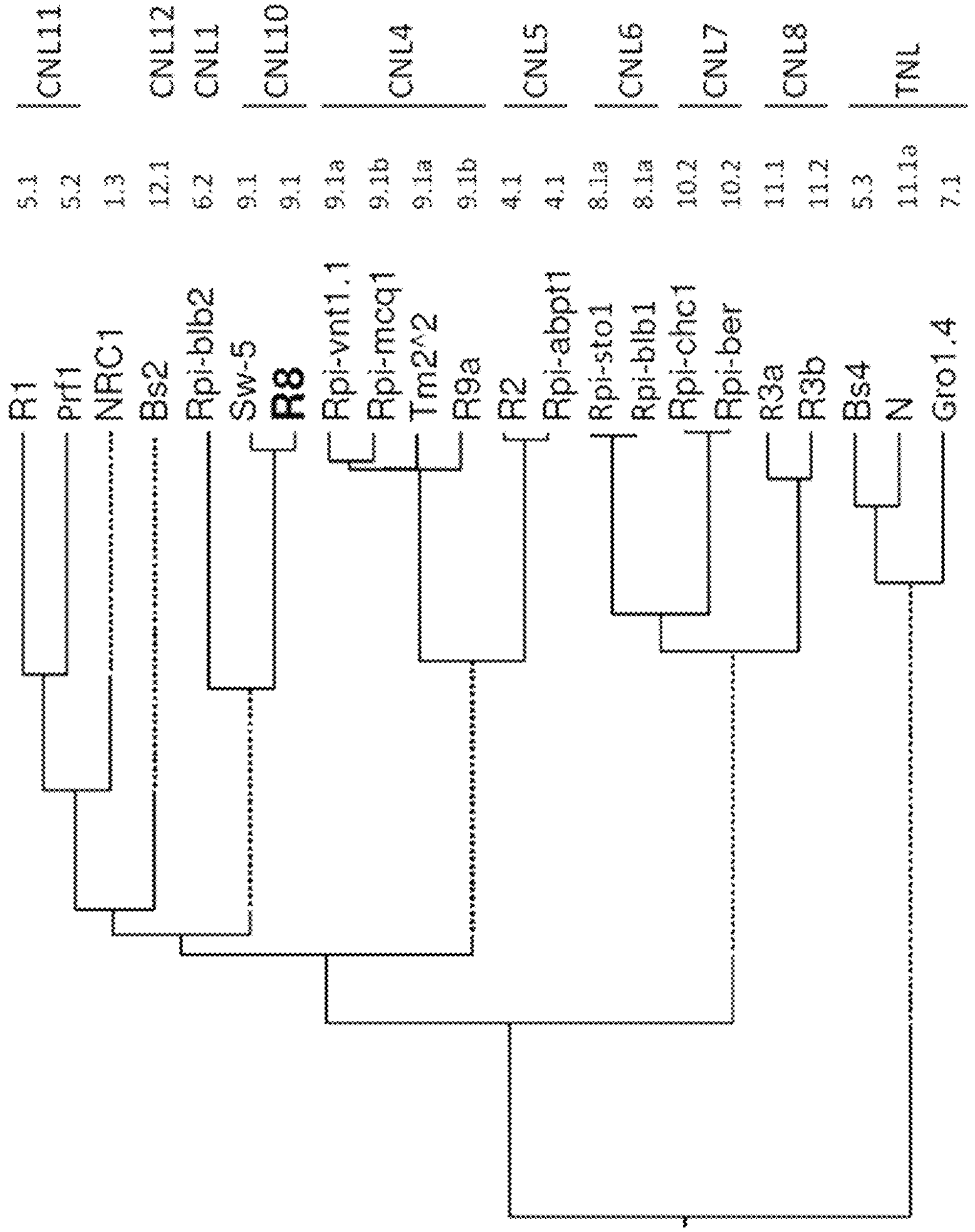

FIG. 12. Phylogenetic analysis of R8 and other R proteins from Solanaceae. The column on the right of the protein names contains the genetic location of the encoding genes (chromosome, and RGA cluster number; Vossen et al. 2013). Clades observed in this tree match the sequence groups defined previously (extreme right column; Andolfo et al. 2014).

Figure 13:
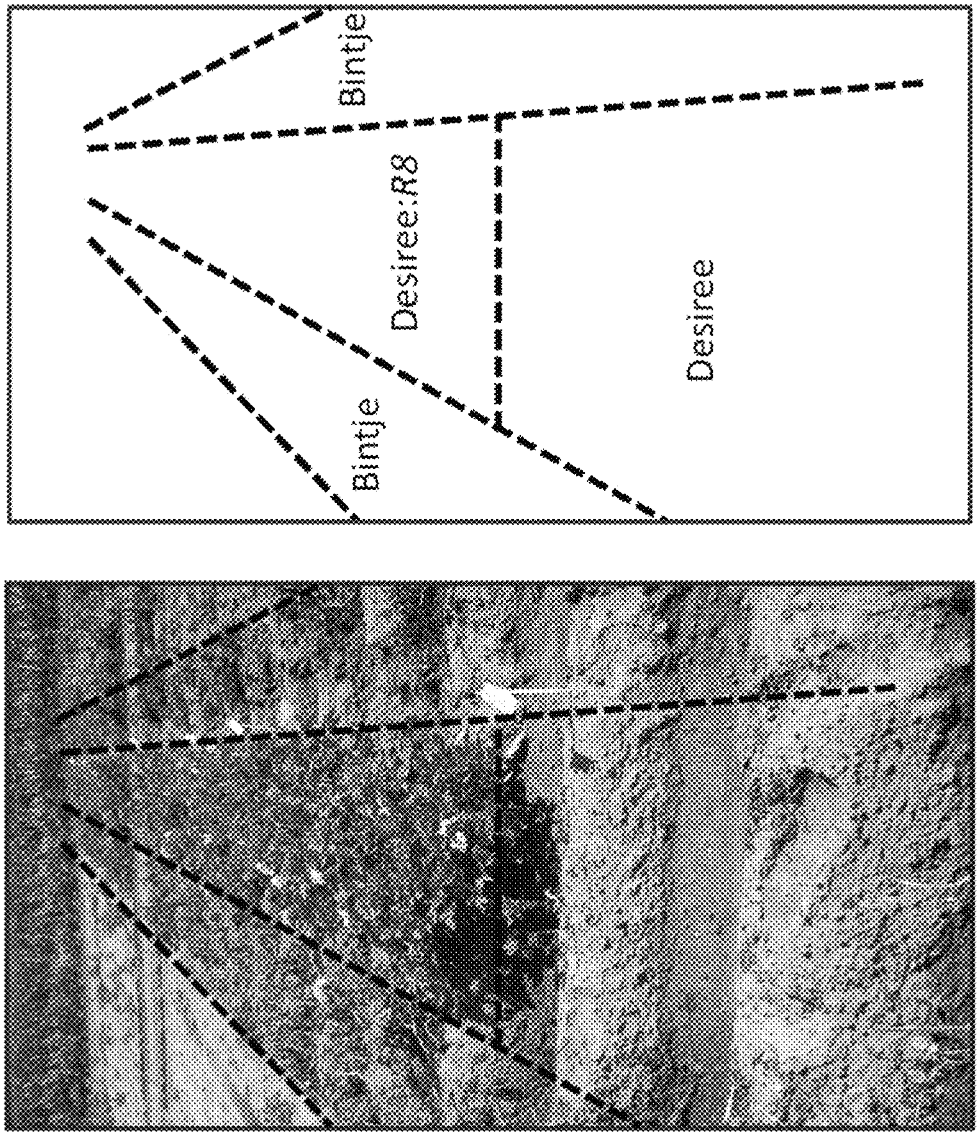

FIG. 13. R8 mediated broad spectrum resistance in field trials in 2014. Bintje spreader rows were derived from seed tubers. Desiree and Desiree transformants were planted from in vitro culture. At the onset of the natural late blight epidemic the Bintje plants were much taller than the Desiree and R8 transgenics (Desiree:R8). This explains the difference in the height of the deceased Bintje and Desiree plants, while the R8 transgenics kept growing.

DETAILED DESCRIPTION

As used herein, the term "plant or part thereof" means any complete or partial plant, single cells and cell tissues such as plant cells that are intact in plants, cell clumps and tissue cultures from which potato plants can be regenerated. Examples of plant parts include, but are not limited to, single cells and tissues from pollen, ovules, leaves, embryos, roots, root tips, anthers, flowers, fruits, stems shoots, tubers, including potato tubers for consumption or 'seed tubers' for cultivation or clonal propagation, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "variety" is as defined in the UPOV treaty and refers to any plant grouping within a single botanical taxon of the lowest known rank, which grouping can be: (a) defined by the expression of the characteristics that results from a given genotype or combination of genotypes, (b) distinguished from any other plant grouping by the expression of at least one of the said characteristics, and (c) considered as a unit with regard to its suitability for being propagated unchanged.

The term "cultivar" (for cultivated variety) as used herein is defined as a variety that is not normally found in nature but that has been cultivated by humans, i.e. having a biological status other than a "wild" status, which "wild" status indicates the original non-cultivated, or natural state of a plant or accession. The term "cultivar" specifically relates to a potato plant having a ploidy level that is tetraploid. The term "cultivar" further includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar.

As used herein, "crossing" means the fertilization of female plants (or gametes) by male plants (or gametes). The term "gamete" refers to the haploid or diploid reproductive cell (egg or sperm) produced in plants by meiosis, or by first or second restitution, or double reduction from a gametophyte and involved in sexual reproduction, during which two gametes of opposite sex fuse to form a diploid or polyploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from genetically the same individual.

The term "backcrossing" as used herein means the process wherein the plant resulting from a cross between two parental lines is crossed with one of its parental lines, wherein the parental line used in the backcross is referred to as the recurrent parent. Repeated backcrossing results in the genome becoming more and more similar to the recurrent parent, as far as this can be achieved given the level of homo- or heterozygosity of said parent.

As used herein, "selfing" is defined as refers to the process of self-fertilization wherein an individual is pollinated or fertilized with its own pollen.

The term "marker" as used herein means any indicator that is used in methods for inferring differences in characteristics of genomic sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, "locus" is defined as the genetic or physical position that a given gene occupies on a chromosome of a plant.

The term “allele(s)” as used herein means any of one or more alternative forms of a gene, all of which alleles relate to the presence or absence of a particular phenotypic trait or characteristic in a plant. In a diploid cell or organism, the two alleles of a given gene occupy corresponding loci on a pair of homologous chromosomes. It is in some instance more accurate to refer to “haplotypes” (i.e. an allele of a chromosomal segment) in stead of “allele”, however, in these instances, the term “allele” should be understood to comprise the term “haplotype”.

The term “heterozygous” as used herein, and confined to diploids, means a genetic condition existing when different alleles reside at corresponding loci on homologous chromosomes.

As used herein, and confined to diploids, “homozygous” is defined as a genetic condition existing when identical alleles reside at corresponding loci on homologous chromosomes.

As used herein, and confined to tetraploids, the term “nulliplex”, “simplex”, “duplex”, “triplex” and “quadruplex”, is defined as a genetic condition existing when a specific allele at a corresponding locus on corresponding homologous chromosomes is present 0, 1, 2, 3 or 4 times, respectively. At the tetraploid level the phenotypic effect associated with a recessive allele is only observed when the allele is present in quadruplex condition, whereas the phenotypic effect associated with a dominant allele is already observed when the allele is present in a simplex or higher condition.

The terms “haploid”, “diploid” and “tetraploid” as used herein are defined as having respectively one, two and four pairs of each chromosome in each cell (excluding reproductive cells).

The term “haplotype” as used herein means a combination of alleles at multiple loci that are transmitted together on the same chromosome. This includes haplotypes referring to as few as two loci, and haplotypes referring to an entire chromosome depending on the number of recombination events that have occurred between a given set of loci.

As used herein, the term “infer” or “inferring”, when used in reference to assessing the presence of the fungal resistance as related to the expression of the R8 gene, means drawing a conclusion about the presence of said gene in a plant or part thereof using a process of analyzing individually or in combination nucleotide occurrence(s) of said gene in a nucleic acid sample of the plant or part thereof. As disclosed herein, the nucleotide occurrence(s) can be identified directly by examining the qualitative differences or quantitative differences in expression levels of nucleic acid molecules, or indirectly by examining (the expression level of) a the R8 protein.

The term “primer” as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. A “pair of bi-directional primers” as used herein refers to one forward and one reverse primer as commonly used in the art of DNA amplification such as in PCR amplification.

As used herein, the term “probe” means a single-stranded oligonucleotide sequence that will recognize and form a hydrogen-bonded duplex with a complementary sequence in a target nucleic acid sequence or its cDNA derivative.

The terms “stringency” or “stringent hybridization conditions” refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer.

Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or “conditions of reduced stringency” include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

The present invention describes the cloning of the R8 gene (also identified as Rpi-Smira2 gene). R8 was mapped to a new R gene locus on chromosome IX using a *S. demissum* MaR8 mapping population. The R gene locus contains at least 10 paralogous sequences, that are closely related to the R8 gene. Only 1 of the six tested paralogs provided recognition of the *P. infestans* Avr8 effector protein. The R8 gene codes for a protein which is denominated as R8 and the protein encoding nucleotide and its 5' and 3' UTR sequences may be found in FIG. 10 of the present application. As can be derived from Table 8, outside the R gene cluster described in this invention, R8 does not share high identities with known R genes that are known to be specific for *Phytophthora*. The R8 gene and its paralogs share, however, a high identity with a gene from tomato, that is known to provide resistance to tomato spotted wilt virus (TSWV). This Sw-5 protein and R8 share 88.6% homology. Within genes that are known or have been reported to confer resistance against *P. infestans*, the highest amino acid sequence identity (26.1%) is to a protein Rpi-blb2 derived from *Solanum bulbocastanum* (Van de Vossen et al., 2005, The Plant Journal 44, 208-222).

In a first embodiment, the invention provides an isolated or recombinant nucleic acid sequence comprising a nucleic acid sequence encoding the R8 amino acid sequence as as encoded by the nucleic acid presented in FIG. 10 or a functional fragment thereof, i.e. a functional fragment of the amino sequence as encoded by the nucleotide sequence of FIG. 10. Further encompassed in the present invention are sequences that code for a protein that has more than 95% identity of the R8 protein. More preferably, the nucleic acid encoding for such a protein has at least 95% identity with the nucleotide sequence presented in FIG. 10 with respect to the coding part.

The term "nucleic acid" means a single or double stranded DNA or RNA molecule.

Also included are the complementary sequences of the herein described nucleotide sequences.

The term "functional fragment thereof" is typically used to refer to a fragment of the R8 protein that is capable of providing at least partial resistance or increasing resistance in a plant of the Solanaceae family against an oomycete infection. Such a fragment is, for example, a truncated version of the R8 protein as presented in FIG. 10. A truncated version/fragment of the R8 protein is a fragment that is smaller than 1245 amino acids and preferably comprises part of the LRR domain (i.e. part of the leucine-rich repeats domain which stretches from about amino acid 896 to amino acid 1245 of R8 and/or the N-terminal parts of the R8 protein.

Also included are protein sequences that are highly homologous to or have a high identity with the herein described R8 protein, where such proteins are capable of providing at least partial resistance or increasing resistance in a plant of the Solanaceae family against an oomycete infection. Included are artificial changes or amino acid residue substitutions that at least partly maintain the effect of the R8 protein. Preferably such proteins would maintain the ability to recognize the *P. infestans* Avr8 effector protein and induce a defense response. Such proteins are highly homologous or have a high identity with the herein described R8 protein, for example, certain amino acid residues of the original R8 protein can conventionally be replaced by others of comparable nature, e.g. a basic residue by another basic residue, an acidic residue by another acidic residue, a hydrophobic residue by another hydrophobic residue, and so on. Examples of hydrophobic amino acids are valine, leucine and isoleucine. Phenylalanine, tyrosine and tryptophan are examples of amino acids with an aromatic side chain and cysteine as well as methionine are examples of amino acids with sulphur-containing side chains. Serine and threonine contain aliphatic hydroxyl groups and are considered to be hydrophilic. Aspartic acid and glutamic acid are examples of amino acids with an acidic side chain. In short, the term "highly homologous" or "having a high identity" include variants of the R8 protein in which amino acids have been inserted, replaced or deleted and which at least partly maintain the effect of the R8 protein (i.e. at least partly providing or increasing resistance in a plant of the Solanaceae family against an oomycete infection). Preferred variants are variants which only contain conventional amino acid replacements as described above. A high identity in the definition as mentioned above means an identity of at least 95%. Most preferred are amino acids that have an identity of 96, 97, 98 or 99% with the amino acid sequence of R8.

Also included are nucleic acid sequences that encode a highly homologous protein as described above. Preferred are nucleotide sequences that have a high identity with respect to their nucleic acid sequence with the nucleic acid sequence depicted in FIG. 12, at least the coding portion of the nucleic acid sequence of FIG. 12.

Homology and/or identity percentages can for example be determined after sequence alignments with computer programs such as BLAST, ClustalW or ClustalX. Preferably, for the purposes of the present invention, identity of proteins s determined by the alignment method labeled ClustalW found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the ClustalW program, it is possible to obtain a "percent identity" by viewing the "sequence distances" table in the same program.

For nucleotide sequences the BLASTN method is used, which alignment is an algorithm provided by the National Center for Biotechnology Information (NCBI) to compare nucleotide sequences using default parameters.

Many nucleic acid sequences code for a protein that is 100% identical to the R8 protein as presented in FIG. 13. This is because nucleotides in a nucleotide triplet may vary without changing the corresponding amino acid (wobble in the nucleotide triplets). Thus, without having an effect on the amino acid sequence of a protein the nucleotide sequence coding for this protein can be varied. However, in a preferred embodiment, the invention provides an isolated or recombinant nucleic acid sequence as depicted in FIG. 10. In a preferred embodiment, the invention provides an isolated, synthetic, or recombinant nucleic acid that represents the coding sequence (CDS) of the R8 protein, i.e. the bold nucleotides of FIG. 10 or a functional fragment thereof. For the purposes of this invention, this coding sequence may be combined with regulatory nucleotide sequences needed for a proper expression A further preferred variant of the nucleic acid sequence as defined above is the nucleic acid sequence that is found in the Rpi-smira2 gene of the potato variety Sarpo Mira. This gene was retrieved from this potato variety by PCR amplification and successive cloning using R8 specific primers. The nucleotide sequence of this gene had one polymorphism when compared with the R8 gene (T>C at position -723 in the 5'UTR in R8 vs Rpi-smira2).

Fragments as well as highly homologous genes of the herein described R8 gene and protein can for example be tested for their functionality by using an *Agrobacterium tumefaciens* transient transformation assays (agro-infiltration) and/or by using a detached leaf assay as described in the experimental section.

The experimental part for example describes a functional screen for testing candidate genes using agroinfiltration, whereby 4 week old wild type *Nicotiana benthamiana* plants are infiltrated with *Agrobacterium* strains containing the candidate R8 homologues. The infiltrated leaves are subsequently challenged one day after infiltration with a *P. infestans* strain that is virulent on *N. benthamiana*, for example IPO-C or 90128, in detached leaf assays. This system is equally suitable for testing candidate homologous fragments of R8. A person skilled in the art thus can easily determine whether or not an R8 fragment can be considered to be a functional fragment.

Transient gene expression, as is achieved through agroinfiltration, is a fast, flexible and reproducible approach to high-level expression of useful proteins. In plants, recombinant strains of *Agrobacterium tumefaciens* can be used for transient expression of genes that have been inserted into the T-DNA region of the bacterial Ti plasmid. A bacterial culture is infiltrated into leaves, and upon T-DNA transfer, there is ectopic expression of the gene of interest in the plant cells. However, the utility of the system is limited because the ectopic RNA expression ceases after 2-3 days. It is shown that post-transcriptional gene silencing (PTGS) is a major cause for this lack of efficiency. A system based on co-expression of a viral-encoded suppressor of gene silencing, the p19 protein of tomato bushy stunt virus (TBSV), prevents the onset of PTGS in the infiltrated tissues and allows high level of transient expression. Expression of a range of proteins was enhanced 50-fold or more in the presence of p19 so that protein purification could be achieved from as little as 100 mg of infiltrated leaf material. Although it is clear that the use of p19 has advantages, an agroinfiltration without p19 can also be used to test the functionality of candidate fragments and functional homologues.

Alternatively, each candidate gene (for example being a fragment or homologue) construct is targeted for transformation to a susceptible potato cultivar, for example Desiree. Primary transformants are challenged in detached leaf assays using for example isolates IPO-0, IPO-C or 90128. Transformants that are resistant to these isolates harbour for example functional fragments or highly homologous sequences of R8.

In yet another embodiment, the invention provides a vector comprising a nucleic acid as provided herein, i.e. a nucleic acid capable of providing at least partial resistance or increasing resistance in a plant of the Solanaceae family against an oomycete infection. More particularly, the invention provides a vector comprising an isolated, synthetic or recombinant nucleic acid sequence comprising a nucleic acid sequence encoding the amino acid sequence R8 of FIG. 13 or a functional fragment or a functional highly homologous sequence thereof. The invention also provides a vector comprising a nucleic acid sequence as depicted in FIG. 10 or as described above.

Examples of a suitable vector are pBeloBACII, pBINplus, pKGW-MG, or any commercially available cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector. Another suitable means is by crossing a plant which contains the gene encoding R8 to a plant that does not contain the gene and to identify those progeny of the cross that have inherited the R8 gene.

The invention further provides a host cell comprising a nucleic acid as described herein or a vector as described herein. Examples of a preferred host cell are an *E. coli* cell suitable for BAC clones (e.g. DH10B) or an *Agrobacterium* (host) cell. In another embodiment, said host cell comprises a plant cell. A preferred plant cell is a cell derived from a member of the Solanaceae family and even more preferred said plant cell comprises a cell from *Solanum tuberosum, Solanum lycopersicum*, formerly known as *Lycopersicon esculentum*, pepper and eggplant. From such a cell, a transgenic or genetically modified plant (for example a potato or tomato plant) can be obtained by methods known by the skilled person (for example regeneration protocols).

The invention further provides a leaf, tuber, fruit or seed or part or progeny of a genetically modified plant as described herein.

In yet another embodiment, the invention provides a protein encoded by the herein described isolated or recombinant nucleic acid or a functional fragment or a functional homologue thereof. In a preferred embodiment, the invention provides a protein encoded by a nucleic acid sequence as depicted in FIG. 10. In yet another preferred embodiment, the invention provides a protein comprising the amino acid sequence of FIG. 11 or a functional fragment or a highly homologous sequence thereof.

The herein described R8 protein comprises 1245 amino acids and the LRR domains of R8 consist of 13 imperfect repeats (FIG. 11). Interestingly, R8 shares the highest homology (>80%) with a gene from *S. lycopersicon* and not with R genes that are known to associate with *P. infestans* resistance (Table 9). Further, it appeared that of the 7 tested paralogs that were found in the cluster, of which R8 is one, only R8 could recognize the Avr8 protein of *P. infestans*. Further, as can be derived from table 7, the other paralogs were not effective in whole-plant assays and field assays. It can thus be concluded that it is surprising that a gene which has a very low homology (about 15-25%) with other known R genes against *Phytophthora infestans* infection is able to provide a high and during resistance in the field, while genes that are highly homologous with the R8 gene are not able to provide resistance.

As already described, a functional fragment or a functional highly homologous sequence of R8 is a fragment or homologue that is capable of providing at least partial resistance or increasing resistance in a plant of the Solanaceae family against an oomycete infection and/or recognition of the *P. infestans* Avr8 effector protein. This means that at least the 6 paralogs (RGA 1.0, 1.1, 1.2, 0.21, 3.1 and 3.2) that have been tested as described in the experimental part are not considered to be functional highly homologous sequences to R8.

Means to test the functionality of a functional fragment or a functional homologue of R8 have been provided above and may be found in some detail in the experimental section of the present application. Recognition of the Avr8 effector protein can be achieved according to methods as found in the experimental description.

Based on the herein described nucleic acid sequences, the invention also provides probes and primers (i.e. oligonucleotide sequences complementary to one of the (complementary) DNA strands as described herein). Probes are for example useful in Southern or northern analysis and primers are for example useful in PCR analysis. Primers based on the herein described nucleic acid sequences are very useful to assist plant breeders active in the field of classical breeding and/or breeding by genetic modification of the nucleic acid content of a plant (preferably said plant is a *Solanum tuberosum, Solanum lycopersicum*, formerly known as *Lycopersicon esculentum*), pepper or eggplant in selecting a plant that is capable of expressing for example R8 or a functional fragment or functional highly homologous sequence thereof.

Hence, in a further embodiment, the invention provides a binding molecule capable of binding to a nucleic acid encoding R8 or a functional fragment or functional highly homologous sequence thereof as described herein or its complementary nucleic acid. In a preferred embodiment, said binding molecule is a primer or a probe. As mentioned, such a binding molecule is very useful for plant breeders and hence the invention further provides a method for selecting a plant or plant material or progeny thereof for its susceptibility or resistance to an oomycete infection. Preferably, the nucleic acid of a plant to be tested is isolated from said plant and the obtained isolated nucleic acid is brought in contact with one or multiple (preferably different) binding molecule(s). One can for example use a PCR analysis to test plants for the presence of absence of R8 in the plant genome. Such a method would be especially preferable in marker-free transformation protocols, such as described in WO 03/010319.

The herein described R8 protein can also be used to elicit antibodies by means known to the skilled person. The invention thus also provides an antibody that (specifically) binds to the protein encoded by the herein described isolated or recombinant nucleic acid (for example the nucleic acid sequence of FIG. 10) or an antibody that (specifically) binds to a protein as depicted in FIG. 11 or a functional fragment or a functional homolog thereof. Such an antibody is for example useful in protein analysis methods such as Western blotting or ELISA, and hence can be used in selecting plants that successfully express the R8 gene.

Based on the herein provided nucleic acid sequences, the invention also provides the means to introduce or increase resistance against an oomycete infection in a plant. The invention therefore also provides a method for providing at least partial resistance or increasing resistance in a plant against an oomycete infection comprising providing a plant or a part thereof with:

an isolated or recombinant nucleic acid sequence comprising a nucleic acid sequence encoding the R8 amino acid sequence of FIG. 13 or a functional fragment or a functional highly homologous sequence thereof, or an isolated or recombinant nucleic acid sequence as depicted in FIG. 10, or a vector comprising the herein described nucleic acid sequences, or a host cell as described herein.

Such a method for providing at least partial resistance or increasing resistance in a plant against an oomycete infection may be based on classical breeding, departing from a parent plant that already contains the R8 gene or a functional homolog thereof, or it involves the transfer of DNA into a plant, i.e., involves a method for transforming a plant cell comprising providing said plant cell with a nucleic acid as described herein or a vector as described herein or a host cell as described herein.

There are multiple ways in which a recombinant nucleic acid can be transferred to a plant cell, for example Agrobacterium mediated transformation. However, besides by Agrobacterium infection, there are other means to effectively deliver DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. Nos. 5,302,523; and 5,464,765), and by acceleration of DNA coated particles (U.S. Pat. Nos. 5,550,318; 5,538,877; and 5,538,880). Through the application of techniques such as these, cells from virtually any plant species may be stably transformed, and these cells may be developed into transgenic plants.

In case Agrobacterium mediated transfer is used, it is preferred to use a substantially virulent Agrobacterium such as A. tumefaciens, as exemplified by strain A281 or a strain derived thereof or another virulent strain available in the art. These Agrobacterium strains carry a DNA region originating from the virulence region of the Ti plasmid pTiBo542, which coordinates the processing of the T-DNA and its transfer into plant cells. Agrobacterium-based plant transformation is well known in the art (as e.g. described in, for example by Komari, T. et al.: Plant Transformation Technology: Agrobacterium-Mediated Transformation, in: Handbook of Plant Biotechnology, Eds. Christou, P. and Klee, H., John Wiley & Sons, Ltd, Chichester, UK, 2004, pp. 233-262). Preferably a marker-free transformation protocol is used, such as described in WO03/010319.

Alternatively, the nucleic acid of the R8 gene or a functional highly homologous sequence thereof may be introduced into a plant by crossing. Such a crossing scheme starts off with the selection of a suitable parent plant. This may for instance be an original Solanum demissum variety or a plant from the S. tuberosum variety 'Sarpo Mira' or a plant that has obtained the desired nucleic acid by genetic engineering as described above.

Any suitable method known in the art for crossing selected plants may be applied in the method according to the invention. This includes both in vivo and in vitro methods. A person skilled in the art will appreciate that in vitro techniques such as protoplast fusion or embryo rescue may be applied when deemed suitable.

Selected plants that are used for crossing purposes in the methods according to the invention may have any type of ploidy. For example, selected plants may be haploid, diploid or tetraploid. Most cultured potato plants are diploid, and preferably tetraploid. Solanum demissum is a hexaploid plant. Crossing a hexaploid plant with a diploid or a tetraploid plant will generally result in offspring that is sterile.

Thus, when plants are selected that are hexaploid, their ploidy must be decreased to diploid or tetraploid level before they can be crossed with another diploid or tetraploid plant in the methods according to the invention. Methods for decreasing the ploidy of a plant are well known in the art and can be readily applied by a person skilled in the art. For example, ploidy of a diploid plant for crossing purposes can be increased by using 2N gametes of said diploid plant. Ploidy can also be increased by inhibiting chromosome segregation during meiosis, for example by treating a diploid plant with colchicine. By applying such methods on a diploid plant, embryos or gametes are obtained that comprise double the usual number of chromosomes. Such embryos or gametes can then be used for crossing purposes. For potatoes a resistant tetraploid plant is preferred, since tetraploid plants are known to have higher yields of tubers. A decrease in ploidy can for instance be achieved by a meiotic division and parthenogenesis from said meiotically divided cell. It is also possible to cross hexaploid cells with diploid cells to obtain (in general a low yield of) tetraploid offspring.

Since the resistance characteristic has appeared to be a dominant trait, it is sufficient if only one allele with the functional gene is present.

Preferably, selected plants are crossed with each other using classical in vivo crossing methods that comprise one or more crossing steps including selfing. By applying such classical crossing steps characteristics of both the parents can be combined in the progeny. For example, a plant that provides a high yield can be crossed with a plant that contains large amounts of a certain nutrient. Such a crossing would provide progeny comprising both characteristics, i.e. plants that not only comprise large amounts of the nutrient but also provide high yields.

When applying backcrossing, F1 progeny is crossed with one of its high-yielding parents P to ensure that the characteristics of the F2 progeny resemble those of the high-yielding parent. For example, a selected diploid potato with oomycete resistance is made tetraploid by using colchicine and then crossed with a selected high-yielding tetraploid potato cultivar, with the purpose of ultimately providing a high-yielding tetraploid progeny having oomycete resistance. Also selfing may be applied. Selected plants, either parent or progeny, are then crossed with themselves to produce inbred varieties for breeding. For example, selected specimens from the above mentioned F1 progeny are crossed with themselves to provide an F2 progeny from which specimens can be selected that have an increased level of resistance.

It is also possible to use a potato breeding technology as described in WO 2011/053135 and WO 2012/144902.

After transfer of a nucleic acid into a plant or plant cell, it must be determined which plants or plant cells have been provided with said nucleic acid. When selecting and crossing a parental genotype in a method according to the invention, a marker is used to assist selection in at least one selection step. It is known in the art that markers, indicative for a certain trait or condition, can be found in vivo and in vitro at different biological levels. For example, markers can be found at peptide level or at gene level. At gene level, a marker can be detected at RNA level or DNA level. Preferably, in the present invention the presence of such a marker is detected at DNA level, using the above described primers and/or probes. Alternatively, proper expression of the R8 protein or a functional homolog thereof can be assessed in plant parts by performing an immunoassay with an antibody that specifically binds the protein. Next to the primers and probes according to the invention, use can also be made of specific markers that are to be found in the vicinity of the coding sequence. Such markers are indicated in the experimental part below and comprise for instance the markers At5-2FspBI and 184-81-Rsa 1, and especially the markers 10-SCAR and 993-DraI (see FIG. 7).

In case of transgenic approaches selecting a transformed plant may be accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. Suitable examples of reporter genes are beta-glucuronidase (GUS), beta-galactosidase, luciferase and green fluorescent protein (GFP).

In a preferred embodiment, the invention provides a method for providing at least partial resistance or increasing resistance in a plant against an oomycete infection comprising providing a plant or a part thereof with:

an isolated or recombinant nucleic acid sequence comprising a nucleic acid sequence encoding the R8 amino acid sequence of FIG. 13 or a functional fragment or functional highly homologous sequence thereof, or an isolated or recombinant nucleic acid sequence as depicted in FIG. 10 comprising at least the coding part of said sequence, a vector comprising the herein described nucleic acid sequences, or a host cell as described herein, wherein said oomycete comprises *Phytophthora*, preferably *Phytophthora infestans* and/or wherein said plant comprises a plant from the Solanaceae family, preferably a potato or tomato plant, more preferably a tetraploid potato plant.

In a further preferred embodiment, the invention comprises introduction into a plant cell or plant of an isolated or recombinant nucleic acid sequence comprising a nucleic acid sequence encoding the R8 amino acid sequence of FIG. 11 or a functional fragment or functional highly homologous sequence thereof and next to this nucleic acid another nucleic acid encoding a resistance gene that provides protection against oomycete infection, in particular infection with *Phytophthora*, more particularly *P. infestans*. Preferably such other resistance genes are selected from Table 1, and preferably selected from the genes Rpi-chc1, Rpi-ber, Rpi-sto1, Rpi-blb3, Rpi-edn2, Rpi-vnt1.1 and Rpi-blb2. Most preferred are Rpi-edn2, Rpi-vnt1.1 and Rpi-blb2. The invention also provides a plant that is obtainable by using a method for providing at least partial resistance or increasing resistance in a plant against an oomycete infection as described above. A preferred plant is a plant from the Solanaceae family and even more preferred said plant is a *Solanum tuberosum* or a *Solanum lycopersicum*, formerly known as *Lycopersicon esculentum, Solanum melononga, Capsicum* spp., such as *C. annuum, C. baccatum, C. chinense, C. frutescens* and *C. pubescens*. The invention thus also provides a plant that has been provided with a nucleic acid encoding a R8 protein or a functional fragment or a functional homologue thereof.

The invention further provides a plant part or progeny of a plant according to the invention comprising a nucleic acid encoding the R8 amino acid sequence of FIG. 13 or a functional fragment or a functional highly homologous sequence thereof.

In a preferred embodiment, the herein described nucleic acid is transferred to a *Solanum* variety other than *Solanum demissum*, i.e. the herein described nucleic acid is preferably provided to a non-*demissum* background, preferably *S. lycopersicon* or *S. tuberosum*. Of the latter most preferred is a tetraploid variety and more preferably to a commercial interesting variety such as Bintje, Desiree or Premiere, Spunta, Nicola, Favorit, Russet Burbank, Aveka or Lady Rosetta.

It is also possible to provide the resistance according to the invention to a plant that is already partially resistant to an oomycete infection, wherein said plant is provided with a nucleic acid encoding a further resistance gene, such as R3a, R3b, R4, Rpi-chc1, Rpi-blb1,-2, -3, Rpi-vnt1 or Rpi-mcq1.

The invention further provides use of an isolated or recombinant nucleic acid sequence comprising a nucleic acid sequence encoding the R8 amino acid sequence of FIG. 11 or a functional fragment or a functional highly homologous sequence thereof or use of an isolated or recombinant nucleic acid sequence as depicted in FIG. 10 or use of a vector comprising any of said nucleic acid sequences or use of a host cell comprising any of said nucleic acid sequences or said vector for providing a plant with at least partial resistance against an oomycete infection. In a preferred embodiment, said oomycete comprises *Phytophthora* and even more preferably *Phytophthora infestans*. In yet another preferred embodiment said plant comprises *Solanum tuberosum* or *Solanum lycopersicum*, formerly known as *Lycopersicon esculentum.*

In yet another embodiment, the invention provides a method for producing R8 protein or a functional fragment or a functional homologue thereof comprising functionally linking a nucleic acid as described herein to a regulatory sequence and allowing said nucleic acid to be expressed in a host cell. Examples of a regulatory sequence are a promoter and/or terminator sequence. Further, the R8 sequence may be expressed under control of its own promoter and terminator, but also other strong or inducible promoters and or vectors may be provided. Therefore, the invention further provides the promoter and/or terminator sequences of R8 (FIG. 10). FIG. 10 shows the nucleotide sequence of R8 (7011 bp) containing the R8 gene and regulatory sequences. The R8 coding region of 3735 bp is in bold font. The upstream nucleotides (nt 1-1679) and the downstream nucleotides harbour the regulatory sequences that ensure correct expression of the gene. The skilled person is very well capable of cloning (part of) said regulatory sequences and testing their efficiency in transcription. It has further been found that even a better expression is obtained with a truncated promoter, i.e. a promoter containing less than 1000, preferably not more than 900 base pairs upstream of the gene sequence.

The invention will be explained in more detail in the following, non-limiting examples.

EXPERIMENTAL PART

Example 1: Mapping of *S. demissum* Late Blight Resistance Gene R8

Plant Material and Mapping Population

MaR8, corresponding to 2424a(5) and PI 303149 (Black et al. 1953; Malcolmson and Black 1966), and cultivar Concurrent were maintained and in vitro and multiplied in the Laboratory of Plant Breeding, Wageningen University. MaR8, as resistant female parent, and the susceptible cultivar Concurrent were crossed to generate a F1 mapping population in the summer of 2008 (population code R8*C). Seeds were sown under sterile conditions and 100 plants were maintained in in vitro culture.

*Phytophthora infestans* Isolates and Disease Testing

*Phytophthora infestans* isolate IPO-C (race 1, 2, 3, 4, 5, 6, 7, 10, 11) was kindly provided by Prof. Francine Govers (Laboratory of Phytopathology, Wageningen University). IPO-C was used in detached leaf assays as described by Vleeshouwers et al. (1999) but also to inoculate field trials. In 2009 and 2010, respectively, four and two in vitro plants per genotype from population R8*C were planted in the beginning of June. Spreader rows and the border rows consisted of the susceptible potato cultivars Bintje and Nicola, which served to support a local late blight epidemic. In the beginning of July, the trial fields were inoculated. For the inoculum production, a large number of detached leaves of potato cultivar Bintje were inoculated with isolate IPO-C. After 6 days, spores were washed off to prepare a spore suspension in large containers. Zoospore release was induced by incubating the containers at 10° C. After the release of the zoospores, the inoculum was adjusted to a concentration of $5\times10^4$ zoospores/ml. At nightfall, the zoospore suspension was sprayed on the potato field using a tractor using a spraying arm. After 2 weeks severe late blight symptoms were observed in susceptible plants and a clear segregation of resistance and susceptibility was observed in population R8*C. Scoring was performed in a qualitative way (resistant or susceptible).

DNA Isolation and Marker Analysis

Genomic DNA was isolated as described by Fulton et al. (1995). Young leaf tissue was collected for DNA isolation according to the CTAB protocol with the Retsch machine (RETSCH Inc., Hannover, Germany). Primers used for marker analysis are listed in Table 2. PCR reactions were performed using DreamTaq™ polymerase (Fermentas) in a standard PCR program (start: 94° C. for 30 s; amplification: 35 cycles of 94° C. for 30 s, 55° C. for 30 s; 72° C. for 1 min; termination: 72° C. for 2 min). NBS profiling was performed as described by Van der Linden et al. (2004), with minor modifications. The restriction enzyme digestion of genomic DNA and the ligation of adapters were made in one incubation step. Restriction enzymes MseI, HaeIII and RsaI were used for restriction ligation reactions and NBS primers NBS1, NBS2, NBS3, NBS5a6 and NBS9 in combination with the adaptor primer were used for the successive PCR reactions. Primers with corresponding names and sequences have been described previously (Van der Linden et al. 2004; Wang et al. 2008; Mantovani et al. 2006; Brugmans et al. 2008). Totally, 15 primer enzyme combinations were used for NBS profiling. For R gene CDP, R2 and Tm-22 primers (R2LF1, R2LF2, R2LF3, R2LF4, R2LR2, R2LR3, R2LR4, Tm1F, Tm1R, Tm3F, Tm3R, Tm6F, Tm15F, Tm15R, Tm19F, Tm19R, Mcq19F, Mcq21R and Mcq23F) were used as described by Verzaux (2010). HotStarTaq™ polymerase (QIAGEN) was used in the first PCR and DreamTaq™ polymerase (Fermentas) in a second PCR. For designing Hero-CDP-primers, Hero-like sequences available from NCBI (ncbi.nlm.nih.gov) and *S. phureja* DM1-3 516R44 (CIP801092) whole genome assembly scaffold sv3 available from the Potato Genome Sequencing Consortium (PGSC; potatogenome.net) were collected and aligned. Primers were designed on cluster specific conserved domains encoding CC and LRR. A total of six Hero-CDP degenerate primers were designed and one produced a marker that was linked to R8 (Table 2). For Sw-5-CDP seven specific primers described by Dianese et al. (2010) were used. Like in NBS profiling, the CDP primers were used in combination with a labeled adaptor primer (fluorescent dye IRD700) to enable visualization on a denaturing polyacrylamide gel using a NEN_IR2 DNA analyser (LI-COR_Biosciences, Lincoln, Nebr., USA). NBS profiling was carried out first on a set of 10 resistant and 10 susceptible F1 plants, including the parents. If in this first round polymorphic bands between the parents and co-segregation of these bands with resistance in the F1 plants were found, a second round of NBS profiling was carried out on genomic DNA of the remaining F1 progeny. If multiple markers are found with one primer/enzyme combination, numbers behind the dash are consecutive numbers ordered from low to high molecular weight produced by the same primer enzyme combination. For example, marker CDPTm21-1 and CDPTm21-2 were produced using primer/enzyme combination Tm15R/MseI. In order to screen for cleaved amplified polymorphic sequences (CAPS), PCR was done using primers listed in Table 2 and successively the PCR products were digested using the restriction enzymes listed in Table 2. 5 μl of PCR product were added to a 15 μl of restriction enzyme digestion according to the manufacturers' instructions.

TABLE 2

Markers used for mapping of R8 in the F1 population MaR8 x Concurrent

| Marker name | Primer name | Primer sequence (5'→3')* | SEQ ID NO | Polymorphism | Reference |
|---|---|---|---|---|---|
| NBS5a6H | NBS5a6 | YYTKRTHGTMITKGATGAYRTITGG | 1 | HaeIII | Van der Linden et al. 2004 |
| NBS1 M | NBS1 | GCIARWGTWGTYTTICCYRAICC | 2 | MseI | |
| CDP$^{Tm2}$1-1 | Tm15R | GTAACAAGTCATGTATGCGAC | 3 | MseI | Verzaux 2010 |
| CDP$^{Tm2}$1-2 | Tm15R | GTAACAAGTCATGTATGCGAC | 3 | MseI | Verzaux 2010 |
| CDP$^{Hero}$2 | Tm19F | GCCAAATAGTATTGTCAAGCTC | 4 | MseI | Verzaux 2010 |
| CDP$^{Tm2}$3 | Hero4064F | RRAGATTCAGCCATKGARATTAAGAAA | 5 | HaeIII | This study |
| CDP$^{Sw5}$4 | Sw55F | AGTCTCCAAACATTCCTGCTTCTC | 6 | MseI | Dianese et al. 2010 |
| CDP$^{Sw5}$5 | Sw55F | AGTCTCCAAACATTCCTGCTTCTC | 6 | HaeIII | Dianese et al. 2010 |
| Stm1021 | STM1021 F<br>STM1021 R | GGAGTCAAAGTTTGCTCACATC<br>CACCCTCAACCCCCATATC | 7<br>8 | SSR | Collins et al. 1999 |
| TG328 | TG328F<br>TG328R | TGAATGGACTGGTGATCTGC<br>TTGGAAAGAATTGGCTTTTGA | 9<br>10 | SCAR | This study |
| 184-81 | 184-81F<br>184-81R | CCACCGTATGCTCCGCCGTC<br>GTTCCACTTAGCCTTGTCTTGCTCA | 11<br>12 | CAPS, RsaI | This study |
| General primers for profiling | | | | | |
| MseI adaptor | Mse-ad-top<br>Mse-ad-bottom | CCCGAAAGTATAGATCCCAT<br>TAATGGGATCTATACTT | 13<br>14 | | Van der Linden etal. 2004 |
| Blunt adaptor | B-ad-top<br>B-ad-bottom | ACTCGATTCTCAACCCGAAAGTATAGATCCCA<br>TGGGATCTATACTT | 15<br>16 | | Van der Linden etal. 2004 |
| Adaptor primer | | ACTCGATTCTCAACCCGAAAG | 17 | | Van der Linden etal. 2004 |

F; forward primer, R; reverse primer. *All markers were produced using a standard PCR program

Isolation and Sequence Analysis of NBS Fragments

Fragments were excised as described in the Odyssey manual for band extraction (Westburg, The Netherlands) and re-amplified with the specific profiling primer and the adapter primer. PCR products were checked on agarose gels and purified with QIAquick PCR purification spin columns (QIAGEN Benelux, The Netherlands). Fragments were cloned into the pGEM-T Easy vector (Promega, USA) prior to sequencing with M13 primers. Sequencing was carried out with the BigDye Terminator kit and an ABI 3700 automated sequencer from Applied Biosystems (USA). Blast analysis of the sequences was performed using the websites from NCBI, PGCS and SGN (blast.ncbi.nlm.nih-.gov/; potatogenomics.plantbiology.msu.edu/; solgenomics-.net). ClustalX (Jeanmougin et al. 1998) was used to align sequences.

Map Construction

Co-segregating, simplex-inherited NBS and CDP markers from the tetraploid female parent (MaR8) were scored as dominant markers (Wu et al. 1992). The marker order was determined by TetraploidMap (Hackett and Luo 2003; bioss.ac.uk). The map distance was calculated based on the frequency of the recombination between markers. Publicly available potato and tomato genetic maps from the SH×RH population (Van Os et al 2006), SGN sgn.cornell.edu/cview/map.pl?map_id=9&show_offsets=1&show_ruler=1) and GABI (gabipd.org/database/) databases were included for comparison of marker positions and synteny.

Results

Segregation of Resistance in the Mapping Population

F1 progeny and the parental clones MaR8 and cv. Concurrent were screened for resistance against *P. infestans* isolate IPO-C. The detached leaf assay with leaves from greenhouse grown plants turned out not to be suitable for the F1 population. In contrast to the mother plant MaR8, the F1 plants showed no clear resistance. Initial screens indicated some variation in resistance; however, these findings were not reproducible for most of the individuals. In contrast, highly reproducible results were obtained in two field trials performed in Wageningen, The Netherlands, in the summer of 2009 and 2010. MaR8 plants remained devoid of late blight symptoms, while cv. Concurrent was completely infected within 2 weeks after inoculation. Among 100 F1 genotypes screened, 52 were resistant, 46 were susceptible and 2 showed intermediate phenotypes. This demonstrates that the resistance in MaR8 is inherited as a dominant simplex allele ($\chi 2=0.54$, $P>0.05$) at a single locus. The corresponding gene is referred to as R8 hereafter.

Identification of R8 Flanking Markers

In order to identify markers linked to R8, we used NBS profiling since this technique can also give an indication about the R gene family of the targeted gene. Initially, NBS profiling experiments were carried out using combinations of the NBS5a6 primer and three enzymes (HaeIII, RsaI and MseI) on both parents and 10 resistant and 10 susceptible F1 individuals from the mapping population. Marker NBS5a6H was linked to the resistance phenotype and was found at a frequency of one recombinant in twenty F1 plants. Subsequently, an additional set of NBS primers (NBS1, NBS2, NBS3 and NBS9) was used which resulted in the identification of an additional marker, NBS1M showing linkage to the resistance but without recombinants in twenty F1 plants. The NBS5a6H and NBS1M markers were tested on the complete F1 progeny. 22 additional recombinants were found between NBS5a6H and R8, and three recombinants were identified between NBS1M and R8. These recombinants were not overlapping resulting in 26 recombinants between NBS1M and NBS5a6. This showed that the two NBS profiling markers flank the R8 gene (FIG. 1).

Localization of R8 Flanking Markers in the Genome

The NBS5a6H (361 bp) and NBS1M (301 bp) fragments were cut out of the gel and sequenced (genbank accession numbers: JF317286 and JF317287 respectively). In potato scaffold PGSC0003DMS000000483, a 93% identity match was found for the NBS5a6H sequence. PGSC0003DMS000000483 could be located to chromosome IX using genetic and physical maps of tomato (FIG. 1). NBS1M showed 97% identity to potato scaffold PGSC0003DM S000001347. This scaffold could be linked to the telomeric region at the long arm of chromosome IX using markers C2_At1g09815 and C2_At3g24160 (FIG. 1). The proposed inversions between potato and tomato on chromosome IX (Tanksley et al. 1992) did not affect the positioning of the R8 flanking markers. For marker NBS1M, there was no similarity to sequences with known function. The sequence of marker NBS5a6H, however, showed 90% identity to the tomato Hero gene (Ernst et al. 2002), which is located on chromosome IV. Apparently, Hero-like genes are not only present on chromosome IV but are located in other genomic regions as well (FIG. 1).

Localisation of R8 on Chromosome IX

In order to verify that R8 and its flanking markers were on chromosome IX, more closely linked markers near the R8 gene were required. Therefore, R gene CDP was performed. Two R gene clusters known to locate on chromosome IV (R2 and Hero), and two clusters known to locate on chromosome IX (Tm-22 and Sw-5) were targeted for R gene-CDP. Using R2-CDP no bands linked to the resistance were found among 24 primer/enzyme combinations (data not shown). Three linked markers, CDPTm21-1 (240 bp), CDPTm21-2 (345 bp) and CDPTm22 (120 bp), were identified using Tm-22 primers out of 36 primer/enzyme combinations. CDPTm21-1 and CDPTm21-2 were identified using the same primer enzyme combination (Tm15R/MseI). All Tm-22-CDP markers are at 2 cM distance (proximal) from R8 (FIG. 2). Two markers, CDPSw54 (277 bp) and CDPSw55 (165 bp), were identified using Sw-5-CDP. Both markers were located at 1 cM to the opposite side (distal) of the R8 gene as CDPTm21-1, CDPTm21-2 and CDPTm22 (FIG. 2). Interestingly, one fully co-segregating marker, CDPHero3 (500 bp), was found using Hero-CDP out of 18 primer/enzyme combinations. All CDP markers were excised from the gel and subjected to sequence analysis. CDPTm21-1 and CDPTm22 indeed showed similarity to Tm-22. CDPSw54 and CDPSw55 were confirmed to be similar to Sw-5, a *S. lycopersicon* tospovirus resistance gene (Brommonschenkel and Tanksley 1997; Spassova et al. 2001). Unfortunately, the sequences of CDPTm21-2 and CDP3 remained unresolved due to technical reasons. The relative positions of the Tm-22 and Sw-5 homologous markers in the R8 map are in agreement with relative positions of Rpi-moc1, which is homologous to Tm-22 (Foster et al. 2009) and Sw-5, as inferred from publically available genetic maps of chromosome IX (FIG. 2). In addition, the draft sequence of the complete tomato chromosome IX shows that Tm-22 and Sw-5 like sequences are located close to each other near the telomere (FIG. 1). To further confirm the map position of R8 and the newly identified profiling markers on chromosome IX, known markers (GP101, S2g3, TG591A, GP41, CT220, T0521, S1d11, S1d5-a, T1065, TG328, TG424, and St_At3g23400) from the SGN and GABI databases on the long arm of chromosome IX were selected and tested for linked polymorphisms after digestion with 24 selected restriction enzymes. Only TG328 did display an informative SCAR type polymorphism. A segregation of 87 presence to 12 absence genotypes was found which fits a 5:1 ratio ($\chi2=0.23$, $p>0.05$), indicating that the TG328 marker allele is present in duplex in MaR8. Also three SSR markers (Stm1010, Stm1021, Stm0017) (Milbourne et al. 1998; Collins et al. 1999) were screened and one SSR marker, Stm1021, present in RH9 BIN65 of the SH×RH map located at 9 cM proximal to R8. Since no other useful polymorphisms could be found in known genetic markers in this region, we mined for potential polymorphic regions in the potato genome covering this region. TG328 located to SH9 BIN77 of the SH×RH map, was linked to Rpi-moc1 in the GABI map, and located 2 cM proximal relative to R8 (FIG. 2). Scaffold PGSC0003DM S000000184 which contained the flanking markers TG328, CDPTm21-1 and CDPTm22, was aligned to the tomato genome and several polymorphic regions were identified. PCR screens within these regions eventually identified additional polymorphic marker (184-81), which located 1 cM proximal to R8 (FIG. 2).

Example 2: The Avirulence Factor AVR8 for the Mexican *S. demissum* Late Blight Resistance Gene R8 is Recognized by cv. Sarpo Mira and Resistant Wild *Solanum* Species from South America

Materials and Methods

Plant Material

The potato differential plant MaR8, also known as 2424a (5), was used as female parent in a cross with the susceptible cultivar Concurrent to generate a F1 mapping population (R8*C). Cultivar Sarpo Mira was crossed with the susceptible clone RH89-039-16, a donor of the potato genome sequence, to produce population SM*RH. A hundred or thirty of genotypes of populations R8*C or SM*RH, respectively, and their parents, were clonally maintained in vitro culture containing Murashige and Skoog medium (Murashige and Skoog, 1962) supplemented with 3% (w/v) sucrose at 20° C. The wild *Solanum* plant materials which were maintained in vitro at Wageningen University, Laboratory of Plant Breeding, were used for effector screening and functional allele mining. Information on species, origin, collection site, GPS coordinates and other genbank code are accessible on the SolRgene database.

*Phytophthora infestans* Isolate and Blight Resistance Tests

*Phytophthora infestans* isolate IPO-C (race 1, 2, 3, 4, 5, 6, 7, 10, 11) was used in field trials. Field trials for the mapping populations were done in 2009, 2010 and 2011 in Wageningen, The Netherlands, as described in previous studies (Jo et al. 2011; Rietman et al. 2012). Field trials for germplasm accessions were performed in the growing seasons of the years 2005 and 2007 in Wageningen, The Netherlands (Vleeshouwers et al. 2011b). Disease assessments were made in four replicates per genotype by estimating the percentage of leaf area covered with late blight lesions at multiple time points after inoculation. From these readings, the AUDPC was calculated (Fry 1978) and the AUDPC values were transformed to 1 (susceptible)-9 (resistant) scale.

Screening of in Planta-Induced RXLR Effectors

A genome-wide collection of RXLR effectors was selected from the *P. infestans* genome sequence based on presence of a predicted signal peptide, an RXLR motif, and an elevated gene expression at 6 hours post inoculation (hpi) to 3 days post inoculation (dpi) (Haas et al. 2009). Using Gateway™ technology, effectors were subcloned into pK7WG2 and transformed into *Agrobacterium tumefaciens* strain AGL1, pSoup, and pVirG cells by electroporation. Agroinfiltration was performed as previously described (Rietman et al. 2012). Briefly, *A. tumefaciens* strains from frozen glycerol stocks were grown overnight at 28° C. in 3 ml of LB medium supplemented with appropriate antibiotics. The next day these cultures were used to inoculate 15 ml of YEB medium (5 g beef extract, 5 g bacteriological peptone, 5 g sucrose, 1 g yeast extract, 2 ml 1 M MgSO4 in 1 L of milli-Q water) supplemented with antibiotics, 10 µl/L of 200 mM acetosyringone and 1000 µl/L of 1M MES. On the third day, the cells were harvested and resuspended to a final OD600 of 0.3 in MMA (20 g sucrose, 5 g MS salts and 1.95 g MES in 1 liter of distilled water, adjusted to pH 5.6 with KOH supplemented with 1 ml/L of 200 mM acetosyringone). Leaves of plants were infiltrated with this suspension. Two leaves per plant and three replicate plants of 4 to 5 weeks old were infiltrated with the following constructs: effectors, R3a (Huang et al. 2005) and Avr3a (Armstrong et al. 2005) as the positive control and empty pK7WG2 (Karimi et al. 2002) as the negative control. Responses were scored 3 to 4 days after infiltration.

DNA Isolation and Marker Analysis

Total genomic DNA was isolated from young leaves as described by Fulton et al. (1995). The Retsch homogenizer (RETSCH Inc., Hannover, Germany) was used to grind young plant materials frozen in liquid nitrogen. For mapping Avr8-responsiveness in F1 populations markers described by Jo et al. (2011) were used (Table 3). For the identification of markers associated with the recognition of AVR8 in various *Solanum* genotypes, a modification of the NBS profiling protocol of Van der Linden et al. (2004) was carried out as described in Jo et al. (2011). The concentrations of genomic DNA for all samples were adjusted to 300 ng/µl prior to profiling experiments. PCR reactions for markers 184-81 and Stm1021 were performed using the primers in Table 3 and DreamTaq™ polymerase (Fermentas) in a simple PCR program (94° C. for 60 s followed by 30 cycles of 94° C. for 30 s, 58° C. for 60 s, 72° C. for 90 s and a final extension time of 5 min at 72° C.). The polymorphism for marker 184-81 was detected by digesting the PCR product with the restriction enzyme listed in Table 3 and 1% agarose gel electrophoresis. Marker Stm1021 is a simple sequence repeat marker. Polymorphisms were detected using polyacrylamide gel electrophoresis. Fragments were prepared using a labelled forward primer (fluorescent dye IRD800) to enable visualization on a denaturing polyacrylamide gel using a NENR IR2 DNA analyser (LI-CORR Biosciences, Lincoln, Nebr., USA).

TABLE 3

Markers used for mapping of Rpi-Smira2 in the F1 population (Sarpo Mira x RH)

| Marker | Primer Sequence (5′→3′) | SEQ ID NO | Marker type | Tm (° C.) | Product size (bp) | References |
|---|---|---|---|---|---|---|
| CDP3 | Hero4064F: RRAGATTCAGCCATKGARATTAAGAAA | 5 | CDP/HaeIII | 55 | 500 bp | Jo et al. (2011) |
| 184-81 | 184-81F: CCACCGTATGCTCCGCCGTC<br>184-81R: GTTCCACTTAGCCTTGTCTTGCTCA | 11<br>12 | CAP SIRsaI | 58 | 480 bp | Jo et al. (2011) |
| CDP4 | Sw55F: AGTCTCCAAACATTCCTGCTTCTC | 6 | CDP/MseI | 55 | 277 bp | Jo et al. (2011) |
| Stm1021 | Stm1021F: GGAGTCAAAGTTTGCTCACATC<br>Stm1021R: CACCCTCAACCCCCATATC | 7<br>8 | SSR | 58 | 210 bp | Collins et al. (1999) |
| Sequences of adapter and adapter primer for CDP profiling | | | | | | |
| MseI adapter | Mse-ad-top: CCCGAAAGTATAGATCCCAT<br>Mse-ad-bottom: TAATGGGATCTATACTT | 13<br>14 | | | | |
| Blunt adapter | B-ad-top: ACTCGATTCTCAACCCGAAAGTATAGATCCCA<br>B-ad-bottom: TGGGATCTATACTT | 15<br>16 | | | | van der Linden et al. (2004) |
| Adapter primer | ACTCGATTCTCAACCCGAAAG | 17 | | | | |

Map Construction

The marker order was determined by TetraploidMap (Hackett and Luo, 2003; bioss.ac.uk/knowledge/tetraploid-map/). The map distance was calculated based on the frequency of the recombination between markers.

Results

In Planta-Induced RXLR Effector Screening Reveals Candidate Genes for Avr8

MaR8 was functionally profiled for response to a collection of 234 predicted RXLR effectors selected from the *Phytophthora infestans* genome sequence described by Haas et al. (2009). Responses to effectors were quantitatively scored for the level of cell death, ranging from 0% (no symptoms) to 100% (confluent cell death in all replicates) four days after agroinfiltration. Out of the 234 tested effectors, 13 effectors triggered more than 30% of cell death in the MaR8 plant. Among those 13 effectors, four effectors, i.e., Avr3a, Avr3b, Avr4 and AvrSmira2 (PITG_07558), were described previously to confer avirulence activity in Sarpo Mira (Rietman 2011).

Response to AVR8 is Co-Segregating with R8 Specific Resistance

To investigate which of the identified effectors had an avirulence function towards R8, we adopted a genetic approach. MaR8 was crossed with the susceptible cultivar Concurrent and 100 F1 genotypes (population R8*C) were assessed for resistance to *P. infestans* isolate IPO-C in detached leaf tests and in replicate field trials (Jo et al. 2011). This isolate is virulent on potatoes carrying R3a, R3b, and R4, and therefore, those R genes are expected not to interfere with the R8 phenotype. The population R8*C showed a clear segregation of 1:1 ratio for resistance and susceptibility in field trials but not in laboratory tests (data not shown). Subsequently, we tested this population for response to the effectors that were recognized in MaR8 (Table 4).

TABLE 4

RXLR effectors that trigger cell death response on the differential plant MaR8

| Effector [a] | | SignalP [b] | | | | Expression in potato [c] | | |
|---|---|---|---|---|---|---|---|---|
| Gene or construct ID | Gene annotation | HMM Prob. | NN mean NS score | RXLR | RXLR Tribe [d] | 16 hpi | 48 hpi | Response MaR8(%) [e] |
| PITG_15039 | | 0.993 | 0.928 | RILV | 1 | 0.83 | 1.12 | 100 |
| PITG_22880 | | 0.999 | 0.928 | na | 1 | 0.74 | 0.09 | 100 |
| PITG_07558 | Avr8 | 1.000 | 0.963 | RSLR | 2 | 1.11 | 0.24 | 95 |
| PITG_04097 | | 1.000 | 0.786 | RSLR | 5 | 1.40 | 1.28 | 75 |
| PITG_18683 | | 1.000 | 0.862 | RSLR | 5 | −0.54 | 2.61 | 47 |
| PITG_04169 | | 0.995 | 0.918 | RSLR | 10 | 0.13 | 0.65 | 83 |
| PITG_07387 | Avr4 | 0.999 | 0.903 | RFLR | 52 | 0.03 | 2.00 | 100 |
| PITG_10540 | | 0.999 | 0.850 | RFLR | 57 | −0.06 | 1.37 | 86 |
| PITG_14371_KI [f] | Avr3a (KI) | na | na | RLLR | 58 | na | na | 100 |
| PITG_14374 | | 0.992 | na | RFLR | 58 | 0.44 | 0.91 | 100 |
| PITG_18215 | Avr3b | 0.999 | 0.857 | RSLR | 124 | 1.51 | 3.07 | 100 |
| PITG_23129 | | 0.956 | 0.452 | RLLR | 128 | 1.38 | 1.28 | 78 |
| PITG_23131 | | 0.983 | 0.831 | RLLR | 128 | 0.97 | 1.09 | 94 |
| pMDC32 | Neg control | — | | — | | na | na | 0 |
| R3a:Avr3a | Pos control | — | | — | | na | na | 100 |

[a] Description of predicted RXLR effectors from the *P. infestans* genome reference strain T30-4.

[b] Hidden Markov model (HMM) score and S-mean value predicted using SignalPv2.0. NN = neutral networks output, NS = S score (signal peptide score).

[c] Gene induction on potato in T30-4 reference genome strain. In planta-gene induction was estimated relative to the expression levels in mycelium. Hours post inoculation (hpi).

[d] RXLR Tribe ID as described by Haas et al. (2009).

[e] Percentage of cell death response upon agroinfiltration, based on an average of quantitative scores in at least nine replicates.

[f] AVR3aKI is the avirulent allele of AVR3a.

na; not assessed.

In an initial screen, agroinfiltration was done on ten resistant and ten susceptible individuals of population R8*C. Co-infiltration of R3a/Avr3a and the empty vector pK7WG2 were included as positive and negative controls, respectively. High levels of necrosis in the range of 30%-80% were observed in the negative control for five plants in the resistant set and six in the susceptible set. Also, the Concurrent parent displayed nonspecific response to agroinfiltration (FIG. 3). To establish a subset of the population that does not show nonspecific cell death to the negative control, we tested an additional 23 individuals of population R8*C for their responses to the empty vector pK7WG2 and R3a/Avr3a (co)infiltration. Altogether, nine resistant and nine susceptible plants showed no cell death to the negative control but did show cell death to the positive control. We subjected this mini-population to an agroinfiltration experiment with the Avr8 candidates in Table 4. The response to one effector PITG_07558 fully matched with the resistance to *P. infestans* isolate IPO-C in field trials (FIG. 3). To further confirm these co-segregation results on a large set of the R8*C population, 56 additional genotypes of population R8*C were tested. Despite the occurrence of certain levels of cell death responses to negative controls in five plants, for the remaining progeny clear distinction between PITG_07558-infiltrated spots (90-100%) and negative control spots (30-60%) was observed.

All 34 plants that responded to PITG_07558 were resistant to *P. infestans* in the field, whereas all 31 plants that failed to respond to PITG_07558 were susceptible. Thus, response to PITG_07558 fully co-segregated with R8 specific resistance to *P. infestans* and we designated PITG_07558 "Avr8". To test whether the response to Avr8 co-segregates with the presence of a R8 specific marker, we tested 65 genotypes which were used in agroinfiltration with marker CDP3 (Jo et al. 2011). All 34 resistant AVR8-responding plants contained CDP3, whereas all 31 susceptible non-responding plants did not. These data further confirm that the response to Avr8 is associated with R8 specific resistance.

Avr8 Gene Structure and Expression

Avr8 (PITG_07558) is a single copy gene in the T30-4 reference genome located at supercontig 11 (Haas et al. 2009; FIG. 4A). Indeed, the *P. infestans* transcripts database displayed only one expressed Avr8 copy (broadinstitute.org). Avr8 encodes a secreted protein with a typical RXLR effector of 244 amino acids and most likely an EER-like motif in its N-terminal domain and a WY-domain in its C-terminal domain (FIG. 4B). Similar to other *P. infestans* Avr genes, Avr8 resides in a gene-sparse repeat-rich region (GSR) of the *P. infestans* genome (FIG. 4A). The Avr8 gene is present in all thus far sequenced *P. infestans* isolates 90128, PIC99189, 06_3928A (13_A2), NL07434 and P17777 (US22) (Haas et al. 2009, Cooke et al. 2012 and unpublished), and no polymorphisms have been found thus far. Additional studies for genetic variation of Avr8 are underway (data not shown). Sequencing of the closely related *P. mirabilis* showed that Avr8 is also conserved in that species, but not in other clade 1c *Phytophthora* species.

Rpi-Smira2 is Localized on Chromosome IX

In previous studies, it was shown that the response to PITG_07558 correlates with field resistance that is conferred by the late blight resistance gene Rpi-Smira2 in cv. Sarpo Mira (Rietman et al. 2012). The fact that Rpi-Smira2 interacts with the same effector as R8 suggests that both genes localize on a similar position of chromosome IX. In order to prove this, the flanking markers to R8, 184-81 and CDP4 (Jo et al. 2011), were tested in Sarpo Mira×RH population (population SM*RH). In population SM*RH, flanking marker CDP4 located 1 cM distal to HR responses to AVR8 upon agroinfiltration (AVR8-HR) and the opposite flanking marker 184-81 2 cM proximal to AVR8-HR (FIG. 5). This position is similar to position of the R8 gene (Jo et al. 2011). For CDP3, a segregation of 22 presence to 4 absence in the tested genotypes was found which fitted a 5:1 ratio ($\chi2$=0.87, >0.05). Some CDP3 positive genotypes were not responsive to AVR8 while none of the AVR8 responsive genotypes lacked the marker band.

TABLE 5

Markers used for mapping of Rpi-Smira2 in the F1 population (Sarpo Mira x RH)

| Marker | Primer Sequence (5′→3′) | SEQ ID NO | Marker type | Tm[a] (° C.) | Product size (bp) | References |
|---|---|---|---|---|---|---|
| CDP3 | Hero4064F: RRAGATTCAGCCATKGARATTAAGAAA | 5 | CDP/HaeIII | 55 | 500 bp | Jo et al. (2011) |
| 184-81 | 184-81F: CCACCGTATGCTCCGCCGTC<br>184-81R: GTTCCACTTAGCCTTGTCTTGCTCA | 11<br>12 | CAP SIRsaI | 58 | 480 bp | Jo et al. (2011) |
| CDP4 | Sw55F: AGTCTCCAAACATTCCTGCTTCTC | 6 | CDP/MseI | 55 | 277 bp | Jo et al. (2011) |
| Stm1021 | Stm1021F: GGAGTCAAAGTTTGCTCACATC<br>Stm1021R: CACCCTCAACCCCCATATC | 7<br>8 | SSR | 58 | 210 bp | Collins et al. (1999) |
| Sequences of adapter and adapter primer for CDP profiling | | | | | | |
| MseI adapter | Mse-ad-top: CCCGAAAGTATAGATCCCAT<br>Mse-ad-bottom: TAATGGGATCTATACTT | 13<br>14 | | | | |
| Blunt adapter | B-ad-top: ACTCGATTCTCAACCCGAAAGTATAGATCCCA<br>B-ad-bottom: TGGGATCTATACTT | 15<br>16 | | | | van der Linden et al. (2004) |
| Adapter primer | ACTCGATTCTCAACCCGAAAG | 17 | | | | |

This suggested that CDP3 was present in duplex and that only one marker allele was linked to Rpi-Smira2 which was present in simplex. Therefore, we concluded that Rpi-Smira2 resides in the R8 locus on chromosome IX.

Functional Profiling of Wild *Solanum* Species for Response to AVR8

To determine the representation of R8 functional homologs in wild *Solanum* species, 98 genotypes (72 accessions of 40 species) which are geographically and phylogenetically diverse were selected from wild *Solanum* section *Petota* germplasm (Vleeshouwers et al. 2011b). Wild *Solanum* genotypes that display resistance to *P. infestans* isolate IPO-C in detached leaf tests as well as in field trials were selected. The plants were functionally tested for cell death responses to AVR8 by agroinfiltration. Also, the potato differential set MaR1 to MaR11 were included in this study. From these 109 genotypes, 60 genotypes showed nonspecific cell death responses to *Agrobacterium* or did not produce a response to the positive control construct and therefore could not be accurately grouped as responsive or nonresponsive. 35 genotypes that were well amenable to agroinfiltration did not show an Avr8 response. Twelve genotypes from various wild *Solanum* accessions and two genotypes from the potato differential set displayed specific cell death in response to AVR8 (Table 6). These include genotypes from *S. demissum, S. tarijense, S. microdontum gigantophyllum, S. stoloniferum, S. schenkii* and two unclassified *Solanum* section *Petota* species. From the potato differential set MaR1 to MaR11, as expected, MaR8 as well as MaR9 showed the response to AVR8 (Table 6). The presence of R8 in MaR9 confirms the conclusion of a previous study (Kim et al. 2012). We further tested all AVR8 responding genotypes using R8 flanking markers, and found that *S. microdontum* spp. *gigantophyllum* genotypes GIG712-6 and GIG715-4 had distinctive marker patterns, which lack the target bands that linked to the R8 resistance (data not shown). This suggests that AVR8 recognition specificity of these plants may be conferred by R gene(s) different from R8.

we detected response to AVR8 in various *Solanum* species that originate from both the Central and the South American center of diversity of *Solanum* section *Petota. Solanum*, previously named *S. ugentii.*

Example 3: Cloning and Sequencing of the R8 Gene

Materials and Methods

Plant Material

The potato differential plant MaR8, corresponding to plant 2424a(5) described by Black et al. (1953), was used for bacterial artificial chromosome (BAC) library construction.

TABLE 6

AVR8 response in a selection of *Solanum* germplasm material and the Mastenbroek late blight differential set

| Species | Genotype[a] | Series[b] | Country of origin | Avr8 | pK7WG2 | R3a/ Avr3a | Resistance (IPO-C field)[c] |
|---|---|---|---|---|---|---|---|
| *S.* species | spp114-5[f] | Demissa | BOL | + | − | + | R |
| *S. demissum* | DMS345-1 | Demissa | MEX | + | − | + | R |
| *S. demissum* | DMS343-1 | Demissa | MEX | + | − | + | R |
| *S. demissum* | DMS344-18 | Demissa | GTM | + | − | + | R |
| *S. demissum* | DMS585-7 | Demissa | MEX | + | − | + | R |
| *S. demissum* | DMS585-1 | Demissa | MEX | + | − | + | R |
| *S. microdontum gigantophyllum* | GIG712-6 | Tuberosa | BOL | + | − | + | R |
| *S. microdontum gigantophyllum* | GIG715-4 | Tuberosa | ARG | + | − | + | M |
| *S. schenckii* | SNK213-1 | Demissa | MEX | + | − | + | R |
| *S.* species | spp891-1[g] | Tuberosa | BOL | + | − | + | R |
| *S. tarijense* | TAR852-5 | Yungasensa | BOL | + | − | + | M |
| *S. stoloniferum* | STO389-4 | Longipedicellata | MEX | + | − | + | R |
| (*S. demissum*)[d] | MaR1 | | (MEX)[e] | − | − | + | S |
| (*S. demissum*)[d] | MaR2 | | (MEX)[e] | − | − | + | S |
| (*S. demissum*)[d] | MaR3 | | (MEX)[e] | − | − | + | S |
| (*S. demissum*)[d] | MaR4 | | (MEX)[e] | − | − | + | S |
| (*S. demissum*)[d] | MaR5 | | (MEX)[e] | − | − | − | M |
| (*S. demissum*)[d] | MaR6 | | (MEX)[e] | − | − | + | S |
| (*S. demissum*)[d] | MaR7 | | (MEX)[e] | − | − | + | S |
| (*S. demissum*)[d] | MaR8 | | (MEX)[e] | + | − | + | R |
| (*S. demissum*)[d] | MaR9 | | (MEX)[e] | + | − | + | R |
| (*S. demissum*)[d] | MaR10 | | (MEX)[e] | − | − | + | S |
| (*S. demissum*)[d] | MaR11 | | (MEX)[e] | − | − | + | S |

[a]The three letter code represents the *Solanum* species (Simmonds 1962). The first number represents the CBSG number for the accession followed by a genotype number. MEX: Mexico, BOL: Bolivia, ARG: Argentina, GTM: Guatemala.
[b]Classified according to Hawkes (1990).
[c]R (highly resistant): >8.5, M (moderately resistant): 4.5-8.0, phenotype data for two years' field trials (Vleeshouwers et al. 2011b).
[d,e]The resistance of potato differential set is originating from *S. demissum* from Mexico.
[f]Unclassified *Solanum*, previously named *S. astleyi*.
[g]Unclassified Response to Avr8 occurs in Central and South American *Solanum* species.

An AFLP-based phylogenetic tree of the *Solanum* species that were tested for response to AVR8 was created using the SolRgene database (FIG. 6; Jacobs et al. 2011; Vleeshouwers et al. 2011b). Basically, the tested wild genotypes were arranged into five different groups (FIG. 6). Group I and IV included genotypes from South America while groups II and V are from Central America. Genotypes from both Central and South America belong to group III. The AVR8 responding genotypes belonged to groups IV and V, which consist of genotypes derived from Mexico (Central America) and from Bolivia and Argentina (South America) (FIG. 6, Table 6). All five *S. demissum* genotypes were responsive to AVR8. The two unclassified genotypes that also respond to AVR8 were classified with *S. demissum* (based on AFLP patterns, Jacobs 2008). From the Mexican polyploid species *S. stoloniferum* and *S. schenckii*, additional responsive genotypes were identified. From South American origin, genotypes of *S. tarijense* and *S. microdontum* spp. *gigantophyllum* were found to respond to AVR8 (FIG. 6). In summary, MaR8*Concurrent population (R8*C) was used for genetic mapping. These plant materials and cv Desiree, which was used for transformation, were maintained in vitro at Wageningen UR Plant Breeding. *Nicotiana benthamiana* was maintained as seed stock.

Bacterial Artificial Chromosome Library Construction and Screening

A first BAC library was produced by mechanical shearing of MaR8 genomic DNA and ligation of high molecular weight fragments into pCC1 at RxBiosciences (Rockville, USA). This first BAC library consisted of 768 simple pools of 200 individual BAC clones. Simple pools were stored at −80° C. The average insert size was 55 kb, resulting in a 2.5* coverage of a haploid genome. A second BAC library was produced by Bio S&T (Montreal, Canada). MaR8 genomic DNA was fragmented by partial digestion with HindIII. Size selected fragments were cloned into pIndigoBAC-5. The average insert size was 100 kb (FIG. S1) and 750 simple pools of 400 individual BACs, representing a 10* coverage of the haploid genome, were stored at −80° C. Markers described in Table S2 were used to screen the BAC libraries. Bacterial suspensions of positive pools were diluted and plated on LB agar plates containing chloramphenicol (12.5 μg $ml^{-1}$). After determining the bacterial titer of a positive pool, 2× 96 subpools containing 50 individuals each were grown for 8 hours in deepwell blocks. After culture, PCR positive sub pools were plated on LB plates containing chloramphenicol and individual colonies were picked into 96 flat bottom microtitre plates. Positive BAC clones were subsequently identified by a third round of PCR screening.

DNA Sequencing and Bioinformatics Analysis

BAC clone sequencing was carried out using a shotgun strategy. Fragmentation, library production, 454 sequencing and contig assembly was performed at Macrogen (Seoul, Korea). BAC n2A2 was sequenced using PACBIO (GATC, Germany). Gene structures were predicted using FGENESH2.6 (Softberry) and protein sequences were deduced by translation of ORF using the standard genetic code. Multiple sequence alignments and phylogenetic analyses were conducted using CLUSTALX 1.81 (Thompson et al. 1997) available in the MegAlign Lasergene 9.0 software package (DNASTAR Inc., USA).

Subcloning of Candidate Genes

Primers were designed for subcloning RGA0.20-3.2 (FIG. 7) using Primer Select from the Lasergene 9.0 software package (DNASTAR Inc., USA) and were extended at the 5' end with recognition sites for eight cutter restriction enzymes (Table S3). Long-range PCR reactions were performed using Phusion® High-Fidelity DNA Polymerase (New England Biolabs, Ipswich, USA) in a simple PCR program (98° C. for 30 s followed by 24 cycles of 98° C. for 10 s, 62-65° C. for 30 s, 72° C. for 5.5 min and a final extension time of 15 min at 72° C.), and using BAC clones 3E3, 6A5, or n2E2 as templates. The resulting PCR products were subjected to G50 Sephadex purification using Illustra MicroSpin columns (GE Healthcare) followed by ligation to the PCR-BluntII-Topo vector using the Zero Blunt Topo PCR Cloning Kit (Invitrogen). Ligation products were transformed to ElectroMAX *E. coli* DH10B competent cells (Life technologies, Paisley, UK). The inserts of PCR positive colonies were sequenced using a primer walking strategy (700 bp by 700 bp) to confirm that no mutations were introduced. The purified PCR-BluntII-Topo clones were digested with AscI and SbfI, or with XmaI and SbfI which were present in the 5' extensions of the primer (Table 7), Sticky ends were subsequently dephosphorylated using TSAP (Pomega) and all enzymes were heat inactivated. The digestion mix was ligated to the AscI and SbfI or XmaI and SbfI sites of the binary vector pBINPLUS-PASSA or pBINPLUS-ASSAP (Jo et al. 2015), which are modified versions of pBINPLUS containing eight cutter multiple cloning sites (PASSA: P=PacI; A=AbsI; S=SrfI; S=SbfI; A=AscI, or the inversed orientation for pBINPLUS-ASSAP). Recombinant clones were selected that contained R8 between the SrfI and SbfI sites (pBINPLUS-PAS:R8:SA) or between the SbfI and AscI sites (pBINPLUS-PASS:R8:A or pBINPLUS-A:R8:SSAP).

TABLE 7

Primer used for RGA amplification and subcloning

| Target | Orien-tation | Restriction site | Tm (° C.) | Sequence (5′...3′) | SEQ ID NO |
|---|---|---|---|---|---|
| RGA0.20 | F | SrfI | 63 | catgcccgggcAAAACTTTCACGCACCCATAGGA | 18 |
| | R | SbfI | | gcacctgcaggAACAAGAGATGAATTAAGTCGGTAGC | 19 |
| RGA0.21 | F | SrfI | 65 | catgcccgggcTTTGTATTATGATTGGCCCTGTTCTGA | 20 |
| | R | SbfI | | gcacctgcaggCTGCGAGTATTGGTGGCTGACAT | 21 |
| RGA1.0 | F | SrfI | 65 | catgcccgggcCAACAATGCGGCGCTTTAGGA | 22 |
| | R | SbfI | | gcacctgcaggTGGTGCACTTGCCTGGACTTTA | 23 |
| RGA1.1 | F | SrfI | 62 | catgcccgggcCCTCCATTTTCCATTAAGTCTTGC | 24 |
| | R | SbfI | | gcacctgcaggAATGGTTTCATCAATGAATCTTTC | 25 |
| RGA1.2 | F | AscI | 65 | catggcgcgccTATTAAACAGGAAACACAAAAGCAGT CA | 26 |
| | R | XmaI | | catgcccgggcTTCCTTGCAAAAATCTCACTCACTATG | 27 |
| RGA3.1 | F | SrfI | 62 | catgcccgggcCACCTAACTGATTTGCTTC | 28 |
| | R | SbfI | | gcacctgcaggTCAAACTAAGACACTTAAATTA | 29 |
| RGA3 .2 | F | SbfI | 65 | gcacctgcaggTCTTGTGGTTGTCTTGGTAGCAGGAG | 30 |
| | R | XmaI | | catgcccgggcGTAGAGAAAAAGGAGAAAGCACAGA | 31 |
| Rpi-smira2 CDS | F | | 63 | CTGGATTTCTTCAAGATTCGTCGT | 32 |
| | R | | | TTCAATCTCTTCGACTTCTTCTTACG | 33 |
| Rpi-smira2 5′ end | F | | 63 | AAAACTTTCACGCACCCATAGGA | 34 |
| | R | | | AGTAAACTTTGACACCTTTAGTTCACCAT | 35 |

*Agrobacterium*-Mediated Transient Co-Expression in *N. benthamiana*

Binary plasmids harbouring RGAs or Avr8 (Jo 2013) were transformed to *A. tumefaciens* strain AGL1 with an additional plasmid borne copy of VirG (van der Fits et al. 2000). Two leaves per plant and three replicates of 4 weeks old *N. benthamiana* seedlings were agroinfiltrated. A mixture of R3b and Avr3b (Li et al. 2011) were used as the positive control and empty pBINPLUS was used as a negative control. *A. tumefaciens* strains from frozen glycerol stocks were grown overnight at 28° C. in 3 ml of LB medium supplemented with appropriate antibiotics. The next day these cultures were used to inoculate 15 ml of YEB medium (5 g beef extract, 5 g bacteriological peptone, 5 g sucrose, 1 g yeast extract, 2 ml 1 M $MgSO_4$ in 1 liter of milliQ water) supplemented with antibiotics, 10 µl/l of 200 mM acetosyringone and 1000 µl/l of 1 M MES. On the third day, the cells were harvested and resuspended to a final OD600 of 0.2 in MMA (20 g sucrose, 5 g MS salts and 1.95 g MES in 1 liter of distilled water, adjusted to pH5.6 with KOH) supplemented with 1 ml/l of 200 mM acetosyringone in DMSO. Responses were scored 3 to 4 days after infiltration.

Transformation of Potato

Binary plasmids harbouring RGAs were transferred to *A. tumefaciens* strain AGL1 containing the helper plasmid pVirG (van der Fits et al. 2000). The stability of these clones in *Agrobacterium* was tested and overnight cultures of the transformed *A. tumefaciens* strain were used to transform susceptible cultivar Desiree (Heeres et al. 2002). The kanamycin resistant regenerants (transgenic events) were analysed by PCR to determine the presence of the desired R8 gene. Two replicates per transgenic event were transferred to the greenhouse for successive climate chamber assays or for planting in the field, respectively.

Late Blight Resistance Tests

*P. infestans* isolates and their corresponding (a)-virulence spectra that were used in this study are listed in Table 3. The late blight epidemic in Wageningen in the 2014 and 2015 field trials was a result of natural *P. infestans* infection that started at the end of June (2014) or half July (2015). Field trials in Wageningen in the years 2012 and 2013, in which recombinant plants from the extended 3020 population were tested, were inoculated at July $1^{st}$ with IPO-C as described earlier (Jo et al. 2011). Field trials contained four replicates per genotype and late blight was assessed at weekly intervals after inoculation or after the first late blight symptoms were visible in susceptible control plants by observing late blight lesions, in a qualitative way. Resistant plants remained unaffected untill the end of the experiment mid August, while susceptible plants had died already mid July.

Climate cell whole plant assays: Two replicates of transgenic Desiree or recombinant seedlings from population R8*C were propagated in vitro. The plants were transferred to potting soil and grown in the greenhouse at 22° C. with a 10 h day/14 h night photoperiod and a relative humidity of 70-80%. One month after potting of the plants, they were transferred into a growth chamber and inoculated. Inoculum was prepared by washing of the oospores from two weeks old rye sucrose agar plates containing the isolates of interest. Plants were inoculated by placing four 141 droplets of inoculum ($5\times10^4$ zoospores/ml) on the adaxial side of at least three leaves per plant. Inoculated plants were kept for seven days in a climate chamber at 15° C. and 100% humidity with a photoperiod of 16 h/8 h day/night. Late blight levels could be classified in three groups, resistant (no symptoms, limited hypersensitive response (HR)); intermediate resistance (large HR lesions or spreading HR lesions without sporulation) or susceptible (sporulating lesions). Genotypes classified in the resistant group or intermediate resistant group in climate chamber assays did not show significant late blight lesions until the end of the field trial experiments (resistant) and could easily be distinguished from the susceptible group.

Results

R8 Fine Mapping

In order to fine map R8, molecular markers were required to perform a recombinant screen in F1 population R8*C. R8 is located at the bottom end of chromosome 9, flanked by Tm-$2^2$-like CDP markers at the centromer proximal side and by Sw-5 CDP markers on the distal side (Jo et al. 2011). The CDP markers were not suitable for high throughput recombinant screens and simple PCR markers needed to be developed. On the proximal side marker 184_81 had been described before, but a marker on the distal side of R8 remained to be developed. Screening of the tomato marker database revealed marker C2_At5g06360, which is located near the telomer of Chr9. MaR8 and cv Concurrent derived amplicons of this marker were screened for cleaved amplified polymorphisms, linked to resistance and this resulted in marker At5g06360_2-FspBI. Population R8*C was expanded to 1720 individuals and recombinants between markers At5g06360_2-FspBI and 184_81-RsaI (FIG. 7) were screened for. In total 36 recombinants were found and their resistance phenotype was determined in a whole plant late blight assay in a climate chamber. Marker $CDP^{Hero}3$, which was identified previously, was still fully linked to resistance in this expanded population. Two recombinants were found between At5g06360_2-FspBI and $CDP^{Hero}3$, while 34 recombinants were found between 184_81 and $CDP^{Hero}$3 (FIG. 1).

BAC Landing and BAC Walking

A first BAC library was constructed from the genomic DNA of MaR8 plants. The library was screened using marker $CDP^{Hero}3$ and BAC clones 1A6, 3E3 and 6G9 were identified. The insert of 3E3 was sequenced and revealed the presence of four complete (RGA1.1, 1.2, 3.1 and 3.2) and one truncated R gene analog (RGA3.3). The newly obtained sequences were used for new marker development. A screen for markers in the intergenic regions successfully identified two polymorphic markers named 3E3_5-HRM and 3E3_10-SCAR. Mapping of the new markers revealed that the right end of BAC 3E3 fell outside the mapping interval, excluding RGA3.3 as a R8 candidate (FIG. 7). No recombinants were found at the left end of the BAC indicating that RGAs 1.0, 1.1, 3.1, 3.2 and, so far unidentified additional RGAs could be R8 candidates. In order to close the genetic window, marker 3E3_10-SCAR was used for screening the BAC library and resulted in the isolation of BAC clone 6A5 (FIG. 7). Sequence analysis revealed one additional complete RGA (RGA1.0). A marker developed on the 6A5 BAC end (6A5F_3-HpyCH4IV) still did not show any recombinants with R8 resistance, so the genetic window was not closed yet. Marker 6A5F_3-HpyCH4IV was used to screen the BAC library but unfortunately no new positive BACs were identified. A new BAC library was generated using a different genome fragmentation method (partial restriction enzyme digestion instead of mechanical shearing that was used in constructing the first BAC library). Screening of the new library identified BAC clone n2E2. Sequence analysis revealed the presence of four additional complete RGAs (0.10, 0.11, 0.20, and 0.21.). A screen for markers in the intergenic regions revealed marker 2E2_1-hin1II. One recombinant was found between this marker and the late blight resistance and it was concluded that the genetic interval was now closed. A genomic region of 174 kb (FIG. 8) containing a cluster of 10 paralogous sequences was found and all sequences had high homology to Sw-5, a R gene from tomato that provides resistance to tomato spotted wilt virus (Brommonschenkel et al. 2000).

R8 Candidate Cloning and Complementation Analysis

Figure 9A:
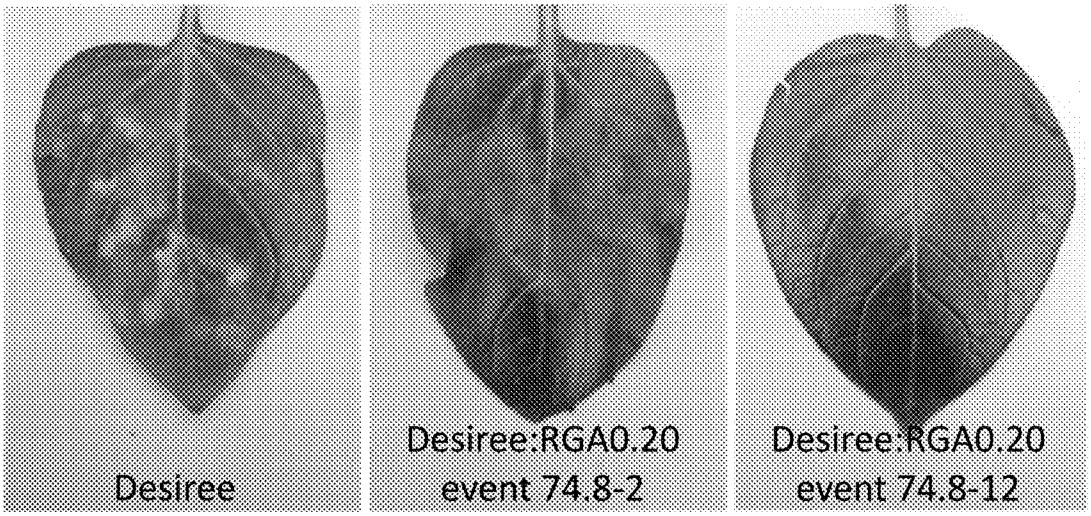
Figure 9B:
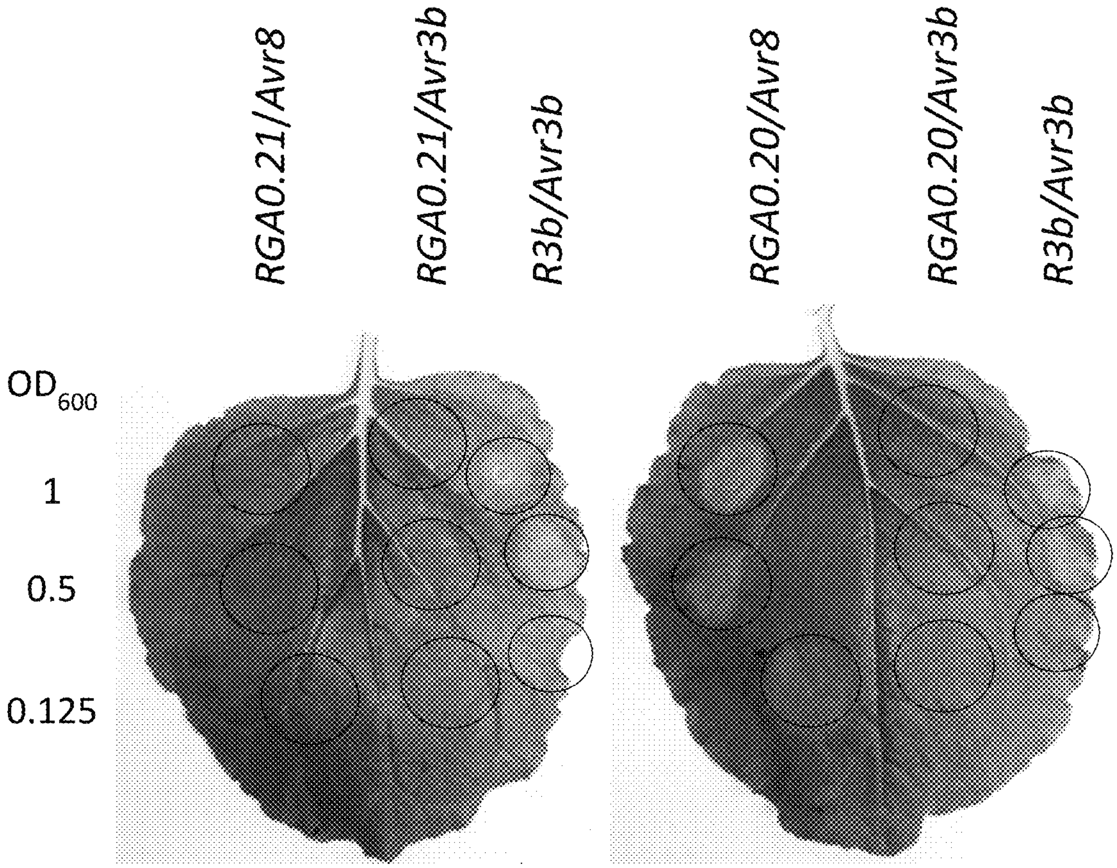

The seven RGAs in the genetic window were subcloned in the binary vector pBINPLUS-PASSA for *Agrobacterium* mediated transformation of plants. Stable transgenic plants of the susceptible potato variety Desiree were produced and 10 to 47 events per construct were selected. Six out of seven constructs produced only transformation events that were susceptible to *P. infestans* isolate IPO-C (Table 8). Eight out of 47 events transformed with RGA0.20 were susceptible, while 39 events showed intermediate to strong late blight resistance in a whole plant assay in climate chambers (FIG. 9A). PCR analysis revealed that the 8 susceptible events contained only partial inserts of the T-DNA. RGA0.20 was therefore denoted as a strong R8 candidate. This idea was confirmed when the RGAs were co-expressed with Avr8 in the *Nicotiana benthamiana*. Only RGA0.20 induced a hypersensitive response (HR) when co-infiltrated with Avr8. The observed HR was a result of specific recognition since co-infiltration of Avr3b with RGA0.20 did not result in a HR (FIG. 9B). From these results we conclude that RGA0.20 is R8.

TABLE 8

Complementation analysis of R8 resistance in Desiree

| construct | Avr8 response in *N. benthamiana* | Tested events# | Climate chamber whole plant assay# S | IR | R | Field trial# S | R |
|---|---|---|---|---|---|---|---|
| RGA3.2 | − | 12 | 12 | 0 | 0 | nd | nd |
| RGA3.1 | − | 10 | 10 | 0 | 0 | nd | nd |
| RGA1.2 | − | 10 | 10 | 0 | 0 | nd | nd |
| RGA1.1 | − | 10 | 10 | 0 | 0 | nd | nd |
| RGA1.0 | − | 10 | 10 | 0 | 0 | nd | nd |
| RGA0.21 | − | 15 | 15 | 0 | 0 | nd | nd |
| RGA0.20 | + | 47 | 8 | 14 | 25 | 8 | 39 |
| empty | − | 12 | 12 | 0 | 0 | 12 | 0 |

nd: not determined;
#: number of events

R8 Sequence Annotation

The binary vector containing R8 that was used for complementation studies had an insert of 7011 bp. A 1680 bp 5' untranslated region, encompassing a functional promotor, is followed by a single open reading frame of 3738 bp, representing the R8 coding sequence, which is followed by a 1594 bp 3' untranslated region which encompasses a functional transcriptional terminator (FIG. 10). The encoded R8 protein shows a tripartite domain structure CC NB-ARC LRR, which is typical for intracellular plant disease resistance proteins. Conserved protein sub-domains can be distinguished in the central NB-ARC region and a set of 13 C-terminal leucine rich repeats are found (FIG. 11). When the R8 protein sequence was aligned with known R proteins from Solanaceae and phylogenetic analysis was performed, it was found that R8 constitutes a distinct clade with the tomato Sw-5 protein (Brommonschenkel, 2000), which provides resistance to tomato spotted wilt virus (FIG. 12). Sw-5 and R8 shared 88.6% homology, while homology to other R proteins that were aligned was 26.1%, in the case of Rpi-blb2, or less (Table 9).

TABLE 9

Percentages of homology between R proteins from Solanaceae.

| R8 | R1 | Sw-5 | Rpi-blb2 | Prf1 | Rpi-chc1 | Rpi-tar1 | Rpi-vnt1 | Rpi-sto1 | Bs2 | Bs4 | gro1.4 |
|---|---|---|---|---|---|---|---|---|---|---|---|
| 26 | 27.1 | 25 | 23.7 | 28.4 | 21.8 | 22.1 | 24.4 | 22.1 | 28.6 | 14.9 | 16.2 |
| *** | 22.8 | 88.6 | 26.1 | 23.1 | 19.9 | 20.3 | 24.1 | 20.8 | 25.7 | 15.1 | 15 |
| | *** | 22.6 | 23.6 | 27.2 | 19.9 | 19.5 | 24.5 | 20.4 | 26.6 | 13.9 | 14.4 |
| | | *** | 26 | 22.9 | 19.5 | 19.9 | 24.5 | 19.5 | 25.4 | 15 | 14.6 |
| | | | *** | 22.5 | 19.3 | 19.3 | 21.4 | 21.1 | 25 | 16 | 16.4 |
| | | | | *** | 21.6 | 21.6 | 22.7 | 18.7 | 27.1 | 14.8 | 15.5 |
| | | | | | *** | 98.2 | 19.9 | 34.7 | 21.7 | 15.6 | 15.5 |
| | | | | | | *** | 19.9 | 34.6 | 21.9 | 15.2 | 15.6 |
| | | | | | | | *** | 23.3 | 23.2 | 14.4 | 14.9 |
| | | | | | | | | *** | 20.7 | 16.2 | 16.1 |
| | | | | | | | | | *** | 16.1 | 15.9 |
| | | | | | | | | | | *** | 40.3 |
| | | | | | | | | | | | *** |

| R2 | R3a | R3b | Rpi-abpt | Tm2^2 | R9a | mcq1 | N | |
|---|---|---|---|---|---|---|---|---|
| 26.1 | 20.7 | 20.3 | 26.4 | 25.4 | 26.3 | 24.9 | 15.8 | NRC1 |
| 24.6 | 21.1 | 19.7 | 24.3 | 24.3 | 25.9 | 24.6 | 15.4 | R8 |
| 25.3 | 20.7 | 19.7 | 25 | 25.5 | 26.3 | 24.8 | 14.4 | R1 |
| 23.3 | 20.8 | 19.2 | 23.2 | 24.9 | 25.9 | 24.6 | 15 | Sw-5 |
| 22.9 | 21.8 | 20.2 | 22.7 | 21.7 | 22.1 | 21.5 | 16.2 | Rpi-blb2 |
| 23.9 | 18.7 | 18.3 | 23.3 | 23.6 | 24.3 | 22.7 | 14.3 | Prf1 |
| 23.9 | 29.2 | 28.7 | 23.9 | 21.1 | 21.6 | 20.1 | 15.1 | Rpi-chc1 |
| 24 | 28.8 | 28.3 | 24 | 20.9 | 21.7 | 20.1 | 14.9 | Rpi-tar1 |
| 29.9 | 20.9 | 20.4 | 29.1 | 76.6 | 78.7 | 82 | 14.8 | Rpi-vnt1 |

TABLE 9-continued

| Percentages of homology between R proteins from Solanaceae. | | | | | | | | |
|---|---|---|---|---|---|---|---|---|
| 26 | 30.8 | 30.7 | 26.3 | 22.2 | 23.6 | 22.7 | 15 | Rpi-sto1 |
| 23.8 | 21.3 | 19.3 | 23.6 | 23.7 | 23.6 | 23.1 | 15.3 | Bs2 |
| 15.6 | 15.8 | 14.9 | 15.4 | 15.4 | 15.1 | 15.4 | 61.1 | BS4 |
| 15.2 | 17.1 | 16.3 | 14.7 | 14.7 | 15 | 15.3 | 39.6 | gro1.4 |
| *** | 24.4 | 24.2 | 95.5 | 28.9 | 28.9 | 28.8 | 15 | R2 |
| | *** | 72.4 | 24.2 | 20.5 | 22 | 20.6 | 16.1 | R3a |
| | | *** | 24 | 19.9 | 20.7 | 20.3 | 15.2 | R3b |
| | | | *** | 28.3 | 27.9 | 28.2 | 14.9 | Rpi-abpt |
| | | | | *** | 74 | 79 | 15.3 | Tm2^2 |
| | | | | | *** | 81.7 | 14.9 | R9a |
| | | | | | | *** | 15.4 | Rpi-mcq1 |
| | | | | | | | *** | N |

Example 4: Late Blight Challenges

Materials and Methods

Construction of Vectors Harbouring Combinations of R8 with Other Late Blight Resistance Genes Combinations of R8 with other late blight R genes were made by inserting Rpi-sto1, Rpi-blb3, Rpi-edn2, Rpi-vnt1.1, or Rpi-blb2 into the SbfI and AscI or SrfI and SbfI sites of the recipient vectors containing R8 (pBINPLUS-PAS:R8:SA, pBINPLUS-PASS:R8:A or pBINPLUS-A:R8:SSAP). This resulted in pBINPLUS-PAS:R8:S:Rpi-sto1:A, pBINPLUS-A:R8:S:Rpi-blb3:SAP, pBINPLUS-PAS:R8:S:Rpi-edn2:A, pBINPLUS-PA:Rpi-vnt1.1:SS:R8:A, pBINPLUS-PAS:Rpi-blb2:S:R8:A.

Late Blight Resistance Tests

*P. infestans* isolates and their corresponding (a)-virulence spectra that were used in this study are listed in Table 9. The late blight epidemic in Wageningen, the Netherlands, in the 2014 and 2015 field trial was a result of natural *P. infestans* infection that started at the end of June. Field trials contained four replicates per genotype and late blight was assessed by observing late blight lesions after inoculation or after the first late blight symptoms were visible in susceptible control plants (2014), in a qualitative way. Resistant plants remained unaffected until the end of the experiment mid August, while susceptible plants had died already mid July.

Climate cell whole plant assays: Two replicates of transgenic Desiree or recombinant seedlings from population 3020 were propagated in vitro. The plants were transferred to potting soil and grown in the greenhouse at 22° C. with a 10 h day/14 h night photoperiod and a relative humidity of 70-80%. One month after potting of the plants, they were transferred into a growth chamber and inoculated. Inoculum was prepared by washing of the oospores from two weeks old rye sucrose agar plates containing the isolates of interest. Plants were inoculated by placing four 10 μl droplets of inoculum (5×104 zoospores/ml) on the adaxial side of at least three leaves per plant. Inoculated plants were kept for seven days in a climate chamber at 15° C. and 100% humidity with a photoperiod of 16 h day/8 h night. Late blight levels could be classified in three groups, resistant (no symptoms, limited hypersensitive response (HR)); intermediate resistance (large HR lesions or spreading HR lesions without sporulation) or susceptible (sporulating lesions). Genotypes classified in the resistant group or intermediate resistant group in climate chamber assays did not show significant late blight lesions until the end of the field trial experiments (resistant) and could easily be distinguished from the susceptible group.

TABLE 10

Virulence spectra of different *P. infestans* isolates used in this study.

| Isolate | Origin | A-virulence spectrum | Reference |
|---|---|---|---|
| NL09066 | The Netherlands | avrsto1, Avrblb3, Avr8, Avredn2, Avrblb2, Avrvnt1 | G. Kessel |
| IPO-C | The Netherlands | Avrsto1, avrblb3, Avr8, Avredn2, Avrblb2, Avrvnt1 | (Zhu et al. 2014) |
| US-22 | USA (US090017) | Avrsto1, Avrblb3, avr8, Avredn2, Avrblb2, Avrvnt1 | G. Kessel |
| NL12097 | The Netherlands | Avrsto1, Avrblb3, Avr8, avredn2, Avrblb2, Avrvnt1 | G. Kessel |
| NL12003 | The Netherlands | Avrsto1, Avrblb3, Avr8, Avredn2, avrblb2, Avrvnt1 | G. Kessel |
| Ec-1 | Ecuador | Avrsto1, Avrblb3, Avr8, Avredn2, Avrblb2, avrvnt1 | (Pel 2010) |

Transformation of Potato

Binary plasmids harbouring combinations of late blight R genes were transferred to *A. tumefaciens* strain AGL1 containing the helper plasmid pVirG (Van der Fits et al. 2000). The stability of these clones in *Agrobacterium* was tested and overnight cultures of the transformed *A. tumefaciens* strain were used to transform susceptible cultivar Desiree (Heeres et al. 2002). The kanamycin resistant regenerants (transgenic events) were analysed by PCR to determine the presence of the R8 and the second late blight resistance gene. Two or four plants per transgenic event were transferred to the greenhouse for climate chamber assays or for planting in the field, respectively.

Results

Potential of R8 for Protection Against Late Blight

Not only the Avr8 recognition was maintained by the cloned R8 gene (Table 8), but also the broad resistance spectrum of R8 against the current *P. infestans* population was maintained. 39 transgenic events provided excellent late blight resistance to natural late blight infection in 2014 and 2015 in field trials in Wageningen, The Netherlands (Table 1, FIG. 3).

It was described previously that R8 is the same or a similar gene as Rpi-smira2, the major constituent of the durably late blight resistant variety Sarpo Mira (Jo 2013). To confirm this suggestion, we set out to clone the Rpi-smira2 gene using R8 specific primers (Table S3) that amplified the coding sequence (CDS) or 1690 nucleotides of the 5' untranslated region (UTR) and the first 745 bp of the CDS. Three independent Rpi-smira2 clones of each amplicon were sequenced and the consensus showed 100% identity with R8 in the CDS. At position -723 in the 5'UTR there was one T>C polymorphism in R8 vs Rpi-smira2. This clearly confirmed that Rpi-smira2 is the same gene as R8.

Stacking of R8 with Other Late Blight R Genes to Achieve Durable Resistance

The durability of Sarpo mira's resistance was associated with the stacking of multiple R genes (Rietman et al. 2012). To pursue similar or even better durability, we set out to produce stacks of R8 with other late blight R genes in order to create material for future durability challenges. Combinations of R8 with Rpi-sto1, Rpi-blb3, Rpi-edn2, Rpi-vnt1.1 and Rpi-blb2 were made in binary vectors and these constructs were transformed to potato variety Desiree. From each construct 21 transformation events were harvested and tested for the presence and functional expression of both R genes. For this purpose, the events were inoculated with differential *P. infestans* isolates (Table 10) that had overcome one of the R genes in the stack. There was a remarkable difference in the frequency by which events were produced that were resistant to both differential isolates (Table 3). The most efficient combinations were R8:Rpi-edn2, Rpi-vnt1.1:R8 and Rpi-blb2:R8. In 2015 these plants were exposed to durability challenges in field trials in 2015. Indeed, the plants that functionally expressed both R8 and the second R gene remained devoid of any late blight symptoms (Table 11).

TABLE 11

Combinations of R8 with other late blight R genes in one binary vector transformed to Desiree.

| Insert in binary vector | Frequency that both R genes are active in transgenic events* | Frequency of Immune** plants among events with both R genes active in the field |
|---|---|---|
| R8:Rpi-sto1 | 0.00 | — |
| Rpi-blb3:R8 | 0.08 | — |
| R8:Rpi-edn2 | 0.55 | 1.0 |
| Rpi-vnt1.1:R8 | 0.86 | 1.0 |
| Rpi-blb2:R8 | 0.95 | 1.0 |

*21 events per construct were tested for the activity of both R genes using differential isolates.
**immunity is defined as absence of symptoms until the end of the growing season of 2015

The invention claimed is:

1. A method for providing at least partial resistance or increasing resistance in a plant against *Phytophthora infestans* infection, comprising providing a plant or a part thereof with a. an isolated nucleic acid encoding a resistance protein that is able to confer resistance to *Phytophthora infestans* when expressed in a plant, wherein said isolated nucleic acid is a transgene and i. comprises the nucleic acid sequence of SEQ ID NO: 36, ii. encodes a protein having the amino acid sequence of SEQ ID NO: 37, or iii. comprises a nucleic acid sequence that codes for a protein that has an identity of at least 95% with said protein having the amino acid sequence of SEQ ID NO: 37 wherein resistance is increased compared to a plant without said nucleic acid; and b. one or more further *Phytophthora infestans* resistance genes selected from Rpi-edn2, Rpivnt1.1 and Rpi-blb2.

2. The method according to claim 1, wherein said plant or part thereof is also provided with a nucleic acid sequence encoding a further *Phytophthora infestans* resistance gene selected from:

c. the R-genes of *S. berthaultii, S. bulbocastanum, S. caripense, S. demissum, S. mkrodontum, S. mochiquense, S. papita, S. paucissectum, S. phureja, S. pinnatisectum, S. stoloniferum, S. venturii, S. vernei*, or hybrids with *S. tuberosum*; and/or d. Rpi-ber, Rpi-ber1, Rpi-ber2, RB/Rpi-blb1, Rpi-blb3, R1, R2, R3, R3a, R3b, R5, R6, R7, R8, R9, R10, R11, Rpi-mcq1, Rpi-pta1, Rpi-phu1, Rpi-pn1, Rpi-sto1, Rpi-vnt1.3, Rpi-abpt, or R2-like.

3. A method for obtaining a potato plant that is resistant against *Phytophthora infestans* infection by crossing a donor potato plant that has the R8 gene from *Solanum demissum* with a potato plant of interest and testing the offspring plant of said cross for a. the presence of a nucleic acid, wherein said nucleic acid i. comprises the nucleic acid sequence of SEQ ID NO: 36, ii. encodes a protein having the amino acid sequence of SEQ ID NO: 37, iii. comprises a nucleic acid sequence that codes for a protein that has an identity of at least 95% with said protein having the amino acid sequence of SEQ ID NO: 37; and b. the presence of one or more further *Phytophthora infestans* resistance genes selected from Rpi-edn2, Rpivnt1.1, and Rpi-blb2.

4. The method according to claim 3, wherein said donor potato plant that has the R8 gene is of the variety 'Sarpo Mira'.

5. A method for breeding a *Phytophthora infestans* resistant tetraploid offspring plant, said method comprising a. doubling the ploidy level of the gametes of a diploid donor plant that already contains the nucleic acid sequence and the one or more further *Phytophthora infestans* resistance genes as defined in claim 3;

b. using said gametes in a cross with gametes of a tetraploid plant; and c. selecting the offspring of said cross for the presence of said nucleic acid sequence.

6. The method according to claim 3, wherein said *Phytophthora infestans* resistant offspring plant further comprises one or more further resistance genes selected from:

a. the R-genes of *S. berthaultii, S. bulbocastanum, S. caripense, S. demissum, S. microdontum, S. mochiquense, S. papita, S. paucissectum, S. phureja, S. pinnatisectum, S. stoloniferum, S. venturii, S. vernei*, or hybrids with *S. tuberosum*; and/or b. Rpi-ber, Rpi-ber1, Rpi-ber2, RB/Rpi-blb1, Rpi-blb3, R1, R2, R3, R3a, R3b, R5, R6, R7, R8, R9, R10, R11, Rpi-mcq1, Rpi-pta1, Rpi-phu1, Rpi-pnt1, Rpi-sto1, Rpi-vnt1.3, Rpi-abpt, or R2-like.

7. A method for selecting a plant or plant material or progeny thereof for its susceptibility or resistance to *Phytophthora infestans* infection, said method comprising the steps of testing at least part of said plant or plant material or progeny thereof for the presence or absence of the nucleic acid and the one or more further *Phytophthora infestans* resistance genes as defined in claim 3.

8. The method according to claim 3, wherein said testing involves detecting the presence of at least part of the nucleic acid sequence as shown in SEQ ID NO. 36 and is performed with a primer or a probe that specifically binds to said nucleic acid sequence.

9. A transgenic or tetraploid cell comprising the nucleic acid and one or more further *Phytophthora infestans* resistance genes as defined in claim 3 as a transgene.

10. A vector comprising the nucleic acid and one or more further *Phytophthora infestans* resistance genes as defined in claim 3.

11. The vector according to claim 10, further comprising a promoter and/or terminator with which the nucleic acid sequence is naturally associated.

12. A transgenic or tetraploid host cell comprising the nucleic acid and one or more further *Phytophthora infestans* resistance genes as defined in claim 3 as a transgene or a vector according to claim 10.

13. A transgenic or tetraploid plant cell comprising the nucleic acid and one or more further *Phytophthora infestans* resistance genes as defined in claim 3 as a transgene or the vector according to claim 10.

14. A transgenic or tetraploid plant comprising the cell according to claim 13.

15. A plant part taken from the plant according to claim 14.

16. The method according to claim 1, wherein said plant or part thereof or said offspring plant further comprises or is provided with one or more further *Phytophthora infestans* resistance genes selected from Rpi-chc1, Bpi-ber, Rpi-sto1, and Rpi-blb3.

17. The method according to claim 3, wherein said plant or part thereof or said offspring plant further comprises or is provided with one or more further *Phytophthora infestans* resistance genes selected from Rpi-chc1, Bpi-ber, Rpi-sto1, and Rpi-blb3.

18. The plant of claim 14, wherein said plant or part thereof or said offspring plant further comprises or is provided with one or more further *Phytophthora infestans* resistance genes selected from Rpi-chc1, Rpi-ber, Rpi-sto1, and Rpi-blb3.

* * * * *